US009856253B2

(12) United States Patent
Breinlinger et al.

(10) Patent No.: US 9,856,253 B2
(45) Date of Patent: Jan. 2, 2018

(54) TRICYCLIC MODULATORS OF TNF SIGNALING

(71) Applicant: AbbVie Inc., North Chicago, IL (US)

(72) Inventors: Eric C. Breinlinger, Charlton, MA (US); Phil B. Cox, Grayslake, IL (US); Justin Dietrich, Lindenhurst, IL (US); Kristine E. Frank, Grayslake, IL (US); Michael M. Friedman, Brookline, MA (US); Huan-Qui Li, Wilmette, IL (US); Kenton Longenecker, Grayslake, IL (US); Augustine Osuma, Lindenhurst, IL (US); Ann Marie Rowley, Libertyville, IL (US); Anil Vasudevan, Union Grove, WI (US); Noel Wilson, Kenosha, WI (US)

(73) Assignee: AbbVie, Inc., North Chicago, IL (US)

( * ) Notice: Subject to any disclaimer, the term of this patent is extended or adjusted under 35 U.S.C. 154(b) by 0 days.

(21) Appl. No.: 15/130,362

(22) Filed: Apr. 15, 2016

(65) Prior Publication Data

US 2016/0304517 A1 Oct. 20, 2016

Related U.S. Application Data

(60) Provisional application No. 62/149,280, filed on Apr. 17, 2015.

(51) Int. Cl.

| C07D 227/00 | (2006.01) |
| C07D 471/04 | (2006.01) |
| C07D 471/14 | (2006.01) |
| C07D 487/04 | (2006.01) |
| C07D 498/04 | (2006.01) |
| C07D 498/14 | (2006.01) |
| C07D 498/18 | (2006.01) |
| C07D 498/20 | (2006.01) |
| C07D 498/22 | (2006.01) |
| C07D 519/00 | (2006.01) |
| C07D 471/18 | (2006.01) |
| C07D 491/147 | (2006.01) |
| C07D 491/22 | (2006.01) |

(52) U.S. Cl.
CPC ......... *C07D 471/04* (2013.01); *C07D 471/14* (2013.01); *C07D 471/18* (2013.01); *C07D 487/04* (2013.01); *C07D 491/147* (2013.01); *C07D 491/22* (2013.01); *C07D 498/04* (2013.01); *C07D 498/14* (2013.01); *C07D 498/18* (2013.01); *C07D 498/20* (2013.01); *C07D 498/22* (2013.01); *C07D 519/00* (2013.01)

(58) Field of Classification Search
CPC .................................................. C07D 227/00
See application file for complete search history.

(56) References Cited

U.S. PATENT DOCUMENTS

| 2007/0021337 | A1 | 1/2007 | Lee et al. |
| 2007/0213337 | A1 | 9/2007 | Wacker et al. |
| 2008/0287448 | A1 | 11/2008 | Zoller et al. |
| 2010/0029616 | A1 | 2/2010 | Kinney et al. |
| 2010/0204214 | A1 | 8/2010 | Chytil et al. |
| 2014/0235675 | A1 | 8/2014 | Papeo et al. |
| 2016/0039811 | A1 | 2/2016 | Yoshida et al. |

FOREIGN PATENT DOCUMENTS

| JP | 2009035531 A | 2/2009 |
| WO | WO-2004/063163 A1 | 7/2004 |
| WO | WO-2004/093872 A1 | 11/2004 |
| WO | WO-2005/100353 A1 | 10/2005 |
| WO | 2005121096 | 12/2005 |
| WO | WO-2006/047516 | 5/2006 |
| WO | 2006108948 | 10/2006 |
| WO | 2007042178 | 4/2007 |
| WO | WO-2007/110216 A1 | 10/2007 |
| WO | 2007126122 | 11/2007 |
| WO | 2007126128 | 11/2007 |
| WO | WO-2008/008432 A2 | 1/2008 |
| WO | 2008051403 | 5/2008 |
| WO | 2008051493 | 5/2008 |
| WO | 2008141385 | 11/2008 |
| WO | WO-2010/054278 A2 | 5/2010 |
| WO | 2010084402 | 7/2010 |
| WO | 2010115491 | 10/2010 |
| WO | WO-2011/062864 A2 | 5/2011 |
| WO | 2011119565 | 9/2011 |
| WO | WO-2011/116356 A2 | 9/2011 |
| WO | 2012072019 | 6/2012 |
| WO | 2012088124 | 6/2012 |
| WO | 2013000994 | 1/2013 |
| WO | WO-2013/186229 A1 | 12/2013 |

(Continued)

OTHER PUBLICATIONS

Chimirri et al, "Synethsis and Antitumour Activity of 1H,3H-thiazolo[3,4-a]benzimidazole Derivatives", Archiv der Pharmazie, vol. 334, No. 6, Jun. 1, 2001, pp. 203-208.
Kumar K.S., et al., "A New Three-Component Reaction: Green Synthesis of Novel Soindolo[2,1-a]quinazoline Derivatives as Potent Inhibitors of TNF-α," Chemical Communications, 2011, vol. 47 (17), pp. 5010-5012.
Database CAPLUS in STN, Acc. No. 2009:1290752, Vidal'-Khuan et al., RU 2370496 C2 (Oct. 20, 2009) (abstract).
Database CAPLUS in STN, Acc. No. 2008:276955, Cappelli et al., Journal of Medicinal Chemistry (2008), 51(7), pp. 2137-2146 (abstract).
Database CAPLUS in STN, Acc. No. 2005:1154552, Vidal et al., WO 2005/100353 A 1 (Oct. 27, 2005) (abstract).
Chimirri et al, "Synthesis and Antitumour Activity of 1 H,3H-thiazolo[3,4-a]benzimidazole Derivatives", Archiv der Pharmazie, vol. 334, No. 6, Jun. 1, 2001, pp. 203-208.
U.S. Appl. No. 15/130,279, filed Apr. 15, 2016.
U.S. Appl. No. 15/130,323, filed Apr. 15, 2016.

(Continued)

*Primary Examiner* — Bruck Kifle
(74) *Attorney, Agent, or Firm* — Dana M. Gordon; Foley Hoag LLP

(57) ABSTRACT

The invention provides tricyclic heterocyclic compounds, pharmaceutically acceptable salts, pro-drugs, biologically active metabolites, stereoisomers and isomers thereof wherein the variables are defined herein. The compounds of the invention may be useful for treating immunological and oncological conditions.

19 Claims, No Drawings

(56) References Cited

FOREIGN PATENT DOCUMENTS

| | | |
|---|---|---|
| WO | 2014009295 | 1/2014 |
| WO | WO-2014/009296 A1 | 1/2014 |
| WO | WO-2014/157569 A1 | 10/2014 |
| WO | 2015086526 | 6/2015 |
| WO | 2015086527 | 6/2015 |
| WO | WO-2015/086496 A1 | 6/2015 |
| WO | WO-2015/086498 A1 | 6/2015 |
| WO | WO-2015/086499 A1 | 6/2015 |
| WO | WO-2015/086500 A1 | 6/2015 |
| WO | WO-2015/086501 A1 | 6/2015 |
| WO | WO-2015/086502 A1 | 6/2015 |
| WO | WO-2015/086503 A1 | 6/2015 |
| WO | WO-2015/086504 A1 | 6/2015 |
| WO | WO-2015/086505 A1 | 6/2015 |
| WO | WO-2015/086506 A1 | 6/2015 |
| WO | WO-2015/086507 A1 | 6/2015 |
| WO | WO-2015/086508 A1 | 6/2015 |
| WO | WO-2015/086509 A1 | 6/2015 |
| WO | WO-2015/086511 A1 | 6/2015 |
| WO | WO-2015/086512 A1 | 6/2015 |
| WO | WO-2015/086513 A1 | 6/2015 |
| WO | WO-2015/086519 A1 | 6/2015 |
| WO | WO-2015/086520 A1 | 6/2015 |
| WO | WO-2015/086521 A1 | 6/2015 |
| WO | WO-2015/086523 A1 | 6/2015 |
| WO | WO-2016/050975 A1 | 4/2016 |
| WO | 2015086525 | 6/2016 |
| WO | WO-2016/149436 A1 | 9/2016 |
| WO | WO-2016/149437 A1 | 9/2016 |
| WO | WO-2016/149439 A1 | 9/2016 |
| WO | WO-2016/168633 A1 | 10/2016 |
| WO | WO-2016/168638 A1 | 10/2016 |
| WO | WO-2016/168641 A1 | 10/2016 |
| WO | WO-2016/198398 A1 | 12/2016 |
| WO | WO-2016/198400 A1 | 12/2016 |
| WO | WO-2016/198401 A1 | 12/2016 |
| WO | WO-2016/202411 A1 | 12/2016 |
| WO | WO-2016/202412 A1 | 12/2016 |
| WO | WO-2016/202413 A1 | 12/2016 |
| WO | WO-2016/202414 A1 | 12/2016 |
| WO | WO-2016/202415 A1 | 12/2016 |
| WO | WO-2017/023902 A1 | 2/2017 |
| WO | WO-2017/023905 A1 | 2/2017 |

OTHER PUBLICATIONS

U.S. Appl. No. 62/134,769, filed Mar. 18, 2015, Bristol-Myers Squibb Company.

Cappelli et al., "Design, Synthesis, and Biological Evaluation of AT1 Angiotensin II Receptor antagonists Based on the Pyrazolo[3,4-b]pyridine and Related Heteroaromatic Bicyclic Systems," J Med Chem, 51: 2137-2146 (2008).

International Search Report and Written Opinion for International Application No. PCT/2016/027799 dated [May 25, 2016].

International Search Report and Written Opinion for International Application No. PCT/2016/027808 dated [Jun. 1, 2016].

International Search Report and Written Opinion for International Application No. PCT/2016/027814 dated [Jun. 10, 2016].

Notice of Allowance for U.S. Appl. No. 15/130,279 dated May 8, 2017.

TRICYCLIC MODULATORS OF TNF SIGNALING

PRIORITY CLAIM

This application claims the benefit of U.S. Provisional Application No. 62/149,280, filed Apr. 17, 2015, which is hereby incorporated by reference in its entirety.

FIELD OF THE INVENTION

The present invention relates to a class of tricyclic heterocycles, and to their use in therapy. More particularly, this invention is concerned with pharmacologically active substituted tricyclic heterocycles. These compounds are modulators of the signaling of TNFα, and are accordingly of benefit as pharmaceutical agents, especially in the treatment of adverse inflammatory and autoimmune disorders, neurological and neurodegenerative disorders, pain and nociceptive disorders, cardiovascular disorders, metabolic disorders, ocular disorders, and oncological disorders.

BACKGROUND

TNFα is the prototypical member of the Tumor Necrosis Factor (TNF) superfamily of proteins that share a primary function of regulating cell survival and cell death. One structural feature common to all known members of the TNF superfamily is the formation of trimeric complexes that bind to, and activate, specific TNF superfamily receptors. By way of example, TNFα exists in soluble and transmembrane forms and signals through two receptors, known as TNFR1 and TNFR2, with distinct functional endpoints.

Various products capable of modulating TNFα activity are already commercially available. All are approved for the treatment of inflammatory and autoimmune disorders such as rheumatoid arthritis and Crohn's disease. All currently approved products are macromolecular and act by inhibiting the binding of human TNFα to its receptor. Typical macromolecular TNFα inhibitors include anti-TNFα antibodies and soluble TNFα receptor fusion proteins. Examples of commercially available anti-TNFα antibodies include fully human antibodies such as adalimumab (Humira®) and golimumab (Simponi®), chimeric antibodies such as infliximab (Remicade®), and pegylated Fab' fragments such as certulizumab pegol (Cimzia®). An example of a commercially available soluble TNFα receptor fusion protein is etanercept (Enbrel®).

TNF superfamily members, including TNFα itself, are implicated in a variety of physiological and pathological functions that are believed to play a part in a range of conditions of significant medical importance (see, for example, M. G. Tansey & D. E. Szymkowski, Drug Discovery Today, 2009, 14, 1082-1088; and F. S. Carneiro et al., J. Sexual Medicine, 2010, 7, 3823-3834).

SUMMARY OF THE INVENTION

The compounds in accordance with the present invention, being potent modulators of human TNFα activity, may be beneficial in the treatment and/or prevention of various human ailments. These include autoimmune and inflammatory disorders; neurological and neurodegenerative disorders; pain and nociceptive disorders; cardiovascular disorders; metabolic disorders; ocular disorders; and oncological disorders.

In addition, the compounds in accordance with the present invention may be beneficial as pharmacological standards for use in the development of new biological tests and in the search for new pharmacological agents. Thus, in one embodiment, the compounds of this invention may be useful as radioligands in assays for detecting pharmacologically active compounds. In an alternative embodiment, certain compounds of this invention may be useful for coupling to a fluorophore to provide fluorescent conjugates that can be utilized in assays (e.g., a fluorescence polarization assay) for detecting pharmacologically active compounds.

In a first embodiment the invention provides a compound of Formula (I):

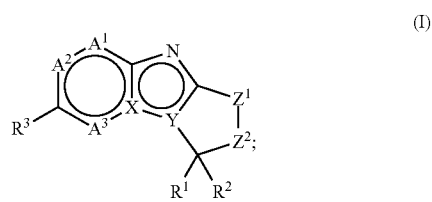

or a pharmaceutically acceptable salt, prodrug or stereoisomer thereof, wherein:

$R^1$ is H, OH, F or optionally substituted $(C_1-C_3)$alkyl;

$R^2$ is optionally substituted aryl, optionally substituted $(C_3-C_8)$cycloalkyl, optionally substituted heteroaryl or optionally substituted heterocyclyl; or $R^1$ and $R^2$ together can form an optionally substituted saturated or partially saturated carbocyclic ring or optionally substituted saturated or partially saturated heterocyclic ring;

up to two of $A^1$, $A^2$, and $A^3$ are N, and the rest are independently $C(R^{42})$;

X is N and Y is C, wherein:
  $Z^1$ is —$C(R^z)_2$— and $Z^2$ is —$C(R^z)_2$—, —$N(R^{z1})$— or —O—; or
  $Z^1$ is —$CH_2$— and $Z^2$ is —$Z^{2a}$—$Z^{2b}$—,
    wherein $Z^{2a}$ is attached to $Z^1$ and $Z^{2b}$ is attached to $C(R^1)(R^2)$; and
    $Z^{2a}$ and $Z^{2b}$ are independently —$C(R^z)_2$—, —$C(R^z)_2C(R^z)_2$—, —O— or —$N(R^{z1})$— provided that one of $Z^{2a}$ and $Z^{2b}$ is —$C(R^z)_2$— or —$C(R^z)_2C(R^z)_2$—; or
    —$Z^{2a}$—$Z^{2b}$— form —$N(R^{z1})C(O)$— or —$C(O)N(R^{z1})$—;

or

X is C and Y is N, provided that $R^1$ is not —OH or —F, wherein:
  $Z^1$ is —$C(R^z)_2$— and $Z^2$ is —$C(R^z)_2$—; or
  $Z^1$ is —$C(R^z)_2$— and $Z^2$ is —$Z^{2a}$—$Z^{2b}$—,
    wherein $Z^{2a}$ is attached to $Z^1$ and $Z^{2b}$ is attached to $C(R^1)(R^2)$, and
    $Z^{2a}$ is —$C(R^z)_2$—, —$C(R^z)_2C(R^z)_2$—, —O— or —$N(R^{z1})$, and $Z^{2b}$ is —$C(R^z)_2$—, or
    —$Z^{2a}$—$Z^{2b}$— form —$N(R^{z1})C(O)$— or —$C(O)N(R^{z1})$—;

$R^3$ is —$R^{3a}$—$R^{3b}$, wherein:
$R^{3a}$ is an optionally substituted aryl, optionally substituted saturated or partially saturated heterocyclyl or optionally substituted heteroaryl;
$R^{3b}$ is H, —$CF_3$, —CN, —C(O)OH, —N($R^a$)($R^b$), —C(O)N($R^a$)($R^b$), —C(O)-optionally substituted heterocyclyl, —O($R^a$), —S(O)$_2$(C$_1$-C$_3$)alkyl, —S(O)$_2$N($R^c$)($R^d$), —S—(C$_1$-C$_3$)alkyl, —S(O)$_2$—$R^c$ optionally substituted (C$_1$-C$_5$)alkyl, —(CH$_2$)$_p$-optionally substituted (C$_3$-C$_6$)cycloalkyl, —(CH$_2$)$_p$-optionally substituted heteroaryl or —(CH$_2$)$_p$-optionally substituted saturated, unsaturated or partially saturated heterocyclyl; provided that R3$^b$ is not H or methoxy when R$^2$ is optionally substituted phenyl;

R$^a$ and R$^b$ are independently selected from H, optionally substituted (C$_1$-C$_5$)alkyl, —C(O)-optionally substituted (C$_1$-C$_5$)alkyl, optionally substituted —(CH$_2$)$_p$—(C$_3$-C$_6$)cycloalkyl and —(CH$_2$)$_p$-optionally substituted heterocyclyl;

R$^c$ and R$^d$ are independently selected from H, optionally substituted (C$_1$-C$_5$)alkyl, optionally substituted —(CH$_2$)$_p$—(C$_3$-C$_6$)cycloalkyl and —(CH$_2$)$_p$-optionally substituted heterocyclyl;

R$^{42}$ is independently H, CF$_3$, halo or (C$_1$-C$_3$)alkyl;

R$^z$ is independently H, F, CF$_3$, —OH or (C$_1$-C$_3$)alkyl;

R$^{z1}$ is independently H or (C$_1$-C$_3$)alkyl; and p is independently 0, 1 or 2;

provided that R$^2$ is not phenyl substituted with —OCHF$_2$; and provided the compound is not 1-(2-methylphenyl)-7-[2-(morpholin-4-yl)pyrimidin-5-yl]-2,3-dihydro-1H-pyrrolo[1,2-a]benzimidazole;

7-[2-(morpholin-4-yl)pyrimidin-5-yl]-1-phenyl-2,3-dihydro-1H-pyrrolo[1,2-a]benzimidazole;

(1R or S)-7-(6-methylsulfonyl-3-pyridyl)-1-phenyl-2,3-dihydro-1H-pyrrolo[1,2-a]benzimidazole;

[5-[(1R or S)-1-phenyl-2,3-dihydro-1H-pyrrolo[1,2-a]benzimidazol-7-yl]-2-pyridyl]methanol;

tert-butyl 4-[5-[(1R or S)-1-phenyl-2,3-dihydro-1H-pyrrolo[1,2-a]benzimidazol-7-yl]-2-pyridyl]piperazine-1-carboxylate;

(1R or S)-7-[(6-chloromethyl)-3-pyridyl]-1-phenyl-2,3-dihydro-1H-pyrrolo[1,2-a]benzimidazole;

(1R or S)-7-[(6-(methylsulfonylmethyl)-3-pyridyl]-1-phenyl-2,3-dihydro-1H-pyrrolo[1,2-a]benzimidazole; or (1R or S)-1-phenyl-7-[6-(piperazin-1-yl)pyridine-3-yl]-2,3-dihydro-1H-pyrrolo[1,2-a]benzimidazole.

In a second embodiment the invention provides a compound according to the first embodiment, wherein R$^2$ is phenyl, tetrahydropyranyl, pyridinyl or cyclohexyl, each of which is independently optionally substituted with 1 to 3 groups selected from halogen, —CN, —NR$^a$, —OR$^a$, —CF$_3$, —(C$_1$-C$_6$)alkyl, —(C$_1$-C$_6$)haloalkyl, —(C$_1$-C$_6$)alkylene-OR$^a$, —(C$_1$-C$_6$)alkylene-NR$^a$R$^a$, and —(C$_1$-C$_6$)haloalkoxy, wherein R$^a$ is H or —(C$_1$-C$_6$)alkyl; and R$^1$ is H, OH or optionally substituted (C$_1$-C$_3$)alkyl; or R$^1$ and R$^2$ together form an optionally substituted spirocycle selected from

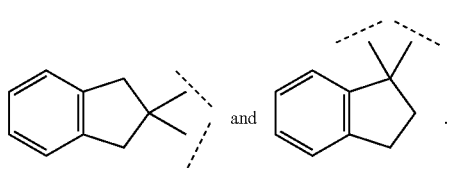

In a third embodiment the invention provides a compound according to any of the foregoing embodiments, wherein R$^2$ is phenyl or cyclohexyl, each of which is independently optionally substituted with 1 to 3 groups selected from halogen, —OR$^a$, —(C$_1$-C$_6$)alkyl, and —(C$_1$-C$_6$)haloalkoxy, and R$^1$ is H, OH or CH$_3$; or R$^1$ and R$^2$ together form

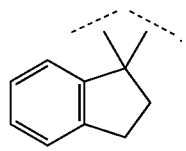

In a fourth embodiment the invention provides a compound according to any of the foregoing embodiments, wherein R$^{3a}$ is optionally substituted phenyl, optionally substituted imidazo[4,5-b]pyridinyl, optionally substituted [1,2,5]oxadiazolo[3,4-b]pyridinyl, optionally substituted piperazinyl, optionally substituted piperidinyl, optionally substituted pyrimidinyl, optionally substituted pyridinyl, optionally substituted pyrazinyl, optionally substituted pyridin-2(1H)-one, optionally substituted 3,4-dihydro-2H-pyrido[3,2-b][1,4]oxazinyl, optionally substituted furo[3,2-b]pyridinyl, optionally substituted benzo[d][1,3]dioxolyl, optionally substituted 1H-pyrazolyl, optionally substituted 3,4-dihydro-2H-pyrido[3,2-b][1,4]oxazinyl, optionally substituted pyrrolyl, optionally substituted [1,2,5]oxadiazolo[3,4-b]pyridinyl, optionally substituted pyrido[2,3-b]pyrazinyl, optionally substituted 3H-imidazo[4,5-b]pyridinyl, optionally substituted pyridin-2(1H)-onyl, or optionally substituted thienyl.

In a fifth embodiment the invention provides a compound according to any of the foregoing embodiments, wherein R$^{3b}$ is H, CF$_3$, CN, —C(O)OH, —C(O)N(R$^a$)$_2$, optionally substituted (C$_1$-C$_3$)alkyl, optionally substituted (C$_3$-C$_6$)cycloalkyl, —CH$_2$-optionally substituted heteroaryl, —N(R$^a$)$_2$, —N(R$^c$)S(O)$_2$-optionally substituted (C$_1$-C$_3$) alkyl, —OR$^a$, —S-optionally substituted (C$_1$-C$_3$)alkyl, —S(O)$_2$-optionally substituted (C$_1$-C$_3$)alkyl, —S(O)$_2$—N(R$^a$)$_2$, —S(O)$_2$-morpholinyl, optionally substituted azepanyl, optionally substituted 6-azaspiro[3.4]nonanyl, optionally substituted 7-azaspiro[3.5]nonanyl, optionally substituted azaspiro[3.4]octanyl, optionally substituted azetidinyl, optionally substituted 2,7-diazaspiro[4.4]nonanyl, optionally substituted diazepanyl, optionally substituted 3,10-diazabicyclo[4.3.1]decanyl, optionally substituted oxetanyl, hexahydroimidazo[1,2-a]pyrimidin-2(3H)-one, optionally substituted imidazolyl, hexahydroimidazo[1,2-c]pyrimidin-2(3H)-one, optionally substituted hexahydroimidazo[1,5a]pyrazin-3(2H)-one, optionally substituted hexahydroimidazo[1,5-c]pyrazin-3(2H)-one, optionally substituted morpholinyl, optionally substituted oxazolo[3,4-a]pyrazine-3-one, 1,4-oxepanyl, optionally substituted piperazinyl, optionally substituted piperidinyl, optionally substituted pyrazinyl, optionally substituted pyrazolyl, optionally substituted pyrimidinyl, optionally substituted pyrrolidinyl, tetrahydro-1H-oxazolo[3,4-a]pyrazin-3(5H)-one, optionally substituted tetrahydropyranyl, thiomorpholinyl 1,1-dioxide, 5,6,7,8-tetrahydro-[1,2,4]triazolo[4,3-a]pyrazinyl, optionally substituted 1,3,8-triazaspiro[4.5]decanyl.

In a sixth embodiment the invention provides a compound according to any of the foregoing embodiments, wherein R$^{3a}$ is optionally substituted phenyl, optionally substituted piperazinyl, optionally substituted piperidinyl, optionally substituted pyrimidinyl, optionally substituted pyridinyl, optionally substituted 3,4-dihydro-2H-pyrido[3,2-b][1,4]oxazinyl, optionally substituted furo[3,2-b]pyridinyl, optionally substituted benzo[d][1,3]dioxolyl, or optionally substituted thienyl.

In a seventh embodiment the invention provides a compound according to any of the foregoing embodiments, wherein $R^{3b}$ is H, $CF_3$, CN, —C(O)OH, —C(O)N(H)$_2$, —C(O)N(H), optionally substituted ($C_1$-$C_3$)alkyl, —C(O)N(H)(cyclopropyl), optionally substituted ($C_1$-$C_3$)alkyl, optionally substituted cyclobutyl, optionally substituted cyclopropyl, —N(H)(optionally substituted ($C_1$-$C_3$)alkyl), —N(optionally substituted ($C_1$-$C_3$)alkyl))$_2$, —N(H)(cyclopropyl), —N(H)(cyclopentyl), —N($R^c$)S(O)$_2$-optionally substituted ($C_1$-$C_3$)alkyl, —O-tetrahydropyranyl, —O-optionally substituted ($C_1$-$C_3$)alkyl, —S(O)$_2$—CH$_3$, —S(O)$_2$—N($R^c$)$_2$, —S(O)$_2$-morpholinyl, optionally substituted azepanyl, optionally substituted 6-azaspiro[3.4]nonanyl, optionally substituted 7-azaspiro[3.5]nonanyl, optionally substituted azaspiro[3.4]octanyl, optionally substituted 2,7-diazaspiro[4.4]nonanyl, optionally substituted diazepanyl, optionally substituted 3,10-diazabicyclo[4.3.1]decanyl, optionally substituted oxetanyl, hexahydroimidazo[1,2-a]pyrimidin-2(3H)-one, optionally substituted imidazolyl, hexahydroimidazo[1,2-c]pyrimidin-2(3H)-one, optionally substituted hexahydroimidazo[1,5-a]pyrazin-3 (2H)-one, optionally substituted hexahydroimidazo[1,5-c]pyrazin-3 (2H)-one, optionally substituted morpholinyl, optionally substituted oxazolo[3,4-a]pyrazine-3-one, 1,4-oxepanyl, optionally substituted piperazinyl, optionally substituted piperidinyl, optionally substituted pyrazinyl, optionally substituted pyrazolyl, optionally substituted pyrimidinyl, optionally substituted pyrrolidinyl, tetrahydro-1H-oxazolo[3,4-a]pyrazin-3(5H)-one, optionally substituted tetrahydropyranyl, thiomorpholinyl 1,1-dioxide, 5,6,7,8-tetrahydro-[1,2,4]triazolo[4,3-a]pyrazinyl, optionally substituted 1,3,8-triazaspiro[4.5]decanyl.

In an eighth embodiment the invention provides a compound according to any of the foregoing embodiments, wherein $R^{3b}$ is optionally substituted by one or more substituents independently selected from —F, —CH$_3$, —CH$_2$OH, —CN, —CH$_2$C(O)OCH$_2$CH$_3$, —C(O)CH$_2$OH, —C(O)CH$_3$, —C(O)OH, —NH$_2$, —N(H)S(O)$_2$CH$_3$, —OH, and =O.

In a ninth embodiment the invention provides a compound according to any of the foregoing embodiments, wherein $R^{3a}$ is optionally substituted phenyl, or optionally substituted pyrimidinyl.

In a tenth embodiment the invention provides a compound according to any of the foregoing embodiments, wherein $R^{3b}$ is optionally substituted ($C_1$-$C_3$)alkyl, optionally substituted cyclobutyl, —O-optionally substituted ($C_1$-$C_3$)alkyl, —S(O)$_2$-optionally substituted ($C_1$-$C_3$)alkyl-S(O)$_2$—N(H)(optionally substituted ($C_1$-$C_3$)alkyl), optionally substituted azepanyl, optionally substituted 7-azaspiro[3.5]nonanyl, optionally substituted 3,10-diazabicyclo[4.3.1]decanyl, optionally substituted oxetanyl, optionally substituted hexahydroimidazo[1,5-a]pyrazin-3 (2H)-one, optionally substituted morpholinyl, 1,4-oxepanyl, optionally substituted piperazinyl, optionally substituted piperidinyl, r optionally substituted tetrahydropyranyl, or thiomorpholinyl 1,1-dioxide.

In an eleventh embodiment $A^1$ is N.
In a twelfth embodiment $A^1$ is CH.
In a thirteenth embodiment $A^2$ is N.
In a fourteenth embodiment $A^2$ is CH.
In a fifteenth embodiment $A^3$ is N.
In an sixteenth embodiment $A^3$ is CH.
In a seventeenth embodiment $Z^1$ is —CH$_2$—.

In a eighteenth embodiment $Z^2$ is —CH$_2$—.
In a nineteenth embodiment $Z^2$ is —NH—.
In a twentieth embodiment $Z^2$ is —O—.
In a twenty-first embodiment $Z^{2a}$ is —CH$_2$—.
In a twenty-second embodiment $Z^{2a}$ is —CH$_2$CH$_2$—.
In a twenty-third embodiment $Z^{2a}$ is —O—.
In a twenty-fourth embodiment $Z^{2a}$ is —NH—.
In a twenty-fifth embodiment $Z^{2b}$ is —CH$_2$—.
In a twenty-sixth embodiment $Z^{2b}$ is —CH$_2$CH$_2$—.
In a twenty-seventh embodiment $Z^{2b}$ is —O—.
In a twenty-eighth embodiment $Z^{2b}$ is —NH—.
In a twenty-ninth embodiment $Z^{2a}$-$Z^{2b}$ form —N(H$^1$)C(O)—.
In a thirtieth embodiment $Z^{2a}$-$Z^{2b}$ form —C(O)N(H)—;
In an thirty-first embodiment the invention provides a compound according to any of the foregoing embodiments, wherein $R^{3b}$ is optionally substituted by one or more substituents independently selected from —CH$_3$, —CH$_2$OH, —C(O)OCH$_2$CH$_3$, —C(O)OH, —NH$_2$, —OH, and =O.

In a thirty-second embodiment the invention provides a compound according to any of the foregoing embodiments, wherein in the compound is
2-(5-(1-(2-methoxyphenyl)-2,3-dihydro-1H-benzo[d]pyrrolo[1,2-a]imidazol-7-yl)pyrimidin-2-yl)propan-2-ol;
4-(3-fluorophenyl)-7-(2-morpholinopyrimidin-5-yl)-3,4-dihydro-1H-benzo[4,5]imidazo[2,1-c][1,4]oxazine;
(R)-1-phenyl-7-(2-((tetrahydro-2H-pyran-4-yl)oxy)pyridin-4-yl)-2,3-dihydro-1H-benzo[d]pyrrolo[1,2-a]imidazole;
(S)-2-(2-morpholinopyrimidin-5-yl)-9-phenyl-8,9-dihydro-6H-pyrido[3',2':4,5]imidazo[2,1-c][1,4]oxazine;
2-(5-(8-methyl-8-phenyl-7,8-dihydro-6H-pyrrolo[2',1':2,3]imidazo[4,5-b]pyridin-2-yl)pyrimidin-2-yl)propan-2-ol;
2-(5-(1-(tetrahydro-2H-pyran-4-yl)-2,3-dihydro-1H-benzo[d]pyrrolo[1,2-a]imidazol-7-yl)pyrimidin-2-yl)propan-2-ol;
(S)-7-(2-((1R,6S)-3,10-diazabicyclo[4.3.1]decan-10-yl)pyrimidin-5-yl)-4-phenyl-3,4-dihydro-1H-benzo[4,5]imidazo[2,1-c][1,4]oxazine;
(S)-7-(5-(4-phenyl-3,4-dihydro-1H-benzo[4,5]imidazo[2,1-c][1,4]oxazin-7-yl)pyrimidin-2-yl)-7-azaspiro[3.5]nonan-2-amine;
7-(5-((S)-4-phenyl-3,4-dihydro-1H-benzo[4,5]imidazo[2,1-c][1,4]oxazin-7-yl)pyrimidin-2-yl)hexahydroimidazo[1,5-a]pyrazin-3(2H)-one;
7-(5-(8-(2-methoxyphenyl)-7,8-dihydro-6H-cyclopenta[4,5]imidazo[1,2-b]pyridazin-2-yl)pyrimidin-2-yl)hexahydroimidazo[1,5-a]pyrazine-3 (2H)-one;
1-(5-(8-phenyl-7,8-dihydro-6H-cyclopenta[4,5]imidazo[1,2-b]pyridazin-2-yl)pyrimidin-2-yl)piperidin-4-ol;
2-(5-(4-(2-methoxyphenyl)-3,4-dihydro-1H-pyran[3',4':4,5]imidazo[1,2-a]pyridin-7-yl)pyrimidin-2-yl)propan-2-ol;
(S)-7-(5-((R)-8-phenyl-7,8-dihydro-6H-pyrrolo[2',1':2,3]imidazo[4,5-b]pyridin-2-yl)pyrimidin-2-yl)hexahydroimidazo[1,5-a]pyrazin-3 (2H)-one;
(R)-7-(5-((R)-1-phenyl-2,3-dihydro-1H-benzo[d]pyrrolo[1,2-a]imidazol-7-yl)pyrimidin-2-yl)hexahydroimidazo[1,5-a]pyrazin-3 (2H)-one;
2-(5-(8-(pyridin-2-yl)-7,8-dihydro-6H-pyrrolo[2',1':2,3]imidazo[4,5-b]pyridin-2-yl)pyrimidin-2-yl)propan-2-ol;
2-(5-(1-(pyridin-2-yl)-2,3-dihydro-1H-benzo[d]pyrrolo[1,2-a]imidazol-7-yl)pyrimidin-2-yl)propan-2-ol;
(S)-7-(5-((S)-4-phenyl-3,4-dihydro-1H-benzo[4,5]imidazo[2,1-c][1,4]oxazin-7-yl)pyrimidin-2-yl)hexahydroimidazo[1,5-a]pyrazin-3 (2H)-one;
(R)-7-(5-((S)-4-phenyl-3,4-dihydro-1H-benzo[4,5]imidazo[2,1-c][1,4]oxazin-7-yl)pyrimidin-2-yl)hexahydroimidazo[1,5-a]pyrazin-3 (2H)-one;

7-(5-(9-(2-methoxyphenyl)-6,7,8,9-tetrahydrobenzo[4,5]imidazo[1,2-a]pyridin-2-yl)pyrimidin-2-yl)-7-azaspiro[3.5]nonan-2-ol;

4-(5-(9-(2-methoxyphenyl)-6,7,8,9-tetrahydrobenzo[4,5]imidazo[1,2-a]pyridin-2-yl)pyrimidin-2-yl)-1,4-oxazepane;

7-(5-(9-(2-methoxyphenyl)-6,7,8,9-tetrahydrobenzo[4,5]imidazo[1,2-a]pyridin-2-yl)pyrimidin-2-yl)hexahydroimidazo[1,5-a]pyrazin-3 (2H)-one;

1-(5-(9-(2-methoxyphenyl)-6,7,8,9-tetrahydrobenzo[4,5]imidazo[1,2-a]pyridin-2-yl)pyrimidin-2-yl)-4-methylpiperidin-4-ol;

(4-fluoro-1-(5-(9-(2-methoxyphenyl)-6,7,8,9-tetrahydrobenzo[4,5]imidazo[1,2-a]pyridin-2-yl)pyrimidin-2-yl)piperidin-4-yl)methanol;

(4-fluoro-1-(5-(9-(2-methoxyphenyl)-6,7,8,9-tetrahydrobenzo[4,5]imidazo[1,2-a]pyridin-2-yl)pyrimidin-2-yl)piperidin-4-yl)methanol;

1-(5-(9-(2-methoxyphenyl)-6,7,8,9-tetrahydrobenzo[4,5]imidazo[1,2-a]pyridin-2-yl)pyrimidin-2-yl)azepan-4-ol;

1-(5-(9-(2-methoxyphenyl)-6,7,8,9-tetrahydrobenzo[4,5]imidazo[1,2-a]pyridin-2-yl)pyrimidin-2-yl)piperidin-4-ol;

1-(5-(8-methyl-8-phenyl-7,8-dihydro-6H-pyrrolo[2',1':2,3]imidazo[4,5-b]pyridin-2-yl)pyrimidin-2-yl)piperidin-4-ol;

1-(5-(9-(3-fluorophenyl)-8,9-dihydro-6H-pyrido[3',2':4,5]imidazo[2,1-c][1,4]oxazin-2-yl)pyrimidin-2-yl)piperidin-4-ol;

7-(5-(8-methyl-8-phenyl-7,8-dihydro-6H-pyrrolo[2',1':2,3]imidazo[4,5-b]pyridin-2-yl)pyrimidin-2-yl)hexahydroimidazo[1,5-a]pyrazin-3(2H)-one;

7-(5-(9-(3-fluorophenyl)-8,9-dihydro-6H-pyrido[3',2':4,5]imidazo[2,1-c][1,4]oxazin-2-yl)pyrimidin-2-yl)hexahydroimidazo[1,5-a]pyrazin-3(2H)-one;

7-(5-(8-cyclohexyl-7,8-dihydro-6H-pyrrolo[2',1':2,3]imidazo[4,5-b]pyridin-2-yl)pyrimidin-2-yl)hexahydroimidazo[1,5-a]pyrazin-3(2H)-one;

7-(5-((R)-8-cyclohexyl-7,8-dihydro-6H-pyrrolo[2',1':2,3]imidazo[4,5-b]pyridin-2-yl)pyrimidin-2-yl)hexahydroimidazo[1,5-a]pyrazin-3 (2H)-one;

7-(5-((S)-4-(2-chlorophenyl)-3,4-dihydro-1H-benzo[4,5]imidazo[2,1-c][1,4]oxazin-7-yl)pyrimidin-2-yl)hexahydroimidazo[1,5-a]pyrazin-3 (2H)-one;

7-(5-(4-(3-chlorophenyl)-3,4-dihydro-1H-benzo[4,5]imidazo[2,1-c][1,4]oxazin-7-yl)pyrimidin-2-yl)hexahydroimidazo[1,5-a]pyrazin-3 (2H)-one;

7-(5-(4-(2-fluorophenyl)-3,4-dihydro-1H-benzo[4,5]imidazo[2,1-c][1,4]oxazin-7-yl)pyrimidin-2-yl)hexahydroimidazo[1,5-a]pyrazin-3 (2H)-one;

4-(5-(1-(2-methoxyphenyl)-2,3-dihydro-1H-cyclopenta[4,5]imidazo[1,2-a]pyridin-7-yl)pyrimidin-2-yl)morpholine;

(R)-7-(5-((R)-9-phenyl-8,9-dihydro-6H-pyrano[3',4':4,5]imidazo[1,2-b]pyridazin-2-yl)pyrimidin-2-yl)hexahydroimidazo[1,5-a]pyrazin-3 (2H)-one;

(R)-7-(5-((R)-4-phenyl-3,4-dihydro-1H-pyrano[3',4':4,5]imidazo[1,2-a]pyridin-7-yl)pyrimidin-2-yl)hexahydroimidazo[1,5-a]pyrazin-3(2H)-one;

1-(5-(9-(2-methoxyphenyl)-6,7,8,9-tetrahydroimidazo[1,2-a:5,4-b']dipyridin-2-yl)pyrimidin-2-yl)piperidin-4-ol;

7-(5-(8-(2-methoxyphenyl)-7,8-dihydro-6H-pyrrolo[2',1':2,3]imidazo[4,5-b]pyridin-2-yl)pyrimidin-2-yl)hexahydroimidazo[1,5-a]pyrazin-3(2H)-one;

1-(5-(8-(2-methoxyphenyl)-7,8-dihydro-6H-pyrrolo[2',1':2,3]imidazo[4,5-b]pyridin-2-yl)pyrimidin-2-yl)piperidin-4-ol;

(S)-1-(5-(9-(2-methoxyphenyl)-8,9-dihydro-6H-pyrido[3',2':4,5]imidazo[2,1-c][1,4]oxazin-2-yl)pyrimidin-2-yl)piperidin-4-ol;

7-(5-((S)-9-phenyl-8,9-dihydro-6H-pyrido[3',2':4,5]imidazo[2,1-c][1,4]oxazin-2-yl)pyrimidin-2-yl)hexahydroimidazo[1,5-a]pyrazin-1(5H)-one;

(S)-1-(5-(9-phenyl-8,9-dihydro-6H-pyrido[3',2':4,5]imidazo[2,1-c][1,4]oxazin-2-yl)pyrimidin-2-yl)piperidin-4-ol;

(S)-4-(5-(9-phenyl-8,9-dihydro-6H-pyrido[3',2':4,5]imidazo[2,1-c][1,4]oxazin-2-yl)pyrimidin-2-yl)piperazin-2-one;

(S)-2-(5-(9-phenyl-8,9-dihydro-6H-pyrido[3',2':4,5]imidazo[2,1-c][1,4]oxazin-2-yl)pyrimidin-2-yl)propan-2-ol;

(S)-7-(5-((R)-1-phenyl-2,3-dihydro-1H-benzo[d]pyrrolo[1,2-a]imidazol-7-yl)pyrimidin-2-yl)hexahydroimidazo[1,5-a]pyrazin-3(2H)-one;

(R)-3-(5-(1-phenyl-2,3-dihydro-1H-benzo[d]pyrrolo[1,2-a]imidazol-7-yl)pyrimidin-2-yl)oxetan-3-ol;

(R)-1-(5-(1-phenyl-2,3-dihydro-1H-benzo[d]pyrrolo[1,2-a]imidazol-7-yl)pyrimidin-2-yl)cyclobutanol;

(R)-4-(5-(1-phenyl-2,3-dihydro-1H-benzo[d]pyrrolo[1,2-a]imidazol-7-yl)pyrimidin-2-yl)tetrahydro-2H-pyran-4-ol;

(R)-7-(5-((R)-1-phenyl-2,3-dihydro-1H-benzo[d]pyrrolo[1,2-a]imidazol-7-yl)pyrimidin-2-yl)hexahydroimidazo[1,5-a]pyrazin-3(2H)-one;

2-(5-(4-(2,6-dichlorophenyl)-3,4-dihydro-1H-benzo[4,5]imidazo[2,1-c][1,4]oxazin-7-yl)pyrimidin-2-yl)propan-2-ol;

(S)-2-(5-(4-(2-methoxyphenyl)-3,4-dihydro-1H-benzo[4,5]imidazo[2,1-c][1,4]oxazin-7-yl)pyrimidin-2-yl)propan-2-ol;

7-(5-((S)-4-phenyl-3,4-dihydro-1H-benzo[4,5]imidazo[2,1-c][1,4]oxazin-7-yl)pyrimidin-2-yl)hexahydroimidazo[1,5-a]pyrazin-3 (2H)-one;

7-(5-(4-(2-chlorophenyl)-3,4-dihydro-1H-benzo[4,5]imidazo[2,1-c][1,4]oxazin-7-yl)pyrimidin-2-yl)hexahydroimidazo[1,5-a]pyrazin-3 (2H)-one;

7-(5-(1,2',3,3'-tetrahydrospiro[benzo[4,5]imidazo[2,1-c][1,4]oxazine-4,1'-inden]-7-yl)pyrimidin-2-yl)hexahydroimidazo[1,5-a]pyrazin-3(2H)-one;

(S)-2-hydroxy-1-(4-(5-(4-phenyl-3,4-dihydro-1H-benzo[4,5]imidazo[2,1-c][1,4]oxazin-7-yl)pyrimidin-2-yl)piperazin-1-yl)ethanone;

7-(5-((S)-4-phenyl-3,4-dihydro-1H-benzo[4,5]imidazo[2,1-c][1,4]oxazin-7-yl)pyrimidin-2-yl)-7-azaspiro[3.5]nonan-1-ol;

(R)-1-(5-(8-(3-fluorophenyl)-7,8-dihydro-6H-pyrrolo[2',1':2,3]imidazo[4,5-b]pyridin-2-yl)pyrimidin-2-yl)piperidin-4-ol;

(R)-1-(5-(8-phenyl-7,8-dihydro-6H-pyrrolo[2',1':2,3]imidazo[4,5-b]pyridin-2-yl)pyrimidin-2-yl)piperidin-4-ol;

(R)-4-(5-(8-phenyl-7,8-dihydro-6H-pyrrolo[2',1':2,3]imidazo[4,5-b]pyridin-2-yl)pyrimidin-2-yl)morpholine;

(S)-2-(5-(1-(2,5-dimethylphenyl)-2,3-dihydro-H-benzo[d]pyrrolo[1,2-a]imidazol-7-yl)pyrimidin-2-yl)propan-2-ol;

(R)-2-(5-(1-(2,5-dimethylphenyl)-2,3-dihydro-1H-benzo[d]pyrrolo[1,2-a]imidazol-7-yl)pyrimidin-2-yl)propan-2-ol;

(S)-4-(3-fluorophenyl)-7-(2-morpholinopyrimidin-5-yl)-3,4-dihydro-1H-benzo[4,5]imidazo[2,1-c][1,4]oxazine;

7-(5-(8-(2,5-dimethylphenyl)-7,8-dihydro-6H-pyrrolo[2',1':2,3]imidazo[4,5-b]pyridin-2-yl)pyrimidin-2-yl)hexahydroimidazo[1,5-a]pyrazin-3(2H)-one compound with ethane (1:1);

7-(5-(8-(3-fluorophenyl)-7,8-dihydro-6H-pyrrolo[2',1':2,3]imidazo[4,5-b]pyridin-2-yl)pyrimidin-2-yl)hexahydroimidazo[1,5-a]pyrazin-3(2H)-one;

(R)-1-(5-(1-phenyl-2,3-dihydro-1H-benzo[d]pyrrolo[1,2-a]imidazol-7-yl)pyrimidin-2-yl)piperidin-4-ol;

(R)-4-(5-(1-phenyl-2,3-dihydro-1H-benzo[d]pyrrolo[1,2-a]imidazol-7-yl)pyrimidin-2-yl)thiomorpholine 1,1-dioxide;

-(5-(8-phenyl-7,8-dihydro-6H-pyrrolo[2',1':2,3]imidazo[4,5-b]pyridin-2-yl)pyrimidin-2-yl)hexahydroimidazo[1,5-a]pyrazin-3 (2H)-one;

7-(5-((R)-1-phenyl-2,3-dihydro-1H-benzo[d]pyrrolo[1,2-a]imidazol-7-yl)pyrimidin-2-yl)hexahydroimidazo[1,5-a]pyrazin-3(2H)-one;

3,3-difluoro-1-(5-((R)-1-phenyl-2,3-dihydro-1H-benzo[d]pyrrolo[1,2-a]imidazol-7-yl)pyrimidin-2-yl)piperidin-4-ol;

(S)-2-(5-(4-(2-(difluoromethoxy)phenyl)-3,4-dihydro-H-benzo[4,5]imidazo[2,1-c][1,4]oxazin-7-yl)pyrimidin-2-yl)propan-2-ol;

(S)-2-(5-(9-(2-methoxyphenyl)-6,7,8,9-tetrahydrobenzo[4,5]imidazo[1,2-a]pyridin-2-yl)pyrimidin-2-yl)propan-2-ol;

(R)-7-(5-(1-phenyl-2,3-dihydro-1H-benzo[d]pyrrolo[1,2-a]imidazol-7-yl)pyrimidin-2-yl)-7-azaspiro[3.5]nonan-2-ol;

1-(5-(8-(2,5-dimethylphenyl)-7,8-dihydro-6H-pyrrolo[2',1':2,3]imidazo[4,5-b]pyridin-2-yl)pyrimidin-2-yl)piperidin-4-ol;

4-(5-(10-(2-methoxyphenyl)-7,8,9,10-tetrahydro-6H-cyclohepta[4,5]imidazo[1,2-a]pyridin-2-yl)pyrimidin-2-yl)morpholine;

(R)-4-(5-(1-phenyl-2,3-dihydro-1H-benzo[d]pyrrolo[1,2-a]imidazol-7-yl)pyrimidin-2-yl)morpholine;

7-(5-((S)-4-phenyl-3,4-dihydro-1H-benzo[4,5]imidazo[2,1-c][1,4]oxazin-7-yl)pyrimidin-2-yl)hexahydroimidazo[1,5-a]pyrazin-3(2H)-one;

4-(5-(8-(2,5-dimethylphenyl)-7,8-dihydro-6H-pyrrolo[2',1':2,3]imidazo[4,5-b]pyridin-2-yl)pyrimidin-2-yl)piperazin-2-one;

2-(5-(1-(2,5-dimethylphenyl)-2,3-dihydro-1H-benzo[d]pyrrolo[1,2-a]imidazol-7-yl)pyrimidin-2-yl)propan-2-ol;

3,3-difluoro-1-(5-((S)-4-phenyl-3,4-dihydro-1H-benzo[4,5]imidazo[2,1-c][1,4]oxazin-7-yl)pyrimidin-2-yl)piperidin-4-ol;

7-(5-(4-(3-fluorophenyl)-3,4-dihydro-1H-benzo[4,5]imidazo[2,1-c][1,4]oxazin-7-yl)pyrimidin-2-yl)hexahydroimidazo[1,5-a]pyrazin-3(2H)-one;

(R)-2-(5-(1-(2-methoxyphenyl)-2,3-dihydro-H-cyclopenta[4,5]imidazo[1,2-a]pyridin-7-yl)pyrimidin-2-yl)propan-2-ol;

7-(4-(isopropylsulfonyl)phenyl)-1-phenyl-2,3-dihydro-1H-benzo[d]pyrrolo[1,2-a]imidazole;

2-(5-(9-(2-methoxyphenyl)-6,7,8,9-tetrahydrobenzo[4,5]imidazo[1,2-a]pyridin-2-yl)pyrimidin-2-yl)propan-2-ol;

4-(5-(8-(2,5-dimethylphenyl)-7,8-dihydro-6H-pyrrolo[2',1':2,3]imidazo[4,5-b]pyridin-2-yl)pyrimidin-2-yl)morpholine;

(S)-7-(5-(4-phenyl-3,4-dihydro-1H-benzo[4,5]imidazo[2,1-c][1,4]oxazin-7-yl)pyrimidin-2-yl)-7-azaspiro[3.5]nonan-2-ol;

4-(5-(9-(2-methoxyphenyl)-6,7,8,9-tetrahydrobenzo[4,5]imidazo[1,2-a]pyridin-2-yl)pyrimidin-2-yl)morpholine;

(S)-1-(5-(4-phenyl-3,4-dihydro-1H-benzo[4,5]imidazo[2,1-c][1,4]oxazin-7-yl)pyrimidin-2-yl)piperidin-4-ol;

1-(5-(9-phenyl-6,7,8,9-tetrahydroimidazo[1,2-a:5,4-b']dipyridin-2-yl)pyrimidin-2-yl)piperidin-4-ol;

(R)-2-(5-(1-phenyl-2,3-dihydro-1H-benzo[d]pyrrolo[1,2-a]imidazol-7-yl)pyrimidin-2-yl)propan-2-ol;

4-(5-(8-(3-fluorophenyl)-7,8-dihydro-6H-pyrrolo[2',1':2,3]imidazo[4,5-b]pyridin-2-yl)pyrimidin-2-yl)morpholine;

2-(5-(10-(2-methoxyphenyl)-7, 8,9,10-tetrahydro-6H-cyclohepta[4,5]imidazo[1,2-a]pyridin-2-yl)pyrimidin-2-yl)propan-2-ol;

N-methyl-4-(1-phenyl-2,3-dihydro-1H-benzo[d]pyrrolo[1,2-a]imidazol-7-yl)benzenesulfonamide;

1-(5-(8-(3-fluorophenyl)-7,8-dihydro-6H-pyrrolo[2',1':2,3]imidazo[4,5-b]pyridin-2-yl)pyrimidin-2-yl)piperidin-4-ol;

7-(4-(ethylsulfonyl)phenyl)-1-phenyl-2,3-dihydro-1H-benzo[d]pyrrolo[1,2-a]imidazole;

(S)-7-(2-morpholinopyrimidin-5-yl)-4-phenyl-3,4-dihydro-1H-benzo[4,5]imidazo[2,1-c][1,4]oxazine;

4-(5-(8-phenyl-7,8-dihydro-6H-pyrrolo[2',1':2,3]imidazo[4,5-b]pyridin-2-yl)pyrimidin-2-yl)morpholine;

4-(5-(8-phenyl-7,8-dihydro-6H-pyrrolo[2',1':2,3]imidazo[4,5-b]pyridin-2-yl)pyrimidin-2-yl)morpholine;

(S)-7-(5-(4-phenyl-3,4-dihydro-1H-benzo[4,5]imidazo[2,1-c][1,4]oxazin-7-yl)pyrimidin-2-yl)-7-azaspiro[3.5]nonan-2-ol;

1-(5-(8-phenyl-7,8-dihydro-6H-pyrrolo[2',1':2,3]imidazo[4,5-b]pyridin-2-yl)pyrimidin-2-yl)piperidin-4-ol;

(S)-7-(2-(1,4-oxazepan-4-yl)pyrimidin-5-yl)-4-phenyl-3,4-dihydro-1H-benzo[4,5]imidazo[2,1-c][1,4]oxazine;

4-(5-(1-phenyl-2,3-dihydro-1H-benzo[d]pyrrolo[1,2-a]imidazol-7-yl)pyrimidin-2-yl)morpholine;

3,3-difluoro-1-(5-(4-(3-fluorophenyl)-3,4-dihydro-1H-benzo[4,5]imidazo[2,1-c][1,4]oxazin-7-yl)pyrimidin-2-yl)piperidin-4-ol;

(1-(5-((S)-4-phenyl-3,4-dihydro-1H-benzo[4,5]imidazo[2,1-c][1,4]oxazin-7-yl)pyrimidin-2-yl)piperidin-3-yl)methanol;

1-(5-((S)-4-phenyl-3,4-dihydro-1H-benzo[4,5]imidazo[2,1-c][1,4]oxazin-7-yl)pyrimidin-2-yl)azepan-4-ol;

(S)-4-(5-(4-phenyl-3,4-dihydro-1H-benzo[4,5]imidazo[2,1-c][1,4]oxazin-7-yl)pyrimidin-2-yl)piperazine-1-sulfonamide;

N-(4-(1-phenyl-2,3-dihydro-1H-benzo[d]pyrrolo[1,2-a]imidazol-7-yl)benzyl)methanesulfonamide;

2-(5-(1-(2-methoxyphenyl)-2,3-dihydro-1H-cyclopenta[4,5]imidazo[1,2-a]pyridin-7-yl)pyrimidin-2-yl)propan-2-ol;

7-(4-(methylsulfonyl)phenyl)-1-phenyl-2,3-dihydro-1H-benzo[d]pyrrolo[1,2-a]imidazole;

7-(2-(1,4-oxazepan-4-yl)pyrimidin-5-yl)-4-(3-fluorophenyl)-3,4-dihydro-1H-benzo[4,5]imidazo[2,1-c][1,4]oxazine;

4-(1-phenyl-2,3-dihydro-1H-benzo[d]pyrrolo[1,2-a]imidazol-7-yl)benzenesulfonamide;

(4-(5-((S)-4-phenyl-3,4-dihydro-1H-benzo[4,5]imidazo[2,1-c][1,4]oxazin-7-yl)pyrimidin-2-yl)morpholin-2-yl)methanol;

(S)-4-(5-(4-phenyl-3,4-dihydro-1H-benzo[4,5]imidazo[2,1-c][1,4]oxazin-7-yl)pyrimidin-2-yl)thiomorpholine 1,1-dioxide;

4-(5-(9-phenyl-6,7,8,9-tetrahydroimidazo[1,2-a:5,4-b']dipyridin-2-yl)pyrimidin-2-yl)morpholine;

(R)-4-(5-(1-phenyl-1,2,3,4-tetrahydrobenzo[4,5]imidazo[1,2-a]pyridin-8-yl)pyrimidin-2-yl)morpholine;

2-(5-(1-(3-fluorophenyl)-2,3-dihydro-1H-benzo[d]pyrrolo[1,2-a]imidazol-7-yl)pyrimidin-2-yl)propan-2-ol;

(S)-(4-fluoro-1-(5-(4-phenyl-3,4-dihydro-1H-benzo[4,5]imidazo[2,1-c][1,4]oxazin-7-yl)pyrimidin-2-yl)piperidin-4-yl)methanol;

4-(5-(9-(3-chlorophenyl)-6,7,8,9-tetrahydrobenzo[4,5]imidazo[1,2-a]pyridin-2-yl)pyrimidin-2-yl)morpholine;

(R)-2-(5-(1-phenyl-1,2,3,4-tetrahydrobenzo[4,5]imidazo[1,2-a]pyridin-8-yl)pyrimidin-2-yl)propan-2-ol;

(S)-7-(2-(1'-methyl-[4, 4'-bipiperidin]-1-yl)pyrimidin-5-yl)-4-phenyl-3,4-dihydro-1H-benzo[4,5]imidazo[2, 1-c][1,4]oxazine;
2-(5-(9-phenyl-6,7,8,9-tetrahydroimidazo[1,2-a:5, 4-b']dipyridin-2-yl)pyrimidin-2-yl)propan-2-ol;
7-(2-Morpholinopyrimidin-5-yl)-4-phenyl-3,4-dihydro-1H-benzo[4,5]imidazo[2,1-c][1,4]oxazine;
(4S)-7-(2-(2-methylmorpholino)pyrimidin-5-yl)-4-phenyl-3,4-dihydro-1H-benzo[4,5]imidazo[2,1-c][1,4]oxazine;
7-(5-(4-(3-fluorophenyl)-3,4-dihydro-1H-benzo[4,5]imidazo[2,1-c][1,4]oxazin-7-yl)pyrimidin-2-yl)-7-azaspiro[3.5]nonan-2-ol;
4-(5-(1-phenyl-1,2,3,4-tetrahydrobenzo[4,5]imidazo[1,2-a]pyridin-8-yl)pyrimidin-2-yl)morpholine;
Ethyl 2-[[5-[9-(2-methoxyphenyl)-6,7,8,9-tetrahydropyrido[1,2-a]benzimidazol-2-yl]pyrimidin-2-yl]amino]acetate;
(S)-7-(2-(5,6-dihydro-[1,2,4]triazolo[4,3-a]pyrazin-7(8H)-yl)pyrimidin-5-yl)-4-phenyl-3,4-dihydro-1H-benzo[4,5]imidazo[2,1-c][1,4]oxazine;
2-(5-(8-(3-fluorophenyl)-7,8-dihydro-6H-pyrrolo[2',1':2,3]imidazo[4,5-b]pyridin-2-yl)pyrimidin-2-yl)propan-2-ol;
(S)-7-(2-(4-(methylsulfonyl)piperazin-1-yl)pyrimidin-5-yl)-4-phenyl-3,4-dihydro-1H-benzo[4,5]imidazo[2, 1-c][1,4]oxazine;
2-(5-(8-phenyl-7,8-dihydro-6H-pyrrolo[2',1':2,3]imidazo[4,5-b]pyridin-2-yl)pyrimidin-2-yl)propan-2-ol;
2-(4-(1-phenyl-2,3-dihydro-1H-benzo[d]pyrrolo[1,2-a]imidazol-7-yl)phenyl)acetonitrile;
4-(5-(8-phenyl-7,8-dihydro-6H-pyrrolo[2',1':2,3]imidazo[4,5-b]pyridin-2-yl)pyrimidin-2-yl)piperazin-2-one;
7-(2-cyclopropylpyrimidin-5-yl)-1-phenyl-2,3-dihydro-1H-benzo[d]pyrrolo[1,2-a]imidazole;
(S)-4-(5-(4-phenyl-3,4-dihydro-1H-benzo[4,5]imidazo[2,1-c][1,4]oxazin-7-yl)pyrimidin-2-yl)piperazin-2-one;
2-((5-(9-(2-methoxyphenyl)-6,7,8,9-tetrahydrobenzo[4,5]imidazo[1,2-a]pyridin-2-yl)pyridin-2-yl)oxy)acetic acid;
7-(6-(ethylsulfonyl)pyridin-3-yl)-1-phenyl-2,3-dihydro-1H-benzo[d]pyrrolo[1,2-a]imidazole;
4-(5-(8-(3-fluorophenyl)-7,8-dihydro-6H-pyrrolo[2',1':2,3]imidazo[4,5-b]pyridin-2-yl)pyrimidin-2-yl)piperazin-2-one;
10-(3-fluorophenyl)-2-(2-morpholinopyrimidin-5-yl)-7,8,9,10-tetrahydro-6H-cyclohepta[4,5]imidazo[1,2-a]pyridin-10-ol;
4-(5-(9-phenyl-6,7,8,9-tetrahydroimidazo[1,2-a:5,4-b']dipyridin-2-yl)pyrimidin-2-yl)piperazin-2-one;
(S)-6-(5-(4-phenyl-3,4-dihydro-1H-benzo[4,5]imidazo[2,1-c][1,4]oxazin-7-yl)pyrimidin-2-yl)-6-azaspiro[3.4]octan-2-ol;
N,N-dimethyl-4-(1-phenyl-2,3-dihydro-1H-benzo[d]pyrrolo[1,2-a]imidazol-7-yl)benzamide;
N-ethyl-N-methyl-4-(1-phenyl-2,3-dihydro-1H-benzo[d]pyrrolo[1,2-a]imidazol-7-yl)benzamide;
7-(6-morpholinopyridin-3-yl)-4-phenyl-3,4-dihydro-1H-benzo[4,5]imidazo[2,1-c][1,4]oxazine;
2-(5-(1-phenyl-1,2,3,4-tetrahydrobenzo[4,5]imidazo[1,2-a]pyridin-8-yl)pyrimidin-2-yl)propan-2-ol;
2-(5-(1-Phenyl-2,3-dihydro-1H-benzo[d]pyrrolo[1,2-a]imidazol-7-yl)pyrimidin-2-yl)propan-2-ol;
(S)-4-(2-hydroxyethyl)-1-(5-(4-phenyl-3,4-dihydro-1H-benzo[4,5]imidazo[2,1-c][1,4]oxazin-7-yl)pyrimidin-2-yl)piperidin-4-ol;
(S)-7-(2-(2-oxa-7-azaspiro[3.5]nonan-7-yl)pyrimidin-5-yl)-4-phenyl-3,4-dihydro-1H-benzo[4,5]imidazo[2,1-c][1,4]oxazine;
2-(1-(5-((S)-4-phenyl-3,4-dihydro-1H-benzo[4,5]imidazo[2,1-c][1,4]oxazin-7-yl)pyrimidin-2-yl)piperidin-3-yl)acetic acid;
7-(5-methyl-6-morpholinopyridin-3-yl)-4-phenyl-3,4-dihydro-1H-benzo[4,5]imidazo[2,1-c][1,4]oxazine;
7-(5-(2-methyl-1H-imidazol-1-yl)pyrazin-2-yl)-4-phenyl-3,4-dihydro-1H-benzo[4,5]imidazo[2,1-c][1,4]oxazine;
2-(5-(1-cyclohexyl-2,3-dihydro-1H-benzo[d]pyrrolo[1,2-a]imidazol-7-yl)pyrimidin-2-yl)propan-2-ol;
2-(5-(4-phenyl-3,4-dihydro-1H-benzo[4,5]imidazo[2,1-c][1,4]oxazin-7-yl)pyrimidin-2-yl)propan-2-ol;
(S)-(4-(methylsulfonyl)-1-(5-(4-phenyl-3,4-dihydro-1H-benzo[4,5]imidazo[2,1-c][1,4]oxazin-7-yl)pyrimidin-2-yl)piperidin-4-yl)methanol;
1-(1-(5-((S)-4-phenyl-3,4-dihydro-1H-benzo[4,5]imidazo[2,1-c][1,4]oxazin-7-yl)pyrimidin-2-yl)piperidin-4-yl)ethanol;
(S)-4-(5-(4-phenyl-3,4-dihydro-1H-benzo[4,5]imidazo[2,1-c][1,4]oxazin-7-yl)pyrimidin-2-yl)-1,4-diazepan-2-one;
2-(4-(1-phenyl-2,3-dihydro-1H-benzo[d]pyrrolo[1,2-a]imidazol-7-yl)phenoxy)acetonitrile;
(S)—N-(1-(5-(4-phenyl-3,4-dihydro-1H-benzo[4,5]imidazo[2,1-c][1,4]oxazin-7-yl)pyrimidin-2-yl)piperidin-4-yl)methanesulfonamide;
(S)-3-(1-(5-(4-phenyl-3,4-dihydro-1H-benzo[4,5]imidazo[2,1-c][1,4]oxazin-7-yl)pyrimidin-2-yl)piperidin-4-yl)propanoic acid;
4-phenyl-7-(6-(trifluoromethyl)pyridin-3-yl)-3,4-dihydro-1H-benzo[4,5]imidazo[2,1-c][1,4]oxazine;
4-(5-(1-phenyl-1,2,3,4-tetrahydrobenzo[4,5]imidazo[1,2-a]pyridin-8-yl)pyrimidin-2-yl)piperazin-2-one;
7-(5-fluoro-6-methoxypyridin-3-yl)-4-phenyl-3,4-dihydro-1H-benzo[4,5]imidazo[2,1-c][1,4]oxazine;
N,N-dimethyl-5-(1-phenyl-2,3-dihydro-1H-benzo[d]pyrrolo[1,2-a]imidazol-7-yl)pyridin-2-amine;
7-(2-methylpyridin-4-yl)-1-phenyl-2,3-dihydro-1H-benzo[d]pyrrolo[1,2-a]imidazole;
(4S)-4-phenyl-7-(2-(2-(trifluoromethyl)morpholino)pyrimidin-5-yl)-3,4-dihydro-1H-benzo[4,5]imidazo[2,1-c][1,4]oxazine;
7-(5-((S)-4-phenyl-3,4-dihydro-1H-benzo[4,5]imidazo[2,1-c][1,4]oxazin-7-yl)pyrimidin-2-yl)-2,7-diazaspiro[4.4]nonan-1-one;
N-cyclopentyl-5-(4-phenyl-3,4-dihydro-H-benzo[4,5]imidazo[2,1-c][1,4]oxazin-7-yl)pyrimidin-2-amine;
7-(2-(1H-pyrazol-1-yl)pyrimidin-5-yl)-4-phenyl-3,4-dihydro-1H-benzo[4,5]imidazo[2,1-c][1,4]oxazine;
(4S)-7-(2-(2,6-dimethylmorpholino)pyrimidin-5-yl)-4-phenyl-3,4-dihydro-1H-benzo[4,5]imidazo[2,1-c][1,4]oxazine;
7-(6-methylpyridin-3-yl)-1-phenyl-2,3-dihydro-1H-benzo[d]pyrrolo[1,2-a]imidazole;
7-(5-ethoxypyridin-3-yl)-1-phenyl-2,3-dihydro-1H-benzo[d]pyrrolo[1,2-a]imidazole;
2-(2-morpholinopyrimidin-5-yl)-9-(m-tolyl)-6,7,8,9-tetrahydrobenzo[4,5]imidazo[1,2-a]pyridin-9-ol;
7-(6-(methylthio)pyridin-3-yl)-1-phenyl-2,3-dihydro-1H-benzo[d]pyrrolo[1,2-a]imidazole;
ethyl 2-((5-(10-(2-methoxyphenyl)-7,8,9,10-tetrahydro-6H-cyclohepta[4,5]imidazo[1,2-a]pyridin-2-yl)pyrimidin-2-yl)amino)acetate;
(S)-3-(4-(5-(4-phenyl-3,4-dihydro-1H-benzo[4,5]imidazo[2,1-c][1,4]oxazin-7-yl)pyrimidin-2-yl)piperazin-1-yl)propan-1-ol;
9-(3-fluorophenyl)-2-(2-morpholinopyrimidin-5-yl)-6,7,8,9-tetrahydrobenzo[4,5]imidazo[1,2-a]pyridin-9-ol;

2-(2-morpholinopyrimidin-5-yl)-9-phenyl-6,7,8,9-tetrahydrobenzo[4,5]imidazo[1,2-a]pyridin-9-ol;

4-(2,5-difluorophenyl)-7-(2-morpholinopyrimidin-5-yl)-3,4-dihydro-1H-benzo[4,5]imidazo[2,1-c][1,4]oxazine;

1-phenyl-7-(6-(piperazin-1-yl)pyridin-3-yl)-2,3-dihydro-1H-benzo[d]pyrrolo[1,2-a]imidazole;

9-(2-Methoxyphenyl)-2-(2-morpholinopyrimidin-5-yl)-6,7,8,9-tetrahydrobenzo[4,5]imidazo[1,2-a]pyridin-9-ol;

(S)-7-(2-(2-oxa-6-azaspiro[3.4]octan-6-yl)pyrimidin-5-yl)-4-phenyl-3,4-dihydro-1H-benzo[4,5]imidazo[2,1-c][1,4]oxazine;

7-(5-(1H-imidazol-1-yl)pyrazin-2-yl)-4-phenyl-3,4-dihydro-1H-benzo[4,5]imidazo[2,1-c][1,4]oxazine;

7-(furo[3,2-b]pyridin-6-yl)-4-phenyl-3,4-dihydro-1H-benzo[4,5]imidazo[2,1-c][1,4]oxazine;

10-(3-chlorophenyl)-2-(2-morpholinopyrimidin-5-yl)-7,8,9,10-tetrahydro-6H-cyclohepta[4,5]imidazo[1,2-a]pyridin-10-ol;

N-ethyl-4-(1-phenyl-2,3-dihydro-1H-benzo[d]pyrrolo[1,2-a]imidazol-7-yl)benzamide;

2-(3-(1-phenyl-2,3-dihydro-1H-benzo[d]pyrrolo[1,2-a]imidazol-7-yl)phenoxy)acetonitrile;

2-(2-morpholinopyrimidin-5-yl)-10-(m-tolyl)-7,8,9,10-tetrahydro-6H-cyclohepta[4,5]imidazo[1,2-a]pyridin-10-ol;

2-((5-(10-(2-methoxyphenyl)-7,8,9,10-tetrahydro-6H-cyclohepta[4,5]imidazo[1,2-a]pyridin-2-yl)pyrimidin-2-yl)amino)acetic acid;

N-cyclopropyl-4-(1-phenyl-2,3-dihydro-1H-benzo[d]pyrrolo[1,2-a]imidazol-7-yl)benzamide;

4-(1-phenyl-2,3-dihydro-1H-benzo[d]pyrrolo[1,2-a]imidazol-7-yl)benzamide;

1-(4-(5-(4-phenyl-3,4-dihydro-1H-benzo[4,5]imidazo[2,1-c][1,4]oxazin-7-yl)pyridin-2-yl)piperazin-1-yl)ethanone;

7-(6-(4-methylpiperazin-1-yl)pyridin-3-yl)-1-phenyl-2,3-dihydro-1H-benzo[d]pyrrolo[1,2-a]imidazole;

7-(benzo[d][1,3]dioxol-5-yl)-1-phenyl-2,3-dihydro-1H-benzo[d]pyrrolo[1,2-a]imidazole;

9-(3-fluoro-2-methylphenyl)-2-(2-morpholinopyrimidin-5-yl)-6,7,8,9-tetrahydrobenzo[4,5]imidazo[1,2-a]pyridin-9-ol;

8-Phenyl-2-(4-(pyrimidin-2-yl)piperazin-1-yl)-7,8-dihydro-6H-pyrrolo[2',1':2,3]imidazo[4,5-b]pyridine;

9-(4-fluorophenyl)-2-(2-morpholinopyrimidin-5-yl)-6,7,8,9-tetrahydrobenzo[4,5]imidazo[1,2-a]pyridin-9-ol;

7-(5-((S)-4-phenyl-3,4-dihydro-1H-benzo[4,5]imidazo[2,1-c][1,4]oxazin-7-yl)pyrimidin-2-yl)tetrahydro-1H-oxazolo[3,4-a]pyrazin-3 (5H)-one;

2-((5-(9-(2-methoxyphenyl)-6,7,8,9-tetrahydrobenzo[4,5]imidazo[1,2-a]pyridin-2-yl)pyrimidin-2-yl)amino)acetic acid;

10-(4-fluorophenyl)-2-(2-morpholinopyrimidin-5-yl)-7,8,9,10-tetrahydro-6H-cyclohepta[4,5]imidazo[1,2-a]pyridin-10-ol;

9-(3-chlorophenyl)-2-(2-morpholinopyrimidin-5-yl)-6,7,8,9-tetrahydrobenzo[4,5]imidazo[1,2-a]pyridin-9-ol;

N-cyclopropyl-5-(4-phenyl-3,4-dihydro-1H-benzo[4,5]imidazo[2,1-c][1,4]oxazin-7-yl)pyrimidin-2-amine;

9-(3-chloro-5-fluorophenyl)-2-(2-morpholinopyrimidin-5-yl)-6,7,8,9-tetrahydrobenzo[4,5]imidazo[1,2-a]pyridin-9-ol;

N,N-dimethyl-5-(4-phenyl-3,4-dihydro-1H-benzo[4,5]imidazo[2,1-c][1,4]oxazin-7-yl)pyrimidin-2-amine;

1-(5-(1-phenyl-1,2,3,4-tetrahydrobenzo[4,5]imidazo[1,2-a]pyridin-8-yl)pyrimidin-2-yl)piperidine-4-carboxylic acid;

7-(6-isopropoxypyridin-3-yl)-4-phenyl-3,4-dihydro-1H-benzo[4,5]imidazo[2,1-c][1,4]oxazine;

7-(6-isopropoxypyridin-3-yl)-4-phenyl-3,4-dihydro-1H-benzo[4,5]imidazo[2,1-c][1,4]oxazine;

4-(5-(6-phenyl-7,8-dihydro-6H-pyrrolo[1',2':1,2]imidazo[4,5-c]pyridin-3-yl)pyrimidin-2-yl)morpholine;

1-phenyl-7-(1-(pyridin-3-ylmethyl)-1H-pyrazol-4-yl)-2,3-dihydro-1H-benzo[d]pyrrolo[1,2-a]imidazole;

5-(4-phenyl-3,4-dihydro-1H-benzo[4,5]imidazo[2,1-c][1,4]oxazin-7-yl)picolinonitrile;

7-(4-methyl-3,4-dihydro-2H-pyrido[3,2-b][1,4]oxazin-7-yl)-4-phenyl-3,4-dihydro-1H-benzo[4,5]imidazo[2,1-c][1,4]oxazine;

2-(2-morpholinopyrimidin-5-yl)-9-(p-tolyl)-6,7,8,9-tetrahydrobenzo[4,5]imidazo[1,2-a]pyridin-9-ol;

7-(6-(methylsulfonyl)pyridin-3-yl)-4-phenyl-3,4-dihydro-1H-benzo[4,5]imidazo[2,1-c][1,4]oxazine;

N-(2-methoxyethyl)-4-(1-phenyl-2,3-dihydro-1H-benzo[d]pyrrolo[1,2-a]imidazol-7-yl)benzamide;

N-methyl-4-(1-phenyl-2,3-dihydro-1H-benzo[d]pyrrolo[1,2-a]imidazol-7-yl)benzamide;

4-phenyl-7-(6-(2,2,2-trifluoroethoxy)pyridin-3-yl)-3,4-dihydro-1H-benzo[4,5]imidazo[2,1-c][1,4]oxazine;

1-(5-(4-phenyl-3,4-dihydro-1H-benzo[4,5]imidazo[2,1-c][1,4]oxazin-7-yl)pyrimidin-2-yl)piperidine-4-carboxylic acid;

7-(5-methyl-6-(4-methylpiperazin-1-yl)pyridin-3-yl)-4-phenyl-3,4-dihydro-1H-benzo[4,5]imidazo[2,1-c][1,4]oxazine;

5-(9-(2-Methoxyphenyl)-6,7,8,9-tetrahydrobenzo[4,5]imidazo[1,2-a]pyridin-2-yl)thiophene-2-carboxylic acid;

7-(6-(4-methylpiperazin-1-yl)pyridin-3-yl)-4-phenyl-3,4-dihydro-1H-benzo[4,5]imidazo[2,1-c][1,4]oxazine;

(S)-7-(2-(1'-methyl-[4, 4'-bipiperidin]-1-yl)pyrimidin-5-yl)-4-phenyl-3,4-dihydro-1H-benzo[4,5]imidazo[2,1-c][1,4]oxazine;

7-(2-methoxypyrimidin-5-yl)-4-phenyl-3,4-dihydro-1H-benzo[4,5]imidazo[2,1-c][1,4]oxazine;

10-(3-chloro-5-fluorophenyl)-2-(2-morpholinopyrimidin-5-yl)-7,8,9,10-tetrahydro-6H-cyclohepta [4,5]imidazo[1,2-a]pyridin-10-ol;

3-(2-hydroxyethyl)-1-(5-((S)-4-phenyl-3,4-dihydro-1H-benzo[4,5]imidazo[2,1-c][1,4]oxazin-7-yl)pyrimidin-2-yl)pyrrolidin-3-ol;

4-(5-(9-(2-Methoxyphenyl)-6,7-dihydrobenzo[4,5]imidazo[1,2-a]pyridin-2-yl)pyrimidin-2-yl)morpholine;

10-(4-methoxyphenyl)-2-(2-morpholinopyrimidin-5-yl)-7,8,9,10-tetrahydro-6H-cyclohepta [4,5]imidazo[1,2-a]pyridin-10-ol;

7-(5-(1H-pyrazol-1-yl)pyrazin-2-yl)-4-phenyl-3,4-dihydro-1H-benzo[4,5]imidazo[2,1-c][1,4]oxazine;

1-phenyl-7-(pyridin-3-yl)-2, 3-dihydro-1H-benzo[d]pyrrolo[1,2-a]imidazole;

5-(1-phenyl-2,3-dihydro-1H-benzo[d]pyrrolo[1,2-a]imidazol-7-yl)pyrimidin-2-amine;

2-(2-morpholinopyrimidin-5-yl)-10-(p-tolyl)-7,8,9,10-tetrahydro-6H-cyclohepta[4,5]imidazo[1,2-a]pyridin-10-ol;

5-(4-phenyl-3,4-dihydro-1H-benzo[4,5]imidazo[2,1-c][1,4]oxazin-7-yl)pyrimidine-2-carbonitrile;

(R)-2-(5-(9-(2-methoxyphenyl)-6,7,8,9-tetrahydrobenzo[4,5]imidazo[1,2-a]pyridin-2-yl)pyrimidin-2-yl)propan-2-ol;

(S)-7-(2-((R)-3-(methylsulfonyl)pyrrolidin-1-yl)pyrimidin-5-yl)-4-phenyl-3,4-dihydro-1H-benzo[4,5]imidazo[2,1-c][1,4]oxazine;

7-([1,2,5]oxadiazolo[3,4-b]pyridin-6-yl)-4-phenyl-3,4-dihydro-1H-benzo[4,5]imidazo[2,1-c][1,4]oxazine;

2-(5-(6-phenyl-7,8-dihydro-6H-pyrrolo[1,2':1,2]imidazo[4,5-c]pyridin-3-yl)pyrimidin-2-yl)propan-2-ol;

7-(2-methylpyrimidin-5-yl)-4-phenyl-3,4-dihydro-1H-benzo[4,5]imidazo[2,1-c][1,4]oxazine;

1-phenyl-7-(pyrimidin-5-yl)-2,3-dihydro-1H-benzo[d]pyrrolo[1,2-a]imidazole;

7-(6-methoxy-5-methylpyridin-3-yl)-4-phenyl-3,4-dihydro-1H-benzo[4,5]imidazo[2,1-c][1,4]oxazine;

10-(4-chlorophenyl)-2-(2-morpholinopyrimidin-5-yl)-7,8,9,10-tetrahydro-6H-cyclohepta [4,5]imidazo[1,2-a]pyridin-10-ol;

2-(3-(1-phenyl-2,3-dihydro-1H-benzo[d]pyrrolo[1,2-a]imidazol-7-yl)phenyl)acetonitrile;

N-(3-(1-phenyl-2,3-dihydro-1H-benzo[d]pyrrolo[1,2-a]imidazol-7-yl)benzyl)methanesulfonamide;

7-(6-methylpyridin-3-yl)-4-phenyl-3,4-dihydro-H-benzo[4,5]imidazo[2,1-c][1,4]oxazine;

(S)-2-(5-(1-phenyl-1,2,3,4-tetrahydrobenzo[4,5]imidazo[1,2-a]pyridin-8-yl)pyrimidin-2-yl)propan-2-ol;

(S)-7-(2-(4-(1-methylpiperidin-4-yl)piperazin-1-yl)pyrimidin-5-yl)-4-phenyl-3,4-dihydro-1H-benzo[4,5]imidazo[2,1-c][1,4]oxazine;

4-phenyl-7-(6-(piperazin-1-yl)pyridin-3-yl)-3,4-dihydro-1H-benzo[4,5]imidazo[2,1-c][1,4]oxazine;

(4S)-7-(2-(3-(methylsulfonyl)pyrrolidin-1-yl)pyrimidin-5-yl)-4-phenyl-3,4-dihydro-1H-benzo[4,5]imidazo[2,1-c][1,4]oxazine;

(S)-8-(5-(4-phenyl-3,4-dihydro-1H-benzo[4,5]imidazo[2,1-c][1,4]oxazin-7-yl)pyrimidin-2-yl)-1,3,8-triazaspiro[4.5]decan-4-one;

7-(6-isopropoxy-5-methylpyridin-3-yl)-4-phenyl-3,4-dihydro-1H-benzo[4,5]imidazo[2,1-c][1,4]oxazine;

7-(5-methylpyridin-3-yl)-1-phenyl-2,3-dihydro-1H-benzo[d]pyrrolo[1,2-a]imidazole;

N-methyl-3-(1-phenyl-2,3-dihydro-1H-benzo[d]pyrrolo[1,2-a]imidazol-7-yl)benzamide;

4-(1-phenyl-2,3-dihydro-1H-benzo[d]pyrrolo[1,2-a]imidazol-7-yl)-N-((tetrahydrofuran-2-yl)methyl)benzamide;

(S)-4-(5-(1-phenyl-2,3-dihydro-H-benzo[d]pyrrolo[1,2-a]imidazol-7-yl)pyrimidin-2-yl)morpholine;

N-(5-(4-phenyl-3,4-dihydro-1H-benzo[4,5]imidazo[2,1-c][1,4]oxazin-7-yl)pyridin-2-yl)acetamide;

N-ethyl-N-methyl-3-(1-phenyl-2,3-dihydro-1H-benzo[d]pyrrolo[1,2-a]imidazol-7-yl)benzamide;

5-(1-phenyl-2,3-dihydro-1H-benzo[d]pyrrolo[1,2-a]imidazol-7-yl)pyridin-2-amine;

7-(3-methyl-3H-imidazo[4,5-b]pyridin-6-yl)-4-phenyl-3,4-dihydro-1H-benzo[4,5]imidazo[2,1-c][1,4]oxazine;

10-(3,5-dimethoxyphenyl)-2-(2-morpholinopyrimidin-5-yl)-7,8,9,10-tetrahydro-6H-cyclohepta [4,5]imidazo[1,2-a]pyridin-10-ol;

N,N-dimethyl-3-((5-(4-phenyl-3,4-dihydro-1H-benzo[4,5]imidazo[2,1-c][1,4]oxazin-7-yl)pyridin-2-yl)oxy)propan-1-amine;

(3R,4R)-1-(5-((S)-4-phenyl-3,4-dihydro-1H-benzo[4,5]imidazo[2,1-c][1,4]oxazin-7-yl)pyrimidin-2-yl)pyrrolidine-3,4-diol;

N-(2-(dimethylamino)ethyl)-3-(1-phenyl-2,3-dihydro-1H-benzo[d]pyrrolo[1,2-a]imidazol-7-yl)benzamide;

10-(3-methoxyphenyl)-2-(2-morpholinopyrimidin-5-yl)-7,8,9,10-tetrahydro-6H-cyclohepta [4,5]imidazo[1,2-a]pyridin-10-ol;

7-(1,5-dimethyl-1H-pyrazol-4-yl)-1-phenyl-2,3-dihydro-1H-benzo[d]pyrrolo[1,2-a]imidazole;

N,N-dimethyl-3-(1-phenyl-2,3-dihydro-1H-benzo[d]pyrrolo[1,2-a]imidazol-7-yl)benzamide;

7-(3-(methylsulfonyl)phenyl)-1-phenyl-2,3-dihydro-1H-benzo[d]pyrrolo[1,2-a]imidazole;

4-phenyl-7-(pyrido[2,3-b]pyrazin-7-yl)-3,4-dihydro-1H-benzo[4,5]imidazo[2,1-c][1,4]oxazine;

1-methyl-5-(1-phenyl-2,3-dihydro-1H-benzo[d]pyrrolo[1,2-a]imidazol-7-yl)pyridin-2(1H)-one;

(3S,4S)-1-(5-((S)-4-phenyl-3,4-dihydro-1H-benzo[4,5]imidazo[2,1-c][1,4]oxazin-7-yl)pyrimidin-2-yl)pyrrolidine-3,4-diol;

4-phenyl-7-(pyrimidin-5-yl)-3,4-dihydro-1H-benzo[4,5]imidazo[2,1-c][1,4]oxazine;

(S)-2-(5-(1-(2-Methoxyphenyl)-2,3-dihydro-1H-cyclopenta[4,5]imidazo[1,2-a]pyridin-7-yl)pyrimidin-2-yl)propan-2-ol;

(S)-2-(5-(1-phenyl-2,3-dihydro-1H-benzo[d]pyrrolo[1,2-a]imidazol-7-yl)pyrimidin-2-yl)propan-2-ol;

2-(2-(2-(2-hydroxypropan-2-yl)pyrimidin-5-yl)-6,7,8,9-tetrahydrobenzo[4,5]imidazo[1,2-a]pyridin-9-yl)phenol;

4-(5-(6-phenyl-6,7,8,9-tetrahydroimidazo[1,2-a:4,5-b']dipyridin-3-yl)pyrimidin-2-yl)piperazin-2-one;

(S)-7-(2-(3-morpholinoazetidin-1-yl)pyrimidin-5-yl)-4-phenyl-3,4-dihydro-1H-benzo[4,5]imidazo[2,1-c][1,4]oxazine;

7-(5-(methylsulfonyl)pyridin-3-yl)-1-phenyl-2,3-dihydro-1H-benzo[d]pyrrolo[1,2-a]imidazole;

(R)-7-(2-Morpholinopyrimidin-5-yl)-4-phenyl-3,4-dihydro-1H-benzo[4,5]imidazo[2,1-c][1,4]oxazine;

7-(2-methylpyridin-3-yl)-1-phenyl-2,3-dihydro-1H-benzo[d]pyrrolo[1,2-a]imidazole;

1-(5-(1-phenyl-1,2,3,4-tetrahydrobenzo[4,5]imidazo[1,2-a]pyridin-8-yl)pyrimidin-2-yl)azetidine-3-carboxylic acid;

7-(1-methyl-1H-pyrrol-3-yl)-1-phenyl-2,3-dihydro-1H-benzo[d]pyrrolo[1,2-a]imidazole; or N-(2-morpholinoethyl)-5-(4-phenyl-3,4-dihydro-H-benzo[4,5]imidazo[2,1-c][1,4]oxazin-7-yl)pyridin-2-amine.

In a thirty-third embodiment the invention provides a compound according to any of the foregoing embodiments wherein the compound is 7-(5-((R)-1-Phenyl-2,3-dihydro-1H-benzo[d]pyrrolo[1,2-a]imidazol-7-yl)pyrimidin-2-yl)hexahydroimidazo[1,5-a]pyrazin-3(2H)-one;

3,3-difluoro-1-(5-((R)-1-phenyl-2,3-dihydro-1H-benzo[d]pyrrolo[1,2-a]imidazol-7-yl)pyrimidin-2-yl)piperidin-4-ol;

(S)-2-(5-(4-(2-(Difluoromethoxy)phenyl)-3,4-dihydro-1H-benzo[4,5]imidazo[2,1-c][1,4]oxazin-7-yl)pyrimidin-2-yl)propan-2-ol;

(S)-2-(5-(9-(2-methoxyphenyl)-6,7,8,9-tetrahydrobenzo[4,5]imidazo[1,2-a]pyridin-2-yl)pyrimidin-2-yl)propan-2-ol;

(R)-7-(5-(1-phenyl-2,3-dihydro-1H-benzo[d]pyrrolo[1,2-a]imidazol-7-yl)pyrimidin-2-yl)-7-azaspiro[3.5]nonan-2-ol;

1-(5-(8-(2,5-dimethylphenyl)-7,8-dihydro-6H-pyrrolo[2',1':2,3]imidazo[4,5-b]pyridin-2-yl)pyrimidin-2-yl)piperidin-4-ol;

4-(5-(10-(2-methoxyphenyl)-7,8,9,10-tetrahydro-6H-cyclohepta[4,5]imidazo[1,2-a]pyridin-2-yl)pyrimidin-2-yl)morpholine;

(R)-4-(5-(1-phenyl-2,3-dihydro-1H-benzo[d]pyrrolo[1,2-a]imidazol-7-yl)pyrimidin-2-yl)morpholine;

7-(5-((S)-4-phenyl-3,4-dihydro-1H-benzo[4,5]imidazo[2,1-c][1,4]oxazin-7-yl)pyrimidin-2-yl)hexahydroimidazo[1,5-a]pyrazin-3 (2H)-one;

7-(5-((S)-4-phenyl-3,4-dihydro-1H-benzo[4,5]imidazo[2,1-c][1,4]oxazin-7-yl)pyrimidin-2-yl)hexahydroimidazo[1,5-a]pyrazin-3 (2H)-one;

4-(5-(8-(2,5-dimethylphenyl)-7,8-dihydro-6H-pyrrolo[2',1': 2,3]imidazo[4,5-b]pyridin-2-yl)pyrimidin-2-yl)piperazin-2-one;

2-(5-(1-(2,5-dimethylphenyl)-2,3-dihydro-1H-benzo[d]pyrrolo[1,2-a]imidazol-7-yl)pyrimidin-2-yl)propan-2-ol;

3,3-difluoro-1-(5-((S)-4-phenyl-3,4-dihydro-1H-benzo[4,5]imidazo[2,1-c][1,4]oxazin-7-yl)pyrimidin-2-yl)piperidin-4-ol;

7-(5-(4-(3-fluorophenyl)-3,4-dihydro-1H-benzo[4,5]imidazo[2,1-c][1,4]oxazin-7-yl)pyrimidin-2-yl)hexahydroimidazo[1,5-a]pyrazin-3 (2H)-one;

(R)-2-(5-(1-(2-methoxyphenyl)-2,3-dihydro-H-cyclopenta[4,5]imidazo[1,2-a]pyridin-7-yl)pyrimidin-2-yl)propan-2-ol;

7-(4-(isopropylsulfonyl)phenyl)-1-phenyl-2,3-dihydro-1H-benzo[d]pyrrolo[1,2-a]imidazole;

2-(5-(9-(2-Methoxyphenyl)-6,7,8,9-tetrahydrobenzo[4,5]imidazo[1,2-a]pyridin-2-yl)pyrimidin-2-yl)propan-2-ol;

4-(5-(8-(2,5-dimethylphenyl)-7,8-dihydro-6H-pyrrolo[2',1': 2,3]imidazo[4,5-b]pyridin-2-yl)pyrimidin-2-yl)morpholine;

(S)-7-(5-(4-phenyl-3,4-dihydro-1H-benzo[4,5]imidazo[2,1-c][1,4]oxazin-7-yl)pyrimidin-2-yl)-7-azaspiro[3.5]nonan-2-ol;

4-(5-(9-(2-methoxyphenyl)-6,7,8,9-tetrahydrobenzo[4,5]imidazo[1,2-a]pyridin-2-yl)pyrimidin-2-yl)morpholine;

1-(5-(9-phenyl-6,7,8,9-tetrahydroimidazo[1,2-a:5,4-b']dipyridin-2-yl)pyrimidin-2-yl)piperidin-4-ol;

(R)-2-(5-(1-Phenyl-2,3-dihydro-1H-benzo[d]pyrrolo[1,2-a]imidazol-7-yl)pyrimidin-2-yl)propan-2-ol;

2-(5-(10-(2-methoxyphenyl)-7,8,9,10-tetrahydro-6H-cyclohepta[4,5]imidazo[1,2-a]pyridin-2-yl)pyrimidin-2-yl)propan-2-ol;

N-methyl-4-(1-phenyl-2,3-dihydro-1H-benzo[d]pyrrolo[1,2-a]imidazol-7-yl)benzenesulfonamide;

(S)-7-(2-morpholinopyrimidin-5-yl)-4-phenyl-3,4-dihydro-1H-benzo[4,5]imidazo[2,1-c][1,4]oxazine;

(S)-7-(5-(4-phenyl-3,4-dihydro-1H-benzo[4,5]imidazo[2,1-c][1,4]oxazin-7-yl)pyrimidin-2-yl)-7-azaspiro[3.5]nonan-2-ol;

2-(5-(1-(2-methoxyphenyl)-2,3-dihydro-H-cyclopenta[4,5]imidazo[1,2-a]pyridin-7-yl)pyrimidin-2-yl)propan-2-ol;

(R)-2-(5-(1-phenyl-1,2,3,4-tetrahydrobenzo[4,5]imidazo[1,2-a]pyridin-8-yl)pyrimidin-2-yl)propan-2-ol;

ethyl 2-[[5-[9-(2-methoxyphenyl)-6,7,8,9-tetrahydropyrido[1,2-a]benzimidazol-2-yl]pyrimidin-2-yl]amino]acetate.r 2-((5-(9-(2-methoxyphenyl)-6,7,8,9-tetrahydrobenzo[4,5]imidazo[1,2-a]pyridin-2-yl)pyridin-2-yl)oxy)acetic acid.

In a thirty-third embodiment the invention provides a compound of Formula (I):

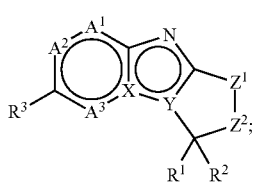

(I)

or a pharmaceutically acceptable salt, prodrug or stereoisomer thereof, wherein:

$R^1$ is H, $OR^4$, $N(R^4)_2$ or optionally substituted $(C_1-C_3)$ alkyl;

$R^2$ is optionally substituted $(C_1-C_3)$alkyl, or optionally substituted aryl; or $R^1$ and $R^2$ together can form an optionally substituted saturated or partially saturated carbocyclic or optionally substituted saturated or partially saturated heterocyclic ring;

$A^1$, $A^2$, and $A^3$ are independently $C(R^{A2})$ or N, provided that at least one is $C(R^{A2})$;

X is N and Y is C, wherein:
$Z^1$ is —$C(R^z)_2$— or —O— and $Z^2$ is —$C(R^z)_2$; or
$Z^1$ is —$CH_2$— or —O— and $Z^2$ is —$Z^{2a}$—$Z^{2b}$—, wherein $Z^{2a}$ is attached to $Z^1$ and $Z^{2b}$ is attached to $C(R^1)(R^2)$; and
$Z^{2a}$ and $Z^{2b}$ are independently —$C(R)_2$ or —O—, provided that neither $Z^{2a}$ nor $Z^{2b}$ is —O— when $Z^1$ is —O—;

or

X is C and Y is N wherein:
$Z^1$ is —$C(R^z)_2$— and $Z^2$ is —$C(R^z)_2$; or
$Z^1$ is —$C(R^z)_2$— and $Z^2$ is $Z^2$ is —$Z^{2a}$—$Z^{2b}$—; wherein $Z^{2a}$ is attached to $Z^1$ and $Z^{2b}$ is attached to $C(R^1)(R^2)$; and
$Z^{2a}$ and $Z^{2b}$ are independently —$C(R^z)_2$ or —O—;

$R^3$ is —$R^{3a}$—$R^{3b}$, wherein:
$R^{3a}$ is an optionally substituted aryl, optionally substituted saturated or partially saturated heterocyclyl, or optionally substituted heteroaryl;
$R^{3b}$ is H, —$N(R^a)(R^b)$, —C(O)-optionally substituted $(C_1-C_3)$alkyl, —C(O)-optionally substituted heterocyclyl, —$O(R^a)$, —$S(O)_2(C_1-C_3)$alkyl, —$(C(R^e)_2)_q$-optionally substituted cycloalkyl; or —$C(R^e)_q$-optionally substituted heterocyclyl; provided that $R3^b$ is not H or methoxy when $R^2$ is optionally substituted phenyl;

$R^4$ is independently H or optionally substituted $(C_1-C_3)$ alkyl;

$R^a$ and $R^b$ are independently selected from H, optionally substituted $(C_1-C_5)$alkyl, —$(CH_2)_p$—$(C_3-C_6)$cycloalkyl and —$(CH_2)_p$-optionally substituted heterocyclyl;

$R^e$ is independently H, OH or $CH_3$;
$R^{A2}$ is independently H, $CF_3$, or $(C_1-C_3)$alkyl;
$R^z$ is independently H, F, $CF_3$, —OH or $(C_1-C_3)$alkyl;
$R^{z1}$ is independently H, OH or $(C_1-C_3)$alkyl;
p is independently 0, 1 or 2; and
q is independently 0, 1 or 2;
provided that $R^2$ is not phenyl substituted with —$OCHF_2$; and
provided the compound is not 1-(2-methylphenyl)-7-[2-(morpholin-4-yl)pyrimidin-5-yl]-2,3-dihydro-1H-pyrrolo[1,2-a]benzimidazole;

7-[2-(morpholin-4-yl)pyrimidin-5-yl]-1-phenyl-2,3-dihydro-1H-pyrrolo[1,2-a]benzimidazole;

(1R or S)-7-(6-methylsulfonyl-3-pyridyl)-1-phenyl-2,3-dihydro-1H-pyrrolo[1,2-a]benzimidazole;

[5-[(1R or S)-1-phenyl-2,3-dihydro-1H-pyrrolo[1,2-a]benzimidazol-7-yl]-2-pyridyl]methanol;

tert-butyl 4-[5-[(1R or S)-1-phenyl-2,3-dihydro-1H-pyrrolo[1,2-a]benzimidazol-7-yl]-2-pyridyl]piperazine-1-carboxylate;

(1R or S)-7-(6-chloromethyl-3-pyridyl)-1-phenyl-2,3-dihydro-1H-pyrrolo[1,2-a]benzimidazole;

(1R or S)-7-[(6-(methylsulfonylmethyl)-3-pyridyl]-1-phenyl-2,3-dihydro-1H-pyrrolo[1,2-a]benzimidazole; or (1R or S)-1-phenyl-7-[6-(piperazin-1-yl)pyridine-3-yl]-2,3-dihydro-1H-pyrrolo[1,2-a]benzimidazole.

In a thirty-fourth embodiment the invention provides a compound according to any of the foregoing embodiments, wherein $R^2$ is optionally substituted $(C_1-C_3)$alkyl or phenyl, each of which is independently optionally substituted with 1 to 3 groups independently selected from —OR$^a$, and —(C$_1$-C$_6$)alkylene-OR$^a$, wherein R$^a$ is H or —(C$_1$-C$_6$)alkyl; and R$^1$ is H, or optionally substituted (C$_1$-C$_3$)alkyl; or R$^1$ and R$^2$ together form an optionally substituted spirocycle selected from

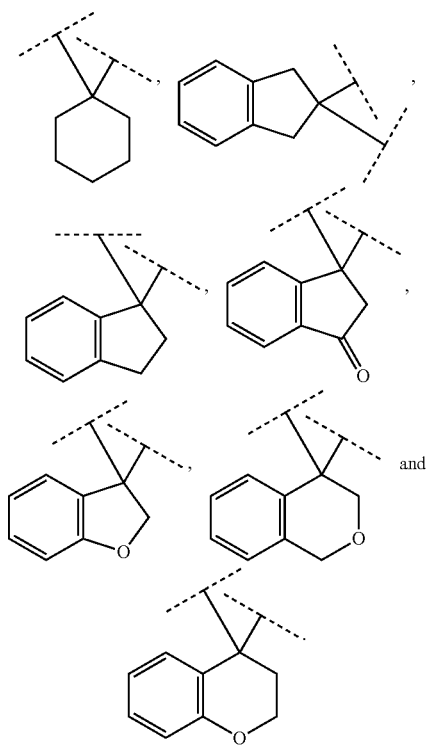

In a thirty-fifth embodiment the invention provides a compound according to any of the foregoing embodiments wherein R$^{3a}$ is optionally substituted cyclohexenyl, optionally substituted pyrazolyl, optionally substituted pyridinyl, optionally substituted 1,2,3,6-tetrahydropyridinyl, pyridine-2(1H)-one, optionally substituted pyrimidinyl, optionally substituted tetrahydropyridinyl or 2,5-dihydro-1H-pyrrolyl.

In a thirty-sixth embodiment the invention provides a compound according to any of the foregoing embodiments wherein the compound is a compound of Formula (Ia) or Formula (Ib)

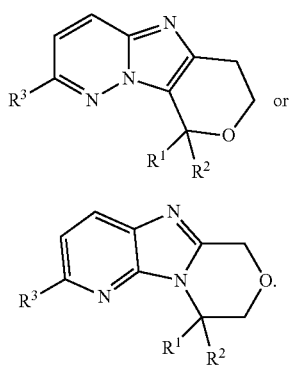

In a thirty-seventh embodiment the invention provides a compound according to any of the foregoing embodiments wherein R$^1$ and R$^2$ together form an optionally substituted spirocycle selected from

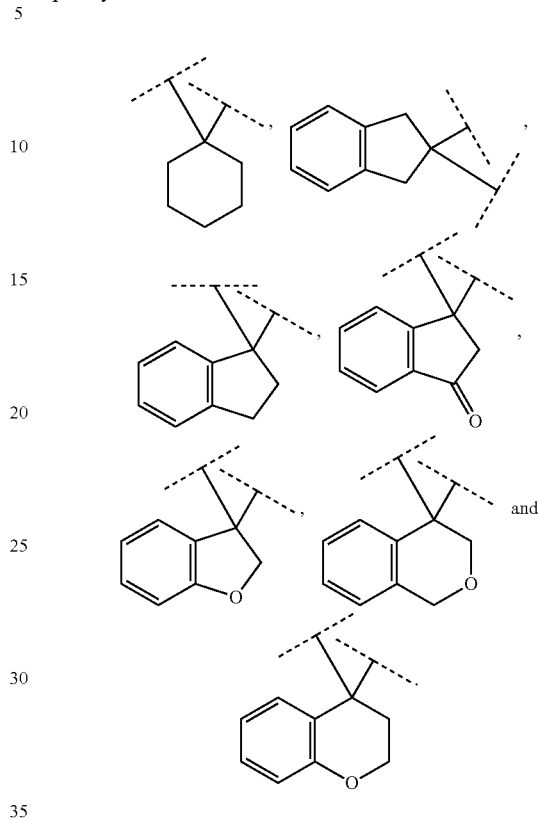

In a thirty-eighth embodiment the invention provides a compound according to any of the foregoing embodiments wherein R$^{3b}$ is H, —C(O)-optionally substituted (C$_1$-C$_3$) alkyl, —C(O)-optionally substituted piperidinyl, optionally substituted (C$_1$-C$_4$)alkyl, —N(H)-optionally substituted (C$_1$-C$_3$)alkyl, —N(H)-optionally substituted cyclobutyl, —N(H)-optionally substituted tetrayhydrofuranyl, —O-optionally substituted (C$_1$-C$_3$)alkyl, —O-optionally substituted cyclohexyl, —O-optionally substituted cyclopentyl, —O-optionally substituted tetrahydropyranyl, —S(O)$_2$-optionally substituted (C$_1$-C$_3$)alkyl, -optionally substituted azepanyl, optionally substituted azetidinyl, optionally substituted diazepanyl, optionally substituted hexahydroimidazo[1,5-α]pyrazin-3(2H)-one, optionally substituted morpholinyl, 1,4-oxazepanyl, optionally substituted piperazinyl, optionally substituted piperidinyl or optionally substituted pyrrolidinyl.

In a thirty-ninth embodiment the invention provides a compound according to any of the foregoing embodiments wherein the compound is (8aR)-7-(5-(6',8'-dihydro-2H-spiro[benzofuran-3,9'-pyrido[3',2':4,5]imidazo[2,1-c][1,4]oxazin]-2'-yl)pyrimidin-2-yl)hexahydroimidazo[1,5-a]pyrazin-3(2H)-one;

3-((5-(6',8'-dihydro-2H-spiro[benzofuran-3,9'-pyrido[3',2':4,5]imidazo[2,1-c][1,4]oxazin]-2'-yl)pyrimidin-2-yl)amino)cyclobutanol;

5-(6',8'-dihydro-2H-spiro[benzofuran-3,9'-pyrido[3',2':4,5]imidazo[2,1-c][1,4]oxazin]-2'-yl)-N-(tetrahydrofuran-3-yl)pyrimidin-2-amine;

1-(5-(6',8'-dihydro-2H-spiro[benzofuran-3,9'-pyrido[3',2':4,5]imidazo[2,1-c][1,4]oxazin]-2'-yl)pyrimidin-2-yl)piperidin-3-ol;

2'-(2-(4-methylpiperazin-1-yl)pyrimidin-5-yl)-6',8'-dihydro-2H-spiro[benzofuran-3,9'-pyrido[3',2':4,5]imidazo[2, 1-c][1,4]oxazine];

2'-(2-morpholinopyrimidin-5-yl)-6',8'-dihydro-2H-spiro[benzofuran-3,9'-pyrido[3',2':4,5]imidazo[2, 1-c][1,4]oxazine];

1-(5-(1,2',3,3'-tetrahydrospiro[benzo[4,5]imidazo[2,1-c][1,4]oxazine-4,1'-inden]-7-yl)pyrimidin-2-yl)piperidin-4-ol;

(1-(5-(2,3,6',8'-tetrahydrospiro[indene-1,9'-pyrido[3',2':4,5]imidazo[2,1-c][1,4]oxazin]-2'-yl)pyrimidin-2-yl)piperidin-3-yl)methanol;

(8aS)-7-(5-(2,3,6',8'-tetrahydrospiro[indene-1,9'-pyrido[3',2':4,5]imidazo[2,1-c][1,4]oxazin]-2'-yl)pyrimidin-2-yl)hexahydroimidazo[1,5-a]pyrazin-3(2H)-one;

2'-(2-(1,4-oxazepan-4-yl)pyrimidin-5-yl)-2,3,6',8'-tetrahydrospiro[indene-1,9'-pyrido[3',2':4,5]imidazo[2,1-c][1,4]oxazine];

3,3-difluoro-1-(5-(2,3,6',8'-tetrahydrospiro[indene-1,9'-pyrido[3',2':4,5]imidazo[2, 1-c][1,4]oxazin]-2'-yl)pyrimidin-2-yl)piperidin-4-ol;

2-hydroxy-1-(4-(5-(2,3,6',8'-tetrahydrospiro[indene-1,9'-pyrido[3',2':4,5]imidazo[2,1-c][1,4]oxazin]-2'-yl)pyrimidin-2-yl)piperazin-1-yl)propan-1-one;

2-hydroxy-1-(4-(5-(2,3,6',8'-tetrahydrospiro[indene-1,9'-pyrido[3',2':4,5]imidazo[2,1-c][1,4]oxazin]-2'-yl)pyrimidin-2-yl)piperazin-1-yl)ethanone;

(4-fluoro-1-(5-(2,3,6',8'-tetrahydrospiro[indene-1,9'-pyrido[3',2':4,5]imidazo[2,1-c][1,4]oxazin]-2'-yl)pyrimidin-2-yl)piperidin-4-yl)methanol;

2'-(2-morpholinopyrimidin-5-yl)-2,3,6',8'-tetrahydrospiro[indene-1,9'-pyrido[3',2':4,5]imidazo[2,1-c][1,4]oxazine];

1-(5-(2,3,6',8'-tetrahydrospiro[indene-1,9'-pyrido[3',2':4,5]imidazo[2,1-c][1,4]oxazin]-2'-yl)pyrimidin-2-yl)azepan-4-ol;

(S)-2-(5-(6',8'-dihydrospiro[chroman-4,9'-pyrido[3',2':4,5]imidazo[2,1-c][1,4]oxazin]-2'-yl)pyrimidin-2-yl)propan-2-ol;

(R)-2-(5-(6',8'-dihydrospiro[chroman-4,9'-pyrido[3',2':4,5]imidazo[2,1-c][1,4]oxazin]-2'-yl)pyrimidin-2-yl)propan-2-ol;

(8aR)-7-(5-(6',8'-dihydro-2H-spiro[benzofuran-3,9'-pyrido[3',2':4,5]imidazo[2,1-c][1,4]oxazin]-2'-yl)pyrimidin-2-yl)hexahydroimidazo[1,5-a]pyrazin-3(2H)-one;

3-((5-(6',8'-dihydro-2H-spiro[benzofuran-3,9'-pyrido[3',2':4,5]imidazo[2,1-c][1,4]oxazin]-2'-yl)pyrimidin-2-yl)amino)cyclobutanol;

5-(6',8'-dihydro-2H-spiro[benzofuran-3,9'-pyrido[3',2':4,5]imidazo[2,1-c][1,4]oxazin]-2'-yl)-N-(tetrahydrofuran-3-yl)pyrimidin-2-amine;

1-(5-(6',8'-dihydro-2H-spiro[benzofuran-3,9'-pyrido[3',2':4,5]imidazo[2,1-c][1,4]oxazin]-2'-yl)pyrimidin-2-yl)piperidin-3-ol;

2'-(2-(4-methylpiperazin-1-yl)pyrimidin-5-yl)-6',8'-dihydro-2H-spiro[benzofuran-3,9'-pyrido[3',2':4,5]imidazo[2,1-c][1,4]oxazine];

2'-(2-morpholinopyrimidin-5-yl)-6',8'-dihydro-2H-spiro[benzofuran-3,9'-pyrido[3',2':4,5]imidazo[2,1-c][1,4]oxazine];

1-(5-(1,2',3,3'-tetrahydrospiro[benzo[4,5]imidazo[2,1-c][1,4]oxazine-4,1'-inden]-7-yl)pyrimidin-2-yl)piperidin-4-ol;

(1-(5-(2,3,6',8'-tetrahydrospiro[indene-1,9'-pyrido[3',2':4,5]imidazo[2,1-c][1,4]oxazin]-2'-yl)pyrimidin-2-yl)piperidin-3-yl)methanol;

(8aR)-7-(5-(2,3,6',8'-tetrahydrospiro[indene-1,9'-pyrido[3',2':4,5]imidazo[2,1-c][1,4]oxazin]-2'-yl)pyrimidin-2-yl)hexahydroimidazo[1,5-a]pyrazin-3(2H)-one;

2'-(2-(1,4-oxazepan-4-yl)pyrimidin-5-yl)-2,3,6',8'-tetrahydrospiro[indene-1,9'-pyrido[3',2':4,5]imidazo[2,1-c][1,4]oxazine];

3,3-difluoro-1-(5-(2,3,6',8'-tetrahydrospiro[indene-1,9'-pyrido[3',2':4,5]imidazo[2, 1-c][1,4]oxazin]-2'-yl)pyrimidin-2-yl)piperidin-4-ol;

2-hydroxy-1-(4-(5-(2,3,6',8'-tetrahydrospiro[indene-1,9'-pyrido[3',2':4,5]imidazo[2,1-c][1,4]oxazin]-2'-yl)pyrimidin-2-yl)piperazin-1-yl)propan-1-one;

2-hydroxy-1-(4-(5-(2,3,6',8'-tetrahydrospiro[indene-1,9'-pyrido[3',2':4,5]imidazo[2,1-c][1,4]oxazin]-2'-yl)pyrimidin-2-yl)piperazin-1-yl)ethanone;

(4-fluoro-1-(5-(2,3,6',8'-tetrahydrospiro[indene-1,9'-pyrido[3',2':4,5]imidazo[2,1-c][1,4]oxazin]-2'-yl)pyrimidin-2-yl)piperidin-4-yl)methanol;

2'-(2-morpholinopyrimidin-5-yl)-2,3,6',8'-tetrahydrospiro[indene-1,9'-pyrido[3',2':4,5]imidazo[2,1-c][1,4]oxazine];

1-(5-(2,3,6',8'-tetrahydrospiro[indene-1,9'-pyrido[3',2':4,5]imidazo[2,1-c][1,4]oxazin]-2'-yl)pyrimidin-2-yl)azepan-4-ol;

(R)-1-((4,4-difluorocyclohexyl)methyl)-4-(8-phenyl-7,8-dihydro-6H-pyrrolo [2',1':2,3]imidazo[4,5-b]pyridin-2-yl)pyridin-2(1H)-one;

(1r,4r)-4-((4-(6',8'-dihydro-2H-spiro[benzofuran-3,9'-pyrido[3',2':4,5]imidazo[2,1-c][1,4]oxazin]-2'-yl)pyridin-2-yl)oxy)cyclohexanol;

(1s,4s)-4-((4-(6',8'-dihydro-2H-spiro[benzofuran-3,9'-pyrido[3',2':4,5]imidazo[2,1-c][1,4]oxazin]-2'-yl)pyridin-2-yl)oxy)cyclohexanol;

3-((4-(6',8'-dihydro-2H-spiro[benzofuran-3,9'-pyrido[3',2':4,5]imidazo[2,1-c][1,4]oxazin]-2'-yl)pyridin-2-yl)oxy)cyclopentanol;

2'-(2-morpholinopyrimidin-5-yl)-6',7'-dihydrospiro[cyclohexane-1,9'-pyrano[4',3':4,5]imidazo[1,2-b]pyridazine];

2'-(2-morpholinopyrimidin-5-yl)-6',7'-dihydrospiro[chroman-4,9'-pyrano[4',3':4,5]imidazo[1,2-b]pyridazine];

2'-(2-(piperazin-1-yl)pyrimidin-5-yl)-6'H,8'H-spiro[chromane-4,9'-pyrido[3',2':4,5]imidazo[2,1-c][1,4]oxazine];

2'-(2-methoxypyrimidin-5-yl)-6',8'-dihydrospiro[chroman-4,9'-pyrido[3,2':4,5]imidazo[2,1-c][1,4]oxazine];

2'-(2-ethoxypyrimidin-5-yl)-6',8-dihydrospiro[chroman-4,9'-pyrido[3,2':4,5]imidazo[2,1-c][1,4]oxazine];

2'-(2-(methylsulfonyl)pyrimidin-5-yl)-6',8'-dihydrospiro[chroman-4,9'-pyrido[3',2':4,5]imidazo[2, 1-c][1,4]oxazine];

2'-(2-(1,4-diazepan-1-yl)pyrimidin-5-yl)-6',8'-dihydrospiro[chroman-4,9'-pyrido[3',2':4,5]imidazo[2, 1-c][1,4]oxazine];

5-(6',8'-dihydrospiro[chroman-4,9'-pyrido[3',2':4,5]imidazo[2,1-c][1,4]oxazin]-2'-yl)-N-isopropylpyrimidin-2-amine;

2'-(2-morpholinopyrimidin-5-yl)-6',8-dihydrospiro[chroman-4,9'-pyrido[3',2':4,5]imidazo[2,1-c][1,4]oxazine];

2-(5-(6',8'-dihydrospiro[chroman-4,9'-pyrido[3',2':4,5]imidazo[2, 1-c][1,4]oxazin]-2'-yl)pyrimidin-2-yl)propan-2-ol;

2'-(2-((tetrahydro-2H-pyran-4-yl)oxy)pyridin-4-yl)-6',8'-dihydrospiro[chroman-4,9'-pyrido[3',2':4,5]imidazo[2, 1-c][1,4]oxazine];

5-(6'H,8'H-Spiro[chromane-4,9'-pyrido[3',2':4,5]imidazo[2, 1-c][1,4]oxazin]-2'-yl)-N-(tetrahydrofuran-3-yl)pyrimidin-2-amine;

(8aR)-7-(5-(6',8'-dihydrospiro[chroman-4,9'-pyrido[3',2':4, 5]imidazo[2, 1-c][1,4]oxazin]-2'-yl)pyrimidin-2-yl)hexahydroimidazo[1,5-a]pyrazin-3 (2H)-one;

1-(5-(6',8'-dihydrospiro[chroman-4,9'-pyrido[3',2':4,5]imidazo[2,1-c][1,4]oxazin]-2'-yl)pyrimidin-2-yl)piperidin-4-ol;

1-(5-(6',8'-dihydrospiro[chroman-4,9'-pyrido[3',2':4,5]imidazo[2,1-c][1,4]oxazin]-2'-yl)pyrimidin-2-yl)piperidin-3-ol;

1-(5-(6',8'-dihydrospiro[chroman-4,9'-pyrido[3',2':4,5]imidazo[2,1-c][1,4]oxazin]-2'-yl)pyrimidin-2-yl)azetidin-3-ol;

1-(5-(6',8'-dihydrospiro[chroman-4,9'-pyrido[3',2':4,5]imidazo[2,1-c][1,4]oxazin]-2'-yl)pyrimidin-2-yl)pyrrolidin-3-ol;

3-((5-(6',8'-dihydrospiro[chroman-4,9'-pyrido[3',2':4,5]imidazo[2,1-c][1,4]oxazin]-2'-yl)pyrimidin-2-yl)amino)cyclobutanol;

1-(5-(6',8'-dihydrospiro[chroman-4,9'-pyrido[3',2':4,5]imidazo[2,1-c][1,4]oxazin]-2'-yl)pyrimidin-2-yl)-3-methylazetidin-3-ol;

2'-(2-(4-methylpiperazin-1-yl)pyrimidin-5-yl)-6',8'-dihydrospiro[chroman-4,9'-pyrido[3',2':4,5]imidazo[2,1-c][1,4]oxazine];

2'-(5,5-Dimethyl-2,5-dihydro-1H-pyrrol-3-yl)-2H,6'H,8'H-spiro[benzofuran-3,9'-pyrido[3',2':4,5]imidazo[2,1-c][1,4]oxazine];

2'-(2,5-dihydro-1H-pyrrol-3-yl)-6',8'-dihydro-2H-spiro[benzofuran-3,9'-pyrido[3',2':4,5]imidazo[2,1-c][1,4]oxazine];

2'-(2-(piperazin-1-yl)pyrimidin-5-yl)-2H,6'H,8'H-spiro[benzofuran-3,9'-pyrido[3',2':4,5]imidazo[2,1-c][1,4]oxazine];

2'-(2-((tetrahydro-2H-pyran-4-yl)oxy)pyridin-4-yl)-6',8'-dihydro-2H-spiro[benzofuran-3,9'-pyrido[3',2':4,5]imidazo[2,1-c][1,4]oxazine];

2'-(2-methoxypyrimidin-5-yl)-6',8'-dihydro-2H-spiro[benzofuran-3,9'-pyrido[3',2':4,5]imidazo[2,1-c][1,4]oxazine];

2-(tert-butoxy)-1-((2S)-4-(5-(6',8'-dihydro-2H-spiro[benzofuran-3,9'-pyrido[3',2':4,5]imidazo[2,1-c][1,4]oxazin]-2'-yl)pyrimidin-2-yl)-2-methylpiperazin-1-yl)ethanone;

2-(tert-butoxy)-1-((3S)-4-(5-(6',8'-dihydro-2H-spiro[benzofuran-3,9'-pyrido[3',2':4,5]imidazo[2,1-c][1,4]oxazin]-2'-yl)pyrimidin-2-yl)-3-methylpiperazin-1-yl)ethanone;

2-(tert-butoxy)-1-((3R)-4-(5-(6',8'-dihydro-2H-spiro[benzofuran-3,9'-pyrido[3',2':4,5]imidazo[2,1-c][1,4]oxazin]-2'-yl)pyrimidin-2-yl)-3-methylpiperazin-1-yl)ethanone;

2-(tert-butoxy)-1-((2R)-4-(5-(6',8'-dihydro-2H-spiro[benzofuran-3,9'-pyrido[3',2':4,5]imidazo[2,1-c][1,4]oxazin]-2'-yl)pyrimidin-2-yl)-2-methylpiperazin-1-yl)ethanone;

1-((2S)-4-(5-(2H,6'H,8'H-spiro[benzofuran-3,9'-pyrido[3',2':4,5]imidazo[2,1-c][1,4]oxazin]-2'-yl)pyrimidin-2-yl)-2-methylpiperazin-1-yl)-2-hydroxyethan-1-one 1-((3 S)-4-(5-(6',8'-dihydro-2H-spiro[benzofuran-3,9'-pyrido[3',2':4,5]imidazo[2,1-c][1,4]oxazin]-2'-yl)pyrimidin-2-yl)-3-methylpiperazin-1-yl)-2-hydroxyethanone;

1-((3R)-4-(5-(6',8'-dihydro-2H-spiro[benzofuran-3,9'-pyrido[3',2':4,5]imidazo[2,1-c][1,4]oxazin]-2'-yl)pyrimidin-2-yl)-3-methylpiperazin-1-yl)-2-hydroxyethanone;

1-((2R)-4-(5-(6',8'-dihydro-2H-spiro[benzofuran-3,9'-pyrido[3',2':4,5]imidazo[2,1-c][1,4]oxazin]-2'-yl)pyrimidin-2-yl)-2-methylpiperazin-1-yl)-2-hydroxyethanone;

2-(5-(2,3-dihydro-6'H,8'H-spiro[indene-1,9'-pyrido[3',2':4,5]imidazo[2,1-c][1,4]oxazin]-2'-yl)pyrimidin-2-yl)propan-2-ol;

2'-(2-(2-hydroxypropan-2-yl)pyrimidin-5-yl)-6',8'-dihydrospiro[indene-1,9'-pyrido[3',2':4,5]imidazo[2,1-c][1,4]oxazin]-3(2H)-one;

2'-(2-(2-hydroxypropan-2-yl)pyrimidin-5-yl)-2,3-dihydro-6'H,8'H-spiro[indene-1,9'-pyrido[3',2':4,5]imidazo[2,1-c][1,4]oxazin]-6'-ol;

2'-(1-(pyrimidin-4-yl)-1,2,3,6-tetrahydropyridin-4-yl)-2H,6'H,8'H-spiro[benzofuran-3,9'-pyrido[3',2':4,5]imidazo[2, 1-c][1,4]oxazine];

1-(4-(6',8'-dihydro-2H-spiro[benzofuran-3,9'-pyrido[3',2':4,5]imidazo[2,1-c][1,4]oxazin]-2'-yl)-5,6-dihydropyridin-1(2H)-yl)-3-methoxy-3-methylbutan-1-one;

(S)-1-(5-(6',8'-dihydro-2H-spiro[benzofuran-3,9'-pyrido[3',2':4,5]imidazo[2,1-c][1,4]oxazin]-2'-yl)pyrimidin-2-yl)piperidin-4-ol;

(R)-7-(5-((S)-6',8'-dihydro-2H-spiro[benzofuran-3,9'-pyrido[3',2':4,5]imidazo[2,1-c][1,4]oxazin]-2'-yl)pyrimidin-2-yl)hexahydroimidazo[1,5-a]pyrazin-3(2H)-one;

(1S,4r)-4-((4-((S)-6',8'-Dihydro-2H-spiro[benzofuran-3,9'-pyrido[3',2':4,5]imidazo[2,1-c][1,4]oxazin]-2'-yl)pyridin-2-yl)oxy)cyclohexanol;

1-((S)-4-(5-((S)-6',8'-dihydro-2H-spiro[benzofuran-3,9'-pyrido[3',2':4,5]imidazo[2,1-c][1,4]oxazin]-2'-yl)pyrimidin-2-yl)-2-methylpiperazin-1-yl)-2-hydroxyethanone;

1-((R)-4-(5-((S)-6',8'-dihydro-2H-spiro[benzofuran-3,9'-pyrido[3',2':4,5]imidazo[2,1-c][1,4]oxazin]-2'-yl)pyrimidin-2-yl)-2-methylpiperazin-1-yl)-2-hydroxyethanone;

1-((R)-4-(5-((R)-6',8'-dihydro-2H-spiro[benzofuran-3,9'-pyrido[3',2':4,5]imidazo[2,1-c][1,4]oxazin]-2'-yl)pyrimidin-2-yl)-2-methylpiperazin-1-yl)-2-hydroxyethanone;

1-((S)-4-(5-((R)-6',8'-dihydro-2H-spiro[benzofuran-3,9'-pyrido[3',2':4,5]imidazo[2,1-c][1,4]oxazin]-2'-yl)pyrimidin-2-yl)-2-methylpiperazin-1-yl)-2-hydroxyethanone;

1-(5-(6',8'-dihydrospiro[isochroman-4,9'-pyrido[3',2':4,5]imidazo[2,1-c][1,4]oxazin]-2'-yl)pyrimidin-2-yl)piperidin-4-ol;

(8aR)-7-(5-(6',8'-dihydrospiro[isochroman-4,9'-pyrido[3',2':4,5]imidazo[2,1-c][1,4]oxazin]-2'-yl)pyrimidin-2-yl)hexahydroimidazo[1,5-a]pyrazin-3(2H)-one;

2'-(2-morpholinopyrimidin-5-yl)-6',8'-dihydrospiro[isochroman-4,9'-pyrido[3',2':4,5]imidazo[2,1-c][1,4]oxazine];

2-(5-(2,3-dihydro-6'H,8'H-spiro[indene-1,9'-pyrido[3',2':4,5]imidazo[2,1-c][1,4]oxazin]-2'-yl)pyrimidin-2-yl)propan-2-amine;

(S)-2-(5-(6',8'-dihydro-2H-spiro[benzofuran-3,9'-pyrido[3',2':4,5]imidazo[2,1-c][1,4]oxazin]-2'-yl)pyrimidin-2-yl)propan-2-amine; or 2'-(2-(2-hydroxypropan-2-yl)pyrimidin-5-yl)-2,3,6',8'-tetrahydrospiro[indene-1,9'-pyrido[3',2':4,5]imidazo[2,1-c][1,4]oxazin]-3-ol.

In a fortieth embodiment the invention provides a compound according to any of the foregoing embodiments wherein $R^{3b}$ is optionally substituted $(C_1-C_4)$alkyl, optionally substituted $(C_3-C_6)$cycloalkyl, —$OR^a$, —$S(O)_2$-optionally substituted $(C_1-C_3)$alkyl, optionally substituted azepanyl, optionally substituted diazepanyl, optionally substituted hexahydroimidazo[1,5-a]pyrazin-3(2H)-one, optionally substituted morpholinyl, 1,4-oxepanyl, optionally substituted piperazinyl, optionally substituted piperidinyl, optionally substituted pyrrolidinyl, optionally substituted tetrahydrofuranyl, optionally substituted tetrahydropyranyl, —C(H)(OH)CH$_2$-optionally substituted cycloalkyl, —C(H)(CH$_3$)CH$_2$-optionally substituted cycloalkyl, —CH$_2$-optionally substituted cycloalkyl, —CH$_2$-optionally substituted heterocylyl, —C(H)(CH$_3$)CH$_2$-optionally substituted heterocyclyl or —C(H)(OH)-optionally substituted heterocyclyl;

wherein $R^a$ is optionally substituted $(C_1-C_4)$alkyl, optionally substituted cyclohexyl, —CH$_2$-optionally substituted cyclohexyl, optionally substituted cyclopentyl, —CH$_2$-optionally substituted oxetanyl, —CH$_2$-optionally substituted tetrahydropyranyl, optionally substituted 6-azaspiro[3.5]nonanyl, optionally substituted 6-azaspiro[3.4]octanyl, optionally substituted piperidinyl, optionally substituted pyrrolidinyl, optionally substituted tetrahydrofuranyl or optionally substituted tetrahydropyranyl.

In a forty-first embodiment the invention provides a compound according to any of the foregoing embodiments wherein R$^{3b}$ is optionally substituted by one or more substituents independently selected from —F, —CH$_3$, —CH$_2$OH, CH$_2$CH$_2$OCH$_3$, —C(O)CH$_2$OH, —C(O)C(H)(OH)CH$_3$, —C(O)CH$_2$OC(CH$_3$)$_3$, —C(O)CH$_3$, —C(O)OCH$_3$, —OC(O)C(H)(NH$_2$)C(H)(CH$_3$)$_2$, —OH, —P(=O)(OH)$_2$, and —S(O)$_2$CH$_3$.

In a forty-second embodiment the invention provides a compound according to any of the foregoing embodiments wherein one of A$^1$, A$^2$, and A$^3$ of N, and the rest are CH.

In a forty-third embodiment the invention provides a compound according to any of the foregoing embodiments wherein the compound is ((R)-1-(5-((R)-8-phenyl-7,8-dihydro-6H-pyrrolo[2',1':2,3]imidazo[4,5-b]pyridin-2-yl)pyrimidin-2-yl)pyrrolidin-2-yl)methanol;

((S)-1-(5-((R)-8-phenyl-7,8-dihydro-6H-pyrrolo[2',1':2,3]imidazo[4,5-b]pyridin-2-yl)pyrimidin-2-yl)pyrrolidin-2-yl)methanol;

(R)-1-(2-(methylsulfonyl)ethyl)-4-(8-phenyl-7,8-dihydro-6H-pyrrolo[2',1':2,3]imidazo[4,5-b]pyridin-2-yl)pyridin-2(1H)-one;

(R)-1-(2-hydroxy-2-methylpropyl)-4-(8-phenyl-7,8-dihydro-6H-pyrrolo [2',1':2,3]imidazo[4,5-b]pyridin-2-yl)pyridin-2(1H)-one;

1-(5-((R)-8-phenyl-7,8-dihydro-6H-pyrrolo[2',1':2,3]imidazo[4,5-b]pyridin-2-yl)pyrimidin-2-yl)ethanol;

2-cyclopropyl-1-(5-((R)-8-phenyl-7,8-dihydro-6H-pyrrolo[2',1':2,3]imidazo[4,5-b]pyridin-2-yl)pyrimidin-2-yl)ethanol;

(5-((R)-8-phenyl-7,8-dihydro-6H-pyrrolo[2',1':2,3]imidazo[4,5-b]pyridin-2-yl)pyrimidin-2-yl)(tetrahydro-2H-pyran-4-yl)methanol;

1-(5-((R)-8-phenyl-7,8-dihydro-6H-pyrrolo[2',1':2,3]imidazo[4,5-b]pyridin-2-yl)pyrimidin-2-yl)-1-(tetrahydro-2H-pyran-4-yl)ethanol;

1-cyclopropyl-2-(5-((R)-8-phenyl-7,8-dihydro-6H-pyrrolo[2',1':2,3]imidazo[4,5-b]pyridin-2-yl)pyrimidin-2-yl)propan-2-ol;

1-((R)-2-methyl-4-(5-((R)-8-phenyl-7,8-dihydro-6H-pyrrolo[2',1':2,3]imidazo[4,5-b]pyridin-2-yl)pyrimidin-2-yl)piperazin-1-yl)ethanone;

1-((S)-2-methyl-4-(5-((R)-8-phenyl-7,8-dihydro-6H-pyrrolo[2',1':2,3]imidazo[4,5-b]pyridin-2-yl)pyrimidin-2-yl)piperazin-1-yl)ethanone;

(1R,3R)-3-((4-((R)-8-phenyl-7,8-dihydro-6H-pyrido[3,2-b]pyrrolizin-2-yl)pyridin-2-yl)oxy)cyclopentanecarbonitrile;

(R)-1-((4,4-difluorocyclohexyl)methyl)-4-(8-phenyl-7,8-dihydro-6H-pyrrolo [2',1':2,3]imidazo[4,5-b]pyridin-2-yl)pyridin-2(1H)-one;

2-(5-(8-(pyridin-2-yl)-7,8-dihydro-6H-pyrrolo[2',1':2,3]imidazo[4,5-b]pyridin-2-yl)pyrimidin-2-yl)propan-2-ol;

1-((S)-2-methyl-4-(5-((R)-8-phenyl-7,8-dihydro-6H-pyrrolo[2',1':2,3]imidazo[4,5-b]pyridin-2-yl)pyrimidin-2-yl)piperazin-1-yl)ethanone;

2-hydroxy-1-((R)-2-methyl-4-(5-((R)-8-phenyl-7,8-dihydro-6H-pyrrolo [2',1':2,3]imidazo[4,5-b]pyridin-2-yl)pyrimidin-2-yl)piperazin-1-yl)ethanone;

(R)-7-(5-((R)-8-(3-methoxyphenyl)-7,8-dihydro-6H-pyrrolo[2',1':2,3]imidazo[4,5-b]pyridin-2-yl)pyrimidin-2-yl)hexahydroimidazo[1,5-a]pyrazin-3 (2H)-one;

1-((R)-4-(5-((R)-8-(3-methoxyphenyl)-7,8-dihydro-6H-pyrrolo[2',1':2,3]imidazo[4,5-b]pyridin-2-yl)pyrimidin-2-yl)-2-methylpiperazin-1-yl)ethanone;

(R)-7-(5-((S)-8-(3-methoxyphenyl)-7,8-dihydro-6H-pyrrolo[2',1':2,3]imidazo[4,5-b]pyridin-2-yl)pyrimidin-2-yl)hexahydroimidazo[1,5-a]pyrazin-3 (2H)-one;

(R)-7-(5-((R)-8-(2-methoxyphenyl)-7,8-dihydro-6H-pyrrolo[2',1':2,3]imidazo[4,5-b]pyridin-2-yl)pyrimidin-2-yl)hexahydroimidazo[1,5-a]pyrazin-3 (2H)-one;

(S)-7-(5-((R)-8-(2-methoxyphenyl)-7,8-dihydro-6H-pyrrolo[2',1':2,3]imidazo[4,5-b]pyridin-2-yl)pyrimidin-2-yl)hexahydroimidazo[1,5-a]pyrazin-3 (2H)-one;

(R)-1-(5-(8-(2-methoxyphenyl)-7,8-dihydro-6H-pyrrolo[2',1': 2, 3]imidazo[4,5-b]pyridin-2-yl)pyrimidin-2-yl)piperidin-4-ol;

2-hydroxy-1-((R)-4-(5-((R)-8-(2-methoxyphenyl)-7,8-dihydro-6H-pyrrolo [2',1':2,3]imidazo[4,5-b]pyridin-2-yl)pyrimidin-2-yl)-2-methylpiperazin-1-yl)ethanone;

(R)-7-(5-((S)-8-(2-methoxyphenyl)-7,8-dihydro-6H-pyrrolo[2',1':2,3]imidazo[4,5-b]pyridin-2-yl)pyrimidin-2-yl)hexahydroimidazo[1,5-a]pyrazin-3 (2H)-one;

1-((R)-4-(5-((R)-8-(3-(Hydroxymethyl)phenyl)-7,8-dihydro-6H-pyrrolo [2',1':2,3]imidazo[4,5-b]pyridin-2-yl)pyrimidin-2-yl)-2-methylpiperazin-1-yl)ethanone;

1-((R)-4-(5-((R)-8-(3-(Hydroxymethyl)phenyl)-7,8-dihydro-6H-pyrrolo [2',1': 2, 3]imidazo[4,5-b]pyridin-2-yl)pyrimidin-2-yl)-2-methylpiperazin-1-yl) ethanone;

(S)-1-(5-((R)-8-phenyl-7,8-dihydro-6H-pyrrolo[2',1':2,3]imidazo[4,5-b]pyridin-2-yl)pyrimidin-2-yl)piperidin-4-yl 2-amino-3-methylbutanoate;

(R)-1-(5-(8-phenyl-7,8-dihydro-6H-pyrrolo[2',1':2,3]imidazo[4,5-b]pyridin-2-yl)pyrimidin-2-yl)piperidin-4-yl dihydrogen phosphate hydrochloride;

(R)-8-phenyl-2-(2-((tetrahydro-2H-pyran-4-yl)oxy)pyridin-4-yl)-7,8-dihydro-6H-pyrrolo [2',1':2,3]imidazo[4,5-b]pyridine;

3-((4-((R)-8-phenyl-7,8-dihydro-6H-pyrrolo[2',1':2,3]imidazo[4,5-b]pyridin-2-yl)pyridin-2-yl)oxy)cyclopentanol;

(R)-4-((4-(8-phenyl-7,8-dihydro-6H-pyrrolo[2',1':2,3]imidazo[4,5-b]pyridin-2-yl)pyridin-2-yl)oxy)cyclohexanol;

(R)-2-(2-(oxetan-3-yloxy)pyridin-4-yl)-8-phenyl-7,8-dihydro-6H-pyrrolo [2',1':2,3]imidazo[4,5-b]pyridine;

3-((4-((R)-8-phenyl-7,8-dihydro-6H-pyrrolo[2',1':2,3]imidazo[4,5-b]pyridin-2-yl)pyridin-2-yl)oxy)cyclohexanol;

(R)-2-(2-(oxetan-3-ylmethoxy)pyridin-4-yl)-8-phenyl-7,8-dihydro-6H-pyrrolo [2',1':2,3]imidazo[4,5-b]pyridine;

(R)-2-(2-(((R)-1-methylpyrrolidin-3-yl)oxy)pyridin-4-yl)-8-phenyl-7,8-dihydro-6H-pyrrolo [2',1':2,3]imidazo[4,5-b]pyridine;

(R)-2-((4-(8-phenyl-7,8-dihydro-6H-pyrrolo[2',1':2,3]imidazo[4,5-b]pyridin-2-yl)pyridin-2-yl)oxy)ethanol;

(R)-2-(2-(((S)-1-methylpyrrolidin-3-yl)oxy)pyridin-4-yl)-8-phenyl-7,8-dihydro-6H-pyrrolo [2',1':2,3]imidazo[4,5-b]pyridine;

(1S,4s)-4-((4-((R)-8-phenyl-7,8-dihydro-6H-pyrrolo[2',1':2, 3]imidazo[4,5-b]pyridin-2-yl)pyridin-2-yl)oxy)cyclohexanol;

(8R)-8-phenyl-2-(2-((tetrahydro-2H-pyran-3-yl)oxy)pyridin-4-yl)-7,8-dihydro-6H-pyrrolo [2',1':2,3]imidazo[4,5-b]pyridine;

(8R)-8-phenyl-2-(2-((tetrahydrofuran-3-yl)oxy)pyridin-4-yl)-7,8-dihydro-6H-pyrrolo [2',1':2,3]imidazo[4,5-b]pyridine;

(R)-2-(2-(cyclopentyloxy)pyridin-4-yl)-8-phenyl-7,8-dihydro-6H-pyrrolo [2',1':2,3]imidazo[4,5-b]pyridine;

(R)-2-(2-(cyclohexyloxy)pyridin-4-yl)-8-phenyl-7,8-dihydro-6H-pyrrolo [2',1':2,3]imidazo[4,5-b]pyridine;

(R)-methyl 4-((4-(8-phenyl-7,8-dihydro-6H-pyrrolo[2',1':2,3]imidazo[4,5-b]pyridin-2-yl)pyridin-2-yl)oxy)cyclohexanecarboxylate;

methyl 3-((4-((R)-8-phenyl-7,8-dihydro-6H-pyrrolo[2',1':2,3]imidazo[4,5-b]pyridin-2-yl)pyridin-2-yl)oxy)cyclopentanecarboxylate;

(R)-2-(2-butoxypyridin-4-yl)-8-phenyl-7,8-dihydro-6H-pyrido[3,2-b]pyrrolizine;

(1R,3R)-3-((4-((R)-8-phenyl-7,8-dihydro-6H-pyrido[3,2-b]pyrrolizin-2-yl)pyridin-2-yl)oxy)cyclopentanecarbonitrile;

(R)-8-phenyl-2-(2-((S)-pyrrolidin-3-yloxy)pyridin-4-yl)-7,8-dihydro-6H-pyrrolo [2',1':2,3]imidazo[4,5-b]pyridine;

(8R)-8-phenyl-2-(2-(piperidin-3-yloxy)pyridin-4-yl)-7,8-dihydro-6H-pyrrolo [2',1':2,3]imidazo[4,5-b]pyridine;

(R)-8-phenyl-2-(2-((R)-pyrrolidin-3-yloxy)pyridin-4-yl)-7,8-dihydro-6H-pyrrolo [2',1':2,3]imidazo[4,5-b]pyridine;

(8R)-2-(2-(6-azaspiro[3.4]octan-1-yloxy)pyridin-4-yl)-8-phenyl-7,8-dihydro-6H-pyrrolo [2',1':2,3]imidazo[4,5-b]pyridine;

(R)-2-(2-(6-azaspiro[3.4]octan-2-yloxy)pyridin-4-yl)-8-phenyl-7,8-dihydro-6H-pyrrolo [2',1':2,3]imidazo[4,5-b]pyridine;

(8R)-2-(2-(6-azaspiro[3.5]nonan-1-yloxy)pyridin-4-yl)-8-phenyl-7,8-dihydro-6H-pyrrolo [2',1':2,3]imidazo[4,5-b]pyridine;

1-(5-(6',8'-sihydro-2H-spiro[benzofuran-3,9'-pyrido[3',2':4,5]imidazo[2,1-c][1,4]oxazin]-2'-yl)pyrimidin-2-yl)piperidin-4-ol;

(R)-1-((4,4-difluorocyclohexyl)methyl)-4-(8-phenyl-7,8-dihydro-6H-pyrrolo [2',1':2,3]imidazo[4,5-b]pyridin-2-yl)pyridin-2(1H)-one;

(R)-1-(2-methoxyethyl)-4-(8-phenyl-7,8-dihydro-6H-pyrrolo[2',1':2,3]imidazo[4,5-b]pyridin-2-yl)pyridin-2(1H)-one;

(R)-4-(8-phenyl-7,8-dihydro-6H-pyrrolo[2',1':2,3]imidazo[4,5-b]pyridin-2-yl)-1-((tetrahydro-2H-pyran-4-yl)methyl)pyridin-2(1H)-one;

4-((R)-8-phenyl-7,8-dihydro-6H-pyrrolo[2',1':2,3]imidazo[4,5-b]pyridin-2-yl)-1-(tetrahydrofuran-3-yl)pyridin-2(1H)-one;

(R)-4-(8-phenyl-7,8-dihydro-6H-pyrrolo[2',1':2,3]imidazo[4,5-b]pyridin-2-yl)-1-(tetrahydro-2H-pyran-4-yl)pyridin-2(1H)-one;

(R)-8-phenyl-2-(1-(tetrahydro-2H-pyran-4-yl)-1H-pyrazol-4-yl)-7,8-dihydro-6H-pyrrolo [2',1':2,3]imidazo[4,5-b]pyridine;

4-((4-(6',8'-dihydro-2H-spiro[benzofuran-3,9'-pyrido[3',2':4,5]imidazo[2,1-c][1,4]oxazin]-2'-yl)pyridin-2-yl)oxy)cyclohexanol;

(R)-1-(5-(3-fluoro-8-phenyl-7,8-dihydro-6H-pyrrolo[2',1':2,3]imidazo[4,5-b]pyridin-2-yl)pyrimidin-2-yl)piperidin-4-ol;

2-(2-morpholinopyrimidin-5-yl)-9-phenyl-7,9-dihydro-6H-pyran[4',3':4,5]imidazo[1,2-b]pyridazine;

trans-4-((4-(4-(2-methoxyphenyl)-3,4-dihydro-2H-pyran[2',3':4,5]imidazo[1,2-a]pyridin-7-yl)pyridin-2-yl)oxy)cyclohexanol;

(8aS)-7-(5-(9-phenyl-8,9-dihydro-6H-pyrido[3',2':4,5]imidazo[2,1-c][1,4]oxazin-2-yl)pyrimidin-2-yl)hexahydroimidazo[1,5-a]pyrazin-3 (2H)-one;

3,3-difluoro-1-(5-(9-phenyl-8,9-dihydro-6H-pyrido[3',2':4,5]imidazo[2,1-c][1,4]oxazin-2-yl)pyrimidin-2-yl)piperidin-4-ol;

1-(5-(9-phenyl-8,9-dihydro-6H-pyrido[3',2':4,5]imidazo[2,1-c][1,4]oxazin-2-yl)pyrimidin-2-yl)piperidin-4-ol;

2-(2-(1,4-oxazepan-4-yl)pyrimidin-5-yl)-9-phenyl-8,9-dihydro-6H-pyrido [3',2':4,5]imidazo[2,1-c][1,4]oxazine;

(1-(5-(9-phenyl-8,9-dihydro-6H-pyrido[3',2':4,5]imidazo[2,1-c][1,4]oxazin-2-yl)pyrimidin-2-yl)piperidin-3-yl) methanol;

(4-fluoro-1-(5-(9-phenyl-8,9-dihydro-6H-pyrido[3',2':4,5]imidazo[2,1-c][1,4]oxazin-2-yl)pyrimidin-2-yl)piperidin-4-yl)methanol;

2-hydroxy-1-(4-(5-(9-phenyl-8,9-dihydro-6H-pyrido[3',2':4,5]imidazo[2,1-c][1,4]oxazin-2-yl)pyrimidin-2-yl)piperazin-1-yl)propan-1-one;

2-hydroxy-1-(4-(5-(9-phenyl-8,9-dihydro-6H-pyrido[3',2':4,5]imidazo[2,1-c][1,4]oxazin-2-yl)pyrimidin-2-yl)piperazin-1-yl)ethanone;

(R)-8-phenyl-2-(2-((tetrahydro-2H-pyran-4-yl)methoxy)pyridin-4-yl)-7,8-dihydro-6H-pyrrolo [2',1':2,3]imidazo[4,5-b]pyridine;

(R)-2-(2-(2-methoxyethoxy)pyridin-4-yl)-8-phenyl-7,8-dihydro-6H-pyrrolo [2',1':2,3]imidazo[4,5-b]pyridine;

(R)-2-methyl-1-((4-(8-phenyl-7,8-dihydro-6H-pyrrolo[2',1':2,3]imidazo[4,5-b]pyridin-2-yl)pyridin-2-yl)oxy)propan-2-ol;

(R)-8-phenyl-2-(1,2,3,6-tetrahydropyridin-4-yl)-7,8-dihydro-6H-pyrrolo [2',1':2,3]imidazo[4,5-b]pyridine;

(1S,4s)-4-(((4-((R)-8-phenyl-7,8-dihydro-6H-pyrrolo[2',1':2,3]imidazo[4,5-b]pyridin-2-yl)pyridin-2-yl)oxy)methyl)cyclohexanol;

(1R,4r)-4-(((4-((R)-8-phenyl-7,8-dihydro-6H-pyrrolo[2',1':2,3]imidazo[4,5-b]pyridin-2-yl)pyridin-2-yl)oxy)methyl)cyclohexanol;

((1R,4r)-4-(((4-((R)-8-phenyl-7,8-dihydro-6H-pyrrolo[2',1':2,3]imidazo[4,5-b]pyridin-2-yl)pyridin-2-yl)oxy)methyl)cyclohexyl)methanol;

(R)-8-Phenyl-2-(1-(pyrimidin-4-yl)-1,2,3,6-tetrahydropyridin-4-yl)-7,8-dihydro-6H-pyrrolo [2',1':2,3]imidazo[4,5-b]pyridine;

methyl 2-(4-((R)-8-phenyl-7,8-dihydro-6H-pyrrolo[2',1':2,3]imidazo[4,5-b]pyridin-2-yl)cyclohex-3-en-1-yl)acetate;

1-(5-(8-methyl-8-phenyl-7,8-dihydro-6H-pyrrolo[2',1':2,3]imidazo[4,5-b]pyridin-2-yl)pyrimidin-2-yl)piperidin-4-ol;

(S)-1-(5-(8-methyl-8-phenyl-7,8-dihydro-6H-pyrrolo[2',1':2,3]imidazo[4,5-b]pyridin-2-yl)pyrimidin-2-yl)piperidin-4-ol;

(R)-1-(5-(8-methyl-8-phenyl-7,8-dihydro-6H-pyrrolo[2',1':2,3]imidazo[4,5-b]pyridin-2-yl)pyrimidin-2-yl)piperidin-4-ol;

(S)-2-(5-(8-methyl-8-phenyl-7,8-dihydro-6H-pyrrolo[2',1':2,3]imidazo[4,5-b]pyridin-2-yl)pyrimidin-2-yl)propan-2-ol;

(R)-2-(5-(8-methyl-8-phenyl-7,8-dihydro-6H-pyrrolo[2',1':2,3]imidazo[4,5-b]pyridin-2-yl)pyrimidin-2-yl)propan-2-ol;

(R)-2-(5-(8-phenyl-7,8-dihydro-6H-pyrrolo[2',1':2,3]imidazo[4,5-b]pyridin-2-yl)pyrimidin-2-yl)propan-2-amine;

2-(2-(4,4-difluoropiperidin-1-yl)pyrimidin-5-yl)-9-phenyl-8,9-dihydro-6H-pyrido-[3',2':4,5]imidazo[2,1-c][1,4]oxazine; or (1R,4R)-4-((4-((R)-8-phenyl-7,8-dihydro-6H-pyrrolo[2',1':2,3]imidazo[4,5-b]pyridin-2-yl)pyridin-2-yl)oxy)cyclohexanol.

In a forty-fourth embodiment the invention provides a compound of Formula (II)

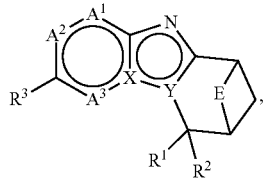

(II)

or a pharmaceutically acceptable salt, prodrug or stereoisomer thereof, wherein:

$R^1$ is H, or optionally substituted $(C_1-C_3)$alkyl;

$R^2$ is optionally substituted aryl;

$A^1$, $A^2$, and $A^3$ are independently $C(R^{A2})$ or N, provided that at least one is $C(R^{A2})$;

or

X is C and Y is N, and E is —O— or $CH_2$;

$R^3$ is —$R^{3a}$—$R^{3b}$, wherein:

$R^{3a}$ is optionally substituted heteroaryl;

$R^{3b}$ is —$O(R^a)$, optionally substituted $(C_1-C_3)$alkyl, —$C(R^e)_2)_q$-optionally substituted cycloalklyl; or —$C(R^e)_q$-optionally substituted heterocyclyl;

$R^a$ and $R^b$ are independently selected from optionally substituted $(C_1-C_5)$alkyl, and —$(CH_2)_p$-optionally substituted heterocyclyl;

$R^e$ is independently H, OH or $CH_3$;

$R^{A2}$ is independently H, or $(C_1-C_3)$alkyl; and q is independently 0, 1 or 2.

In a forty-fifth embodiment the invention provides a compound according to any of the foregoing embodiments wherein $R^2$ is optionally substituted phenyl.

In a forty-sixth embodiment the invention provides a compound according to any of the foregoing embodiments wherein $R^{3a}$ is optionally substituted pyrimidine.

In a forty-seventh embodiment the invention provides a compound according to any of the foregoing embodiments wherein $R^{3b}$ is optionally substituted $(C_1-C_4)$alkyl, —O-tetrahydropyranyl, optionally substituted morpholinyl, or optionally substituted piperidinyl.

In a forty-eighth embodiment the invention provides a compound according to any of the foregoing embodiments wherein the compound is 2-(5-(9-phenyl-6,7,8,9-tetrahydro-6,8-methanoimidazo[1,2-a:5,4-b']dipyridin-2-yl)pyrimidin-2-yl)propan-2-ol;

9-phenyl-2-(2-((tetrahydro-2H-pyran-4-yl)oxy)pyridin-4-yl)-6,7,8,9-tetrahydro-6, 8-methanoimidazo[1,2-a:5,4-b']dipyridine;

4-(5-(9-phenyl-6,7,8,9-tetrahydro-6,8-methanoimidazo[1,2-a:5,4-b']dipyridin-2-yl)pyrimidin-2-yl)morpholine;

1-(5-(9-phenyl-6,7,8,9-tetrahydro-6,8-methanoimidazo[1,2-a:5,4-b']dipyridin-2-yl)pyrimidin-2-yl)piperidin-4-ol;

2-(5-((6R,8S,9S)-9-phenyl-6,7,8,9-tetrahydro-6,8-epoxy-imidazo[1,2-a:5,4-b']dipyridin-2-yl)pyrimidin-2-yl)propan-2-ol;

1-(5-((6R,8S,9S)-9-phenyl-6,7,8,9-tetrahydro-6,8-epoxy-imidazo[1,2-a:5,4-b']dipyridin-2-yl)pyrimidin-2-yl)piperidin-4-ol;

2-(5-(9-phenyl-6,7,8,9-tetrahydro-6,8-methanoimidazo[1,2-a:5,4-b']dipyridin-2-yl)pyrimidin-2-yl)propan-2-ol;

9-phenyl-2-(2-((tetrahydro-2H-pyran-4-yl)oxy)pyridin-4-yl)-6,7,8,9-tetrahydro-6,8-methanoimidazo[1,2-a:5,4-b']dipyridine;

1-(5-(9-phenyl-6,7,8,9-tetrahydro-6,8-methanoimidazo[1,2-a:5,4-b']dipyridin-2-yl)pyrimidin-2-yl)piperidin-4-ol;

4-(5-(9-phenyl-6,7,8,9-tetrahydro-6,8-methanoimidazo[1,2-a:5,4-b']dipyridin-2-yl)pyrimidin-2-yl)morpholine;

2-(5-((6R,8S,9S)-9-phenyl-6,7,8,9-tetrahydro-6,8-epoxy-imidazo[1,2-a:5,4-b']dipyridin-2-yl)pyrimidin-2-yl)propan-2-ol; or 1-(5-((6R,8S,9S)-9-phenyl-6,7,8,9-tetrahydro-6,8-epoxy-imidazo[1,2-a:5,4-b']dipyridin-2-yl)pyrimidin-2-yl)piperidin-4-ol.

In a forty-eighth embodiment the invention provides a method of treating a disease comprising administering a therapeutically effective amount of a compound of any of the foregoing claims to a patient in need thereof.

In a forty-ninth embodiment the invention provides a method according to any of the forty-eighth embodiment, wherein the disease is rheumatoid arthritis, juvenile rheumatoid arthritis, psoriasis, psoriatic arthritis, Crohn's disease, inflammatory bowel disease, ulcerative colitis, psoriatic arthritis, psoriasis, ankylosing spondylitis, systemic lupus erythematosus, lupus nephritis, multiple sclerosis or hidraenitis suppurativa.

In a fiftieth embodiment the invention provides a pharmaceutical composition comprising a compound according to any of the foregoing embodiments and one or more pharmaceutically acceptable excipients.

In a fifty-first embodiment the invention provides a method of treating a disease comprising administering a therapeutically effective amount of a compound according to any of the preceding embodiments to a patient in need thereof.

In a fifty-second embodiment the invention provides a kit comprising a packaged product comprising components with which to administer a compound according to any of the foregoing embodiments for treatment of an autoimmune disorder.

In a fifty-third embodiment the invention provides a kit according to the thirty-sixth embodiment, wherein the packaged product comprises a compound according to any of the foregoing embodiments and instructions for use.

DETAILED DESCRIPTION OF THE INVENTION

Definitions

In this disclosure, the following definitions are applicable:

A "therapeutically effective amount" is an amount of a compound of Formula (I) or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

"Pharmaceutically acceptable salts" refers to those salts which retain the biological effectiveness and properties of the free bases and which are obtained by reaction with inorganic acids, for example, hydrochloric acid, hydrobromic acid, sulfuric acid, nitric acid, and phosphoric acid or organic acids such as sulfonic acid, carboxylic acid, organic phosphoric acid, methanesulfonic acid, ethanesulfonic acid, p-toluenesulfonic acid, citric acid, fumaric acid, maleic acid, succinic acid, benzoic acid, salicylic acid, lactic acid, tartaric acid (e.g., (+) or (−)-tartaric acid or mixtures thereof), amino acids (e.g., (+) or (−)-amino acids or mixtures thereof), and the like. These salts can be prepared by methods known to those skilled in the art.

As used herein the term "pro-drug" refers to an agent which is converted into the parent drug in vivo by some physiological chemical process (e.g., a prodrug on being brought to the physiological pH is converted to the desired drug form). Pro-drugs are often useful because, in some situations, they may be easier to administer than the parent drug. They may, for instance, be bioavailable by oral administration whereas the parent drug is not. The pro-drug may also have improved solubility in pharmacological compositions over the parent drug. An example, without limitation, of a pro-drug would be a compound of the present invention wherein it is administered as an ester (the "pro-drug") to facilitate transmittal across a cell membrane where water solubility is not beneficial, but then it is metabolically hydrolyzed to the carboxylic acid once inside the cell where water solubility is beneficial.

The term "heterocycle," "heterocyclic," "heterocyclyl" or "heterocyclylene," as used herein, include non-aromatic, ring systems, including, but not limited to, monocyclic, bicyclic, tricyclic and spirocyclic rings, which can be completely saturated or which can contain one or more units of unsaturation, for the avoidance of doubt, the degree of unsaturation does not result in an aromatic ring system) and have 5 to 12 atoms including at least one heteroatom, such as nitrogen, oxygen, or sulfur. For purposes of exemplification, which should not be construed as limiting the scope of this invention, the following are examples of heterocyclic rings: azepinyl, azetidinyl, indolinyl, isoindolinyl, morpholinyl, piperazinyl, piperidinyl, pyrrolidinyl, quinucludinyl, thiomorpholinyl, tetrahydropyranyl, tetrahydrofuranyl, tetrahydroindolyl, thiomorpholinyl and tropanyl.

The term "heteroaryl" or "heteroarylene" as used herein, include aromatic ring systems, including, but not limited to, monocyclic, bicyclic and tricyclic rings, and have 5 to 12 atoms including at least one heteroatom, such as nitrogen, oxygen, or sulfur. For purposes of exemplification, which should not be construed as limiting the scope of this invention: azaindolyl, benzo(b)thienyl, benzimidazolyl, benzofuranyl, benzoxazolyl, benzothiazolyl, benzothiadiazolyl, benzoxadiazolyl, furanyl, imidazolyl, imidazopyridinyl, indolyl, indazolyl, isoxazolyl, isothiazolyl, oxadiazolyl, oxazolyl, purinyl, pyranyl, pyrazinyl, pyrazolyl, pyridinyl, pyrimidinyl, pyrrolyl, pyrrolo[2,3-d]pyrimidinyl, pyrazolo[3,4-d]pyrimidinyl, quinolinyl, quinazolinyl, triazolyl, thiazolyl, thiophenyl, tetrazolyl, thiadiazolyl, thienyl, 6H-pyrrolo[2,3-e][1,2,4]triazolo[4,3-a]pyrazinyl, 6H-imidazo[1,5-a]pyrrolo[2,3-e]pyrazinyl, 1,6-dihydropyrazolo[3,4-d]pyrrolo[2,3-b]pyridine, 3H-3,4,6,8a-tetraaza-asindacenyl, 3H-imidazo[1,2-a]pyrrolo[2,3-e]pyrazinyl, pyrazolo[3,4-d]pyrrolo[2,3-b]pyridinyl, 1,6-dihydro-1,2,5,6-tetraza-as-indacenyl, 3H-3,4,8a-triaza-as-indacenyl, 6H-3-oxa-2,5,6-triaza-as-indacenyl, 3,6-dihydro-2,3,6-tetraaza-as-indacenyl, 1,6-dihydro-dipyrrolo[2,3-b; 2'3'-d]pyridinyl, 6H-3-thia-2,5,6-triaza-as-indacenyl, 4,5-dihydro-1H-benzo[b]azepin-2 (3H)-one, 3,4-dihydroquinolin-2(1H)-one, 2H-benzo[b][1,4]oxazin-3(4H)-one, or 6,7-dihydro-4H-pyrazolo[5,1-c][1,4]oxazinyl or 1,6-dihydroimidazo[4,5-d]pyrrolo[2,3-b]pyridine.

As used herein, "alkyl," "alkylene" or notations such as "$(C_1-C_8)$" include straight chained or branched hydrocarbons which are completely saturated. An alkyl is a monovalent radical while an alkylene is a bivalent radical. Examples of alkyls are methyl, ethyl, propyl, isopropyl, butyl, pentyl, hexyl and isomers thereof. Examples of alkylenes include methylene (—$CH_2$—), ethylene (—$CH_2CH_2$—), propylene (—$CH_2CH_2CH_2$—), isopropylene (—$CH(CH_3)CH_2$—) and the like. As used herein, "alkenyl," "alkenylene," "alkynylene" and "alkynyl" means $C_2$-$C_8$ and includes straight chained or branched hydrocarbons which contain one or more units of unsaturation, one or more double bonds for alkenyl and one or more triple bonds for alkynyl.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkoxyalkyl" as used herein, refers to an alkoxy group, as defined herein, appended to the parent molecular moiety through an alkyl group, as defined herein. Representative examples of alkoxyalkyl include, but are not limited to, methoxymethyl, methoxyethyl, and methoxypropyl. As used herein, "aromatic" groups (or "aryl" or "arylene" groups) include aromatic carbocyclic ring systems (e.g., phenyl) and fused polycyclic aromatic ring systems (e.g., naphthyl, biphenyl and 1,2,3,4-tetrahydronaphthyl).

As used herein, "cycloalkyl" or "cycloalkylene" means $C_3$-$C_{12}$ monocyclic or multicyclic (e.g., bicyclic, tricyclic, spirocyclic, etc.) hydrocarbons that are completely saturated. Examples of cycloalkyl groups are cyclopropyl, cyclobutyl, cyclopentyl, bicyclo[1.1.1]pentyl, and cyclohexyl.

As used herein, "cycloalkenyl" means $C_3$-$C_{12}$ monocyclic or multicyclic (e.g., bicyclic, tricyclic, spirocyclic, etc.) hydrocarbons that has one or more unsaturated bonds but does not amount to an aromatic group. Examples of cycloalkenyl groups are cyclopentenyl and cyclohexenyl.

As used herein, many moieties or substituents are termed as being either "substituted" or "optionally substituted." When a moiety is modified by one of these terms, unless otherwise noted, it denotes that any portion of the moiety that is known to one skilled in the art as being available for substitution can be substituted, which includes one or more substituents, where if more than one substituent then each substituent is independently selected. Such means for substitution are well-known in the art and/or taught by the instant disclosure. For purposes of exemplification, which should not be construed as limiting the scope of this invention, some examples of groups that are substituents are: ($C_1$-$C_8$)alkyl groups, ($C_2$-$C_8$)alkenyl groups, ($C_2$-$C_8$)alkynyl groups, ($C_3$-$C_{10}$)cycloalkyl groups, halogen (F, Cl, Br or I), halogenated ($C_1$-$C_8$)alkyl groups (for example but not limited to —$CF_3$), —O—($C_1$-$C_8$)alkyl groups, =O, =$CH_2$, —OH, —$CH_2$OH, —$CH_2NH_2$, ($C_1$-$C_4$)alkyl-OH, —$CH_2CH_2OCH_2CH_3$, —S—($C_1$-$C_8$)alkyl groups, —SH, —NH($C_1$-$C_8$)alkyl groups, —N(($C_1$-$C_8$)alkyl)$_2$ groups, —$NH_2$, —C(O)$NH_2$, —$CH_2$NHC(O)($C_1$-$C_4$)alkyl, —$CH_2$NHC(O)$CH_2$Cl, —$CH_2$NHC(O)$CH_2$CN, —$CH_2$NHC(O)$CH_2CH_2$N($CH_3$)$_2$, —$CH_2$NHC(O)C (=$CH_2$)$CH_3$, —$CH_2$NHC(O)($C_2$-$C_4$)alkynyl, —$CH_2$NHC(O)$CH_2CH_2$-piperidinyl, —($C_1$-$C_4$)alkyl-morpholinyl, —$CH_2$NHC(O)$CH_2$O-phenyl wherein the phenyl is optionally substituted with halogen, ($C_1$-$C_4$)alkoxy, —C(O)($C_1$-$C_4$)alkyl, —C(O)($C_1$-$C_4$)alkoxy, —C(O)N(H)$_2$, —C(O)N($CH_3$)$_2$, —C(O)($C_1$-$C_6$)heteroaryl, —N($CH_3$)$_2$, —NHC(O)($C_1$-$C_4$)alkyl, —NHC(O)($C_2$-$C_4$)alkenyl, —NHC(O)$CH_2$CN, —S(O)$_2$($C_1$-$C_4$)alkyl, —S(O)$_2$($C_1$-$C_6$)heteroaryl, —S(O)$_2$($C_1$-$C_6$)($C_1$-$C_6$)heterocyclyl, 4-methylpiperazinecarbonyl, —($C_1$-$C_4$)alkyl-C(O)$NH_2$, —C(O)NH($C_1$-$C_8$) alkyl groups, —C(O)N(($C_1$-$C_8$)alkyl)$_2$, —C(O)N(H)($C_3$-$C_8$)cycloalkyl groups, —C(O)($C_1$-$C_4$)alkoxy, —NHC(O)H, —NHC(O)($C_1$-$C_8$)alkyl groups, —NHC(O)($C_3$-$C_8$)cycloalkyl groups, —N(($C_1$-$C_8$)alkyl)C(O)H, —N(($C_1$-$C_8$)alkyl)C(O)($C_1$-$C_8$)alkyl groups, —NHC(O)$NH_2$, —NHC(O)NH($C_1$-$C_8$)alkyl groups, —N(($C_1$-$C_8$)alkyl)C(O)$NH_2$ groups, —NHC(O)N(($C_1$-$C_8$)alkyl)$_2$ groups, —N(($C_1$-$C_8$)alkyl)C(O)N(($C_1$-$C_8$)alkyl)$_2$ groups, —N(($C_1$-$C_8$)alkyl)C(O)NH(($C_1$-$C_8$)alkyl), —NHCH$_2$-heteroaryl, benzyl, —OCH$_2$-heteroaryl, —C(O)H, —C(O)($C_1$-$C_8$)alkyl groups, —CN, —NO$_2$, —S(O)($C_1$-$C_8$)alkyl groups, —S(O)$_2$($C_1$-$C_8$)alkyl groups, —S(O)$_2$N(($C_1$-$C_8$)alkyl)$_2$ groups, —S(O)$_2$NH($C_1$-$C_8$)alkyl groups, —S(O)$_2$NH($C_3$-$C_8$)cycloalkyl groups, —S(O)$_2$NH$_2$ groups, —NHS(O)$_2$($C_1$-$C_8$)alkyl groups, —N(($C_1$-$C_8$)alkyl)S(O)$_2$($C_1$-$C_8$)alkyl groups, —($C_1$-$C_8$)alkyl-O—($C_1$-$C_8$)alkyl groups, —O—($C_1$-$C_8$)alkyl-O—($C_1$-$C_8$)alkyl groups, —C(O)OH, —C(O)O($C_1$-$C_8$)alkyl groups, NHOH, NHO($C_1$-$C_8$)alkyl groups, —O-halogenated ($C_1$-$C_8$)alkyl groups (for example but not limited to —OCF$_3$), —S(O)$_2$-halogenated ($C_1$-$C_8$)alkyl groups (for example but not limited to —S(O)$_2$CF$_3$), —S-halogenated ($C_1$-$C_8$)alkyl groups (for example but not limited to —SCF$_3$), —($C_1$-$C_6$)heterocyclyl (for example but not limited to pyrrolidine, tetrahydrofuran, pyran or morpholine), —($C_1$-$C_6$)heteroaryl (for example but not limited to tetrazole, imidazole, furan, pyrazine or pyrazole), -phenyl, optionally substituted benzyl, —NHC(O)O—($C_1$-$C_6$)alkyl groups, —N(($C_1$-$C_6$)alkyl)C(O)O—($C_1$-$C_6$)alkyl groups, —C(=NH)—($C_1$-$C_6$)alkyl groups, —C(=NOH)—($C_1$-$C_6$)alkyl groups, or —C(=N—O—($C_1$-$C_6$)alkyl)-($C_1$-$C_6$)alkyl groups.

The term "kit" as used herein refers to a packaged product comprising components with which to administer a compound of Formula (I) of the invention for treatment of an autoimmune disorder. The kit preferably comprises a box or container that holds the components of the kit. The box or container is affixed with a label or a Food and Drug Administration approved protocol. The box or container holds components of the invention which are preferably contained within plastic, polyethylene, polypropylene, ethylene, or propylene vessels. The vessels can be capped-tubes or bottles. The kit can also include instructions for administering a compound of Formula (I).

Compounds

Compounds of this invention include compounds of Formula (I):

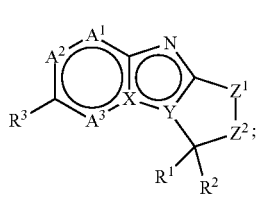

(I)

or a pharmaceutically acceptable salt, prodrug or stereoisomer thereof, wherein:

$R^1$ is H, OH, F or optionally substituted ($C_1$-$C_3$)alkyl;

$R^2$ is optionally substituted aryl, optionally substituted ($C_3$-$C_8$)cycloalkyl, optionally substituted heteroaryl or optionally substituted heterocyclyl; or $R^1$ and $R^2$ together can form an optionally substituted saturated or partially saturated carbocyclic ring or optionally substituted saturated or partially saturated heterocyclic ring;

up to two of $A^1$, $A^2$, and $A^3$ are N, and the rest are independently C($R^{A2}$);

X is N and Y is C, wherein:

$Z^1$ is —C($R^z$)$_2$— and $Z^2$ is —C($R^z$)$_2$—, —N($R^{z1}$)— or —O—; or $Z^1$ is —CH$_2$— and $Z^2$ is —$Z^{2a}$—$Z^{2b}$—, wherein $Z^{2a}$ is attached to $Z^1$ and $Z^{2b}$ is attached to C($R^1$)($R^2$); and $Z^{2a}$ and $Z^{2b}$ are independently —C($R^z$)$_2$—, —C($R^z$)$_2$C($R^z$)$_2$—, —O— or —N($R^{z1}$)— provided that one of $Z^{2a}$ and $Z^{2b}$ is —C($R^z$)$_2$— or —C($R^z$)$_2$C(R)$_2$—; or —$Z^{2a}$—$Z^{2b}$— form —N($R^{z1}$)C(O)— or —C(O)N($R^{z1}$)—;

or

X is C and Y is N, provided that $R^1$ is not —OH or —F, wherein:

$Z^1$ is —C($R^z$)$_2$— and $Z^2$ is —C($R^z$)$_2$—; or $Z^1$ is —C($R^z$)$_2$— and $Z^2$ is —$Z^{2a}$—$Z^{2b}$— wherein $Z^{2a}$ is attached to $Z^1$ and $Z^{2b}$ is attached to C($R^1$)($R^2$), and $Z^{2a}$ is —C($R^z$)$_2$—, —C($R^z$)$_2$C($R^z$)$_2$—, —O— or —N($R^{z1}$), and $Z^{2b}$ is —C($R^z$)$_2$—, or —$Z^{2a}$—$Z^{2b}$— form —N($R^{z1}$)C(O)— or —C(O)N($R^{z1}$)—;

$R^3$ is —$R^{3a}$—$R^{3b}$, wherein:

$R^{3a}$ is an optionally substituted aryl, optionally substituted saturated or partially saturated heterocyclyl or optionally substituted heteroaryl;

$R^{3b}$ is H, —CF$_3$, —CN, —C(O)OH, —N($R^a$)($R^b$), —C(O)N($R^a$)($R^b$), —C(O)-optionally substituted heterocyclyl, —O($R^a$), —S(O)$_2$($C_1$-$C_3$)alkyl, —S(O)$_2$N($R^c$)($R^d$)—, alkyl, —S(O)$_2$—$R^c$ optionally substituted ($C_1$-$C_5$)alkyl, —(CH$_2$)$_p$-optionally substituted ($C_3$-$C_6$)cycloalkyl, —(CH$_2$)$_p$-optionally substituted heteroaryl or —(CH$_2$)$_p$-optionally substituted saturated, unsaturated or partially saturated heterocyclyl;

$R^a$ and $R^b$ are independently selected from H, optionally substituted ($C_1$-$C_5$)alkyl, —C(O)-optionally substituted ($C_1$-$C_5$)alkyl, optionally substituted —(CH$_2$)$_p$—($C_3$-$C_6$)cycloalkyl and —(CH$_2$)$_p$-optionally substituted heterocyclyl;

$R^c$ and $R^d$ are independently selected from H, optionally substituted ($C_1$-$C_5$)alkyl, optionally substituted —(CH$_2$)$_p$—($C_3$-$C_6$)cycloalkyl and —(CH$_2$)$_p$-optionally substituted heterocyclyl;

$R^{A2}$ is independently H, CF$_3$, halo or ($C_1$-$C_3$)alkyl;

$R^z$ is independently H, F, CF$_3$, —OH or ($C_1$-$C_3$)alkyl;

$R^{z1}$ is independently H or ($C_1$-$C_3$)alkyl; and p is independently 0, 1 or 2.

In some embodiments, $R^2$ is phenyl, tetrahydropyranyl, pyridinyl or cyclohexyl, each of which is independently optionally substituted with 1 to 3 groups selected from halogen, —CN, —NR$^a$, —OR$^a$, —CF$_3$, —($C_1$-$C_6$)alkyl, —($C_1$-$C_6$)haloalkyl, —($C_1$-$C_6$)alkylene-OR$^a$, —($C_1$-$C_6$)alkylene-NR$^a$R$^a$, and —($C_1$-$C_6$)haloalkoxy, wherein R$^a$ is H or —($C_1$-$C_6$)alkyl; and $R^1$ is H, OH or optionally substituted ($C_1$-$C_3$)alkyl; or $R^1$ and $R^2$ together form an optionally substituted spirocycle selected from

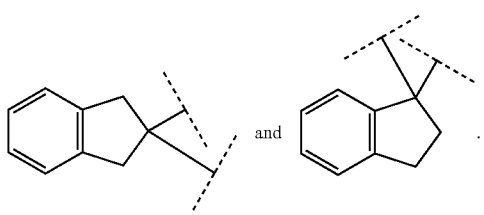

and

In some embodiments R² is phenyl or cyclohexyl, each of which is independently optionally substituted with 1 to 3 groups selected from halogen (e.g., F, Cl), —OR$^a$ (e.g., —OCH$_3$), —(C$_1$-C$_6$)alkyl (e.g., methyl), and —(C$_1$-C$_6$) haloalkoxy (e.g., —OCHF$_2$), and R¹ is H, OH or CH$_3$; or
R¹ and R² together form

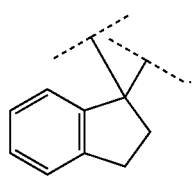

For example, R² may be unsubstituted phenyl, unsubstituted cyclohexyl, unsubstituted pyridinyl or unsubstituted tetrahydropyranyl. In some embodiments, R² is unsubstituted phenyl. In some embodiments, R² is phenyl that is substituted with 1 or 2 substituents selected from halogen (e.g., F, Cl), —OR$^a$ (e.g., —OCH$_3$), —(C$_1$-C$_6$)alkyl (e.g., methyl), and —(C$_1$-C$_6$)haloalkoxy (e.g., —OCHF$_2$).

In some embodiments, R¹ is H. In some embodiments, R¹ is OH. In some embodiments, R¹ is CH$_3$.

In some embodiments, R$^{3a}$ is optionally substituted phenyl, optionally substituted imidazo[4,5-b]pyridinyl, optionally substituted [1,2,5]oxadiazolo[3,4-b]pyridinyl, optionally substituted piperazinyl, optionally substituted piperidinyl, optionally substituted pyrimidinyl, optionally substituted pyridinyl, optionally substituted pyrazinyl, optionally substituted pyridin-2(1H)-one, optionally substituted 3,4-dihydro-2H-pyrido[3,2-b][1,4]oxazinyl, optionally substituted furo[3,2-b]pyridinyl, optionally substituted benzo[d][1,3]dioxolyl, optionally substituted 1H-pyrazolyl, optionally substituted 3,4-dihydro-2H-pyrido [3,2-b][1,4]oxazinyl, optionally substituted pyrrolyl, optionally substituted [1,2,5]oxadiazolo[3,4-b]pyridinyl, optionally substituted pyrido[2,3-b]pyrazinyl, optionally substituted 3H-imidazo[4,5-b]pyridinyl, optionally substituted pyridin-2(1H)-onyl, or optionally substituted thienyl.

In some embodiments, R$^{3b}$ is H, CF$_3$, CN, —C(O)OH, —C(O)N(R$^a$)$_2$, optionally substituted (C$_1$-C$_3$)alkyl, optionally substituted (C$_3$-C$_6$)cycloalkyl, —CH$_2$-optionally substituted heteroaryl, —N(R$^a$)$_2$, —N(R$^c$)S(O)$_2$-optionally substituted (C$_1$-C$_3$)alkyl, —OR$^a$, —S-optionally substituted (C$_1$-C$_3$)alkyl, —S(O)$_2$-optionally substituted (C$_1$-C$_3$)alkyl, —S(O)$_2$—N(R)$_2$, —S(O)$_2$-morpholinyl, optionally substituted azepanyl, optionally substituted 6-azaspiro[3.4]nonanyl, optionally substituted 7-azaspiro[3.5]nonanyl, optionally substituted azaspiro[3.4]octanyl, optionally substituted azetidinyl, optionally substituted 2,7-diazaspiro[4.4]nonanyl, optionally substituted diazepanyl, optionally substituted 3,10-diazabicyclo[4.3.1]decanyl, optionally substituted oxetanyl, hexahydroimidazo[1,2-a]pyrimidin-2(3H)-one, optionally substituted imidazolyl, hexahydroimidazo[1,2-c]pyrimidin-2(3H)-one, optionally substituted hexahydroimidazo[1,5-a]pyrazin-3 (2H)-one, optionally substituted hexahydroimidazo[1,5-c]pyrazin-3(2H)-one, optionally substituted morpholinyl, optionally substituted oxazolo[3,4-a]pyrazine-3-one, 1,4-oxepanyl, optionally substituted piperazinyl, optionally substituted piperidinyl, optionally substituted pyrazinyl, optionally substituted pyrazolyl, optionally substituted pyrimidinyl, optionally substituted pyrrolidinyl, tetrahydro-1H-oxazolo[3,4-a]pyrazin-3 (5H)-one, optionally substituted tetrahydropyranyl, thiomorpholinyl 1,1-dioxide, 5,6,7,8-tetrahydro-[1,2,4]triazolo[4,3-a]pyrazinyl, optionally substituted 1,3,8-triazaspiro[4.5]decanyl.

In some embodiments, R$^{3a}$ is optionally substituted phenyl, optionally substituted piperazinyl, optionally substituted piperidinyl, optionally substituted pyrimidinyl, optionally substituted pyridinyl, optionally substituted 3,4-dihydro-2H-pyrido[3,2-b][1,4]oxazinyl, optionally substituted furo[3,2-b]pyridinyl, optionally substituted benzo[d][1,3]dioxolyl, or optionally substituted thienyl.

In some embodiments, R$^{3b}$ is H, CF$_3$, CN, —C(O)OH, —C(O)N(H)$_2$, —C(O)N(H), optionally substituted (C$_1$-C$_3$)alkyl, —C(O)N(H)(cyclopropyl), optionally substituted (C$_1$-C$_3$)alkyl, optionally substituted cyclobutyl, optionally substituted cyclopropyl, —N(H)(optionally substituted (C$_1$-C$_3$)alkyl), —N(optionally substituted (C$_1$-C$_3$)alkyl))$_2$, —N(H)(cyclopropyl), —N(H)(cyclopentyl), —N(R)S(O)$_2$-optionally substituted (C$_1$-C$_3$)alkyl, —O-tetrahydropyranyl, —O-optionally substituted (C$_1$-C$_3$)alkyl, —S—CH$_3$, —S(O)$_2$—CH$_3$, —S(O)$_2$—N(R)$_2$, —S(O)$_2$-morpholinyl, optionally substituted azepanyl, optionally substituted 6-azaspiro[3.4]nonanyl, optionally substituted 7-azaspiro[3.5]nonanyl, optionally substituted azaspiro[3.4]octanyl, optionally substituted 2,7-diazaspiro[4.4]nonanyl, optionally substituted diazepanyl, optionally substituted 3,10-diazabicyclo[4.3.1]decanyl, optionally substituted oxetanyl, hexahydroimidazo[1,2-a]pyrimidin-2(3H)-one, optionally substituted imidazolyl, hexahydroimidazo[1,2-c]pyrimidin-2(3H)-one, optionally substituted hexahydroimidazo[1,5-a]pyrazin-3(2H)-one, optionally substituted hexahydroimidazo[1,5-c]pyrazin-3 (2H)-one, optionally substituted morpholinyl, optionally substituted oxazolo[3,4-a]pyrazine-3-one, 1,4-oxepanyl, optionally substituted piperazinyl, optionally substituted piperidinyl, optionally substituted pyrazinyl, optionally substituted pyrazolyl, optionally substituted pyrimidinyl, optionally substituted pyrrolidinyl, tetrahydro-1H-oxazolo[3,4-a]pyrazin-3(5H)-one, optionally substituted tetrahydropyranyl, thiomorpholinyl 1,1-dioxide, 5,6,7,8-tetrahydro-[1,2,4]triazolo[4,3-a]pyrazinyl, optionally substituted 1,3,8-triazaspiro[4.5]decanyl.

In some embodiments, R$^{3b}$ is optionally substituted by one or more substituents independently selected from —F, —CH$_3$, —CH$_2$OH, —CN, —CH$_2$C(O)OCH$_2$CH$_3$, —C(O) CH$_2$OH, —C(O)CH$_3$, —C(O)OH, —NH$_2$, —N(H)S(O)$_2$ CH$_3$, —OH, and =O.

In some embodiments, R$^{3a}$ is optionally substituted phenyl, or optionally substituted pyrimidinyl. In some embodiments, R$^{3a}$ is phenyl. In some embodiments, R$^{3a}$ is pyrimidinyl. In some embodiments, R$^{3a}$ is a six-membered ring, such as phenyl or pyrimidinyl, wherein R$^{3b}$ is attached at the para position relative to the remainder of the compound of Formula (I).

In some embodiments, R$^{3b}$ is optionally substituted (C$_1$-C$_3$)alkyl, optionally substituted cyclobutyl, —O-optionally substituted (C$_1$-C$_3$)alkyl, —S(O)$_2$-optionally substituted (C$_1$-C$_3$)alkyl-S(O)$_2$—N(H)(optionally substituted (C$_1$-C$_3$) alkyl), optionally substituted azepanyl, optionally substituted 7-azaspiro[3.5]nonanyl, optionally substituted 3,10-diazabicyclo[4.3.1]decanyl, optionally substituted oxetanyl, optionally substituted hexahydroimidazo[1,5-a]pyrazin-3(2H)-one, optionally substituted morpholinyl, 1,4-oxepanyl, optionally substituted piperazinyl, optionally substituted piperidinyl, r optionally substituted tetrahydropyranyl, or thiomorpholinyl 1,1-dioxide.

In some embodiments, $R^{3b}$ is optionally substituted by one or more substituents independently selected from —$CH_3$, —$CH_2OH$, —$C(O)OCH_2CH_3$, —$C(O)OH$, —$NH_2$, —OH, and =O.

In some embodiments, $A^1$ is N. In some embodiments, $A^1$ is CH. In some embodiments, $A^2$ is N. In some embodiments, $A^2$ is CH. In some embodiments, $A^3$ is N. In some embodiments, $A^3$ is CH. In some embodiments, $A^1$, $A^2$ and $A^3$ are all CH. In some embodiments, $A^1$ is CH, $A^2$ is CH and $A^3$ is N. In some embodiments, $A^1$ is CH, $A^2$ is N and $A^3$ is CH. In some embodiments, $A^1$ is N, $A^2$ is CH and $A^3$ is CH.

In some embodiments, $Z^1$ is —$CH_2$—. In some embodiments, $Z^2$ is —$CH_2$—. In some embodiments, $Z^2$ is —NH—. In some embodiments, $Z^2$ is —O—. In some embodiments, $Z^{2a}$ is —$CH_2$—. In some embodiments, $Z^{2a}$ is —$CH_2CH_2$—. In some embodiments, $Z^{2a}$ is —O—. In some embodiments, $Z^{2a}$ is —NH—. In some embodiments, $Z^{2b}$ is —$CH_2$—. In some embodiments, $Z^{2b}$ is —$CH_2CH_2$—. In some embodiments, $Z^{2b}$ is —O—. In some embodiments, $Z^{2b}$ is —NH—. In some embodiments, $Z^{2a}$—$Z^{2b}$ form —$N(H^1)C(O)$—. In some embodiments, $Z^{2a}$—$Z^{2b}$ form —$C(O)N(H)$—.

In some embodiments, X is N, Y is C, $Z^1$ is —$C(R^z)_2$— and $Z^2$ is —$C(R^z)_2$—, wherein each $R^z$ is H. In some embodiments, X is N, Y is C, $Z^1$ is —$CH_2$— and $Z^2$ is —$Z^{2a}$—$Z^{2b}$—, wherein $Z^{2a}$ is O and $Z^{2b}$ is —$CH_2$. In some embodiments, X is N, Y is C, $Z^1$ is —$CH_2$— and $Z^2$ is —$Z^{2a}$—$Z^{2b}$—, wherein $Z^{2a}$ is —$CH_2$— and $Z^{2b}$ is —$CH_2$—. In some embodiments, X is N, Y is C, $Z^{2a}$ is —$C(R^z)_2C(R^z)_2$— and $Z^{2b}$ is —$C(R^z)_2C(R^z)_2$—, wherein each $R^z$ is H.

In some embodiments, X is C, Y is N, $Z^1$ is —$C(R^z)_2$— and $Z^2$ is —$C(R^z)_2$—, wherein each $R^z$ is H. In some embodiments, X is C, Y is N, $Z^1$ is —$C(R^z)_2$— and $Z^2$ is —$Z^{2a}$—$Z^{2b}$—, $Z^{2a}$ is —$C(R^z)_2$—, and $Z^{2b}$ is —$C(R^z)_2$—, wherein each $R^z$ is H. In some embodiments, X is C, Y is N, $Z^1$ is —$C(R^z)_2$— and $Z^2$ is —$Z^{2a}$—$Z^{2b}$—, $Z^{2a}$ is —O—, and $Z^{2b}$ is —$C(R^z)_2$—, wherein each $R^z$ is H.

Compounds of Formula (I) include:
2-(5-(1-(2-methoxyphenyl)-2,3-dihydro-1H-benzo[d]pyrrolo[1,2-a]imidazol-7-yl)pyrimidin-2-yl)propan-2-ol;
4-(3-fluorophenyl)-7-(2-morpholinopyrimidin-5-yl)-3,4-dihydro-1H-benzo[4,5]imidazo[2,1-c][1,4]oxazine;
(R)-1-phenyl-7-(2-((tetrahydro-2H-pyran-4-yl)oxy)pyridin-4-yl)-2,3-dihydro-1H-benzo [d]pyrrolo[1,2-a]imidazole;
(S)-2-(2-morpholinopyrimidin-5-yl)-9-phenyl-8,9-dihydro-6H-pyrido[3',2':4,5]imidazo[2,1-c][1,4]oxazine;
2-(5-(8-methyl-8-phenyl-7,8-dihydro-6H-pyrrolo[2',1':2,3]imidazo[4,5-b]pyridin-2-yl)pyrimidin-2-yl)propan-2-ol;
2-(5-(1-(tetrahydro-2H-pyran-4-yl)-2,3-dihydro-1H-benzo[d]pyrrolo[1,2-a]imidazol-7-yl)pyrimidin-2-yl)propan-2-ol;
(S)-7-(2-((1R,6S)-3,10-diazabicyclo[4.3.1]decan-10-yl)pyrimidin-5-yl)-4-phenyl-3,4-dihydro-1H-benzo[4,5]imidazo[2,1-c][1,4]oxazine;
(S)-7-(5-(4-phenyl-3,4-dihydro-1H-benzo[4,5]imidazo[2,1-c][1,4]oxazin-7-yl)pyrimidin-2-yl)-7-azaspiro[3.5]nonan-2-amine;
7-(5-((S)-4-phenyl-3,4-dihydro-1H-benzo[4,5]imidazo[2,1-c][1,4]oxazin-7-yl)pyrimidin-2-yl)hexahydroimidazo[1,5-a]pyrazin-3(2H)-one;
7-(5-(8-(2-methoxyphenyl)-7,8-dihydro-6H-cyclopenta[4,5]imidazo[1,2-b]pyridazin-2-yl)pyrimidin-2-yl)hexahydroimidazo[1,5-a]pyrazine-3(2H)-one;
1-(5-(8-phenyl-7,8-dihydro-6H-cyclopenta[4,5]imidazo[1,2-b]pyridazin-2-yl)pyrimidin-2-yl)piperidin-4-ol;
2-(5-(4-(2-methoxyphenyl)-3,4-dihydro-1H-pyrano[3',4':4,5]imidazo[1,2-a]pyridin-7-yl)pyrimidin-2-yl)propan-2-ol;
(S)-7-(5-((R)-8-phenyl-7,8-dihydro-6H-pyrrolo[2',1':2,3]imidazo[4,5-b]pyridin-2-yl)pyrimidin-2-yl)hexahydroimidazo[1,5-a]pyrazin-3 (2H)-one;
(R)-7-(5-((R)-1-phenyl-2,3-dihydro-1H-benzo[d]pyrrolo[1,2-a]imidazol-7-yl)pyrimidin-2-yl)hexahydroimidazo[1,5-a]pyrazin-3(2H)-one;
2-(5-(8-(pyridin-2-yl)-7,8-dihydro-6H-pyrrolo[2',1':2,3]imidazo[4,5-b]pyridin-2-yl)pyrimidin-2-yl)propan-2-ol;
2-(5-(1-(pyridin-2-yl)-2,3-dihydro-1H-benzo[d]pyrrolo[1,2-a]imidazol-7-yl)pyrimidin-2-yl)propan-2-ol;
(S)-7-(5-((S)-4-phenyl-3,4-dihydro-1H-benzo[4,5]imidazo[2,1-c][1,4]oxazin-7-yl)pyrimidin-2-yl)hexahydroimidazo[1,5-a]pyrazin-3(2H)-one;
(R)-7-(5-((S)-4-phenyl-3,4-dihydro-1H-benzo[4,5]imidazo[2,1-c][1,4]oxazin-7-yl)pyrimidin-2-yl)hexahydroimidazo[1,5-a]pyrazin-3(2H)-one;
7-(5-(9-(2-methoxyphenyl)-6,7,8,9-tetrahydrobenzo[4,5]imidazo[1,2-a]pyridin-2-yl)pyrimidin-2-yl)-7-azaspiro[3.5]nonan-2-ol;
4-(5-(9-(2-methoxyphenyl)-6,7,8,9-tetrahydrobenzo[4,5]imidazo[1,2-a]pyridin-2-yl)pyrimidin-2-yl)-1,4-oxazepane;
7-(5-(9-(2-methoxyphenyl)-6,7,8,9-tetrahydrobenzo[4,5]imidazo[1,2-a]pyridin-2-yl)pyrimidin-2-yl)hexahydroimidazo[1,5-a]pyrazin-3(2H)-one;
1-(5-(9-(2-methoxyphenyl)-6,7,8,9-tetrahydrobenzo[4,5]imidazo[1,2-a]pyridin-2-yl)pyrimidin-2-yl)-4-methylpiperidin-4-ol;
(4-fluoro-1-(5-(9-(2-methoxyphenyl)-6,7,8,9-tetrahydrobenzo[4,5]imidazo[1,2-a]pyridin-2-yl)pyrimidin-2-yl)piperidin-4-yl)methanol;
(4-fluoro-1-(5-(9-(2-methoxyphenyl)-6,7,8,9-tetrahydrobenzo[4,5]imidazo[1,2-a]pyridin-2-yl)pyrimidin-2-yl)piperidin-4-yl)methanol;
1-(5-(9-(2-methoxyphenyl)-6,7,8,9-tetrahydrobenzo[4,5]imidazo[1,2-a]pyridin-2-yl)pyrimidin-2-yl)azepan-4-ol;
1-(5-(9-(2-methoxyphenyl)-6,7,8,9-tetrahydrobenzo[4,5]imidazo[1,2-a]pyridin-2-yl)pyrimidin-2-yl)piperidin-4-ol;
1-(5-(8-methyl-8-phenyl-7,8-dihydro-6H-pyrrolo[2',1':2,3]imidazo[4,5-b]pyridin-2-yl)pyrimidin-2-yl)piperidin-4-ol;
1-(5-(9-(3-fluorophenyl)-8,9-dihydro-6H-pyrido[3',2':4,5]imidazo[2,1-c][1,4]oxazin-2-yl)pyrimidin-2-yl)piperidin-4-ol;
7-(5-(8-methyl-8-phenyl-7,8-dihydro-6H-pyrrolo[2',1':2,3]imidazo[4,5-b]pyridin-2-yl)pyrimidin-2-yl)hexahydroimidazo[1,5-a]pyrazin-3(2H)-one;
7-(5-(9-(3-fluorophenyl)-8,9-dihydro-6H-pyrido[3',2':4,5]imidazo[2,1-c][1,4]oxazin-2-yl)pyrimidin-2-yl)hexahydroimidazo[1,5-a]pyrazin-3(2H)-one;
7-(5-(8-cyclohexyl-7,8-dihydro-6H-pyrrolo[2',1':2,3]imidazo[4,5-b]pyridin-2-yl)pyrimidin-2-yl)hexahydroimidazo[1,5-a]pyrazin-3 (2H)-one;

7-(5-((R)-8-cyclohexyl-7,8-dihydro-6H-pyrrolo[2',1':2,3] imidazo[4,5-b]pyridin-2-yl)pyrimidin-2-yl)hexahydroimidazo[1,5-a]pyrazin-3(2H)-one;

7-(5-((S)-4-(2-chlorophenyl)-3,4-dihydro-1H-benzo[4,5] imidazo[2,1-c][1,4]oxazin-7-yl)pyrimidin-2-yl)hexahydroimidazo[1,5-a]pyrazin-3(2H)-one;

7-(5-(4-(3-chlorophenyl)-3,4-dihydro-1H-benzo[4,5]imidazo[2,1-c][1,4]oxazin-7-yl)pyrimidin-2-yl)hexahydroimidazo[1,5-a]pyrazin-3(2H)-one;

7-(5-(4-(2-fluorophenyl)-3,4-dihydro-1H-benzo[4,5]imidazo[2,1-c][1,4]oxazin-7-yl)pyrimidin-2-yl)hexahydroimidazo[1,5-a]pyrazin-3(2H)-one;

4-(5-(1-(2-methoxyphenyl)-2,3-dihydro-1H-cyclopenta[4,5]imidazo[1,2-a]pyridin-7-yl)pyrimidin-2-yl)morpholine;

(R)-7-(5-((R)-9-phenyl-8,9-dihydro-6H-pyrano[3',4':4,5] imidazo[1,2-b]pyridazin-2-yl)pyrimidin-2-yl)hexahydroimidazo[1,5-a]pyrazin-3(2H)-one;

(R)-7-(5-((R)-4-phenyl-3,4-dihydro-1H-pyrano[3',4':4,5] imidazo[1,2-a]pyridin-7-yl)pyrimidin-2-yl)hexahydroimidazo[1,5-a]pyrazin-3(2H)-one;

1-(5-(9-(2-methoxyphenyl)-6,7,8,9-tetrahydroimidazo[1,2-a:5,4-b']dipyridin-2-yl)pyrimidin-2-yl)piperidin-4-ol;

7-(5-(8-(2-methoxyphenyl)-7,8-dihydro-6H-pyrrolo[2',1':2,3]imidazo[4,5-b]pyridin-2-yl)pyrimidin-2-yl)hexahydroimidazo[1,5-a]pyrazin-3(2H)-one;

1-(5-(8-(2-methoxyphenyl)-7,8-dihydro-6H-pyrrolo[2',1':2,3]imidazo[4,5-b]pyridin-2-yl)pyrimidin-2-yl)piperidin-4-ol;

(S)-1-(5-(9-(2-methoxyphenyl)-8,9-dihydro-6H-pyrido[3',2':4,5]imidazo[2,1-c][1,4]oxazin-2-yl)pyrimidin-2-yl)piperidin-4-ol;

7-(5-((S)-9-phenyl-8,9-dihydro-6H-pyrido[3',2':4,5]imidazo[2,1-c][1,4]oxazin-2-yl)pyrimidin-2-yl)hexahydroimidazo[1,5-a]pyrazin-1(5H)-one;

(S)-1-(5-(9-phenyl-8,9-dihydro-6H-pyrido[3',2':4,5]imidazo[2,1-c][1,4]oxazin-2-yl)pyrimidin-2-yl)piperidin-4-ol;

(S)-4-(5-(9-phenyl-8,9-dihydro-6H-pyrido[3',2':4,5]imidazo[2,1-c][1,4]oxazin-2-yl)pyrimidin-2-yl)piperazin-2-one;

(S)-2-(5-(9-phenyl-8,9-dihydro-6H-pyrido[3',2':4,5]imidazo[2,1-c][1,4]oxazin-2-yl)pyrimidin-2-yl)propan-2-ol;

(S)-7-(5-((R)-1-Phenyl-2,3-dihydro-1H-benzo[d]pyrrolo[1,2-a]imidazol-7-yl)pyrimidin-2-yl)hexahydroimidazo[1,5-a]pyrazin-3(2H)-one;

(R)-3-(5-(1-phenyl-2,3-dihydro-1H-benzo[d]pyrrolo[1,2-a]imidazol-7-yl)pyrimidin-2-yl)oxetan-3-ol;

(R)-1-(5-(1-phenyl-2,3-dihydro-1H-benzo[d]pyrrolo[1,2-a]imidazol-7-yl)pyrimidin-2-yl)cyclobutanol;

(R)-4-(5-(1-phenyl-2,3-dihydro-1H-benzo[d]pyrrolo[1,2-a]imidazol-7-yl)pyrimidin-2-yl)tetrahydro-2H-pyran-4-ol;

(R)-7-(5-((R)-1-Phenyl-2,3-dihydro-1H-benzo[d]pyrrolo[1,2-a]imidazol-7-yl)pyrimidin-2-yl)hexahydroimidazo[1,5-a]pyrazin-3(2H)-one;

2-(5-(4-(2,6-dichlorophenyl)-3,4-dihydro-1H-benzo[4,5]imidazo[2,1-c][1,4]oxazin-7-yl)pyrimidin-2-yl)propan-2-ol;

(S)-2-(5-(4-(2-methoxyphenyl)-3,4-dihydro-1H-benzo[4,5]imidazo[2,1-c][1,4]oxazin-7-yl)pyrimidin-2-yl)propan-2-ol;

7-(5-((S)-4-phenyl-3,4-dihydro-1H-benzo[4,5]imidazo[2,1-c][1,4]oxazin-7-yl)pyrimidin-2-yl)hexahydroimidazo[1,5-a]pyrazin-3(2H)-one;

7-(5-(4-(2-chlorophenyl)-3,4-dihydro-1H-benzo[4,5]imidazo[2,1-c][1,4]oxazin-7-yl)pyrimidin-2-yl)hexahydroimidazo[1,5-a]pyrazin-3(2H)-one;

7-(5-(1,2',3,3'-tetrahydrospiro[benzo[4,5]imidazo[2,1-c][1,4]oxazine-4,1'-inden]-7-yl)pyrimidin-2-yl)hexahydroimidazo[1,5-a]pyrazin-3(2H)-one;

(S)-2-hydroxy-1-(4-(5-(4-phenyl-3,4-dihydro-1H-benzo[4,5]imidazo[2,1-c][1,4]oxazin-7-yl)pyrimidin-2-yl)piperazin-1-yl)ethanone;

7-(5-((S)-4-phenyl-3,4-dihydro-1H-benzo[4,5]imidazo[2,1-c][1,4]oxazin-7-yl)pyrimidin-2-yl)-7-azaspiro[3.5] nonan-1-ol;

(R)-1-(5-(8-(3-fluorophenyl)-7,8-dihydro-6H-pyrrolo[2',1':2,3]imidazo[4,5-b]pyridin-2-yl)pyrimidin-2-yl)piperidin-4-ol;

(R)-1-(5-(8-phenyl-7,8-dihydro-6H-pyrrolo[2',1':2,3]imidazo[4,5-b]pyridin-2-yl)pyrimidin-2-yl)piperidin-4-ol;

(R)-4-(5-(8-phenyl-7,8-dihydro-6H-pyrrolo[2',1':2,3]imidazo[4,5-b]pyridin-2-yl)pyrimidin-2-yl)morpholine;

(S)-2-(5-(1-(2,5-dimethylphenyl)-2,3-dihydro-1H-benzo[d]pyrrolo[1,2-a]imidazol-7-yl)pyrimidin-2-yl)propan-2-ol;

(R)-2-(5-(1-(2,5-dimethylphenyl)-2,3-dihydro-1H-benzo[d]pyrrolo[1,2-a]imidazol-7-yl)pyrimidin-2-yl)propan-2-ol;

(S)-4-(3-fluorophenyl)-7-(2-morpholinopyrimidin-5-yl)-3,4-dihydro-1H-benzo[4,5]imidazo[2,1-c][1,4]oxazine;

7-(5-(8-(2,5-dimethylphenyl)-7,8-dihydro-6H-pyrrolo[2',1':2,3]imidazo[4,5-b]pyridin-2-yl)pyrimidin-2-yl)hexahydroimidazo[1,5-a]pyrazin-3(2H)-one compound with ethane (1:1);

7-(5-(8-(3-fluorophenyl)-7,8-dihydro-6H-pyrrolo[2',1':2,3] imidazo[4,5-b]pyridin-2-yl)pyrimidin-2-yl)hexahydroimidazo[1,5-a]pyrazin-3(2H)-one;

(R)-1-(5-(1-phenyl-2,3-dihydro-1H-benzo[d]pyrrolo[1,2-a]imidazol-7-yl)pyrimidin-2-yl)piperidin-4-ol;

(R)-4-(5-(1-phenyl-2,3-dihydro-1H-benzo[d]pyrrolo[1,2-a]imidazol-7-yl)pyrimidin-2-yl)thiomorpholine 1,1-dioxide;

-(5-(8-phenyl-7,8-dihydro-6H-pyrrolo[2',1':2,3]imidazo[4,5-b]pyridin-2-yl)pyrimidin-2-yl)hexahydroimidazo[1,5-a]pyrazin-3(2H)-one;

7-(5-((R)-1-phenyl-2,3-dihydro-1H-benzo[d]pyrrolo[1,2-a] imidazol-7-yl)pyrimidin-2-yl)hexahydroimidazo[1,5-a] pyrazin-3(2H)-one;

3,3-difluoro-1-(5-((R)-1-phenyl-2,3-dihydro-1H-benzo[d] pyrrolo[1,2-a]imidazol-7-yl)pyrimidin-2-yl)piperidin-4-ol;

(S)-2-(5-(4-(2-(Difluoromethoxy)phenyl)-3,4-dihydro-1H-benzo[4,5]imidazo[2,1-c][1,4]oxazin-7-yl)pyrimidin-2-yl)propan-2-ol;

(S)-2-(5-(9-(2-methoxyphenyl)-6,7,8,9-tetrahydrobenzo[4,5]imidazo[1,2-a]pyridin-2-yl)pyrimidin-2-yl)propan-2-ol;

(R)-7-(5-(1-phenyl-2,3-dihydro-1H-benzo[d]pyrrolo[1,2-a] imidazol-7-yl)pyrimidin-2-yl)-7-azaspiro[3.5]nonan-2-ol;

1-(5-(8-(2,5-dimethylphenyl)-7,8-dihydro-6H-pyrrolo[2',1':2,3]imidazo[4,5-b]pyridin-2-yl)pyrimidin-2-yl)piperidin-4-ol;

4-(5-(10-(2-methoxyphenyl)-7,8,9,10-tetrahydro-6H-cyclohepta[4,5]imidazo[1,2-a]pyridin-2-yl)pyrimidin-2-yl) morpholine;

(R)-4-(5-(1-phenyl-2,3-dihydro-1H-benzo[d]pyrrolo[1,2-a] imidazol-7-yl)pyrimidin-2-yl)morpholine;

7-(5-((S)-4-phenyl-3,4-dihydro-1H-benzo[4,5]imidazo[2,1-c][1,4]oxazin-7-yl)pyrimidin-2-yl)hexahydroimidazo[1,5-a]pyrazin-3(2H)-one;

4-(5-(8-(2,5-dimethylphenyl)-7,8-dihydro-6H-pyrrolo[2',1':2,3]imidazo[4,5-b]pyridin-2-yl)pyrimidin-2-yl)piperazin-2-one;

2-(5-(1-(2,5-dimethylphenyl)-2,3-dihydro-1H-benzo[d]pyrrolo[1,2-a]imidazol-7-yl)pyrimidin-2-yl)propan-2-ol;
3,3-difluoro-1-(5-((S)-4-phenyl-3,4-dihydro-1H-benzo[4,5]imidazo[2,1-c][1,4]oxazin-7-yl)pyrimidin-2-yl)piperidin-4-ol;
7-(5-(4-(3-fluorophenyl)-3,4-dihydro-1H-benzo[4,5]imidazo[2,1-c][1,4]oxazin-7-yl)pyrimidin-2-yl)hexahydroimidazo[1,5-a]pyrazin-3(2H)-one;
(R)-2-(5-(1-(2-methoxyphenyl)-2,3-dihydro-H-cyclopenta[4,5]imidazo[1,2-a]pyridin-7-yl)pyrimidin-2-yl)propan-2-ol;
7-(4-(isopropylsulfonyl)phenyl)-1-phenyl-2,3-dihydro-1H-benzo[d]pyrrolo[1,2-a]imidazole;
2-(5-(9-(2-methoxyphenyl)-6,7,8,9-tetrahydrobenzo[4,5]imidazo[1,2-a]pyridin-2-yl)pyrimidin-2-yl)propan-2-ol;
4-(5-(8-(2,5-dimethylphenyl)-7,8-dihydro-6H-pyrrolo[2',1':2,3]imidazo[4,5-b]pyridin-2-yl)pyrimidin-2-yl)morpholine;
(S)-7-(5-(4-phenyl-3,4-dihydro-1H-benzo[4,5]imidazo[2,1-c][1,4]oxazin-7-yl)pyrimidin-2-yl)-7-azaspiro[3.5]nonan-2-ol;
4-(5-(9-(2-methoxyphenyl)-6,7,8,9-tetrahydrobenzo[4,5]imidazo[1,2-a]pyridin-2-yl)pyrimidin-2-yl)morpholine;
(S)-1-(5-(4-phenyl-3,4-dihydro-1H-benzo[4,5]imidazo[2,1-c][1,4]oxazin-7-yl)pyrimidin-2-yl)piperidin-4-ol;
1-(5-(9-phenyl-6,7,8,9-tetrahydroimidazo[1,2-a:5,4-b']dipyridin-2-yl)pyrimidin-2-yl)piperidin-4-ol;
(R)-2-(5-(1-Phenyl-2,3-dihydro-1H-benzo[d]pyrrolo[1,2-a]imidazol-7-yl)pyrimidin-2-yl)propan-2-ol;
4-(5-(8-(3-fluorophenyl)-7,8-dihydro-6H-pyrrolo[2',1':2,3]imidazo[4,5-b]pyridin-2-yl)pyrimidin-2-yl)morpholine;
2-(5-(10-(2-methoxyphenyl)-7,8,9,10-tetrahydro-6H-cyclohepta[4,5]imidazo[1,2-a]pyridin-2-yl)pyrimidin-2-yl)propan-2-ol;
N-methyl-4-(1-phenyl-2,3-dihydro-1H-benzo[d]pyrrolo[1,2-a]imidazol-7-yl)benzenesulfonamide;
1-(5-(8-(3-fluorophenyl)-7,8-dihydro-6H-pyrrolo[2',1':2,3]imidazo[4,5-b]pyridin-2-yl)pyrimidin-2-yl)piperidin-4-ol;
7-(4-(ethylsulfonyl)phenyl)-1-phenyl-2, 3-dihydro-1H-benzo[d]pyrrolo[1, 2-a]imidazole;
(S)-7-(2-morpholinopyrimidin-5-yl)-4-phenyl-3,4-dihydro-1H-benzo[4,5]imidazo[2,1-c][1,4]oxazine;
4-(5-(8-phenyl-7,8-dihydro-6H-pyrrolo[2',1':2,3]imidazo[4,5-b]pyridin-2-yl)pyrimidin-2-yl)morpholine;
4-(5-(8-phenyl-7,8-dihydro-6H-pyrrolo[2',1':2,3]imidazo[4,5-b]pyridin-2-yl)pyrimidin-2-yl)morpholine;
(S)-7-(5-(4-phenyl-3,4-dihydro-1H-benzo[4,5]imidazo[2,1-c][1,4]oxazin-7-yl)pyrimidin-2-yl)-7-azaspiro[3.5]nonan-2-ol;
1-(5-(8-phenyl-7,8-dihydro-6H-pyrrolo[2',1':2,3]imidazo[4,5-b]pyridin-2-yl)pyrimidin-2-yl)piperidin-4-ol;
(S)-7-(2-(1,4-oxazepan-4-yl)pyrimidin-5-yl)-4-phenyl-3,4-dihydro-1H-benzo[4,5]imidazo[2,1-c][1,4]oxazine;
4-(5-(1-phenyl-2,3-dihydro-1H-benzo[d]pyrrolo[1,2-a]imidazol-7-yl)pyrimidin-2-yl)morpholine;
3,3-difluoro-1-(5-(4-(3-fluorophenyl)-3,4-dihydro-1H-benzo[4,5]imidazo[2,1-c][1,4]oxazin-7-yl)pyrimidin-2-yl)piperidin-4-ol;
(1-(5-((S)-4-phenyl-3,4-dihydro-1H-benzo[4,5]imidazo[2,1-c][1,4]oxazin-7-yl)pyrimidin-2-yl)piperidin-3-yl)methanol;
1-(5-((S)-4-phenyl-3,4-dihydro-1H-benzo[4,5]imidazo[2,1-c][1,4]oxazin-7-yl)pyrimidin-2-yl)azepan-4-ol;
(S)-4-(5-(4-phenyl-3,4-dihydro-1H-benzo[4,5]imidazo[2,1-c][1,4]oxazin-7-yl)pyrimidin-2-yl)piperazine-1-sulfonamide;

N-(4-(1-phenyl-2,3-dihydro-1H-benzo[d]pyrrolo[1,2-a]imidazol-7-yl)benzyl)methanesulfonamide;
2-(5-(1-(2-methoxyphenyl)-2,3-dihydro-1H-cyclopenta[4,5]imidazo[1,2-a]pyridin-7-yl)pyrimidin-2-yl)propan-2-ol;
7-(4-(methylsulfonyl)phenyl)-1-phenyl-2,3-dihydro-1H-benzo[d]pyrrolo[1,2-a]imidazole;
7-(2-(1,4-oxazepan-4-yl)pyrimidin-5-yl)-4-(3-fluorophenyl)-3,4-dihydro-1H-benzo[4,5]imidazo[2,1-c][1,4]oxazine;
4-(1-phenyl-2,3-dihydro-1H-benzo[d]pyrrolo[1,2-a]imidazol-7-yl)benzenesulfonamide;
(4-(5-((S)-4-phenyl-3,4-dihydro-1H-benzo[4,5]imidazo[2,1-c][1,4]oxazin-7-yl)pyrimidin-2-yl)morpholin-2-yl)methanol;
(S)-4-(5-(4-phenyl-3,4-dihydro-1H-benzo[4,5]imidazo[2,1-c][1,4]oxazin-7-yl)pyrimidin-2-yl)thiomorpholine 1,1-dioxide;
4-(5-(9-phenyl-6,7,8,9-tetrahydroimidazo[1,2-a:5,4-b']dipyridin-2-yl)pyrimidin-2-yl)morpholine;
(R)-4-(5-(1-phenyl-1,2,3,4-tetrahydrobenzo[4,5]imidazo[1,2-a]pyridin-8-yl)pyrimidin-2-yl)morpholine;
2-(5-(1-(3-fluorophenyl)-2,3-dihydro-1H-benzo[d]pyrrolo[1,2-a]imidazol-7-yl)pyrimidin-2-yl)propan-2-ol;
(S)-(4-fluoro-1-(5-(4-phenyl-3,4-dihydro-1H-benzo[4,5]imidazo[2,1-c][1,4]oxazin-7-yl)pyrimidin-2-yl)piperidin-4-yl)methanol;
4-(5-(9-(3-chlorophenyl)-6,7,8,9-tetrahydrobenzo[4,5]imidazo[1,2-a]pyridin-2-yl)pyrimidin-2-yl)morpholine;
(R)-2-(5-(1-phenyl-1,2,3,4-tetrahydrobenzo[4,5]imidazo[1,2-a]pyridin-8-yl)pyrimidin-2-yl)propan-2-ol;
(S)-7-(2-(1'-methyl-[4,4'-bipiperidin]-1-yl)pyrimidin-5-yl)-4-phenyl-3,4-dihydro-1H-benzo[4,5]imidazo[2,1-c][1,4]oxazine;
2-(5-(9-phenyl-6,7,8,9-tetrahydroimidazo[1,2-a:5,4-b']dipyridin-2-yl)pyrimidin-2-yl)propan-2-ol;
7-(2-morpholinopyrimidin-5-yl)-4-phenyl-3,4-dihydro-1H-benzo[4,5]imidazo[2,1-c][1,4]oxazine;
(4S)-7-(2-(2-methylmorpholino)pyrimidin-5-yl)-4-phenyl-3,4-dihydro-1H-benzo[4,5]imidazo[2,1-c][1,4]oxazine;
7-(5-(4-(3-fluorophenyl)-3,4-dihydro-1H-benzo[4,5]imidazo[2,1-c][1,4]oxazin-7-yl)pyrimidin-2-yl)-7-azaspiro[3.5]nonan-2-ol;
4-(5-(1-phenyl-1,2,3,4-tetrahydrobenzo[4,5]imidazo[1,2-a]pyridin-8-yl)pyrimidin-2-yl)morpholine;
ethyl 2-[[5-[9-(2-methoxyphenyl)-6,7,8,9-tetrahydropyrido[1,2-a]benzimidazol-2-yl]pyrimidin-2-yl]amino]acetate;
(S)-7-(2-(5,6-dihydro-[1,2,4]triazolo[4,3-a]pyrazin-7(8H)-yl)pyrimidin-5-yl)-4-phenyl-3,4-dihydro-1H-benzo[4,5]imidazo[2,1-c][1,4]oxazine;
2-(5-(8-(3-fluorophenyl)-7,8-dihydro-6H-pyrrolo[2',1':2,3]imidazo[4,5-b]pyridin-2-yl)pyrimidin-2-yl)propan-2-ol;
(S)-7-(2-(4-(methylsulfonyl)piperazin-1-yl)pyrimidin-5-yl)-4-phenyl-3,4-dihydro-1H-benzo[4,5]imidazo[2, 1-c][1,4]oxazine;
2-(5-(8-phenyl-7,8-dihydro-6H-pyrrolo[2',1':2,3]imidazo[4,5-b]pyridin-2-yl)pyrimidin-2-yl)propan-2-ol;
2-(4-(1-phenyl-2,3-dihydro-1H-benzo[d]pyrrolo[1,2-a]imidazol-7-yl)phenyl)acetonitrile;
4-(5-(8-phenyl-7,8-dihydro-6H-pyrrolo[2',1':2,3]imidazo[4,5-b]pyridin-2-yl)pyrimidin-2-yl)piperazin-2-one;
7-(2-cyclopropylpyrimidin-5-yl)-1-phenyl-2,3-dihydro-1H-benzo[d]pyrrolo[1,2-a]imidazole;
(S)-4-(5-(4-phenyl-3,4-dihydro-1H-benzo[4,5]imidazo[2,1-c][1,4]oxazin-7-yl)pyrimidin-2-yl)piperazin-2-one;
2-((5-(9-(2-methoxyphenyl)-6,7,8,9-tetrahydrobenzo[4,5]imidazo[1,2-a]pyridin-2-yl)pyridin-2-yl)oxy)acetic acid;

7-(6-(ethylsulfonyl)pyridin-3-yl)-1-phenyl-2,3-dihydro-1H-benzo[d]pyrrolo[1,2-a]imidazole;
4-(5-(8-(3-fluorophenyl)-7,8-dihydro-6H-pyrrolo[2',1':2,3]imidazo[4,5-b]pyridin-2-yl)pyrimidin-2-yl)piperazin-2-one;
10-(3-fluorophenyl)-2-(2-morpholinopyrimidin-5-yl)-7,8,9,10-tetrahydro-6H-cyclohepta[4,5]imidazo[1,2-a]pyridin-10-ol;
4-(5-(9-phenyl-6,7,8,9-tetrahydroimidazo[1,2-a:5,4-b']dipyridin-2-yl)pyrimidin-2-yl)piperazin-2-one;
(S)-6-(5-(4-phenyl-3,4-dihydro-1H-benzo[4,5]imidazo[2,1-c][1,4]oxazin-7-yl)pyrimidin-2-yl)-6-azaspiro[3.4]octan-2-ol;
N,N-dimethyl-4-(1-phenyl-2,3-dihydro-1H-benzo[d]pyrrolo[1,2-a]imidazol-7-yl)benzamide;
N-ethyl-N-methyl-4-(1-phenyl-2,3-dihydro-1H-benzo[d]pyrrolo[1,2-a]imidazol-7-yl)benzamide;
7-(6-morpholinopyridin-3-yl)-4-phenyl-3,4-dihydro-1H-benzo[4,5]imidazo[2,1-c][1,4]oxazine;
2-(5-(1-phenyl-1,2,3,4-tetrahydrobenzo[4,5]imidazo[1,2-a]pyridin-8-yl)pyrimidin-2-yl)propan-2-ol;
2-(5-(1-phenyl-2,3-dihydro-1H-benzo[d]pyrrolo[1,2-a]imidazol-7-yl)pyrimidin-2-yl)propan-2-ol;
(S)-4-(2-hydroxyethyl)-1-(5-(4-phenyl-3,4-dihydro-1H-benzo[4,5]imidazo[2,1-c][1,4]oxazin-7-yl)pyrimidin-2-yl)piperidin-4-ol;
(S)-7-(2-(2-oxa-7-azaspiro[3.5]nonan-7-yl)pyrimidin-5-yl)-4-phenyl-3,4-dihydro-1H-benzo[4,5]imidazo[2,1-c][1,4]oxazine;
2-(1-(5-((S)-4-phenyl-3,4-dihydro-1H-benzo[4,5]imidazo[2,1-c][1,4]oxazin-7-yl)pyrimidin-2-yl)piperidin-3-yl)acetic acid;
7-(5-methyl-6-morpholinopyridin-3-yl)-4-phenyl-3,4-dihydro-1H-benzo[4,5]imidazo[2,1-c][1,4]oxazine;
7-(5-(2-methyl-1H-imidazol-1-yl)pyrazin-2-yl)-4-phenyl-3,4-dihydro-1H-benzo[4,5]imidazo[2,1-c][1,4]oxazine;
2-(5-(1-cyclohexyl-2,3-dihydro-1H-benzo[d]pyrrolo[1,2-a]imidazol-7-yl)pyrimidin-2-yl)propan-2-ol;
2-(5-(4-phenyl-3,4-dihydro-1H-benzo[4,5]imidazo[2,1-c][1,4]oxazin-7-yl)pyrimidin-2-yl)propan-2-ol;
(S)-(4-(methylsulfonyl)-1-(5-(4-phenyl-3,4-dihydro-1H-benzo[4,5]imidazo[2,1-c][1,4]oxazin-7-yl)pyrimidin-2-yl)piperidin-4-yl)methanol;
1-(1-(5-((S)-4-phenyl-3,4-dihydro-1H-benzo[4,5]imidazo[2,1-c][1,4]oxazin-7-yl)pyrimidin-2-yl)piperidin-4-yl)ethanol;
(S)-4-(5-(4-phenyl-3,4-dihydro-1H-benzo[4,5]imidazo[2,1-c][1,4]oxazin-7-yl)pyrimidin-2-yl)-1,4-diazepan-2-one;
2-(4-(1-phenyl-2,3-dihydro-1H-benzo[d]pyrrolo[1,2-a]imidazol-7-yl)phenoxy)acetonitrile;
(S)—N-(1-(5-(4-phenyl-3,4-dihydro-1H-benzo[4,5]imidazo[2,1-c][1,4]oxazin-7-yl)pyrimidin-2-yl)piperidin-4-yl)methanesulfonamide;
(S)-3-(1-(5-(4-phenyl-3,4-dihydro-1H-benzo[4,5]imidazo[2,1-c][1,4]oxazin-7-yl)pyrimidin-2-yl)piperidin-4-yl)propanoic acid;
4-phenyl-7-(6-(trifluoromethyl)pyridin-3-yl)-3,4-dihydro-1H-benzo[4,5]imidazo[2,1-c][1,4]oxazine;
4-(5-(1-phenyl-1,2,3,4-tetrahydrobenzo[4,5]imidazo[1,2-a]pyridin-8-yl)pyrimidin-2-yl)piperazin-2-one;
7-(5-fluoro-6-methoxypyridin-3-yl)-4-phenyl-3,4-dihydro-1H-benzo[4,5]imidazo[2,1-c][1,4]oxazine;
N,N-dimethyl-5-(1-phenyl-2,3-dihydro-1H-benzo[d]pyrrolo[1,2-a]imidazol-7-yl)pyridin-2-amine;
7-(2-methylpyridin-4-yl)-1-phenyl-2,3-dihydro-1H-benzo[d]pyrrolo[1,2-a]imidazole;
(4S)-4-phenyl-7-(2-(2-(trifluoromethyl)morpholino)pyrimidin-5-yl)-3,4-dihydro-1H-benzo[4,5]imidazo[2,1-c][1,4]oxazine;
7-(5-((S)-4-phenyl-3,4-dihydro-1H-benzo[4,5]imidazo[2,1-c][1,4]oxazin-7-yl)pyrimidin-2-yl)-2,7-diazaspiro[4.4]nonan-1-one;
N-cyclopentyl-5-(4-phenyl-3,4-dihydro-H-benzo[4,5]imidazo[2,1-c][1,4]oxazin-7-yl)pyrimidin-2-amine;
7-(2-(1H-pyrazol-1-yl)pyrimidin-5-yl)-4-phenyl-3,4-dihydro-1H-benzo[4,5]imidazo[2,1-c][1,4]oxazine;
(4S)-7-(2-(2,6-dimethylmorpholino)pyrimidin-5-yl)-4-phenyl-3,4-dihydro-1H-benzo[4,5]imidazo[2,1-c][1,4]oxazine;
7-(6-methylpyridin-3-yl)-1-phenyl-2,3-dihydro-1H-benzo[d]pyrrolo[1,2-a]imidazole;
7-(5-ethoxypyridin-3-yl)-1-phenyl-2,3-dihydro-1H-benzo[d]pyrrolo[1,2-a]imidazole;
2-(2-morpholinopyrimidin-5-yl)-9-(m-tolyl)-6,7,8,9-tetrahydrobenzo[4,5]imidazo[1,2-a]pyridin-9-ol;
7-(6-(methylthio)pyridin-3-yl)-1-phenyl-2,3-dihydro-1H-benzo[d]pyrrolo[1,2-a]imidazole;
ethyl 2-((5-(10-(2-methoxyphenyl)-7,8,9,10-tetrahydro-6H-cyclohepta[4,5]imidazo[1,2-a]pyridin-2-yl)pyrimidin-2-yl)amino)acetate;
(S)-3-(4-(5-(4-phenyl-3,4-dihydro-1H-benzo[4,5]imidazo[2,1-c][1,4]oxazin-7-yl)pyrimidin-2-yl)piperazin-1-yl)propan-1-ol;
9-(3-fluorophenyl)-2-(2-morpholinopyrimidin-5-yl)-6,7,8,9-tetrahydrobenzo[4,5]imidazo[1,2-a]pyridin-9-ol;
2-(2-morpholinopyrimidin-5-yl)-9-phenyl-6,7,8,9-tetrahydrobenzo[4,5]imidazo[1,2-a]pyridin-9-ol;
4-(2,5-difluorophenyl)-7-(2-morpholinopyrimidin-5-yl)-3,4-dihydro-1H-benzo[4,5]imidazo[2,1-c][1,4]oxazine;
1-phenyl-7-(6-(piperazin-1-yl)pyridin-3-yl)-2,3-dihydro-1H-benzo[d]pyrrolo[1,2-a]imidazole;
9-(2-Methoxyphenyl)-2-(2-morpholinopyrimidin-5-yl)-6,7,8,9-tetrahydrobenzo[4,5]imidazo[1,2-a]pyridin-9-ol;
(S)-7-(2-(2-oxa-6-azaspiro[3.4]octan-6-yl)pyrimidin-5-yl)-4-phenyl-3,4-dihydro-1H-benzo[4,5]imidazo[2,1-c][1,4]oxazine;
7-(5-(1H-imidazol-1-yl)pyrazin-2-yl)-4-phenyl-3,4-dihydro-1H-benzo[4,5]imidazo[2,1-c][1,4]oxazine;
7-(furo[3,2-b]pyridin-6-yl)-4-phenyl-3,4-dihydro-1H-benzo[4,5]imidazo[2,1-c][1,4]oxazine;
10-(3-chlorophenyl)-2-(2-morpholinopyrimidin-5-yl)-7,8,9,10-tetrahydro-6H-cyclohepta[4,5]imidazo[1,2-a]pyridin-10-ol;
N-ethyl-4-(1-phenyl-2,3-dihydro-1H-benzo[d]pyrrolo[1,2-a]imidazol-7-yl)benzamide;
2-(3-(1-phenyl-2,3-dihydro-1H-benzo[d]pyrrolo[1,2-a]imidazol-7-yl)phenoxy)acetonitrile;
2-(2-morpholinopyrimidin-5-yl)-10-(m-tolyl)-7,8,9,10-tetrahydro-6H-cyclohepta[4,5]imidazo[1,2-a]pyridin-10-ol;
2-((5-(10-(2-methoxyphenyl)-7,8,9,10-tetrahydro-6H-cyclohepta[4,5]imidazo[1,2-a]pyridin-2-yl)pyrimidin-2-yl)amino)acetic acid;
N-cyclopropyl-4-(1-phenyl-2,3-dihydro-1H-benzo[d]pyrrolo[,2-a]imidazol-7-yl)benzamide;
4-(1-phenyl-2,3-dihydro-1H-benzo[d]pyrrolo[1,2-a]imidazol-7-yl)benzamide;
1-(4-(5-(4-phenyl-3,4-dihydro-1H-benzo[4,5]imidazo[2,1-c][1,4]oxazin-7-yl)pyridin-2-yl)piperazin-1-yl)ethanone;
7-(6-(4-methylpiperazin-1-yl)pyridin-3-yl)-1-phenyl-2,3-dihydro-1H-benzo[d]pyrrolo[1,2-a]imidazole;
7-(benzo[d][1,3]dioxol-5-yl)-1-phenyl-2,3-dihydro-1H-benzo[d]pyrrolo[1,2-a]imidazole;

9-(3-fluoro-2-methylphenyl)-2-(2-morpholinopyrimidin-5-yl)-6,7,8,9-tetrahydrobenzo[4,5]imidazo[1,2-a]pyridin-9-ol;

8-Phenyl-2-(4-(pyrimidin-2-yl)piperazin-1-yl)-7,8-dihydro-6H-pyrrolo[2',1':2,3]imidazo[4,5-b]pyridine;

9-(4-fluorophenyl)-2-(2-morpholinopyrimidin-5-yl)-6,7,8,9-tetrahydrobenzo[4,5]imidazo[1,2-a]pyridin-9-ol;

7-(5-((S)-4-phenyl-3,4-dihydro-1H-benzo[4,5]imidazo[2,1-c][1,4]oxazin-7-yl)pyrimidin-2-yl)tetrahydro-1H-oxazolo[3,4-a]pyrazin-3(5H)-one;

2-((5-(9-(2-methoxyphenyl)-6,7,8,9-tetrahydrobenzo[4,5]imidazo[1,2-a]pyridin-2-yl)pyrimidin-2-yl)amino)acetic acid;

10-(4-fluorophenyl)-2-(2-morpholinopyrimidin-5-yl)-7,8,9,10-tetrahydro-6H-cyclohepta[4,5]imidazo[1,2-a]pyridin-10-ol;

9-(3-chlorophenyl)-2-(2-morpholinopyrimidin-5-yl)-6,7,8,9-tetrahydrobenzo[4,5]imidazo[1,2-a]pyridin-9-ol;

N-cyclopropyl-5-(4-phenyl-3,4-dihydro-1H-benzo[4,5]imidazo[2,1-c][1,4]oxazin-7-yl)pyrimidin-2-amine;

9-(3-chloro-5-fluorophenyl)-2-(2-morpholinopyrimidin-5-yl)-6,7,8,9-tetrahydrobenzo[4,5]imidazo[1,2-a]pyridin-9-ol;

N,N-dimethyl-5-(4-phenyl-3,4-dihydro-1H-benzo[4,5]imidazo[2,1-c][1,4]oxazin-7-yl)pyrimidin-2-amine;

1-(5-(1-phenyl-1,2,3,4-tetrahydrobenzo[4,5]imidazo[1,2-a]pyridin-8-yl)pyrimidin-2-yl)piperidine-4-carboxylic acid;

7-(6-isopropoxypyridin-3-yl)-4-phenyl-3,4-dihydro-1H-benzo[4,5]imidazo[2,1-c][1,4]oxazine;

7-(6-isopropoxypyridin-3-yl)-4-phenyl-3,4-dihydro-1H-benzo[4,5]imidazo[2,1-c][1,4]oxazine;

4-(5-(6-phenyl-7,8-dihydro-6H-pyrrolo[1',2':1,2]imidazo[4,5-c]pyridin-3-yl)pyrimidin-2-yl)morpholine;

1-phenyl-7-(1-(pyridin-3-ylmethyl)-1H-pyrazol-4-yl)-2,3-dihydro-1H-benzo[d]pyrrolo[1,2-a]imidazole;

5-(4-phenyl-3,4-dihydro-1H-benzo[4,5]imidazo[2,1-c][1,4]oxazin-7-yl)picolinonitrile;

7-(4-methyl-3,4-dihydro-2H-pyrido[3,2-b][1,4]oxazin-7-yl)-4-phenyl-3,4-dihydro-1H-benzo[4,5]imidazo[2,1-c][1,4]oxazine;

2-(2-morpholinopyrimidin-5-yl)-9-(p-tolyl)-6,7,8,9-tetrahydrobenzo[4,5]imidazo[1,2-a]pyridin-9-ol;

7-(6-(methylsulfonyl)pyridin-3-yl)-4-phenyl-3,4-dihydro-1H-benzo[4,5]imidazo[2,1-c][1,4]oxazine;

N-(2-methoxyethyl)-4-(1-phenyl-2,3-dihydro-1H-benzo[d]pyrrolo[1,2-a]imidazol-7-yl)benzamide;

N-methyl-4-(1-phenyl-2,3-dihydro-1H-benzo[d]pyrrolo[1,2-a]imidazol-7-yl)benzamide;

4-phenyl-7-(6-(2,2,2-trifluoroethoxy)pyridin-3-yl)-3,4-dihydro-1H-benzo[4,5]imidazo[2,1-c][1,4]oxazine;

1-(5-(4-phenyl-3,4-dihydro-1H-benzo[4,5]imidazo[2,1-c][1,4]oxazin-7-yl)pyrimidin-2-yl)piperidine-4-carboxylic acid;

7-(5-methyl-6-(4-methylpiperazin-1-yl)pyridin-3-yl)-4-phenyl-3,4-dihydro-1H-benzo[4,5]imidazo[2,1-c][1,4]oxazine;

5-(9-(2-methoxyphenyl)-6,7,8,9-tetrahydrobenzo[4,5]imidazo[,2-a]pyridin-2-yl)thiophene-2-carboxylic acid;

7-(6-(4-methylpiperazin-1-yl)pyridin-3-yl)-4-phenyl-3,4-dihydro-1H-benzo[4,5]imidazo[2,1-c][1,4]oxazine;

(S)-7-(2-(1'-methyl-[4, 4'-bipiperidin]-1-yl)pyrimidin-5-yl)-4-phenyl-3,4-dihydro-1H-benzo[4,5]imidazo[2,1-c][1,4]oxazine;

7-(2-methoxypyrimidin-5-yl)-4-phenyl-3,4-dihydro-1H-benzo[4,5]imidazo[2,1-c][1,4]oxazine;

10-(3-chloro-5-fluorophenyl)-2-(2-morpholinopyrimidin-5-yl)-7,8,9,10-tetrahydro-6H-cyclohepta[4,5]imidazo[1,2-a]pyridin-10-ol;

3-(2-hydroxyethyl)-1-(5-((S)-4-phenyl-3,4-dihydro-1H-benzo[4,5]imidazo[2,1-c][1,4]oxazin-7-yl)pyrimidin-2-yl)pyrrolidin-3-ol;

4-(5-(9-(2-methoxyphenyl)-6,7-dihydrobenzo[4,5]imidazo[1,2-a]pyridin-2-yl)pyrimidin-2-yl)morpholine;

10-(4-methoxyphenyl)-2-(2-morpholinopyrimidin-5-yl)-7,8,9,10-tetrahydro-6H-cyclohepta[4,5]imidazo[1,2-a]pyridin-10-ol;

7-(5-(1H-pyrazol-1-yl)pyrazin-2-yl)-4-phenyl-3,4-dihydro-1H-benzo[4,5]imidazo[2,1-c][1,4]oxazine;

1-phenyl-7-(pyridin-3-yl)-2, 3-dihydro-1H-benzo[d]pyrrolo[1,2-a]imidazole;

5-(1-phenyl-2,3-dihydro-1H-benzo[d]pyrrolo[1,2-a]imidazol-7-yl)pyrimidin-2-amine;

2-(2-morpholinopyrimidin-5-yl)-10-(p-tolyl)-7,8,9,10-tetrahydro-6H-cyclohepta[4,5]imidazo[1,2-a]pyridin-10-ol;

5-(4-phenyl-3,4-dihydro-1H-benzo[4,5]imidazo[2,1-c][1,4]oxazin-7-yl)pyrimidine-2-carbonitrile;

(R)-2-(5-(9-(2-methoxyphenyl)-6,7,8,9-tetrahydrobenzo[4,5]imidazo[1,2-a]pyridin-2-yl)pyrimidin-2-yl)propan-2-ol;

(S)-7-(2-((R)-3-(methylsulfonyl)pyrrolidin-1-yl)pyrimidin-5-yl)-4-phenyl-3,4-dihydro-1H-benzo[4,5]imidazo[2,1-c][1,4]oxazine;

7-([1,2,5]oxadiazolo[3,4-b]pyridin-6-yl)-4-phenyl-3,4-dihydro-1H-benzo[4,5]imidazo[2,1-c][1,4]oxazine;

2-(5-(6-phenyl-7,8-dihydro-6H-pyrrolo[1,2':1,2]imidazo[4,5-c]pyridin-3-yl)pyrimidin-2-yl)propan-2-ol;

7-(2-methylpyrimidin-5-yl)-4-phenyl-3,4-dihydro-1H-benzo[4,5]imidazo[2,1-c][1,4]oxazine;

1-phenyl-7-(pyrimidin-5-yl)-2,3-dihydro-1H-benzo[d]pyrrolo[1,2-a]imidazole;

7-(6-methoxy-5-methylpyridin-3-yl)-4-phenyl-3,4-dihydro-1H-benzo[4, 5]imidazo[2,1-c][1,4]oxazine;

10-(4-chlorophenyl)-2-(2-morpholinopyrimidin-5-yl)-7, 8, 9,10-tetrahydro-6H-cyclohepta[4,5]imidazo[1,2-a]pyridin-10-ol;

2-(3-(1-phenyl-2,3-dihydro-1H-benzo[d]pyrrolo[1,2-a]imidazol-7-yl)phenyl)acetonitrile;

N-(3-(1-phenyl-2,3-dihydro-1H-benzo[d]pyrrolo[1,2-a]imidazol-7-yl)benzyl)methanesulfonamide;

7-(6-methylpyridin-3-yl)-4-phenyl-3,4-dihydro-H-benzo[4,5]imidazo[2,1-c][1,4]oxazine;

(S)-2-(5-(1-phenyl-1,2,3,4-tetrahydrobenzo[4,5]imidazo[1,2-a]pyridin-8-yl)pyrimidin-2-yl)propan-2-ol;

(S)-7-(2-(4-(1-methylpiperidin-4-yl)piperazin-1-yl)pyrimidin-5-yl)-4-phenyl-3,4-dihydro-1H-benzo[4,5]imidazo[2,1-c][1,4]oxazine;

4-phenyl-7-(6-(piperazin-1-yl)pyridin-3-yl)-3,4-dihydro-1H-benzo[4,5]imidazo[2,1-c][1,4]oxazine;

(4S)-7-(2-(3-(methylsulfonyl)pyrrolidin-1-yl)pyrimidin-5-yl)-4-phenyl-3,4-dihydro-1H-benzo[4,5]imidazo[2,1-c][1,4]oxazine;

(S)-8-(5-(4-phenyl-3,4-dihydro-1H-benzo[4,5]imidazo[2,1-c][1,4]oxazin-7-yl)pyrimidin-2-yl)-1,3,8-triazaspiro[4.5]decan-4-one;

7-(6-isopropoxy-5-methylpyridin-3-yl)-4-phenyl-3,4-dihydro-1H-benzo[4,5]imidazo[2,1-c][1,4]oxazine;

7-(5-methylpyridin-3-yl)-1-phenyl-2,3-dihydro-1H-benzo[d]pyrrolo[1,2-a]imidazole;

N-methyl-3-(1-phenyl-2,3-dihydro-1H-benzo[d]pyrrolo[1,2-a]imidazol-7-yl)benzamide;

4-(1-phenyl-2,3-dihydro-1H-benzo[d]pyrrolo[1,2-a]imidazol-7-yl)-N-((tetrahydrofuran-2-yl)methyl)benzamide;

(S)-4-(5-(1-phenyl-2,3-dihydro-1H-benzo[d]pyrrolo[1,2-a]imidazol-7-yl)pyrimidin-2-yl)morpholine;
N-(5-(4-phenyl-3,4-dihydro-1H-benzo[4,5]imidazo[2,1-c][1,4]oxazin-7-yl)pyridin-2-yl)acetamide;
N-ethyl-N-methyl-3-(1-phenyl-2,3-dihydro-1H-benzo[d]pyrrolo[1,2-a]imidazol-7-yl)benzamide;
5-(1-phenyl-2,3-dihydro-1H-benzo[d]pyrrolo[1,2-a]imidazol-7-yl)pyridin-2-amine;
7-(3-methyl-3H-imidazo[4,5-b]pyridin-6-yl)-4-phenyl-3,4-dihydro-1H-benzo[4,5]imidazo[2,1-c][1,4]oxazine;
10-(3,5-dimethoxyphenyl)-2-(2-morpholinopyrimidin-5-yl)-7,8,9,10-tetrahydro-6H-cyclohepta[4,5]imidazo[1,2-a]pyridin-10-ol;
N,N-dimethyl-3-((5-(4-phenyl-3,4-dihydro-1H-benzo[4,5]imidazo[2,1-c][1,4]oxazin-7-yl)pyridin-2-yl)oxy)propan-1-amine;
(3R,4R)-1-(5-((S)-4-phenyl-3,4-dihydro-1H-benzo[4,5]imidazo[2,1-c][1,4]oxazin-7-yl)pyrimidin-2-yl)pyrrolidine-3,4-diol;
N-(2-(dimethylamino)ethyl)-3-(1-phenyl-2,3-dihydro-1H-benzo[d]pyrrolo[1,2-a]imidazol-7-yl)benzamide;
10-(3-methoxyphenyl)-2-(2-morpholinopyrimidin-5-yl)-7,8,9,10-tetrahydro-6H-cyclohepta [4,5]imidazo[1,2-a]pyridin-10-ol;
7-(1,5-dimethyl-H-pyrazol-4-yl)-1-phenyl-2,3-dihydro-1H-benzo[d]pyrrolo[1,2-a]imidazole;
N,N-dimethyl-3-(1-phenyl-2,3-dihydro-1H-benzo[d]pyrrolo[1,2-a]imidazol-7-yl)benzamide;
7-(3-(methylsulfonyl)phenyl)-1-phenyl-2,3-dihydro-1H-benzo[d]pyrrolo[1,2-a]imidazole;
4-phenyl-7-(pyrido[2,3-b]pyrazin-7-yl)-3,4-dihydro-1H-benzo[4,5]imidazo[2,1-c][1,4]oxazine;
1-methyl-5-(1-phenyl-2,3-dihydro-1H-benzo[d]pyrrolo[1,2-a]imidazol-7-yl)pyridin-2(1H)-one;
(3S,4S)-1-(5-((S)-4-phenyl-3,4-dihydro-1H-benzo[4,5]imidazo[2,1-c][1,4]oxazin-7-yl)pyrimidin-2-yl)pyrrolidine-3,4-diol;
4-phenyl-7-(pyrimidin-5-yl)-3,4-dihydro-1H-benzo[4,5]imidazo[2,1-c][1,4]oxazine;
(S)-2-(5-(1-(2-Methoxyphenyl)-2,3-dihydro-1H-cyclopenta[4,5]imidazo[1,2-a]pyridin-7-yl)pyrimidin-2-yl)propan-2-ol;
(S)-2-(5-(1-phenyl-2,3-dihydro-1H-benzo[d]pyrrolo[1,2-a]imidazol-7-yl)pyrimidin-2-yl)propan-2-ol;
2-(2-(2-(2-hydroxypropan-2-yl)pyrimidin-5-yl)-6,7,8,9-tetrahydrobenzo[4,5]imidazo[1,2-a]pyridin-9-yl)phenol;
4-(5-(6-phenyl-6,7,8,9-tetrahydroimidazo[1,2-a:4,5-b']dipyridin-3-yl)pyrimidin-2-yl)piperazin-2-one;
(S)-7-(2-(3-morpholinoazetidin-1-yl)pyrimidin-5-yl)-4-phenyl-3,4-dihydro-1H-benzo[4,5]imidazo[2,1-c][1,4]oxazine;
7-(5-(methylsulfonyl)pyridin-3-yl)-1-phenyl-2,3-dihydro-1H-benzo[d]pyrrolo[1,2-a]imidazole;
(R)-7-(2-morpholinopyrimidin-5-yl)-4-phenyl-3,4-dihydro-1H-benzo[4,5]imidazo[2,1-c][1,4]oxazine;
7-(2-methylpyridin-3-yl)-1-phenyl-2,3-dihydro-1H-benzo[d]pyrrolo[1,2-a]imidazole;
1-(5-(1-phenyl-1,2,3,4-tetrahydrobenzo[4,5]imidazo[1,2-a]pyridin-8-yl)pyrimidin-2-yl)azetidine-3-carboxylic acid;
7-(1-methyl-1H-pyrrol-3-yl)-1-phenyl-2,3-dihydro-1H-benzo[d]pyrrolo[1,2-a]imidazole; or
N-(2-morpholinoethyl)-5-(4-phenyl-3,4-dihydro-1H-benzo[4,5]imidazo[2,1-c][1,4]oxazin-7-yl)pyridin-2-amine.
Compounds of Formula (I) also include:
7-(5-((R)-1-Phenyl-2,3-dihydro-1H-benzo[d]pyrrolo[1,2-a]imidazol-7-yl)pyrimidin-2-yl)hexahydroimidazo[1,5-a]pyrazin-3(2H)-one;
3,3-difluoro-1-(5-((R)-1-phenyl-2,3-dihydro-1H-benzo[d]pyrrolo[1,2-a]imidazol-7-yl)pyrimidin-2-yl)piperidin-4-ol;
(S)-2-(5-(4-(2-(Difluoromethoxy)phenyl)-3,4-dihydro-1H-benzo[4,5]imidazo[2,1-c][1,4]oxazin-7-yl)pyrimidin-2-yl)propan-2-ol;
(S)-2-(5-(9-(2-methoxyphenyl)-6,7,8,9-tetrahydrobenzo[4,5]imidazo[1,2-a]pyridin-2-yl)pyrimidin-2-yl)propan-2-ol;
(R)-7-(5-(1-phenyl-2,3-dihydro-1H-benzo[d]pyrrolo[1,2-a]imidazol-7-yl)pyrimidin-2-yl)-7-azaspiro[3.5]nonan-2-ol;
1-(5-(8-(2,5-dimethylphenyl)-7,8-dihydro-6H-pyrrolo[2',1':2,3]imidazo[4,5-b]pyridin-2-yl)pyrimidin-2-yl)piperidin-4-ol;
4-(5-(10-(2-methoxyphenyl)-7,8,9,10-tetrahydro-6H-cyclohepta[4,5]imidazo[1,2-a]pyridin-2-yl)pyrimidin-2-yl)morpholine;
(R)-4-(5-(1-phenyl-2,3-dihydro-1H-benzo[d]pyrrolo[1,2-a]imidazol-7-yl)pyrimidin-2-yl)morpholine;
7-(5-((S)-4-phenyl-3,4-dihydro-1H-benzo[4,5]imidazo[2,1-c][1,4]oxazin-7-yl)pyrimidin-2-yl)hexahydroimidazo[1,5-a]pyrazin-3(2H)-one;
7-(5-((S)-4-phenyl-3,4-dihydro-1H-benzo[4,5]imidazo[2,1-c][1,4]oxazin-7-yl)pyrimidin-2-yl)hexahydroimidazo[1,5-a]pyrazin-3(2H)-one;
4-(5-(8-(2,5-dimethylphenyl)-7,8-dihydro-6H-pyrrolo[2',1':2,3]imidazo[4,5-b]pyridin-2-yl)pyrimidin-2-yl)piperazin-2-one;
2-(5-(1-(2,5-dimethylphenyl)-2,3-dihydro-1H-benzo[d]pyrrolo[1,2-a]imidazol-7-yl)pyrimidin-2-yl)propan-2-ol;
3,3-difluoro-1-(5-((S)-4-phenyl-3,4-dihydro-1H-benzo[4,5]imidazo[2,1-c][1,4]oxazin-7-yl)pyrimidin-2-yl)piperidin-4-ol;
7-(5-(4-(3-fluorophenyl)-3,4-dihydro-1H-benzo[4,5]imidazo[2,1-c][1,4]oxazin-7-yl)pyrimidin-2-yl)hexahydroimidazo[1,5-a]pyrazin-3 (2H)-one;
(R)-2-(5-(1-(2-methoxyphenyl)-2,3-dihydro-H-cyclopenta[4,5]imidazo[1,2-a]pyridin-7-yl)pyrimidin-2-yl)propan-2-ol;
7-(4-(isopropylsulfonyl)phenyl)-1-phenyl-2,3-dihydro-1H-benzo[d]pyrrolo[1,2-a]imidazole;
2-(5-(9-(2-methoxyphenyl)-6,7,8,9-tetrahydrobenzo[4,5]imidazo[1,2-a]pyridin-2-yl)pyrimidin-2-yl)propan-2-ol;
4-(5-(8-(2,5-dimethylphenyl)-7,8-dihydro-6H-pyrrolo[2',1':2,3]imidazo[4,5-b]pyridin-2-yl)pyrimidin-2-yl)morpholine;
(S)-7-(5-(4-phenyl-3,4-dihydro-1H-benzo[4,5]imidazo[2,1-c][1,4]oxazin-7-yl)pyrimidin-2-yl)-7-azaspiro[3.5]nonan-2-ol;
4-(5-(9-(2-Methoxyphenyl)-6,7,8,9-tetrahydrobenzo[4,5]imidazo[1,2-a]pyridin-2-yl)pyrimidin-2-yl)morpholine;
1-(5-(9-phenyl-6,7,8,9-tetrahydroimidazo[1,2-a:5,4-b']dipyridin-2-yl)pyrimidin-2-yl)piperidin-4-ol;
(R)-2-(5-(1-phenyl-2,3-dihydro-1H-benzo[d]pyrrolo[1,2-a]imidazol-7-yl)pyrimidin-2-yl)propan-2-ol;
2-(5-(10-(2-methoxyphenyl)-7,8,9,10-tetrahydro-6H-cyclohepta[4,5]imidazo[1,2-a]pyridin-2-yl)pyrimidin-2-yl)propan-2-ol;
N-methyl-4-(1-phenyl-2,3-dihydro-1H-benzo[d]pyrrolo[1,2-a]imidazol-7-yl)benzenesulfonamide;
(S)-7-(2-morpholinopyrimidin-5-yl)-4-phenyl-3,4-dihydro-1H-benzo[4,5]imidazo[2,1-c][1,4]oxazine;
(S)-7-(5-(4-phenyl-3,4-dihydro-1H-benzo[4,5]imidazo[2,1-c][1,4]oxazin-7-yl)pyrimidin-2-yl)-7-azaspiro[3.5]nonan-2-ol;

2-(5-(1-(2-methoxyphenyl)-2,3-dihydro-1H-cyclopenta[4,5]imidazo[1,2-a]pyridin-7-yl)pyrimidin-2-yl)propan-2-ol;

(R)-2-(5-(1-phenyl-1,2,3,4-tetrahydrobenzo[4,5]imidazo[1,2-a]pyridin-8-yl)pyrimidin-2-yl)propan-2-ol;

ethyl 2-[[5-[9-(2-methoxyphenyl)-6,7,8,9-tetrahydropyrido[1,2-a]benzimidazol-2-yl]pyrimidin-2-yl]amino]acetate; or 2-((5-(9-(2-methoxyphenyl)-6,7,8,9-tetrahydrobenzo[4,5]imidazo[1,2-a]pyridin-2-yl)pyridin-2-yl)oxy)acetic acid. Compounds of the invention also include 7-(6-(ethylsulfonyl)pyridin-3-yl)-1-phenyl-2,3-dihydro-1H-benzo[d]pyrrolo[1,2-a]imidazole;

4-(5-(8-(3-fluorophenyl)-7,8-dihydro-6H-pyrrolo[2',1':2,3]imidazo[4,5-b]pyridin-2-yl)pyrimidin-2-yl)piperazin-2-one;

10-(3-fluorophenyl)-2-(2-morpholinopyrimidin-5-yl)-7,8,9,10-tetrahydro-6H-cyclohepta [4,5]imidazo[1,2-a]pyridin-10-ol;

4-(5-(9-phenyl-6,7,8,9-tetrahydroimidazo[1,2-a:5,4-b']dipyridin-2-yl)pyrimidin-2-yl)piperazin-2-one;

(S)-6-(5-(4-phenyl-3,4-dihydro-1H-benzo[4,5]imidazo[2,1-c][1,4]oxazin-7-yl)pyrimidin-2-yl)-6-azaspiro[3.4]octan-2-ol;

N,(S)-(4-(methylsulfonyl)-1-(5-(4-phenyl-3,4-dihydro-1H-benzo[4,5]imidazo[2,1-c][1,4]oxazin-7-yl)pyrimidin-2-yl)piperidin-4-yl)methanol;

1-(1-(5-((S)-4-phenyl-3,4-dihydro-1H-benzo[4,5]imidazo[2,1-c][1,4]oxazin-7-yl)pyrimidin-2-yl)piperidin-4-yl)ethanol;

(S)-4-(5-(4-phenyl-3,4-dihydro-1H-benzo[4,5]imidazo[2,1-c][1,4]oxazin-7-yl)pyrimidin-2-yl)-1,4-diazepan-2-one;

2-(4-(1-phenyl-2,3-dihydro-1H-benzo[d]pyrrolo[1,2-a]imidazol-7-yl)phenoxy)acetonitrile;

(S)—N-(1-(5-(4-phenyl-3,4-dihydro-1H-benzo[4,5]imidazo[2,1-c][1,4]oxazin-7-yl)pyrimidin-2-yl)piperidin-4-yl)methanesulfonamide;

(S)-3-(1-(5-(4-phenyl-3,4-dihydro-1H-benzo[4,5]imidazo[2,1-c][1,4]oxazin-7-yl)pyrimidin-2-yl)piperidin-4-yl)propanoic acid;

4-phenyl-7-(6-(trifluoromethyl)pyridin-3-yl)-3,4-dihydro-1H-benzo[4,5]imidazo[2,1-c][1,4]oxazine;

4-(5-(1-phenyl-1,2,3,4-tetrahydrobenzo[4,5]imidazo[1,2-a]pyridin-8-yl)pyrimidin-2-yl)piperazin-2-one;

7-(5-fluoro-6-methoxypyridin-3-yl)-4-phenyl-3,4-dihydro-1H-benzo[4,5]imidazo[2,1-c][1,4]oxazine;

N,N-dimethyl-5-(1-phenyl-2,3-dihydro-1H-benzo[d]pyrrolo[1,2-a]imidazol-7-yl)pyridin-2-amine;

7-(2-methylpyridin-4-yl)-1-phenyl-2,3-dihydro-1H-benzo[d]pyrrolo[1,2-a]imidazole;

(4S)-4-phenyl-7-(2-(2-(trifluoromethyl)morpholino)pyrimidin-5-yl)-3,4-dihydro-1H-benzo[4,5]imidazo[2,1-c][1,4]oxazine;

7-(5-((S)-4-phenyl-3,4-dihydro-1H-benzo[4,5]imidazo[2,1-c][1,4]oxazin-7-yl)pyrimidin-2-yl)-2,7-diazaspiro[4.4]nonan-1-one;

N-cyclopentyl-5-(4-phenyl-3,4-dihydro-1H-benzo[4,5]imidazo[2,1-c][1,4]oxazin-7-yl)pyrimidin-2-amine;

N-dimethyl-4-(1-phenyl-2,3-dihydro-1H-benzo[d]pyrrolo[1,2-a]imidazol-7-yl)benzamide;

N-ethyl-N-methyl-4-(1-phenyl-2,3-dihydro-1H-benzo[d]pyrrolo[,2-a]imidazol-7-yl)benzamide;

7-(6-morpholinopyridin-3-yl)-4-phenyl-3,4-dihydro-1H-benzo[4,5]imidazo[2,1-c][1,4]oxazine; 7

2-(5-(1-phenyl-1,2,3,4-tetrahydrobenzo[4,5]imidazo[1,2-a]pyridin-8-yl)pyrimidin-2-yl)propan-2-ol;

2-(5-(1-phenyl-2,3-dihydro-1H-benzo[d]pyrrolo[,2-a]imidazol-7-yl)pyrimidin-2-yl)propan-2-ol;

(S)-4-(2-hydroxyethyl)-1-(5-(4-phenyl-3,4-dihydro-1H-benzo[4,5]imidazo[2,1-c][1,4]oxazin-7-yl)pyrimidin-2-yl)piperidin-4-ol;

(S)-7-(2-(2-oxa-7-azaspiro[3.5]nonan-7-yl)pyrimidin-5-yl)-4-phenyl-3,4-dihydro-1H-benzo[4,5]imidazo[2,1-c][1,4]oxazine;

2-(1-(5-((S)-4-phenyl-3,4-dihydro-1H-benzo[4,5]imidazo[2,1-c][1,4]oxazin-7-yl)pyrimidin-2-yl)piperidin-3-yl)acetic acid;

7-(5-methyl-6-morpholinopyridin-3-yl)-4-phenyl-3,4-dihydro-1H-benzo[4,5]imidazo[2,1-c][1,4]oxazine; 7

7-(5-(2-methyl-1H-imidazol-1-yl)pyrazin-2-yl)-4-phenyl-3,4-dihydro-1H-benzo[4,5]imidazo[2,1-c][1,4]oxazine;

2-(5-(1-cyclohexyl-2,3-dihydro-1H-benzo[d]pyrrolo[1,2-a]imidazol-7-yl)pyrimidin-2-yl)propan-2-ol;

2-(5-(4-phenyl-3,4-dihydro-1H-benzo[4,5]imidazo[2,1-c][1,4]oxazin-7-yl)pyrimidin-2-yl)propan-2-ol;

7-(2-(1H-pyrazol-1-yl)pyrimidin-5-yl)-4-phenyl-3,4-dihydro-1H-benzo[4,5]imidazo[2,1-c][1,4]oxazine;

(4S)-7-(2-(2,6-dimethylmorpholino)pyrimidin-5-yl)-4-phenyl-3,4-dihydro-1H-benzo[4,5]imidazo[2,1-c][1,4]oxazine;

7-(6-methylpyridin-3-yl)-1-phenyl-2,3-dihydro-1H-benzo[d]pyrrolo[1,2-a]imidazole;

7-(5-ethoxypyridin-3-yl)-1-phenyl-2,3-dihydro-1H-benzo[d]pyrrolo[1,2-a]imidazole;

2-(2-morpholinopyrimidin-5-yl)-9-(m-tolyl)-6,7,8,9-tetrahydrobenzo[4,5]imidazo[1,2-a]pyridin-9-ol;

7-(6-(methylthio)pyridin-3-yl)-1-phenyl-2,3-dihydro-1H-benzo[d]pyrrolo[1,2-a]imidazole;

ethyl 2-((5-(10-(2-methoxyphenyl)-7,8,9,10-tetrahydro-6H-cyclohepta[4,5]imidazo[1,2-a]pyridin-2-yl)pyrimidin-2-yl)amino)acetate;

(S)-3-(4-(5-(4-phenyl-3,4-dihydro-1H-benzo[4,5]imidazo[2,1-c][1,4]oxazin-7-yl)pyrimidin-2-yl)piperazin-1-yl)propan-1-ol;

9-(3-fluorophenyl)-2-(2-morpholinopyrimidin-5-yl)-6,7,8,9-tetrahydrobenzo[4,5]imidazo[1,2-a]pyridin-9-ol;

2-(2-morpholinopyrimidin-5-yl)-9-phenyl-6,7,8,9-tetrahydrobenzo[4,5]imidazo[1,2-a]pyridin-9-ol;

4-(2,5-difluorophenyl)-7-(2-morpholinopyrimidin-5-yl)-3,4-dihydro-1H-benzo[4,5]imidazo[2,1-c][1,4]oxazine;

1-phenyl-7-(6-(piperazin-1-yl)pyridin-3-yl)-2,3-dihydro-1H-benzo[d]pyrrolo[1,2-a]imidazole;

9-(2-methoxyphenyl)-2-(2-morpholinopyrimidin-5-yl)-6,7,8,9-tetrahydrobenzo[4,5]imidazo[1,2-a]pyridin-9-ol;

(S)-7-(2-(2-oxa-6-azaspiro[3.4]octan-6-yl)pyrimidin-5-yl)-4-phenyl-3,4-dihydro-1H-benzo[4,5]imidazo[2,1-c][1,4]oxazine;

7-(5-(1H-imidazol-1-yl)pyrazin-2-yl)-4-phenyl-3,4-dihydro-1H-benzo[4,5]imidazo[2,1-c][1,4]oxazine;

7-(furo[3,2-b]pyridin-6-yl)-4-phenyl-3,4-dihydro-1H-benzo[4,5]imidazo[2,1-c][1,4]oxazine;

10-(3-chlorophenyl)-2-(2-morpholinopyrimidin-5-yl)-7,8,9,10-tetrahydro-6H-cyclohepta [4,5]imidazo[1,2-a]pyridin-10-ol;

N-ethyl-4-(1-phenyl-2,3-dihydro-1H-benzo[d]pyrrolo[1,2-a]imidazol-7-yl)benzamide;

2-(3-(1-phenyl-2,3-dihydro-1H-benzo[d]pyrrolo[1,2-a]imidazol-7-yl)phenoxy)acetonitrile;

2-(2-morpholinopyrimidin-5-yl)-10-(m-tolyl)-7,8,9,10-tetrahydro-6H-cyclohepta [4,5]imidazo[1,2-a]pyridin-10-ol;

2-((5-(10-(2-methoxyphenyl)-7,8,9,10-tetrahydro-6H-cyclohepta[4,5]imidazo[1,2-a]pyridin-2-yl)pyrimidin-2-yl)amino)acetic acid;

N-cyclopropyl-4-(1-phenyl-2,3-dihydro-1H-benzo[d]pyrrolo[1,2-a]imidazol-7-yl)benzamide;

4-(1-phenyl-2,3-dihydro-1H-benzo[d]pyrrolo[1,2-a]imidazol-7-yl)benzamide;

1-(4-(5-(4-phenyl-3,4-dihydro-1H-benzo[4,5]imidazo[2,1-c][1,4]oxazin-7-yl)pyridin-2-yl)piperazin-1-yl)ethanone;

7-(6-(4-methylpiperazin-1-yl)pyridin-3-yl)-1-phenyl-2,3-dihydro-1H-benzo[d]pyrrolo[1,2-a]imidazole;

7-(benzo[d][1,3]dioxol-5-yl)-1-phenyl-2,3-dihydro-1H-benzo[d]pyrrolo[1,2-a]imidazole;

9-(3-fluoro-2-methylphenyl)-2-(2-morpholinopyrimidin-5-yl)-6,7,8,9-tetrahydrobenzo[4,5]imidazo[1,2-a]pyridin-9-ol;

8-phenyl-2-(4-(pyrimidin-2-yl)piperazin-1-yl)-7,8-dihydro-6H-pyrrolo[2',1':2,3]imidazo[4,5-b]pyridine;

9-(4-fluorophenyl)-2-(2-morpholinopyrimidin-5-yl)-6,7,8,9-tetrahydrobenzo[4,5]imidazo[1,2-a]pyridin-9-ol;

7-(5-((S)-4-phenyl-3,4-dihydro-1H-benzo[4,5]imidazo[2,1-c][1,4]oxazin-7-yl)pyrimidin-2-yl)tetrahydro-1H-oxazolo[3,4-a]pyrazin-3 (5H)-one; 7

2-((5-(9-(2-methoxyphenyl)-6,7,8,9-tetrahydrobenzo[4,5]imidazo[1,2-a]pyridin-2-yl)pyrimidin-2-yl)amino)acetic acid;

10-(4-fluorophenyl)-2-(2-morpholinopyrimidin-5-yl)-7,8,9,10-tetrahydro-6H-cyclohepta [4,5]imidazo[1,2-a]pyridin-10-ol;

9-(3-chlorophenyl)-2-(2-morpholinopyrimidin-5-yl)-6,7,8,9-tetrahydrobenzo[4,5]imidazo[1,2-a]pyridin-9-ol;

N-cyclopropyl-5-(4-phenyl-3,4-dihydro-1H-benzo[4,5]imidazo[2,1-c][1,4]oxazin-7-yl)pyrimidin-2-amine;

9-(3-chloro-5-fluorophenyl)-2-(2-morpholinopyrimidin-5-yl)-6,7,8,9-tetrahydrobenzo[4,5]imidazo[1,2-a]pyridin-9-ol;

N,N-dimethyl-5-(4-phenyl-3,4-dihydro-1H-benzo[4,5]imidazo[2,1-c][1,4]oxazin-7-yl)pyrimidin-2-amine;

1-(5-(1-phenyl-1,2,3,4-tetrahydrobenzo[4,5]imidazo[1,2-a]pyridin-8-yl)pyrimidin-2-yl)piperidine-4-carboxylic acid;

7-(6-isopropoxypyridin-3-yl)-4-phenyl-3,4-dihydro-1H-benzo[4,5]imidazo[2,1-c][1,4]oxazine;

7-(6-isopropoxypyridin-3-yl)-4-phenyl-3,4-dihydro-1H-benzo[4,5]imidazo[2,1-c][1,4]oxazine;

4-(5-(6-phenyl-7,8-dihydro-6H-pyrrolo[1',2':1,2]imidazo[4,5-c]pyridin-3-yl)pyrimidin-2-yl)morpholine;

1-phenyl-7-(1-(pyridin-3-ylmethyl)-1H-pyrazol-4-yl)-2,3-dihydro-1H-benzo[d]pyrrolo[1,2-a]imidazole;

5-(4-phenyl-3,4-dihydro-1H-benzo[4,5]imidazo[2,1-c][1,4]oxazin-7-yl)picolinonitrile;

7-(4-methyl-3,4-dihydro-2H-pyrido[3,2-b][1,4]oxazin-7-yl)-4-phenyl-3,4-dihydro-1H-benzo[4,5]imidazo[2,1-c][1,4]oxazine;

2-(2-morpholinopyrimidin-5-yl)-9-(p-tolyl)-6,7,8,9-tetrahydrobenzo[4,5]imidazo[1,2-a]pyridin-9-ol;

7-(6-(methylsulfonyl)pyridin-3-yl)-4-phenyl-3,4-dihydro-1H-benzo[4,5]imidazo[2,1-c][1,4]oxazine;

N-(2-methoxyethyl)-4-(1-phenyl-2,3-dihydro-1H-benzo[d]pyrrolo[1,2-a]imidazol-7-yl)benzamide;

N-methyl-4-(1-phenyl-2,3-dihydro-1H-benzo[d]pyrrolo[1,2-a]imidazol-7-yl)benzamide;

4-phenyl-7-(6-(2,2,2-trifluoroethoxy)pyridin-3-yl)-3,4-dihydro-1H-benzo[4,5]imidazo[2,1-c][1,4]oxazine;

1-(5-(4-phenyl-3,4-dihydro-1H-benzo[4,5]imidazo[2,1-c][1,4]oxazin-7-yl)pyrimidin-2-yl)piperidine-4-carboxylic acid;

7-(5-methyl-6-(4-methylpiperazin-1-yl)pyridin-3-yl)-4-phenyl-3,4-dihydro-1H-benzo[4,5]imidazo[2,1-c][1,4]oxazine;

5-(9-(2-methoxyphenyl)-6,7,8,9-tetrahydrobenzo[4,5]imidazo[1,2-a]pyridin-2-yl)thiophene-2-carboxylic acid;

7-(6-(4-methylpiperazin-1-yl)pyridin-3-yl)-4-phenyl-3,4-dihydro-1H-benzo[4,5]imidazo[2,1-c][1,4]oxazine;

(S)-7-(2-(1'-methyl-[4,4'-bipiperidin]-1-yl)pyrimidin-5-yl)-4-phenyl-3,4-dihydro-1H-benzo[4,5]imidazo[2,1-c][1,4]oxazine;

7-(2-methoxypyrimidin-5-yl)-4-phenyl-3,4-dihydro-1H-benzo[4,5]imidazo[2,1-c][1,4]oxazine;

10-(3-chloro-5-fluorophenyl)-2-(2-morpholinopyrimidin-5-yl)-7,8,9,10-tetrahydro-6H-cyclohepta [4,5]imidazo[1,2-a]pyridin-10-ol;

3-(2-hydroxyethyl)-1-(5-((S)-4-phenyl-3,4-dihydro-1H-benzo[4,5]imidazo[2,1-c][1,4]oxazin-7-yl)pyrimidin-2-yl)pyrrolidin-3-ol;

4-(5-(9-(2-methoxyphenyl)-6,7-dihydrobenzo[4,5]imidazo[1,2-a]pyridin-2-yl)pyrimidin-2-yl)morpholine;

10-(4-methoxyphenyl)-2-(2-morpholinopyrimidin-5-yl)-7,8,9,10-tetrahydro-6H-cyclohepta [4,5]imidazo[1,2-a]pyridin-10-ol;

7-(5-(1H-pyrazol-1-yl)pyrazin-2-yl)-4-phenyl-3,4-dihydro-1H-benzo[4,5]imidazo[2,1-c][1,4]oxazine;

1-phenyl-7-(pyridin-3-yl)-2,3-dihydro-1H-benzo[d]pyrrolo[1,2-a]imidazole;

5-(1-phenyl-2,3-dihydro-1H-benzo[d]pyrrolo[1,2-a]imidazol-7-yl)pyrimidin-2-amine;

2-(2-morpholinopyrimidin-5-yl)-10-(p-tolyl)-7,8,9,10-tetrahydro-6H-cyclohepta[4,5]imidazo[1,2-a]pyridin-10-ol;

5-(4-phenyl-3,4-dihydro-1H-benzo[4,5]imidazo[2,1-c][1,4]oxazin-7-yl)pyrimidine-2-carbonitrile;

(R)-2-(5-(9-(2-methoxyphenyl)-6,7,8,9-tetrahydrobenzo[4,5]imidazo[1,2-a]pyridin-2-yl)pyrimidin-2-yl)propan-2-ol;

(S)-7-(2-((R)-3-(methylsulfonyl)pyrrolidin-1-yl)pyrimidin-5-yl)-4-phenyl-3,4-dihydro-1H-benzo[4,5]imidazo[2,1-c][1,4]oxazine;

7-([1,2,5]oxadiazolo[3,4-b]pyridin-6-yl)-4-phenyl-3,4-dihydro-1H-benzo[4,5]imidazo[2,1-c][1,4]oxazine;

2-(5-(6-phenyl-7,8-dihydro-6H-pyrrolo[1',2':1,2]imidazo[4,5-c]pyridin-3-yl)pyrimidin-2-yl)propan-2-ol;

7-(2-methylpyrimidin-5-yl)-4-phenyl-3,4-dihydro-1H-benzo[4,5]imidazo[2,1-c][1,4]oxazine;

1-phenyl-7-(pyrimidin-5-yl)-2,3-dihydro-1H-benzo[d]pyrrolo[1,2-a]imidazole;

7-(6-methoxy-5-methylpyridin-3-yl)-4-phenyl-3,4-dihydro-1H-benzo[4,5]imidazo[2,1-c][1,4]oxazine;

10-(4-chlorophenyl)-2-(2-morpholinopyrimidin-5-yl)-7,8,9,10-tetrahydro-6H-cyclohepta [4,5]imidazo[1,2-a]pyridin-10-ol;

2-(3-(1-phenyl-2,3-dihydro-1H-benzo[d]pyrrolo[1,2-a]imidazol-7-yl)phenyl)acetonitrile;

N-(3-(1-phenyl-2,3-dihydro-1H-benzo[d]pyrrolo[1,2-a]imidazol-7-yl)benzyl)methanesulfonamide;

7-(6-methylpyridin-3-yl)-4-phenyl-3,4-dihydro-1H-benzo[4,5]imidazo[2,1-c][1,4]oxazine;

(S)-2-(5-(1-phenyl-1,2,3,4-tetrahydrobenzo[4,5]imidazo[1,2-a]pyridin-8-yl)pyrimidin-2-yl)propan-2-ol;

(S)-7-(2-(4-(1-methylpiperidin-4-yl)piperazin-1-yl)pyrimidin-5-yl)-4-phenyl-3,4-dihydro-1H-benzo[4,5]imidazo[2,1-c][1,4]oxazine;

4-phenyl-7-(6-(piperazin-1-yl)pyridin-3-yl)-3,4-dihydro-1H-benzo[4,5]imidazo[2,1-c][1,4]oxazine;

(4S)-7-(2-(3-(methylsulfonyl)pyrrolidin-1-yl)pyrimidin-5-yl)-4-phenyl-3,4-dihydro-1H-benzo[4,5]imidazo[2,1-c][1,4]oxazine;

(S)-8-(5-(4-phenyl-3,4-dihydro-1H-benzo[4,5]imidazo[2,1-c][1,4]oxazin-7-yl)pyrimidin-2-yl)-1,3,8-triazaspiro[4.5]decan-4-one;

7-(6-isopropoxy-5-methylpyridin-3-yl)-4-phenyl-3,4-dihydro-1H-benzo[4,5]imidazo[2,1-c][1,4]oxazine;

7-(5-methylpyridin-3-yl)-1-phenyl-2,3-dihydro-1H-benzo[d]pyrrolo[1,2-a]imidazole;

N-methyl-3-(1-phenyl-2,3-dihydro-1H-benzo[d]pyrrolo[1,2-a]imidazol-7-yl)benzamide;

4-(1-phenyl-2,3-dihydro-1H-benzo[d]pyrrolo[1,2-a]imidazol-7-yl)-N-((tetrahydrofuran-2-yl)methyl)benzamide;

(S)-4-(5-(1-phenyl-2,3-dihydro-1H-benzo[d]pyrrolo[1,2-a]imidazol-7-yl)pyrimidin-2-yl)morpholine;

N-(5-(4-phenyl-3,4-dihydro-1H-benzo[4,5]imidazo[2,1-c][1,4]oxazin-7-yl)pyridin-2-yl)acetamide;

N-ethyl-N-methyl-3-(1-phenyl-2,3-dihydro-1H-benzo[d]pyrrolo[1,2-a]imidazol-7-yl)benzamide;

5-(1-phenyl-2,3-dihydro-1H-benzo[d]pyrrolo[1,2-a]imidazol-7-yl)pyridin-2-amine;

7-(3-methyl-3H-imidazo[4,5-b]pyridin-6-yl)-4-phenyl-3,4-dihydro-1H-benzo[4,5]imidazo[2,1-c][1,4]oxazine;

10-(3,5-dimethoxyphenyl)-2-(2-morpholinopyrimidin-5-yl)-7,8,9,10-tetrahydro-6H-cyclohepta[4,5]imidazo[1,2-a]pyridin-10-ol;

N,N-dimethyl-3-((5-(4-phenyl-3,4-dihydro-1H-benzo[4,5]imidazo[2,1-c][1,4]oxazin-7-yl)pyridin-2-yl)oxy)propan-1-amine;

(3R,4R)-1-(5-((S)-4-phenyl-3,4-dihydro-1H-benzo[4,5]imidazo[2,1-c][1,4]oxazin-7-yl)pyrimidin-2-yl)pyrrolidine-3,4-diol;

N-(2-(dimethylamino)ethyl)-3-(1-phenyl-2,3-dihydro-1H-benzo[d]pyrrolo[1,2-a]imidazol-7-yl)benzamide;

10-(3-methoxyphenyl)-2-(2-morpholinopyrimidin-5-yl)-7,8,9,0-tetrahydro-6H-cyclohepta[4,5]imidazo[1,2-a]pyridin-10-ol;

7-(1,5-dimethyl-H-pyrazol-4-yl)-1-phenyl-2,3-dihydro-1H-benzo[d]pyrrolo[,2-a]imidazole;

N,N-dimethyl-3-(1-phenyl-2,3-dihydro-1H-benzo[d]pyrrolo[1,2-a]imidazol-7-yl)benzamide;

7-(3-(methylsulfonyl)phenyl)-1-phenyl-2,3-dihydro-1H-benzo[d]pyrrolo[1,2-a]imidazole;

4-phenyl-7-(pyrido[2,3-b]pyrazin-7-yl)-3,4-dihydro-1H-benzo[4,5]imidazo[2,1-c][1,4]oxazine;

1-methyl-5-(1-phenyl-2,3-dihydro-1H-benzo[d]pyrrolo[1,2-a]imidazol-7-yl)pyridin-2(1H)-one;

(3 S,4S)-1-(5-((S)-4-phenyl-3,4-dihydro-1H-benzo[4,5]imidazo[2,1-c][1,4]oxazin-7-yl)pyrimidin-2-yl)pyrrolidine-3,4-diol;

4-phenyl-7-(pyrimidin-5-yl)-3,4-dihydro-1H-benzo[4,5]imidazo[2,1-c][1,4]oxazine;

(S)-2-(5-(1-(2-Methoxyphenyl)-2,3-dihydro-H-cyclopenta[4,5]imidazo[1,2-a]pyridin-7-yl)pyrimidin-2-yl)propan-2-ol;

(S)-2-(5-(1-phenyl-2,3-dihydro-1H-benzo[d]pyrrolo[1,2-a]imidazol-7-yl)pyrimidin-2-yl)propan-2-ol;

2-(2-(2-(2-hydroxypropan-2-yl)pyrimidin-5-yl)-6,7,8,9-tetrahydrobenzo[4,5]imidazo[1,2-a]pyridin-9-yl)phenol;

4-(5-(6-phenyl-6,7,8,9-tetrahydroimidazo[1,2-a:4,5-b']dipyridin-3-yl)pyrimidin-2-yl)piperazin-2-one;

(S)-7-(2-(3-morpholinoazetidin-1-yl)pyrimidin-5-yl)-4-phenyl-3,4-dihydro-1H-benzo[4,5]imidazo[2,1-c][1,4]oxazine;

7-(5-(methylsulfonyl)pyridin-3-yl)-1-phenyl-2,3-dihydro-1H-benzo[d]pyrrolo[1,2-a]imidazole;

(R)-7-(2-morpholinopyrimidin-5-yl)-4-phenyl-3,4-dihydro-1H-benzo[4,5]imidazo[2,1-c][1,4]oxazine;

7-(2-methylpyridin-3-yl)-1-phenyl-2,3-dihydro-1H-benzo[d]pyrrolo[1,2-a]imidazole;

1-(5-(1-phenyl-1,2,3,4-tetrahydrobenzo[4,5]imidazo[1,2-a]pyridin-8-yl)pyrimidin-2-yl)azetidine-3-carboxylic acid;

7-(1-methyl-1H-pyrrol-3-yl)-1-phenyl-2,3-dihydro-1H-benzo[d]pyrrolo[1,2-a]imidazole;

N-(2-morpholinoethyl)-5-(4-phenyl-3,4-dihydro-H-benzo[4,5]imidazo[2,1-c][1,4]oxazin-7-yl)pyridin-2-amine. Compounds of the invention also include 3,3-difluoro-1-(5-((R)-1-phenyl-2,3-dihydro-1H-benzo[d]pyrrolo[1,2-a]imidazol-7-yl)pyrimidin-2-yl)piperidin-4-ol;

(S)-2-(5-(4-(2-(difluoromethoxy)phenyl)-3,4-dihydro-1H-benzo[4,5]imidazo[2,1-c][1,4]oxazin-7-yl)pyrimidin-2-yl)propan-2-ol;

(S)-2-(5-(9-(2-methoxyphenyl)-6,7,8,9-tetrahydrobenzo[4,5]imidazo[,2-a]pyridin-2-yl)pyrimidin-2-yl)propan-2-ol;

(R)-7-(5-(1-phenyl-2,3-dihydro-1H-benzo[d]pyrrolo[1,2-a]imidazol-7-yl)pyrimidin-2-yl)-7-azaspiro[3.5]nonan-2-ol;

1-(5-(8-(2,5-dimethylphenyl)-7,8-dihydro-6H-pyrrolo[2',1':2,3]imidazo[4,5-b]pyridin-2-yl)pyrimidin-2-yl)piperidin-4-ol;

4-(5-(10-(2-methoxyphenyl)-7,8,9,10-tetrahydro-6H-cyclohepta[4,5]imidazo[1,2-a]pyridin-2-yl)pyrimidin-2-yl)morpholine;

(R)-4-(5-(1-phenyl-2,3-dihydro-1H-benzo[d]pyrrolo[1,2-a]imidazol-7-yl)pyrimidin-2-yl)morpholine;

7-(5-((S)-4-phenyl-3,4-dihydro-1H-benzo[4,5]imidazo[2,1-c][1,4]oxazin-7-yl)pyrimidin-2-yl)hexahydroimidazo[1,5-a]pyrazin-3(2H)-one;

7-(5-((S)-4-phenyl-3,4-dihydro-1H-benzo[4,5]imidazo[2,1-c][1,4]oxazin-7-yl)pyrimidin-2-yl)hexahydroimidazo[1,5-a]pyrazin-3(2H)-one;

4-(5-(8-(2,5-dimethylphenyl)-7,8-dihydro-6H-pyrrolo[2',1':2,3]imidazo[4,5-b]pyridin-2-yl)pyrimidin-2-yl)piperazin-2-one;

2-(5-(1-(2,5-dimethylphenyl)-2,3-dihydro-H-benzo[d]pyrrolo[1,2-a]imidazol-7-yl)pyrimidin-2-yl)propan-2-ol;

3,3-difluoro-1-(5-((S)-4-phenyl-3,4-dihydro-1H-benzo[4,5]imidazo[2,1-c][1,4]oxazin-7-yl)pyrimidin-2-yl)piperidin-4-ol;

7-(5-(4-(3-fluorophenyl)-3,4-dihydro-1H-benzo[4,5]imidazo[2,1-c][1,4]oxazin-7-yl)pyrimidin-2-yl)hexahydroimidazo[1,5-a]pyrazin-3(2H)-one;

(R)-2-(5-(1-(2-methoxyphenyl)-2,3-dihydro-H-cyclopenta[4,5]imidazo[1,2-a]pyridin-7-yl)pyrimidin-2-yl)propan-2-ol;

7-(4-(isopropylsulfonyl)phenyl)-1-phenyl-2,3-dihydro-1H-benzo[d]pyrrolo[1,2-a]imidazole;

2-(5-(9-(2-methoxyphenyl)-6,7,8,9-tetrahydrobenzo[4,5]imidazo[1,2-a]pyridin-2-yl)pyrimidin-2-yl)propan-2-ol;

4-(5-(8-(2,5-dimethylphenyl)-7,8-dihydro-6H-pyrrolo[2',1':2,3]imidazo[4,5-b]pyridin-2-yl)pyrimidin-2-yl)morpholine;

(S)-7-(5-(4-phenyl-3,4-dihydro-1H-benzo[4,5]imidazo[2,1-c][1,4]oxazin-7-yl)pyrimidin-2-yl)-7-azaspiro[3.5]nonan-2-ol;

4-(5-(9-(2-methoxyphenyl)-6,7,8,9-tetrahydrobenzo[4,5]imidazo[1,2-a]pyridin-2-yl)pyrimidin-2-yl)morpholine;

1-(5-(9-phenyl-6,7,8,9-tetrahydroimidazo[1,2-a:5,4-b']dipyridin-2-yl)pyrimidin-2-yl)piperidin-4-ol;

(R)-2-(5-(1-phenyl-2,3-dihydro-1H-benzo[d]pyrrolo[1,2-a]imidazol-7-yl)pyrimidin-2-yl)propan-2-ol;

2-(5-(10-(2-methoxyphenyl)-7,8,9,10-tetrahydro-6H-cyclohepta[4,5]imidazo[1,2-a]pyridin-2-yl)pyrimidin-2-yl)propan-2-ol;

N-methyl-4-(1-phenyl-2,3-dihydro-1H-benzo[d]pyrrolo[1,2-a]imidazol-7-yl)benzenesulfonamide;
(S)-7-(2-morpholinopyrimidin-5-yl)-4-phenyl-3,4-dihydro-1H-benzo[4,5]imidazo[2,1-c][1,4]oxazine;
(S)-7-(5-(4-phenyl-3,4-dihydro-1H-benzo[4,5]imidazo[2,1-c][1,4]oxazin-7-yl)pyrimidin-2-yl)-7-azaspiro[3.5]nonan-2-ol;
2-(5-(1-(2-methoxyphenyl)-2,3-dihydro-1H-cyclopenta[4,5]imidazo[1,2-a]pyridin-7-yl)pyrimidin-2-yl)propan-2-ol;
(R)-2-(5-(1-phenyl-1,2,3,4-tetrahydrobenzo[4,5]imidazo[1,2-a]pyridin-8-yl)pyrimidin-2-yl)propan-2-ol;
ethyl 2-[[5-[9-(2-methoxyphenyl)-6,7,8,9-tetrahydropyrido[1,2-a]benzimidazol-2-yl]pyrimidin-2-yl]amino]acetate; or
2-((5-(9-(2-methoxyphenyl)-6,7,8,9-tetrahydrobenzo[4,5]imidazo[1,2-a]pyridin-2-yl)pyridin-2-yl)oxy)acetic acid.

In another embodiment the invention includes a compound of Formula (I):

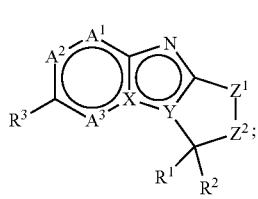

(I)

or a pharmaceutically acceptable salt, prodrug or stereoisomer thereof, wherein:

$R^1$ is H, $OR^4$, $N(R^4)_2$ or optionally substituted $(C_1-C_3)$ alkyl;

$R^2$ is optionally substituted $(C_1-C_3)$alkyl, or optionally substituted aryl; or $R^1$ and $R^2$ together can form an optionally substituted saturated or partially saturated carbocyclic or optionally substituted saturated or partially saturated heterocyclic ring;

$A^1$, $A^2$, and $A^3$ are independently $C(R^{A2})$ or N, provided that at least one is $C(R^{A2})$;

X is N and Y is C, wherein:
$Z^1$ is —$C(R^z)_2$— or —O— and $Z^2$ is —$C(R^z)_2$; or
$Z^1$ is —$CH_2$— or —O— and $Z^2$ is —$Z^{2a}$—$Z^{2b}$—,
wherein $Z^{2a}$ is attached to $Z^1$ and $Z^{2b}$ is attached to $C(R^1)(R^2)$; and
$Z^{2a}$ and $Z^{2b}$ are independently —$C(R^z)_2$ or —O—, provided that neither $Z^{2a}$ nor $Z^{2b}$ is —O— when $Z^1$ is —O—;

or

X is C and Y is N wherein:
$Z^1$ is —$C(R^z)_2$— and $Z^2$ is —$C(R^z)_2$; or
$Z^1$ is —$C(R^z)_2$— and $Z^2$ is $Z^2$ is —$Z^{2a}$—$Z^{2b}$—;
wherein $Z^{2a}$ is attached to $Z^1$ and $Z^{2b}$ is attached to $C(R^1)(R^2)$; and
$Z^{2a}$ and $Z^{2b}$ are independently —$C(R^z)_2$ or —O—;

$R^3$ is —$R^{3a}$—$R^{3b}$, wherein:
$R^{3a}$ is an optionally substituted aryl, optionally substituted saturated or partially saturated heterocyclyl, or optionally substituted heteroaryl;

$R^{3b}$ is H, —$N(R^a)(R^b)$, —C(O)-optionally substituted $(C_1-C_3)$alkyl, —C(O)-optionally substituted heterocyclyl, —$O(R^a)$, —$S(O)_2(C_1-C_3)$alkyl, —$(C(R^e)_2)_q$-optionally substituted cycloalkyl; or —$C(R^e)_q$-optionally substituted heterocyclyl;

$R^4$ is independently H or optionally substituted $(C_1-C_3)$alkyl;

$R^a$ and $R^b$ are independently selected from H, optionally substituted $(C_1-C_5)$alkyl, —$(CH_2)_p$—$(C_3-C_6)$cycloalkyl and —$(CH_2)_p$-optionally substituted heterocyclyl;

$R^e$ is independently H, OH or $CH_3$;
$R^{A2}$ is independently H, $CF_3$, halo or $(C_1-C_3)$alkyl;
$R^z$ is independently H, F, $CF_3$, —OH or $(C_1-C_3)$alkyl;
$R^{z1}$ is independently H, OH or $(C_1-C_3)$alkyl;
p is independently 0, 1 or 2; and
q is independently 0, 1 or 2.

In another embodiment, the invention includes the compound of any of the foregoing embodiments, wherein $R^2$ is optionally substituted $(C_1-C_3)$alkyl or phenyl, each of which is independently optionally substituted with 1 to 3 groups independently selected from —$OR^a$, and —$(C_1-C_6)$alkylene-$OR^a$, wherein $R^a$ is H or —$(C_1-C_6)$alkyl; and $R^1$ is H, or optionally substituted $(C_1-C_3)$alkyl; or
$R^1$ and $R^2$ together form an optionally substituted spirocycle selected from

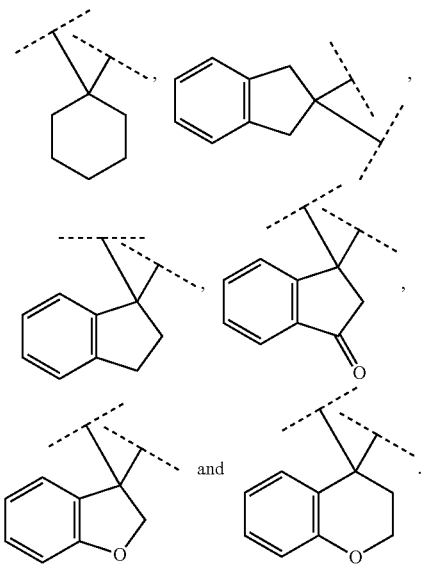

In another embodiment the invention includes the compound according to any of the foregoing embodiments wherein the compound is a compound of Formula (Ia) or Formula (Ib)

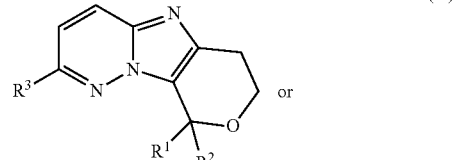

(Ia)

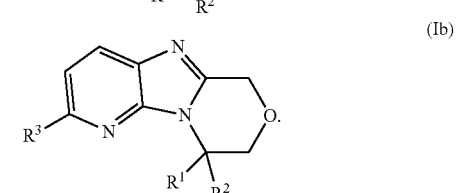

(Ib)

In another embodiment the invention includes the compound according to any of the foregoing embodiments wherein R³ᵃ is optionally substituted pyridinyl, 1,2,3,6-tetrahydropyridinyl, optionally substituted pyrimidinyl, optionally substituted tetrahydropyridinyl or 1H-pyrrolyl.

In another embodiment the invention includes the compound according to any of the foregoing embodiments wherein R¹ and R² together form an optionally substituted spirocycle selected from

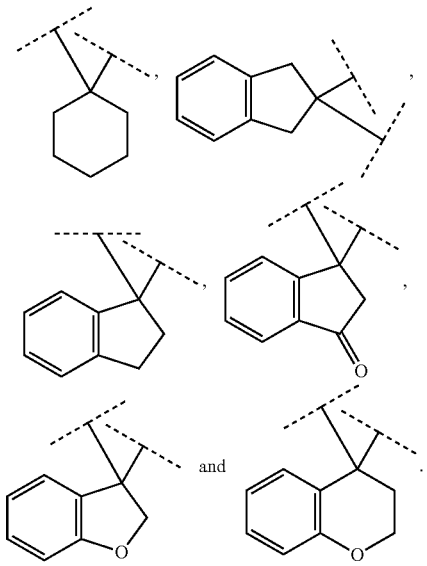

and .

In another embodiment the invention includes the compound according to any of the foregoing embodiments wherein $R^{3b}$ is H, —C(O)-optionally substituted ($C_1$-$C_3$) alkyl, —C(O)-optionally substituted piperidinyl, optionally substituted ($C_1$-$C_4$)alkyl, —N(H)-optionally substituted ($C_1$-$C_3$)alkyl, —N(H)-optionally substituted cyclobutyl, —N(H)-optionally substituted tetrayhydrofuranyl, —O-optionally substituted ($C_1$-$C_3$)alkyl, —O-optionally substituted cyclohexyl, —O-optionally substituted cyclopentyl, —O-optionally substituted tetrahydropyranyl, —S(O)$_2$-optionally substituted ($C_1$-$C_3$)alkyl, -optionally substituted azepanyl, optionally substituted azetidinyl, optionally substituted diazepanyl, optionally substituted hexahydroimidazo[1,5-a]pyrazin-3(2H)-one, optionally substituted morpholinyl, 1,4-oxazepanyl, optionally substituted piperazinyl, optionally substituted piperidinyl or optionally substituted pyrrolidinyl.

In another embodiment compounds of the invention include
(8aR)-7-(5-(6',8'-dihydro-2H-spiro[benzofuran-3,9'-pyrido[3',2':4,5]imidazo[2,1-c][1,4]oxazin]-2'-yl)pyrimidin-2-yl)hexahydroimidazo[1,5-a]pyrazin-3(2H)-one;
3-((5-(6',8'-dihydro-2H-spiro[benzofuran-3,9'-pyrido[3',2':4,5]imidazo[2,1-c][1,4]oxazin]-2'-yl)pyrimidin-2-yl)amino)cyclobutanol;
5-(6',8'-dihydro-2H-spiro[benzofuran-3,9'-pyrido[3',2':4,5]imidazo[2,1-c][1,4]oxazin]-2'-yl)-N-(tetrahydrofuran-3-yl)pyrimidin-2-amine;
1-(5-(6',8'-dihydro-2H-spiro[benzofuran-3,9'-pyrido[3',2':4,5]imidazo[2,1-c][1,4]oxazin]-2'-yl)pyrimidin-2-yl)piperidin-3-ol;
2'-(2-(4-methylpiperazin-1-yl)pyrimidin-5-yl)-6',8'-dihydro-2H-spiro[benzofuran-3,9'-pyrido[3',2':4,5]imidazo[2,1-c][1,4]oxazine];
2'-(2-Morpholinopyrimidin-5-yl)-6',8'-dihydro-2H-spiro[benzofuran-3,9'-pyrido[3',2':4,5]imidazo[2,1-c][1,4]oxazine];
1-(5-(1,2',3,3'-tetrahydrospiro[benzo[4,5]imidazo[2,1-c][1,4]oxazine-4,1'-inden]-7-yl)pyrimidin-2-yl)piperidin-4-ol;
(1-(5-(2,3,6',8'-tetrahydrospiro[indene-1,9'-pyrido[3',2':4,5]imidazo[2,1-c][1,4]oxazin]-2'-yl)pyrimidin-2-yl)piperidin-3-yl)methanol;
(8aS)-7-(5-(2,3,6',8'-tetrahydrospiro[indene-1,9'-pyrido[3',2':4,5]imidazo[2,1-c][1,4]oxazin]-2'-yl)pyrimidin-2-yl)hexahydroimidazo[1,5-a]pyrazin-3 (2H)-one;
2'-(2-(1,4-oxazepan-4-yl)pyrimidin-5-yl)-2,3,6',8'-tetrahydrospiro[indene-1,9'-pyrido[3',2':4,5]imidazo[2, 1-c][1,4]oxazine]; 0
3,3-difluoro-1-(5-(2,3,6',8'-tetrahydrospiro[indene-1,9'-pyrido[3',2':4,5]imidazo[2,1-c][1,4]oxazin]-2'-yl)pyrimidin-2-yl)piperidin-4-ol;
2-hydroxy-1-(4-(5-(2,3,6',8'-tetrahydrospiro[indene-1,9'-pyrido[3',2':4,5]imidazo[2,1-c][1,4]oxazin]-2'-yl)pyrimidin-2-yl)piperazin-1-yl)propan-1-one;
2-hydroxy-1-(4-(5-(2,3,6',8'-tetrahydrospiro[indene-1,9'-pyrido[3',2':4,5]imidazo[2,1-c][1,4]oxazin]-2'-yl)pyrimidin-2-yl)piperazin-1-yl)ethanone;
(4-fluoro-1-(5-(2,3,6',8'-tetrahydrospiro[indene-1,9'-pyrido[3',2':4,5]imidazo[2,1-c][1,4]oxazin]-2'-yl)pyrimidin-2-yl)piperidin-4-yl)methanol;
2'-(2-morpholinopyrimidin-5-yl)-2,3,6',8'-tetrahydrospiro[indene-1,9'-pyrido[3',2':4,5]imidazo[2, 1-c][1,4]oxazine];
1-(5-(2,3,6',8'-tetrahydrospiro[indene-1,9'-pyrido[3',2':4,5]imidazo[2,1-c][1,4]oxazin]-2'-yl)pyrimidin-2-yl)azepan-4-ol; 0
(S)-2-(5-(6',8'-dihydrospiro[chroman-4,9'-pyrido[3',2':4,5]imidazo[2,1-c][1,4]oxazin]-2'-yl)pyrimidin-2-yl)propan-2-ol;
(R)-2-(5-(6',8'-dihydrospiro[chroman-4,9'-pyrido[3',2':4,5]imidazo[2,1-c][1,4]oxazin]-2'-yl)pyrimidin-2-yl)propan-2-ol;
(8aR)-7-(5-(6',8'-dihydro-2H-spiro[benzofuran-3,9'-pyrido[3',2':4,5]imidazo[2,1-c][1,4]oxazin]-2'-yl)pyrimidin-2-yl)hexahydroimidazo[1,5-a]pyrazin-3(2H)-one;
3-((5-(6',8'-dihydro-2H-spiro[benzofuran-3,9'-pyrido[3',2':4,5]imidazo[2,1-c][1,4]oxazin]-2'-yl)pyrimidin-2-yl)amino)cyclobutanol;
5-(6',8'-dihydro-2H-spiro[benzofuran-3,9'-pyrido[3',2':4,5]imidazo[2,1-c][1,4]oxazin]-2'-yl)-N-(tetrahydrofuran-3-yl)pyrimidin-2-amine;
1-(5-(6',8'-dihydro-2H-spiro[benzofuran-3,9'-pyrido[3',2':4,5]imidazo[2,1-c][1,4]oxazin]-2'-yl)pyrimidin-2-yl)piperidin-3-ol;
2'-(2-(4-methylpiperazin-1-yl)pyrimidin-5-yl)-6',8'-dihydro-2H-spiro[benzofuran-3,9'-pyrido[3',2':4,5]imidazo[2,1-c][1,4]oxazine];
2'-(2-Morpholinopyrimidin-5-yl)-6',8'-dihydro-2H-spiro[benzofuran-3,9'-pyrido[3',2':4,5]imidazo[2,1-c][1,4]oxazine];
1-(5-(1,2',3,3'-Tetrahydrospiro[benzo[4,5]imidazo[2,1-c][1,4]oxazine-4,1'-inden]-7-yl)pyrimidin-2-yl)piperidin-4-ol;
(1-(5-(2,3,6',8'-tetrahydrospiro[indene-1,9'-pyrido[3',2':4,5]imidazo[2,1-c][1,4]oxazin]-2'-yl)pyrimidin-2-yl)piperidin-3-yl)methanol;
(8aR)-7-(5-(2,3,6',8'-tetrahydrospiro[indene-1,9'-pyrido[3',2':4,5]imidazo[2,1-c][1,4]oxazin]-2'-yl)pyrimidin-2-yl)hexahydroimidazo[1,5-a]pyrazin-3(2H)-one;
2'-(2-(1,4-oxazepan-4-yl)pyrimidin-5-yl)-2,3,6',8'-tetrahydrospiro[indene-1,9'-pyrido[3',2':4,5]imidazo[2,1-c][1,4]oxazine];
3,3-difluoro-1-(5-(2,3,6',8'-tetrahydrospiro[indene-1,9'-pyrido[3',2':4,5]imidazo[2,1-c][1,4]oxazin]-2'-yl)pyrimidin-2-yl)piperidin-4-ol;

2-hydroxy-1-(4-(5-(2,3,6',8'-tetrahydrospiro[indene-1,9'-pyrido[3',2':4,5]imidazo[2,1-c][1,4]oxazin]-2'-yl)pyrimidin-2-yl)piperazin-1-yl)propan-1-one;

2-hydroxy-1-(4-(5-(2,3,6',8'-tetrahydrospiro[indene-1,9'-pyrido[3',2':4,5]imidazo[2,1-c][1,4]oxazin]-2'-yl)pyrimidin-2-yl)piperazin-1-yl)ethanone;

(4-fluoro-1-(5-(2,3,6',8'-tetrahydrospiro[indene-1,9'-pyrido[3',2':4,5]imidazo[2,1-c][1,4]oxazin]-2'-yl)pyrimidin-2-yl)piperidin-4-yl)methanol;

2'-(2-morpholinopyrimidin-5-yl)-2,3,6',8'-tetrahydrospiro[indene-1,9'-pyrido[3',2':4,5]imidazo[2,1-c][1,4]oxazine];

1-(5-(2,3,6',8'-tetrahydrospiro[indene-1,9'-pyrido[3',2':4,5]imidazo[2,1-c][1,4]oxazin]-2'-yl)pyrimidin-2-yl)azepan-4-ol;

(R)-1-((4,4-Difluorocyclohexyl)methyl)-4-(8-phenyl-7,8-dihydro-6H-pyrrolo [2',1':2,3]imidazo[4,5-b]pyridin-2-yl)pyridin-2(1H)-one;

(1r,4r)-4-((4-(6',8'-dihydro-2H-spiro[benzofuran-3,9'-pyrido[3',2':4,5]imidazo[2,1-c][1,4]oxazin]-2'-yl)pyridin-2-yl)oxy)cyclohexanol;

(1s,4s)-4-((4-(6',8'-dihydro-2H-spiro[benzofuran-3,9'-pyrido[3',2':4,5]imidazo[2,1-c][1,4]oxazin]-2'-yl)pyridin-2-yl)oxy)cyclohexanol;

3-((4-(6',8'-dihydro-2H-spiro[benzofuran-3,9'-pyrido[3',2':4,5]imidazo[2,1-c][1,4]oxazin]-2'-yl)pyridin-2-yl)oxy)cyclopentanol;

2'-(2-morpholinopyrimidin-5-yl)-6',7'-dihydrospiro[cyclohexane-1,9'-pyrano[4',3':4,5]imidazo[1,2-b]pyridazine];

2'-(2-morpholinopyrimidin-5-yl)-6',7'-dihydrospiro[chroman-4,9'-pyrano[4',3':4,5]imidazo[1,2-b]pyridazine];

2'-(2-(piperazin-1-yl)pyrimidin-5-yl)-6'H,8'H-spiro[chromane-4,9'-pyrido[3',2':4,5]imidazo[2,1-c][1,4]oxazine];

2'-(2-methoxypyrimidin-5-yl)-6',8'-dihydrospiro[chroman-4,9'-pyrido[3',2':4,5]imidazo[2,1-c][1,4]oxazine];

2'-(2-ethoxypyrimidin-5-yl)-6',8'-dihydrospiro[chroman-4,9'-pyrido[3',2':4,5]imidazo[2,1-c][1,4]oxazine];

2'-(2-(methylsulfonyl)pyrimidin-5-yl)-6',8'-dihydrospiro[chroman-4,9'-pyrido[3',2':4,5]imidazo[2, 1-c][1,4]oxazine];

2'-(2-(1,4-diazepan-1-yl)pyrimidin-5-yl)-6',8'-dihydrospiro[chroman-4,9'-pyrido[3',2':4,5]imidazo[2, 1-c][1,4]oxazine];

5-(6',8'-dihydrospiro[chroman-4,9'-pyrido[3',2':4,5]imidazo[2,1-c][1,4]oxazin]-2'-yl)-N-isopropylpyrimidin-2-amine;

2'-(2-morpholinopyrimidin-5-yl)-6',8'-dihydrospiro[chroman-4,9'-pyrido[3',2':4,5]imidazo[2,1-c][1,4]oxazine];

2-(5-(6',8'-dihydrospiro[chroman-4,9'-pyrido[3',2':4,5]imidazo[2,1-c][1,4]oxazin]-2'-yl)pyrimidin-2-yl)propan-2-ol;

2'-(2-((tetrahydro-2H-pyran-4-yl)oxy)pyridin-4-yl)-6',8'-dihydrospiro[chroman-4,9'-pyrido[3',2':4,5]imidazo[2, 1-c][1,4]oxazine];

5-(6'H,8'H-Spiro[chromane-4,9'-pyrido[3',2':4,5]imidazo[2,1-c][1,4]oxazin]-2'-yl)-N-(tetrahydrofuran-3-yl)pyrimidin-2-amine;

(8aR)-7-(5-(6',8'-dihydrospiro[chroman-4,9'-pyrido[3',2':4,5]imidazo[2,1-c][1,4]oxazin]-2'-yl)pyrimidin-2-yl)hexahydroimidazo[1,5-a]pyrazin-3(2H)-one;

1-(5-(6',8'-dihydrospiro[chroman-4,9'-pyrido[3',2':4,5]imidazo[2,1-c][1,4]oxazin]-2'-yl)pyrimidin-2-yl)piperidin-4-ol;

1-(5-(6',8'-dihydrospiro[chroman-4,9'-pyrido[3',2':4,5]imidazo[2,1-c][1,4]oxazin]-2'-yl)pyrimidin-2-yl)piperidin-3-ol;

1-(5-(6',8'-dihydrospiro[chroman-4,9'-pyrido[3',2':4,5]imidazo[2,1-c][1,4]oxazin]-2'-yl)pyrimidin-2-yl)azetidin-3-ol;

1-(5-(6',8'-dihydrospiro[chroman-4,9'-pyrido[3',2':4,5]imidazo[2,1-c][1,4]oxazin]-2'-yl)pyrimidin-2-yl)pyrrolidin-3-ol;

3-((5-(6',8'-dihydrospiro[chroman-4,9'-pyrido[3',2':4,5]imidazo[2,1-c][1,4]oxazin]-2'-yl)pyrimidin-2-yl)amino)cyclobutanol;

1-(5-(6',8'-dihydrospiro[chroman-4,9'-pyrido[3',2':4,5]imidazo[2,1-c][1,4]oxazin]-2'-yl)pyrimidin-2-yl)-3-methylazetidin-3-ol;

2'-(2-(4-methylpiperazin-1-yl)pyrimidin-5-yl)-6',8'-dihydrospiro[chroman-4,9'-pyrido[3',2':4,5]imidazo[2, 1-c][1, 4]oxazine];

2'-(5,5-Dimethyl-2,5-dihydro-1H-pyrrol-3-yl)-2H,6'H,8'H-spiro[benzofuran-3,9'-pyrido[3',2':4,5]imidazo[2, 1-c][1, 4]oxazine];

2'-(2,5-dihydro-1H-pyrrol-3-yl)-6',8'-dihydro-2H-spiro[benzofuran-3,9'-pyrido[3',2':4,5]imidazo[2, 1-c][1,4]oxazine];

2'-(2-(piperazin-1-yl)pyrimidin-5-yl)-2H,6'H,8'H-spiro[benzofuran-3,9'-pyrido[3',2':4,5]imidazo[2, 1-c][1,4]oxazine];

2'-(2-((tetrahydro-2H-pyran-4-yl)oxy)pyridin-4-yl)-6',8'-dihydro-2H-spiro[benzofuran-3,9'-pyrido[3',2':4,5]imidazo[2, 1-c][1,4]oxazine];

2'-(2-methoxypyrimidin-5-yl)-6',8'-dihydro-2H-spiro[benzofuran-3,9'-pyrido[3',2':4,5]imidazo[2, 1-c][1,4]oxazine];

2-(tert-butoxy)-1-((2S)-4-(5-(6',8'-dihydro-2H-spiro[benzofuran-3,9'-pyrido[3',2':4,5]imidazo[2,1-c][1,4]oxazin]-2'-yl)pyrimidin-2-yl)-2-methylpiperazin-1-yl)ethanone;

2-(tert-butoxy)-1-((3 S)-4-(5-(6',8'-dihydro-2H-spiro[benzofuran-3,9'-pyrido[3',2':4,5]imidazo[2,1-c][1,4]oxazin]-2'-yl)pyrimidin-2-yl)-3-methylpiperazin-1-yl)ethanone;

2-(tert-butoxy)-1-((3R)-4-(5-(6',8'-dihydro-2H-spiro[benzofuran-3,9'-pyrido[3',2':4,5]imidazo[2,1-c][1,4]oxazin]-2'-yl)pyrimidin-2-yl)-3-methylpiperazin-1-yl)ethanone;

2-(tert-butoxy)-1-((2R)-4-(5-(6',8'-dihydro-2H-spiro[benzofuran-3,9'-pyrido[3',2':4,5]imidazo[2,1-c][1,4]oxazin]-2'-yl)pyrimidin-2-yl)-2-methylpiperazin-1-yl)ethanone;

1-((2S)-4-(5-(2H,6'H,8'H-Spiro[benzofuran-3,9'-pyrido[3',2':4,5]imidazo[2,1-c][1,4]oxazin]-2'-yl)pyrimidin-2-yl)-2-methylpiperazin-1-yl)-2-hydroxyethan-1-one 1-((3 S)-4-(5-(6',8'-dihydro-2H-spiro[benzofuran-3,9'-pyrido[3',2':4,5]imidazo[2,1-c][1,4]oxazin]-2'-yl)pyrimidin-2-yl)-3-methylpiperazin-1-yl)-2-hydroxyethanone;

1-((3R)-4-(5-(6',8'-dihydro-2H-spiro[benzofuran-3,9'-pyrido[3',2':4,5]imidazo[2,1-c][1,4]oxazin]-2'-yl)pyrimidin-2-yl)-3-methylpiperazin-1-yl)-2-hydroxyethanone;

1-((2R)-4-(5-(6',8'-dihydro-2H-spiro[benzofuran-3,9'-pyrido[3',2':4,5]imidazo[2,1-c][1,4]oxazin]-2'-yl)pyrimidin-2-yl)-2-methylpiperazin-1-yl)-2-hydroxyethanone;

2-(5-(2,3-Dihydro-6'H,8'H-spiro[indene-1,9'-pyrido[3',2':4,5]imidazo[2,1-c][1,4]oxazin]-2'-yl)pyrimidin-2-yl)propan-2-ol;

2'-(2-(2-Hydroxypropan-2-yl)pyrimidin-5-yl)-6',8'-dihydrospiro[indene-1,9'-pyrido[3',2':4,5]imidazo[2,1-c][1,4]oxazin]-3(2H)-one;

2'-(2-(2-hydroxypropan-2-yl)pyrimidin-5-yl)-2,3-dihydro-6'H,8'H-spiro[indene-1,9'-pyrido[3',2':4,5]imidazo[2,1-c][1,4]oxazin]-6'-ol;

2'-(1-(pyrimidin-4-yl)-1,2,3,6-tetrahydropyridin-4-yl)-2H,6'H,8'H-spiro[benzofuran-3,9'-pyrido[3',2':4,5]imidazo[2, 1-c][1,4]oxazine];

1-(4-(6',8'-dihydro-2H-spiro[benzofuran-3,9'-pyrido[3',2':4, 5]imidazo[2,1-c][1,4]oxazin]-2'-yl)-5,6-dihydropyridin-1 (2H)-yl)-3-methoxy-3-methylbutan-1-one;

(S)-1-(5-(6',8'-dihydro-2H-spiro[benzofuran-3,9'-pyrido[3', 2':4,5]imidazo[2,1-c][1,4]oxazin]-2'-yl)pyrimidin-2-yl) piperidin-4-ol;

(R)-7-(5-((S)-6',8'-dihydro-2H-spiro[benzofuran-3,9'-pyrido[3',2':4,5]imidazo[2,1-c][1,4]oxazin]-2'-yl)pyrimidin-2-yl)hexahydroimidazo[1,5-a]pyrazin-3(2H)-one;

(1S,4r)-4-((4-((S)-6',8'-Dihydro-2H-spiro[benzofuran-3,9'-pyrido[3',2':4,5]imidazo[2,1-c][1,4]oxazin]-2'-yl)pyridin-2-yl)oxy)cyclohexanol;

1-((S)-4-(5-((S)-6',8'-dihydro-2H-spiro[benzofuran-3,9'-pyrido[3',2':4,5]imidazo[2,1-c][1,4]oxazin]-2'-yl)pyrimidin-2-yl)-2-methylpiperazin-1-yl)-2-hydroxyethanone;

1-((R)-4-(5-((S)-6',8'-dihydro-2H-spiro[benzofuran-3,9'-pyrido[3',2':4,5]imidazo[2,1-c][1,4]oxazin]-2'-yl)pyrimidin-2-yl)-2-methylpiperazin-1-yl)-2-hydroxyethanone;

1-((R)-4-(5-((R)-6',8'-dihydro-2H-spiro[benzofuran-3,9'-pyrido[3',2':4,5]imidazo[2,1-c][1,4]oxazin]-2'-yl)pyrimidin-2-yl)-2-methylpiperazin-1-yl)-2-hydroxyethanone;

1-((S)-4-(5-((R)-6',8'-dihydro-2H-spiro[benzofuran-3,9'-pyrido[3',2':4,5]imidazo[2,1-c][1,4]oxazin]-2'-yl)pyrimidin-2-yl)-2-methylpiperazin-1-yl)-2-hydroxyethanone;

1-(5-(6',8'-dihydrospiro[isochroman-4,9'-pyrido[3',2':4,5] imidazo[2,1-c][1,4]oxazin]-2'-yl)pyrimidin-2-yl)piperidin-4-ol;

(8aR)-7-(5-(6',8'-dihydrospiro[isochroman-4,9'-pyrido[3',2': 4,5]imidazo[2,1-c][1,4]oxazin]-2'-yl)pyrimidin-2-yl) hexahydroimidazo[1,5-a]pyrazin-3(2H)-one;

2'-(2-morpholinopyrimidin-5-yl)-6',8'-dihydrospiro[isochroman-4,9'-pyrido[3',2':4,5]imidazo[2,1-c][1,4]oxazine];

2-(5-(2,3-dihydro-6'H,8'H-spiro[indene-1,9'-pyrido[3',2':4, 5]imidazo[2,1-c][1,4]oxazin]-2'-yl)pyrimidin-2-yl)propan-2-amine;

(S)-2-(5-(6',8'-dihydro-2H-spiro[benzofuran-3,9'-pyrido[3', 2':4,5]imidazo[2,1-c][1,4]oxazin]-2'-yl)pyrimidin-2-yl) propan-2-amine; or 2'-(2-(2-hydroxypropan-2-yl)pyrimidin-5-yl)-2,3,6',8'-tetrahydrospiro[indene-1,9'-pyrido[3',2':4,5]imidazo[2,1-c][1, 4]oxazin]-3-ol.

In another embodiment the invention includes the compound according to any of the foregoing embodiments wherein $R^{3b}$ is H, optionally substituted $(C_1-C_4)$alkyl, optionally substituted $(C_3-C_6)$cycloalkyl, —OR$^a$—S(O)$_2$-optionally substituted $(C_1-C_3)$alkyl, optionally substituted azepanyl, optionally substituted diazepanyl, optionally substituted hexahydroimidazo[1,5-a]pyrazin-3(2H)-one, optionally substituted morpholinyl, 1,4-oxepanyl, optionally substituted piperazinyl, optionally substituted piperidinyl, optionally substituted pyrrolidinyl, optionally substituted tetrahydrofuranyl, optionally substituted tetrahydropyranyl, —C(H)(OH)CH$_2$-optionally substituted cycloalkyl, —C(H) (CH$_3$)CH$_2$-optionally substituted cycloalkyl, —CH$_2$-optionally substituted cycloalkyl, —CH$_2$-optionally substituted heterocylyl, —C(H)(CH$_3$)CH$_2$-optionally substituted heterocyclyl or —C(H)(OH)-optionally substituted heterocyclyl;

wherein $R^a$ is optionally substituted $(C_1-C_4)$alkyl, optionally substituted cyclohexyl, optionally substituted cyclopentyl, —CH$_2$-optionally substituted oxetanyl, —CH$_2$-optionally substituted tetrahydorpyranyl optionally substituted 6-azaspiro[3.5]nonanyl, optionally substituted pyrrolidinyl, optionally substituted tetrahydrofuranyl or optionally substituted tetrahydropyranyl.

In another embodiment, the invention includes the compounds according to any of the foregoing embodiments wherein $R^{3b}$ is optionally substituted by one or more substituents independently selected from —F, —CH$_3$, —CH$_2$OH, CH$_2$CH$_2$OCH$_3$, —C(O)CH$_2$OH, —C(O)C(H) (OH)CH$_3$, —C(O)CH$_2$OC(CH$_3$)$_3$, —C(O)CH$_3$, —C(O) OCH$_3$, —OC(O)C(H)(NH$_2$)C(H)(CH$_3$)$_2$, —OH, —P(=O) (OH)$_2$, and —S(O)$_2$CH$_3$.

In another embodiment, the invention includes the compounds according to foregoing embodiments wherein one of $A^1$, $A^2$, and $A^3$ of N, and the rest are CH.

In another embodiment the invention includes compound ((R)-1-(5-((R)-8-phenyl-7,8-dihydro-6H-pyrrolo[2',1':2,3] imidazo[4,5-b]pyridin-2-yl)pyrimidin-2-yl)pyrrolidin-2-yl)methanol;

((S)-1-(5-((R)-8-phenyl-7,8-dihydro-6H-pyrrolo[2',1':2,3] imidazo[4,5-b]pyridin-2-yl)pyrimidin-2-yl)pyrrolidin-2-yl)methanol;

(R)-1-(2-(methylsulfonyl)ethyl)-4-(8-phenyl-7,8-dihydro-6H-pyrrolo[2',1':2,3]imidazo[4,5-b]pyridin-2-yl)pyridin-2(1H)-one;

(R)-1-(2-hydroxy-2-methylpropyl)-4-(8-phenyl-7,8-dihydro-6H-pyrrolo[2',1':2,3]imidazo[4,5-b]pyridin-2-yl) pyridin-2(1H)-one;

1-(5-((R)-8-phenyl-7,8-dihydro-6H-pyrrolo[2',1':2,3]imidazo[4,5-b]pyridin-2-yl)pyrimidin-2-yl)ethanol;

2-cyclopropyl-1-(5-((R)-8-phenyl-7,8-dihydro-6H-pyrrolo [2',1':2,3]imidazo[4,5-b]pyridin-2-yl)pyrimidin-2-yl) ethanol;

(5-((R)-8-phenyl-7,8-dihydro-6H-pyrrolo[2',1':2,3]imidazo [4,5-b]pyridin-2-yl)pyrimidin-2-yl)(tetrahydro-2H-pyran-4-yl)methanol;

1-(5-((R)-8-phenyl-7,8-dihydro-6H-pyrrolo[2',1':2,3]imidazo[4,5-b]pyridin-2-yl)pyrimidin-2-yl)-1-(tetrahydro-2H-pyran-4-yl)ethanol;

1-cyclopropyl-2-(5-((R)-8-phenyl-7,8-dihydro-6H-pyrrolo [2',1':2,3]imidazo[4,5-b]pyridin-2-yl)pyrimidin-2-yl)propan-2-ol;

1-((R)-2-methyl-4-(5-((R)-8-phenyl-7,8-dihydro-6H-pyrrolo[2',1':2,3]imidazo[4,5-b]pyridin-2-yl)pyrimidin-2-yl) piperazin-1-yl)ethanone;

1-((S)-2-methyl-4-(5-((R)-8-phenyl-7,8-dihydro-6H-pyrrolo[2',1':2,3]imidazo[4,5-b]pyridin-2-yl)pyrimidin-2-yl) piperazin-1-yl)ethanone;

(1R,3R)-3-((4-((R)-8-phenyl-7,8-dihydro-6H-pyrido[3,2-b] pyrrolizin-2-yl)pyridin-2-yl)oxy)cyclopentanecarbonitrile;

(R)-1-((4,4-difluorocyclohexyl)methyl)-4-(8-phenyl-7,8-dihydro-6H-pyrrolo [2',1':2,3]imidazo[4,5-b]pyridin-2-yl) pyridin-2(1H)-one;

2-(5-(8-(pyridin-2-yl)-7,8-dihydro-6H-pyrrolo[2',1':2,3]imidazo[4,5-b]pyridin-2-yl)pyrimidin-2-yl)propan-2-ol;

1-((S)-2-methyl-4-(5-((R)-8-phenyl-7,8-dihydro-6H-pyrrolo[2',1':2,3]imidazo[4,5-b]pyridin-2-yl)pyrimidin-2-yl) piperazin-1-yl)ethanone;

2-hydroxy-1-((R)-2-methyl-4-(5-((R)-8-phenyl-7,8-dihydro-6H-pyrrolo [2',1':2,3]imidazo[4,5-b]pyridin-2-yl) pyrimidin-2-yl)piperazin-1-yl)ethanone;

(R)-7-(5-((R)-8-(3-methoxyphenyl)-7,8-dihydro-6H-pyrrolo[2',1':2,3]imidazo[4,5-b]pyridin-2-yl)pyrimidin-2-yl) hexahydroimidazo[1,5-a]pyrazin-3 (2H)-one;

1-((R)-4-(5-((R)-8-(3-methoxyphenyl)-7,8-dihydro-6H-pyrrolo[2',1':2,3]imidazo[4,5-b]pyridin-2-yl)pyrimidin-2-yl)-2-methylpiperazin-1-yl)ethanone;

(R)-7-(5-((S)-8-(3-methoxyphenyl)-7,8-dihydro-6H-pyrrolo [2',1':2,3]imidazo[4,5-b]pyridin-2-yl)pyrimidin-2-yl) hexahydroimidazo[1,5-a]pyrazin-3(2H)-one;

(R)-7-(5-((R)-8-(2-methoxyphenyl)-7,8-dihydro-6H-pyrrolo[2',1':2,3]imidazo[4,5-b]pyridin-2-yl)pyrimidin-2-yl)hexahydroimidazo[1,5-a]pyrazin-3 (2H)-one;

(S)-7-(5-((R)-8-(2-methoxyphenyl)-7,8-dihydro-6H-pyrrolo[2',1':2,3]imidazo[4,5-b]pyridin-2-yl)pyrimidin-2-yl)hexahydroimidazo[1,5-a]pyrazin-3 (2H)-one;

(R)-1-(5-(8-(2-methoxyphenyl)-7,8-dihydro-6H-pyrrolo[2',1':2,3]imidazo[4,5-b]pyridin-2-yl)pyrimidin-2-yl)piperidin-4-ol;

2-hydroxy-1-((R)-4-(5-((R)-8-(2-methoxyphenyl)-7,8-dihydro-6H-pyrrolo[2',1':2,3]imidazo[4,5-b]pyridin-2-yl)pyrimidin-2-yl)-2-methylpiperazin-1-yl)ethanone;

(R)-7-(5-((S)-8-(2-methoxyphenyl)-7,8-dihydro-6H-pyrrolo[2',1':2,3]imidazo[4,5-b]pyridin-2-yl)pyrimidin-2-yl)hexahydroimidazo[1,5-a]pyrazin-3 (2H)-one;

1-((R)-4-(5-((R)-8-(3-(Hydroxymethyl)phenyl)-7,8-dihydro-6H-pyrrolo[2',1':2,3]imidazo[4,5-b]pyridin-2-yl)pyrimidin-2-yl)-2-methylpiperazin-1-yl)ethanone;

1-((R)-4-(5-((R)-8-(3-(Hydroxymethyl)phenyl)-7,8-dihydro-6H-pyrrolo[2',1':2,3]imidazo[4,5-b]pyridin-2-yl)pyrimidin-2-yl)-2-methylpiperazin-1-yl)ethanone;

(S)-1-(5-((R)-8-Phenyl-7,8-dihydro-6H-pyrrolo[2',1':2,3]imidazo[4,5-b]pyridin-2-yl)pyrimidin-2-yl)piperidin-4-yl 2-amino-3-methylbutanoate;

(R)-1-(5-(8-Phenyl-7,8-dihydro-6H-pyrrolo[2',1':2,3]imidazo[4,5-b]pyridin-2-yl)pyrimidin-2-yl)piperidin-4-yl dihydrogen phosphate hydrochloride;

(R)-8-Phenyl-2-(2-((tetrahydro-2H-pyran-4-yl)oxy)pyridin-4-yl)-7,8-dihydro-6H-pyrrolo [2',1':2,3]imidazo[4,5-b]pyridine)

3-((4-((R)-8-phenyl-7,8-dihydro-6H-pyrrolo[2',1':2,3]imidazo[4,5-b]pyridin-2-yl)pyridin-2-yl)oxy)cyclopentanol;

(R)-4-((4-(8-phenyl-7,8-dihydro-6H-pyrrolo[2',1':2,3]imidazo[4,5-b]pyridin-2-yl)pyridin-2-yl)oxy)cyclohexanol;

(R)-2-(2-(oxetan-3-yloxy)pyridin-4-yl)-8-phenyl-7,8-dihydro-6H-pyrrolo[2',1':2,3]imidazo[4,5-b]pyridine;

3-((4-((R)-8-phenyl-7,8-dihydro-6H-pyrrolo[2',1':2,3]imidazo[4,5-b]pyridin-2-yl)pyridin-2-yl)oxy)cyclohexanol;

(R)-2-(2-(oxetan-3-ylmethoxy)pyridin-4-yl)-8-phenyl-7,8-dihydro-6H-pyrrolo [2',1':2,3]imidazo[4,5-b]pyridine;

(R)-2-(2-(((R)-1-methylpyrrolidin-3-yl)oxy)pyridin-4-yl)-8-phenyl-7,8-dihydro-6H-pyrrolo [2',1':2,3]imidazo[4,5-b]pyridine;

(R)-2-((4-(8-phenyl-7,8-dihydro-6H-pyrrolo[2',1':2,3]imidazo[4,5-b]pyridin-2-yl)pyridin-2-yl)oxy)ethanol;

(R)-2-(2-(((S)-1-methylpyrrolidin-3-yl)oxy)pyridin-4-yl)-8-phenyl-7,8-dihydro-6H-pyrrolo [2',1':2,3]imidazo[4,5-b]pyridine;

(1S,4s)-4-((4-((R)-8-phenyl-7,8-dihydro-6H-pyrrolo[2',1':2,3]imidazo[4,5-b]pyridin-2-yl)pyridin-2-yl)oxy)cyclohexanol;

(8R)-8-phenyl-2-(2-((tetrahydro-2H-pyran-3-yl)oxy)pyridin-4-yl)-7,8-dihydro-6H-pyrrolo [2',1':2,3]imidazo[4,5-b]pyridine;

(8R)-8-phenyl-2-(2-((tetrahydrofuran-3-yl)oxy)pyridin-4-yl)-7,8-dihydro-6H-pyrrolo [2',1':2,3]imidazo[4,5-b]pyridine;

(R)-2-(2-(cyclopentyloxy)pyridin-4-yl)-8-phenyl-7,8-dihydro-6H-pyrrolo[2',1':2,3]imidazo[4,5-b]pyridine;

(R)-2-(2-(cyclohexyloxy)pyridin-4-yl)-8-phenyl-7,8-dihydro-6H-pyrrolo[2',1':2,3]imidazo[4,5-b]pyridine;

(R)-methyl 4-((4-(8-phenyl-7,8-dihydro-6H-pyrrolo[2',1':2,3]imidazo[4,5-b]pyridin-2-yl)pyridin-2-yl)oxy)cyclohexanecarboxylate;

methyl 3-((4-((R)-8-phenyl-7,8-dihydro-6H-pyrrolo[2',1':2,3]imidazo[4,5-b]pyridin-2-yl)pyridin-2-yl)oxy)cyclopentanecarboxylate;

(R)-2-(2-butoxypyridin-4-yl)-8-phenyl-7,8-dihydro-6H-pyrido[3,2-b]pyrrolizine;

(1R,3R)-3-((4-((R)-8-phenyl-7,8-dihydro-6H-pyrido[3,2-b]pyrrolizin-2-yl)pyridin-2-yl)oxy)cyclopentanecarbonitrile;

(R)-8-phenyl-2-(2-((S)-pyrrolidin-3-yloxy)pyridin-4-yl)-7,8-dihydro-6H-pyrrolo [2',1':2,3]imidazo[4,5-b]pyridine;

(8R)-8-phenyl-2-(2-(piperidin-3-yloxy)pyridin-4-yl)-7,8-dihydro-6H-pyrrolo [2',1':2,3]imidazo[4,5-b]pyridine;

(R)-8-phenyl-2-(2-((R)-pyrrolidin-3-yloxy)pyridin-4-yl)-7,8-dihydro-6H-pyrrolo [2',1':2,3]imidazo[4,5-b]pyridine;

(8R)-2-(2-(6-azaspiro[3.4]octan-1-yloxy)pyridin-4-yl)-8-phenyl-7,8-dihydro-6H-pyrrolo [2',1':2,3]imidazo[4,5-b]pyridine;

(R)-2-(2-(6-azaspiro[3.4]octan-2-yloxy)pyridin-4-yl)-8-phenyl-7,8-dihydro-6H-pyrrolo [2',1':2,3]imidazo[4,5-b]pyridine;

(8R)-2-(2-(6-azaspiro[3.5]nonan-1-yloxy)pyridin-4-yl)-8-phenyl-7,8-dihydro-6H-pyrrolo [2',1':2,3]imidazo[4,5-b]pyridine 1-(5-(6',8'-sihydro-2H-spiro[benzofuran-3,9'-pyrido[3',2':4,5]imidazo[2,1-c][1,4]oxazin]-2'-yl)pyrimidin-2-yl)piperidin-4-ol;

(R)-1-((4,4-difluorocyclohexyl)methyl)-4-(8-phenyl-7,8-dihydro-6H-pyrrolo [2',1':2,3]imidazo[4,5-b]pyridin-2-yl)pyridin-2(1H)-one;

(R)-1-(2-methoxyethyl)-4-(8-phenyl-7,8-dihydro-6H-pyrrolo[2',1':2,3]imidazo[4,5-b]pyridin-2-yl)pyridin-2(1H)-one;

(R)-4-(8-phenyl-7,8-dihydro-6H-pyrrolo[2',1':2,3]imidazo[4,5-b]pyridin-2-yl)-1-((tetrahydro-2H-pyran-4-yl)methyl)pyridin-2(1H)-one;

4-((R)-8-phenyl-7,8-dihydro-6H-pyrrolo[2',1':2,3]imidazo[4,5-b]pyridin-2-yl)-1-(tetrahydrofuran-3-yl)pyridin-2 (1H)-one;

(R)-4-(8-phenyl-7,8-dihydro-6H-pyrrolo[2',1':2,3]imidazo[4,5-b]pyridin-2-yl)-1-(tetrahydro-2H-pyran-4-yl)pyridin-2(1H)-one;

(R)-8-phenyl-2-(1-(tetrahydro-2H-pyran-4-yl)-1H-pyrazol-4-yl)-7,8-dihydro-6H-pyrrolo [2',1':2,3]imidazo[4,5-b]pyridine;

4-((4-(6',8'-dihydro-2H-spiro[benzofuran-3,9'-pyrido[3',2':4,5]imidazo[2,1-c][1,4]oxazin]-2'-yl)pyridin-2-yl)oxy)cyclohexanol;

(R)-1-(5-(3-fluoro-8-phenyl-7,8-dihydro-6H-pyrrolo[2',1':2,3]imidazo[4,5-b]pyridin-2-yl)pyrimidin-2-yl)piperidin-4-ol;

2-(2-morpholinopyrimidin-5-yl)-9-phenyl-7,9-dihydro-6H-pyrano[4',3':4,5]imidazo[1,2-b]pyridazine;

trans-4-((4-(4-(2-Methoxyphenyl)-3,4-dihydro-2H-pyrano[2',3':4,5]imidazo[1,2-a]pyridin-7-yl)pyridin-2-yl)oxy)cyclohexanol;

(8aS)-7-(5-(9-Phenyl-8,9-dihydro-6H-pyrido[3',2':4,5]imidazo[2,1-c][1,4]oxazin-2-yl)pyrimidin-2-yl)hexahydroimidazo[1,5-a]pyrazin-3(2H)-one;

3,3-difluoro-1-(5-(9-phenyl-8,9-dihydro-6H-pyrido[3',2':4,5]imidazo[2,1-c][1,4]oxazin-2-yl)pyrimidin-2-yl)piperidin-4-ol;

1-(5-(9-phenyl-8,9-dihydro-6H-pyrido[3',2':4,5]imidazo[2,1-c][1,4]oxazin-2-yl)pyrimidin-2-yl)piperidin-4-ol;

2-(2-(1,4-oxazepan-4-yl)pyrimidin-5-yl)-9-phenyl-8,9-dihydro-6H-pyrido[3',2':4,5]imidazo[2,1-c][1,4]oxazine;

(1-(5-(9-phenyl-8,9-dihydro-6H-pyrido[3',2':4,5]imidazo[2,1-c][1,4]oxazin-2-yl)pyrimidin-2-yl)piperidin-3-yl)methanol (4-fluoro-1-(5-(9-phenyl-8,9-dihydro-6H-pyrido[3',2':4,5]imidazo[2,1-c][1,4]oxazin-2-yl)pyrimidin-2-yl)piperidin-4-yl)methanol 2-hydroxy-1-(4-(5-(9-phenyl-8,9-dihydro-6H-pyrido[3',2':4,5]imidazo[2,1-c][1,4]oxazin-2-yl)pyrimidin-2-yl)piperazin-1-yl)propan-1-one;

2-hydroxy-1-(4-(5-(9-phenyl-8,9-dihydro-6H-pyrido[3',2':4,5]imidazo[2,1-c][1,4]oxazin-2-yl)pyrimidin-2-yl)piperazin-1-yl)ethanone;

(R)-8-Phenyl-2-(2-(((tetrahydro-2H-pyran-4-yl)methoxy)pyridin-4-yl)-7,8-dihydro-6H-pyrrolo [2',1':2,3]imidazo[4,5-b]pyridine;

(R)-2-(2-(2-methoxyethoxy)pyridin-4-yl)-8-phenyl-7,8-dihydro-6H-pyrrolo[2',1':2,3]imidazo[4,5-b]pyridine;

(R)-2-methyl-1-((4-(8-phenyl-7,8-dihydro-6H-pyrrolo[2',1':2,3]imidazo[4,5-b]pyridin-2-yl)pyridin-2-yl)oxy)propan-2-ol;

(R)-8-Phenyl-2-(1,2,3,6-tetrahydropyridin-4-yl)-7,8-dihydro-6H-pyrrolo[2',1':2,3]imidazo[4,5-b]pyridine;

(1S,4s)-4-(((4-((R)-8-phenyl-7,8-dihydro-6H-pyrrolo[2',1':2,3]imidazo[4,5-b]pyridin-2-yl)pyridin-2-yl)oxy)methyl)cyclohexanol;

(1R,4r)-4-(((4-((R)-8-phenyl-7,8-dihydro-6H-pyrrolo[2',1':2,3]imidazo[4,5-b]pyridin-2-yl)pyridin-2-yl)oxy)methyl)cyclohexanol;

((1R,4r)-4-(((4-((R)-8-phenyl-7,8-dihydro-6H-pyrrolo[2',1':2,3]imidazo[4,5-b]pyridin-2-yl)pyridin-2-yl)oxy)methyl)cyclohexyl)methanol;

(R)-8-Phenyl-2-(1-(pyrimidin-4-yl)-1,2,3,6-tetrahydropyridin-4-yl)-7,8-dihydro-6H-pyrrolo [2',1':2,3]imidazo[4,5-b]pyridine;

methyl 2-(4-((R)-8-phenyl-7,8-dihydro-6H-pyrrolo[2',1':2,3]imidazo[4,5-b]pyridin-2-yl)cyclohex-3-en-1-yl)acetate;

1-(5-(8-methyl-8-phenyl-7,8-dihydro-6H-pyrrolo[2',1':2,3]imidazo[4,5-b]pyridin-2-yl)pyrimidin-2-yl)piperidin-4-ol;

(S)-1-(5-(8-methyl-8-phenyl-7,8-dihydro-6H-pyrrolo[2',1':2,3]imidazo[4,5-b]pyridin-2-yl)pyrimidin-2-yl)piperidin-4-ol;

(R)-1-(5-(8-methyl-8-phenyl-7,8-dihydro-6H-pyrrolo[2',1':2,3]imidazo[4,5-b]pyridin-2-yl)pyrimidin-2-yl)piperidin-4-ol;

(S)-2-(5-(8-methyl-8-phenyl-7,8-dihydro-6H-pyrrolo[2',1':2,3]imidazo[4,5-b]pyridin-2-yl)pyrimidin-2-yl)propan-2-ol;

(R)-2-(5-(8-methyl-8-phenyl-7,8-dihydro-6H-pyrrolo[2',1':2,3]imidazo[4,5-b]pyridin-2-yl)pyrimidin-2-yl)propan-2-ol;

(R)-2-(5-(8-phenyl-7,8-dihydro-6H-pyrrolo[2',1':2,3]imidazo[4,5-b]pyridin-2-yl)pyrimidin-2-yl)propan-2-amine;

2-(2-(4,4-difluoropiperidin-1-yl)pyrimidin-5-yl)-9-phenyl-8,9-dihydro-6H-pyrido-[3',2':4,5]imidazo[2,1-c][1,4]oxazine; or (1R,4R)-4-((4-((R)-8-phenyl-7,8-dihydro-6H-pyrrolo[2',1':2,3]imidazo[4,5-b]pyridin-2-yl)pyridin-2-yl)oxy)cyclohexanol.

In another embodiment the invention includes a compound of Formula (II)

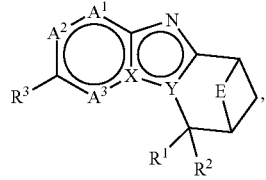

(II)

or a pharmaceutically acceptable salt, prodrug or stereoisomer thereof, wherein:

$R^1$ is H, or optionally substituted $(C_1$-$C_3)$alkyl;

$R^2$ is optionally substituted phenyl;

$A^1$, $A^2$, and $A^3$ are independently $C(R^{A2})$ or N, provided that at least one is $C(R^2)$;

or

X is C and Y is N, and E is —O—;

$R^3$ is —$R^{3a}$—$R^{3b}$, wherein:

$R^{3a}$ is optionally substituted heteroaryl $R^{3b}$ is —O($R^a$), optionally substituted $(C_1$-$C_3)$alkyl, —$C(R^e)_2)_q$-optionally substituted cycloalklyl; or —$C(R^e)_q$-optionally substituted heterocyclyl;

$R^a$ and $R^b$ are independently selected from optionally substituted $(C_1$-$C_5)$alkyl, and —$(CH_2)_p$-optionally substituted heterocyclyl;

$R^e$ is independently H, OH or $CH_3$;

$R^{A2}$ is independently H, or $(C_1$-$C_3)$alkyl; and q is independently 0, 1 or 2.

In another embodiment the invention includes the compound according to any of the foregoing embodiments wherein $R^2$ is optionally substituted phenyl.

In another embodiment the invention includes the compound according to any of the foregoing embodiments wherein $R^{3a}$ is optionally substituted pyrimidine In another embodiment the invention includes the compound according to any of the foregoing embodiments wherein $R^{3b}$ is optionally substituted $(C_1$-$C_4)$alkyl, —O-tetrahydropyranyl, optionally substituted morpholinyl, or optionally substituted piperidinyl.

In another embodiment the invention includes the compound according to any of the foregoing embodiments wherein the compound is 2-(5-(9-phenyl-6,7,8,9-tetrahydro-6,8-methanoimidazo[1,2-a:5,4-b']dipyridin-2-yl)pyrimidin-2-yl)propan-2-ol;

9-phenyl-2-(2-((tetrahydro-2H-pyran-4-yl)oxy)pyridin-4-yl)-6,7,8,9-tetrahydro-6, 8-methanoimidazo[1,2-a:5,4-b']dipyridine;

4-(5-(9-phenyl-6,7,8,9-tetrahydro-6,8-methanoimidazo[1,2-a:5,4-b']dipyridin-2-yl)pyrimidin-2-yl)morpholine;

1-(5-(9-phenyl-6,7,8,9-tetrahydro-6,8-methanoimidazo[1,2-a:5,4-b']dipyridin-2-yl)pyrimidin-2-yl)piperidin-4-ol;

2-(5-((6R,8S,9S)-9-phenyl-6,7,8,9-tetrahydro-6,8-epoxyimidazo[1,2-a:5,4-b']dipyridin-2-yl)pyrimidin-2-yl)propan-2-ol;

1-(5-((6R,8S,9S)-9-phenyl-6,7,8,9-tetrahydro-6,8-epoxyimidazo[1,2-a:5,4-b']dipyridin-2-yl)pyrimidin-2-yl)piperidin-4-ol;

2-(5-(9-Phenyl-6,7,8,9-tetrahydro-6,8-methanoimidazo[1,2-a:5,4-b']dipyridin-2-yl)pyrimidin-2-yl)propan-2-ol;

9-phenyl-2-(2-((tetrahydro-2H-pyran-4-yl)oxy)pyridin-4-yl)-6,7,8,9-tetrahydro-6,8-methanoimidazo[1,2-a:5,4-b']dipyridine;

1-(5-(9-Phenyl-6,7,8,9-tetrahydro-6,8-methanoimidazo[1,2-a:5,4-b']dipyridin-2-yl)pyrimidin-2-yl)piperidin-4-ol;

4-(5-(9-phenyl-6,7,8,9-tetrahydro-6,8-methanoimidazo[1,2-a:5,4-b']dipyridin-2-yl)pyrimidin-2-yl)morpholine;

2-(5-(((6R,8S,9S)-9-phenyl-6,7,8,9-tetrahydro-6,8-epoxy-imidazo[1,2-a:5,4-b']dipyridin-2-yl)pyrimidin-2-yl)propan-2-ol; or 1-(5-(((6R,8S,9S)-9-phenyl-6,7,8,9-tetrahydro-6,8-epoxy-imidazo[1,2-a:5,4-b']dipyridin-2-yl)pyrimidin-2-yl)piperidin-4-ol.

In another emboodimen the invention provides a method of treating a disease comprising administering a therapeutically effective amount of a compound of any of the foregoing claims to a patient in need thereof.

In another emboodimen the invention provides a method wherein the disease is rheumatoid arthritis, juvenile rheumatoid arthritis, psoriasis, psoriatic arthritis, Crohn's disease, inflammatory bowel disease, ulcerative colitis, psoriatic arthritis, psoriasis, ankylosing spondylitis, systemic lupus erythematosus, lupus nephritis, multiple sclerosis or hidraenitis suppurativa.

In another embodiment the invention provides a kit comprising a packaged product comprising components with which to administer a compound of any of the foregoing claims for treatment of an autoimmune disorder.

In another embodiment the invention provides a kit according to the prior embodiment, wherein the packaged product comprises a compound of any of the foregoing claims and instructions for use.

In another embodiment the invention provides a pharmaceutical composition comprising a compound according to any of claims 1-29 and one or more pharmaceutically acceptable excipients.

Certain compounds of Formula (I) which have acidic substituents may exist as salts with pharmaceutically acceptable bases. The present invention includes such salts. Examples of such salts include sodium salts, potassium salts, lysine salts and arginine salts. These salts may be prepared by methods known to those skilled in the art.

Certain compounds of Formula (I) and their salts may exist in more than one crystal form and the present invention includes each crystal form and mixtures thereof.

Certain compounds of Formula (I) and their salts may also exist in the form of solvates, for example hydrates, and the present invention includes each solvate and mixtures thereof.

Certain compounds of Formula (I) may contain one or more chiral centers, and exist in different optically active forms. When compounds of Formula (I) contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of Formula (I) contains more than one chiral center, it may exist in diastereoisomeric forms. The diastereoisomeric compounds may be separated by methods known to those skilled in the art, for example chromatography or crystallization and the individual enantiomers may be separated as described above. The present invention includes each diastereoisomer of compounds of Formula (I) (and mixtures thereof.

Certain compounds of Formula (I) may exist in different tautomeric forms or as different geometric isomers, and the present invention includes each tautomer and/or geometric isomer of compounds of Formula (I) and mixtures thereof.

Certain compounds of Formula (I) may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Formula (I) and mixtures thereof.

Certain compounds of Formula (I) may exist in zwitterionic form and the present invention includes each zwitterionic form of compounds of Formula (I) and mixtures thereof.

Certain compounds of Formula (I) may further be in the form of a pro-drug. Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue.

Exemplary pro-drugs upon cleavage release the corresponding free acid, and such hydrolyzable ester-forming residues of the compounds of this invention include but are not limited to carboxylic acid substituents wherein the free hydrogen is replaced by $(C_1-C_4)$alkyl, $(C_1-C_{12})$alkanoyloxymethyl, $(C_4-C_9)$1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as (3-dimethylaminoethyl), carbamoyl-$(C_1-C_2)$alkyl, N,N-di$(C_1-C_2)$-alkylcarbamoyl-$(C_1-C_2)$alkyl and piperidino-, pyrrolidino- or morpholino$(C_2-C_3)$alkyl.

Other exemplary pro-drugs release an alcohol of Formula (I) wherein the free hydrogen of the hydroxyl substituent (e.g., $R^1$ contains hydroxyl) is replaced by $(C_1-C_6)$alkanoyloxymethyl, 1-(($(C_1-C_6)$alkanoyloxy)ethyl, 1-methyl-1-(($(C_1-C_6)$alkanoyloxy)ethyl, $(C_1-C_{12})$alkoxycarbonyloxymethyl, N—$(C_1-C_6)$alkoxycarbonylamino-methyl, succinoyl, $(C_1-C_6)$alkanoyl, α-amino$(C_1-C_4)$alkanoyl, arylacyl and α-aminoacyl, or α-aminoacyl-α-aminoacyl wherein said α-aminoacyl moieties are independently any of the naturally occurring L-amino acids found in proteins, $P(O)(OH)_2$, —$P(O)(O(C_1-C_6)$alkyl$)_2$ or glycosyl (the radical resulting from detachment of the hydroxyl of the hemiacetal of a carbohydrate).

Compounds of Formula (I) also include compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Methods of Treatment

Many autoimmune diseases and disease associated with chronic inflammation, as well as acute responses, have been linked to excessive or unregulated production or activity of one or more cytokines.

The compounds of the invention are also useful in the treatment of rheumatoid arthritis, asthma, juvenile arthritis, ankylosing spondylitis, hidradenitis supportive, psoriasis, psoriatic arthritis, ulcerative colitis, Crohn's disease, inflammatory bowel disease, Sjögren's disease associated lung disease, ankylosing spondylitis associated lung disease, and Sjögren's syndrome.

Combination Therapies

Compounds of Formula (I) of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the compound of the present invention. The additional agent also can be an agent that imparts a beneficial attribute to the therapeutic composition e.g., an agent that affects the viscosity of the composition.

It should further be understood that the combinations which are to be included within this invention are those combinations useful for their intended purpose. The agents set forth below are illustrative for purposes and not intended to be limited. The combinations, which are part of this invention, can be the compounds of the present invention and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDs which include drugs like ibuprofen. Other preferred combinations are corticosteroids including prednisolone; the well-known side-effects of steroid use can be reduced or even eliminated by tapering the steroid dose required when treating patients in combination with the compounds of this invention. Non-limiting examples of therapeutic agents for rheumatoid arthritis with which a compound of Formula (I) of the invention can be combined include the following: cytokine suppressive anti-inflammatory drug(s) (CSAIDs); antibodies to or antagonists of other human cytokines or growth factors, for example, LT, IL-1, IL-2, IL-3, IL-4, IL-5, IL-6, IL-7, IL-8, IL-12, IL-15, IL-16, IL-21, IL-23, interferons, EMAP-II, GM-CSF, FGF, MMP-13 and PDGF. Compounds of the invention can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include IL-1 inhibitors (Interleukin-1-converting enzyme inhibitors, IL-1RA etc.) may be effective for the same reason. Other preferred combinations include Interleukin 11. Yet other preferred combinations are the other key players of the autoimmune response which may act parallel to, dependent on or in concert with IL-18 function; especially preferred are IL-12 antagonists including IL-12 antibodies or soluble IL-12 receptors, or IL-12 binding proteins. It has been shown that IL-12 and IL-18 have overlapping but distinct functions and a combination of antagonists to both may be most effective. Yet another preferred combination is non-depleting anti-CD4 inhibitors. Yet other preferred combinations include antagonists of the co-stimulatory pathway CD80 (B7.1) or CD86 (B7.2) including antibodies, soluble receptors or antagonistic ligands.

A compound of Formula (I) of the invention may also be combined with agents, such as methotrexate, 6-mercaptopurine, azathioprine sulphasalazine, mesalazine, olsalazine chloroquinine/hydroxychloroquine, pencillamine, aurothiomalate (intramuscular and oral), azathioprine, cochicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signaling by proinflammatory cytokines such as IL-1 (e.g., NIK, IKK, JAK1, JAK2, JAK3, p38 or MAP kinase inhibitors), IL-1β converting enzyme inhibitors, T-cell signaling inhibitors such as kinase inhibitors, metalloproteinase inhibitors, sulfasalazine, 6-mercaptopurines, angiotensin converting enzyme inhibitors, soluble cytokine receptors and derivatives thereof (e.g., sIL-1RI, sIL-1RII, sIL-6R), anti-inflammatory cytokines (e.g., IL-4, IL-10, IL-11, IL-13), celecoxib, folic acid, hydroxychloroquine sulfate, rofecoxib, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl misoprostol, naproxen sodium, omeprazole, cyclophosphamide, rituximab, tofacitinib, IL-1 TRAP, MRA, CTLA4-IG, IL-18 BP, anti-IL-12, Anti-IL15, BIRB-796, SCIO-469, VX-702, AMG-548, VX-740, Roflumilast, IC-485, CDC-801, S1P1 agonists (such as FTY720), PKC family inhibitors (such as Ruboxistaurin or AEB-071) and Mesopram. Preferred combinations include methotrexate or leflunomide and in moderate or severe rheumatoid arthritis cases, and cyclosporine.

Non-limiting examples of therapeutic agents for inflammatory bowel disease with which a compound of Formula (I) of the invention can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β monoclonal antibodies; anti-IL-6 monoclonal antibodies; growth factors; elastase inhibitors; pyridinyl-imidazole compounds; antibodies to or antagonists of other human cytokines or growth factors, for example, LT, IL-1, IL-2, IL-6, IL-7, IL-8, IL-12, IL-15, IL-16, IL-23, EMAP-II, GM-CSF, FGF, and PDGF; cell surface molecules such as CD2, CD3, CD4, CD8, CD25, CD28, CD30, CD40, CD45, CD69, CD90 or their ligands; methotrexate; cyclosporine; FK506; rapamycin; mycophenolate mofetil; leflunomide; NSAIDs, for example, ibuprofen; corticosteroids such as prednisolone; phosphodiesterase inhibitors; adenosine agonists; antithrombotic agents; complement inhibitors; adrenergic agents; agents which interfere with signaling by proinflammatory cytokines such as IL-1 (e.g., NIK, IKK, p38 or MAP kinase inhibitors); IL-1β converting enzyme inhibitors; T-cell signaling inhibitors such as kinase inhibitors; metalloproteinase inhibitors; sulfasalazine; azathioprine; 6-mercaptopurines; angiotensin converting enzyme inhibitors; soluble cytokine receptors and derivatives thereof (e.g., sIL-1RI, sIL-1RII, sIL-6R) and anti-inflammatory cytokines (e.g., IL-4, IL-10, IL-11, IL-13). Preferred examples of therapeutic agents for Crohn's disease with which a compound of Formula (I) can be combined include PDE4 inhibitors. A compound of Formula (I) can be combined with corticosteroids, for example, budenoside and dexamethasone; sulfasalazine, 5-aminosalicylic acid; olsalazine; and agents which interfere with synthesis or action of proinflammatory cytokines such as IL-1, for example, IL-1β converting enzyme inhibitors and IL-1ra; T cell signaling inhibitors, for example, tyrosine kinase inhibitors; 6-mercaptopurine; IL-11; mesalamine; prednisone; azathioprine; mercaptopurine; infliximab; methylprednisolone sodium succinate; diphenoxylate/atropine sulfate; loperamide hydrochloride; methotrexate; omeprazole; folate; ciprofloxacin/dextrose-water; hydrocodone bitartrate/apap; tetracycline hydrochloride; fluocinonide; metronidazole; thimerosal/boric acid; cholestyramine/sucrose; ciprofloxacin hydrochloride; hyoscyamine sulfate; meperidine hydrochloride; midazolam hydrochloride; oxycodone HCl/acetaminophen; promethazine hydrochloride; sodium phosphate; sulfamethoxazole/trimethoprim; celecoxib; polycarbophil; propoxyphene napsylate; hydrocortisone; multivitamins; balsalazide disodium; codeine phosphate/apap; colesevelam HCl; cyanocobalamin; folic acid; levofloxacin; methylprednisolone; natalizumab and interferon-gamma.

Non-limiting examples of therapeutic agents for ankylosing spondylitis with which a compound of Formula (I) can be combined include the following: ibuprofen, diclofenac, misoprostol, naproxen, meloxicam, indomethacin, diclofenac, celecoxib, rofecoxib, sulfasalazine, methotrexate, azathioprine, minocyclin, and prednisone Non-limiting examples of therapeutic agents for psoriasis with which a compound of Formula (I) can be combined include the following: calcipotriene, clobetasol propionate, triamcinolone acetonide, halobetasol propionate, tazarotene, methotrexate, fluocinonide, betamethasone dipropionate augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emollient, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine, ABT-874 and ustekinamab.

Non-limiting examples of therapeutic agents for psoriatic arthritis with which a compound of Formula (I) can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone dipropionate augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, and alefacept.

Compositions and Routes of Administration

One or more compounds of this invention can be administered to a human patient by themselves or in pharmaceutical compositions where they are mixed with biologically suitable carriers or excipient(s) at doses to treat or ameliorate a disease or condition as described herein. Mixtures of these compounds can also be administered to the patient as a simple mixture or in suitable formulated pharmaceutical compositions. A therapeutically effective dose refers to that amount of the compound or compounds sufficient to result in the prevention or attenuation of a disease or condition as described herein. Techniques for formulation and administration of the compounds of the instant application may be found in references well known to one of ordinary skill in the art, such as "Remington's Pharmaceutical Sciences," Mack Publishing Co., Easton, Pa., latest edition.

Suitable routes of administration may, for example, include oral, eye drop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into an edematous site, often in a depot or sustained release formulation.

Furthermore, one may administer the drug in a targeted drug delivery system, for example, in a liposome coated with endothelial cell-specific antibody.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

The compounds can be formulated for parenteral administration by injection, e.g., bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD: 5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counter ions.

Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in a method of the present invention, the therapeutically effective dose can be estimated initially from cellular assays. For example, a dose can be formulated in cellular and animal models to achieve a circulating concentration range that includes the $IC_{50}$ as determined in cellular assays (e.g., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition (see, e.g., Fingl et al., 1975, in *The Pharmacological Basis of Therapeutics*, Ch. 1, p. 1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g., the concentration necessary to achieve 50-90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10-90% of the time, preferably between 30-90% and most preferably between 50-90% until the desired amelioration of symptoms is achieved. In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the following Examples.

a) Capsules

In the preparation of capsules, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared, for example, from the following ingredients.

Parts by Weight

| | |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinylpyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with another therapeutic agent that is known to treat a disease or condition described herein. For example, with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. The compounds of the invention can be administered prior to, subsequent to or simultaneously with the additional pharmaceutical agent, whichever course of administration is appropriate. The additional pharmaceutical agents include, but are not limited to, anti-edemic steroids, NSAIDS, ras inhibitors, anti-IL1 agents, antihistamines, PAF-antagonists, COX-1 inhibitors, COX-2 inhibitors, NO synthase inhibitors, Akt/PTB inhibitors, IGF-1R inhibitors, PKC inhibitors, PI3 kinase inhibitors, calcineurin inhibitors and immunosuppressants. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deleterious effects of a hyperproliferative disorder, angiogenesis, vascular hyperpermeability or edema than the administration of either substance alone. In the treatment of malignant disorders combinations with antiproliferative or cytotoxic chemotherapies or radiation are included in the scope of the present invention.

The present invention also comprises the use of a compound of Formula (I) as a medicament.

A further aspect of the present invention provides the use of a compound of Formula (I) or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of Formula (I) to a mammal, particularly a human being, in need thereof.

EXAMPLES

Abbreviations

| | |
|---|---|
| Ac | Acetyl |
| AcOH | Glacial acetic acid |
| aq. | Aqueous |
| Boc | t-Butoxycarbonyl |
| bs | Broad singlet |
| d | Doublet |
| dd | Doublet of doublets |
| dba | Dibenzylideneacetone |
| DIEA | N,N-Diisopropylethylamine |
| DCM | Dichloromethane (methylene chloride) |
| DEA | Diethanolamine |
| DME | Dimethoxyethane |
| DMEA | N,N-Dimethylethane-1,2-diamine |
| DMF | N,N-Dimethylformamide |
| DMSO | Dimethyl sulfoxide |
| dppf | 1,1'-Bis(diphenylphosphino)ferrocene |
| EDC | 1-Ethyl-3-(3-dimethylaminopropyl)carbodiimide |
| EDTA | Ethylene diamine tetraacetic acid |
| Et | Ethyl |
| Et$_2$O | Diethyl ether |
| EtOAc | Ethyl acetate |
| EtOH | Ethanol |
| g | Gram(s) |
| h | Hour(s) |
| HEPES | N-2-Hydroxyethylpiperazine-N'-2-ethanesulfonic acid |
| HPLC | High-pressure liquid chromatography |
| HOBT | 1-Hydrobenzotriazole |
| IPA | Isopropyl alcohol |
| KOAc | Potassium acetate |
| LC/MS | Liquid chromatography/mass spectrometry |
| m | Multiplet |
| M | Molar |
| MTBE | Methyl tert-butyl ether |
| Me | Methyl |
| MeCN | Acetonitrile |
| MeI | Iodomethane |
| MeOH | Methyl alcohol |
| min | Minute(s) |
| mmol | Millimole |
| MS | Mass spectrometry |
| MsCl | Methanesulfonyl chloride |
| n- | Normal (nonbranched) |
| N | Normal |
| N$_2$ | Nitrogen |
| NaBH(OAc)$_3$ | Sodium triacetoxyhydroborate |
| NH$_4$OAc | Ammonium acetate |
| NMR | Nuclear magnetic resonance |
| OR | optical rotation |
| Pd(OAc)$_2$ | Palladium(II) acetate |
| pH | $-\log[H^+]$ |
| Pd(PPh$_3$)$_4$ | Tetrakis(triphenylphosphine)palladium(0) |
| PPh$_3$ | Triphenylphosphine |
| ppm | Parts per million |
| PCy$_3$ | Tricyclohexylphosphine |
| R$_t$ | Retention time |
| rt | Room temperature |
| SM | Small molecule |
| s | Singlet |
| sat. | Saturated |
| t | Triplet |
| TBDMS | tert-Butyldimethylsilyl |
| TEA | Triethylamine |
| tert- | Tertiary |
| TES- | TriethylsilaneT |
| TFA | Trifluoroacetic acid |
| TES | Triethylsilane |
| THF | Tetrahydrofuran |
| TLC | Thin layer chromotographyn |
| TNFα | Tumor necrosis factor |
| Trt | Triphenylmethyl |
| UV | Ultraviolet |

TNFα FP Competitive Binding Assay

Solution Preparation

1. Assay Buffer: Prepare 1× Assay Buffer (Water with 47 mM HEPES, 47 mM NaCl, 0.9 mM EDTA, 0.0071% Triton X-100) by adding 25 mL of 1 M HEPES, 5 mL of 5 M NaCl, 1 mL of 0.5 M EDTA, and 375 μL of a 10% Triton X-100 stock to a fresh 500 mL bottle of water.

2. Assay Mixture: Prepare fresh Assay Mixture containing 20 nM TNFα trimer (60 nM protein) and 1 nM 2',7'-difluoro-3',6'-dihydroxy-N-(2-(2-(2-((4-(isoquinolin-8-yl)-3-(4-(isoquinolin-8-yl)phenethoxy)benzyl)oxy)

ethoxy)ethoxy)ethyl)-3-oxo-3H-spiro[isobenzofuran-1, 9'-xanthene]-5-carboxamide probe in 1× Assay Buffer.

Compound Plate Preparation

Manual 12-Point 1:3 Dilution Plates: (384 Well Polypropylene Plates)

Top concentration of compounds, 10 mM in DMSO, dispensed in rows A-O in columns 1 and 13.

Compounds are serially diluted 1:3 with DMSO in columns 2-12 or 14-24 using a 16-channel Matrix pipettor. Plates stored at −20° C.

Discovery Preps 12-Point 1:3 Dilution Plates: (384 Well Assay Plates)

Top concentration, 5 mM in DMSO, of compounds placed in rows A-O in columns 1 and 13.

Compounds are serially diluted 1:3 with DMSO in columns 2-12 or 14-24. Compound solutions are dispensed into replicate assay plates at 410 nL per well. Plates stored at 4° C.

TNFα FP Competitive Binding Assay Protocol

1. Compound plates are warmed to rt.
2. Fresh Assay Mixture is prepared.
3. Assay Mixture (20 µL) is dispensed each well of 384 assay plates using a Thermo Multidrop Combi or 16-channel Matrix pipettor. If Manual 12-point 1:3 Dilution Plates are to be tested, Assay Mix is dispensed into empty plates. Discovery Preps 12-point 1:3 Dilution Plates already contain 410 nL compound solution in DMSO.
4. For Manual 12-point 1:3 Dilution Plates, 0.7 µL is manually transferred using a 16-channel Matrix pipettor to replicate assay plates containing 20 µL Assay Mixture for a final top compound concentration of 338 µM (3.4% DMSO).
5. For Discovery Preps 12-point 1:3 Dilution Plates, 20 µL Assay Mixture added the 410 nL compound solution already in the plates yields a final top compound concentration of 100 µM (2.0% DMSO).
6. Background subtraction controls are wells P1-P8 containing only Assay Buffer. The low % inhibition controls are wells P9-P16 containing only Assay Mix. The high % inhibition are wells P17-P24 containing only 1 nM 2',7'-difluoro-3',6'-dihydroxy-N-(2-(2-(2-((4-(isoquinolin-8-yl)-3-(4-(isoquinolin-8-yl)phenethoxy)benzyl)oxy)ethoxy)ethoxy)ethyl)-3-oxo-3H-spiro[isobenzofuran-1, 9'-xanthene]-5-carboxamide probe in 1× Assay Buffer.
7. Plates are incubated at room temperature for 18-24 h in 37° C. incubator ($CO_2$ is off).
8. Prior to reading the assay, the plates are placed in a dark cabinet to equilibrate at rt for one hour.
9. Background-subtracted fluorescence polarization (mP) is measured using a PerkinElmer Envision plate reader.
10. Raw data is entered into Assay Explorer and dose-response curves are generated using a variable slope curve.

Supplies, Materials, and Reagents

| Item | Vendor | Catalog # |
| --- | --- | --- |
| HEPES (1M) | Invitrogen | 15630-080 |
| EDTA (0.5M) | Invitrogen | 15575-038 |
| NaCl (5M) | Sigma | S5150 |
| Triton X-100 | Sigma | T8787 |
| Water | Invitrogen | 10977-015 |

| Item | Vendor | Catalog # |
| --- | --- | --- |
| SM-antiTNFα OregonGreen488 probe | Abbvie | 2',7'-difluoro-3',6'-dihydroxy-N-(2-(2-(2-((4-(isoquinolin-8-yl)-3-(4-(isoquinolin-8-yl)phenethoxy)benzyl)oxy)ethoxy)ethoxy)ethyl)-3-oxo-3H-spiro[isobenzofuran-1,9'-xanthene]-5-carboxamide |
| Corning 3676 Compound Plate: 384 Well Low Volume Black Round Bottom Polystyrene NBS | Corning | 3676 |

SM-antiTNFα OregonGreen488 Probe

Preparation A 2-(4-(Isoquinolin-8-yl)phenyl)ethanol

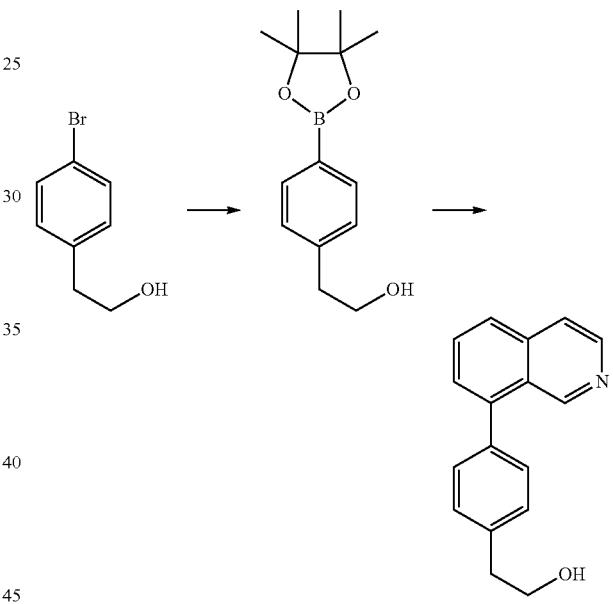

Step 1: 2-(4-(4,4,5,5-Tetramethyl-1,3,2-dioxaborolan-2-yl)phenyl)ethanol

Potassium acetate (4.88 g, 49.7 mmol), 4,4,4',4',5,5,5',5'-octamethyl-2,2'-bi(1,3,2-dioxaborolane) (7.6 g, 30 mmol) and $PdCl_2$(dppf) (0.91 g, 1.2 mmol) were added to a solution of 2-(4-bromophenyl)ethanol (5.0 g, 25 mmol) in 1,4-dioxane (100 mL) under $N_2$. The mixture was purged with $N_2$ then stirred under $N_2$ at about 85° C. for about 12 h. After cooling to rt, water (100 mL) was added and the mixture was extracted with EtOAc (2×100 mL). The combined organic layers were washed with saturated aqueous NaCl (100 mL) and dried over $Na_2SO_4$, filtered and concentrated under reduced pressure. The residue was purified via flash chromatography on silica gel (17% EtOAc/petroleum ether). The appropriate fractions were collected and concentrated under reduced pressure to give the title compound (6.2 g, 100%). $^1$H NMR (400 MHz, $CDCl_3$) δ 7.78 (d, J=7.9 Hz, 2H), 7.29-7.23 (m, 2H), 3.87 (t, J=6.6 Hz, 2H), 2.90 (t, J=6.6 Hz, 2H), 1.36 (s, 12H).

Step 2: 2-(4-(Isoquinolin-8-yl)phenyl)ethanol 1,1'-Bis(diphenylphosphino)ferrocenepalladium(II) dichloride dichloromethane complex (0.30 g, 0.40 mmol) was added to a mixture of 2-(4-(4,4,5,5-tetramethyl-1,3,2-dioxaborolan-2-yl)phenyl)ethanol (6.15 g, 24.8 mmol), 8-bromoisoquinoline (5.67 g, 27.3 mmol), cesium carbonate (16.6 g, 50.8 mmol), and 1,4-dioxane (60 mL) under $N_2$. The mixture was purged with $N_2$ and then stirred at about 95° C. for about 2 h. After cooling to rt, water (200 mL), chloroform (450 mL), and isopropyl alcohol (150 mL) were added then the layers were separated. The organic layer was dried over $Na_2SO_4$, filtered, and concentrated under reduced pressure. The residue was purified via flash chromatography on silica gel (0-100% EtOAc/heptane). The appropriate fractions were collected and concentrated under reduced pressure to give the title compound (3.72 g, 60%). MS m/z: 250 $(M+H)^+$.

For the purpose of the examples and tables below, the TNFα FP binding assay $IC_{50}$ (TNF $IC_{50}$) of each compound is expressed as follows; A=a compound with a TNF $IC_{50}$ less than 1.0 μM, B=a compound with a TNF $IC_{50}$ within the range of 1.0 to 10.0 μM, and C=a compound with a TNF $IC_{50}$ within the range of 10.0 to 100 μM.

Preparation B

Methyl 3-hydroxy-4-(isoquinolin-8-yl)benzoate

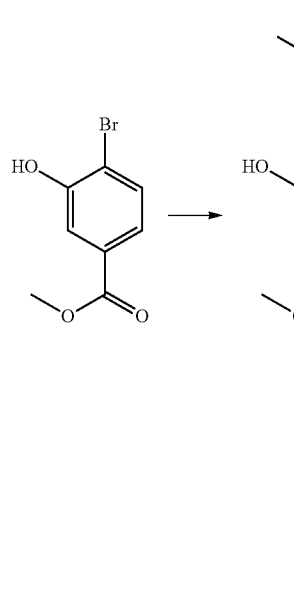

Step 1: Methyl 3-hydroxy-4-(4,4,5,5-tetramethyl-1,3,2-dioxaborolan-2-yl)benzoate KOAc (1.27 g, 13.0 mmol) was added to a solution of methyl 4-bromo-3-hydroxybenzoate (1.0 g, 4.3 mmol) in 1,4-dioxane (20 mL) under $N_2$ followed by addition of 4,4,4',4',5,5,5',5'-octamethyl-2,2'-bi(1,3,2-dioxaborolane) (2.2 g, 8.7 mmol) and $PdCl_2(dppf)$ (0.18 g, 0.22 mmol). The mixture was purged with $N_2$ then stirred at about 80° C. for about 3 h. The reaction mixture was cooled to rt and water (50 mL) was added. The mixture was extracted with EtOAc (3×50 mL). The combined organics were dried over $Na_2SO_4$, filtered, and concentrated under reduced pressure. The residue was purified by flash chromatography on silica gel (0-10% MeOH/DCM). The appropriate fractions were combined and concentrated under reduced pressure to afford the title product (1.13 g, 94%). $^1$H NMR (400 MHz, $CDCl_3$) δ 7.81 (s, 1H), 7.60 (d, J=8.1 Hz, 1H), 7.50-7.40 (m, 2H), 3.84 (s, 3H), 1.31 (s, 12H).

Step 2: Methyl 3-hydroxy-4-(isoquinolin-8-yl)benzoate

EtOH (100 mL) was added to a mixture of sodium carbonate (2.04 g, 19.2 mmol), $Pd(OAc)_2$ (0.022 g, 0.096 mmol), 8-bromoisoquinoline (2.00 g, 9.61 mmol), methyl 3-hydroxy-4-(4,4,5,5-tetramethyl-1,3,2-dioxaborolan-2-yl)benzoate (2.67 g, 9.61 mmol), and dicyclohexyl(2',6'-dimethoxy-[1,1'-biphenyl]-2-yl)phosphine (0.079 g, 0.19 mmol) under $N_2$. The mixture was degassed with $N_2$ and then heated to about 80° C. for about 16 h. Water (200 mL) was added and the resulting solid was collected by filtration then dried to afford the title product (1.27 g, 47%). MS m/z: 280 $(M+H)^+$.

Preparation #C

2',7'-Difluoro-3',6'-dihydroxy-N-(2-(2-(2-((4-(isoquinolin-8-yl)-3-(4-(isoquinolin-8-yl)phenethoxy)benzyl)oxy)ethoxy)ethoxy)ethyl)-3-oxo-3H-spiro[isobenzofuran-1,9'-xanthene]-5-carboxamide

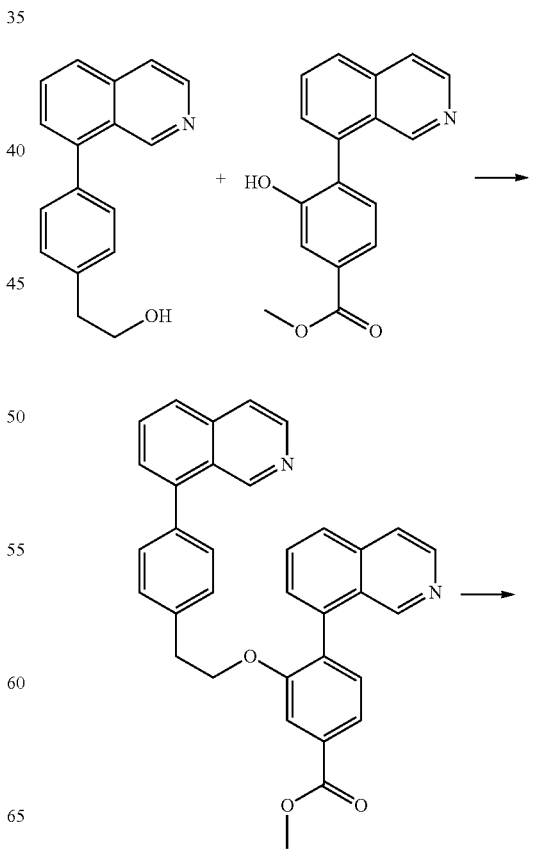

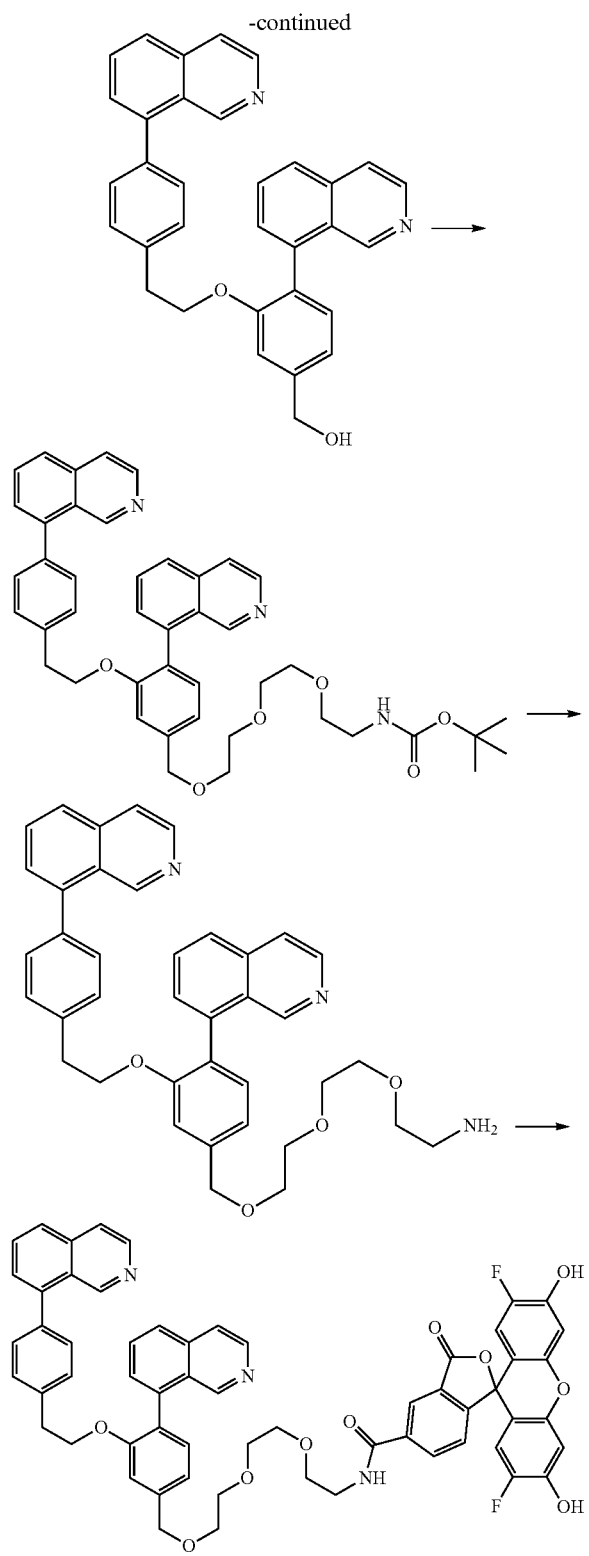

Step 1: Methyl 4-(isoquinolin-8-yl)-3-(4-(isoquinolin-8-yl)phenethoxy)benzoate

Cyanomethylenetributylphosphorane (0.90 mL, 3.4 mmol) was added to a mixture of methyl 3-hydroxy-4-(isoquinolin-8-yl)benzoate (800 mg, 2.86 mmol), 2-(4-(isoquinolin-8-yl)phenyl)ethanol (714 mg, 2.86 mmol), and toluene (30 mL). After stirring for about 4 h at about 100° C., the reaction mixture was allowed to cool to rt. Tri-n-butylphosphine (0.71 mL, 2.9 mmol) and (E)-N1,N1,N2,N2-tetramethyldiazene-1,2-dicarboxamide (493 mg, 2.86 mmol) were added respectively. After stirring at rt for about 18 h, the organic volatiles were removed under reduced pressure. The residue was purified by flash chromatography on silica gel (20% acetone/hexanes). The appropriate fractions were collected and concentrated under reduced pressure to afford the title product (1.07 g, 73%). MS m/z: 511 (M+H)+.

Step 2: (4-(Isoquinolin-8-yl)-3-(4-(isoquinolin-8-yl)phenethoxy)phenyl)methanol

Lithium aluminum hydride (1 M solution in THF, 0.4 mL, 0.4 mmol) was added to a solution of methyl 4-(isoquinolin-8-yl)phenethoxy)benzoate (204 mg, 0.400 mmol) and THF (3.6 mL) under $N_2$ at about 0° C. After about 1 h, 10% aqueous sodium potassium tartrate (6 mL) was added. The reaction was allowed to warm to rt. After about 10 min at rt, EtOAc (10 mL) was added. The layers were separated and the aqueous layer was extracted with EtOAc (10 mL). The combined organics were washed with sat. aq. NaCl (10 mL), dried over $MgSO_4$, filtered and concentrated under reduced pressure. The residue was purified by flash chromatography on silica gel (0-5% MeOH/$CHCl_3$). The appropriate fractions were collected and concentrated under reduced pressure to afford the title product (169 mg, 88%). MS m/z: 483 (M+H)+.

Step 3: 2-(2-(2-((4-(Isoquinolin-8-yl)-3-(4-(isoquinolin-8-yl)phenethoxy)benzyl)oxy)ethoxy)ethoxy)ethanamine (4-(Isoquinolin-8-yl)-3-(4-(isoquinolin-8-yl)phenethoxy)phenyl)methanol (31 mg, 0.064 mmol) and 2,2-dimethyl-4-oxo-3,8,11-trioxa-5-azatridecan-13-yl methanesulfonate (32 mg, 0.096 mmol) were combined in DMF (1 mL). Sodium hydride (10 mg, 0.26 mmol) was added in one portion. The reaction was stirred at rt for about 16 h. 50% MeCN/water (1 mL) was added and the resulting mixture was lyophilized to dryness. The residue was diluted with 90% DMSO/water (3 mL) and purified in one injection using RP-HPLC (Waters Deltapak C18 200×25 mm column) with time collection. The appropriate peak was collected and lyophilized. The residue was dissolved in TFA (2 mL) and shaken at rt for about 1 min. The volatiles were evaporated under a stream of dry nitrogen gas. The film was dissolved in 50% MeCN/water (1 mL) and lyophilized to afford a trifluoroacetate salt of the title compound (10 mg, 19%). MS m/z: 614 (M+H)+.

Step 4: 2',7'-difluoro-3',6'-dihydroxy-N-(2-(2-(2-((4-(isoquinolin-8-yl)-3-(4-(isoquinolin-8-yl)phenethoxy)benzyl)oxy)ethoxy)ethoxy)ethyl)-3-oxo-3H-spiro[isobenzofuran-1,9'-xanthene]-5-carboxamide 2-(2-(2-((4-(Isoquinolin-8-yl)-3-(4-(isoquinolin-8-yl)phenethoxy)benzyl)oxy)ethoxy)ethoxy)ethanamine (9.38 mg, 9.82 μmol) and 2,5-dioxopyrrolidin-1-yl 2',7'-difluoro-3',6'-dihydroxy-3-oxo-3H-spiro [isobenzofuran-1,9'-xanthene]-5-carboxylate (5 mg, 10 μmol) were combined in 1% DIEA/DMF (1 mL) and shaken at rt. After completion, the reaction was diluted with 90% DMSO/water (2 mL) and purified in one injection using RP-HPLC (Waters Deltapak C18 200×25 mm column) with slope collection. The appropriate peak was collected and lyophilized to afford the title product (4.1 mg, 41%). MS m/z: 1008 (M+H)$^+$.

Analytical Methods

Analytical data was included within the procedures below, in the illustrations of the general procedures, or in the tables of examples. Unless otherwise stated, all $^1$H NMR data were collected on a Varian 400 MHz Mercury Plus, Inova, or 400-MR instrument and chemical shifts are quoted in parts per million (ppm). LC/MS and HPLC data are referenced to the table of LC/MS and HPLC conditions using the lower case method letter provided in Table 1.

TABLE 1

LC/MS and HPLC methods

| Method | Conditions |
|---|---|
| a | LC/MS: The gradient was 1-90% B for 3.4 min, 90-100% B in 0.45 min, 100-1% B in 0.01 min, and then held at 1% B for 0.65 min (0.8 mL/min flow rate). Mobile phase A was 0.0375% TFA in water, mobile phase B was 0.018% TFA in MeCN. The column used for the chromatography was a 2.0 × 50 mm Phenomenex Luna-C18 column (5 μm particles). Detection methods are diode array (DAD) and evaporative light scattering (ELSD) detection as well as positive electrospray ionization (MS). |
| b | LC/MS: The gradient was 10-90% B for 1.15 min, with a hold at 90% B for 0.40 min, 90-10% B in 0.01 min, and then hold at 10% B for 0.54 min (1.0 mL/min flow rate). Mobile phase A was 0.0375% TFA in water, mobile phase B was 0.018% TFA in MeCN. The column used for the chromatography was a 2.1 × 30 mm Halo C18 column (2.7 μm particles). Detection methods are diode array (DAD) and positive/negative electrospray ionization. |
| c | Prep HPLC: The column is a Phenomenex Luna C18 10 μm column (250 mm × 50 mm). A gradient of acetonitrile (A) and 0.75% TFA in water (B) is used, at a flow rate of 80 mL/min. A linear gradient is used from about 3% of A to about 30% of A over about 20 min. Detection method is UV at wave length of 220 nM and 254 nM. |
| d | LC/MS: The gradient was 3% B for 0.02 min, 3-100% B in 1.28 min with a hold at 100% B for 0.15 min then 100-3% B in 0.05 min (1.5 mL/min flow rate). Mobile phase A was 0.1% TFA in water, mobile phase B was HPLC grade MeCN. The column used for the chromatography was a 2.1 × 30 mm Phenomenex Kinetex C8 column (2.6 μm particles) at a temperature of 65° C. Detection methods are diode array (DAD) and evaporative light scattering (ELSD) detection under positive APCI ionization conditions. |
| e | LC/MS: The gradient was 5% B for 0.1 min, 5-100% B in 2.5 min with a hold at 100% B for 0.3 min then 100-5% B in 0.1 min (2.0 mL/min flow rate). Mobile phase A was 0.1% TFA in water, mobile phase B was HPLC grade MeCN. The column used for the chromatography was a 2.1 × 50 mm Phenomenex Luna C8 (5.0 μm particles) at a temperature of 55° C. Detection methods are diode array (DAD) and evaporative light scattering (ELSD) detection under positive ESI ionization conditions. |
| f | LC/MS: The gradient was 3% B for 0.02 min, 3-100% B in 1.28 min with a hold at 100% B for 0.15 min then 100-3% B in 0.05 min (1.5 mL/min flow rate). Mobile phase A was 0.1% TFA in water, mobile phase B was HPLC grade MeCN. The column used for the chromatography was a 2.1 × 30 mm Phenomenex Kinetex C8 column (2.6 μm particles) at a temperature of 65° C. Detection methods are diode array (DAD) and evaporative light scattering (ELSD) detection under positive ESI ionization conditions. |
| g | LC/MS: The gradient was 5% B for 0.1 min, 5-100% B in 5.1 min with a hold at 100% B for 0.5 min then 100-5% B in 0.3 min (1.5 mL/min flow rate). Mobile phase A was 0.1% TFA in water, mobile phase B was HPLC grade MeCN. The column used for the chromatography was a 2.1 × 30 mm Phenomenex Kinetex C8 column (2.6 μm particles) at a temperature of 65° C. Detection methods are diode array (DAD) detection under positive APCI ionization conditions. |
| h | UPLC/MS: The gradient was 5% B for 0.1 min, 5-100% B in 5.1 min with a hold at 100% B for 0.5 min then 100-5% B in 0.3 min (1.5 mL/min flow rate). Mobile phase A was 0.1% TFA in water, mobile phase B was HPLC grade MeCN. The column used for the chromatography was a 2.1 × 30 mm Phenomenex Kinetex C8 column (2.6 μm particles) at a temperature of 65° C. Detection methods are diode array (DAD) detection under positive ESI ionization conditions. |
| i | LC/MS: The gradient was 10% B for 0.1 min, 10-100% B in 1.0 min with a hold at 100% B for 0.2 min then 100-10% B in 0.1 min (1.0 mL/min flow rate). Mobile phase A was 0.1% TFA in water, mobile phase B was HPLC grade MeCN. The column used for the chromatography was a 2.1 × 30 mm Waters BEH C8 column (1.7 μm particles) at a temperature of 55° C. Detection methods are diode array (DAD) detection under positive APCI ionization conditions. |
| j | Prep HPLC: The column is a Phenomenex Luna C18(2) 10 μm 100 Å AXIA column (250 mm × 21.2 mm). A gradient of MeCN (A) and 0.1% TFA in water (B) is used, at a flow rate of 25 mL/min. A linear gradient is used from about 5% of A to about 95% of A over about 10 min. Detection method is UV at wave length of 220 nM and 254 nM. |
| k | Prep HPLC: The column is a Phenomenex Luna C8(2) 5 μm 100 Å AXIA column (30 mm × 150 mm). A gradient of MeCN (A) and 0.1% TFA in water (B) was used, at a flow rate of 50 mL/min (0-0.5 min 5% A, 0.5-8.5 min linear gradient 5-100% A, 8.7-10.7 min 100% A, 10.7-11.0 min linear gradient 100-5% A). Fraction collection was automatically triggered when the extracted ion chromatogram (EIC) for the target mass exceeded the threshold specified in the method. |

TABLE 1-continued

LC/MS and HPLC methods

| Method | Conditions |
|---|---|
| l | Prep HPLC: The column is a Waters Sunfire C8, 5 μm 100 Å columns (30 mm × 75 mm). A gradient of MeCN (A) and 10 mM NH$_4$OAc in water (B) was used, at a flow rate of 50 mL/min (0-1.0 min 5-30% A, 1.0-8.5 min linear gradient 30-60% A, 8.7-10.7 min 100% A, 10.7-11 min linear gradient 100-5% A). Fraction collection was automatically triggered when the extracted ion chromatogram (EIC) for the target mass exceeded the threshold specified in the method. |
| m | Prep HPLC: The column is a Waters Sunfire C8, 5 um 100 Å column (30 mm × 75 mm). A gradient of MeCN (A) and 0.1% TFA in water (B) was used, at a flow rate of 40 mL/min (0-2.0 min 40% A, 2.0-10 min linear gradient 40-60% A, 10-11 min 60-100% A, 11-12 min linear gradient 100 Å). Fraction collection was automatically triggered when the extracted ion chromatogram (EIC) for the target mass exceeded the threshold specified in the method. |
| n | LC/MS: The gradient was 3% B for 0.02 min, 3-100% B in 1.78 min with a hold at 100% B for 0.15 min then 100-3% B in 0.05 min (1.5 mL/min flow rate). Mobile phase A was 0.1% TFA in water, mobile phase B was HPLC grade MeCN. The column used for the chromatography was a 2.1 × 30 mm Phenomenex Kinetex C8 column (2.6 μm particles) at a temperature of 65° C. Detection methods are diode array (DAD) and evaporative light scattering (ELSD) detection under positive ESI ionization conditions. |
| o | Prep HPLC: The column is a Waters Sunfire C8, 5 μm 100 Å columns (30 mm × 75 mm). A gradient of MeCN (A) and 0.1% TFA in water (B) was used, at a flow rate of 50 mL/min (0-1.5 min 5-25% A, 1.5-8.5 min linear gradient 25-55% A, 8.5-8.7 min linear gradient 55-100% A 8.7-10.7 min 100% A, 10.7-11 min linear gradient 100-5% A). Fraction collection was automatically triggered when the extracted ion chromatogram (EIC) for the target mass exceeded the threshold specified in the method. |
| p | Prep HPLC: The column is a Waters Sunfire C8, 5 um 100 Å column (30 mm × 75 mm). A gradient of MeCN (A) and 0.1% TFA in water (B) was used, at a flow rate of 50 mL/min (0-1.5 min 5-30% A, 1.5-8.5 min linear gradient 30-60% A, 8.5-8.7 min linear gradient 60-100% A 8.7-10.7 min 100% A, 10.7-11 min linear gradient 100-5% A). Fraction collection was automatically triggered when the extracted ion chromatogram (EIC) for the target mass exceeded the threshold specified in the method. |
| q | Prep HPLC: The column is a Waters Sunfire C8, 5 μm 100 Å columns (30 mm × 75 mm). A gradient of MeCN (A) and 0.1% TFA in water (B) was used, at a flow rate of 50 mL/min (0-0.5 min 5% A, 0.5-8.5 min linear gradient 05-100% A, 8.7-10.7 min 100% A, 10.7-11 min linear gradient 100-05% A. Fraction collection was automatically triggered when the extracted ion chromatogram (EIC) for the target mass exceeded the threshold specified in the method. |
| r | LC/MS: The gradient was 5-60% B in 1.5 min then 60-95% B to 2.5 min with a hold at 95% B for 1.2 min (1.3 mL/min flow rate). Mobile phase A was 10 mM NH$_4$OAc and mobile phase B was HPLC grade MeCN. The column used for the chromatography is a 4.6 × 50 mm MAC-MOD Halo C8 column (2.7 μm particles). Detection methods are diode array (DAD) and evaporative light scattering (ELSD) detection as well as positive/negative electrospray ionization.) |
| s | LC/MS: The gradient was 3% B for 0.3 min, 3-100% B in 4.95 min with a hold at 100% B for 0.6 min then 100-3% B in 0.15 min (0.5 mL/min flow rate). Mobile phase A was 0.1% TFA in water, mobile phase B was HPLC grade MeCN. The column used for the chromatography was a 2.1 × 30 mm Phenomenex Kinetex C8 column (2.6 μm particles) at a temperature of 65° C. Detection methods are diode array (DAD) detection under positive ESI ionization conditions. |
| t | LC/MS (The gradient was 0-80% B in 3.4 min, 80-100% B in 0.45 min, 100-0% B in 0.01 min, and then held at 0% B for 0.65 min (0.6 mL/min flow rate). Mobile phase A was 0.0375% TFA in water, mobile phase B was 0.018% TFA in MeCN. The column used for the chromatography was a 2.0 × 50 mm Phenomenex Luna-C18 column (5 μm particles). Detection methods are diode array (DAD) and evaporative light scattering (ELSD) detection as well as positive electrospray ionization(MS). |
| u | LC/MS: A gradient of 3-100% MeCN (A) and 10 mM NH$_4$OAc in water (B) was used, at a flow rate of 1.25 mL/min (0-0.02 min 3% A, 0.02-1.3 min 3-100% A, 1.3-1.45 min 100% A, 1.45-1.5 min 100-3% A. 0.25 min post-run delay). The column used was a Phenomenex Kinetex C8, 2.6 μm 100 Å (2.1 mm × 30 mm), at a temperature of 65° C. |
| v | LC/MS: The gradient was 5-60% B in 1.50 min then 60-95% B to 2.5 min with a hold at 95% B for 1.2 min (1.3 mL/min flow rate). Mobile phase A was 10 mM NH$_4$OAc, mobile phase B was HPLC grade MeCN. The column used for the chromatography was a 4.6 × 50 mm MAC-MOD Halo C8 column (2.7 μm particles). Detection methods were diode array (DAD) and evaporative light scattering (ELSD) detection as well as positive/negative electrospray ionization. |
| w | LC/MS: The gradient was 5-60% B in 1.5 min then 60-95% B to 2.5 min with a hold at 95% B for 1.2 min (1.3 mL/min flow rate). Mobile phase A was 10 mM NH$_4$OAc, mobile phase B was HPLC grade MeCN. The column used for the chromatography is a 4.6 × 50 mm MAC-MOD Halo C18 column (2.7 μm particles). Detection methods are diode array (DAD) and evaporative light scattering (ELSD) detection as well as positive/negative electrospray ionization. |
| x | LC/MS: The gradient was 3% B for 0.02 min, 3-100% B in 1.28 min with a hold at 100% B for 0.15 min then 100-3% B in 0.05 min (1.5 mL/min flow rate). Mobile phase A was 10 mM NH$_4$OAc in water, mobile phase B was HPLC grade MeCN. The column used for the chromatography was a 2.1 × 30 mm Phenomenex Kinetex C8 column (2.6 μm particles) at a temperature of 65° C. Detection methods are diode array (DAD) and evaporative light scattering (ELSD) detection under positive APCI ionization conditions. |

TABLE 1-continued

LC/MS and HPLC methods

| Method | Conditions |
|---|---|
| y | LC/MS: The gradient was 5-60% B in 1.6 min then 60-95% B to 2.2 min with a hold at 95% B for 0.1 min (1.0 mL/min flow rate). Mobile phase A was 10 mM $NH_4OAc$, mobile phase B was HPLC grade MeCN. The column used for the chromatography is a 2.1 × 30 mm Waters Cortecs C18 column (1.6 μm particles). Detection methods are diode array (DAD) and evaporative light scattering (ELSD) detection as well as positive/negative electrospray ionization. |
| z | LC/MS: The gradient was 5-60% B in 1.6 min then 60-95% B to 2.2 min with a hold at 95% B for 0.1 min (1.0 mL/min flow rate). Mobile phase A was 10 mM $NH_4OAc$, mobile phase B was HPLC grade MeCN. The column used for the chromatography is a 2.1 × 30 mm Waters Cortecs C18 column (1.6 μm particles). Detection methods are diode array (DAD) and evaporative light scattering (ELSD) detection as well as positive/negative electrospray ionization. |
| aa | Halo-2 C8 monitoring method: The gradient was 5-60% B in 1.6 min then 60-95% B to 2.2 min with a hold at 95% B for 0.1 min (1.0 mL/min flow rate). Mobile phase A was 10 mM $NH_4OAc$, mobile phase B was HPLC grade MeCN. The column used for the chromatography is a 2.1 × 30 mm Halo-2 C8 column (2 μm particles). Detection methods are diode array (DAD) and evaporative light scattering (ELSD) detection as well as positive/negative electrospray ionization. |
| ab | LC/MS: A gradient of 3-100% MeCN (A) and 0.1% TFA in water (B) was used, at a flow rate of 1.25 mL/min (0-0.05 min 3% A, 0.05-1.2 min 5-100% A, 1.2-1.4 min 100% A, 1.4-1.5 min 100-3% A. 0.25 min post-run delay). The column used was a Phenomenex Kinetex C8, 2.6 μm 100 Å (2.1 mm × 30 mm), at a temperature of 65° C. Detection methods are diode array (DAD) and evaporative light scattering (ELSD) detection under positive APCI ionization conditions. |
| ac | LC/MS: A gradient of 3-100% MeCN (A) and 10 mM $NH_4OAc$ in water (B) was used, at a flow rate of 1.25 mL/min (0-0.05 min 3% A, 0.05-1.2 min 5-100% A, 1.2-1.4 min 100% A, 1.4-1.5 min 100-3% A. 0.25 min post-run delay). The column used was a Phenomenex Kinetex C8, 2.6 μm 100 Å (2.1 mm × 30 mm), at a temperature of 65° C. Detection methods are diode array (DAD) and evaporative light scattering (ELSD) detection under positive APCI ionization conditions. |
| ad | LC/MS: The gradient was 10-80% B in 2.0 min, 80-80% B in 0.5 min, 80-10% B in 0.01 min, and then hold at 10% B for 0.5 min (1 mL/min flow rate. Mobile phase A was 10 mM $NH_4HCO_3$, mobile phase B was HPLC grade MeCN. The column used for the chromatography is a 2.1 × 50 mm Xbridge C18 column (5 μm particles). Detection methods are diode array (DAD) and evaporative light scattering (ELSD) detection as well as negative electrospray ionization (MS). |
| ae | LC/MS: The gradient was 1-90% B in 3.4 min, 90-100% B in 0.45 min, 100-1% B in 0.01 min, and then held at 1% B for 0.65 min (0.8 mL/min flow rate). Mobile phase A was 10 mM $NH_4HCO_3$, mobile phase B was HPLC grade MeCN. The column used for the chromatography is a 2.1 × 50 mm Xbridge Shield RPC18 column (5 μm particles). Detection methods are diode array (DAD) and evaporative light scattering (ELSD) detection as well as positive electrospray ionization (MS). |
| af | LC/MS (The gradient was 1-90% B in 3.4 min, 90-100% B in 0.45 min, 100-1% B in 0.01 min, and then held at 1% B for 0.65 min (0.8 mL/min flow rate). Mobile phase A was 0.0375% TFA in water, mobile phase B was 0.018% TFA in MeCN. The column used for the chromatography was a 2.0 × 50 mm Phenomenex Luna-C18 column (5 μm particles). Detection methods are diode array (DAD) and evaporative light scattering (ELSD) detection as well as positive electrospray ionization (MS). |
| ag | Prep LC/MS: The column is a Phenomenex Luna C8(2) 5 μm 100 Å AXIA column (50 mm × 30 mm). A gradient of MeCN (A) and 0.1% TFA in $H_2O$ (B) was used at a flow rate of 40 mL/min (0-0.5 min 5% A, 0.5-6.5 min linear gradient 5-100% A, 6.5-8.5 min 100% A, 8.5-9.0 min linear gradient 100-5% A, 9.0-10 min 5% A). Detection methods are diode array (DAD) under positive APCI ionization conditions. |
| ah | Prep LC/MS: The column is a Phenomenex Luna C8(2) 5 μm 100 Å AXIA column (50 mm × 30 mm). A gradient of MeCN (A) and 0.1% $NH_4OAc$ in $H_2O$ (B) was used at a flow rate of 40 mL/min (0-0.5 min 5% A, 0.5-6.5 min linear gradient 5-100% A, 6.5-8.5 min 100% A, 8.5-9.0 min linear gradient 100-5% A, 9.0-10 min 5% A). Detection methods are diode array (DAD) under positive APCI ionization conditions. |
| ai | Prep LC/MS: The column is a Phenomenex Luna C8(2) 5 μm 100 Å AXIA column (50 mm × 30 mm). A gradient of MeCN (A) and 0.1% $NH_4OAc$ in $H_2O$ (B) was used at a flow rate of 40 mL/min (0-0.5 min 5% A, 0.5-6.5 min linear gradient 5-100% A, 6.5-8.5 min 100% A, 8.5-9.0 min linear gradient 100-5% A, 9.0-10 min 5% A). Detection methods are diode array (DAD) under positive APCI ionization conditions. |
| aj | Prep HPLC: The column is a Phenomenex Luna (2) C18 10 μm (50 mm × 250 mm). A gradient of MeCN (A) and 10 mM $NH_4OAc$ in $H_2O$ (B) was used at a flow rate of 80 mL/min (0-20 min linear gradient 30-60% A). Detection method is UV at wave length of 220 nM and 254 nM. |
| ak | LC/MS: The gradient was 0-30% B in 2.6 min, 30-30% B in 0.1 min, 30-0% B in 0.01 min, and then hold at 0% B for 0.5 min (0.8 mL/min flow rate). Mobile phase A was 10 mM $NH_4HCO_3$, mobile phase B was HPLC grade MeCN. The column used for the chromatography is a 2.1 × 50 mm Xbridge C18 column (5 μm particles). Detection methods are diode array (DAD) and evaporative light scattering (ELSD) detection as well as positive electrospray ionization (MS). |

TABLE 1-continued

LC/MS and HPLC methods

| Method | Conditions |
|---|---|
| al | Prep HPLC: The column is a Phenomenex Luna C18 10 μm (50 mm × 250 mm). A gradient of MeCN (A) and 0.09% TFA in $H_2O$ (B) was used at a flow rate of 80 mL/min (0-20 min linear gradient 20-45% A). Detection method is UV at wave length of 220 nM and 254 nM. |
| am | LC/MS: The gradient was 10-100% B in 3.4 min with a hold at 100% B for 0.45 min, 100-10% B in 0.01 min, and then held at 10% B for 0.65 min (0.8 mL/min flow rate). Mobile phase A was 0.0375% TFA in water, mobile phase B was 0.018% TFA in MeCN. The column used for the chromatography was a 2.0 × 50 mm Phenomenex Luna-C18 column (5 μm particles). Detection methods are diode array (DAD) and evaporative light scattering (ELSD) detection as well as positive electrospray ionization (MS). |
| an | LC/MS: A gradient of 3-100% MeCN (A) and 10 mM $NH_4OAc$ in water (B) was used, at a flow rate of 1.25 mL/min (0-0.05 min 3% A, 0.05-1.2 min 5-100% A, 1.2-1.4 min 100% A, 1.4-1.5 min 100-3% A. 0.25 min post-run delay). The column used was a Phenomenex Kinetex C8, 2.6 μm 100 Å (2.1 mm × 30 mm), at a temperature of 65° C. Detection methods are diode array (DAD) and evaporative light scattering (ELSD) detection as well as positive electrospray ionization (MS). |
| ao | Prep HPLC: The column is a Phenomenex Luna C8(2) 5 μm 100 Å AXIA column (30 mm × 75 mm). A gradient of MeCN (A) and 0.1% TFA in water (B) was used, at a flow rate of 50 mL/min (0-0.5 min 5% A, 0.5-8.5 min linear gradient 20-100% A, 8.7-10.7 min 100% A, 10.7-11 min linear gradient 100-05% A). Fractions were collected based upon UV signal threshold and selected fractions subsequently analyzed by flow injection analysis mass spectrometry using positive APCI ionization on a Finnigan Navigator using 70:30 MeOH:10 mM $NH_4OH$ (aq) at a flow rate of 0.8 mL/min. |
| ap | Prep HPLC: The column is a Phenomenex Luna C8(2) 5 μm 100 Å AXIA column (30 mm × 75 mm). A gradient of MeCN (A) and 0.1% TFA in water (B) was used, at a flow rate of 50 mL/min (0-0.5 min 5% A, 0.5-8.5 min linear gradient 10-100% A, 8.7-10.7 min 100% A, 10.7-11 min linear gradient 100-05% A). Fractions were collected based upon UV signal threshold and selected fractions subsequently analyzed by flow injection analysis mass spectrometry using positive APCI ionization on a Finnigan Navigator using 70:30 MeOH:10 mM $NH_4OH$ (aq) at a flow rate of 0.8 mL/min. |
| aq | Prep HPLC: The column is a Phenomenex Luna C8(2) 5 um 100 Å AXIA column (30 mm × 75 mm). A gradient of MeCN (A) and 0.1% TFA in water (B) was used, at a flow rate of 50 mL/min (0-0.7 min 5% A, 0.5-12.71 min linear gradient 30.6-70.6% A, 12.72-12.72 min 100% A, 12.72-15.47 min 100%% A). Fraction collection was automatically triggered when the extracted ion chromatogram (EIC) for the target mass exceeded the threshold specified in the method. |
| ar | Prep HPLC: A gradient of MeOH (A) and 0.1% TFA in water (B) was used, at a flow rate of 40 mL/min (0-1.0 min 30% A, 1.0-6.5 min linear gradient 30-50% A, 6.25-10.5 min linear gradient 50-65% A, 10.5-11 min 100% A, 11-13.0 min 100% A using 30 × 100 mm Waters T3 column and UV collection at 202 nm. |

TABLE 2

Chiral separation methods

| Method | Conditions |
|---|---|
| 1 | Preparative SFC was performed on a THAR/Waters SFC 80 system running under SuperChrom software control. The preparative SFC system was equipped with a $CO_2$ pump, modifier pump, automated back pressure regulator (ABPR), UV detector, injector, and 6-position fraction collector. The mobile phase comprised of supercritical $CO_2$ supplied by a bulk tank of 99.5% bone-dry non-certified $CO_2$ pressurized to 1200 psi with a modifier of MeOH buffered with 0.1% DEA at a flow rate of 70 g/min. UV detection was set to collect at a wavelength of 220 nm, the column was at ambient temperature, and the backpressure regulator was set to maintain 100 bar. The sample was dissolved in MeOH at a concentration of 50 mg/mL and the injection volume was 1 mL. The mobile phase was held isocratically at 20% MeOH (0.1% DEA):$CO_2$. The instrument was fitted with a ChiralPak AD-H, 5 μm (21 mm × 250 mm) column. |
| 2 | Preparative SFC was performed on a THAR/Waters SFC 80 system running under SuperChrom software control. The preparative SFC system was equipped with a $CO_2$ pump, modifier pump, automated back pressure regulator (ABPR), UV detector, injector, and 6-position fraction collector. The mobile phase comprised of supercritical $CO_2$ supplied by a bulk tank of 99.5% bone-dry non-certified $CO_2$ pressurized to 1200 psi with a modifier of MeOH buffered with 0.5% DEA at a flow rate of 70 g/min. UV detection was set to collect at a wavelength of 220 nm, the column was at ambient temperature, and the backpressure regulator was set to maintain 100 bar. The sample was dissolved in MeOH at a concentration of 30 mg/mL and the injection volume was 0.25 mL. The mobile phase was held isocratically at 16% MeOH (0.1% EA):$CO_2$. The instrument was fitted with a YMC Cellulose - C, 5 μm (21 mm × 250 mm) column. |
| 3 | Preparative SFC was performed on a THAR/Waters SFC 80 system running under SuperChrom software control. The preparative SFC system was equipped with a $CO_2$ pump, modifier pump, automated back pressure regulator (ABPR), UV detector, injector, |

TABLE 2-continued

Chiral separation methods

| Method | Conditions |
|---|---|
| | and 6-position fraction collector. The mobile phase comprised of supercritical $CO_2$ supplied by a bulk tank of 99.5% bone-dry non-certified $CO_2$ pressurized to 1200 psi with a modifier of MeOH buffered with 0.1% DEA at a flow rate of 70 g/min. UV detection was set to collect at a wavelength of 220 nm, the column was at ambient temperature, and the backpressure regulator was set to maintain 100 bar. The sample was dissolved in MeOH at a concentration of 10 mg/mL, and the injection volume was 2 mL. The mobile phase was held isocratically at 30% MeOH (0.1% DEA):$CO_2$. The instrument was fitted with a YMC Cellulose - C, 5 μm (21 mm × 250 mm) column. |
| 4 | Preparative SFC was performed on a Jasco Prep 2088 system running under SF-Nav software control. The preparative SFC system was equipped with a $CO_2$ pump, autosampler, modifier pump, makeup pump, column oven, automated back pressure regulator (ABPR), UV detector, injector, and 6-position fraction collector. The mobile phase comprised of supercritical $CO_2$ supplied by a bulk tank of 99.5% bone-dry non-certified $CO_2$ pressurized to 1200 psi with a modifier of MeOH buffered with 0.1% DEA at a flow rate of 70 g/min. UV detection was set to collect at a wavelength of 220 nm, the column was at 40° C., and the backpressure regulator was set to maintain 100 bar. The sample was dissolved in MeOH at a concentration of 10 mg/mL, and the injection volume was 0.5 mL. The mobile phase was held isocratically at 30% MeOH (0.1% DEA):$CO_2$. The instrument was fitted with a ChiralPak AD-H, 5 μm (21 mm × 250 mm) column. |
| 5 | Preparative SFC was performed on a THAR/Waters SFC 80 system running under SuperChrom software control. The preparative SFC system was equipped with a $CO_2$ pump, modifier pump, automated back pressure regulator (ABPR), UV detector, injector, and 6-position fraction collector. The mobile phase comprised of supercritical $CO_2$ supplied by a bulk tank of 99.5% bone-dry non-certified $CO_2$ pressurized to 1200 psi with a modifier of MeOH buffered with 0.5% DEA at a flow rate of 70 g/min. UV detection was set to collect at a wavelength of 220 nm, the column was at ambient temperature, and the backpressure regulator was set to maintain 100 bar. The sample was dissolved in MeOH at a concentration of 15 mg/mL, and the injection volume was 0.1 mL. The mobile phase was held isocratically at 13% MeOH (0.1% DEA):$CO_2$. The instrument was fitted with a ChiralPak IC, 5 μm (21 mm × 250 mm) column. |
| 6 | Preparative SFC was performed on a THAR/Waters SFC 80 system running under SuperChrom software control. The preparative SFC system was equipped with an 8-way preparative column switcher, $CO_2$ pump, modifier pump, automated back pressure regulator (ABPR), UV detector, and 6-position fraction collector. The mobile phase comprised of supercritical $CO_2$ supplied by a dewar of bone-dry non-certified $CO_2$ pressurized to 350 psi with a modifier of MeOH buffered with 0.1% DEA at a flow rate of 70 g/min. UV detection was set to collect at a wavelength of 254 nm, the column was at ambient temperature, and the backpressure regulator was set to maintain 100 bar. The sample was dissolved in MeOH at a concentration of 5 mg/mL. The sample was loaded into the modifier stream in 1 mL (5 mg) injections. The mobile phase was held isocratically at 20% MeOH (0.1% DEA):$CO_2$. Fraction collection was time triggered. The instrument was fitted with a CHIRALPAK OJ-H, 5 μm (21 mm × 250 mm) column. |
| 7 | Preparative SFC was performed on a Jasco Prep 2088 system running under SF-Nav software control. The preparative SFC system was equipped with a $CO_2$ pump, autosampler, modifier pump, makeup pump, column oven, automated back pressure regulator (ABPR), UV detector, injector, and 6-position fraction collector. The mobile phase comprised of supercritical $CO_2$ supplied by a bulk tank of 99.5% bone-dry non-certified $CO_2$ pressurized to 1200 psi with a modifier of MeOH buffered with 0.1% DEA at a flow rate of 70 g/min. UV detection was set to collect at a wavelength of 220 nm, the column was at 40° C., and the backpressure regulator was set to maintain 100 bar. The sample was dissolved in MeOH at a concentration of 10 mg/mL, and the injection volume was 0.25 mL. The mobile phase was held isocratically at 20% MeOH (0.1% DEA):$CO_2$. The instrument was fitted with a YMC Cellulose-C, 5 μm (21 mm × 250 mm) column. |
| 8 | Preparative SFC was performed on a THAR/Waters SFC 80 system running under SuperChrom software control. The preparative SFC system was equipped with a $CO_2$ pump, modifier pump, automated back pressure regulator (ABPR), UV detector, injector, and 6-position fraction collector. The mobile phase was comprised of supercritical $CO_2$ supplied by a bulk tank of 99.5% bone-dry non-certified $CO_2$ pressurized to 1200 psi with a modifier of MeOH buffered with 0.1% DEA at a flow rate of 70 g/min. UV detection was set to collect at a wavelength of 220 nm, the column was at ambient temperature, and the backpressure regulator was set to maintain 100 bar. The sample was dissolved in MeOH at a concentration of 10 mg/mL, and the injection volume was 2 mL. The mobile phase was held isocratically at 20% MeOH (0.1% DEA):$CO_2$. The instrument was fitted with a YMC Cellulose-C, 5 μm (21 mm × 250 mm) column. |
| 9 | Prep HPLC: The column is an YMC SA column (20 × 250 mm). A gradient separation method wherein mobile phase A was EtOH (200 proof), mobile phase B was HPLC grade heptane with 0.20% DEA, at a flow rate was 20 mL/min. Gradient was held at 30% A for 12.4 min, then ramp to 60% A in 0.2 min, hold for 5.4 min. |
| 10 | Preparative SFC was performed on a Jasco Prep 2088 system running under SF-Nav software control. The preparative SFC system was equipped with a $CO_2$ pump, autosampler, modifier pump, makeup pump, column oven, automated back pressure regulator (ABPR), UV detector, injector, and 6-position fraction collector. The mobile phase comprised of supercritical $CO_2$ supplied by a bulk tank of 99.5% bone-dry non-certified $CO_2$ pressurized to 1200 psi with a modifier of MeOH buffered with 0.1% DEA |

TABLE 2-continued

Chiral separation methods

| Method | Conditions |
|---|---|
| | at a flow rate of 100 g/min. UV detection was set to collect at a wavelength of 220 nm, the column was at 40° C., and the backpressure regulator was set to maintain 100 bar. The sample was dissolved in MeOH at a concentration of 100 mg/mL, and the injection volume was 1.0 mL. The mobile phase was held isocratically at 30% MeOH (0.1% DEA):$CO_2$. The instrument was fitted with a YMC Cellulose-C, 5 μm (30 mm × 250 mm) column. |
| 11 | The mobile phase was comprised of supercritical $CO_2$ supplied by a bulk tank of 99.5% bone-dry non-certified $CO_2$ pressurized to 1200 psi with a modifier of MeOH at a flow rate of 75 g/min. UV detection was set to collect at a wavelength of 220 nm, the column was at 38° C., and the backpressure regulator was set to maintain 100 bar. The sample was dissolved in MeOH at a concentration of about 70 mg/mL, and the injection volume was 2.2 mL. The mobile phase was held isocratically at 46% MeOH:$CO_2$. The instrument was fitted with a Chiralpak AS-H, 5 μm (30 mm × 250 mm) column. |
| 12 | 10% B for 11 min then 10-51% B in 3 min and hold at 51% B for 4 min (20 mL/min flow rate). Mobile phase B was 1:1 HPLC grade MeOH: EtOH (200 proof), mobile phase A was HPLC grade heptane with 0.2% diethylamine added. The chromatography used a YMC-SA, 21 × 250 mm column (5 μm particles). |
| 13 | 2-7% B in 5 min and hold at 7% B for 17 min (20 mL/min flow rate). Mobile phase B was HPLC grade isopropanol, mobile phase A was HPLC grade heptane with 0.2% diethylamine added. The chromatography used a YMC-SA, 21 × 250 mm column (5 μm particles). |
| 14 | Preparative SFC was performed on a THAR/Waters SFC 80 system running under SuperChrom software control. The preparative SFC system was equipped with an 8-way preparative column switcher, $CO_2$ pump, modifier pump, automated back pressure regulator (ABPR), UV detector, and 6-position fraction collector. The mobile phase comprised of supercritical $CO_2$ supplied by a bulk-delivery supplied $CO_2$ tank (reagent grade) pressurized to 350 psi with a modifier of MeOH buffered with 0.5% DEA at a flow rate of 70 g/min. The column was at ambient temperature and the backpressure regulator was set to maintain 100 bar. The sample was dissolved in MeOH at a concentration of 20 mg/mL. The sample was loaded into the modifier stream in 0.1 mL (2 mg) injections. The mobile phase was held isocratically at 20% methanol (0.5% diethylamine):$CO_2$. Fraction collection was time triggered. The instrument was fitted with a Regis Whelk-O (S,S) column with dimensions 21 mm i.d. × 250 mm length with 5 μm particles. |
| 15 | Prep HPLC: The column was an [IC] column (20 mm × 250 mm). An isocratic separation method wherein mobile phase A was HPLC grade heptane with 0.20% DEA and mobile phase B was IPA with no modifier at a flow rate was 20 mL/min. 30% B for 21 min. |
| 16 | Prep HPLC: The column was an YMC-SB column (20 × 250 mm). An gradient separation method wherein mobile phase A was HPLC grade heptane with 0.20% DEA and mobile phase B was 1:1 MeOH/EtOH with no modifier at a flow rate was 20 mL/min. 30% B for 21 min. 2% B for 0.5 min then to 11% B in 1 min then 11-16% B in 10 min then hold at 16% for 1 min and re-equilibrate for 4 min |
| 17 | Preparative SFC was performed on a THAR/Waters SFC 80 system running under SuperChrom software control. The preparative SFC system was equipped with an 8-way preparative column switcher, $CO_2$ pump, modifier pump, automated back pressure regulator (ABPR), UV detector, and 6-position fraction collector. The mobile phase comprised of supercritical $CO_2$ supplied by bulk-delivered bone-dry non-certified $CO_2$ pressurized to 350 psi with a modifier of MeOH at a flow rate of 70 g/min. The column was at ambient temperature and the backpressure regulator was set to maintain 100 bar. The sample was dissolved in MeOH at a concentration of 5 mg/mL and loaded into the modifier stream in 1 mL (5 mg) injections. The mobile phase was held isocratically at 30% MeOH: $CO_2$. Fraction collection was time triggered. The instrument was fitted with a ChiralCel OD-H column with dimensions 21 mm i.d. × 250 mm length with 5 μm particles. |
| 18 | Preparative SFC was performed on a THAR/Waters SFC 80 system running under SuperChrom software control. The preparative SFC system was equipped with an 8-way preparative column switcher, $CO_2$ pump, modifier pump, automated back pressure regulator (ABPR), UV detector, and 6-position fraction collector. The mobile phase comprised of supercritical $CO_2$ supplied by bulk-delivered bone-dry non-certified $CO_2$ pressurized to 350 psi with a modifier of MeOH buffered with 0.1% diethylamine at a flow rate of 70 g/min. The column was at ambient temperature and the backpressure regulator was set to maintain 100 bar. The sample was dissolved in MeOH at a concentration of 15 mg/mL and loaded into the modifier stream in 1 mL (15 mg) injections. The mobile phase was held isocratically at 30% MeOH (0.1% DEA): $CO_2$. Fraction collection was time triggered. The instrument was fitted with a ChiralPak IB column with dimensions 21 mm i.d. × 250 mm length with 5 μm particles. |
| 19 | Prep HPLC: The column was a Phenomenex luna C18 (250 × 50 mm × 10 μm). A gradient separation method wherein mobile phase A was $CF_3COOH/H_2O$ = 0.075% v/v B was MeCN at a flow rate was 80 mL/min. 25% B for 21 min. 2% B for 20 min then to 55% B in 0.1 min then 100% B in 0.2 min then hold at 100% for 5 min and re-equilibrate for 1.5 min |
| 20 | Preparative SFC was performed on a THAR/Waters SFC 80 system running under SuperChrom software control. The preparative SFC system was equipped with an 8-way preparative column switcher, $CO_2$ pump, modifier pump, automated back pressure regulator (ABPR), UV detector, and 6-position fraction collector. The mobile phase |

TABLE 2-continued

Chiral separation methods

| Method | Conditions |
|---|---|
| | comprised of supercritical $CO_2$ supplied by bulk-delivered bone-dry non-certified $CO_2$ pressurized to 350 psi with a modifier of methanol at a flow rate of 80 g/min. The column was at ambient temperature and the backpressure regulator was set to maintain 100 bar. The sample was dissolved in methanol at a concentration of 50 mg/mL and loaded into the modifier stream in 0.5 mL (25 mg) injections. The mobile phase was held isocratically at 20% methanol: $CO_2$. Fraction collection was time triggered. The instrument was fitted with a ChiralPak IA column with dimensions 21 mm i.d. × 250 mm length with 5 pm particles. |
| 21 | Preparative SFC was performed on a THAR/Waters SFC 80 system running under SuperChrom software control. The preparative SFC system was equipped with an 8-way preparative column switcher, $CO_2$ pump, modifier pump, automated back pressure regulator (ABPR), UV detector, and 6-position fraction collector. The mobile phase comprised of supercritical $CO_2$ supplied by bulk-delivered bone-dry non-certified $CO_2$ pressurized to 350 psi with a modifier of isopropanol at a flow rate of 45 g/min. The column was at ambient temperature and the backpressure regulator was set to maintain 100 bar. The sample was dissolved in methanol at a concentration of 20 mg/mL and loaded into the modifier stream in 2 mL (40 mg) injections. The mobile phase was held isocratically at 30% isopropanol: $CO_2$. Fraction collection was time triggered. The instrument was fitted with a ChiralCel OD-H column with dimensions 21 mm i.d. × 250 mm length with 5 μm particles. |
| 22 | Preparative SFC was performed on a THAR/Waters SFC 80 system running under SuperChrom software control. The preparative SFC system was equipped with an 8-way preparative column switcher, $CO_2$ pump, modifier pump, automated back pressure regulator (ABPR), UV detector, and 6-position fraction collector. The mobile phase comprised of supercritical $CO_2$ supplied by bulk-delivered bone-dry non-certified $CO_2$ pressurized to 350 psi with a modifier of isopropanol at a flow rate of 70 g/min. The column was at ambient temperature and the backpressure regulator was set to maintain 100 bar. The sample was dissolved in methanol at a concentration of 30 mg/mL and loaded into the modifier stream in 1 mL (30 mg) injections. The mobile phase was held isocratically at 30% isopropanol: $CO_2$. Fraction collection was time triggered. The instrument was fitted with a ChiralCel OD-H column with dimensions 21 mm i.d. × 250 mm length with 5 μm particles. |

Purification Methods

Intermediates and final compounds prepared via the General Procedures can be optionally purified using one or more of the Purification Methods described below. The final compounds may be purified by any technique or combination of techniques known to one skilled in the art. Some examples that are not limiting include flash chromatography with a solid phase (e.g., silica gel, alumina, etc.) and a solvent (or combination of solvents) that elutes the desired compounds (e.g., hexanes, heptane, EtOAc, DCM, MeOH, EtOH, MeCN, water, etc.); preparatory TLC with a solid phase (e.g., silica gel, alumina etc.) and a solvent (or combination of solvents) that elutes the desired compounds (e.g., hexanes, heptane, EtOAc, DCM, MeOH, EtOH, MeCN, water, etc.); reverse phase HPLC (see Table 1 for some non-limiting conditions); recrystallization from an appropriate solvent (e.g., MeOH, EtOH, i-PrOH, EtOAc, toluene, etc.) or combination of solvents (e.g., EtOAc/heptane, EtOAc/MeOH, etc.); chiral LC with a solid phase and an appropriate solvent (e.g., EtOH/heptane, MeOH/heptane, i-PrOH/heptane, etc. with or without a modifier such as DEA, TFA, etc.) to elute the desired compound; chiral SFC (see Table 2 for some non-limiting conditions) with a solid phase and $CO_2$ with an appropriate modifier (e.g., MeOH, EtOH, i-PrOH with or without additional modifier such as DEA, TFA, etc.); precipitation from a combination of solvents (e.g., DMF/water, DMSO/DCM, EtOAc/heptane, etc.); trituration with an appropriate solvent (e.g., EtOAc, DCM, MeCN, MeOH, EtOH, i-PrOH, n-PrOH, etc.); extractions by dissolving a compound in a liquid and washing with an appropriately immiscible liquid (e.g., DCM/water, EtOAc/water, DCM/saturated $NaHCO_3$, EtOAc/saturated $NaHCO_3$, DCM/10% aqueous HCl, EtOAc/10% aqueous HCl, etc.); distillation (e.g., simple, fractional, Kugelrohr, etc.); gas chromatography using an appropriate temperature, carrier gas and flow rate; sublimation at an appropriate temperature and pressure; filtration through a media (e.g., Florosil®, alumina, Celite®, silica gel, etc.) with a solvent (e.g., heptane, hexanes, EtOAc, DCM, MeOH, etc.) or combination of solvents; salt formation with solid support (resin based, e.g., ion exchange) or without. Some descriptions of these techniques can be found in the following references, Gordon, A. J. and Ford, R. A. "The Chemist's Companion", 1972; Palleros, D. R. "Experimental Organic Chemistry", 2000; Still, W. C., Kahn, M. and Mitra, A. J. Org. Chem. 1978, 43, 2923; Yan, B. "Analysis and Purification Methods in Combinatorial Chemistry" 2003; Harwood, L. M., Moody, C. J. and Percy, J. M. "Experimental Organic Chemistry: Standard and Microscale, $2^{nd}$ Edition", 1999; Stichlmair, J. G. and Fair, J. R. "Distillation; Principles and Practices" 1998; Beesley T. E. and Scott, R. P. W. "Chiral Chromatography", 1999; Landgrebe, J. A. "Theory and Practice in the Organic Laboratory, $4^{th}$ Edition", 1993; Skoog, D. A. and Leary, J. J. "Principles of Instrumental Analysis, $4^{th}$ Edition" 1992; Subramanian, G. "Chiral Separation Techniques $3^{rd}$ Edition" 2007; Kazakevich, Y. and Lobrutto, R. "HPLC for Pharmaceutical Scientists" 2007.

Degassing Methods

Preparations of intermediates and final compounds obtained via the General Procedures can be optionally degassed using one or more of the Degassing Methods described below. The reaction mixtures may be degassed by a single or multiple applications of any technique or combination of techniques known to one skilled in the art. Some examples that are not limiting include bubbling a continuous stream of an inert gas (e.g., nitrogen, argon, etc.) through a mixture of reagents and a solvent suitable for the transformation (e.g., THF, 1,4-dioxane, EtOAc, DCM, toluene, MeOH, EtOH, DMF, MeCN, water, etc.), freeze-thawing of a mixture of reagents in a solvent (e.g., THF, 1,4-dioxane, EtOAc, DCM, toluene, MeOH, EtOH, DMF, MeCN, water, etc.) where the resulting solution is cooled below its freezing point and evacuated under reduced pressure, then allowed to warm above the freezing point and purged with an atmosphere of inert gas (e.g., nitrogen, argon, etc.); evacuation under reduced pressure of a mixture of reagents with or without a suitable solvent for the transformation (e.g., THF, 1,4-dioxane, EtOAc, DCM, toluene, MeOH, EtOH, DMF, MeCN, water, etc.) followed by purging of the mixture with an inert gas (e.g., nitrogen, argon, etc.); evacuation under reduced pressure of a mixture of reagents in a suitable solvent for the transformation (e.g., THF, 1,4-dioxane, EtOAc, DCM, toluene, MeOH, EtOH, DMF, MeCN, water, etc.) with the aid of mechanical agitation (e.g., stirring, shaking, sonication, etc.) followed by purging of the mixture with an inert gas (e.g., nitrogen, argon, etc.). Some descriptions of these techniques can be found in the following references, Gordon, A. J. and Ford, R A. *The Chemist's Companion*, 1972; Palleros, D. R. *Experimental Organic Chemistry*, 2000; Harwood, L. M., Moody, C. J. and Percy, J. M. *Experimental Organic Chemistry: Standard and Microscale*, $2^{nd}$ Edition, 1999; Landgrebe, J. A. *Theory and Practice in the Organic Laboratory*, $4^{th}$ Edition, 1993; Leonard, J., Lygo, B. and Procter, G. *Advanced Practical Organic Chemistry*, $2^{nd}$ Edition, 1998; Meyers, A. G.; Dragovich, P. S. *Organic Syntheses*, 1995, 72:104; Hajos, Z. G., Parrish, D. R *Organic Syntheses*, 1985, 63:26.

Compound Syntheses

None of the specific conditions and reagents noted herein are to be construed as limiting the scope of the invention and are provided for illustrative purposes only. All starting materials are commercially available unless otherwise noted after the chemical name. Reagent/reactant names given are as named on the commercial bottle or as generated by IUPAC conventions, CambridgeSoft® ChemDraw Ultra 12.0, CambridgeSoft® ChemDraw Professional 15.0, CambridgeSoft® Chemistry E-Notebook 11, or AutoNom 2000. Compounds designated as salts (e.g., hydrochloride, acetate) may contain more than one molar equivalent of the salt. For reactions run under microwave heating conditions, the parameters were 300 watts with a maximum pressure of 250 psi.

General Synthetic Schemes

Compounds of the invention may be prepared using the synthetic transformations illustrated in Schemes I-VII. Starting materials are commercially available, may be prepared by the procedures described herein, by literature procedures, or by procedures that would be well known to one skilled in the art of organic chemistry. Further functionalization of any of the R groups in the Schemes I-VII below (e.g., R', R") can be performed, if desired, at any point in the reaction sequence using reactions known to one skilled in the art (for example, Larock, R. C. "Comprehensive Organic Transformations: A Guide to Functional Group Preparations, 2nd edition", 1999, Wiley-VCH). For example, formation of amides, ureas, sulfonamides, aryl amines, heteroaryl amines, sulfonyl ureas, substituted amines, or guanidines can be prepared with an R group containing a primary or secondary amine. In a second non-limiting example, an R group containing a halide may be reacted with an amine to give a substituted amine or an alcohol to give substituted ether. In a third non-limiting example, formation of ethers, carbamates, and esters can be prepared with a corresponding R group containing an alcohol. Also, deprotection of an R group to yield deprotected compounds may be performed using conditions such as those described in Greene, T. W. and Wuts, P. G. M. "Protective Groups in Organic Synthesis, 3rd Edition", 1999, Wiley-Interscience and the deprotected compounds may then be reacted further as described above. In addition, prodrug moieties may be introduced to the intermediates or final compounds described herein.

Methods for preparing cycloalkyl[4,5]imidazo[1,2-a]pyridine (wherein $A_1$ is CH) or cycloalkyl[4,5]imidazo[1,2-b]pyridazine (wherein $A_1$ is N) compounds 6 of the invention are illustrated in Scheme I. 1,3-Cycloalkyldiones 1 can be obtained commercially or prepared by one skilled in the art (for example, *JACS* 1980, 102(6), 2095-2096). In Scheme I, step a, bromocycloalkyldiones 2 can be obtained commercially or prepared from bromination of 1,3-cycloalkyldiones 1 using conditions such as those described in step 1 of Preparation #1, #2, and #3. Bromocycloalkyldiones 2 in Scheme I, step b, are reacted with 5-bromopyridin-2-amine with or without a base; such as NaHCO$_3$, to form the cycloaddition products 3, wherein $A_1$ is CH, or reacted with 6-bromopyridazin-3-amine to form the cycloaddition products 3, wherein $A_1$ is N (for example, see Preparation #64). Bromoketones 3 may undergo a variety of reactions known to one skilled in the art (for example, Larock, R. C. [referenced above]) including, but not limited to, a Suzuki coupling (for example, Preparation #37, or *J. Organomet. Chem.* 1999, 576, 147-168) with an aryl or heteroaryl boronic acid or boronate to give cycloalkyl[4,5]imidazo[1,2-a]pyridin-9(6H)-ones 4 as shown in Scheme I, step c. The boronic acids and/or boronic esters used in the Suzuki coupling are either commercially available or can be prepared by methods known to one skilled in the art (Miyaura, N. et al *Chem. Rev.* 1995, 95, 2457-2483). Alcohols 5 in Scheme I, step d, may be obtained by the reaction of ketones 4 with organometallic reagents including, but not limited to, Grignard reagents using methods known to one skilled in the art (for example, see Example #5 or Larock, R. C. [referenced above]). The Grignard reagents used are either commercially available or can be prepared by methods known to one skilled in the art (for example *Synthesis* 1981, 8, 585-604). Tertiary alcohols 5 are ionized with BF$_3$.OEt$_2$ and reacted with TES to provide the deoxygenated products 6 and/or the elimination products 7 (for example, *Synth. Commun.* 1988, 18, 833-839, or see Example #14). Alternatively, in Scheme I, step g, alcohols 8 can be prepared in a similar manner from ketones 3 with organometallic reagents including, but not limited to, Grignard reagents using methods known to one skilled in the art (for example, see Preparation #3, step 3 and Preparation #65, step 1). The Grignard reagents used are either commercially available or can be prepared by methods known to one skilled in the art (for example *Synthesis* 1981, 8, 585-604). In subsequent reaction with boron trifluoride diethyl etherate and TES provides deoxygenated products 10 and/or the elimination products 9 (for example, see *Synth. Commun.* 1988, 18, 833-839, Preparation #3, step 4, Example #10, step 2, or Preparation #65, step 2). In Scheme I, step i, either deoxygenated products 10 and/or the elimination products 9 may undergo a variety of reactions known to one skilled in the art (for example, Larock, R. C. [referenced above]) including, but not limited to, a Suzuki coupling with a boronate ester or boronic acid (for example, see Example #10, step 2, Example #7, or Example #33) to give products 6 and/or the dienes 7. The boronic acids and/or boronic esters used in the Suzuki coupling are either commercially available or can be prepared by methods known to one skilled in the art (Miyaura, N. et al *Chem. Rev.* 1995, 95, 2457-2483) or by further functionalization of any R group containing boronic acids and/or boronic esters or the corresponding halogenated aryl or heteroaryl precusor as described above (see, for example, Preparation #22, or Preparation #34). In Scheme I, step f, alkenes 7 are hydrogenated with Pd/C to give products 6 using methods known to one skilled in the art (for example, see Example #15, or Larock, R. C. [referenced above]).

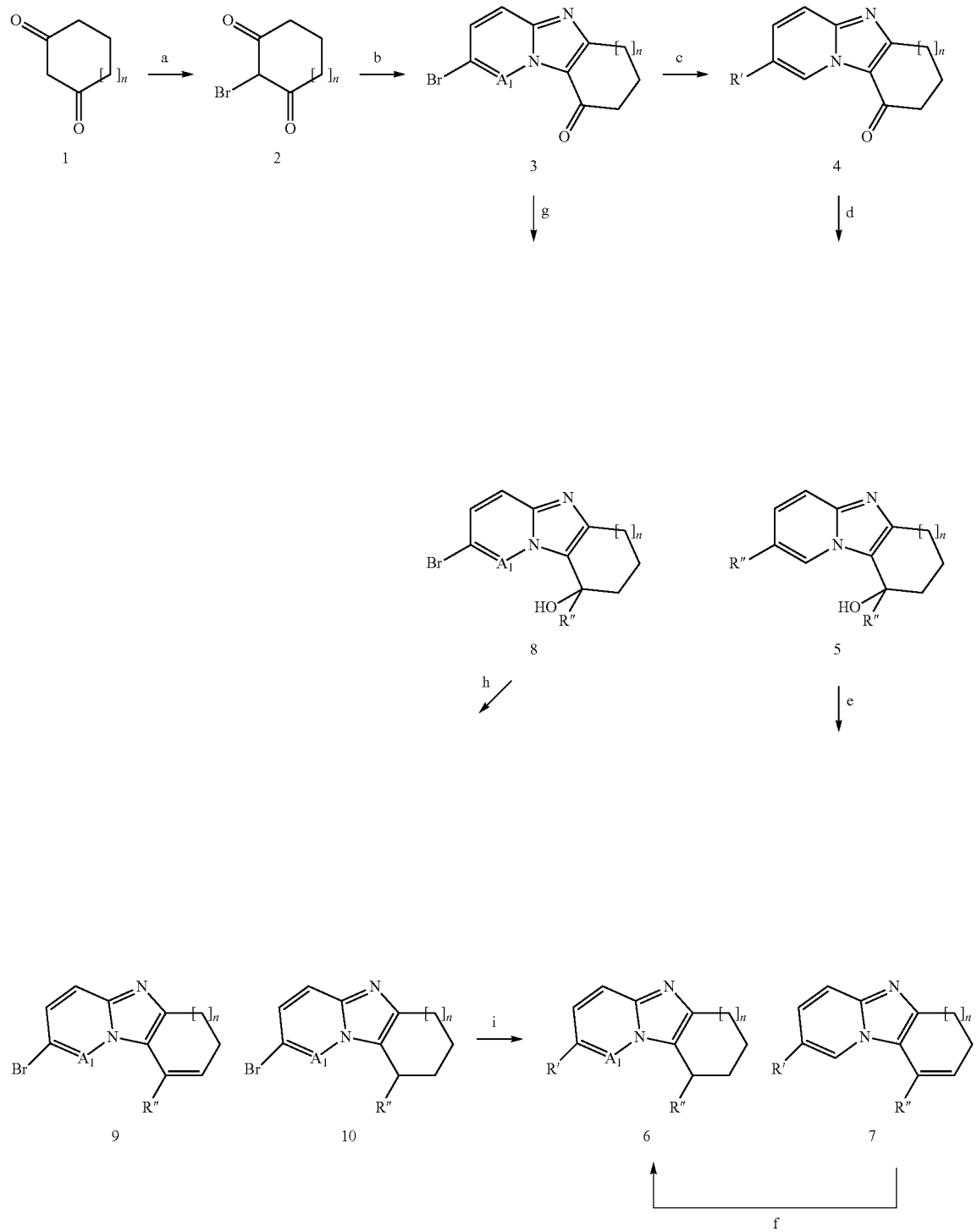

Scheme I n = 0, 1, 2  $A_1$ = N, CH

Methods for preparing imidazo[1,2-a]pyridines 14 of the invention are illustrated in Scheme I. Cyclohex-2-enone 11, Scheme II, step a, can undergo 1,4-addition with arylboronic acids via rhodium-catalyzed conditions known to one skilled in the art (for example, *JOC* 2013, 78, 9975-9980 or see Example #16, step 1). In Scheme II, step b, cyclohexanones 12 are brominated with $Br_2$ and subsequently cyclized with 5-bromopyridin-2-amine using conditions such as those described in Example #16, step 2 to give tricycles 13. Bromocycloalkyl[4,5]imidazo[1,2-a]pyridines 13 may undergo a variety of reactions known to one skilled in the art (for example, Larock, R. C. referenced above) including, but not limited to, a Suzuki coupling (for example, see Example #16, step 3, or *J. Organomet. Chem.* 1999, 576, 147-168) with an aryl or heteroaryl boronic acid or boronate to give the imidazo[1,2-a]pyridines 14. The boronic acids and/or boronic esters used in the Suzuki coupling are either commercially available or can be prepared by methods known to one skilled in the art (for example see Miyaura, N. [referenced above]).

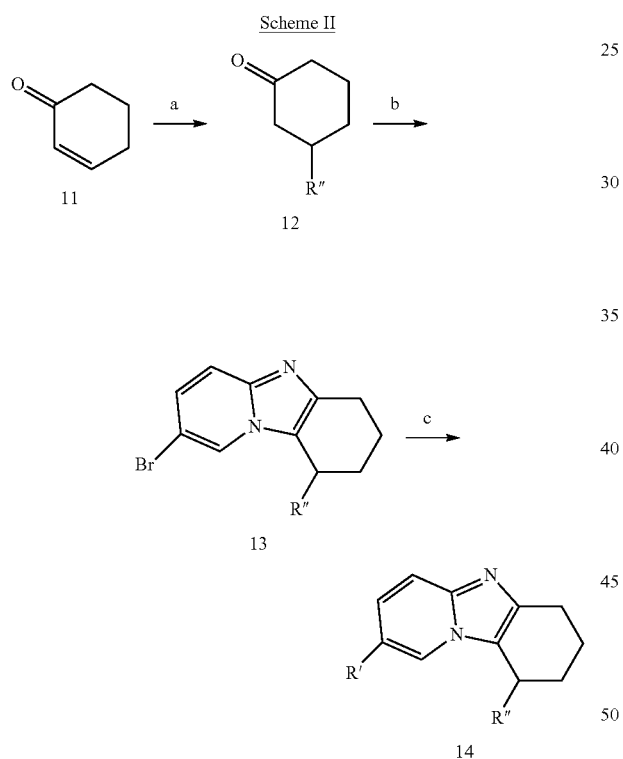

Alternatively, methods for preparing imidazo[1,2-a]pyridines 16 of the invention are illustrated in Scheme III. As shown in step a, alcohols 8 provide the deoxygenated products 10 and/or the elimination products 9 using conditions such as those described above (see, for example, Preparation #51, step 2). Boronic acids 15, step b, can be prepared from the deoxygenated products 10 and/or the elimination products 9 using methods known to one skilled in the art (for example see Miyaura, N. [referenced above] or Preparation #51). Boronic acids 15 may undergo a Suzuki coupling (for example, see Example #AG. 1) with an optionally substituted aryl or heteroaryl halide to give the imidazo[1,2-a]pyridines 16.

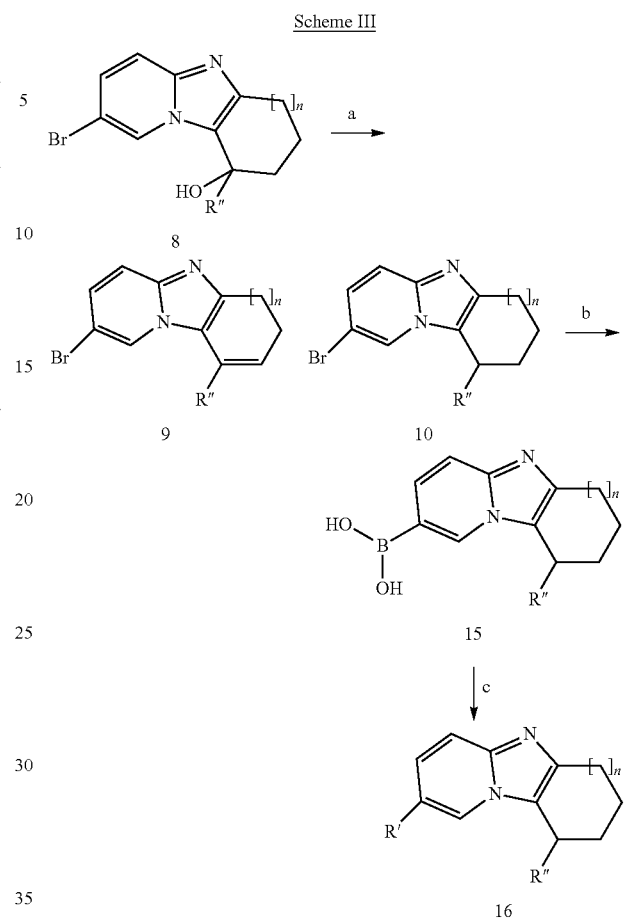

Methods for preparing pyranoimidazo[1,2-a]pyridine (wherein $A_1$ is CH) or pyranoimidazo[1,2-b]pyridazine (wherein $A_1$ is N) compounds 22 of the invention are illustrated in Scheme IV. As shown in step a, 2H-pyran-3,5(4H,6H)-dione may be brominated by methods known to one skilled in the art (see, for example, Larock, R. C. [referenced above] or Preparation #63, step 1). The bromodione 18 are reacted with 5-bromopyridin-2-amine or with 6-bromopyridazin-3-amine to form the cycloaddition products 19, (see, for example, Preparation #63, step 2). Cycloaddition products 19 can be reacted with organometallic reagents including, but not limited to, Grignard reagents using methods known to one skilled in the art (for example, see Preparation #63, step 3 or Larock, R. C. [referenced above]) to afford alcohols 20. These alcohols 20 may then be deoxygenated to pyranoimidazo[1,2-a]pyridine (wherein $A_1$ is CH) or pyranoimidazo[1,2-b]pyridazine (wherein $A_1$ is N) compounds 21 by methods described in Preparation #63, step 4 or Preparation #65, step 2. Further functionalization of compounds 21 via a Suzuki coupling (for example, see Example #AG.1) with a boronate ester or boronic acid (for example, see Example #32 or Example #AF.1) give products 22. The boronic acids and/or boronic esters used in the Suzuki coupling are either commercially available or can be prepared by methods known to one skilled in the art (Miyaura, N. et al *Chem. Rev.* 1995, 95, 2457-2483) or by further functionalization of any R group containing boronic acids and/or boronic esters or corresponding halogenated aryl or heteroaryl precursor as described above (see, for example, Preparation #22, or Preparation #39 and Example #AF. 1).

Methods for preparing tricyclic benzimidazoles 28 (wherein Y is O or $CH_2$) of the invention are illustrated in Scheme IV

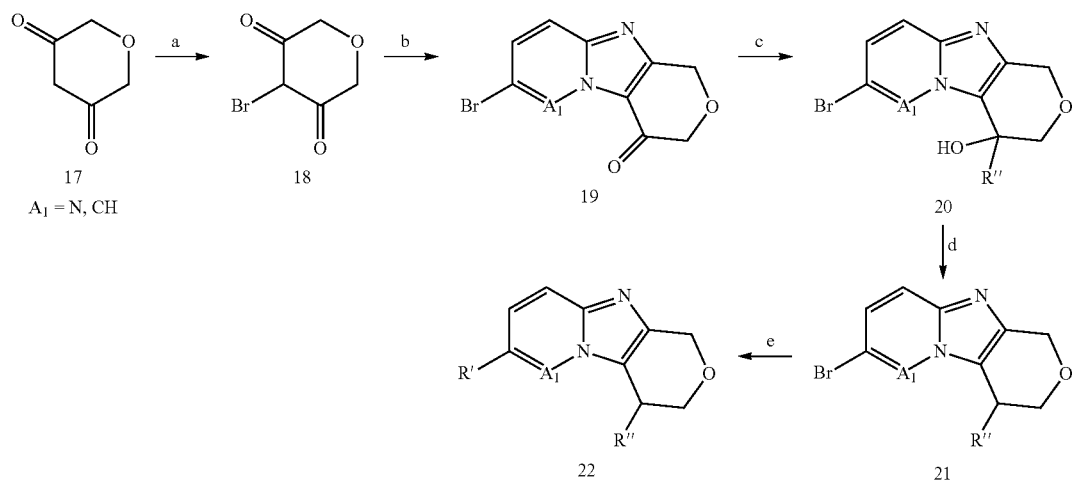

Alternatively, methods for preparing ketones 4 of the invention are illustrated in Scheme V. As shown in step a, (6-aminopyridin-3-yl)boronic acid 23 may undergo Suzuki coupling with an optionally substituted aryl or heteroaryl halide to give substituted pyridin-2-amines 24 by methods known to one skilled in the art or as described in Preparation 10, step 1. Pyridin-2-amines 24 are reacted with, bromocycloalkyldiones 2, obtained commercially or prepared from bromination of 1,3-cycloalkyldiones using conditions such as those described in step 1 of Preparation #1, #2, and #3, to afford the ketones 4 using conditions described in Preparation #10, step 2. Further transformation of ketones 5 can be performed as described in Scheme I.

Scheme V

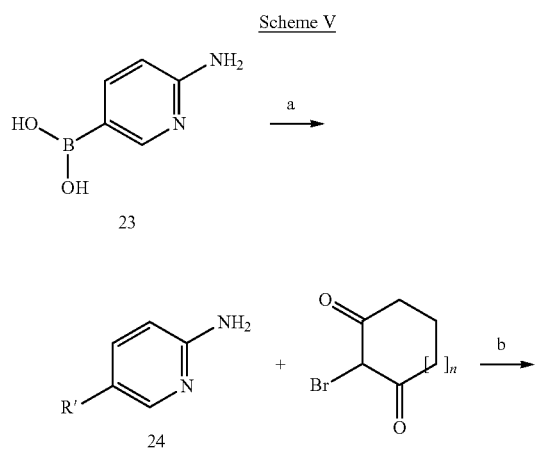

Scheme VI. Cyclic amides 25 are either commercially available or can be prepared by methods known to one skilled in the art (for example Bull. Korean Chem. Soc. 1999, 20, 1253-1254, WO2012034095A1, Preparation #23, or Preparation #53). Amidines 26 in Scheme VI, step a, are prepared using Vilsmeier conditions from cyclic amides 25 and 4-bromo-2-fluoroaniline such as those described in Preparation #9, step 1 or Tetrahedron 2012, 68, 2993-3000. Amidines 26 undergo an intramolecular $S_NAr$ substitution reaction (Scheme VI, step b) conditions known to one skilled in the art (for example, Preparation #9, step 2, or Tetrahedron 2012, 68, 2993-3000). Tricyclic benzimidazoles 27 may undergo a variety of reactions known to one skilled in the art (for example, Larock, R. C. referenced above) including, but not limited to Suzuki coupling (for example, see Example #19 or J. Organometallic Chem. 1999, 576, 147) with a boronic acid or boronate. The boronic acids and/or boronic esters used in the Suzuki coupling are either commercially available or can be prepared by methods known to one skilled in the art (for example see Miyaura, N. [referenced above]) or by further functionalization of any R group containing boronic acids and/or boronic esters or corresponding halogenated aryl or heteroaryl precursor as described above (see, for example, Preparation #22, or Preparation #39 and Example #24). In a second non-limiting example, tricyclic benzimidazoles 4 with an R'" group containing a halide may be reacted with an amine to give a substituted amine (for example, see Example #4, or Larock, R. C. [referenced above]).

Scheme VI

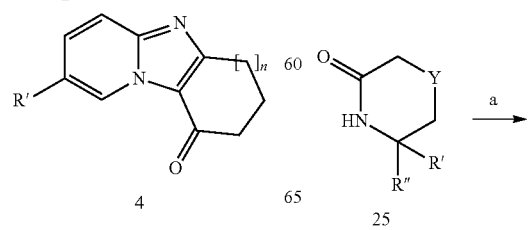

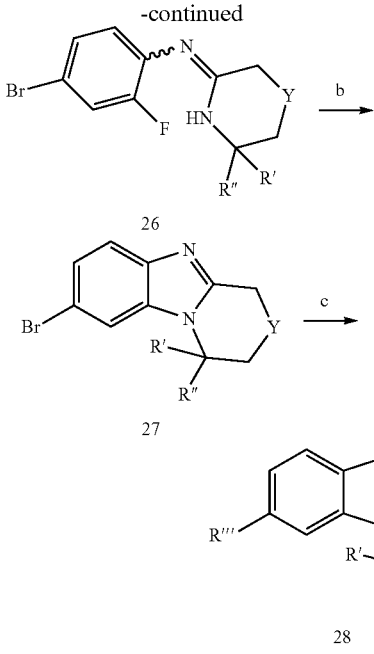

Y = O, CH₂

Methods for preparing tricyclic benzimidazoles 32 (wherein Y is O or CH₂; A₁, A₂, and A₃ are CH; or A₁ is N and A₂ and A₃ are CH; or A₂ is N and A₁ and A₃ are CH; or A₃ is N and A₁ and A₂ are CH) of the invention are illustrated in Scheme VII. Cyclic amides 29 are either commercially available or can be prepared by methods known to one skilled in the art (see, for example, *Bull. Korean Chem. Soc.* 1999, 20, 1253-1254, WO2012034095A1, Preparation #33, or Preparation #80, step 1). Amidines 30 in Scheme VII, step a, are synthesized from cyclic amides 29 and the appropriate ortho bromoanilinic aromatic or heteroaromatic rings 18 (wherein X is Cl or Br; A₁, A₂, and A₃ are CH; or A₁ is N and A₂ and A₃ are CH; or A₂ is N and A₁ and A₃ are CH; or A₃ is N and A₁ and A₂ are CH) using conditions such as those described in Preparation #4, step 1 or *Tetrahedron* 2012, 68, 2993-3000. Amidines 30 undergo copper catalyzed N-arylation (Scheme VII, step b) using conditions known to one skilled in the art (for example, Preparation #4, step 1, Preparation #24, or *Tetrahedron* 2012, 68, 2993-3000). Tricyclic benzimidazoles 31 may undergo a variety of reactions known to one skilled in the art (for example, Larock, R. C. referenced above) including, but not limited to Buchwald with an amine (for example, Hartwig, J. F. *Angew. Chem. Int. Ed.* 1998, 37, 2046 or see Example #18) or Suzuki coupling (for example, see Example #17 or *J. Organometallic Chem.* 1999, 576, 147) with a boronic acid or boronate. The boronic acids and/or boronic esters used in the Suzuki coupling are either commercially available or can be prepared by methods known to one skilled in the art (for example see Miyaura, N. [referenced above]) or by further functionalization of any R group containing boronic acids and/or boronic esters or corresponding halogenated aryl or heteroaryl precusor as described above (see, for example, Preparation #22, or Example #35). In a second non-limiting example, tricyclic benzimidazoles 32 with an R'" group containing a halide may be reacted with an amine to give a substituted amine (for example, see Example #22, or Larock, R. C. [referenced above]) or provide ethers when reacted with an alcohol (for example, see Example #47, Example #48, or Example #74.

Scheme VII

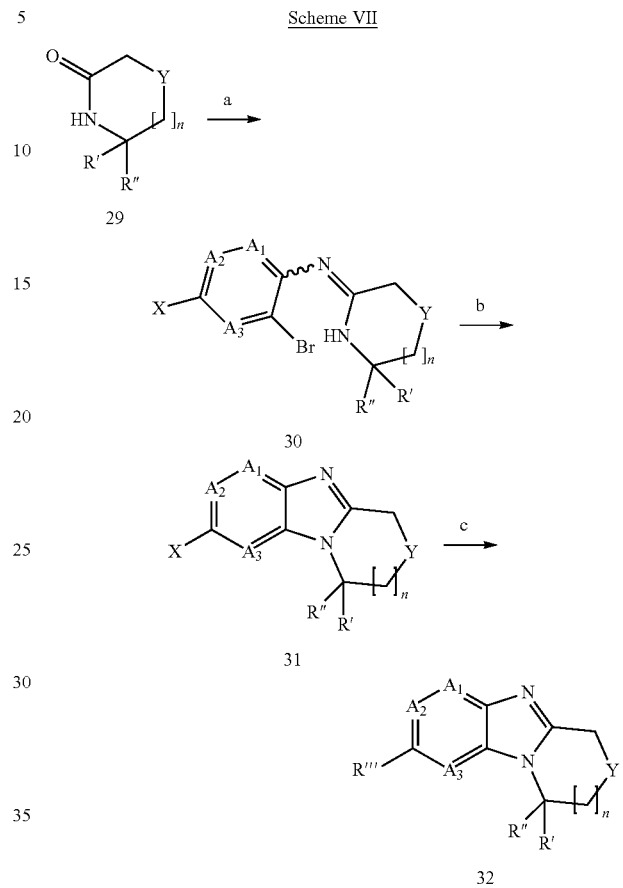

n = 0, 1, 2  Y = O, CH₂

If desired, chiral separation of any of the chiral compounds in Schemes I-III may be done using methods known to one skilled in the art such as chiral SFC (for example, see Example #20 and 21), chiral preparative HPLC, or crystallization of diastereomeric salts.

Preparation #1

2-Bromo-7,8-dihydrobenzo[4,5]imidazo[1,2-a]pyridin-9(6H)-one

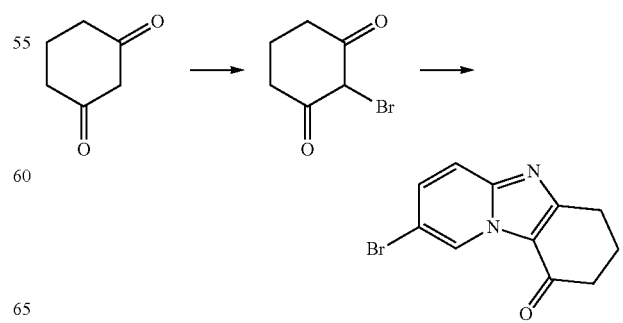

Step 1: 2-Bromocyclohexane-1,3-dione

To a solution of cyclohexane-1,3-dione (15.0 g, 134 mmol) in DMSO (150 mL) was added N-bromosuccinimide (25.0 g, 140 mmol) in portions. The mixture was stirred at about 25° C. for about 1 h and quenched by NH$_4$Cl solution. The solid was collected by filtration and dried to give the title compound (9 g, 35%); $^1$H NMR (400 MHz, DMSO-d$_6$) δ 2.56-2.49 (m, 4H), 1.86 (q, J=6.3 Hz, 2H)

Step 2: 2-Bromo-7,8-dihydrobenzo[4,5]imidazo[1,2-a]pyridin-9(6H)-one

A solution of 5-bromopyridin-2-amine (9.98 g, 57.7 mmol) and 2-bromocyclohexane-1,3-dione (14.0 g, 73.3 mmol) in DME (280 mL) was refluxed overnight. The reaction was cooled to rt, concentrated, and purified using silica gel chromatography (0-15% EtOAc/DCM) to give the title compound (5 g, 33%); LC/MS (Table 1, Method a) R$_t$=2.43 min; MS m/z: 265, 267 (M+H)$^+$

Preparation #2

7-Bromo-2,3-dihydro-1H-cyclopenta[4,5]imidazo[1,2-a]pyridin-1-one

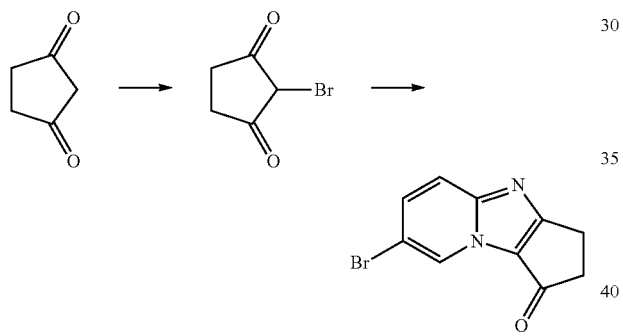

Step 1: 2-Bromocyclopentane-1,3-dione

To a stirred solution of cyclopentane-1,3-dione (20.0 g, 204 mmol) in AcOH (400 mL) at rt was added Br$_2$ (11.6 mL, 224 mmol) dropwise. The reaction mixture was stirred for about 1 h and filtered. The filter cake was washed with MBTE and dried under reduced pressure to give the product (22 g, 61%); LC/MS (Table 1, Method b) R$_t$=0.31 min; MS m/z: 177, 179 (M+H)$^+$

Step 2: 7-Bromo-2,3-dihydro-1H-cyclopenta[4,5]imidazo[1,2-a]pyridin-1-one

To a stirred solution of 2-bromocyclopentane-1,3-dione (10.0 g, 56.5 mmol) in DME (200 mL) was added 5-bromopyridin-2-amine (10.75 g, 62.1 mmol) and NaHCO$_3$ (9.49 g, 113 mmol). The mixture was stirred at about 120° C. for about 12 h then filtered. The filtrate was concentrated and purified by column chromatography on silica gel (0-1% MeOH/DCM) to give a crude product. The crude product was further purified by preparative HPLC (Table 1, Method c) to the title compound (1.38 g, 9.7%); LC/MS (Table 1, Method b) R$_t$=2.38 min; MS m/z: 251, 253 (M+H)$^+$

Preparation #3

2-Bromo-10-(2-methoxyphenyl)-7,8,9,10-tetrahydro-6H-cyclohepta[4,5]imidazo[1,2-a]pyridine

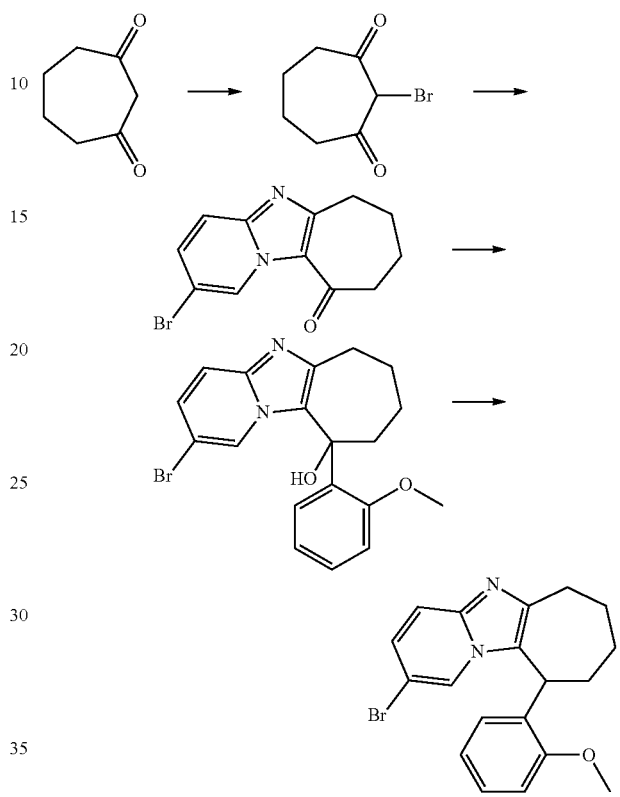

Step 1: 2-Bromocycloheptane-1,3-dione

To the solution of cycloheptane-1,3-dione (9.5 g, 75 mmol) in water (37 mL) was added HBr (40%, 1.03 mL). The mixture was cooled to about 0° C. and a solution of potassium bromate (4.18 g, 25.0 mmol) in water (37 mL) was added drop-wise. The mixture was warmed to about 25° C. with stirring for about 1.5 h. The mixture was extracted with MTBE (100 mL, and the organics washed with brine, dried over Na$_2$SO$_4$, filtered, and concentrated to give product (11 g, 71%); $^1$H NMR (400 MHz, CDCl$_3$) δ 4.93 (s, 1H), 2.88-2.70 (m, 2H), 2.68-2.53 (m, 2H), 2.09-1.92 (m, 4H)

Step 2: 2-Bromo-8,9-dihydro-6H-cyclohepta[4,5]imidazo[1,2-a]pyridin-10(7H)-one The reaction was performed from 2-bromocycloheptane-1,3-dione and 5-bromopyridin-2-amine in a similar fashion to Preparation #2, step 2 to give the title compound (5.5 g, 37%); $^1$H NMR (400 MHz, CDCl$_3$) δ 9.85 (s, 1H), 7.55 (s, 2H), 3.20 (t, J=6.2 Hz, 2H), 2.85-2.83 (m, 2H), 2.06-1.95 (m, 4H)

Step 3: 2-Bromo-10-(2-methoxyphenyl)-7,8,9,10-tetrahydro-6H-cyclohepta[4,5]imidazo[1,2-a]pyridin-10-ol In a round bottom flask was added 2-bromo-8,9-dihydro-6H-cyclohepta[4,5]imidazo[1,2-a]pyridin-10(7H)-one (1.0 g, 3.58 mmol) in THF (20 mL). To this stirring solution at about 0° C. under N₂ was added (2-methoxyphenyl)magnesium bromide (5.37 mL, 5.37 mmol). The mixture was stirred at rt for about 1 h. To the reaction mixture was added saturated aq. NH₄Cl (20 mL), then extracted with EtOAc (3×20 mL). The combined organic phases were washed with brine (25 mL), dried over Na₂SO₄, filtered, and concentrated. The residue was triturated with DCM (about 15 mL) to afford the title product (0.8 g, 58%); LC/MS (Table 1, Method d) R$_f$=0.82 min; MS m/z: 387, 389 (M+H)⁺

Step 4: 2-Bromo-10-(2-methoxyphenyl)-7,8,9,10-tetrahydro-6H-cyclohepta[4,5]imidazo[1,2-a]pyridine To a stirring solution of 2-bromo-10-(2-methoxyphenyl)-7,8,9,10-tetrahydro-6H-cyclohepta [4,5]imidazo[1,2-a]pyridin-10-ol (0.8 g, 2.07 mmol) in DCM (20 mL) at about −78° C. was slowly added triethylsilane (1.32 mL, 8.26 mmol) and (diethyloxonio)trifluoroborate (0.995 mL, 7.85 mmol). The reaction was stirred at about −78° C. for about 90 min under N₂ and then warmed up to rt. The reaction mixture was washed with sat. aq. NaHCO₃ (about 20 mL). Separated layers and extracted aqueous phase with DCM (3×30 mL). The combined organic phases were washed with brine (25 mL), dried over Na₂SO₄, filtered, and concentrated. The crude was purified using silica gel chromatography (30-50% EtOAc/heptane) to give the title product (0.10 g, 13%). LC/MS (Table 1, Method e) R$_f$=1.45 min; MS m/z: 371, 373 (M+H)⁺

Preparation #4

(R)-7-Bromo-1-phenyl-2,3-dihydro-1H-benzo[d]pyrrolo[1,2-a]imidazole and (S)-7-bromo-1-phenyl-2,3-dihydro-1H-benzo[d]pyrrolo[1,2-a]imidazole

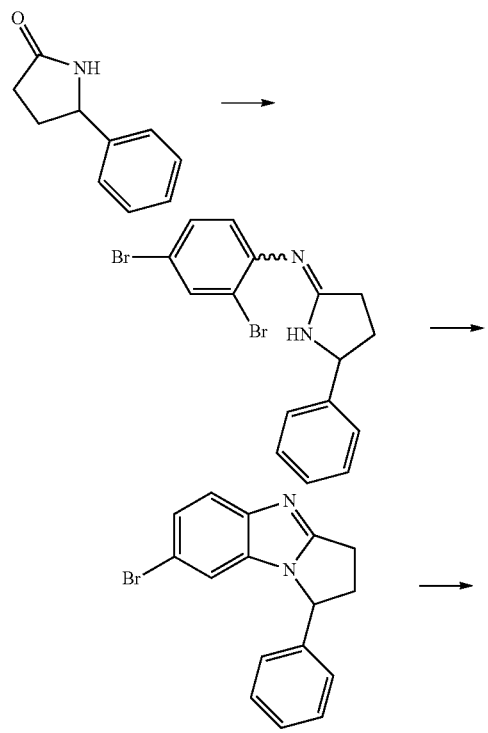

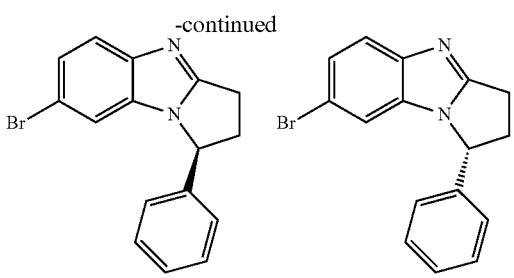

Step 1: 7-Bromo-1-phenyl-2,3-dihydro-1H-benzo[d]pyrrolo[1,2-a]imidazole

5-Phenylpyrrolidin-2-one (1.22 g, 7.57 mmol) was dissolved in dry toluene (18 mL) and POCl₃ (0.353 mL, 3.79 mmol) was added dropwise at about 0° C. with stirring for about 2 h. 2,4-Dibromoaniline (0.95 g, 3.79 mmol) was added in one portion and the resulting mixture was refluxed with stirring for about 4 h.

The residue was dissolved in EtOAc washed with 1M NaOH, brine, dried over MgSO₄, filtered, and concentrated under reduced pressure to give crude 2,4-dibromo-N-(5-phenylpyrrolidin-2-ylidene)aniline (2.03 g). The crude material was dissolved in MeCN (24 mL) was added K₂CO₃ (0.523 g, 3.79 mmol), DMEA (0.041 mL, 0.379 mmol) and CuI (0.036 g, 0.189 mmol). The resulting mixture was refluxed while stirring for about 18 h under a N₂ atmosphere. After cooling DCM (5 mL) was added and the mixture was filtered and the filtrate was evaporated. The residue was purified by column chromatography on silica gel (40-100% EtOAc/heptane) to afford the title compound (0.94 g, 79%). LC/MS (Table 1, Method e) R$_f$=1.06 min; MS m/z: 313, 315 (M+H)⁺

Step 2: (R)-7-Bromo-1-phenyl-2,3-dihydro-1H-benzo[d]pyrrolo[1,2-a]imidazole and (S)-7-bromo-1-phenyl-2,3-dihydro-1H-benzo[d]pyrrolo[1,2-a]imidazole A racemic mixture of 7-bromo-1-phenyl-2,3-dihydro-1H-benzo[d]pyrrolo[1,2-a]imidazole (0.94 g) was separated via chiral SFC (Table 1, Method 1) to give (S)-7-bromo-1-phenyl-2,3-dihydro-1H-benzo [d]pyrrolo[1,2-a]imidazole (0.45 g, 48%, OR=negative) and (R)-7-bromo-1-phenyl-2,3-dihydro-1H-benzo[d]pyrrolo[1,2-a]imidazole (0.44 g, 47%, OR=positive) [Stereochemistry assignment based on optical rotation]; LC/MS (Table 1, Method e) R$_f$=1.05 min; MS m/z: 313, 315 (M+H)⁺

Preparation #5

(R)-7-Chloro-1-phenyl-2,3-dihydro-1H-benzo[d]pyrrolo[1,2-a]imidazole and (S)-7-chloro-1-phenyl-2,3-dihydro-1H-benzo[d]pyrrolo[1,2-a]imidazole

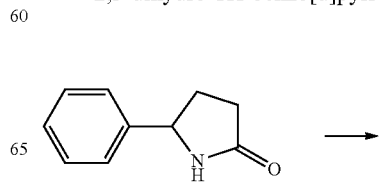

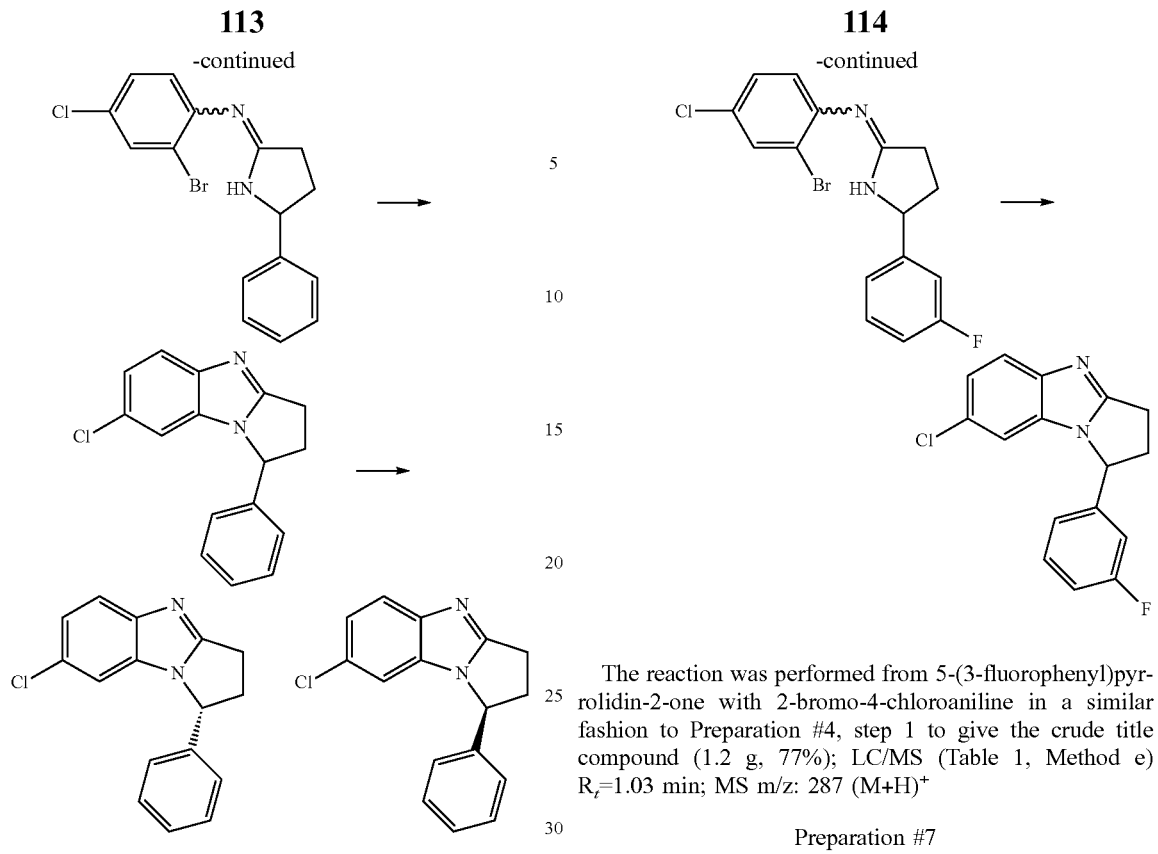

Step 1: 7-Chloro-1-phenyl-2,3-dihydro-1H-benzo[d]pyrrolo[1,2-a]imidazole

The reaction was performed from 5-phenylpyrrolidin-2-one with 2-bromo-4-chloroaniline in a similar fashion to Preparation #4, step 1 to give the crude title compound (0.55 g, 58%); LC/MS (Table 1, Method e) $R_t$=1.35 min; MS m/z: 269 (M+H)

Step 2: (R)-7-Chloro-1-phenyl-2,3-dihydro-1H-benzo[d]pyrrolo[1,2-a]imidazole and (S)-7-chloro-1-phenyl-2,3-dihydro-1H-benzo[d]pyrrolo[1,2-a]imidazole A racemic mixture of 7-chloro-1-phenyl-2,3-dihydro-1H-benzo[d]pyrrolo[1,2-a]imidazole (0.655 g) was separated via chiral SFC (Table 2, Method 2) to give (R)-7-chloro-1-phenyl-2,3-dihydro-1H-benzo [d]pyrrolo[1,2-a]imidazole (0.3 g, 45%, OR=positive); and (S)-7-chloro-1-phenyl-2,3-dihydro-1H-benzo [d]pyrrolo[1,2-a]imidazole (0.24 g, 37%, OR=negative) [Stereochemistry assignment based on optical rotation]; LC/MS (Table 1, Method e) $R_t$=1.32 min; MS m/z: 269 (M+H)$^+$

Preparation #6

7-Chloro-1-(3-fluorophenyl)-2,3-dihydro-1H-benzo[d]pyrrolo[1,2-a]imidazole

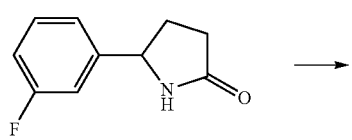

The reaction was performed from 5-(3-fluorophenyl)pyrrolidin-2-one with 2-bromo-4-chloroaniline in a similar fashion to Preparation #4, step 1 to give the crude title compound (1.2 g, 77%); LC/MS (Table 1, Method e) $R_t$=1.03 min; MS m/z: 287 (M+H)$^+$

Preparation #7

7-Chloro-1-(2,5-dimethylphenyl)-2,3-dihydro-1H-benzo[d]pyrrolo[1,2-a]imidazole

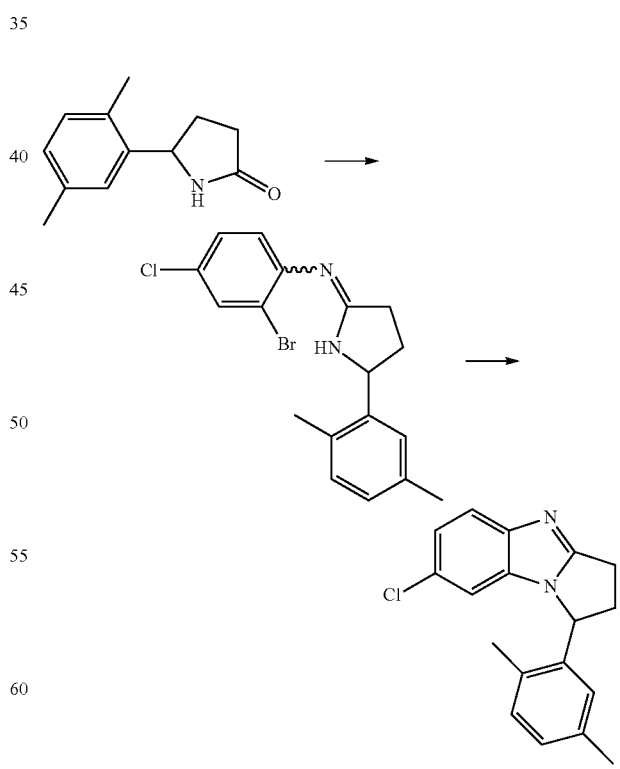

The reaction was performed from 5-(2,5-dimethylphenyl)pyrrolidin-2-one with 2-bromo-4-chloroaniline in a similar fashion to Preparation #4, step 1 to give the crude title compound (1.09 g, 39%); LC/MS (Table 1, Method e) $R_t$=1.14 min; MS m/z: 297 (M+H)$^+$ Preparation #8

7-Bromo-1-cyclohexyl-2,3-dihydro-1H-benzo[d]pyrrolo[1,2-a]imidazole

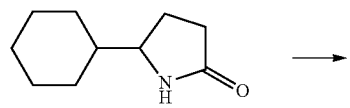

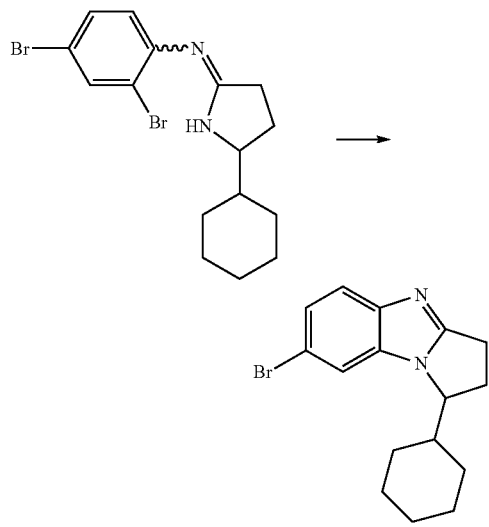

The reaction was performed from 5-cyclohexylpyrrolidin-2-one with 2,4-dibromoaniline in a similar fashion to Preparation #4, step 1 to give the crude title compound (0.265 g, 95%); LC/MS (Table 1, Method f) $R_t$=0.83 min; MS m/z: 319, 321 (M+H)$^+$ Preparation #9

8-(2-Chloropyrimidin-5-yl)-1-phenyl-1,2,3,4-tetrahydrobenzo[4,5]imidazo[1,2-a]pyridine

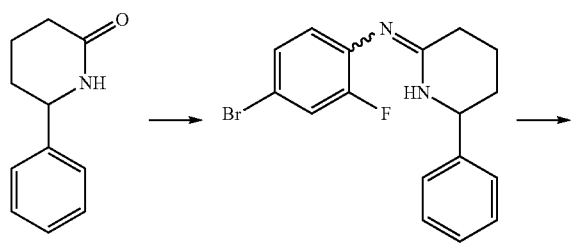

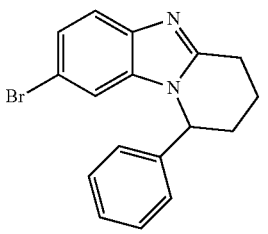

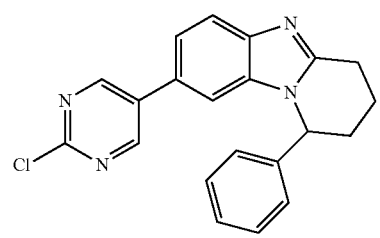

Step 1: 8-Bromo-1-phenyl-1,2,3,4-tetrahydrobenzo[4,5]imidazo[1,2-a]pyridine

To a solution of 6-phenylpiperidin-2-one (0.40 g, 2.3 mmol) in dry toluene (12 mL) at about 0° C. was added POCl$_3$ (0.106 mL, 1.141 mmol) dropwise. The reaction solution was stirred at about 0° C. for about 2 h. 4-Bromo-2-fluoroaniline (0.217 g, 1.141 mmol) was added and the mixture was refluxed while stirring for about 4 h. The organic layer was removed and the residue was dissolved in EtOAc. The organics were washed with 1M NaOH, brine, dried over MgSO$_4$, filtered and concentrated. The residue was purified by flash-column chromatography on silica gel 0-10% MeOH/DCM to give impure 4-bromo-2-fluoro-N-(6-phenylpiperidin-2-ylidene)aniline (0.5 g). To a microwave vial was added the impure material (0.45 g, 1.30 mmol), K$_2$CO$_3$ (1.43 g, 10.37 mmol), and DMA (7 mL). The reaction was heated in the microwave for about 30 min at about 250° C. The reaction was cooled, poured over 20 mL of water and stirred for about 20 min. The resulting precipitate then was collect by filtration and the filter cake was washed with water and dried under vacuum to give the product (0.32 g, 75%); LC/MS (Table 1, Method e) $R_t$=1.28 min; MS m/z: 327, 329 (M+H)$^+$ Step 2: 8-(2-Chloropyrimidin-5-yl)-1-phenyl-1,2,3,4-tetrahydrobenzo[4,5]imidazo[1,2-a]pyridine A mixture of 8-bromo-1-phenyl-1,2,3,4-tetrahydrobenzo[4,5]imidazo[1,2-a]pyridine (0.25 g, 0.76 mmol), (2-chloropyrimidin-5-yl)boronic acid (0.133 g, 0.840 mmol), PdCl$_2$(dppf) (0.056 g, 0.076 mmol), Na$_2$CO$_3$ (0.162 g, 1.53 mmol), 1,4-dioxane (2 mL) and water (2 mL) was heated in a microwave at about 120° C. for about 45 min under a N$_2$ atmosphere. The reaction was cooled to rt, diluted with EtOAc, and the organics collected. The combined organic layer was washed with brine, dried by Na$_2$SO$_4$, filtered and concentrated under reduced pressure. The residue was purified by flash-column chromatography on silica gel (50-100% EtOAc/heptane) to give the title compound (0.110 g, 40%); LC/MS (Table 1, Method e) $R_t$=1.35 min; MS m/z: 361(M+H)$^+$

Preparation #10

2-(2-Morpholinopyrimidin-5-yl)-7,8-dihydrobenzo[4,5]imidazo[1,2-a]pyridin-9(6H)-one

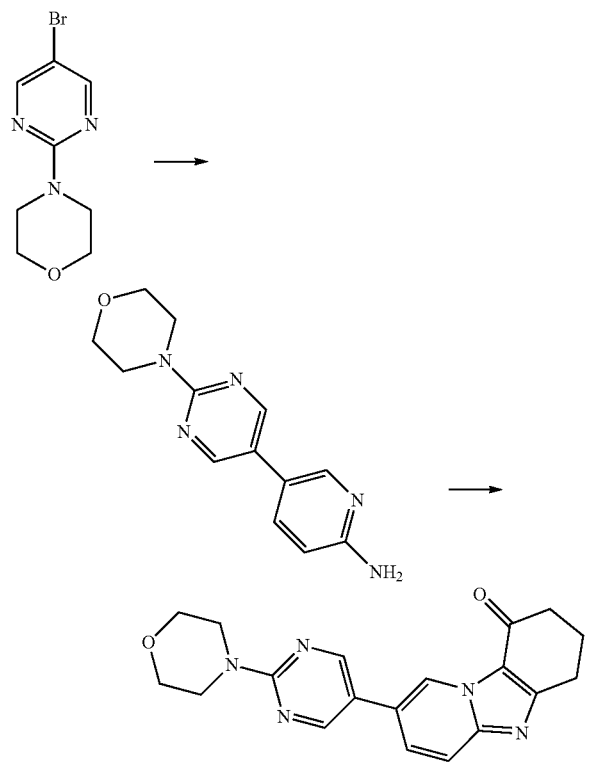

Step 1: 4-Bromo-2-fluoro-N-(6-phenylpiperidin-2-ylidene)aniline

To a solution of 4-(5-bromopyrimidin-2-yl)morpholine (5.5 g, 22.53 mmol), (6-aminopyridin-3-yl)boronic acid (5 g, 36.2 mmol), $K_2CO_3$ (9.34 g, 67.6 mmol) and $Pd(PPh_3)_4$ (1.302 g, 1.127 mmol) in 1,4-dioxane (150 mL) and water (75 mL) was heated to about 85° C. and stirred for about 16 h. The reaction mixture was cooled to rt and filtered. Water was added and a precipitate formed. EtOAc was added and the solid remaining between the phases was collected by filtration, washed with water and EtOAc, and dried under vacuum to give the title compound (3.52 g, 61%). The organic phase from the filtrate was separated and the aqueous phase was extracted once more with EtOAc. The organics were combined, dried over $MgSO_4$, filtered and concentrated in vacuo to give crude product. The residue was purified by flash-column chromatography on silica gel (2 M $NH_3$ in MeOH/DCM 0-15%) to afford additional title compound (0.69 g, 12%); LC/MS (Table 1, Method e) $R_t$=0.67 min; MS m/z: 258 (M+H)$^+$

Step 2: 2-(2-Morpholinopyrimidin-5-yl)-7,8-dihydrobenzo[4,5]imidazo[1,2-a]pyridin-9(6H)-one To a round bottom flask was added 5-(2-morpholinopyrimidin-5-yl)pyridin-2-amine (1.764 g, 6.86 mmol), 2-bromocyclohexane-1,3-dione (1.31 g, 6.86 mmol, Preparation #1) and DME (68.6 mL). The suspension was stirred at reflux for about 18 h. An additional 0.5 equiv of 2-bromocyclohexane-1,3-dione (Preparation #1) was added and the reaction was and stirred for about 24 h. The solvent was removed, and the residue dissolved in 1:1 MeOH/DCM, concentrated on to silica and purified by flash-column chromatography on silica gel (0-10% MeOH/DCM) to give the title compound (0.79 g, 33%); LC/MS (Table 1, Method e) $R_t$=1.09 min; MS m/z: 350 (M+H)$^+$

Preparation #11

2-(2-Bromo-6,7,8,9-tetrahydrobenzo[4,5]imidazo[1,2-a]pyridin-9-yl)phenol

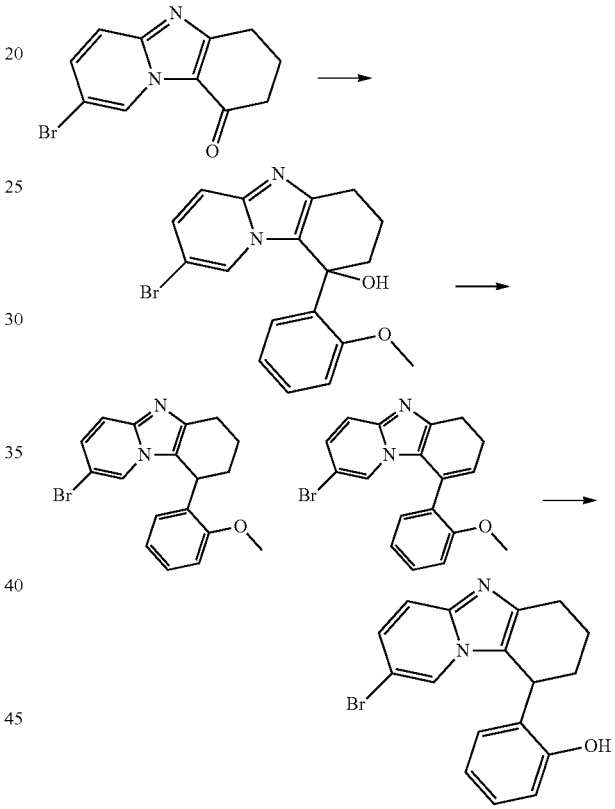

Step 1: 2-Bromo-9-(2-methoxyphenyl)-6,7,8,9-tetrahydrobenzo[4,5]imidazo[1,2-a]pyridin-9-ol To a flask was added 2-bromo-7,8-dihydrobenzo[4,5]imidazo[1,2-a]pyridin-9(6H)-one (0.85 g, 3.21 mmol, Preparation #1) in THF (32 mL). To this stirring solution at about 0° C. under an $N_2$ atmosphere was added (2-methoxyphenyl)magnesium bromide (3.85 mL, 3.85 mmol). The mixture was stirred at rt for about 1 h. The reaction was quenched with sat. $NH_4Cl$ and extracted with EtOAc. The organics were collected, washed with water, filtered through a phase separator, and concentrated under reduced pressure. The residue was purified on silica gel (EtOAc/heptane 40-100%) to give the title compound (1.08 g, 90%); LC/MS (Table 1, Method e) $R_t$=1.31 min; MS m/z: 373, 375 (M+H)$^+$

Step 2: Mixture of 2-bromo-9-(2-methoxyphenyl)-6,7,8,9-tetrahydrobenzo[4,5]imidazo[1,2-a]pyridine and 2-bromo-9-(2-methoxyphenyl)-6,7,8,9-dihydrobenzo[4,5]imidazo[1,2-a]pyridine To a mixture of 2-bromo-9-(2-methoxyphenyl)-6,7,8,9-tetrahydrobenzo[4,5]imidazo[1,2-a]pyridin-9-ol (0.1 g, 0.268 mmol) in DCM (2.5 mL) was added $BF_3 \cdot OEt_2$ (0.112 mL, 0.884 mmol) and TES (0.150 mL, 0.938 mmol). The reaction was stirred for about 30 min at about −78° C. then warmed to rt. The reaction was quenched with sat. $NaHCO_3$. The organics were separated and the aqueous layer extracted with DCM. The organics were combined, filtered through a phase separator, and concentrated under reduced pressure. The residue was purified by column chromatography on silica (EtOAc/heptane 0-100% then MeOH/DCM 0-5%) to give a 8:2 mixture of 2-bromo-9-(2-methoxyphenyl)-6,7,8,9-tetrahydrobenzo[4,5]imidazo[1,2-a]pyridine and 2-bromo-9-(2-methoxyphenyl)-6,7-dihydrobenzo[4,5]imidazo[1,2-a]pyridine (0.07 g, 77%); LC/MS (Table 1, Method e) $R_t$=1.41 min; MS m/z: 357, 359 (M+H)$^+$

Step 3: 2-(2-Bromo-6,7,8,9-tetrahydrobenzo[4,5]imidazo[1,2-a]pyridin-9-yl)phenol The mixture of 2-bromo-9-(2-methoxyphenyl)-6,7,8,9-tetrahydrobenzo[4,5]imidazo[1,2-a]pyridine, 2-bromo-9-(2-methoxyphenyl)-6,7-dihydrobenzo[4,5]imidazo[1,2-a]pyridine (0.73 g, 2.04 mmol) and $BBr_3$ (1 M in DCM, 10.2 mL, 10.2 mmol) was stirred at about 0° C. for about 1 h. The reaction mixture was filtered, diluted with DCM, and washed with water. The aqueous layer was extracted with DCM (×2) and the organics combined, dried over $MgSO_4$ and the solvent removed in vacuo. The residue was purified by column chromatography on silica (MeOH/DCM 0-20%) to give the title compound (0.53 g, 76%); LC/MS (Table 1, Method e) $R_t$=1.18 min; MS m/z: 343, 345 (M+H)$^+$

Preparation #12

2-Bromo-8-phenyl-7,8-dihydro-6H-pyrrolo[2',1':2,3]imidazo[4,5-b]pyridine

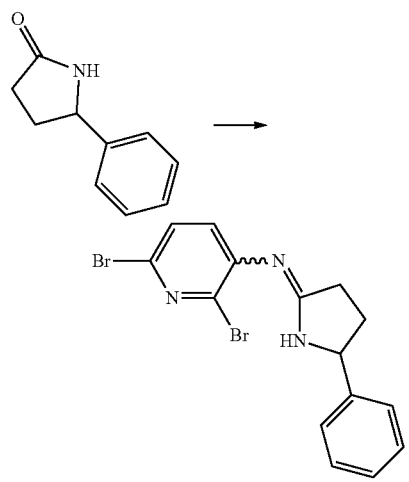

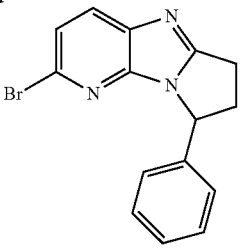

The reaction was performed from 5-phenylpyrrolidin-2-one with 2,6-dibromopyridin-3-amine in a similar fashion to Preparation #4, step 1 to give the crude title compound (0.88 g, 65%); LC/MS (Table 1, Method d) $R_t$=0.72 min; MS m/z: 314, 316 (M+H)$^+$

Preparation #13

2-Bromo-8-(3-fluorophenyl)-7,8-dihydro-6H-pyrrolo[2',1':2,3]imidazo[4,5-b]pyridine

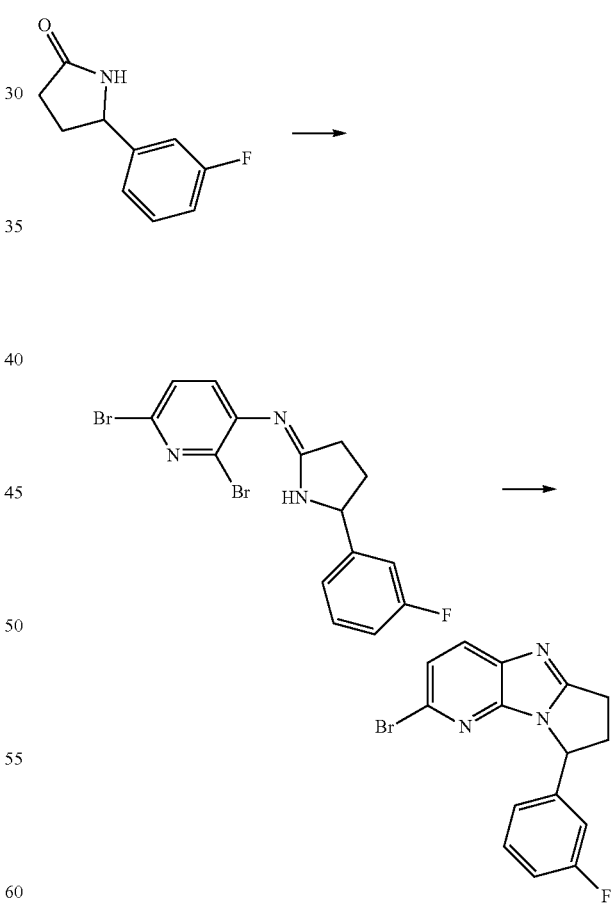

The reaction was performed from 5-(3-fluorophenyl)pyrrolidin-2-one with 2,6-dibromopyridin-3-amine in a similar fashion to Preparation #4, step 1 to give the crude title compound (0.88 g, 44%); LC/MS (Table 1, Method d) $R_t$=0.61 min; MS m/z: 332, 334 (M+H)$^+$

Preparation #14

2-Bromo-9-(2-fluorophenyl)-8,9-dihydro-6H-pyrido[3',2':4,5]imidazo[2,1-c][1,4]oxazine

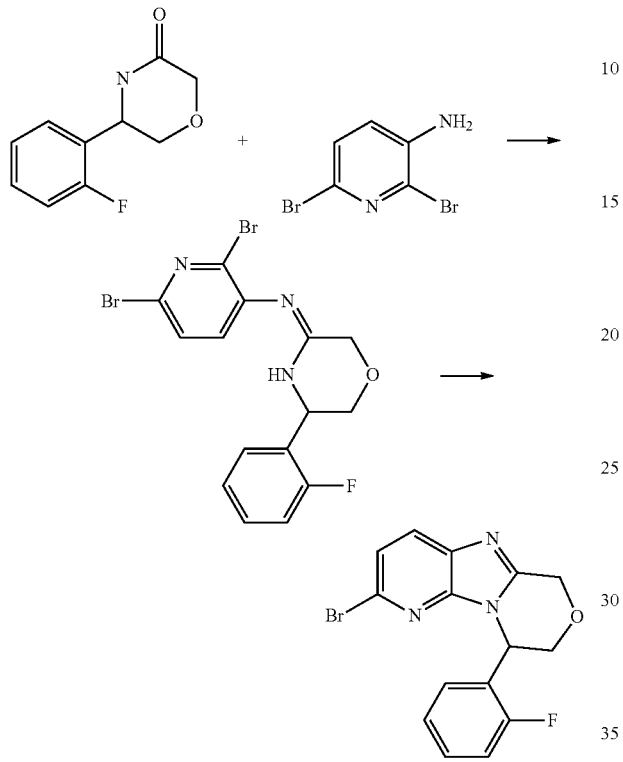

Step 1: 2,6-dibromo-N-(5-(2-fluorophenyl)morpholin-3-ylidene)pyridin-3-amine 5-(2-Fluorophenyl)morpholin-3-one (1.0 g, 5.12 mmol) and 2,6-dibromopyridin-3-amine (1.291 g, 5.12 mmol) were dissolved in dry toluene (25 mL) and $POCl_3$ (0.478 mL, 5.12 mmol) was added slowly at about 0° C. The bath was pulled and allowed to warm to rt. The reaction solution was refluxed while stirring for about 40 min. The reaction mixture was cooled to about rt, concentrated under reduced pressure. DCM (200 mL) was added followed by the addition of 1M NaOH to neutralize the reaction (pH between about 6 and 7). The organics were collected washed with brine (50 mL), dried over $Na_2SO_4$, filtered and concentrated under reduced pressure to give the crude title compound (2.03 g); LC/MS (Table 1, Method e) $R_t$=0.69 min.; MS m/z: 429, 431 (M+H)$^+$.

Step 2: 2-Bromo-9-(2-fluorophenyl)-8,9-dihydro-6H-pyrido[3',2':4,5]imidazo[2,1-c][1,4]oxazine To a solution of 2,6-dibromo-N-(5-(2-fluorophenyl)morpholin-3-ylidene)pyridin-3-amine (2.03 g, 4.73 mmol) in MeCN (30 mL) was added $K_2CO_3$ (0.654 g, 4.73 mmol), DMEA (0.051 mL, 0.473 mmol) and CuI (0.045 g, 0.237 mmol). The result mixture was refluxed with stirring for about 16 h under $N_2$. After cooling DCM (80 mL) was added, and the solution was filtered. The filtrate was concentrated under reduced pressure to give a crude residue that was purified via silica gel chromatography eluting with 30-100% EtOAc/heptane to give title compound (0.85 g, 52%); LC/MS (Table 1, Method e) $R_t$=0.83 min.; MS m/z: 348, 350 (M+H)$^+$.

Preparation #15

2-Bromo-9-(3-fluorophenyl)-8,9-dihydro-6H-pyrido[3',2':4,5]imidazo[2,1-c][1,4]oxazine

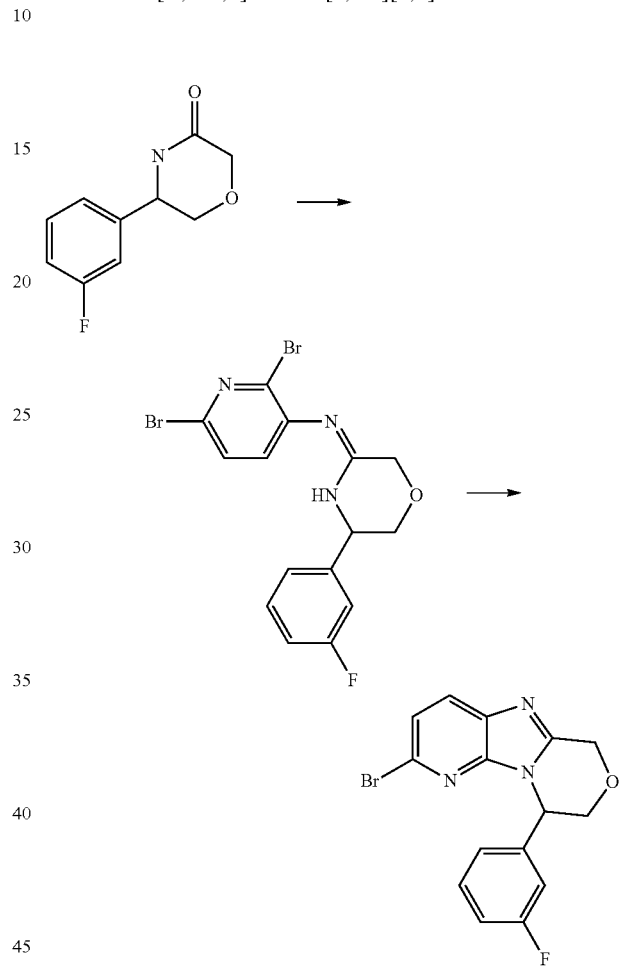

The reaction sequence was performed from 5-(3-fluorophenyl)morpholin-3-one in a similar fashion to Preparation #14 to give the crude title compound (0.71 g, 49%); LC/MS (Table 1, Method e) $R_t$=0.87 min; MS m/z: 348, 350 (M+H)$^+$

Preparation #16

2-Bromo-8-methyl-8-phenyl-7,8-dihydro-6H-pyrrolo[2',1':2,3]imidazo[4,5-b]pyridine

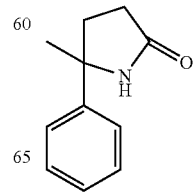

123

-continued

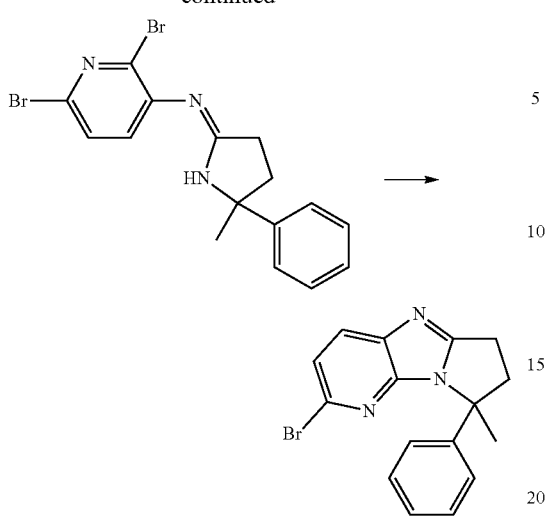

5-Methyl-5-phenylpyrrolidin-2-one (0.50 g, 2.85 mmol) and 2,6-dibromopyridin-3-amine (0.719 g, 2.85 mmol) were dissolved in dry toluene (15 mL) and POCl₃ (0.266 mL, 2.85 mmol) was added slowly at about 0° C. The mixture was warmed to rt then heated to reflux with stirring for about 40 min. The reaction was cooled to rt and solvent was removed under reduced pressure. The residue was dissolved in DCM, and 1M NaOH was added. The organic layer was collected, washed with brine, dried over Na₂SO₄, filtered and concentrated under reduced pressure to afford the crude intermedite (Z)-2,6-dibromo-N-(5-methyl-5-phenylpyrrolidin-2-ylidene)pyridin-3-amine (1.11 g), which was used directly for the next step. To a solution of crude intermedite (Z)-2,6-dibromo-N-(5-methyl-5-phenylpyrrolidin-2-ylidene)pyridin-3-amine (1.11 g, 2.71 mmol) in MeCN (20 mL) was added K₂CO₃ (0.375 g, 2.71 mmol), DMEA (0.029 mL, 0.271 mmol) and CuI (0.026 g, 0.136 mmol). The mixture was refluxed with stirring for about 16 h under N₂ atmoshere. After cooling to rt DCM was added. The mixture was filtered and the filtrate concentrated under reduced pressure. The crude product was purified via silica gel chromatography eluting with 30-100% EtOAc/heptane to give the title compound (0.61 g, 65% over two steps); LC/MS (Table 1, Method e) $R_t$=0.83 min; MS m/z: 328, 330 (M+H)⁺

Preparation #17

2-Bromo-8-(2,5-dimethylphenyl)-7,8-dihydro-6H-pyrrolo[2',1':2,3]imidazo[4,5-b]pyridine

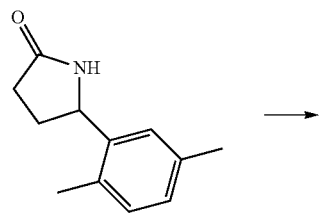

124

-continued

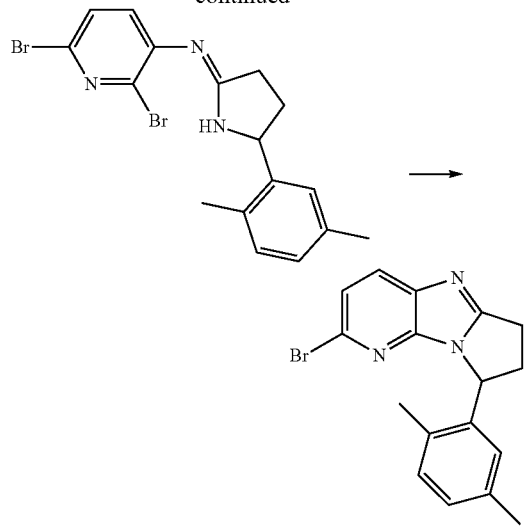

The reaction was performed from 5-(2,5-dimethylphenyl)pyrrolidin-2-one with 2,6-dibromopyridin-3-amine in a similar fashion to Preparation #4, step 1 to give the crude title compound (0.49 g, 47%); LC/MS (Table 1, Method d) $R_t$=0.94 min; MS m/z: 343, 345 (M+H)⁺

Preparation #18

2-Bromo-9-phenyl-6,7,8,9-tetrahydroimidazo[1,2-a:5,4-b']dipyridine

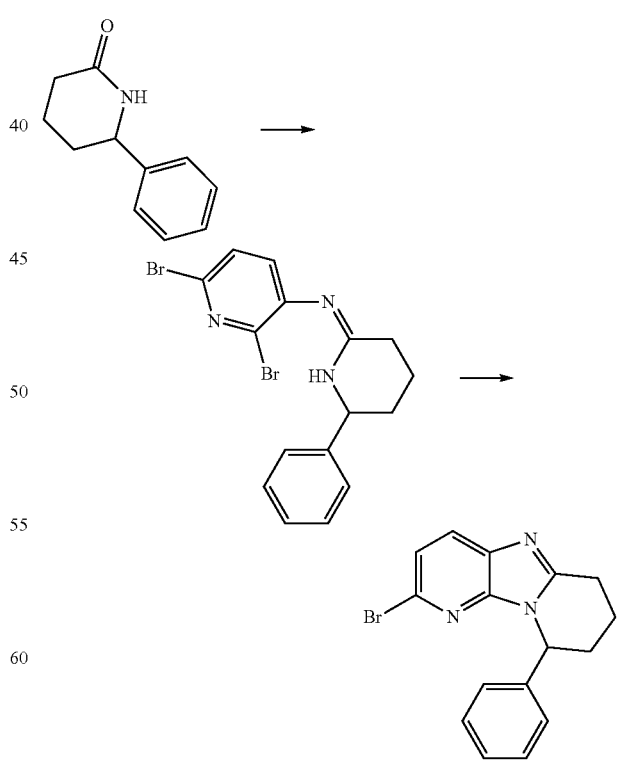

The reaction was performed from 6-phenylpiperidin-2-one with 2,6-dibromopyridin-3-amine in a similar fashion to Preparation #4, step 1 to give the crude title compound (0.44 g, 43%); LC/MS (Table 1, Method d) $R_t$=0.71 min; MS m/z: 328 330 (M+H)$^+$ Preparation #19

3-Bromo-6-phenyl-7,8-dihydro-6H-pyrrolo[1',2':1,2]imidazo[4,5-c]pyridine

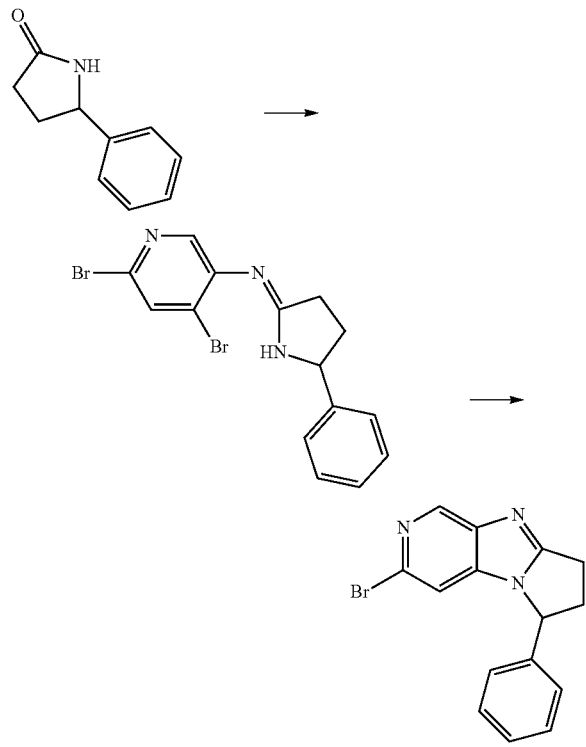

The reaction was performed from 5-phenylpyrrolidin-2-one with 4,6-dibromopyridin-3-amine in a similar fashion to Preparation #4, step 1 to give the crude title compound (0.59 g, 67%); LC/MS (Table 1, Method d) $R_t$=0.84 min; MS m/z: 314, 316 (M+H)$^+$ Preparation #20

3-Chloro-6-phenyl-6,7,8,9-tetrahydroimidazo[1,2-a:4,5-b']dipyridine

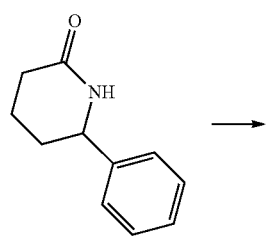

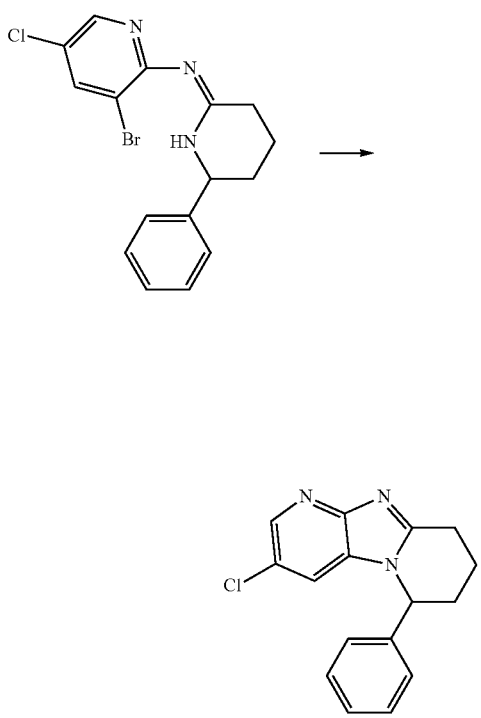

The reaction was performed from 6-phenylpiperidin-2-one with 3-bromo-5-chloropyridin-2-amine in a similar fashion to Preparation #4, step 1 to give the crude title compound (0.66 g, 47%); LC/MS (Table 1, Method d) $R_t$=0.70 min; MS m/z: 284 (M+H)$^+$ Preparation #21

2-(3-Oxopiperazin-1-yl)pyrimidin-5-ylboronic acid

To the 2-chloropyrimidine-5-boronic acid (2.00 g, 12.6 mmol) in 1,4-dioxane (15 mL) was added piperazin-2-one (1.26 g, 12.6 mmol). The mixture was heated in a microwave for about 45 min at about 100° C. The mixture was evaporated to dryness to give the crude title compound (2.8 g, 100%); LC/MS (Table 1, Method d) $R_t$=0.11 min; MS m/z: 223 (M+H)$^+$

Preparation #22

(2-(4-Hydroxypiperidin-1-yl)pyrimidin-5-yl)boronic acid

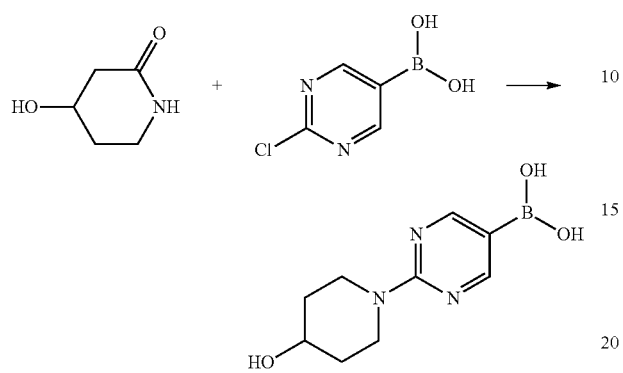

The reaction was performed from piperidin-4-ol in a similar fashion to Preparation #21 to give the crude title compound (2.5 g, 88%); LC/MS (Table 1, Method d) $R_t$=0.12 min; MS m/z: 224 (M+H)$^+$

Preparation #23

(S)-5-Phenylmorpholin-3-one

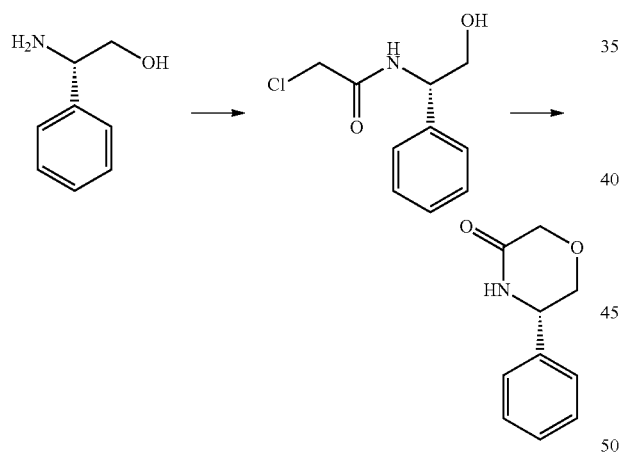

A mixture of (S)-2-amino-2-phenylethanol (15.0 g, 109 mmol) and TEA (22.9 mL, 164 mmol) in THF (109 mL) was cooled to about 0° C. in an ice bath. To this cooled solution was added 2-chloroacetyl chloride (10.6 mL, 131 mmol) in THF (45 mL) via addition funnel over about 20 min. The reaction was stirred for about 40 min and then filtered. The filtrate was diluted with EtOAc (about 150 mL) and was washed with water and brine (about 200 mL each). The organic layer was dried over $Na_2SO_4$, filtered, and concentrated under reduced pressure to give crude (S)-2-chloro-N-(2-hydroxy-1-phenylethyl)acetamide (27.2 g). The crude material was dissolved in THF (240 mL) and cooled to about 0° C. in an ice bath. To this cooled solution was added NaH (60 wt % in mineral oil, 10.93 g, 273 mmol) portion-wise over about 5 min. After about 1 h at about 0-10° C., the reaction was quenched by slow addition of THF/water (1:1, 10 mL) and then partitioned between EtOAc (300 mL) and water (200 mL). The layers were separated. The organic layer was washed with brine (2×150 mL), dried over $Na_2SO_4$, filtered, and concentrated under reduced pressure. The crude product was purified via silica gel chromatography eluting with 50-100% EtOAc in heptane to give the title compound (3.91 g, 20%). The fraction collector was set to collect peaks and the UV signal is very weak at 254 nm. The waste from the chromatography was concentrated under reduced pressure and purified via silica gel chromatography eluting with 50-100% EtOAc in heptane to give additional title compound (7.91 g, 41%); LC/MS (Table 1, Method g) $R_t$=0.50 min; MS m/z: 178 (M+H)$^+$

Preparation #24

(S)-7-Bromo-4-phenyl-3,4-dihydro-1H-benzo[4,5]imidazo[2,1-c][1,4]oxazine

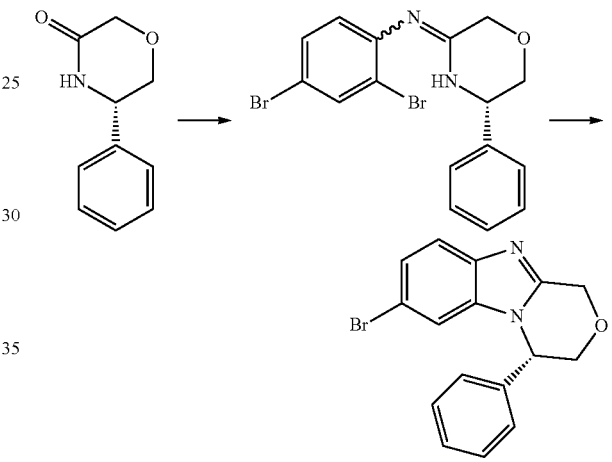

To a mixture of (S)-5-phenylmorpholin-3-one (7.57 g, 42.7 mmol, Preparation #23) in toluene (150 mL) was added $POCl_3$ (4.0 mL, 43 mmol) and 2,4-dibromoaniline (10.7 g, 42.7 mmol). The reaction mixture was heated to about 110° C. After about 45 min, the reaction mixture was cooled to rt and concentrated under reduced pressure. The crude material was dissolved in EtOAc (750 mL) and washed with 1M NaOH (250 mL) and brine (100 mL). The organic layer was dried over $Na_2SO_4$, filtered, and concentrated under reduced pressure to give crude (S)-2,4-dibromo-N-(5-phenylmorpholin-3-ylidene)aniline (17.99 g). To a solution of (S)-2,4-dibromo-N-(5-phenylmorpholin-3-ylidene)aniline (17.99 g crude) in MeCN (285 mL) was added $K_2CO_3$ (7.09 g, 51.3 mmol), DMEA (0.92 mL, 8.5 mmol) and CuI (0.814 g, 4.27 mmol). The reaction mixture was heated at about 80° C. After about 15 h, the reaction mixture was cooled to rt, diluted with DCM (300 mL), and filtered through Florisil® (120 g). The filtrate was concentrated under reduced pressure. To the resulting solid was added $Et_2O$ (70 mL) and stirred vigorously at rt to get a uniform suspension. The resulting solid was collected via vacuum filtration and dried under vacuum at about 60° C. to give the title compound (9.46 g, 67%). The filtrate from above was concentrated to give the crude title compound (1.88 g) that was dissolved in DCM and purified via silica gel chromatography eluting with 0-60% EtOAc in heptane to give additional title compound (0.75 g, 5%) after drying under vacuum at about 60° C.; LC/MS (Table 1, Method g) $R_t$=1.61 min; MS m/z: 329, 331 (M+H)+.

Preparation #25

5-Phenylmorpholin-3-one

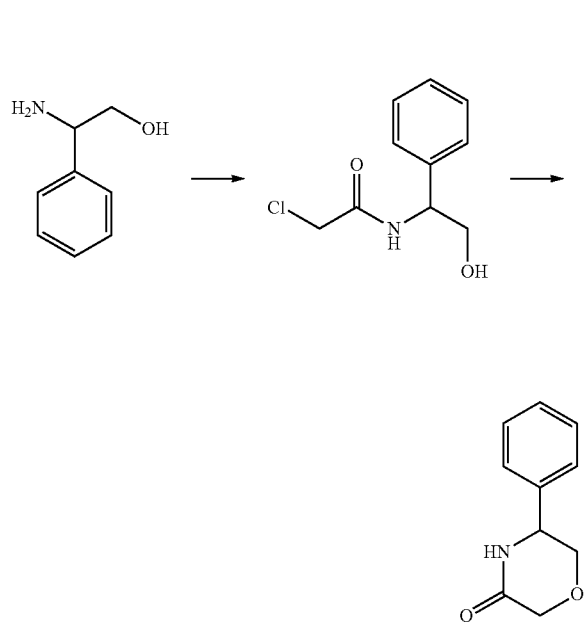

Step 1: 2-Chloro-N-(2-hydroxy-1-phenylethyl)acetamide

In a round bottom flask with magnetic stirrer was added THF (35 mL) followed by the addition of 2-amino-2-phenylethanol (3.5 g, 25.5 mmol) and TEA (5.33 mL, 38.3 mmol). The contents were cooled by ice bath and 2-chloroacetyl chloride (2.058 mL, 25.5 mmol) was diluted with THF (15 mL) and placed in an addition funnel. 2-Chloroacetyl chloride was added drop-wise over the course of about 10 min and the reaction was then allowed to warm to rt. After about 3 h, the reaction contents were filtered and the filtrate was diluted with EtOAc, washed with water and brine. The organic layer was collected, dried over MgSO4 and concentrated to give the crude title compound (3 g, 55%); LC/MS (Table 1, Method f) $R_t$=0.43 min; MS m/z: 214 (M+H)+

Step 2: 5-Phenylmorpholin-3-one

The crude 2-chloro-N-(2-hydroxy-1-phenylethyl)acetamide (3 g, 14.04 mmol) was dissolved in of dry THF (40 mL) and the mixture was cooled to about 0° C. NaH (0.842 g, 35.1 mmol) was added in 2 portions and the reaction was warmed to rt. The reaction was quenched by the slow addition of a 50% solution of THF/water, diluted into EtOAc, washed with aq NaHCO3, water, and brine. The organics were collected and purified by flash chromatography (30-100% EtOAc/heptane) to give the title compound (2.25 g, 90%); LC/MS (Table 1, Method f) $R_t$=0.39 min; MS m/z: 219(M+H+MeCN)+

Preparation #26

7-Bromo-4-phenyl-3,4-dihydro-1H-benzo[4,5]imidazo[2,1-c][1,4]oxazine

To a solution of 5-phenylmorpholin-3-one (2.25 g, 12.7 mmol, Preparation #25) in dry toluene (25 mL) at about 0° C. was added POCl3 (1.18 mL, 5.36 mmol) drop-wise. The reaction was allowed to warm to rt and was stirred for about 2 h and then 4-bromo-2-fluoroaniline (2.41 g, 12.7 mmol) was added in one portion. The mixture was heated to about 120° C. for about 2 h. Upon completion of the reaction, the organic layer was removed. The residue was dissolved in EtOAc and was washed with 1M NaOH, water, and brine. The organic layer was dried over MgSO4 and concentrated under reduced pressure to give crude 4-bromo-2-fluoro-N-(5-phenylmorpholin-3-ylidene)aniline (3.8 g). In a microwave vial with magnetic stirrer was added crude 4-bromo-2-fluoro-N-(5-phenylmorpholin-3-ylidene)aniline (3.8 g crude) dissolved in DMA (10 mL). K2CO3 (6.02 g, 43.5 mmol) was added and the contents were heated to about 230° C. under microwave irradiation for about 25 min. The mixture was concentrated under reduced pressure and purified via silica gel chromatography (30-100% EtOAc/heptane) to give the title compound (1.4 g, 39%); LC/MS (Table 1, Method f) $R_t$=0.76 min; MS m/z: 329, 331 (M+H)+

Preparation #27

5-(2,5-(Difluoro)phenyl)morpholin-3-one

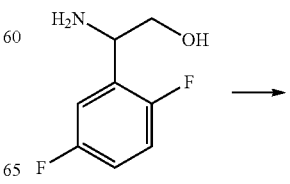

-continued

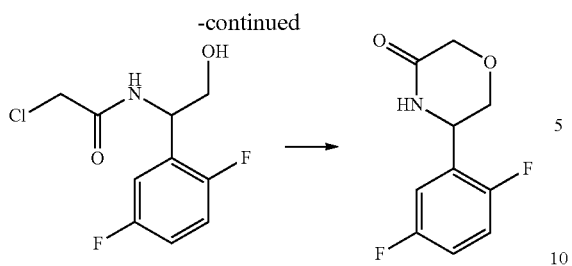

The reaction sequence was performed from 2-amino-2-(2,5-difluorophenyl)ethanol in a similar fashion to Preparation #25 to give the title compound (0.39 g, 76% over 2 steps); LC/MS (Table 1, Method f) $R_t$=0.54 min; MS m/z: 214 (M+H)$^+$ Preparation #28

7-Bromo-4-(2,5-difluorophenyl)-3,4-dihydro-1H-benzo[4,5]imidazo[2,1-c][1,4]oxazine

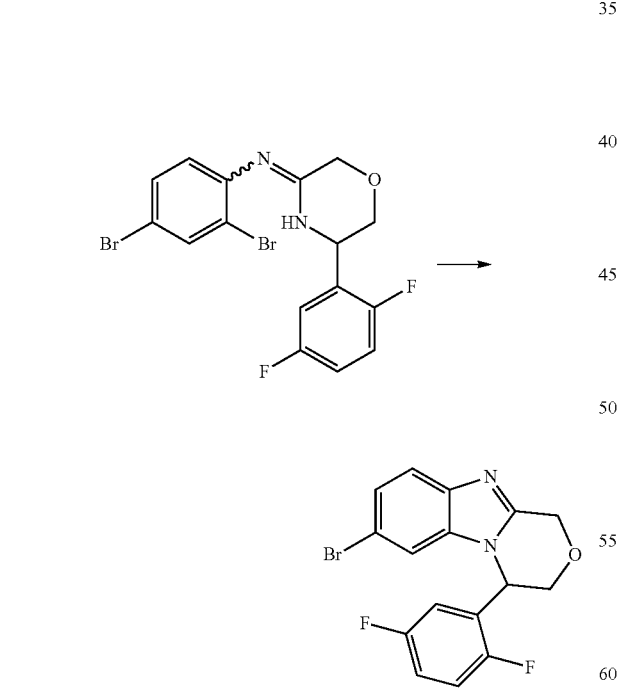

The reaction sequence was performed from 5-(2,5-difluorophenyl)morpholin-3-one (Preparation #27) in a similar fashion to Preparation #24 to give the title compound (0.41 g, 79% over 2 steps); LC/MS (Table 1, Method f) $R_t$=0.77 min; MS m/z: 365, 367(M+H)$^+$ Preparation #29

5-(3-Fluorophenyl)morpholin-3-one

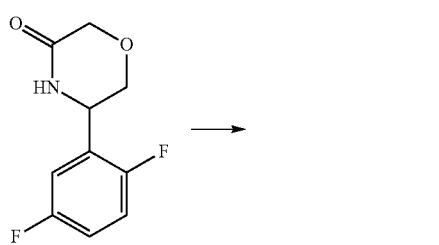

The reaction sequence was performed from 2-amino-2-(3-fluorophenyl)ethanol in a similar fashion to Preparation #25 to give the title compound (0.63 g, 53% over 2 steps); LC/MS (Table 1, Method f) $R_t$=0.34 min; MS m/z: 196 (M+H)$^+$ Preparation #30

7-Bromo-4-(-(3-fluorophenyl)-3,4-dihydro-1H-benzo[4,5]imidazo[2,1-c][1,4]oxazine

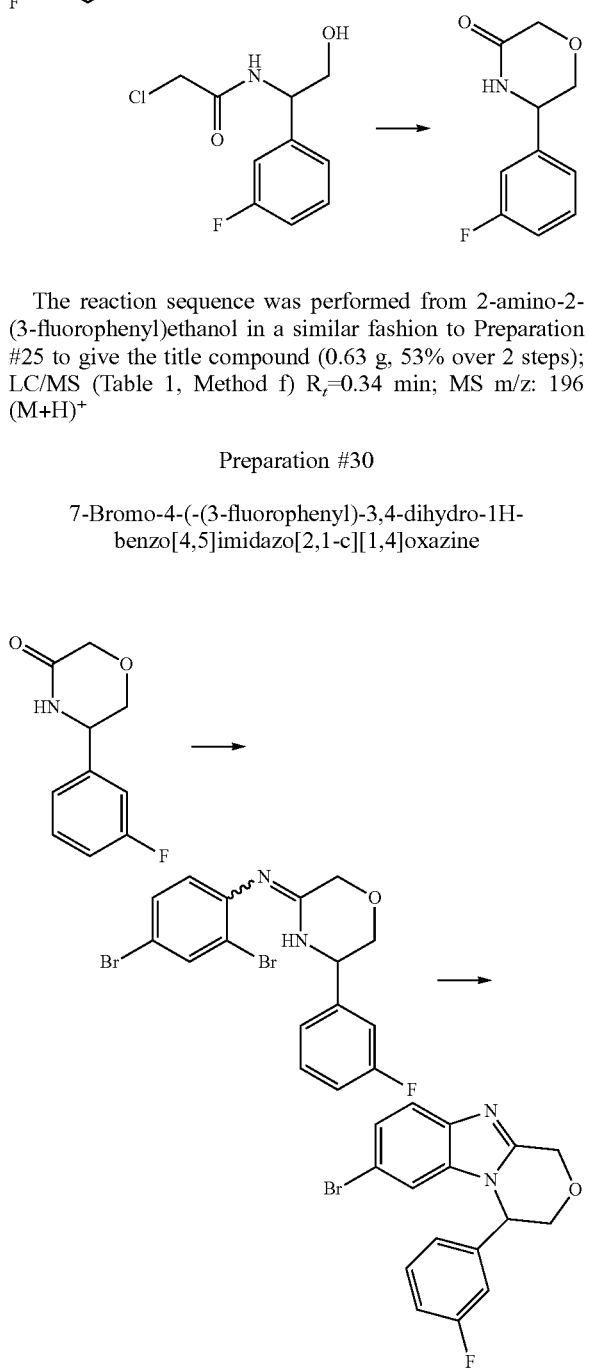

The reaction sequence was performed from 5-(-(3-fluorophenyl)morpholin-3-one (Preparation #29) in a similar fashion to Preparation #24 to give the title compound (0.867 g, 71% over 2 steps); LC/MS (Table 1, Method n) $R_t$=1.11 min; MS m/z: 347,349 (M+H)$^+$.

Preparation #31

5-(2-Chlorophenyl)morpholin-3-one

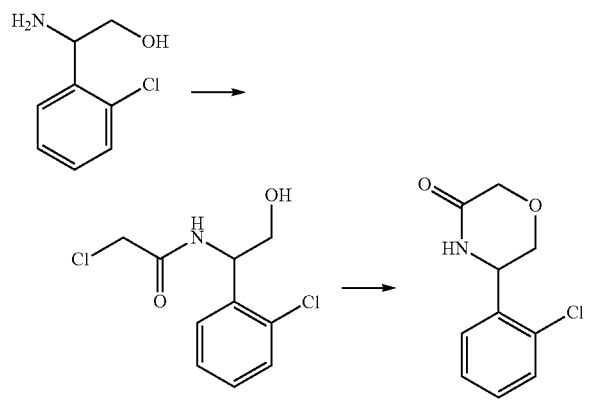

The reaction sequence was performed from 2-amino-2-(2-chlorophenyl)ethanol hydrochloride in a similar fashion to Preparation #25 to give the title compound (0.315 g, 62% over 2 steps); LC/MS (Table 1, Method f) $R_t$=0.62 min; MS m/z: 253 (M+H+MeCN)$^+$.

Preparation #32

7-Bromo-4-(2-(chloro)phenyl)-3,4-dihydro-1H-benzo[4,5]imidazo[2,1-c][1,4]oxazine

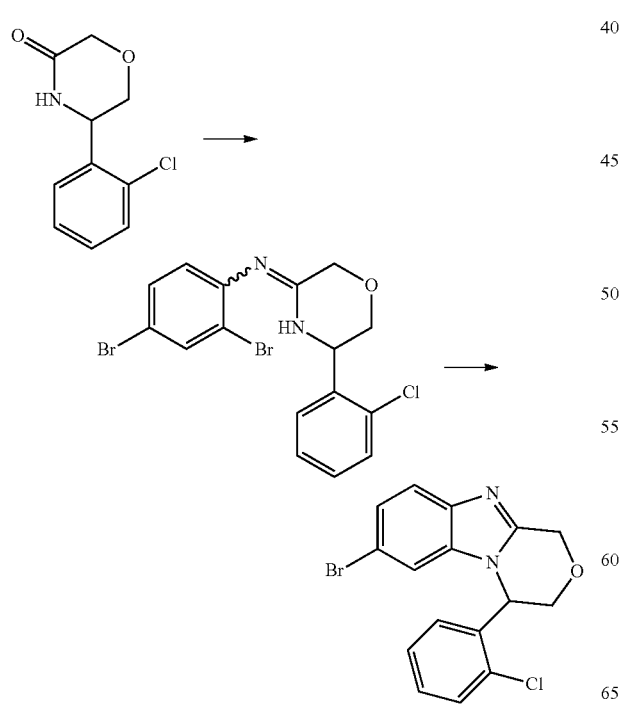

The reaction sequence was performed from 5-(2-(chlorophenyl)morpholin-3-one (Preparation #31) in a similar fashion to Preparation #24 to give the title compound (0.425 g, 68% over 2 steps); LC/MS (Table 1, Method f) $R_t$=0.85 min; MS m/z: 363, 365 (M+H)$^+$.

Preparation #33

2,3-Dihydrospiro[indene-1,3'-morpholin]-5'-one

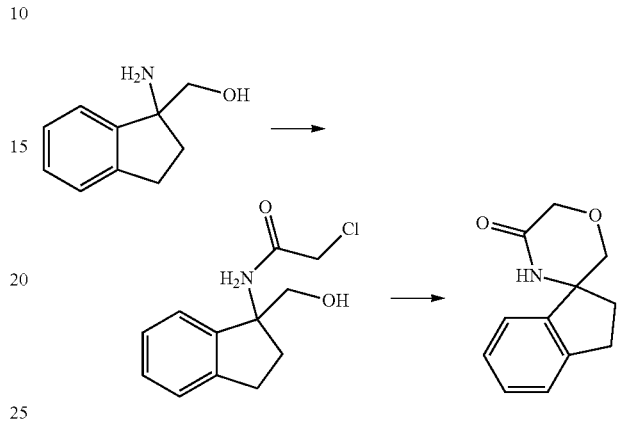

The reaction sequence was performed from (1-amino-2,3-dihydro-1H-inden-1-yl)methanol in a similar fashion to Preparation #25 to give the title compound (0.156 g, 21% over 2 steps); LC/MS (Table 1, Method f) $R_t$=0.77 min; MS m/z: 204 (M+H)$^+$.

Preparation #34

7-Bromo-1,2',3,3'-tetrahydrospiro[benzo[4,5]imidazo[2,1-c][1,4]oxazine-4,1'indene]

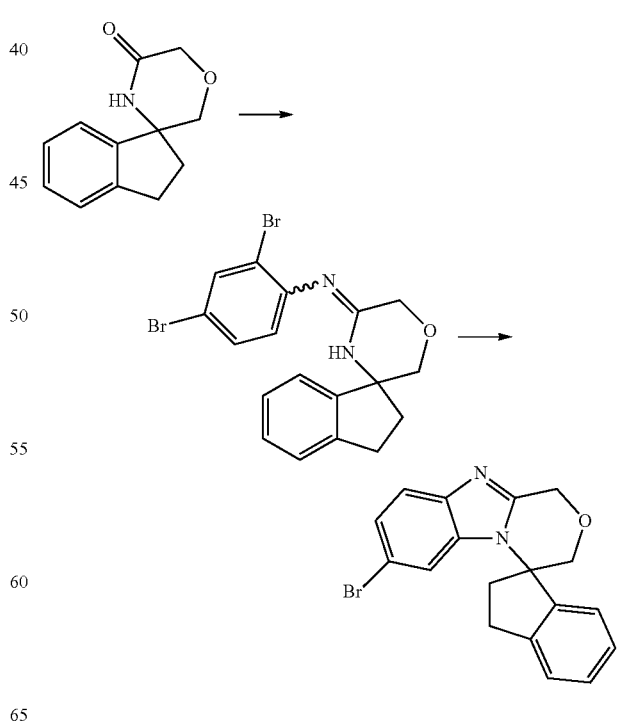

The reaction sequence was performed from 2,3-dihydrospiro[indene-1,3'-morpholin]-5'-one (Preparation #33) in a similar fashion to Preparation #24 to give the title compound (0.154 g, 58% crude over 2 steps); LC/MS (Table 1, Method f) $R_t$=0.84 min; MS m/z: 355, 357 (M+H)$^+$.

Preparation #35

(S)-7-(2-Chloropyrimidin-5-yl)-4-phenyl-3,4-dihydro-1H-benzo[4,5]imidazo[2,1-c][1,4]oxazine

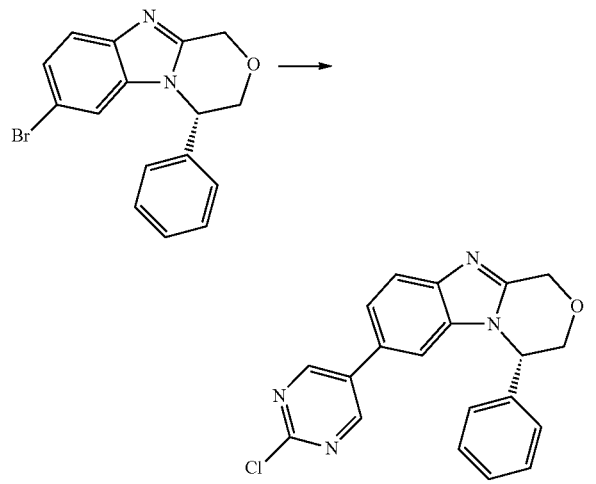

In a 20 mL microwave vial equipped with a magnetic stirrer was added (S)-7-bromo-4-phenyl-3,4-dihydro-1H-benzo[4,5]imidazo[2,1-c][1,4]oxazine (1.5 g, 4.56 mmol, Preparation #24), 2-chloro-5-(4,4,5,5-tetramethyl-1,3,2-dioxaborolan-2-yl)pyrimidine (2.19 g, 9.11 mmol), and Pd(dppf)Cl$_2$.DCM (0.37 g, 0.046 mmol). 8 mL of dry, degassed 1,4-dioxane was added to the vial followed by the addition of Cs$_2$CO$_3$ (2.97 g, 9.11 mmol), and water (2 mL). The vial was capped, reacted under microwave irradiation at about 140° C. for about 30 min. The reaction was cooled to rt, filtered through Celite®, concentrated under reduced pressure and purified via silica gel chromatography (30-100% EtOAc/heptane) to obtain the title compound (0.79 g, 48%); LC/MS (Table 1, Method e) $R_t$=1.41 min; MS m/z: 363 (M+H)$^+$.

Preparation #36

(S)-7-Bromo-4-(2-(difluoromethoxy)phenyl)-3,4-dihydro-1H-benzo[4,5]imidazo[2,1-c][1,4]oxazine

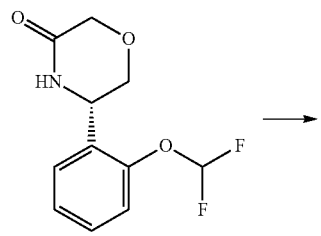

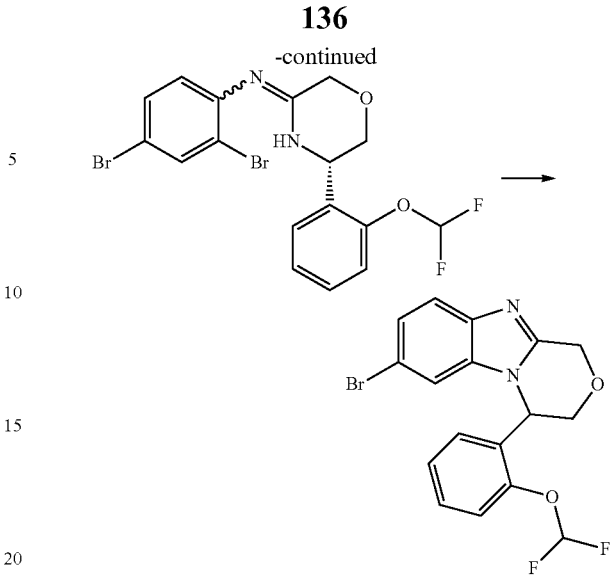

The reaction sequence was performed from (S)-5-(2-(difluoromethoxy)phenyl)morpholin-3-one (Preparation #38) in a similar fashion to Preparation #24 to give the title compound (79% crude over 2 steps); LC/MS (Table 1, Method h) $R_t$=2.43 min; MS m/z: 395,397 (M+H)$^+$.

Preparation #37

2-(2-Morpholinopyrimidin-5-yl)-8,9-dihydro-6H-cyclohepta[4,5]imidazo[1,2-a]pyridin-10(7H)-one

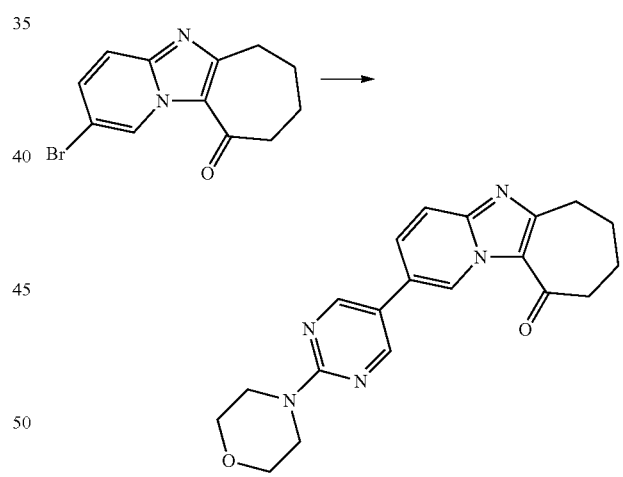

To a vial was added 2-bromo-8,9-dihydro-6H-cyclohepta[4,5]imidazo[1,2-a]pyridin-10(7H)-one (0.8 g, 2.87 mmol, Preparation #3, step 2), (2-morpholinopyrimidin-5-yl)boronic acid (0.50 g, 3.15 mmol), K$_3$PO$_4$ (2.43 g, 11.46 mmol) in a mixture of 1,4-dioxane (8 mL) and MeOH (5.33 mL). The vial was degassed, Pd(PPh$_3$)$_4$(0.33 g, 0.29 mmol) was added, purged with N$_2$, sealed, and heated at about 110° C. for about 1 h. Solvent was removed and the residue was partitioned between water and DCM. The organic phase was separated and concentrated under reduced pressure. The residue was purified by column chromatography on silica (50-100% EtOAc/heptane) to give the title compound (0.56 g, 53%); LC/MS (Table 1, Method e) $R_t$=1.19 min; MS m/z: 364 (M+H)$^+$.

Preparation #38

(S)-5-(2-(Difluoromethoxy)phenyl)morpholin-3-one

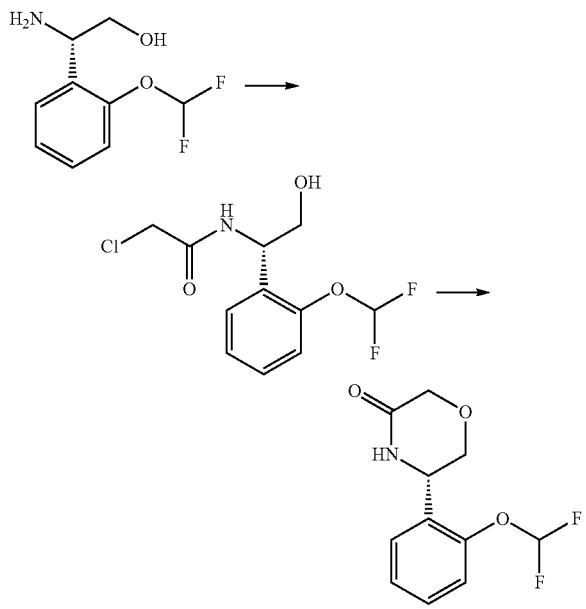

The reaction sequence was performed from (S)-2-amino-2-(2-(difluoromethoxy)phenyl)ethanol hydrochloride in a similar fashion to Preparation #23 to give the title compound (35% over 2 steps): LC/MS (Table 1, Method g) $R_t$=0.80 min; MS m/z: 244 (M+H)$^+$.

Preparation #39

(S)-7-(5-bromopyrimidin-2-yl)hexahydroimidazo[1,5-a]pyrazin-3(2H)-one and (R)-7-(5-bromopyrimidin-2-yl)hexahydroimidazo[1,5-a]pyrazin-3(2H)-one

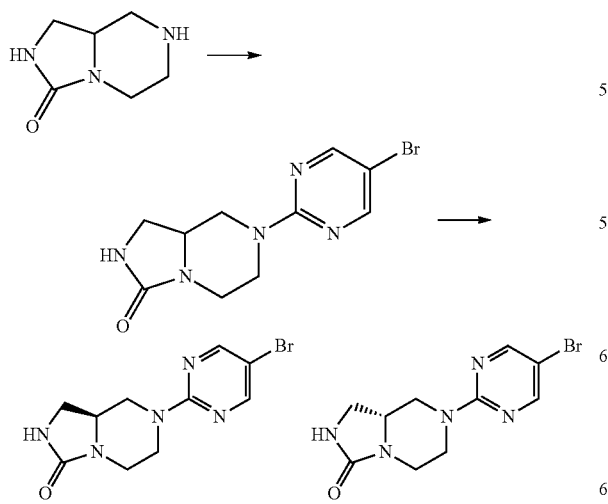

Step 1: 7-(5-Bromopyrimidin-2-yl)hexahydroimidazo[1,5-a]pyrazin-3(2H)-one

A mixture of hexahydroimidazo[1,5-a]pyrazin-3(2H)-one hydrochloride (0.441 g, 2.48 mmol), 5-bromo-2-chloropyrimidine (0.542 g, 2.80 mmol), TEA (1.20 mL, 8.61 mmol), and EtOH (20.0 mL) was warmed to about 78° C. After about 4 h, the solution was allowed to cool to rt. After stirring about 20 h, the volatiles were removed under reduced pressure. The residue was partitioned between 5% MeOH/DCM (50 mL) and water (25 mL). The aqueous layer was extracted with 5% MeOH/DCM (2×25 mL). The combined organics were dried over Na$_2$SO$_4$, filtered, and concentrated under reduced pressure. The crude material was purified by flash chromatography on silica gel eluting with a gradient of 0-5% MeOH/DCM. Product containing fractions were combined and concentrated under reduced pressure to afford the title product as a white solid (0.714 g, 96%); $^1$H NMR (400 MHz, DMSO-d$_6$) δ 8.48 (s, 2H), 6.50 (bs, 1H), 4.65-4.47 (m, 2H), 3.69-3.56 (m, 2H), 3.42-3.35 (m, 1H), 3.01-2.94 (m, 1H), 2.87-2.72 (m, 3H); LC/MS (Table 1, Method r) Rt=1.61 min; MS m/z: 298, 300 (M+H)$^+$.

Step 2: (S)-7-(5-bromopyrimidin-2-yl)hexahydroimidazo[1,5-a]pyrazin-3(2H)-one and (R)-7-(5-bromopyrimidin-2-yl)hexahydroimidazo[1,5-a]pyrazin-3(2H)-one A racemic mixture of 7-(5-bromopyrimidin-2-yl)hexahydroimidazo[1,5-a]pyrazin-3(2H)-one (0.714 g) was separated via preparative HPLC (Table 2, Method 9) to give (S)-7-(5-bromopyrimidin-2-yl)hexahydroimidazo[1,5-a]pyrazin-3(2H)-one (0.32 g, 43%, OR=positive); LC/MS (Table 1, Method r) Rt=1.61 min; MS m/z: 298, 300 (M+H)$^+$ and (R)-7-(5-bromopyrimidin-2-yl)hexahydroimidazo[1,5-a]pyrazin-3(2H)-one (0.34 g, 44%, OR=negative); LC/MS (Table 1, Method r) $R_t$=1.61 min; MS m/z: 298, 300 (M+H)$^+$; [Stereochemistry assignment arbitrarily assigned].

Preparation #40

(R)-Hexahydroimidazo[1,5-a]pyrazin-3(2H)-one

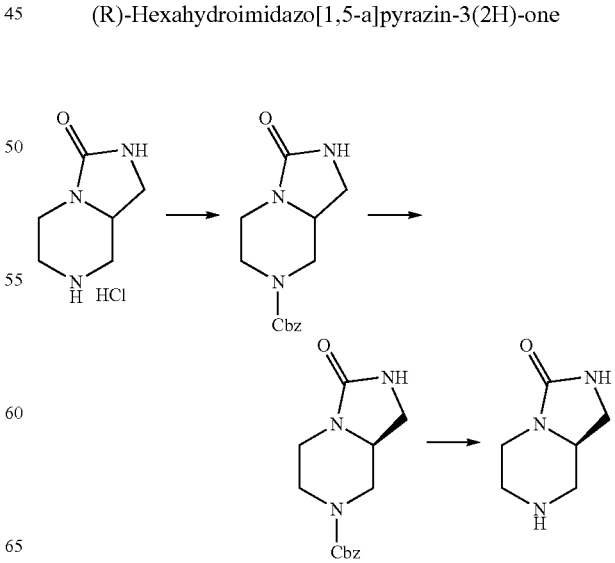

Step 1: Benzyl 3-oxohexahydroimidazo[1,5-a]pyrazine-7(1H)-carboxylate

In a 250 mL round bottom flask with 50 mL DCM was added hexahydroimidazo[1,5-a]pyrazin-3(2H)-one hydrochloride (5 g, 28.1 mmol) and DIEA (14.75 mL, 84 mmol). A solution of benzyl chloroformate (6.03 mL, 42.2 mmol) in 25 mL DCM was then added dropwise and the reaction was allowed to proceed for about 16 hours. Upon completion of the reaction, the organic solution was washed with water and brine and was then concentrated onto silica. The contents were by purified by flash chromatography on silica gel (50-100% EtOAc/heptanes) to give the title compound (6.16 g, 79%); LC/MS (Table 1, Method f) $R_t$=0.91 min; MS m/z: 276(M+H)$^+$

Step 2: (S)-Benzyl 3-oxohexahydroimidazo[1,5-a]pyrazine-7(1H)-carboxylate

The title compound was obtained from chiral SFC purification of 7-(2-morpholinopyrimidin-5-yl)-4-phenyl-3,4-dihydro-1H-benzo[4,5]imidazo[2,1-c][1,4]oxazine Prep Chiral SFC (Table 1, Method 10) $R_t$=4.1 min LC/MS (Table 1, Method f) $R_t$=0.91 min; MS m/z: 276 (M+H)$^+$.

Step 3: (R)-Hexahydroimidazo[1,5-a]pyrazin-3(2H)-one

In a 50 mL pressure bottle was added 20% Pd(OH)$_2$/C, wet (0.54 g, 0.392 mmol) followed by the addition of (S)-benzyl 3-oxohexahydroimidazo[1,5-a]pyrazine-7(1H)-carboxylate (2.7 g, 9.81 mmol) and THF (30 mL). The contents were stirred at 50° C. for about 6 h under 50 psi hydrogen gas. The contents were cooled to rt, filtered through a 0.45 μm syringe filter, and the solvent evaporated to give the title compound (1.15 g, 83%); LC/MS (Table 1, Method f) $R_t$=0.12 min; MS m/z: 276 (M+H)$^+$.

Preparation #41

(S)-Hexahydroimidazo[1,5-a]pyrazin-3(2H)-one

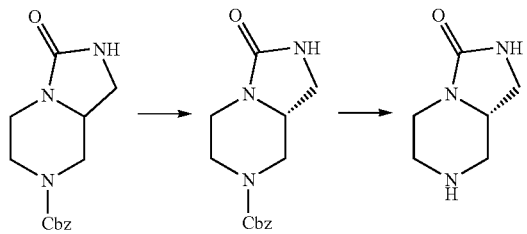 [SMILES: O=C(OCc1ccccc1)N1CCN2C(=O)NCC2C1 ; O=C(OCc1ccccc1)N1CCN2C(=O)NC[C@@H]2C1 ; O=C1NC[C@@H]2CNCCN12]

Step 1: (R)-benzyl 3-oxohexahydroimidazo[1,5-a]pyrazine-7(1H)-carboxylate

The title compound was obtained from chiral SFC purification of 7-(2-morpholinopyrimidin-5-yl)-4-phenyl-3,4-dihydro-1H-benzo[4,5]imidazo[2,1-c][1,4]oxazine Prep Chiral SFC (Table 1, Method 10) $R_t$=5.2 min LC/MS (Table 1, Method f) $R_t$=0.91 min; MS m/z: 276 (M+H)$^+$.

Step 2: (S)-Hexahydroimidazo[1,5-a]pyrazin-3(2H)-one

To a 50 mL pressure bottle was added 20% Pd(OH)$_2$/C, wet (0.54 g, 0.392 mmol) followed by the addition of (R)-benzyl 3-oxohexahydroimidazo[1,5-a]pyrazine-7(1H)-carboxylate (2.7 g, 9.81 mmol) and THF (30 mL). The contents were stirred at 50° C. for about 6 h under 50 psi hydrogen gas. The contents were cooled to rt, filtered through a 0.45 μm syringe filter, and the solvent evaporated to give the title compound (1.05 g, 76%) LC/MS (Table 1, Method f) $R_t$=0.12 min; MS m/z: 276 (M+H)$^+$.

Preparation #42

7-Bromo-1-(2-methoxyphenyl)-2,3-dihydro-1H-benzo[d]pyrrolo[1,2-a]imidazole

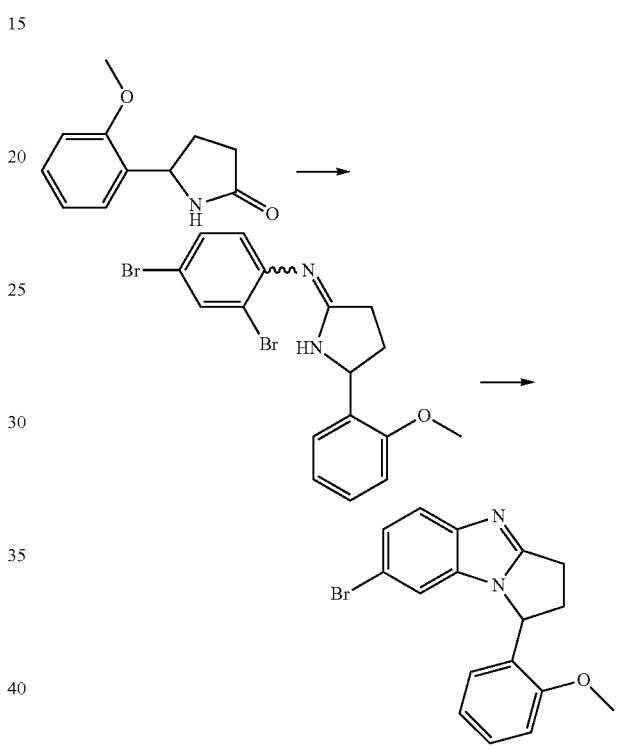

The reaction was performed from 5-(2-methoxyphenyl)pyrrolidin-2-one with 2,4-dibromoaniline in a similar fashion to Preparation #4, step 1 to give the crude title compound (1.65 g, 100%); $^1$H NMR (400 MHz, DMSO-d$_6$) δ 7.65-7.40 (brs, 1H), 7.38-7.28 (m, 1H), 7.28-7.20 (m, J=5.9 Hz, 1H), 7.19-7.04 (m, 2H), 6.89 (td, J=7.4, 1.0 Hz, 1H), 6.73 (dd, J=7.6, 1.8 Hz, 1H), 5.88-5.74 (m, 1H), 3.82 (s, 3H), 3.16-2.92 (m, 3H), 2.47-2.40 (m, 1H).

Preparation #43 and 44

(S)-5-phenylpyrrolidin-2-one and (R)-5-phenylpyrrolidin-2-one

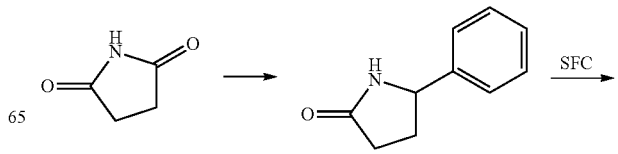

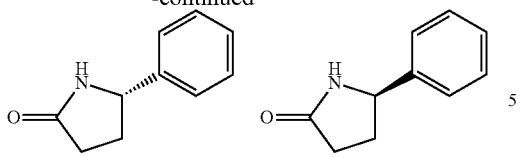

To a suspension of pyrrolidine-2,5-dione (50 g, 505 mmol) in dry DCM (1.2 L) was added dropwise phenylmagnesium bromide (1.26 L, 126 mmol, 1 M in THF) at about −78° C. with stirring. After completion of addition, the cold bath was removed and the mixture was stirred at about 17° C. for about 18 h. Sodium cyanotrihydroborate (38.1 g, 606 mmol) was added in portions to the mixture, followed by a slow addition of 6 M HCl solution to keep the pH about 3 to 4. After stirring for about 45 min, the reaction was neutralized with 4 N aqueous NaOH and extracted with DCM (3×1 L). The combined organic phase was washed with water (1.5 L) and brine (1.5 L), dried over $Na_2SO_4$ and concentrated to give a residue, which was purified by flash chromatography (eluted with a gradient of 0-5% MeOH/DCM) to afford racemic 5-phenylpyrrolidin-2-one (30 g). The racemic mixture was separated via chiral SFC (Table 2, Method 11) to give (S)-5-phenylpyrrolidin-2-one (14.03 g, 17%, OR=negative); LC/MS (Table 1, Method t) $R_t$=2.81 min; MS m/z: 162 (M+H)$^+$, $^1$H NMR (400 MHz, CDCl$_3$) δ 7.39-7.25 (m, 5H), 6.07 (br. s., 1H), 4.74 (t, J=7.1 Hz, 1H), 2.63-2.33 (m, 3H), 2.03-1.89 (m, 1H) and (R)-5-phenylpyrrolidin-2-one (14.25 g, yield 17%, OR=positive); LC/MS (Table 1, Method t, OR=negative) $R_t$=2.81 min; MS m/z: 162 (M+H)$^+$, $^1$H NMR (400 MHz, CDCl$_3$) δ 7.39-7.25 (m, 5H), 6.01 (br. s., 1H), 4.74 (t, J=7.1 Hz, 1H), 2.64-2.32 (m, 3H), 2.04-1.89 (m, 1H).

Preparation #45

4-(5-Bromopyrimidin-2-yl)tetrahydro-2H-pyran-4-ol

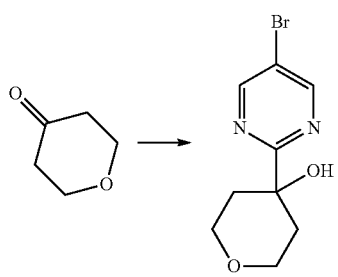 [SMILES: O=C1CCOCC1 ; OC1(c2ncc(Br)cn2)CCOCC1]

n-Butyllithium in hexanes (2.95 mL, 7.38 mmol) was added dropwise to a stirring solution of 5-bromo-2-iodopyrimidine (2.0 g, 7.02 mmol) in Toluene (30 mL) and cooled to about −78° C. under an $N_2$ atmosphere. The mixture was aged for 30 min then dihydro-2H-pyran-4(3H)-one (0.73 mL, 7.72 mmol) was added slowly. The reaction mixture was stirred at about −78° C. for 30 min, then warmed to rt over 1 h. The reaction was diluted with water (about 100 mL) and extracted with EtOAc (3×about 100 mL). The organics were combined, washed with brine, dried over $Mg_2SO_4$, filtered and concentrated under reduced pressure. The residue was purified by flash chromatography on silica gel (0-100% EtOAc/Heptanes) to afford the title compound (0.77 g, 42%); LC/MS (Table 1, Method f) $R_t$=0.50 min; MS m/z: 259, 261 (M+H)$^+$.

Preparation #46

1-(5-Bromopyrimidin-2-yl)cyclobutanol

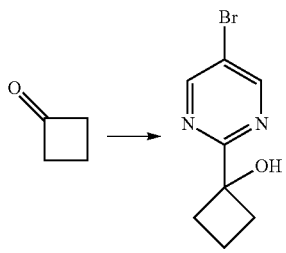

The reaction sequence was performed from cyclobutanone with 5-bromo-2-iodopyrimidine in a similar fashion to Preparation #45 to give the title compound (0.75 g, 46%); LC/MS (Table 1, Method f) $R_t$=0.59 min; MS m/z: 229, 231 (M+H)$^+$.

Preparation #47

3-(5-Bromopyrimidin-2-yl)oxetan-3-ol

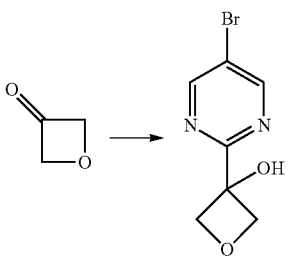 [SMILES: O=C1COC1 ; OC1(c2ncc(Br)cn2)COC1]

The reaction sequence was performed from oxetan-3-one with 5-bromo-2-iodopyrimidine in a similar fashion to Preparation #45 to give the title compound (0.75 g, 46%); LC/MS (Table 1, Method f) $R_t$=0.22 min; MS m/z: 221, 233 (M+H)$^+$.

Preparation #48

4-Bromo-2-((tetrahydro-2H-pyran-4-yl)oxy)pyridine

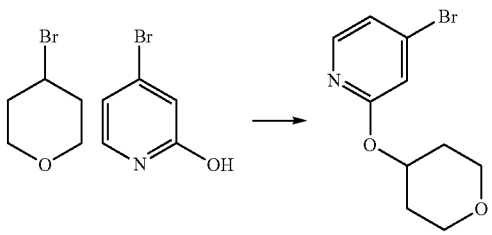

To a solution of 4-bromopyridin-2-ol (1 g, 5.75 mmol) in DMF (10 mL), stirring at rt, was added, potassium tert-butoxide (0.677 g, 6.03 mmol). The mixture was stirred for 30 min then 4-bromotetrahydro-2H-pyran (1.423 g, 8.62 mmol) was added, and the resulting mixture was stirred at 70° C. for 2 h. The mixture was cooled to rt, diluted with EtOAc (50 mL) and quenched with water (20 mL). The organic layer was washed with water (2×20 mL), brine (20 mL), dried over anhydrous MgSO$_4$ and filtered. The filtrate was concentrated in vacuo to afford the title compound (0.13 g, 9%); LC/MS (Table 1, Method f) R$_t$=0.74 min; MS m/z: 258, 260 (M+H)$^+$.

Preparation #49

(R)-7-bromo-1-phenyl-2,3-dihydro-1H-benzo[d]pyrrolo[1,2-a]imidazole

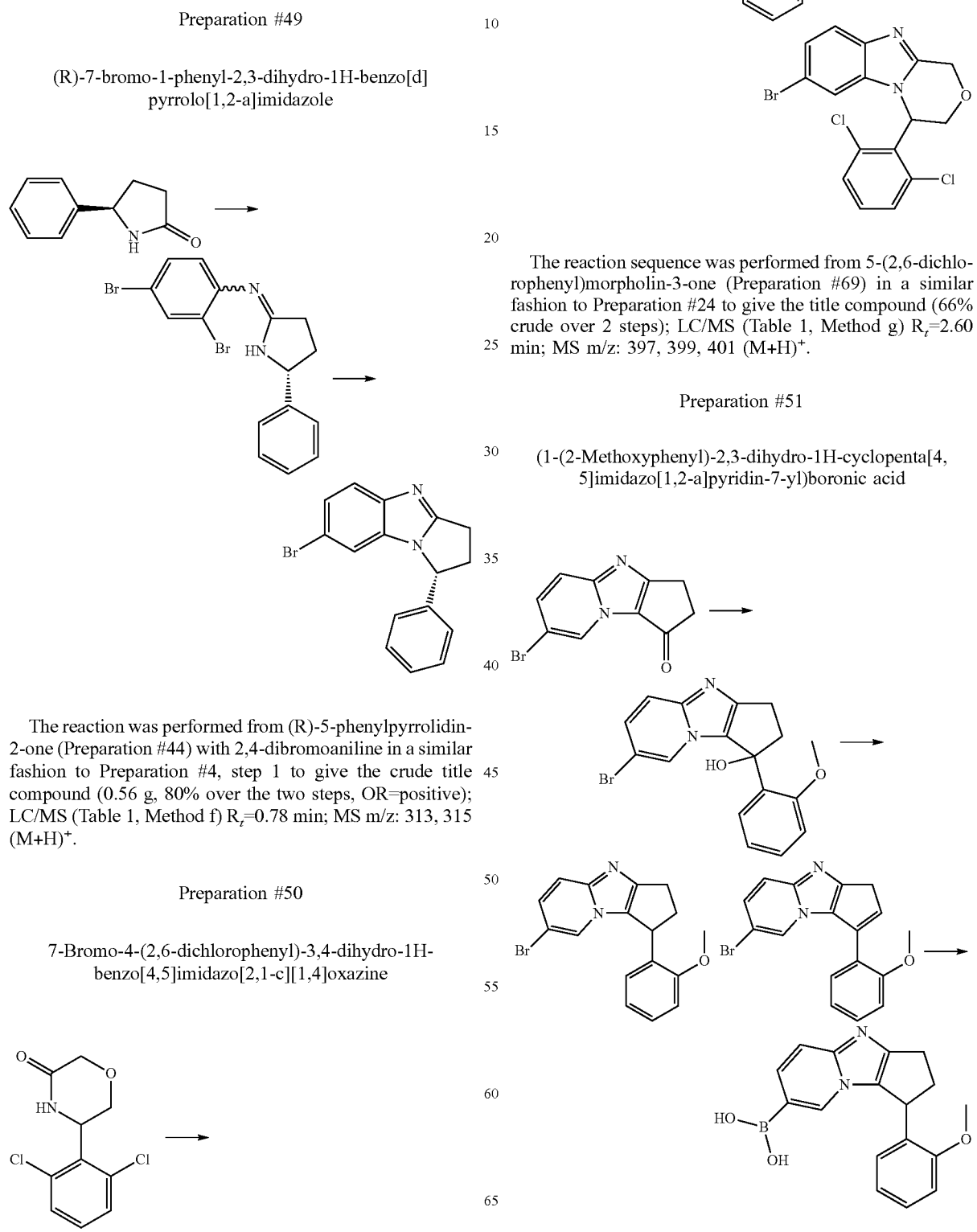

The reaction was performed from (R)-5-phenylpyrrolidin-2-one (Preparation #44) with 2,4-dibromoaniline in a similar fashion to Preparation #4, step 1 to give the crude title compound (0.56 g, 80% over the two steps, OR=positive); LC/MS (Table 1, Method f) R$_t$=0.78 min; MS m/z: 313, 315 (M+H)$^+$.

Preparation #50

7-Bromo-4-(2,6-dichlorophenyl)-3,4-dihydro-1H-benzo[4,5]imidazo[2,1-c][1,4]oxazine The reaction sequence was performed from 5-(2,6-dichlorophenyl)morpholin-3-one (Preparation #69) in a similar fashion to Preparation #24 to give the title compound (66% crude over 2 steps); LC/MS (Table 1, Method g) R$_t$=2.60 min; MS m/z: 397, 399, 401 (M+H)$^+$.

Preparation #51

(1-(2-Methoxyphenyl)-2,3-dihydro-1H-cyclopenta[4,5]imidazo[1,2-a]pyridin-7-yl)boronic acid

Step 1: 7-Bromo-1-(2-methoxyphenyl)-2,3-dihydro-1H-cyclopenta[4,5]imidazo[1,2-a]pyridin-1-ol The reaction sequence was performed from 7-bromo-2,3-dihydro-1H-cyclopenta[4,5]imidazo[1,2-a]pyridin-1-one (Preparation #2) in a similar fashion to Preparation #11, step 1, to afford the crude title compound (0.72 g, 101%); ¹H NMR (500 MHz, DMSO-d₆) δ 7.75 (d, J=2.1 Hz, 1H), 7.64 (dd, J=7.7, 1.8 Hz, 1H), 7.51 (d, J=9.5 Hz, 1H), 7.32-7.24 (m, 2H), 7.01 (td, J=7.5, 1.2 Hz, 1H), 6.96 (dd, J=8.3, 1.1 Hz, 1H), 5.97 (s, 1H), 3.46 (s, 3H), 3.02-2.89 (m, 2H), 2.81 (ddd, J=16.2, 9.3, 3.9 Hz, 1H), 2.68 (ddd, J=12.6, 9.3, 3.9 Hz, 1H).

Step 2: (1-(2-Methoxyphenyl)-2,3-dihydro-1H-cyclopenta[4,5]imidazo[1,2-a]pyridin-7-yl)boronic acid To a mixture of 7-bromo-1-(2-methoxyphenyl)-2,3-dihydro-1H-cyclopenta[4,5]imidazo[1,2-a]pyridin-1-ol (1.69 g, 4.70 mmol) in DCM (40 mL) was added TES (2.48 mL, 15.53 mmol) and (diethyloxonio)trifluoroborate (1.97 mL, 15.53 mmol). The reaction was stirred for about 1 h at about −78° C. under a N₂ atmosphere. The reaction was warmed to rt over about 30 min. The reaction was quenched with sat. NaHCO₃. The layers were separated and the aqueous layer was extracted with DCM. The combined organics were filtered through a phase separator and concentrated under reduced pressure. The residue was purified by flash chromatography on silica gel (40-100% EtOAc/heptanes) to afford approximately a 1:1 mixture of 7-bromo-1-(2-methoxyphenyl)-2,3-dihydro-1H-cyclopenta [4,5]imidazo[1,2-a]pyridine with 7-bromo-1-(2-methoxyphenyl)-3H-cyclopenta [4,5]imidazo[1,2-a]pyridine (1.45 g). To the mixture of 7-bromo-1-(2-methoxyphenyl)-2,3-dihydro-1H-cyclopenta[4,5]imidazo[1,2-a]pyridine compound with 7-bromo-1-(2-methoxyphenyl)-3H-cyclopenta [4,5]imidazo[1,2-a]pyridine (1:1) (0.5 g, 0.731 mmol) was added 4,4,4',4',5,5,5',5'-octamethyl-2,2'-bi(1,3,2-dioxaborolane) (0.22 g, 0.877 mmol), KOAc (0.29 g, 2.92 mmol), Pd(dppf)Cl₂ (0.032 g, 0.044 mmol), and 1,4-dioxane (7 mL) under a N₂ atmosphere. The reaction was stirred at 80° C. for about 26 h. The mixture was cooled to rt, filtered through Celite®, and concentrated under reduced pressure. The crude product was purified by preparative HPLC (Table 1, Method ar) to afford the title compound (0.063 g, 28%); LC/MS (Table 1, Method f) R_f=0.66 min; MS m/z 309 (M+H)⁺.

Preparation #52

(R)-2-Bromo-8-phenyl-7,8-dihydro-6H-pyrrolo[2',1':2,3]imidazo[4,5-b]pyridine

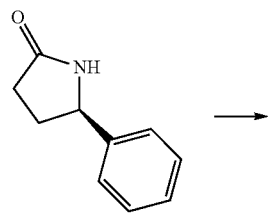

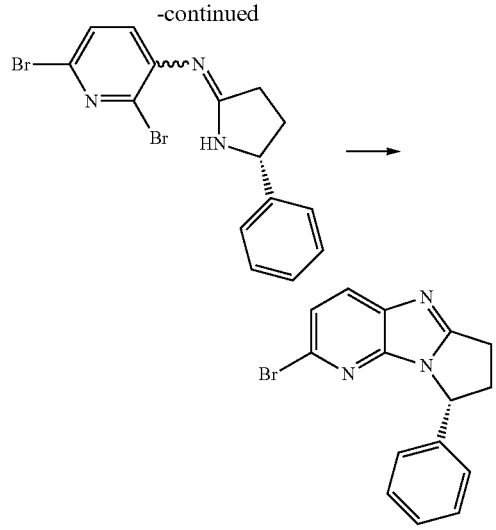

The reaction was performed from (R)-5-phenylpyrrolidin-2-one (Preparation #44) with 2,6-dibromopyridin-3-amine in a similar fashion to Preparation #4, step 1 to give the crude title compound (0.99 g, 54%); LC/MS (Table 1, Method d) R_f=0.76 min; MS m/z: 314, 316 (M+H)⁺.

Preparation #53

6-(2-Methoxyphenyl)piperidin-2-one

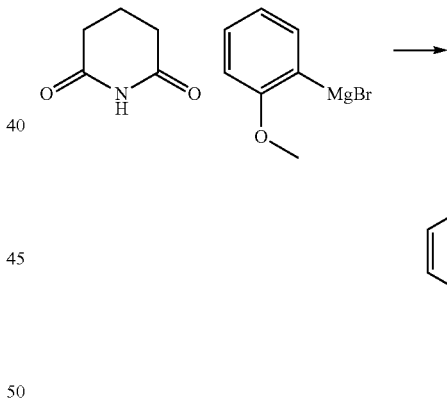

Piperidine-2,6-dione (5.0 g, 44.2 mmol) was dissolved in dry DCM (100 mL) and cooled to −78° C. (2-methoxyphenyl)magnesium bromide (99 mL, 1M in THF) was added and the resulting mixture was stirred for about 18 h at rt. Sodium cyanoborohydride (3.47 g, 55.3 mmol) was added followed by a slow addition of 6M HCl solution to keep the pH between 3 and 4. After about 4 h, the reaction was neutralized with 4N NaOH and extracted into DCM. The organics were washed with excess water and then with brine. Residual water was removed by passing the organics through a Biotage phase separator and the organics evaporated to dryness followed by trituration with hexanes. The resulting solids were collected by filtration to give the title compound (7.4 g, 81%); LC/MS (Table 1, Method d) R_f=0.67 min; MS m/z: 206 (M+H)⁺.

Preparation #54

2-Bromo-9-(2-methoxyphenyl)-6,7,8,9-tetrahydroimidazo[1,2-a:5,4-b']dipyridine

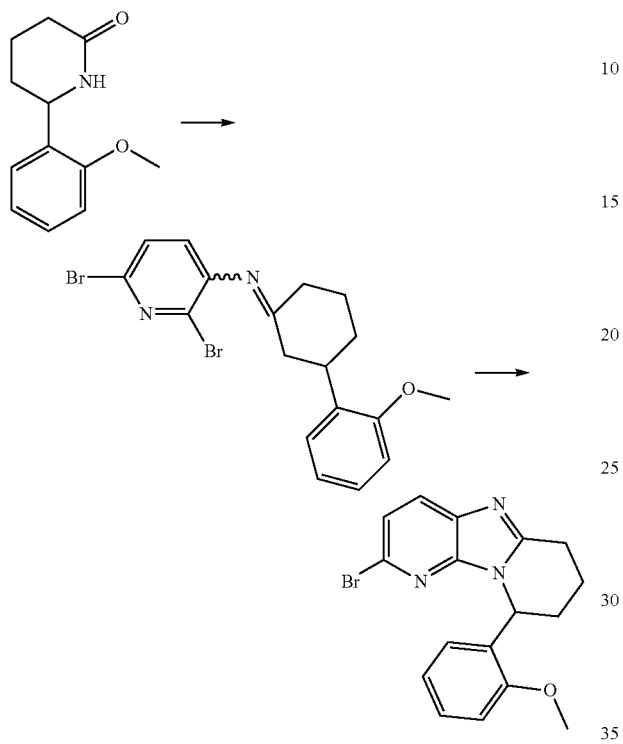

The reaction was performed from (6-(2-methoxyphenyl)piperidin-2-one (Preparation #53) with 2,6-dibromopyridin-3-amine in a similar fashion to Preparation #4, step 1 to give the title compound (2.7 g, 75%); LC/MS (Table 1, Method d) $R_t$=0.71 min; MS m/z: 358, 360 (M+H)+.

Preparation #55

(S)-5-(2-Methoxyphenyl)morpholin-3-one

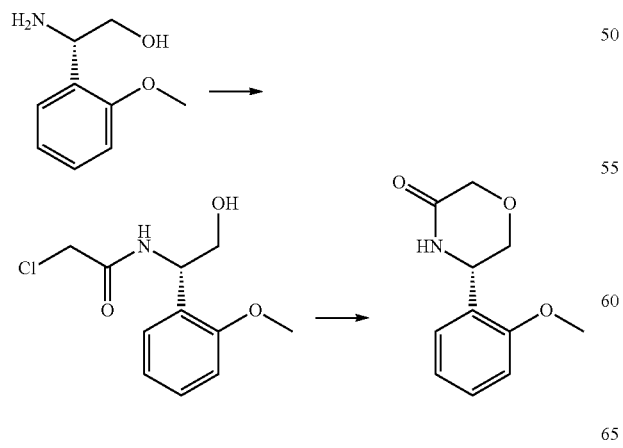

The reaction sequence was performed from (S)-2-amino-2-(2-methoxyphenyl)ethanol hydrochloride in a similar fashion to Preparation #23 to give the title compound (2.53 g, 49% over 2 steps); LC/MS (Table 1, Method h) $R_t$=1.44 min; MS m/z: 208 (M+H)+.

Preparation #56

(S)-2-Bromo-9-phenyl-8,9-dihydro-6H-pyrido[3',2':4,5]imidazo[2,1-c][1,4]oxazine

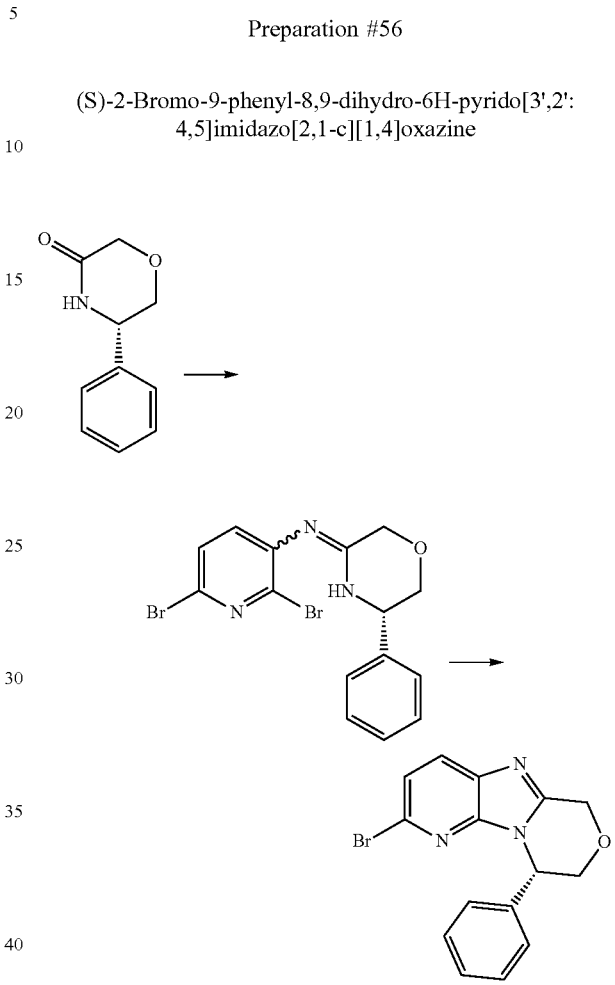

The reaction was performed from (S)-5-phenylmorpholin-3-one (Preparation #23) with 2,6-dibromopyridin-3-amine in a similar fashion to Preparation #4, step 1 to give the title compound (0.98 g, 36%); LC/MS (Table 1, Method d) $R_t$=0.75 min; MS m/z: 330, 332 (M+2H)+.

Preparation #57

(S)-2-Bromo-9-(2-methoxyphenyl)-8,9-dihydro-6H-pyrido[3',2':4,5]imidazo[2,1-c][1,4]oxazine

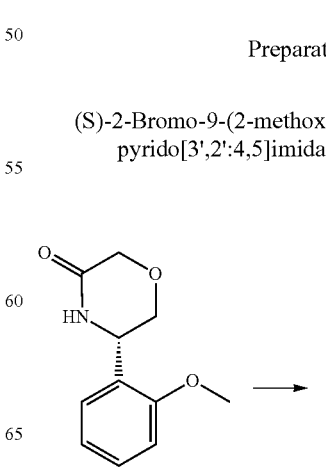

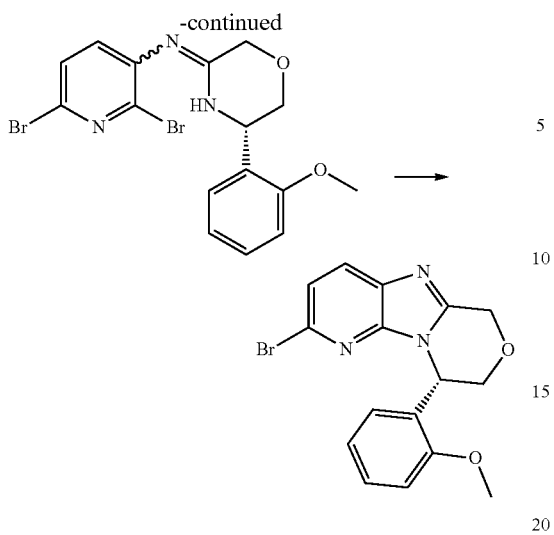

The reaction was performed from (S)-5-(2-methoxyphenyl)morpholin-3-one (Preparation #55) with 2,6-dibromopyridin-3-amine in a similar fashion to Preparation #4, step 1 to give the crude title compound (1.2 g, 84%); LC/MS (Table 1, Method d) $R_t$=0.82 min; MS m/z: 360, 362 (M+2H)$^+$ Preparation #58

7-Bromo-1-(2-methoxyphenyl)-2,3-dihydro-1H-benzo[d]pyrrolo[1,2-a]imidazole

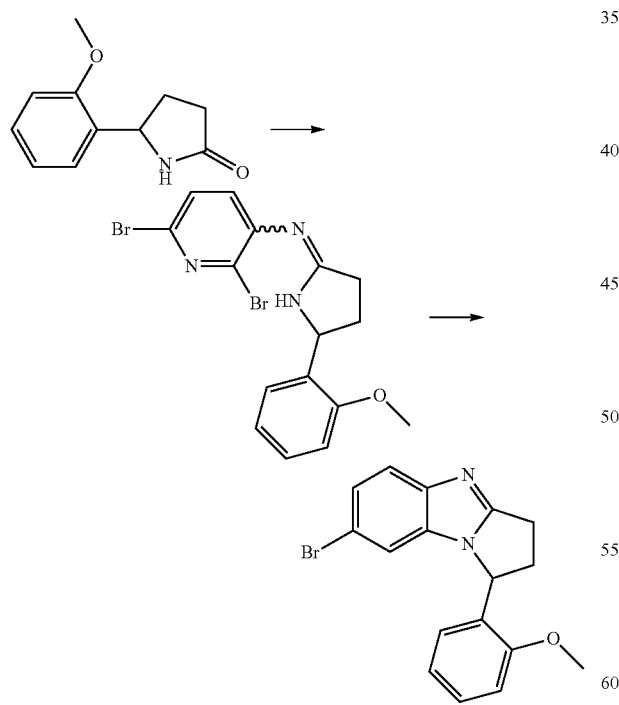

The reaction was performed from (R)-5-phenylpyrrolidin-2-one (Preparation #44) with 2,6-dibromopyridin-3-amine in a similar fashion to Preparation #4, step 1 to give the crude title compound (0.42 g, 55%); LC/MS (Table 1, Method f) $R_t$=0.74 min; MS m/z: 344, 346 (M+H)$^+$.

Preparation #59

(R)-7-Bromo-1-phenyl-2,3-dihydro-1H-benzo[d]pyrrolo[1,2-a]imidazole

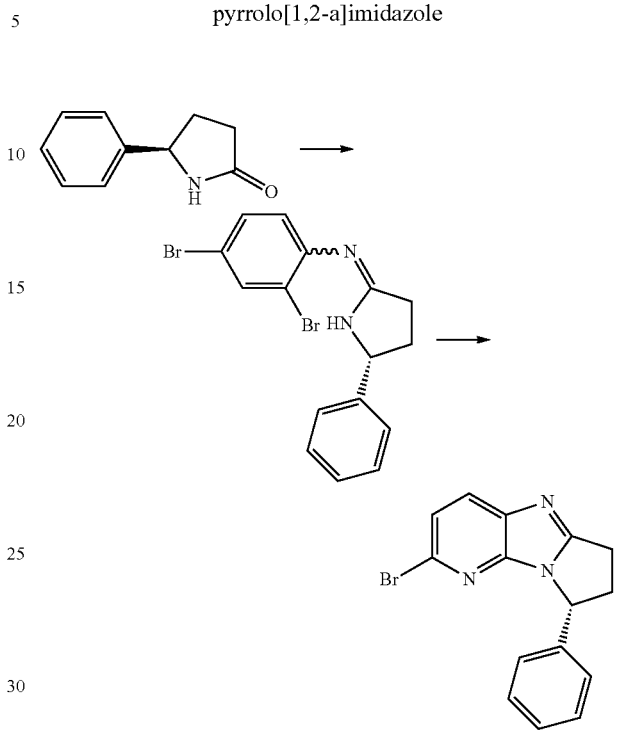

The reaction was performed from (R)-5-phenylpyrrolidin-2-one (Preparation #44) with 2,4-dibromoaniline in a similar fashion to Preparation #4, step 1 to give the crude title compound (0.56 g, 80% over the two steps, OR=positive); LC/MS (Table 1, Method f) $R_t$=0.78 min; MS m/z: 313, 315 (M+H)$^+$ Preparation #60

(S)-7-Bromo-4-(2-methoxyphenyl)-3,4-dihydro-1H-benzo[4,5]imidazo[2,1-c][1,4]oxazine

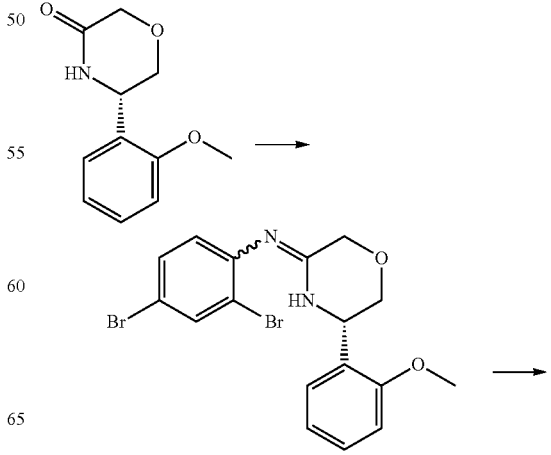

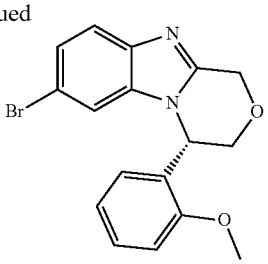

The reaction sequence was performed from (S)-5-(2-methoxyphenyl)morpholin-3-one (Preparation #55) in a similar fashion to Preparation #24 to give the crude title compound (1.81 g, 99% over 2 steps); LC/MS (Table 1, Method g) $R_t$=2.38 min; MS m/z: 359,361 (M+H)$^+$.

Preparation #61

7-Bromo-1-(tetrahydro-2H-pyran-4-yl)-2,3-dihydro-1H-benzo[d]pyrrolo[1,2-a]imidazole

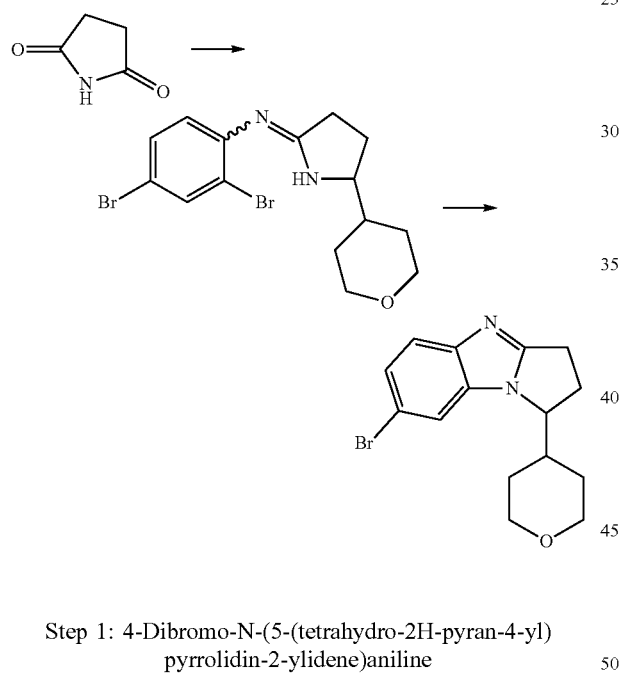

Step 1: 4-Dibromo-N-(5-(tetrahydro-2H-pyran-4-yl)pyrrolidin-2-ylidene)aniline

A solution of pyrrolidine-2,5-dione (1 g, 10.09 mmol) in dry DCM (20 mL) was cooled to about −78° C. (tetrahydro-2H-pyran-4-yl)magnesium chloride (46.4 mL, 23.21 mmol, 0.5 M in THF) was added. After about 5 min, the dry-ice bath was removed and the resulting mixture was stirred for about 18 h at rt. Sodium cyanotrihydroborate (0.761 g, 12.11 mmol) was added followed by a slow addition of 6M HCl solution to keep the pH between about 3 and 4. After about 1 h, the reaction was neutralized with 4N NaOH and extracted with DCM (3×25 mL). The combined organic layers were washed with excess water (25 mL) and then with brine (25 mL), dried over Na$_2$SO$_4$, filtered, and concentrated under reduced pressure to give crude 5-(tetrahydro-2H-pyran-4-yl)pyrrolidin-2-one (1.71 g). 2,4-dibromoaniline (1.47 g, 5.86 mmol) and crude 5-(tetrahydro-2H-pyran-4-yl)pyrrolidin-2-one (1.24 g, 7.33 mmol) were dissolved in dry toluene (30 mL) and POCl$_3$ (0.683 mL, 7.33 mmol) was added slowly at about 0° C. The bath was removed and the reaction was warmed to rt. The reaction solution was refluxed while stirring for about 40 min, cooled to rt, and concentrated under reduced pressure. DCM (200 mL) was added to the crude followed by 1M NaOH adjust the pH between about 6 and 7. The organics were collected washed with brine (50 mL), dried over Na$_2$SO$_4$, filtered and concentrated under reduced pressure. The residue was purified via silica gel chromatography eluting with 0-7% MeOH with 0.5% TEA/DCM to give the impure title compound (0.46 g); LC/MS (Table 1, Method f) $R_t$=0.65 min.; MS m/z: 402, 404 (M+H)$^+$.

Step 2: 7-Bromo-1-(tetrahydro-2H-pyran-4-yl)-2,3-dihydro-1H-benzo[d]pyrrolo[1,2-a]imidazole To a solution of 2,4-dibromo-N-(5-(tetrahydro-2H-pyran-4-yl)pyrrolidin-2-ylidene)aniline (0.46 g, 1.144 mmol) in MeCN (7 mL) was added K$_2$CO$_3$ (0.158 g, 1.144 mmol), DMEA (0.025 mL, 0.229 mmol) and CuI (0.0218 g, 0.114 mmol). The result mixture was refluxed with stirring for about 16 h under N$_2$ atmosphere. After cooling DCM (about 10 mL) was added, filtered. The filtrate was concentrated under reduced pressure. The residue was purified via silica gel chromatography eluting with 30-100% EtOAc/Heptane to give title compound (0.037 g); LC/MS (Table 1, Method f) $R_t$=0.59 min.; MS m/z: 321, 323 (M+H)$^+$.

Preparation #62

7-(5-(4,4,5,5-Tetramethyl-1,3,2-dioxaborolan-2-yl)pyrimidin-2-yl)hexahydroimidazo[1,5-a]pyrazin-3(2H)-one

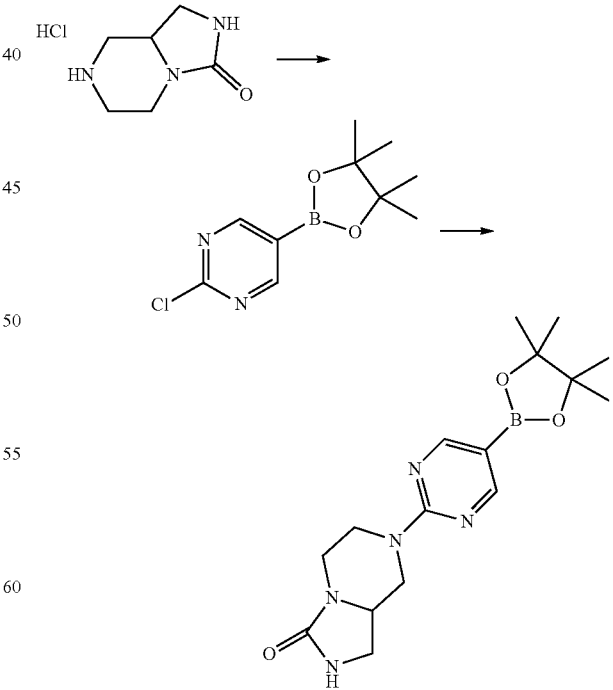

To 2-chloro-5-(4,4,5,5-tetramethyl-1,3,2-dioxaborolan-2-yl)pyrimidine (1.0 g, 4.16 mmol) in 1,4-dioxane (10 mL)

was added hexahydroimidazo[1,5-a]pyrazin-3(2H)-one hydrochloride (0.81 g, 4.57 mmol) and TEA (0.63 g, 6.24 mmol). After about 45 min of heating at about 100° C. in a microwave, the reaction was cooled, the solids were collected by filtration, washed with 1,4-dioxane, water and then with excess diethylether. The filtercake was allowed to air dry to give the crude title compound (1.44 g, 100%); LC/MS (Table 1, Method d) $R_f$=0.14 min; MS m/z: 346 (M+H)+.

Preparation #63

7-Bromo-4-(2-methoxyphenyl)-3,4-dihydro-1H-pyrano[3',4':4,5]imidazo[1,2-a]pyridine

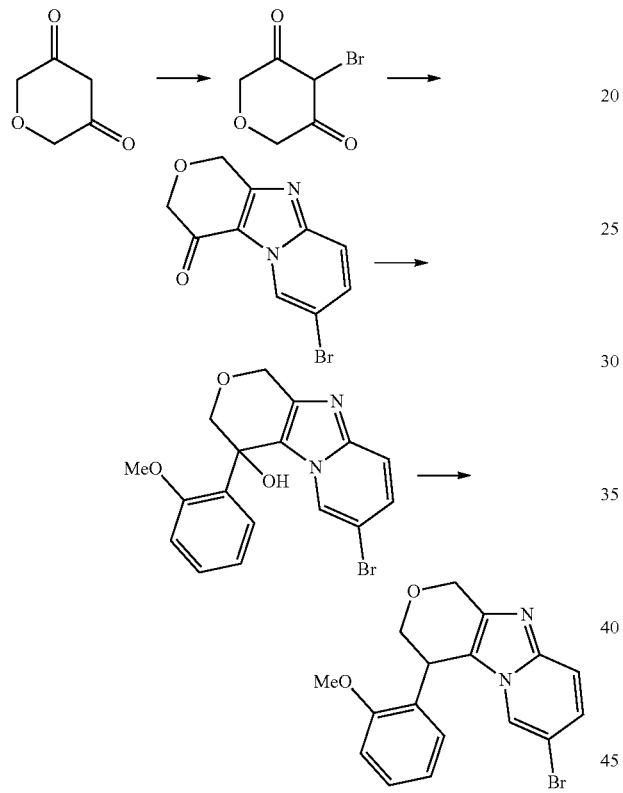

Step 1: 4-Bromo-2H-pyran-3,5(4H, 6H)-dione

To a stirred solution of 2H-pyran-3,5(4H, 6H)-dione (0.7 g, 6.14 mmol) in 31 mL DMSO at rt was added 1-bromopyrrolidine-2,5-dione (1.15 g, 6.44 mmol). The reaction mixture was stirred for about 30 min and then quenched with 10 mL of water. Extracted with 20 mL of EtOAc, dried with MgSO4 and concentrated in vacuo to afford the title compound (0.6 g, 51%) LC/MS (Table 1, Method f) $R_f$=0.1 min; MS m/z: 193, 195 (M+H)+.

Step 2: 7-Bromo-1H-pyrano[3'4':4,5]imidazo[1,2-a]pyridine-4(3H)-one

To a stirred solution of 4-bromo-2H-pyran-3,5(4H,6H)-dione (0.52 g, 2.69 mmol) in DME (10.6 mL) was added 5-bromopyridin-2-amine (0.37 g, 2.69 mmol). The reaction mixture was heated to reflux with stirring for about 12 h, cooled to rt, and concentrated in vacuo. The crude reaction mixture was purified on silica gel (MeOH/DCM 0-5%) to afford the crude title compound (0.23 g, 40%) carried on to the next step.

Step 3: 7-Bromo-4-(2-methoxyphenyl)-3,4-dihydro-1H-pyrano[3',4':4,5]imidazo[1,2-a]pyridin-4-ol To a flask was added crude 7-bromo-1H-pyrano[3',4':4,5]imidazo[1,2-a]pyridin-4(3H)-one (0.13 g, 0.47 mmol) in DCM (2 mL). To this stirring solution at about 0° C. under an N2 atmosphere was added (2-methoxyphenyl)magnesium bromide (1.03 mL, 1.03 mmol). The mixture was stirred at rt for about 1 h. The reaction was quenched with sat. NH4Cl and extracted with 20 mL EtOAc. The organics were collected, washed with water, filtered through a phase separator, and concentrated under reduced pressure. The residue was purified on silica gel (MeOH/DCM 0-30%) to give the title compound (0.11 g, 60%); LC/MS (Table 1, Method u) $R_f$=0.8 min; MS m/z: 375, 377 (M+H)+

Step 4: 7-Bromo-4-(2-methoxyphenyl)-3,4-dihydro-1H-pyrano[3',4':4,5]imidazo[1,2-a]pyridine To a mixture of 7-bromo-4-(2-methoxyphenyl)-3,4-dihydro-1H-pyrano[3',4':4,5]imidazo[1,2-a]pyridin-4-ol (0.05 g, 0.133 mmol) in DCM (1.1 mL) was added boron trifluoride diethyl etherate (0.056 mL, 0.440 mmol) and TES (0.051 mL, 0.44 mmol). The reaction was stirred for about 60 min at about −78° C. then warmed to rt. The reaction was quenched with sat. NaHCO3. The organics were separated and the aqueous layer extracted with DCM. The organics were combined, filtered through a phase separator, and concentrated under reduced pressure. The residue was purified by column chromatography on silica (EtOAc/heptanes 30-100%) to give the title compound (0.022 g, 46%): LC/MS (Table 1, Method f) $R_f$=0.89 min; MS m/z: 360, 362 (M+H)+

Preparation #64

2-Bromo-6H-cyclopenta[4,5]imidazo[1,2-b]byridazin-8(7H-one)

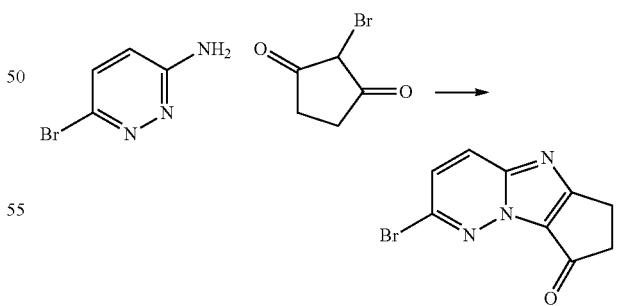

A solution of 2-bromocyclopentane-1,3-dione (1.55 g, 8.76 mmol) and 6-bromopyridazin-3-amine (1.2 g, 6.90 mmol) in DME (35 mL) refluxed at about 100° C. for about 12 h. The reaction was concentrated under reduced pressure. The residue was dissolved in DCM (about 100 mL) and washed with water. The organics were collected, dried over MgSO4, filtered and concentrated under reduced pressure.

The residue was purified by column chromatography on silica (MeOH/DCM 0-10%) to give the title compound in (0.26 g, 15%) LC/MS (Table 1, Method f) $R_f$=0.47 min; MS m/z: 251, 253 (M+H)$^+$.

Preparation #65

2-Bromo-8-phenyl-7,8-dihydro-6H-cyclopenty[4,5]imidazo[1,2-b]pyridazine

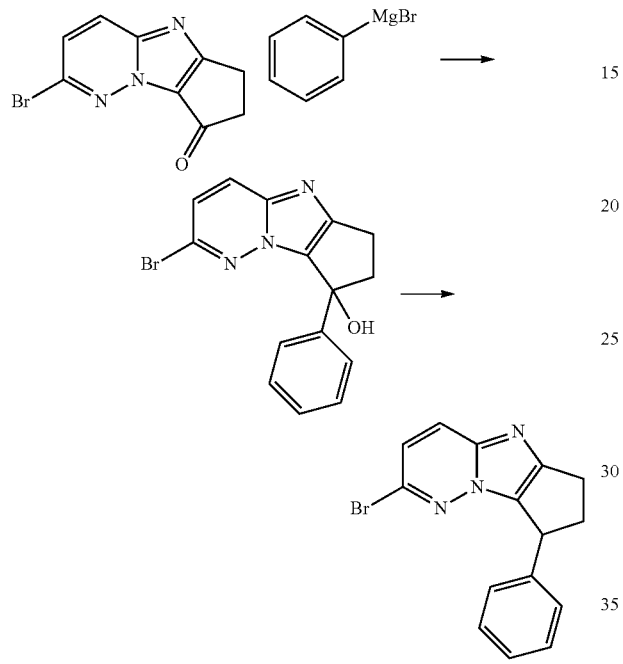

Step 1: 2-Bromo-8-phenyl-7,8-dihydro-6H-cyclopentyl[4,5]imidazo[1,2-b]pyridazin-8-ol A solution of 2-bromo-6H-cyclopenta[4,5]imidazo[1,2-b]pyridazin-8(7H)-one (0.26 g, 1.031 mmol, Preparation #64) in DCM (5.2 mL) was cooled to about 0° C. under N$_2$ atmosphere and 3M phenylmagnesium bromide in THF (0.62 mL, 1.86 mmol) was added dropwise. The mixture was allowed to warm to rt and stirred for about 1 h. The reaction was quenched with 30 mL of aqueous saturated ammonium chloride solution, extracted with 10 mL DCM, dried over MgSO$_4$, and concentrated in vacuo. The residue was purified by column chromatography on silica (0-5-10% MeOH/DCM) to afford the title compound (0.20 g, 59%) LC/MS (Table 1, Method u) $R_f$=0.97 min; MS m/z: 312, 314 (M+H)$^+$ Step 2: 2-Bromo-8-phenyl-7,8-dihydro-6H-cyclopenty[4,5]imidazo[1,2-b]pyridazine To a solution of 2-bromo-8-phenyl-7,8-dihydro-6H-cyclopenta[4,5]imidazo[1,2-b]pyridazin-8-ol (200 mg, 0.606 mmol) in DCM (5.1 mL) was added TES (0.32 mL, 2.0 mmol) and the mixture was stirred for about 5 min. Then (diethyloxonio)trifluoroborate (0.25 mL, 2.0 mmol) was added slowly and the mixture was stirred for about 60 min at about −78° C. under N$_2$ atmosphere. Then the reaction was allowed to warm to rt and stirred for about 30 min. The reaction was quenched with sat. NaHCO$_3$, extracted with DCM and concentrated under reduced pressure. The residue was purified by column chromatography on silica (40-100% EtOAc/heptanes) to afford the title compound (0.020 g, 10.5%) LC/MS (Table 1, Method f) $R_f$=0.77 min; MS m/z: 314, 316 (M+H)$^+$ Preparation #66

2-Bromo-8-(2-methoxyphenyl)-7,8-dihydro-6H-cyclopenta[4,5]imidazo[1,2-b]pyridazine

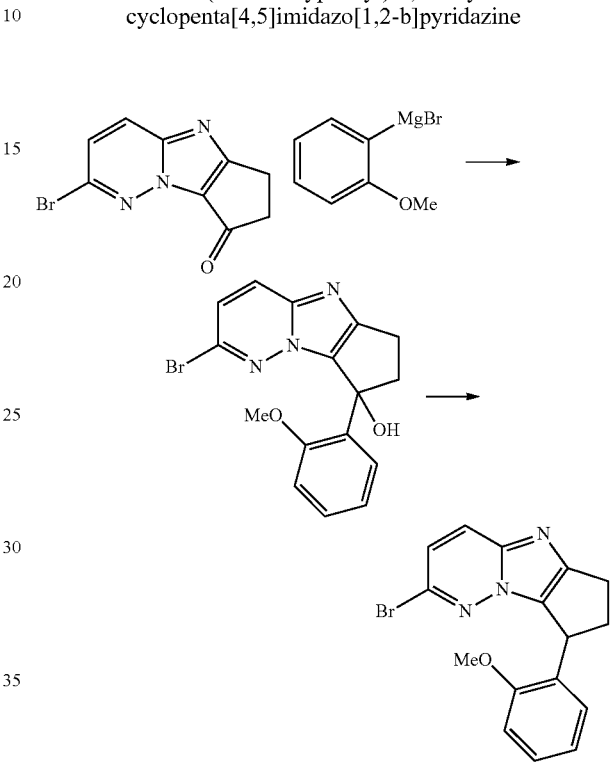

Step 1: 2-Bromo-8-(2-methoxyphenyl)-7,8-dihydro-6H-cyclopenta[4,5]imidazo[1,2-b]pyridazin-8-ol A solution of 2-bromo-6H-cyclopenta[4,5]imidazo[1,2-b]pyridazin-8(7H)-one (0.23 g, 0.91 mmol, Preparation #64) in DCM (4.5 mL) was cooled to about 0° C. under N$_2$ atmosphere and (2-methoxyphenyl)magnesium bromide (1M in THF, 0.35 mL, 1.64 mmol) was added dropwise. The mixture was allowed to warm to rt and stirred for about 1 h. The reaction was quenched with 30 mL of aqueous saturated ammonium chloride solution, extracted with DCM, dried over MgSO$_4$, and concentrated in vacuo. The residue was purified by column chromatography on silica (0-5-10% MeOH/DCM) to afford the title compound (0.30 g, 91%) LC/MS (Table 1, Method u) $R_f$=0.7 min; MS m/z: 359, 361 (M+H)$^+$ Step 2: 2-Bromo-8-(2-methoxyphenyl)-7,8-dihydro-6H-cyclopenta[4,5]imidazo[1,2-b]pyridazine To a solution of 2-Bromo-8-(2-methoxyphenyl)-7,8-dihydro-6H-cyclopenta[4,5]imidazo[1,2-b]pyridazin-8-ol (0.30 g, 0.83 mmol) in DCM (7.1 mL) was added TES (0.44 mL, 2.75 mmol) and stirred for about 5 min. Then, (diethyloxonio)trifluoroborate (0.35 mL, 2.75 mmol) was added slowly and the reaction was stirred for about 60 min at about −78° C. under N$_2$ atmosphere. Then the reaction was allowed to warm to rt and stirred for about 30 min. The reaction was quenched with sat. NaHCO₃, extracted with 10 mL DCM and concentrated under reduced pressure. The residue was purified by column chromatography on silica (40-100% EtOAc/heptanes) to afford the title compound (0.062 g, 22%) LC/MS (Table 1, Method f) $R_f$=0.92 min; MS m/z: 344, 346 (M+H)⁺

Preparation #67

(R)-7-bromo-4-phenyl-3,4-dihydro-1H-pyrano[3',4': 4,5]imidazo[1,2-a]pyridine

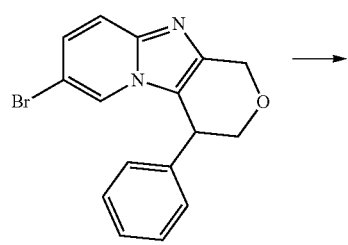

7-Bromo-4-phenyl-3,4-dihydro-1H-pyrano[3',4':4,5]imi-dazo[1,2-a]pyridine (synthesized in a manner similar to Preparation #63 from 7-bromo-1H-pyrano[3'4':4,5]imidazo [1,2-a]pyridine-4(3H)-one with phenyl magnesium bromide) was separated by chiral HPLC (Table 2, Method 12). Fractions from the second eluting component were combined and concentrated under reduced pressure to afford the title compound (0.24 g, 49%); LC/MS (Table 1, Method v) $R_f$=2.14 min; MS m/z: 329, 331 (M+H)⁺

Preparation #68

(R)-2-bromo-9-phenyl-8,9-dihydro-6H-pyrano[3',4': 4,5]imidazo[1,2-b]pyridazine

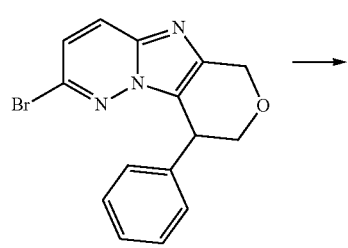

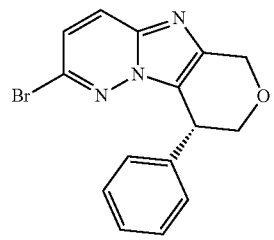

2-Bromo-9-phenyl-8,9-dihydro-6H-pyrano[3',4':4,5]imi-dazo[1,2-b]pyridazine (synthesized in a manner similar to Preparation #63 replacing 5-bromopyridin-2-amine with 6-bromopyridazin-3-amine and (2-methoxyphenyl)magnesium bromide with phenyl magnesium bromide) was submitted for chiral purification (Table 2, Method 13). Fractions from the second eluting component were combined and concentrated under reduced pressure to afford the title compound (0.33 g, 38%); LC/MS (Table 1, Method v) $R_f$=2.08 min; MS m/z: 330, 332 (M+H)⁺

Preparation #69

5-(2,6-Dichlorophenyl)morpholin-3-one

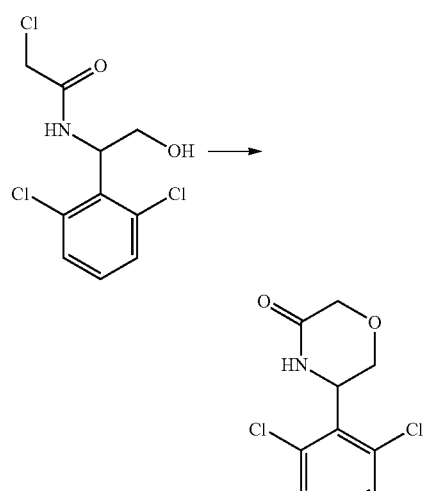

The reaction sequence was performed from 2-amino-2-(2,6-dichlorophenyl)ethanol in a similar fashion to Preparation #23 to give the crude title compound (0.59 g, 40% over 2 steps); LC/MS (Table 1, Method h) $R_f$=1.82 min; MS m/z: 246, 248 (M+H)⁺.

Preparation #70

5-(2-Trifluoromethylphenyl)morpholin-3-one

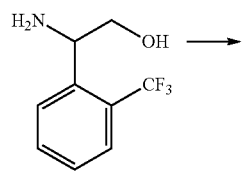

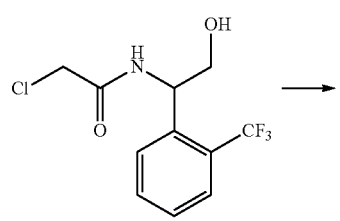

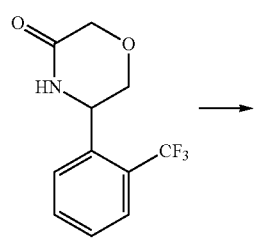

The reaction sequence was performed from 2-amino-2-(2-trifluoromethylphenyl)ethanol in a similar fashion to Preparation #25 to give the title compound (13.0 g, 37.5% over 2 steps); LC/MS (Table 1, Method a) $R_t$=2.62 min; MS m/z: 246 (M+H)$^+$.

Preparation #71

7-Bromo-4-(2-(trifluoromethyl)phenyl)-3,4-dihydro-1H-benzo[4,5]imidazo[2,1-c][1,4]oxazine

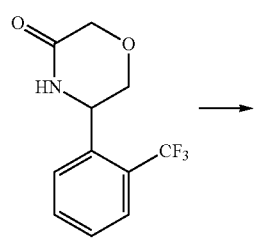

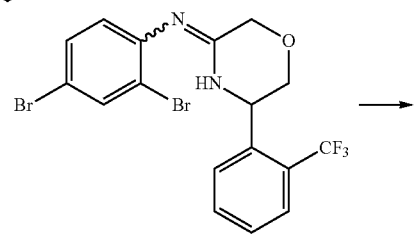

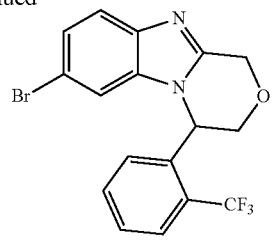

The reaction sequence was performed from 5-(2-(trifluoromethylphenyl)morpholin-3-one (Preparation #70) in a similar fashion to Preparation #24 to give the title compound (0.656 g, 44% over 2 steps); LC/MS (Table 1, Method i) $R_t$=0.79 min; MS m/z: 397, 399 (M+H)$^+$.

Preparation #72

(S)-5-(2-Chlorophenyl)morpholin-3-one

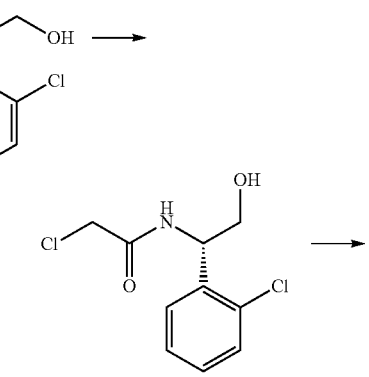

The reaction sequence was performed from (S)-2-amino-2-(2-chlorophenyl) in a similar fashion to Preparation #25 to give the title compound (1.5 g, 32.6% over 2 steps); LC/MS (Table 1, Method a) $R_t$=2.42 min; MS m/z: 212 (M+H)$^+$.

Preparation #73

(S)-7-Bromo-4-(2-chlorophenyl)-3,4-dihydro-1H-benzo[4,5]imidazo[2,1-c][1,4]oxazine

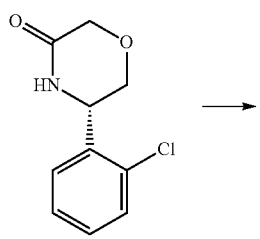

-continued

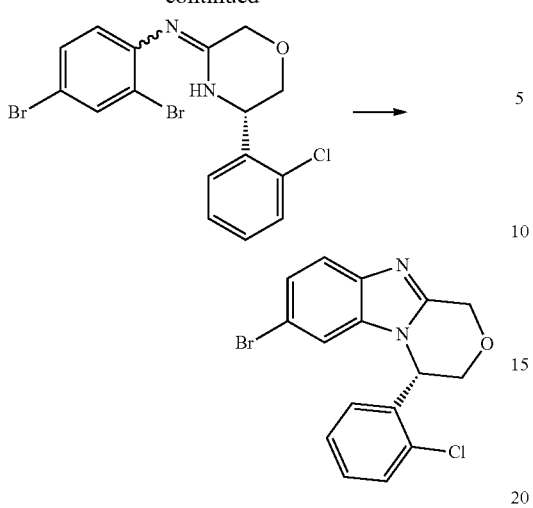

The reaction sequence was performed from (S)-5-(2-(trifluoromethylphenyl)morpholin-3-one (Preparation #72) in a similar fashion to Preparation #24 to give the title compound (0.425 g, 68% over 2 steps); LC/MS (Table 1, Method i) $R_t$=0.74 min; MS m/z: 363, 365 (M+H)$^+$.

Preparation #74

5-(2-Fluorophenyl)morpholin-3-one

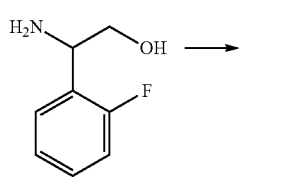

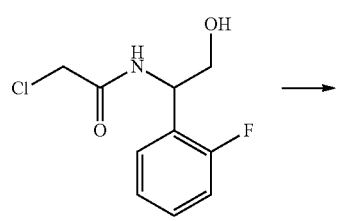

The reaction sequence was performed from 2-amino-2-(2-fluorophenyl)ethanol hydrochloride in a similar fashion to Preparation #25 to give the title compound (5 g, 62% over 2 steps); LC/MS (Table 1, Method a) $R_t$=2.23 min; MS m/z: 196 (M+H)$^+$.

Preparation #75

7-Bromo-4-(2-(fluoro)phenyl)-3,4-dihydro-1H-benzo[4,5]imidazo[2,1-c][1,4]oxazine

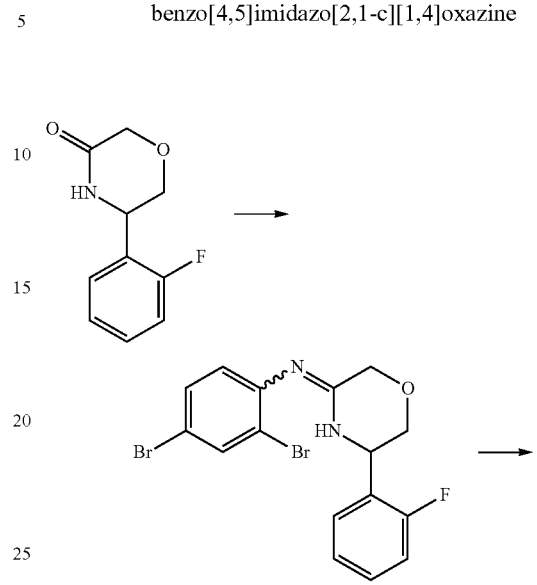

The reaction sequence was performed from 5-(2-(fluorophenyl)morpholin-3-one (Preparation #74) in a similar fashion to Preparation #24 to give the title compound (0.457 g, 32% over 2 steps); LC/MS (Table 1, Method i) $R_t$=0.69 min; MS m/z: 347, 349 (M+H)$^+$.

Preparation #76

5-(3-Chlorophenyl)morpholin-3-one

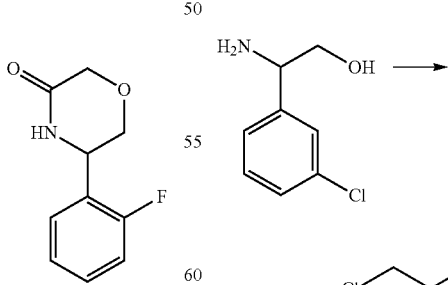

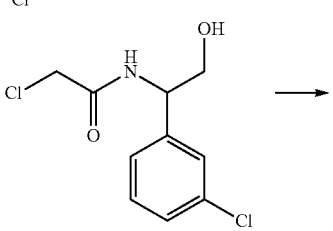

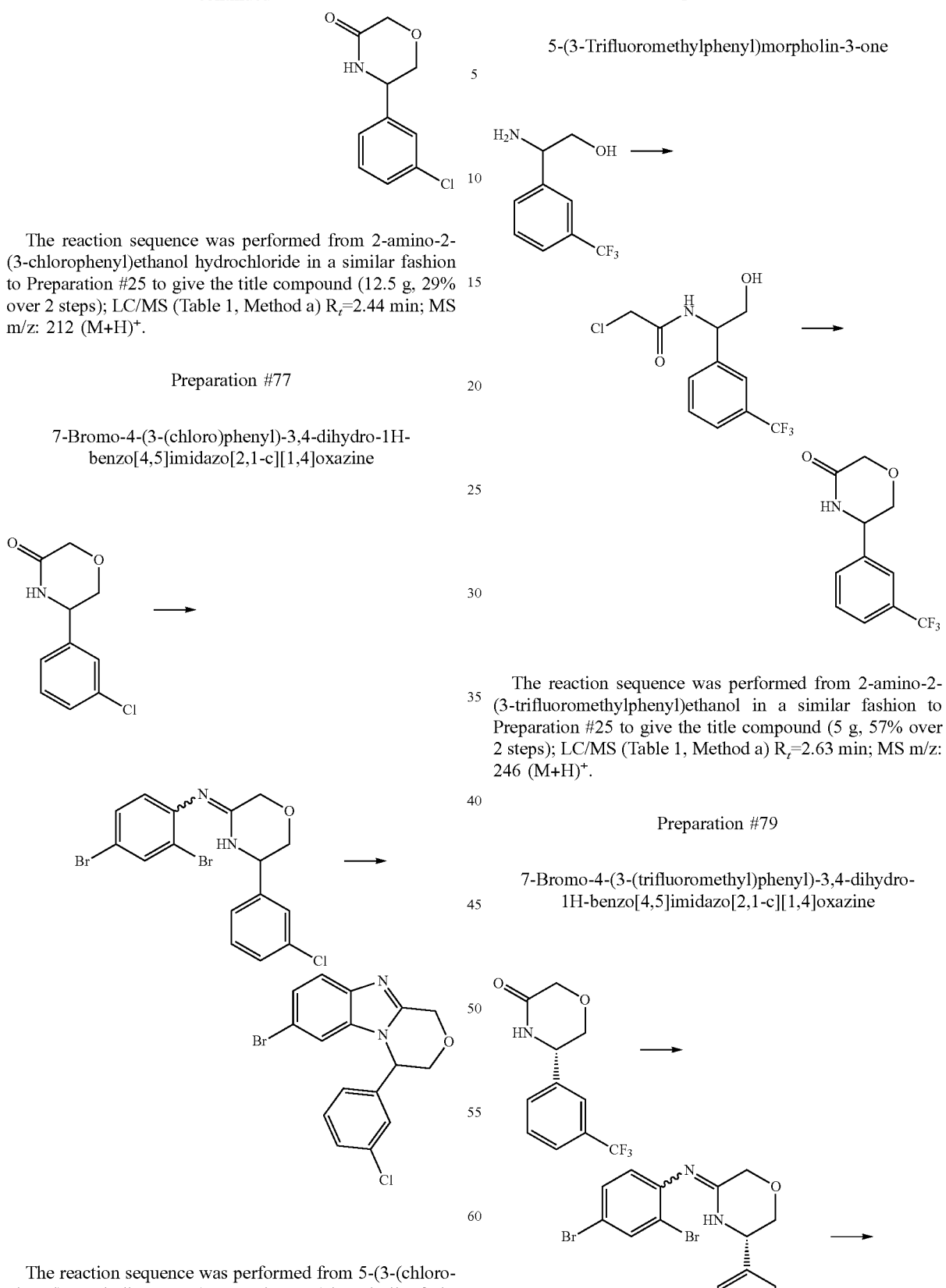

The reaction sequence was performed from 2-amino-2-(3-chlorophenyl)ethanol hydrochloride in a similar fashion to Preparation #25 to give the title compound (12.5 g, 29% over 2 steps); LC/MS (Table 1, Method a) $R_t$=2.44 min; MS m/z: 212 (M+H)+.

Preparation #77

7-Bromo-4-(3-(chloro)phenyl)-3,4-dihydro-1H-benzo[4,5]imidazo[2,1-c][1,4]oxazine The reaction sequence was performed from 5-(3-(chlorophenyl)morpholin-3-one (Preparation #76) in a similar fashion to Preparation #24 to give the title compound (0.370 g, 25% over 2 steps); LC/MS (Table 1, Method i) $R_t$=0.73 min; MS m/z: 363, 365 (M+H)+.

Preparation #78

5-(3-Trifluoromethylphenyl)morpholin-3-one

The reaction sequence was performed from 2-amino-2-(3-trifluoromethylphenyl)ethanol in a similar fashion to Preparation #25 to give the title compound (5 g, 57% over 2 steps); LC/MS (Table 1, Method a) $R_t$=2.63 min; MS m/z: 246 (M+H)+.

Preparation #79

7-Bromo-4-(3-(trifluoromethyl)phenyl)-3,4-dihydro-1H-benzo[4,5]imidazo[2,1-c][1,4]oxazine

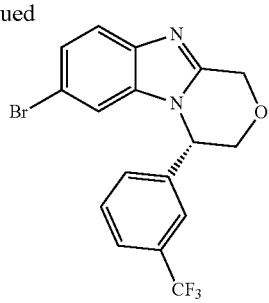

The reaction sequence was performed from 5-(3-(trifluoromethylphenyl)morpholin-3-one (Preparation #78) in a similar fashion to Preparation #24 to give the title compound (0.857 g, 58% over 2 steps); LC/MS (Table 1, Method i) $R_t$=0.76 min; MS m/z: 397, 399 (M+H)$^+$.

Preparation #80

(S)-2-Bromo-8-cyclohexyl-7,8-dihydro-6H-pyrrolo[2',1':2,3]imidazo[4,5-b]pyridine and (R)-2-bromo-8-cyclohexyl-7,8-dihydro-6H-pyrrolo[2',1':2,3]imidazo[4,5-b]pyridine

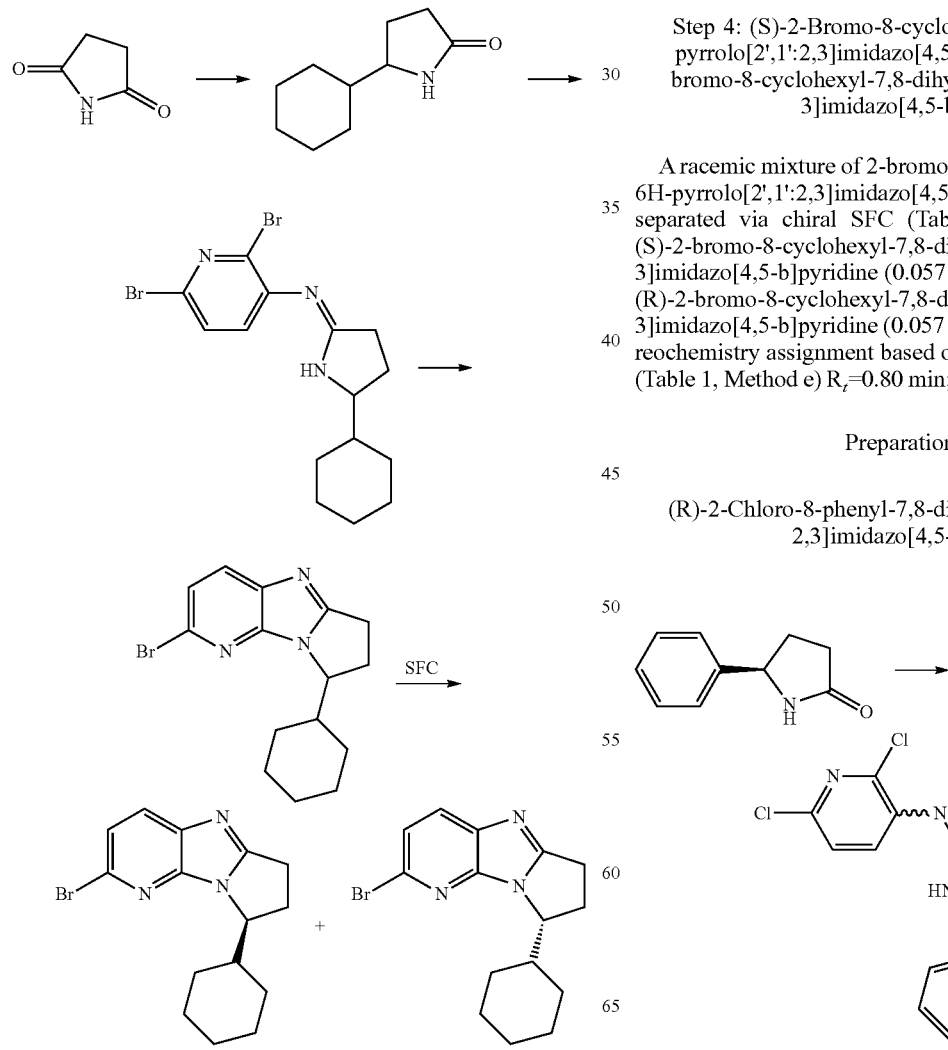

Step 1: 5-Cyclohexylpyrrolidin-2-one

A solution of pyrrolidine-2,5-dione (2.5 g, 25.2 mmol) in dry DCM (60 mL) was cooled to −78° C. cyclohexylmagnesium bromide (63.1 mL, 63.1 mmol, 1M in THF) was added. After about 5 min, the dry-ice bath was removed and the resulting mixture was stirred for about 18 h at rt. Sodium cyanotrihydroborate (1.903 g, 30.3 mmol) was added followed by a slow addition of 6M HCl solution to keep the pH between 3 and 4. After about 1 h, the reaction was neutralized with 4N NaOH and extracted with DCM (3×50 mL). The combined organic layers were washed with excess water (45 mL) and then with brine (35 mL), dried over Na$_2$SO$_4$, filtered, and concentrated under reduced pressure to give crude title compound (1.49 g); LC/MS (Table 1, Method e) $R_t$=0.71 min; MS m/z: 168 (M+H)$^+$ Steps 2 & 3: 2-bromo-8-cyclohexyl-7,8-dihydro-6H-pyrrolo[2',1':2,3]imidazo[4,5-b]pyridine The reaction was performed from 5-cyclohexylpyrrolidin-2-one with 2,6-dibromopyridin-3-amine in a similar fashion to Preparation #4, step 1 to give the crude title compound (0.326 g, 63%); LC/MS (Table 1, Method e) $R_t$=0.81 min; MS m/z: 320, 322 (M+H)$^+$ Step 4: (S)-2-Bromo-8-cyclohexyl-7,8-dihydro-6H-pyrrolo[2',1':2,3]imidazo[4,5-b]pyridine and (R)-2-bromo-8-cyclohexyl-7,8-dihydro-6H-pyrrolo[2',1':2,3]imidazo[4,5-b]pyridine A racemic mixture of 2-bromo-8-cyclohexyl-7,8-dihydro-6H-pyrrolo[2',1':2,3]imidazo[4,5-b]pyridine (0.212 g) was separated via chiral SFC (Table 2, Method 1) to give (S)-2-bromo-8-cyclohexyl-7,8-dihydro-6H-pyrrolo[2',1':2,3]imidazo[4,5-b]pyridine (0.057 g, 27%, OR=negative) and (R)-2-bromo-8-cyclohexyl-7,8-dihydro-6H-pyrrolo[2',1':2,3]imidazo[4,5-b]pyridine (0.057 g, 27%, OR=positive) [Stereochemistry assignment based on optical rotation]; LC/MS (Table 1, Method e) $R_t$=0.80 min; MS m/z: 320, 322 (M+H)$^+$ Preparation #81

(R)-2-Chloro-8-phenyl-7,8-dihydro-6H-pyrrolo[2',1':2,3]imidazo[4,5-b]pyridine

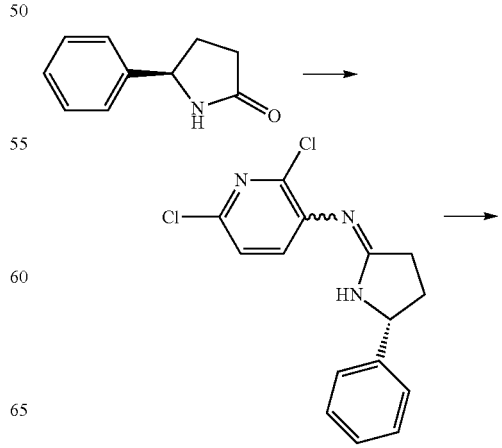

167

-continued

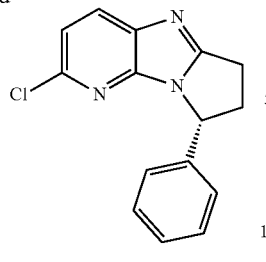

Step 1: (R,Z)-2,6-Dichloro-N-(5-phenylpyrrolidin-2-ylidene)pyridin-3-amine (R)-5-Phenylpyrrolidin-2-one (15.0 g, 93 mmol, Preparation #44) was suspended in toluene (460 mL) under nitrogen. The mixture was stirred at rt for about 30 min then cooled to about 0° C. $POCl_3$ (11.5 mL, 123 mmol) was added dropwise over about 2 min. After completion of addition the mixture was allowed to warm to rt. After about 90 min 2,6-dichloropyridin-3-amine (15.5 g, 95 mmol) was added in one portion then the mixture was warmed to about 110° C. After about 90 min, the reaction mixture was allowed to cool to rt and concentrated under reduced pressure to afford a brown solid. The residue was dissolved in DCM (600 mL) and washed successively with 2 N NaOH (300 mL), water (100 mL) and then sat. NaCl (300 mL). The aqueous layers were extracted with DCM (300 mL). The combined organic layers were dried over $Na_2SO_4$, filtered and concentrated to give the title compound (27.2 g, 95%); LC/MS (Table 1, Method z) $R_t$=0.89 min; MS m/z: 306 $(M+H)^+$.

Step 2: (R)-2-Chloro-8-phenyl-7,8-dihydro-6H-pyrrolo[2',1':2,3]imidazo[4,5-b]pyridine To a mixture of (R,Z)-2,6-dichloro-N-(5-phenylpyrrolidin-2-ylidene)pyridin-3-amine (28.5 g, 93 mmol), $K_2CO_3$ (19.4 g, 140 mmol), and CuI (1.77 g, 9.29 mmol) was added MeCN (500 mL) and DMEA (2.00 mL, 18.56 mmol). The mixture was evacuated then back-filled with $N_2$ three times. The reaction mixture was warmed to about 80° C. for about 14 h then cooled to rt. DCM (500 mL) was added. The mixture was filtered through Celite® rinsing the pad with DCM (500 mL). The filtrate was concentrated under reduced pressure to afford a solid. The residue was dissolved in DCM (500 mL) then washed with water (3×300 mL) then sat. NaCl (300 mL). The aqueous layers were extracted with DCM (100 mL). The combined organic layers were dried over $Na_2SO_4$, filtered, and concentrated to afford a solid which was triturated with $Et_2O$ (100 mL) for about 42 h. The solid was collected by filtration and washed with $Et_2O$ (50 mL). The solid was dried in a vacuum oven at about 50° C. to give the title compound (18.8 g, 73%); LC/MS (Table 1, Method z) $R_t$=1.30 min; MS m/z: 270 $(M+H)^+$.

168

Preparation #82

(S)-2-Chloro-8-(3-methoxyphenyl)-7,8-dihydro-6H-pyrrolo[2',1':2,3]imidazo[4,5-b]pyridine and (R)-2-chloro-8-(3-methoxyphenyl)-7,8-dihydro-6H-pyrrolo[2',1':2,3]imidazo[4,5-b]pyridine

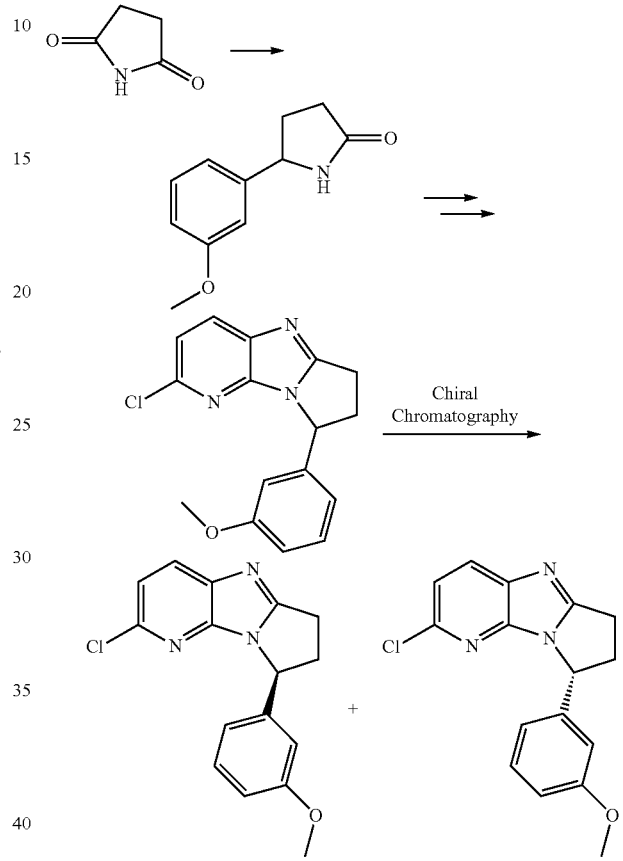

Step 1: 5-(3-Methoxyphenyl)pyrrolidin-2-one

The title compound was synthesized in a manner similar to Preparation #80, step 1 from pyrrolidine-2,5-dione and (3-methoxyphenyl)magnesium bromide; $^1$H NMR (400 MHz, $CDCl_3$) δ 7.60-7.40 (1, 1H), 6.70-6.50 (m, 3H), 6.45 (bs, 1H), 4.75 (t, J=6.6 Hz, 1H), 3.75 (s, 3H), 2.60-2.35 (m, 3H), 2.00-1.85 (m, 1H).

Step 2: 2-Chloro-8-(3-methoxyphenyl)-7,8-dihydro-6H-pyrrolo[2,1':2,3]imidazo[4,5-b]pyridine The title compound was synthesized in a manner similar to Preparation #81, steps 1 and 2 from 5-(3-methoxyphenyl)pyrrolidin-2-one and 2,6-dichloropyridin-3-amine; LC/MS (Table 1, Method z) $R_t$=1.26 m in; MS m/z: 300 $(M+H)^+$.

Step 3: (S)-2-Chloro-8-(3-methoxyphenyl)-7,8-dihydro-6H-pyrrolo[2',1':2,3]imidazo[4,5-b]pyridine and (R)-2-chloro-8-(3-methoxyphenyl)-7,8-dihydro-6H-pyrrolo[2',1':2,3]imidazo[4,5-b]pyridine A racemic mixture of 2-chloro-8-(3-methoxyphenyl)-7,8-dihydro-6H-pyrrolo[2',1':2,3]imidazo[4,5-b]pyridine (0.42 g) was separated via chiral chromatography (Table 2, Method 15) to give (S)-2-chloro-8-(3-methoxyphenyl)-7,8-dihydro-6H-pyrrolo[2',1':2,3]imidazo[4,5-b]pyridine (0.156 g, 350) and (R)-2-chloro-8-(3-methoxyphenyl)-7,8-dihydro-6H-pyrrolo[2,1':2,3]imidazo[4,5-b]pyridine (0.154 g, 35%) [Stereochemistry assignment based on TNFα activity of derivatives]; LC/MS (Table 1, Method z) $R_t$=1.26 min; MS m/z: 300 (M+H)⁺.

Preparation #83

(S)-2-Chloro-8-(2-methoxyphenyl)-7,8-dihydro-6H-pyrrolo[2',1':2,3]imidazo[4,5-b]pyridine and (R)-2-chloro-8-(2-methoxyphenyl)-7,8-dihydro-6H-pyrrolo[2',1':2,3]imidazo[4,5-b]pyridine

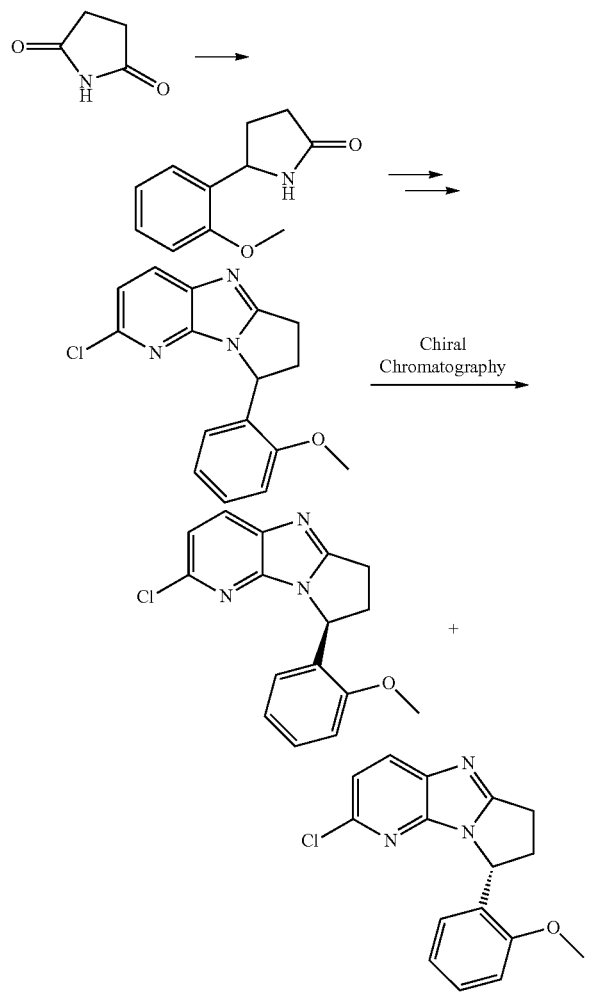

Step 1: 5-(2-Methoxyphenyl)pyrrolidin-2-one

The title compound was synthesized in a manner similar to Preparation #80, step 1 from pyrrolidine-2,5-dione and (2-methoxyphenyl)magnesium bromide; LC/MS (Table 1, Method v) $R_t$=1.56 min; MS m/z: 192 (M+H)⁺.

Step 2: 2-Chloro-8-(2-methoxyphenyl)-7,8-dihydro-6H-pyrrolo[2',1':2,3]imidazo[4,5-b]pyridine The title compound was synthesized in a manner similar to Preparation #81, steps 1 and 2 from 5-(2-methoxyphenyl)pyrrolidin-2-one and 2,6-dichloropyridin-3-amine; LC/MS (Table 1, Method v) $R_t$=2.17 min; MS m/z: 300 (M+H)⁺.

Step 3: (S)-2-Chloro-8-(2-methoxyphenyl)-7,8-dihydro-6H-pyrrolo[2',1':2,3]imidazo[4,5-b]pyridine and (R)-2-chloro-8-(2-methoxyphenyl)-7,8-dihydro-6H-pyrrolo[2',1':2,3]imidazo[4,5-b]pyridine A racemic mixture of 2-chloro-8-(2-methoxyphenyl)-7,8-dihydro-6H-pyrrolo[2',1':2,3]imidazo[4,5-b]pyridine (1.53 g) was separated via chiral chromatography (Table 2, Method 16) to give (S)-2-chloro-8-(2-methoxyphenyl)-7,8-dihydro-6H-pyrrolo[2',1':2,3]imidazo[4,5-b]pyridine (0.55 g, 26%, OR=negative) and (R)-2-chloro-8-(2-methoxyphenyl)-7,8-dihydro-6H-pyrrolo[2',1':2,3]imidazo[4,5-b]pyridine (0.58 g, 27%, OR=positive) [Stereochemistry assignment based on TNFα activity of derivatives]; LC/MS (Table 1, Method v) $R_t$=2.17 min; MS m/z: 300 (M+H)⁺.

Preparation #84

(R)-2-(2-Fluoropyridin-4-yl)-8-phenyl-7,8-dihydro-6H-pyrrolo [2',1':2,3]imidazo[4,5-b]pyridine

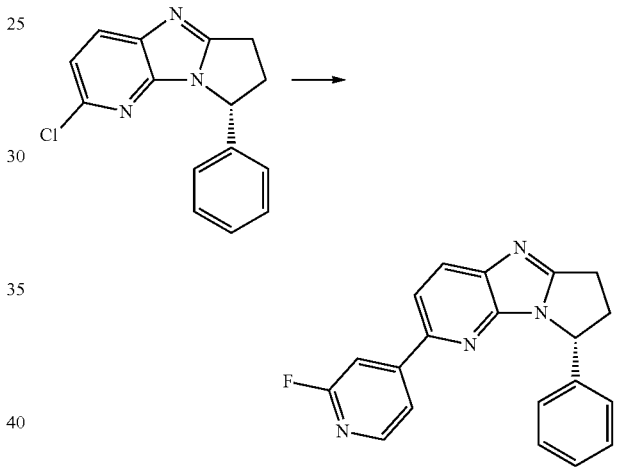

A solution of (R)-2-chloro-8-phenyl-7,8-dihydro-6H-pyrrolo[2',1':2,3]imidazo[4,5-b]pyridine (1 g, 3.71 mmol, Preparation #81), $Cs_2CO_3$ (3.02 g, 9.27 mmol) and $PdCl_2(PPh_3)_2$ (0.26 g, 0.371 mmol) in water (12.50 mL) and 1,4-dioxane (25 mL) was degassed with $N_2$ and heated at about 85° C. overnight. The mixture was cooled to rt, and the organic layer was filtered through a silica gel pad, rinsing with 1,4-dioxane. The filtrate was concentrated under reduced pressure and purified via chromatography eluting with 40-100% EtOAc/heptanes to give the title compound (1.13 g, 92%); LC/MS (Table 1, Method y) $R_t$=0.90 min; MS m/z: 331 (M+H)⁺.

Preparation #85

2'-Bromo-6',8'-dihydro-2H-spiro[benzofuran-3,9'-pyrido[3',2':4,5]imidazo[2,1-c][1,4]oxazine]

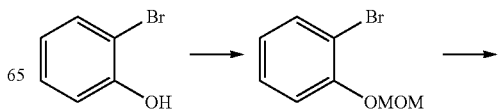

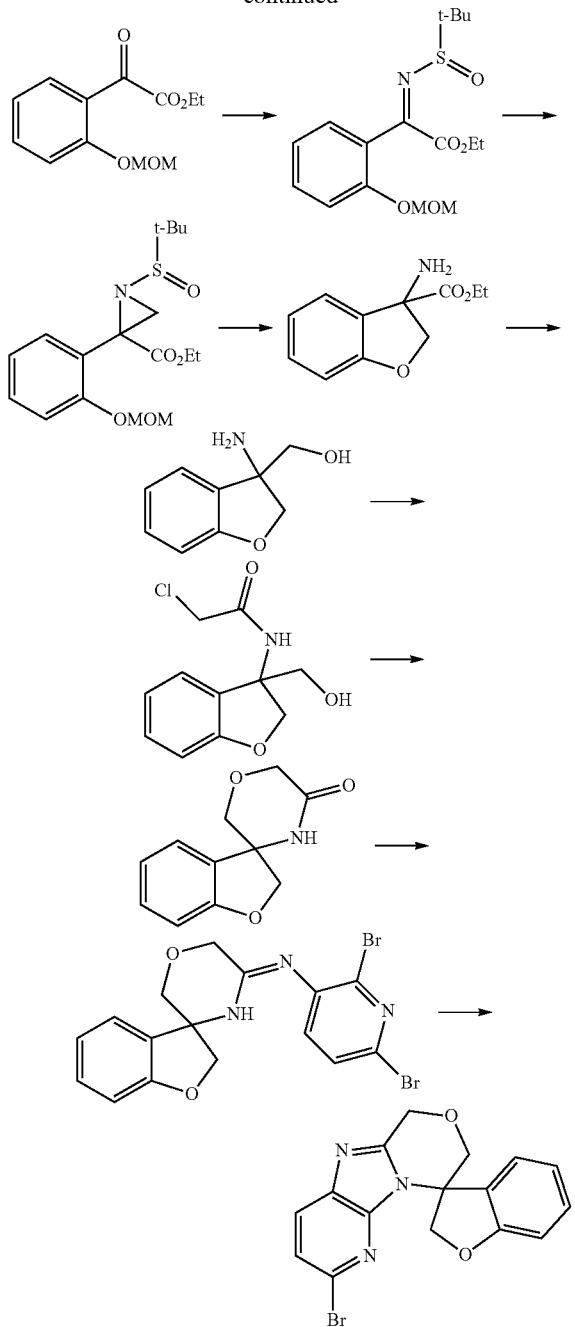

concentrated under reduced pressure to give the title compound (840 g, 83.5%), which was used for next step without further purification. ¹H NMR (400 MHz, CDCl₃) δ 7.55 (d, J=7.5 Hz, 1H), 7.29-7.20 (m, 1H), 7.18-7.11 (m, 1H), 6.89 (t, J=7.5 Hz, 1H), 5.25 (s, 2H), 3.52 (s, 3H).

Step 2: Ethyl 2-(2-(methoxymethoxy)phenyl)-2-oxoacetate

To a solution of 1-bromo-2-(methoxymethoxy)benzene (100 g, 461 mmol) in anhydrous THF (1.5 L) was added n-butyllithium (221 mL, 2.5 M in hexane, 553 mmol) dropwise at −70° C. The mixture was stirred for 1 h. A solution of diethyl oxalate (101 g, 691 mmol) in THF (400 mL) was added dropwise. The mixture was further stirred for 1 h. The reaction was quenched with aq NH₄Cl. Seven additional vials were set up as described above and treated respectively. The mixture were combined and extracted with EtOAc (4×2 L). The organic phases were dried over anhydrous Na₂SO₄ and concentrated under reduced pressure to get a residue, which was purified by column chromatography on silica gel (petroleum ether/EtOAc=I/O to 20/1) to give the title compound (460 g, 55.6%); ¹H NMR (400 MHz, CDCl₃) δ 7.90 (dd, J=1.8, 7.8 Hz, 1H), 7.62-7.53 (m, 1H), 7.21 (d, J=8.4 Hz, 1H), 7.13 (t, J=7.5 Hz, 1H), 5.21 (s, 2H), 4.40 (q, J=7.2 Hz, 2H), 3.49 (s, 3H), 1.41 (t, J=7.2 Hz, 3H).

Step 3: (Z)-Ethyl 2-((tert-butylsulfinyl)imino)-2-(2-(methoxymethoxy)phenyl)acetate To a solution of ethyl-2-(2-(methoxymethoxy)phenyl)-2-oxoacetate (110 g, 491 mmol) in anhydrous THF (770 mL) was added tetraethoxytitanium (224 g, 981 mmol) and 2-methylpropane-2-sulfinamide (71.4 g, 589 mmol). The mixture was stirred at 65° C. until completion. Three additional vials were set up as described above. After cooling rt, all four mixtures were combined and diluted with EtOAc (2 L). The mixture was then poured into a stirring solution of brine (2 L) and vigorously stirred for 15 min. The resulting heterogeneous mixture was filtered through a Celite® pad and washed with EtOAc. The filtrate was transferred to a separatory funnel, the organic layer was separated and the aqueous layer was extracted twice with EtOAc (2×1 L). The combined organic layers were washed with water (3×500 mL) and brine (3×500 mL), dried over MgSO₄, filtered and concentrated under reduced pressure to get a residue, which was purified by column chromatography on silica gel (10:1 petroleum ether/EtOAc) to afford the title compound (340 g, 59.3%); ¹H NMR (400 MHz, CDCl₃) δ 7.82 (d, J=7.5 Hz, 1H), 7.45 (t, J=7.3 Hz, 1H), 7.17 (d, J=8.4 Hz, 1H), 7.07 (t, J=7.5 Hz, 1H), 5.22-5.09 (m, 2H), 4.49-4.29 (m, 2H), 3.47 (s, 3H), 1.41 (t, J=7.3 Hz, 3H), 1.35 (s, 9H).

Step 4: Ethyl 1-(tert-butylsulfinyl)-2-(2-(methoxymethoxy)phenyl)aziridine-2-carboxylate To a mixture of NaH (19.91 g, 498 mmol) and DMSO (615 mL) was added trimethylsulfoxonium iodide (108 g, 498 mmol) in 3 portions over 15 min. The resulting suspension was stirred for 1 h, after which it becomes a clear, homogeneous solution of dimethylsulfoxonium methylide. A solution of (Z)-ethyl 2-((tert-butylsulfinyl)imino)-2-(2-(methoxymethoxy)phenyl)acetate (85 g, 249 mmol) in anhydrous toluene (700 mL) was cooled to 0° C. (ice-water bath). Then the pre-made methylide solution was added via cannula dropwise over 5 min. The mixture was quenched with the addition of sat. NH₄Cl (1 L) and allowed to warm to rt.

Step 1: 1-Bromo-2-(methoxymethoxy)benzene

To a suspension of NaH (27.7 g, 694 mmol) in THF (1.5 L) was added 2-bromophenol (100 g, 578 mmol) dropwise at 0° C. The mixture was allowed to warm up to 20° C. and stirred for 0.5 h. The mixture was re-cooled to 0° C. and chloro(methoxy)methane (55.8 g, 694 mmol) was added dropwise. The resulting mixture was left to warm to 20° C. and stirred for 3 h. Seven additional vials were set up as described above. All the eight mixtures were combined and quenched with aq NaOH (10%, 2 L) and the solvent was removed under reduced pressure. The residue was extracted with 2-methoxy-2-methylpropane (4×2 L) and the organic layer was washed with H₂O, brine, dried over Na₂SO₄ and After transferring to a separatory funnel, the aqueous layer was extracted with EtOAc (3×800 mL). The combined organic layers were washed with water (3×500 mL) and brine (500 mL), dried over MgSO$_4$, filtered and concentrated under reduced pressure. Three additional vials were set up and treated as described above. All the crude mixtures were combined and purified by column chromatography on silica gel (5:1 petroleum ether/EtOAc) to afford the title compound (250 g, 70.6%); $^1$H NMR (400 MHz, CDCl$_3$) δ 7.40 (d, J=7.5 Hz, 1H), 7.31-7.23 (m, 1H), 7.09 (d, J=8.4 Hz, 1H), 6.99 (t, J=7.5 Hz, 1H), 5.21-5.12 (m, 2H), 4.25-4.12 (m, 2H), 3.45 (s, 3H), 3.41 (s, 1H), 2.20 (s, 1H), 1.28 (s, 9H), 1.27-1.22 (m, 3H).

Step 5: Ethyl 3-amino-2,3-dihydrobenzofuran-3-carboxylate

To a solution of ethyl 1-(tert-butylsulfinyl)-2-(2-(methoxymethoxy)phenyl)aziridine-2-carboxylate (50 g, 141 mmol) in EtOH (471 mL) was added HCl in 1,4-dioxane (175 mL, 4 M). The resulting mixture was heated to 70° C. for 3 h. The mixture was cooled to rt and concentrated under reduced pressure. The crude product was suspended in MeCN (2.026 L) and treated with K$_2$CO$_3$ (97 g, 703 mmol) and NaI (4.22 g, 28.1 mmol). Note: the mixture pH≈8. The resulting mixture was heated to 75° C. for 10 h. After cooling to rt, the mixture was filtered and washed with EtOAc (1 L). The filtrate was concentrated under reduced pressure to get a residue, which was re-dissolved in EtOAc, washed with water and brine, dried over MgSO$_4$, filtered and concentrated to give the crude product. Three additional vials were set up and treated as described above. All the crude product was combined and purified by column chromatography on silica gel (10:1 petroleum ether/EtOAc) to give the title compound (96 g, 65.8%); $^1$H NMR (400 MHz, CDCl$_3$) δ7.36-7.27 (m, 2H), 7.04-6.85 (m, 2H), 5.09 (d, J=9.3 Hz, 1H), 4.39 (d, J=9.7 Hz, 1H), 4.35-4.22 (m, 2H), 2.18 (br. s., 2H), 1.31 (t, J=7.1 Hz, 3H).

Step 6: (3-Amino-2,3-dihydrobenzofuran-3-yl)methanol

To a solution of ethyl 3-amino-2,3-dihydrobenzofuran-3-carboxylate (32 g, 154 mmol) in anhydrous THF (1 L) was added lithium aluminium hydride (11.72 g, 309 mmol) in portions at 0° C. The mixture was stirred at 20° C. for 8 h. Water (11.7 mL) was added slowly followed by 15% NaOH (11.7 mL) and water (35 mL). Three additional vials were set up and treated as described above. All the four mixtures were combined, filtered through a Celite® pad and washed with EtOH. The filtrates were combined and concentrated under reduced pressure to get a residue, which was purified by column chromatography on silica gel (50:1 DCM/MeOH) to give the title compound (32 g, 41.3%); $^1$H NMR (400 MHz, CDCl$_3$) δ 7.27-7.17 (m, 2H), 6.95-6.85 (m, 1H), 6.83-6.72 (m, 1H), 4.53 (d, J=9.7 Hz, 1H), 4.16 (d, J=9.7 Hz, 1H), 3.73-3.61 (m, 2H).

Step 7: 2-Chloro-N-(3-(hydroxymethyl)-2,3-dihydrobenzofuran-3-yl)acetamide

To a solution of 3-amino-2,3-dihydrobenzofuran-3-yl)methanol (10.6 g, 64.2 mmol) in anhydrous THF (300 mL) was added TEA (19.48 g, 193 mmol). Then a solution of 2-chloroacetyl chloride (6.52 g, 57.8 mmol) in THF (20 mL) was added dropwise at 0° C. The resulting mixture was stirred for 2 h. The reaction was quenched with water (500 mL) and extracted with EtOAc (3×300 mL). Three additional vials were set up and treated as described above. All the organic layers were combined, washed with brine (2×200 mL), dried over Na$_2$SO$_4$ and concentrated under reduced pressure to get a residue, which was purified by column chromatography on silica gel (80:1 DCM/MeOH) to give the title compound (30 g, 64%); $^1$H NMR (400 MHz, CDCl$_3$) δ 7.32-7.23 (m, 2H), 7.00-6.86 (m, 2H), 4.79-4.73 (m, 1H), 4.70-4.63 (m, 1H), 4.11-3.97 (m, 4H)

Step 8: 2H-Spiro[benzofuran-3,3'-morpholin]-5'-one

To a solution of 2-chloro-N-(3-(hydroxymethyl)-2,3-dihydrobenzofuran-3-yl)acetamide (15 g, 62.1 mmol) in anhydrous THF (300 mL) was added sodium hydride (6.21 g, 155 mmol) in portions at −10° C. The mixture was stirred for 20 mins. The reaction was quenched with water (100 mL). One additional vial was set up as described above. Both reaction mixtures were combined and extracted with EtOAc (3×300 mL). The organic layers were washed with brine, dried over Na$_2$SO$_4$ filtered and concentrated under reduced pressure to get a residue, which was purified by column chromatography on silica gel (1/1 to I/O petroleum ether/EtOAc) to give the title compound (11 g, 43.1%); $^1$H NMR (400 MHz, CDCl$_3$) δ 7.29-7.20 (m, 2), 6.94 (t, J=7.5 Hz, 1H), 6.83 (d, J=8.4 Hz, 1H), 6.42 (br. s., 1H), 4.71 (d, J=9.7 Hz, 1H), 4.33-4.27 (m, 1H), 4.23 (d, J=10.1 Hz, 2H), 3.89 (d, J=11.9 Hz, 1H), 3.69 (d, J=11.9 Hz, 1H)

Step 9: (Z)-2,6-Dibromo-N-(2H-spiro[benzofuran-3,3'-morpholin]-5'-ylidene)pyridin-3-amine A solution of 2H-spiro[benzofuran-3,3'-morpholin]-5'-one (5.5 g, 26.8 mmol) in 1,2-dichloroethane (55 mL) was treated with POCl$_3$ (4.93 g, 32.2 mmol) in 1,2-dichloroethane (55 mL). Then the mixture was stirred for 5 min. To the above solution was added 2,6-dibromopyridin-3-amine (10.13 g, 40.2 mmol) and the reaction was heated to 70° C. After 2 h, the reaction was monitored by LCMS. Another additional vial was set up as described above. After cooling to rt, the two reaction mixtures were combined and then transferred to a separatory funnel with DCM. The organic layer was washed with water and brine, dried with Na$_2$SO$_4$, filtered and concentrated to give crude product (24 g). The crude product was used directly in the next step reaction. LC/MS (Table 1, Method ad) R$_t$=2.31 min; MS m/z: 437.9 (M+H)$^+$

Step 10: 2'-Bromo-6',8'-dihydro-2H-spiro[benzofuran-3,9'-pyrido[3',2':4,5]imidazo[2,1-c][1,4]oxazine]

To a solution of (Z)-2,6-dibromo-N-(2H-spiro[benzofuran-3,3'-morpholin]-5'-ylidene)pyridin-3-amine (12 g, 27.3 mmol) in MeCN (81 mL) and DMSO (27 mL) was added K$_2$CO$_3$ (5.67 g, 41.0 mmol), N1,N1,N2,N2-tetramethylethane-1,2-diamine (1.588 g, 13.66 mmol) and CuI (0.781 g, 4.10 mmol). The mixture was heated to 75° C. for 10 h under nitrogen atmosphere. One additional vial was set up as described above. After cooling to rt, both reaction mixtures were combined and concentrated to remove the MeCN. To the residual mixture was added water (100 mL) with stirring. After 10 min, the formed solid was filtered. The filter cake was dissolved in DCM, washed with brine, then dried over Na$_2$SO$_4$, filtered and concentrated under reduced pressure to get a residue, which was further purified by prep-HPLC (Table 2, Method 19) to give the title compound (4.6 g, 24%); $^1$H NMR (400 MHz, DMSO-d$_6$) δ 7.97 (d, J=8.4 Hz, 1H), 7.39 (d, J=8.4 Hz, 1H), 7.33-7.27 (m, 1H), 7.20 (d, J=6.6 Hz, 1H), 6.99 (d, J=7.9 Hz, 1H), 6.84 (t, J=7.5 Hz, 1H), 5.22-5.04 (m, 2H), 5.00 (d, J=10.1 Hz, 1H), 4.69 (d, J=10.6 Hz, 1H), 4.34-4.20 (m, 2H).

Preparation #86

2'-Bromo-6',8'-dihydrospiro[chroman-4,9'-pyrido[3', 2':4,5]imidazo[2,1-c][1,4]oxazine]

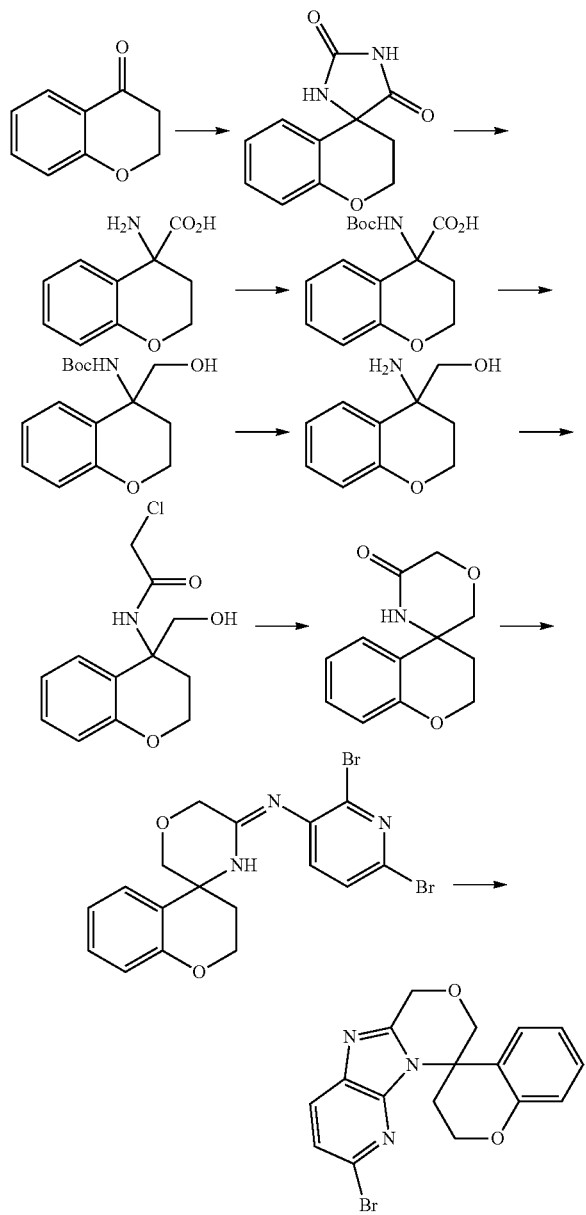

Step 1: Spiro[chroman-4,4'-imidazolidine]-2',5'-dione

To a solution of chroman-4-one (20 g, 135 mmol) in EtOH (150 mL) and water (150 mL) was added (NH$_4$)$_2$CO$_3$ (51.9 g, 540 mmol) and KCN (13.18 g, 202 mmol) at 20° C. The mixture was heated to 65° C. for 48 h. Three additional vials were set up as described above. All four reaction mixtures were combined and concentrated to 150 mL and then filtered. The solid was dried under reduced pressure to give the title compound (80 g, 50.3%); $^1$H NMR (400 MHz, DMSO-d$_6$) δ 10.96 (br, 1H), 8.57 (s, 1H), 7.22-7.19 (t, J=6.8, 7.6 Hz, 1H), 7.05-7.04 (d, J=7.2 Hz, 1H), 6.93-6.91 (t, J=7.6, 7.2 Hz, 1H), 6.84-6.82 (d, J=8.4 Hz, 1H), 4.49-4.45 (m, 1H), 4.19-4.14 (m, 1H), 2.27-2.23 (m, 1H), 2.11-2.09 (m, 1H).

Steps 2 and 3:
4-((tert-Butoxycarbonyl)amino)chroman-4-carboxylic acid

To a solution of spiro[chroman-4,4'-imidazolidine]-2',5'-dione (20 g, 92 mmol) in water (140 mL) was added KOH (36.0 g, 642 mmol) at 20° C. The mixture was heated to 120° C. for 3 days. The mixture was cooled to 30° C. and di-tert-butyl dicarbonate (40.0 g, 183 mmol) was added to the above solution. The mixture was stirred at 30° C. for 12 h. Then the mixture was acidified by the addition of 4 N HCl (186 mL) with stirring. Three additional vials were set up as described above. All four reaction mixtures were combined and transferred to a separatory funnel with DCM and water. The combined organic phases were concentrated under reduced pressure to get a residue. The residue was taken up in MTBE (560 mL) and shaken with 1 N NaOH (1.5 L). The organic phase was discarded. The aqueous phase was washed with an additional portion of MBTE. The remaining aqueous phase was acidified with 1 M HCl (1.8 L) and extracted with DCM (2×500 mL). The organic phases were combined, dried over Na$_2$SO$_4$, filtered and concentrated under reduced pressure to get the title compound (90 g, 84%); $^1$H NMR (400 MHz, DMSO-d$_6$) δ 12.83 (br. s., 1H), 7.47-7.45 (d, J=6.6 Hz, 2H), 7.19-7.16 (m, 1H), 6.88-6.84 (t, J=7.5 Hz, 1H), 6.78-6.76 (d, J=8.4 Hz, 1H), 4.25-4.24 (m, 1H), 4.10-4.06 (m, 1H), 2.55 (m 1H), 2.37-2.32 (m, 1H), 1.37 (s, 9H).

Step 4: tert-Butyl (4-(hydroxymethyl)chroman-4-yl)carbamate

To a solution of 4-((tert-butoxycarbonyl)amino)chroman-4-carboxylic acid (25 g, 85 mmol) in anhydrous THF (625 mL) was added lithium aluminum hydride (7.12 g, 188 mmol) below −5° C. After the addition, the mixture was stirred at 35° C. for 12 h. Then the reaction mixture was carefully quenched with water (7.12 mL), 15% NaOH aqueous (7.12 mL) and then water (21.36 mL). Three additional vials were set up as described above. All four reaction mixtures were combined, filtered and concentrated under reduced pressure to get a crude product, which was purified by silica gel flash column chromatography (2-20% EtOAc/petroleum ether) to get the title compound (56 g, 65.1%); $^1$H NMR (400 MHz, DMSO-d$_6$) δ 7.21-7.19 (d, J=7.7 Hz, 1H), 7.06-7.02 (m, 1H), 6.81-6.78 (t, J=7.2 Hz, 1H), 6.69-6.67 (d, J=8.1 Hz, 1H), 6.62 (br. s., 1H), 5.03 (br. s., 1H), 4.20-4.07 (m, 2H), 3.59-3.32 (m, 2H), 2.60-2.51 (m, 1H), 2.02-1.97 (m, 1H), 1.39-1.02 (m, 9H).

Step 5: (4-Aminochroman-4-yl)methanol

To a solution of tert-butyl (4-(hydroxymethyl)chroman-4-yl)carbamate (28 g, 100 mmol) in MBTE (560 mL) was added MeOH (32.4 mL, 802 mmol) and acetyl chloride (10.63 mL, 200 mmol) below 0° C. The resulting mixture was stirred at 20° C. for 12 h. One additional vial was set up as described above. Both reaction mixtures were combined and filtered. The filter cake was dried in vacuo to give the title compound (19 g, 52.9%); $^1$H NMR (400 MHz, DMSO-$d_6$) δ 8.66 (s, 2H), 7.70-7.68 (d, J=8 Hz, 1H), 7.27-7.23 (m, 1H), 6.98-6.94 (t, J=7.6 Hz, 1H), 6.85-6.83 (d, J=8 Hz, 1H), 5.88-5.85 (t, J=5.2 Hz, 1H), 4.30-4.27 (m, 1H), 4.20-4.17 (m, 1H), 3.80-3.71 (m, 2H), 2.36-2.32 (m, 1H), 2.08-2.02 (m, 1H).

Step 6: 2-Chloro-N-(4-(hydroxymethyl)chroman-4-yl)acetamide

To a solution of (4-aminochroman-4-yl)methanol (19 g, 106 mmol) in anhydrous THF (475 mL) was added TEA (44.3 mL, 318 mmol) and 2-chloroacetyl chloride (11.02 g, 98 mmol) below −5° C. After the addition, the mixture was stirred at 25° C. for 2 h. The mixture was diluted with water (500 mL) and extracted with EtOAc (3×300 mL). The organic layers were dried over $Na_2SO_4$, filtered and concentrated under reduced pressure to get a residue, which was purified by silica gel flash column chromatography (5-30% EtOAc/petroleum ether) to givet the title compound (16 g, 59.0%); $^1$H NMR (400 MHz, DMSO-$d_6$) δ 8.14 (s, 1H), 7.26-7.11 (d, J=7.6 Hz, 1H), 7.09-7.07 (m, 1H), 6.84-6.81 (t, J=7.2 Hz, 1H), 6.74-6.72 (d, J=8.4 Hz, 1H), 5.27-5.24 (t, J=5.6 Hz, 1H), 4.20-4.17 (m, 2H), 4.07 (s, 2H), 3.70-3.69 m, 2H), 2.60-2.54 (m, 1H), 2.08-2.03 (m, 1H).

Step 7: Spiro[chroman-4,3'-morpholin]-5'-one

To a solution of 2-chloro-N-(4-(hydroxymethyl)chroman-4-yl)acetamide (16 g, 62.6 mmol) in anhydrous THF (480 mL), at below −5° C. was added sodium hydride (6.26 g, 156 mmol). Then the mixture was stirred at 25° C. for 1 h. The mixture was quenched below 0° C. with water (500 mL) and extracted with MBTE (3×500 mL). The organic layer was washed with brine (1 L) and dried over $Na_2SO_4$, filtered and concentrated under reduced pressure to get a solid, which was taken up in MBTE, scratched and sonicated then heated to 50° C. After cooling to rt, the mixture was filtered and the filter cake was dried in vacuo to get the title compound (12 g, 87%); $^1$H NMR (400 MHz, DMSO-$d_6$) δ 8.36 (s, 1H), 7.39-7.36 (m, 1H), 7.18-7.16 (m, 1H), 6.95-6.93 (m, 1H), 6.79-6.77 (m, 1H), 4.23-4.05 (m, 4H), 3.94-3.91 (d, J=11.5 Hz, 1H), 3.75-3.72 (d, J=11.9 Hz, 1H), 2.18-2.10 (m, 2H).

Step 8: (Z)-2,6-Dibromo-N-(spiro[chroman-4,3'-morpholin]-5'-ylidene)pyridin-3-amine To a solution of $POCl_3$ (2.04 mL, 21.89 mmol) in 1,2-dichloroethane (80 mL) was added spiro[chroman-4,3'-morpholin]-5'-one (4 g, 18.25 mmol) at 20° C. After stirring for 5 min, 2,6-dibromopyridin-3-amine (5.52 g, 21.89 mmol) was added and the reaction was heated to 70° C. for 2 h. Two additional vials were set up as described above. All three reaction mixtures were combined and cooled to rt. The mixture was filtered and washed with 1,2-dichloroethane (20 mL), then transferred to a separatory funnel with DCM (300 mL). The organic phase was washed with water (300 mL) and brine (300 mL), dried over $Na_2SO_4$, filtered and concentrated under reduced pressure to get the title compound (24 g, 97%), which was used directly for next step without further purification. $^1$H NMR (400 MHz, DMSO-$d_6$) δ 10.16 (s, 1H), 7.93-7.87 (m, 2H), 7.56-7.53 (d, J=7.5 Hz, 1H), 7.26-7.22 (t, J=7.3 Hz, 1H), 7.00-6.98 (t, J=7.3 Hz, 1H), 6.83-6.81 (d, J=7.9 Hz, 1H), 4.98 (s, 1H), 4.29-3.94 (m, 5H), 2.31-2.11 (m, 2H).

Step 9: 2'-Bromo-6',8'-dihydrospiro[chroman-4,9'-pyrido[3',2':4,5]imidazo[2,1-c][1,4]oxazine]

To a solution of (Z)-2,6-dibromo-N-(spiro[chroman-4,3'-morpholin]-5'-ylidene)pyridin-3-amine (8 g, 17.66 mmo) and KOAc (2.079 g, 21.19 mmol) in MeCN (96 mL) and DMSO (24 mL) was added N1,N1,N2,N2-tetramethylethane-1,2-diamine (1.026 g, 8.83 mmol) and CuI (0.336 g, 1.766 mmol) at 20° C. under $N_2$. Then the mixture was heated to 75° C. for 12 h. Two additional vials were set up as described above. All three mixtures were combined. MeCN was removed and to the DMSO solution was added water (300 mL) with stirring. After 10 min, the solid was filtered. The solid was dissolved in DCM (300 mL), washed with brine, then dried over $Na_2SO_4$, filtered and concentrated to get the crude product, which was purified by silica gel flash column chromatography (20-50% EtOAc/petroleum ether) to give the title compound (5.34 g, 25.7%); $^1$H NMR (400 MHz, DMSO-$d_6$) δ 7.97-9.95 (d, J=8.1 Hz, 1H), 7.36-7.34 (d, J=8.3 Hz, 1H), 7.20-7.16 (t, J=7.6 Hz, 1H), 6.91-6.89 (d, J=8.3 Hz, 1H), 6.81-6.79 (m, 1H), 6.75-6.73 (m, 1H), 5.21-5.07 (m, 2H), 4.45-4.42 (d, J=12.1 Hz, 2H), 4.37-4.32 (m, 1H), 4.14-4.11 (d, J=12.3 Hz, 1H), 2.98-2.91 (dt, J=4.1, 13.0 Hz, 1H), 2.34-2.31 (d, J=13.8 Hz, 1H).

Preparation #87

2'-(2-Fluoropyridin-4-yl)-6',8'-dihydro-2H-spiro[benzofuran-3,9'-pyrido[3',2':4,5]imidazo[2,1-c][1,4]oxazine]

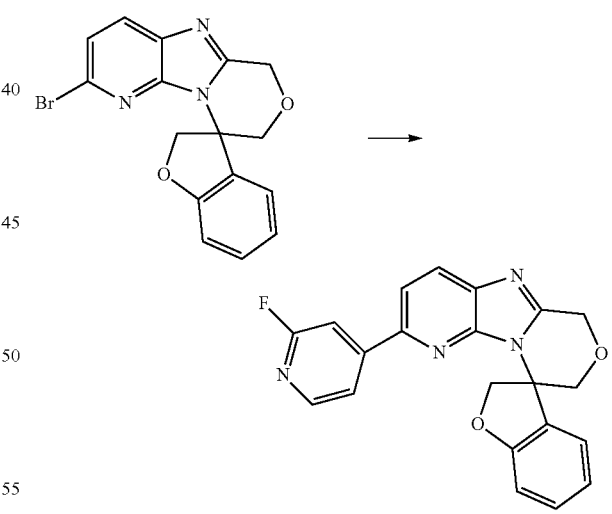

A round bottom flask under nitrogen was charged with 2'-bromo-6',8'-dihydro-2H-spiro[benzofuran-3,9'-pyrido[3',2':4,5]imidazo[2,1-c][1,4]oxazine](1 g, 2.79 mmol, Preparation #85), (2-fluoropyridin-4-yl)boronic acid (0.433 g, 3.07 mmol), $Cs_2CO_3$ (2.00 g, 6.14 mmol) and bis(triphenylphosphine)palladium(II)dichloride (0.196 g, 0.279 mmol) in a mixture of 1,4-dioxane and water. Then the yellowish reaction mixture was degased for 10 min by a flow of nitrogen. Next the reaction was heated in an oil bath to 85° C. After 7 h reaction was cooled then diluted with about 100 mL of EtOAc. The organic layer was washed with water and brine, dried over MgSO$_4$, filtered and evaporated under reduced pressure to provide a solid. The solid was triturated with MeOH affording a solid which was separated by filtration to give the title compound (0.75 g, 70%); LC/MS (Table 1, Method i) R$_t$=0.89 min; MS m/z: 375 (M+H)$^+$.

Preparation #88

(R)-2-Chloro-3-fluoro-8-phenyl-7,8-dihydro-6H-pyrrolo[2',1':2,3]imidazo[4,5-b]pyridine

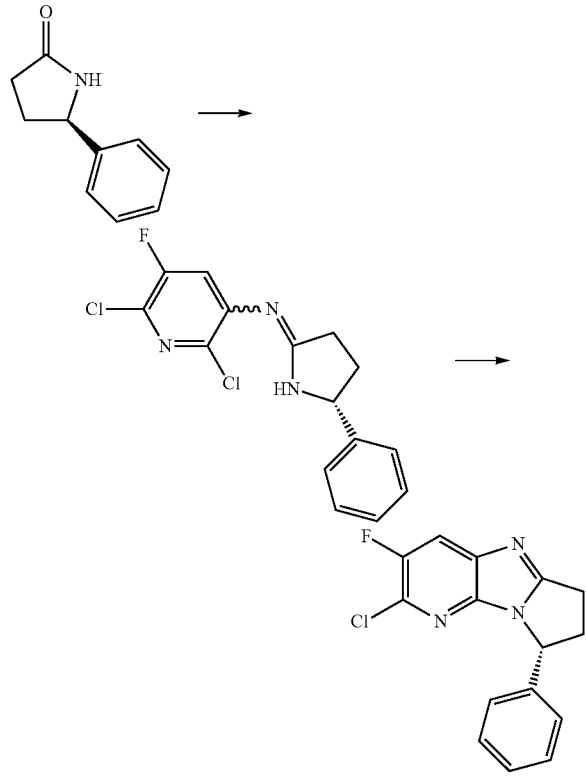

The reaction was performed from (R)-5-phenylpyrrolidin-2-one (Preparation #44) with 2,6-dichloro-5-fluoropyridin-3-amine (ArkPharm) in a similar fashion to Preparation #4, step 1 to give the crude title compound (1.0 g, 60%); LC/MS (Table 1, Method i) R$_t$=0.88 min; MS m/z: 288 (M+H)$^+$.

Preparation #89

2-(6-(2-Morpholinopyrimidin-5-yl)imidazo[1,2-b]pyridazin-2-yl)ethanol

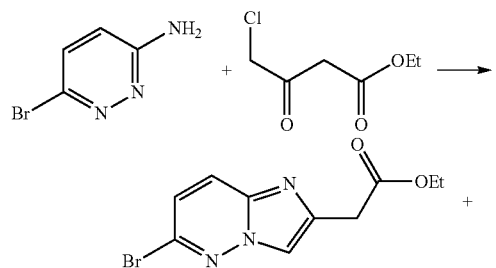

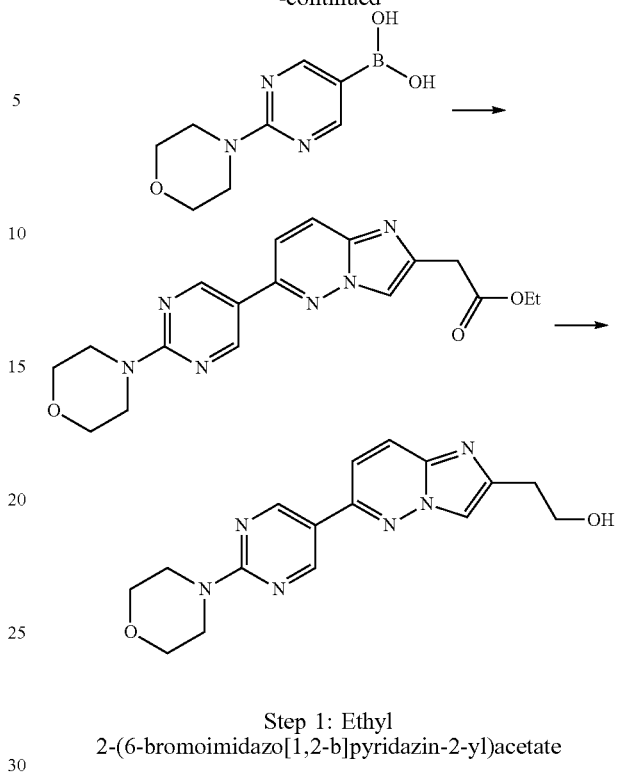

Step 1: Ethyl 2-(6-bromoimidazo[1,2-b]pyridazin-2-yl)acetate

A solution of ethyl 4-chloro-3-oxobutanoate (1.99 g, 811.49 mmol) and 6-bromopyridazin-3-amine (1.0 g, 6.90 mmol, PharmaBlock) in EtOH (15 mL) was heated in a microwave at 120° C. for 2 h. The reaction was concentrated under reduced pressure. The residue was dissolved in EtOAc (about 250 mL) and washed with water, sat. sodium bicarbonate, and then brine. The organics were collected, dried over MgSO$_4$, filtered and concentrated under reduced pressure. The residue was purified by column chromatography on silica (EtOAc/heptane 0-50%) to give the title compound (1.06 g, 65%) LC/MS (Table 1, Method i) R$_t$=0.73 min; MS m/z: 284, 286 (M+H)$^+$.

Step 2: Ethyl 2-(6-(2-morpholinopyrimidin-5-yl) imidazo[1,2-b]pyridazin-2-yl)acetate To a microwave tube were added (2-morpholinopyrimidin-5-yl)boronic acid (0.730 g, 3.49 mmol, ArkPharm), ethyl 2-(6-bromoimidazo[1,2-b]pyridazin-2-yl)acetate (1.141 g. 4.02 mmol), 1,4-dioxane (15 mL) and water (2 mL). Na$_2$CO$_3$ (1.111 g. 10.48 mmol) was added followed by Pd(dppf)Cl$_2$ (0.285 g, 0.349 mmol). The tube was degassed with N$_2$ and heated in a microwave at 100° C. for about 70 min. The reaction mixture was filtered through Celite® washing with excess EtOAc (150 mL). The collected organic layer was washed twice with water, then extracted with 5N HCl (3×100 mL). The combined acid extract was washed with EtOAc (100 mL) then chilled in an ice bath and slowly neutralized with 5N NaOH (pH between about 7-9). The resulting slurry was filtered and washed with ice water (200 mL), dried under vacuum to afford the title compound. LC/MS (Table 1, Method i) R$_t$=0.73 min; MS m/z: 369 (M+H)$^+$ Step 3: 2-(6-(2-Morpholinopyrimidin-5-yl)imidazo [1,2-b]pyridazin-2-yl)ethanol To a solution of ethyl 2-(6-(2-morpholinopyrimidin-5-yl) imidazo[1,2-b]pyridazin-2-yl)acetate (0.100 g, 0.271 mmol)

in THF (1.5 mL) was added 0.5M lithium chloride (0.35 mL, 0.175 mmol) in THF, 1.0M diethylzinc (0.05 mL, 0.050 mmol) in hexanes, and poly(methylhydrosiloxane) (0.05 mL, Fluka). The resulting mixture was stirred for 3 h at ambient temperature, then quenched with 1.5N NaOH (20 mL, 30 mmol). Add THF (10 mL), and stirred overnight at ambient temperature. EtOAc (100 mL) was added and the organic layer was washed with water, brine and dried over Na$_2$SO$_4$, filtered and concentrated under reduced pressure. The residue was purified by column chromatography on silica gel eluting with a gradient of 0-10% MeOH/DCM. LC/MS (Table 1, Method i) R$_t$=0.62 min; MS m/z: 327 (M+H)$^+$ Preparation #90

7-Bromo-4-phenyl-3,4-dihydro-2H-pyrano[2',3':4,5]imidazo[1,2-a]pyridine

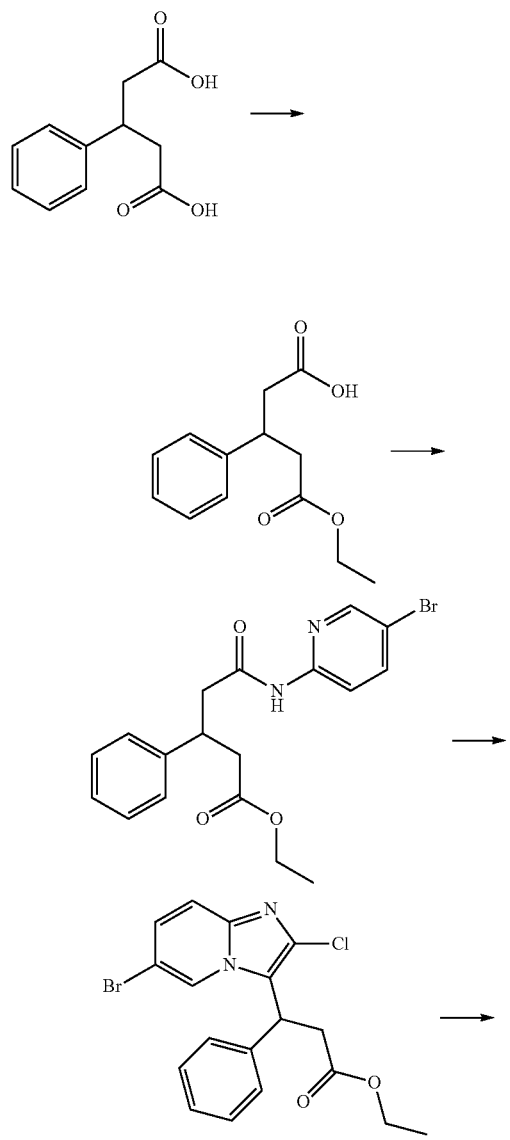

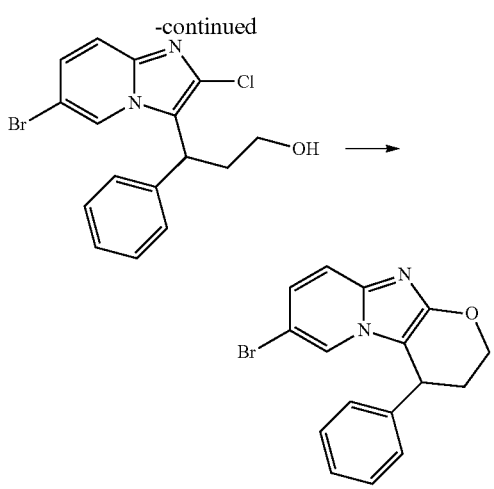

Step 1: 5-Ethoxy-5-oxo-3-phenylpentanoic acid

3-Phenylglutaric acid (4.00 g, 19.21 mmol) was suspended in acetic anhydride (80 mL, 848 mmol), and the reaction mixture was refluxed for 3 h. The yellow solution was concentrated under reduced pressure to afford 3-phenylglutaric anhydride as an oil which solidified upon cooling. This was dissolved in EtOH (120 mL, 2055 mmol), TEA (12 mL, 86 mmol) was added, and the yellow solution was stirred overnight at ambient temperature. The residue was concentrated to an oil, and chromatographed on Grace Reveleris 120 g column with 0-50% EtOAc in 1:1 DCM:heptane (70 mL/min) to give the title compound (4.25 g, 94%); $^1$H NMR (400 MHz, CDCl$_3$) δ 7.37-7.29 (m, 2H), 7.28-7.21 (m, 3H), 4.06 (q, J=7.1 Hz, 2H), 3.66 (p, J=7.5 Hz, 1H), 2.84-2.61 (m, 4H), 1.17 (t, J=7.1 Hz, 3H). MS (ESI+) m/z: 236.9 (M+H)$^+$.

Step 2: Ethyl 5-((5-bromopyridin-2-yl)amino)-5-oxo-3-phenylpentanoate

To a solution of 5-ethoxy-5-oxo-3-phenylpentanoic acid (1.064 g, 4.50 mmol) in DCM (25 mL), a few drops of DMF was added, then oxalyl chloride (1.2 mL, 13.71 mmol) was added dropwise, and the solution was stirred for 2.5 h at ambient temperature. The yellow solution was concentrated to an oil, and dissolved in DCM (25 mL). 5-Bromopyridin-2-amine (0.857 g, 4.95 mmol), TEA (1.0 mL, 7.17 mmol), and catalytic 4-dimethylaminopyridine were added, and the yellow mixture was stirred for 30 min at ambient temperature. EtOAc (200 mL) was added, the mixture was washed with 1N HCl (2×200 mL), sat. NaHCO$_3$ (2×200 mL), and brine, and dried over Na$_2$SO$_4$. Chromatographed on a Grace Reveleris 120 g column, eluted with 0-50% EtOAc in 1:1 DCM:Heptane (70 mL/min). The title compound was obtained (0.552 g, 31.3%); $^1$H NMR (400 MHz, CDCl$_3$) δ 8.29 (d, J=2.4 Hz, 1H), 8.11 (d, J=8.9 Hz, 1H), 7.97 (s, 1H), 7.77 (dd, J=8.9, 2.4 Hz, 1H), 7.37-7.21 (m, 5H), 4.08 (qt, J=7.2, 1.1 Hz, 2H), 3.76 (p, J=7.3 Hz, 1H), 2.84 (ddd, J=20.7, 15.0, 7.0 Hz, 2H), 2.72 (ddd, J=14.7, 7.7, 2.6 Hz, 2H), 1.18 (td, J=7.2, 0.9 Hz, 3H). MS (ESI+) m/z: 391.0 (M+H)$^+$.

Step 3: Ethyl 3-(6-bromo-2-chloroimidazo[1,2-a]pyridin-3-yl)-3-phenylpropanoate

To a solution of ethyl 5-((5-bromopyridin-2-yl)amino)-5-oxo-3-phenylpentanoate (1.384 g, 3.54 mmol) in CHCl$_3$ (23 mL), thionyl chloride (1.14 mL, 15.62 mmol) was added, followed by pyridine (0.60 mL, 7.42 mmol). The yellow solution was heated at 100° C. for 2 h in a sealed vial. EtOAc (200 mL) was added, the mixture was washed with sat. NaHCO$_3$ and brine, and dried over Na$_2$SO$_4$ then concentrated to an oil, chromatographed on Grace Reveleris 120 g column with 0-50% EtOAc in 1:1 DCM:heptane (70 mL/min) affording title compound (0.764 g, 53.0%); $^1$H NMR (400 MHz, DMSO-d$_6$) δ 8.83 (dd, J=1.8, 0.9 Hz, 1H), 7.49 (dd, J=9.5, 0.8 Hz, 1H), 7.41 (dd, J=9.5, 1.8 Hz, 1H), 7.35-7.25 (m, 4H), 7.23-7.17 (m, 1H), 5.16 (dd, J=9.9, 6.6 Hz, 1H), 3.92 (q, J=7.1 Hz, 2H), 3.42 (dd, J=16.3, 9.9 Hz, 1H), 3.35-3.24 (m, 1H), 0.97 (t, J=7.1 Hz, 3H). MS (ESI+) m/z: 409.0 (M+H)$^+$.

Step 4: 3-(6-Bromo-2-chloroimidazo[1,2-a]pyridin-3-yl)-3-phenylpropan-1-ol

To a solution of ethyl 3-(6-bromo-2-chloroimidazo[1,2-a]pyridin-3-yl)-3-phenylpropanoate (0.764 g, 1.874 mmol) in THF (8 mL) was added 0.5M lithium chloride (0.90 mL, 0.450 mmol) in THF, 1.0 M diethylzinc (0.13 mL, 0.130 mmol) in hexanes, and poly(methylhydrosiloxane (0.65 mL). The resulting mixture was stirred for 3 h at ambient temperature. The solution was quenched with 1.5 N NaOH (40 mL, 60 mmol), THF (30 mL) was added, and the mixture stirred overnight at ambient temperature. Added 150 mL EtOAc, washed with water and brine, and dried over Na$_2$SO$_4$, affording the crude title compound (0.764 g, 111%); $^1$H NMR (400 MHz, DMSO-d$_6$) δ 8.65-8.60 (m, 1H), 7.49 (dd, J=9.5, 0.7 Hz, 1H), 7.38 (dd, J=9.5, 1.8 Hz, 1H), 7.38-7.29 (m, 2H), 7.31-7.24 (m, 2H), 7.21-7.14 (m, 1H), 4.77 (dd, J=9.0, 7.0 Hz, 1H), 4.56 (t, J=5.0 Hz, 1H), 3.46-3.34 (m, 1H), 3.34-3.24 (m, 1H), 2.53-2.41 (m, 1H), 2.37-2.23 (m, 1H). MS (ESI+) m/z: 367.1 (M+H)$^+$.

Step 5: 7-Bromo-4-phenyl-3,4-dihydro-2H-pyrano[2',3':4,5]imidazo[1,2-a]pyridine

To a solution of 3-(6-bromo-2-chloroimidazo[1,2-a]pyridin-3-yl)-3-phenylpropan-1-ol (750 mg, 2.05 mmol) in THF (12 mL) was added 1.0 M potassium tert-butoxide (1.5 mL, 1.500 mmol) in THF. The brown mixture was heated for 30 min at 100° C. in a sealed vial. Water (200 mL) was added, extracted twice with EtOAc (100 mL), washed with brine, and dried over Na$_2$SO$_4$. The residue was purified on a Grace Reveleris 40 g column with 0-100% EtOAc in 1:1 DCM:heptane (40 mL/min). Obtained title compound (0.353 g, 52.3%); $^1$H NMR (501 MHz, DMSO-d$_6$) δ 7.67 (dd, J=1.9, 0.8 Hz, 1H), 7.42 (dd, J=9.4, 0.8 Hz, 1H), 7.37-7.31 (m, 2H), 7.30-7.24 (m, 2H), 7.12-7.06 (m, 2H), 4.53 (t, J=5.6 Hz, 1H), 4.27 (ddd, J=11.2, 6.3, 2.9 Hz, 1H), 4.12 (ddd, J=11.3, 9.0, 2.5 Hz, 1H), 2.47-2.40 (m, 1H), 2.00-1.93 (m, 1H). MS (ESI+) m/z 329.1 (M+H). LC/MS (Table 1, AB) R$_t$=0.83 min; MS m/z: 328.9 (M+H)$^+$.

Preparation #91

7-Bromo-4-(2-methoxyphenyl)-3,4-dihydro-2H-pyrano[2',3':4,5]imidazo[1,2-a]pyridine

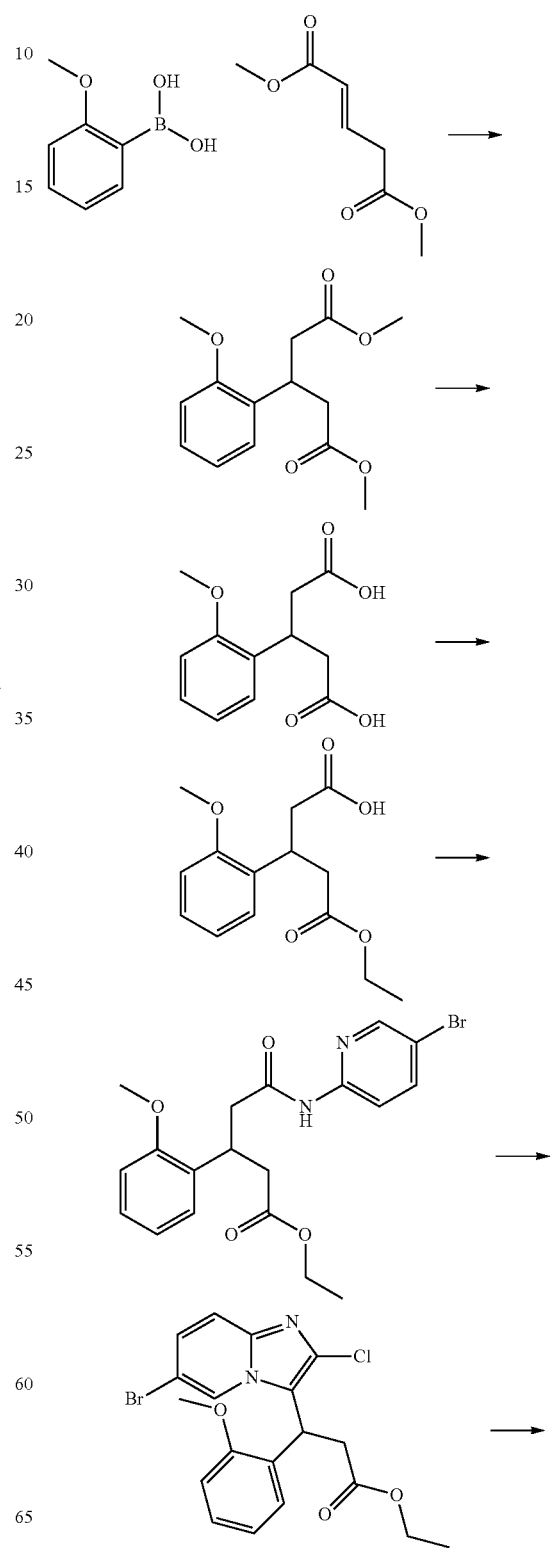

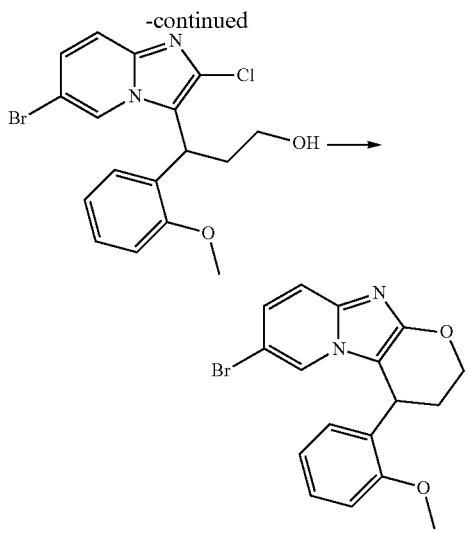

Step 1: Dimethyl 3-(2-methoxyphenyl)pentanedioate

To a solution of (2-methoxyphenyl)boronic acid (8.10 g, 53.3 mmol) and chloro(1,5-cyclooctadiene)rhodium(I) dimer (0.526 g, 1.066 mmol) in 1,4-dioxane (90 mL) and degassed water (15 mL) was added TEA (4.95 mL, 35.5 mmol) and dimethyl glutaconate (5 mL, 35.5 mmol). The orange solution was heated at 50° C. for 3 days. The mixture was quenched with 300 mL 1.0 M citric acid, extracted with 300 mL MTBE, washed with brine, and dried over $Na_2SO_4$. The residue was purified on a Grace Reveleris 220 g column, eluted with 0-100% DCM/heptane, then 0-100% EtOAc/DCM (70 mL/min), affording the title compound (4.69 g, 49.6%); $^1$H NMR (501 MHz, $CDCl_3$) δ 7.22 (ddd, J=8.2, 7.4, 1.8 Hz, 1H), 7.18 (dd, J=7.6, 1.7 Hz, 1H), 6.91 (td, J=7.5, 1.1 Hz, 1H), 6.88 (dd, J=8.2, 1.2 Hz, 1H), 3.93 (p, J=7.4 Hz, 1H), 3.86 (s, 3H), 3.62 (s, 6H), 2.80 (d, J=7.3 Hz, 4H). MS (DCI+) m/z: 284 $(M+NH_4)^+$.

Step 2: 3-(2-Methoxyphenyl)pentanedioic acid

To a solution of dimethyl 3-(2-methoxyphenyl)pentanedioate (4.69 g, 17.61 mmol) in EtOH (50 mL) was added a solution of KOH (2.075 g, 37.0 mmol) in EtOH (50 mL) and water (10 mL). The solution was refluxed overnight. Additional KOH (2.075 g, 37.0 mmol) and water (10 mL) were added, and refluxed for 2 h. The reaction volume was concentrated, acidified with 1N HCl (90 mL), extracted twice with EtOAc (200 mL), washed with brine, and dried over $Na_2SO_4$ affording title compound (3.82 g, 91%); $^1$H NMR (400 MHz, DMSO-$d_6$) δ 12.06 (s, 2H), 7.17-7.11 (m, 2H), 6.92 (dd, J=8.1, 1.0 Hz, 1H), 6.83 (td, J=7.5, 1.2 Hz, 1H), 3.75 (s, 3H), 3.70 (p, J=7.3 Hz, 1H), 2.59-2.48 (m, 4H). MS (ESI−) m/z: 237 (M−H)$^+$.

Step 3: 5-Ethoxy-3-(2-methoxyphenyl)-5-oxopentanoic acid 3-(2-Methoxyphenyl)pentanedioic acid (3.82 g, 16.03 mmol) was suspended in acetic anhydride (80 mL, 848 mmol), and the reaction mixture was refluxed for 3 h. The solution was concentrated under reduced pressure to afford 3-(2-methoxyphenyl)glutaric anhydride as a liquid. This was dissolved in EtOH (100 mL, 1713 mmol), TEA (11 mL, 79 mmol) was added, and the mixture was stirred for 3 days at ambient temperature. The product was concentrated to an oil, and chromatographed on Grace Reveleris 120 g column with 0-50% EtOAc in 1:1 DCM/heptane (70 mL/min) to afford the title compound (2.81 g, 65.8%); $^1$H NMR (400 MHz, DMSO-$d_6$) δ 12.03 (s, 1H), 7.21-7.10 (m, 2H), 6.97-6.90 (m, 1H), 6.84 (td, J=7.5, 1.1 Hz, 1H), 3.91 (q, J=7.1 Hz, 2H), 3.81-3.68 (m, 4H), 2.61 (d, J=7.4 Hz, 2H), 2.56 (d, J=7.4 Hz, 2H), 1.03 (t, J=7.1 Hz, 3H). MS (ESI+) m/z: 267 (M+H)$^+$.

Step 4: Ethyl 5-((5-bromopyridin-2-yl)amino)-3-(2-methoxyphenyl)-5-oxopentanoate To a solution of 5-ethoxy-3-(2-methoxyphenyl)-5-oxopentanoic acid (3.624 g, 13.61 mmol) in DCM (60 mL), a few drops of DMF was added, then oxalyl chloride (5.0 mL, 57.1 mmol) was added dropwise, and the solution was stirred for 3 h at ambient temperature. The solution was concentrated to an oil, and dissolved in DCM (30 mL). The acid chloride solution was added to a suspension of 5-bromopyridin-2-amine (2.59 g, 14.97 mmol), TEA (4.0 mL, 28.7 mmol), and 4-dimethylaminopyridine (0.17 g, 1.392 mmol) in DCM (50 mL), and the solution was stirred overnight at ambient temperature. EtOH (50 mL) and hydrazine hydrate (1.5 mL, 30.8 mmol) were added and the mixture was stirred for 30 min at ambient temperature. Added DCM (200 mL), washed with 1N HCl (2×300 mL), sat $NaHCO_3$ (2×300 mL), and dried over $Na_2SO_4$. The residue was purified on a Grace Reveleris 120 g column, eluted with 0-50% EtOAc in 1:1 DCM/heptane (70 mL/min) to afford title compound (3.04 g, 53.0%); $^1$H NMR (501 MHz, DMSO-$d_6$) δ 10.58 (s, 1H), 8.38 (dd, J=2.5, 0.8 Hz, 1H), 8.01-7.96 (m, 1H), 7.93 (dd, J=8.9, 2.5 Hz, 1H), 7.19-7.12 (m, 2H), 6.92 (dd, J=8.3, 1.1 Hz, 1H), 6.84 (td, J=7.4, 1.2 Hz, 1H), 3.94-3.86 (m, 3H), 3.76 (s, 3H), 2.79-2.69 (m, 2H), 2.68-2.59 (m, 2H), 1.02 (t, J=7.1 Hz, 3H). MS (ESI+) m/z: 423 (M+H)$^+$.

Step 5: Ethyl 3-(6-bromo-2-chloroimidazo[1,2-a]pyridin-3-yl)-3-(2-methoxyphenyl)propanoate To a solution of ethyl 5-((5-bromopyridin-2-yl)amino)-3-(2-methoxyphenyl)-5-oxopentanoate (2.785 g, 6.611 mmol) in $CHCl_3$ (64 mL), thionyl chloride (1.86 mL, 25.48 mmol) was added, followed by pyridine (1.12 mL, 13.85 mmol). The solution was heated at 100° C. for 2 h in a sealed vial. 300 mL EtOAc was added, the mixture was washed with sat. $NaHCO_3$ and brine, and dried over $Na_2SO_4$. The residue was concentrated to an oil, purified on a Grace Reveleris 120 g column with 0-50% EtOAc in 1:1 DCM/heptane (70 mL/min), affording the title compound (1.670 g, 57.7%); $^1$H NMR (501 MHz, DMSO-$d_6$) δ 8.72 (dd, J=2.0, 0.9 Hz, 1H), 7.48 (dd, J=9.5, 0.8 Hz, 1H), 7.44-7.40 (m, 2H), 7.24-7.19 (m, 1H), 6.97-6.91 (m, 2H), 5.17 (dd, J=10.4, 6.0 Hz, 1H), 3.93 (q, J=7.1 Hz, 2H), 3.63 (s, 3H), 3.47 (dd, J=16.5, 10.4 Hz, 1H), 3.23 (dd, J=16.4, 6.1 Hz, 1H), 0.98 (t, J=7.1 Hz, 3H). MS (ESI+) m/z: 439 (M+H)$^+$.

Step 6: 3-(6-Bromo-2-chloroimidazo[1,2-a]pyridin-3-yl)-3-(2-methoxyphenyl)propan-1-ol To a solution of ethyl 3-(6-bromo-2-chloroimidazo[1,2-a]pyridin-3-yl)-3-(2-methoxyphenyl)propanoate (1.67 g, 3.82 mmol) in THF (20 mL) was added 0.5M lithium chloride (2.0 mL, 1.000 mmol) in THF, 1.0M diethylzinc (0.3 mL, 0.300 mmol) in hexanes, and poly(methylhydrosiloxane) (1.5 mL). The resulting mixture was stirred for 4 h at ambient temperature. The solution was quenched with 3N NaOH (40 mL, 120 mmol), THF (60 mL) and water (20 mL) were added, and the solution stirred overnight at ambient temperature. 200 mL EtOAc were added, the mixture was washed with water and brine, and dried over $Na_2SO_4$, to afford the crude title compound (2.25 g, 149%); $^1$H NMR (400 MHz, DMSO-$d_6$) δ 8.56 (dd, J=2.0, 0.9 Hz, 1H), 7.46 (dd, J=9.5, 0.8 Hz, 1H), 7.42 (dd, J=7.6, 1.7 Hz, 1H), 7.38 (dd, J=9.5, 1.8 Hz, 1H), 7.18 (td, J=7.8, 1.7 Hz, 1H), 6.97-6.89 (m, 2H), 4.90 (dd, J=9.7, 6.3 Hz, 1H), 4.55 (t, J=5.0 Hz, 1H), 3.65 (s, 3H), 3.44-3.35 (m, 1H), 3.27-3.19 (m, 1H), 2.53-2.42 (m, 1H), 2.31-2.18 (m, 1H). MS (ESI+) m/z: 397 (M+H)$^+$.

Step 7: 7-Bromo-4-(2-methoxyphenyl)-3,4-dihydro-2H-pyrano[2',3':4,5]imidazo[1,2-a]pyridine To a solution of 3-(6-bromo-2-chloroimidazo[1,2-a]pyridin-3-yl)-3-(2-methoxyphenyl)propan-1-ol (2.09 g, 5.28 mmol) in THF (28 mL) was added 1.0M potassium tert-butoxide (22.6 mL, 22.6 mmol) in THF. The brown mixture was heated for 1 h at 100° C. in a sealed vial. 300 mL water was added, extracted twice with 100 mL EtOAc, washed with brine, and dried over $Na_2SO_4$. The residue was purified on a Grace Reveleris 120 g column with 0-100% EtOAc in 1:1 DCM/heptane (70 mL/min) to afford the title compound (1.024 g, 54.0%); $^1$H NMR (501 MHz, DMSO-$d_6$) δ 7.71 (dd, J=1.9, 0.8 Hz, 1H), 7.42 (dd, J=9.4, 0.8 Hz, 1H), 7.30-7.23 (m, 2H), 7.09 (dd, J=8.3, 1.1 Hz, 1H), 6.79 (td, J=7.5, 1.1 Hz, 1H), 6.47 (dd, J=7.5, 1.7 Hz, 1H), 4.71 (dd, J=6.3, 3.6 Hz, 1H), 4.26 (ddd, J=11.2, 4.9, 3.1 Hz, 1H), 3.98 (td, J=10.9, 2.2 Hz, 1H), 3.87 (s, 3H), 2.36 (dddd, J=14.1, 10.4, 6.3, 3.1 Hz, 1H), 1.99 (dddd, J=14.3, 4.9, 3.7, 2.3 Hz, 1H); LC/MS (Table 1, ab) $R_t$=0.89 min; MS m/z: 359, 361 (M+H)$^+$.

Preparation #92

2'-Bromo-2,3,6',8'-tetrahydrospiro[indene-1,9'-pyrido[3',2':4,5]imidazo[2,1-c][1,4]oxazine]

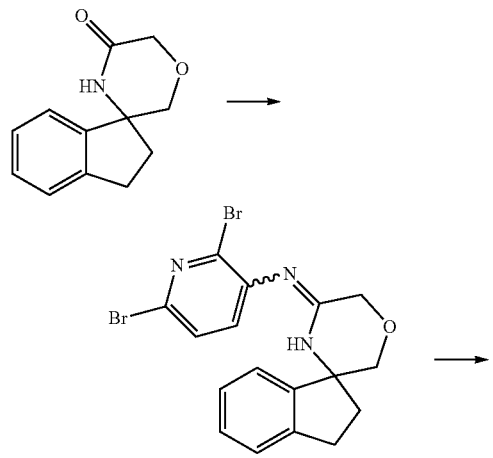

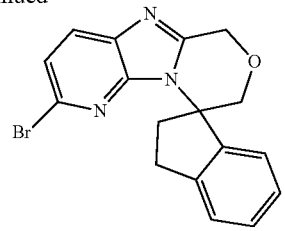

The reaction sequence was performed from 2,3-dihydrospiro[indene-1,3'-morpholin]-5'-one (Preparation #33) in a similar fashion to Preparation #56 to give the title compound (48% crude over 2 steps); LC/MS (Table 1, Method f) $R_t$=0.84 min; MS m/z: 355, 357 (M+H)$^+$. $^1$H NMR (400 MHz, DMSO-$d_6$) δ 7.94 (d, J=8.4 Hz, 1H), 7.40-7.31 (m, 2H), 7.28 (td, J=7.3, 1.3 Hz, 1H), 7.16-7.02 (m, 2H), 5.12 (q, J=16.1 Hz, 2H), 4.12 (d, J=12.1 Hz, 1H), 3.99 (d, J=12.0 Hz, 1H), 3.40-3.34 (m, 1H), 3.16-3.01 (m, 1H), 2.84 (dt, J=13.6, 8.6 Hz, 1H), 2.41 (ddd, J=12.9, 8.6, 3.7 Hz, 1H).

Preparation #93

7-(2-Fluoropyridin-4-yl)-4-(2-methoxyphenyl)-3,4-dihydro-2H-pyrano [2',3':4,5]imidazo[1,2-a]pyridine

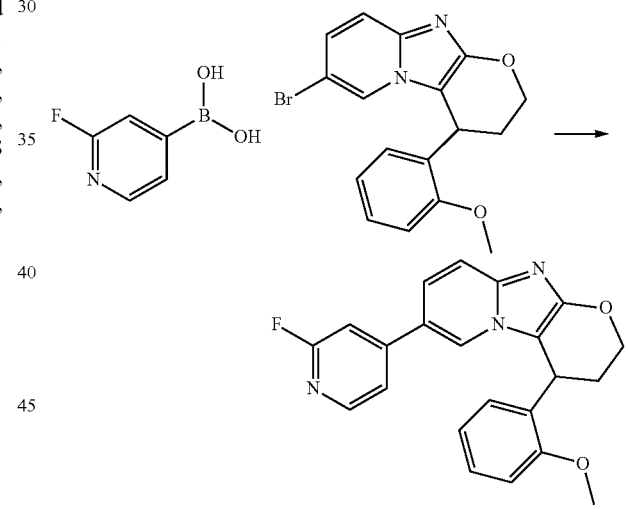

7-Bromo-4-(2-methoxyphenyl)-3,4-dihydro-2H-pyrano [2',3':4,5]imidazo[1,2-a]pyridine (445 mg, 1.239 mmol, Preparation #91), (2-fluoropyridin-4-yl)boronic acid (209 mg, 1.487 mmol), $PdCl_2(PPh_3)_2$ (87 mg, 0.124 mmol), and $Cs_2CO_3$ (1009 mg, 3.10 mmol) were flushed with $N_2$, 1,4-dioxane (10 mL) and water (2 mL) were added, and the mixture was heated at 85° C. for 1.5 h. 200 mL EtOAc was added, the solution was washed with 100 mL water, and dried over $Na_2SO_4$. The residue was purified on a Grace Reveleris 40 g column, eluted with 0-100% 3:1 EtOAc: EtOH in 1:1 DCM:heptane (40 mL/min), affording the title compound (414.8 mg, 89%); $^1$H NMR (400 MHz, DMSO-$d_6$) δ 8.20 (d, J=5.3 Hz, 1H), 8.06 (dd, J=1.9, 1.0 Hz, 1H), 7.62 (dd, J=9.3, 1.9 Hz, 1H), 7.60-7.48 (m, 1H), 7.40-7.37 (m, 1H), 7.21 (ddd, J=8.2, 7.3, 1.7 Hz, 1H), 7.07 (dd, J=8.3, 1.1 Hz, 1H), 6.74 (td, J=7.4, 1.1 Hz, 1H), 6.45 (dd, J=7.6, 1.7 Hz, 1H), 4.82 (dd, J=6.2, 3.4 Hz, 1H), 4.27 (ddd, J=11.3, 4.8, 3.2 Hz, 1H), 3.95 (td, J=11.0, 2.1 Hz, 1H), 3.87 (s, 3H), 2.37 (dddd, J=14.0, 10.6, 6.1, 3.1 Hz, 1H), 2.10-2.02 (m, 1H). MS (ESI+) m/z 376.1 (M+H). LC/MS (Table 1, ab) $R_t$=0.87 min; MS m/z: 376 (M+H)$^+$.

Preparation #94

(6S,8R,9R)-2-Bromo-9-phenyl-6,7,8,9-tetrahydro-6,8-epoxyimidazo[1,2-a:5,4-b"]dipyridine and (6R,8S,9S)-2-bromo-9-phenyl-6,7,8,9-tetrahydro-6,8-epoxy-imidazo[1,2-i:5,4-b']dipyridin

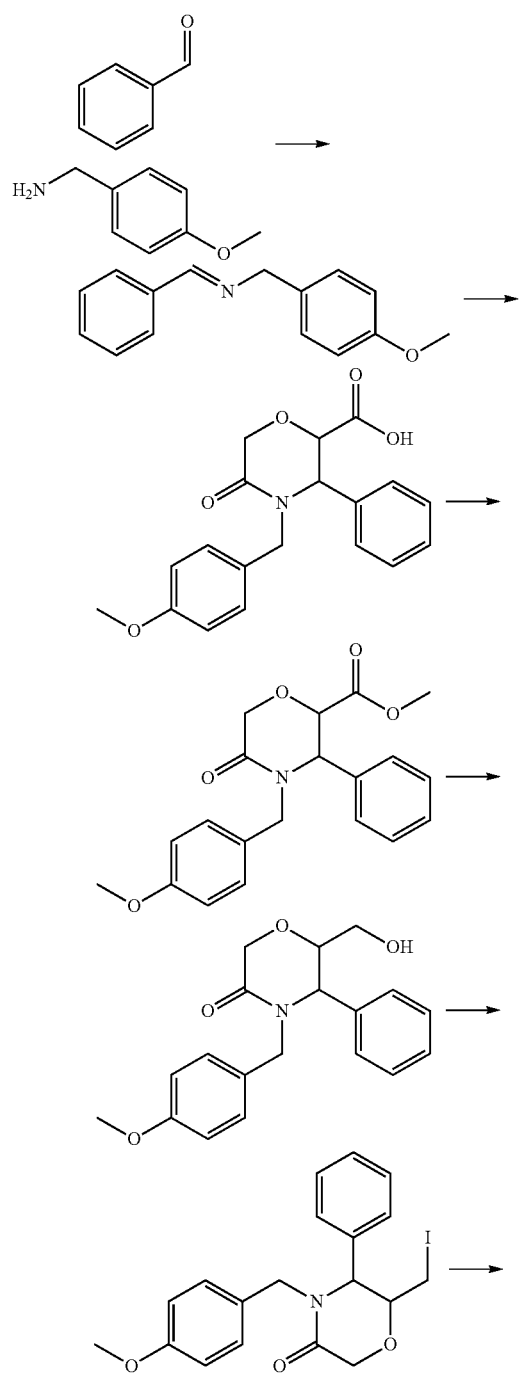

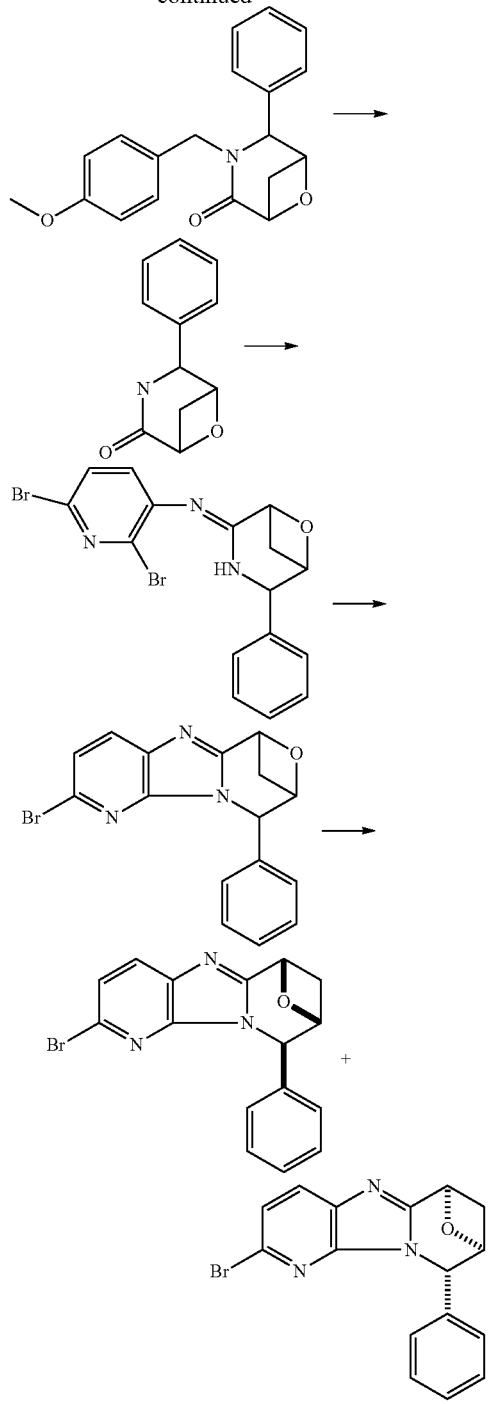

Step 1:
(E)-N-Benzylidene-1-(4-methoxyphenyl)methanamine

To a 500 mL round bottom flask was added 4-methoxybenzylamine (15 mL, 115 mmol) in DCM (200 mL) at rt. Benzaldehyde (11.14 mL, 110 mmol) and MgSO$_4$ (26.4 g, 219 mmol) were added to the mixture and stirred at rt for 96 h, filtered and concentrated in vacuo. The residue was put on Hi-vac overnight to remove any excess solvent to give the title compound (10.25 g, 91%); $^1$H NMR (400 MHz, CDCl$_3$) δ 8.42 (d, J=1.4 Hz, 1H), 7.94-7.81 (m, 2H), 7.55-7.43 (m, 3H), 7.39-7.26 (m, 2H), 7.04-6.88 (m, 2H), 4.83 (d, J=1.4 Hz, 2H), 3.84 (s, 3H). MS (ESI) m/z: 226 (M+H)⁺.

Step 2: 4-(4-Methoxybenzyl)-5-oxo-3-phenylmorpholine-2-carboxylic acid

To a 200 mL round bottom flask was added diglycolic anhydride (9.80 g, 76 mmol), (E)-N-benzylidene-1-(4-methoxyphenyl)methanamine (15.56 g, 69.1 mmol) in xylene (150 mL) and the solution was heated to reflux (about 138° C.) for 2 h. The reaction was complete after heating for 3 h, cooled to rt and extracted with 10% aq Na₂CO₃ (2×30 mL), water (2×30 mL), acidified with 1 N HCl to neutral (see solid suspension) and extracted with EtOAc (200 mL), dried over Na₂SO₄, filtered and concentrated in vacuo. The residue was purified on silica gel and eluted with DCM/MTBE 0-20% over 60 min to give the title compound (18.70 g, 79%); ¹H NMR (501 MHz, DMSO-d₆) δ 7.45-7.37 (m, 2H), 7.31-7.22 (m, 2H), 7.13-7.00 (m, 2H), 6.87-6.79 (m, 3H), 5.13 (d, J=14.7 Hz, 1H), 4.78 (d, J=2.6 Hz, 1H), 4.61 (d, J=16.7 Hz, 1H), 4.45-4.32 (m, 1H), 3.74 (m, J=21.6 Hz, 3H), 2.50 (m, J=1.8 Hz, 1H), 1.04 (d, J=6.1 Hz, 1H). MS (ESI) m/z: 342 (M+H)⁺.

Step 3: Methyl 4-(4-methoxybenzyl)-5-oxo-3-phenylmorpholine-2-carboxylate

To a 1000 mL round bottom flask was added 4-(4-methoxybenzyl)-5-oxo-3-phenylmorpholine-2-carboxylic acid (18.70 g, 54.8 mmol) in MeOH (500 ml) was added concentrated HCl (3 mL) and the mixture heated to 60° C. The reaction was complete after 5 h. The solution was cooled and concentrated. The crude reaction mixture was dissolved in EtOAc (500 mL), washed with sat NaHCO₃ (100 mL), brine (200 mL), dried over Na₂SO₄, filtered and concentrated under reduced pressure. The residue was purified on silica gel and eluted with 0-20% MTBE/DCM over 60 min to give methyl the title compound (15.98 g, 82%); ¹H NMR (400 MHz, CDCl₃) δ 7.47-7.33 (m, 2H), 7.37-7.21 (m, 2H), 7.21-7.10 (m, 2H), 7.10-7.02 (m, 3H), 5.53 (d, J=14.6 Hz, 1H), 5.29 (s, 1H), 4.89-4.76 (m, 1H), 4.70 (d, J=2.6 Hz, 1H), 4.49-4.31 (m, 1H), 3.83 (s, 3H), 3.77 (s, 3H), 1.19 (s, 1H). MS (ESI) m/z: 355 (M+H)⁺.

Step 4: 6-(Hydroxymethyl)-4-(4-methoxybenzyl)-5-phenylmorpholin-3-one

To a 500 mL round bottom flask was added methyl 4-(4-methoxybenzyl)-5-oxo-3-phenylmorpholine-2-carboxylate (15.97 g, 44.9 mmol) in THF (200 mL) and lithium borohydride (58.4 ml, 117 mmol) was added and stirred at rt. After 4 h the reaction was complete. The solution was concentrated under reduced pressure, dissolved in EtOAc (500 mL) and washed with NaHCO₃ (200 mL), brine (100 mL), dried over Na₂SO₄, filtered and concentrated. The residue was purified on silica gel and eluted with DCM/MTBE 0-20% over 60 min to give the title compound (13.13 g, 89%); ¹H NMR (400 MHz, CDCl₃) δ 7.47-7.32 (m, 3H), 7.16 (dd, J=7.3, 2.2 Hz, 2H), 6.99-6.90 (m, 2H), 6.84-6.69 (m, 2H), 5.37 (d, J=14.6 Hz, 1H), 4.47 (d, J=16.4 Hz, 1H), 4.42-4.30 (m, 2H), 3.86-3.63 (m, 2H), 3.51 (ddd, J=12.2, 6.2, 2.7 Hz, 1H), 3.46-3.28 (m, 2H), 1.18 (s, 3H). MS (ESI) m/z: 328 (M+H)⁺.

Step 5: 6-(Iodomethyl)-4-(4-methoxybenzyl)-5-phenylmorpholin-3-one

To a solution of 6-(hydroxymethyl)-4-(4-methoxybenzyl)-5-phenylmorpholin-3-one (4.40 g, 13.44 mmol) in THF (150 mL) at rt was added PPh₃ (7.76 g, 29.6 mmol), imidazole (2.93 g, 43.0 mmol) and iodine (8.53 g, 33.6 mmol) and the reaction was stirred at rt. After 2 h at rt the reaction was complete. The crude reaction mixture was washed with sat. Na₂S2SO₄ (100 mL), 1N HCl (50 mL), sat. NaHCO₃ (2×50 mL), brine (2×50 mL), dried over Na₂SO₄, filtered and concentrated in vacuo. The residue was purified on silica gel and eluted with 0-10% MTBE/DCM over 60 min wth 60 min hold to give the title compound (5.45 g, 93%) ¹H NMR (400 MHz, CDCl₃) δ 7.40 (dd, J=5.0, 1.7 Hz, 2H), 7.18 (dd, J=6.7, 2.8 Hz, 2H), 7.05-6.91 (m, 3H), 6.82 (d, J=8.4 Hz, 2H), 5.49-5.32 (m, 1H), 4.51 (d, J=16.7 Hz, 1H), 4.47-4.21 (m, 2H), 3.81 (3, 3H), 3.58 (tt, J=9.4, 4.7 Hz, 1H), 3.32 (d, J=14.6 Hz, 1H), 3.13 (dd, J=11.0, 3.9 Hz, 1H), 2.99 (dd, J=10.9, 6.4 Hz, 1H). MS (ESI) m/z: 438 (M+H)⁺.

Step 6: 3-(4-Methoxybenzyl)-4-phenyl-6-oxa-3-azabicyclo[3.1.1]heptan-2-one

To a 200 mL flask was added 6-(iodomethyl)-4-(4-methoxybenzyl)-5-phenylmorpholin-3-one (4810 mg, 11.00 mmol) in THF (200 mL) at −74° C. was added potassium bis(trimethylsilyl)amide (13.20 mL, 13.20 mmol) dropwise over 10 min and keeping the internal temperature below −74° C. After 15 min at −74° C., the reaction was quenched with sat. NH₄Cl (5 mL) and stirred for 30 min. The reaction mixture was extracted with EtOAc (2×200 mL), washed with brine (2×20 mL), dried over Na₂SO₄, filtered and concentrated. The residue was purified on silica gel and eluted with heptane/EtOAc 0-50% over 60 min to give the title compound (2.60 g, 76%); ¹H NMR (400 MHz, CDCl₃) δ 7.49-7.22 (m, 5H), 7.20-7.02 (m, 2H), 6.95-6.79 (m, 2H), 5.49 (dd, J=14.5, 11.1 Hz, 1H), 4.63 (dd, J=6.4, 3.7 Hz, 1H), 4.55 (dd, J=6.6, 3.9 Hz, 1H), 4.24 (d, J=19.8 Hz, 1H), 3.81 (s, J=13.1 Hz, 3H), 3.50-3.33 (m, 2H), 2.09 (d, J=9.1 Hz, 1H). MS (ESI) m/z: 310 (M+H)⁺.

Step 7: 4-Phenyl-6-oxa-3-azabicyclo[3.1.1]heptan-2-one

To a 200 mL round bottom flask was added 3-(4-methoxybenzyl)-4-phenyl-6-oxa-3-azabicyclo[3.1.1]heptan-2-one (2.60 g, 8.40 mmol) in MeCN (60 mL) and water (20.00 mL). The mixture was cooled to 0° C. and solid ceric ammonium nitrate (18.40 g, 33.6 mmol) was added in one portion. The reaction was warmed to rt, after stirring for 12 h, the reaction was complete. Reaction mixture was extracted with EtOAc (2×100 mL) and washed with brine (2×50 mL), dried over Na₂SO₄, filtered and concentrated under reduced pressure. The residue was purified on silica gel and eluted with heptane/EtOAc 0-80% over 40 min with 40 min hold to give the title compound (0.72 g, 45.3%); ¹H NMR (500 MHz, CDCl₃) δ 7.47-7.26 (m, 5H), 5.99 (s, 1H), 4.75-4.70 (m, 1H), 4.68 (dddt, J=5.8, 3.4, 2.4, 1.0 Hz, 1H), 4.54 (dddd, J=6.5, 3.5, 2.0, 0.8 Hz, 1H), 3.51 (dt, J=9.3, 6.6 Hz, 1H), 2.37 (dt, J=9.3, 0.9 Hz, 1H). MS (ESI) m/z: 190 (M+H)⁺.

Step 8: (Z)-2,6-Dibromo-N-(4-phenyl-6-oxa-3-azabicyclo[3.1.1]heptan-2-ylidene)pyridin-3-amine To a 100 mL round bottom flask was added 4-phenyl-6-oxa-3-azabicyclo[3.1.1]heptan-2-one (830 mg, 4.39 mmol) in dichloroethane (30 mL). POCl₃ (0.409 mL, 4.39 mmol) was added and the mixture stirred at rt for 20 min. 2,6-Dibromopyridin-3-amine (1216 mg, 4.83 mmol) was added as a solid and stirred at 45° C. After heating overnight, the reaction was concentrated and extracted with EtOAc (2×50 mL), washed with water (2×10 mL), brine (2×10 mL), dried over Na₂SO₄, filtered and concentrated to provide the title compound, which was used without purification in the next step. MS (ESI) m/z: 423 (M+H)⁺.

Step 9: 2-Bromo-9-phenyl-6,7,8,9-tetrahydro-6,8-epoxyimidazo[1,2-a:5,4-b']dipyridine To a 200 mL round bottom flask was added K₂CO₃ (353 mg, 2.55 mmol), CuI (64.8 mg, 0.340 mmol), (Z)-2,6-dibromo-N-(4-phenyl-6-oxa-3-azabicyclo[3.1.1]heptan-2-ylidene)pyridin-3-amine (720 mg, 1.702 mmol), N1,N1,N2,N2-tetramethylethane-1,2-diamine (0.102 mL, 0.681 mmol) in butyronitrile (12 mL) and DMSO (4 mL). The reaction was heated to 100° C. for 1 h. Water (150 mL) was added and reaction mixture was extracted with chloroform (2×200 mL) and IPA (2×40 mL). The organic layer was extracted (2×100 mL chloroform/10% IPA) then washed with brine (150 mL), dried over Na₂SO₄, filtered and concentrated under reduced pressure. The residue was purified on silica gel and eluted with DCM/0-20% MTBE to give the title compound (365 mg, 63%); ¹H NMR (400 MHz, CDCl₃) δ 7.81 (d, J=8.3 Hz, 1H), 7.42-7.22 (m, 4H), 7.04-6.92 (m, 2H), 5.78 (d, J=2.7 Hz, 1H), 3.56 (q, J=5.5 Hz, 1H), 2.99 (qd, J=6.1, 2.7 Hz, 1H), 2.80 (dt, J=9.5, 5.9 Hz, 1H), 2.45-2.32 (m, 1H), 2.08-1.87 (m, 2H). MS (ESI) m/z: 342 (M+H)⁺.

Step 10: (6S,8R,9R)-2-Bromo-9-phenyl-6,7,8,9-tetrahydro-6,8-epoxyimidazo[1,2-a:5,4-b']dipyridine and (6R,8S,9S)-2-bromo-9-phenyl-6,7,8,9-tetrahydro-6,8-epoxyimidazo[1,2-a:5,4-i']dipyridine The enantiomers were separated using sfc with a Chiral Technologies Inc., Chiralpak IA (21×250 mm) 5 micron, eluting with MeOH/CO₂ 70 mL/min flow rate to give the enantiomers. ¹H NMR (400 MHz, DMSO-d₆) δ 8.04 (d, J=8.3 Hz, 1H), 7.41 (d, J=8.3 Hz, 1H), 7.36-7.25 (m, 3H), 7.19-7.08 (m, 2H), 5.88 (s, 1H), 5.42 (dd, J=6.3, 3.0 Hz, 1H), 4.89 (dd, J=6.7, 3.0 Hz, 1H), 3.67 (dt, J=9.4, 6.6 Hz, 1H), 2.39 (d, J=9.5 Hz, 1H). MS (ESI) m/z: 342 (M+H⁺) and ¹H NMR (400 MHz, DMSO-d₆) δ 8.06 (d, J=8.4 Hz, 1H), 7.43 (d, J=8.3 Hz, 1H), 7.39-7.27 (m, 3H), 7.19-7.09 (m, 2H), 5.90 (s, 1H), 5.44 (dd, J=6.2, 3.0 Hz, 1H), 4.90 (dd, J=6.6, 3.0 Hz, 1H), 3.69 (dt, J=9.5, 6.6 Hz, 1H), 2.41 (d, J=9.6 Hz, 1H).
MS (ESI) m/z: 342 (M+H)⁺.

Preparation #95

2-Bromo-9-phenyl-6,7,8,9-tetrahydro-6,8-methanoimidazo[1,2-a:5,4-b']dipyridine

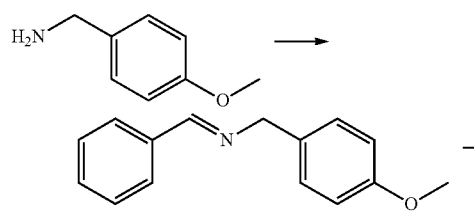

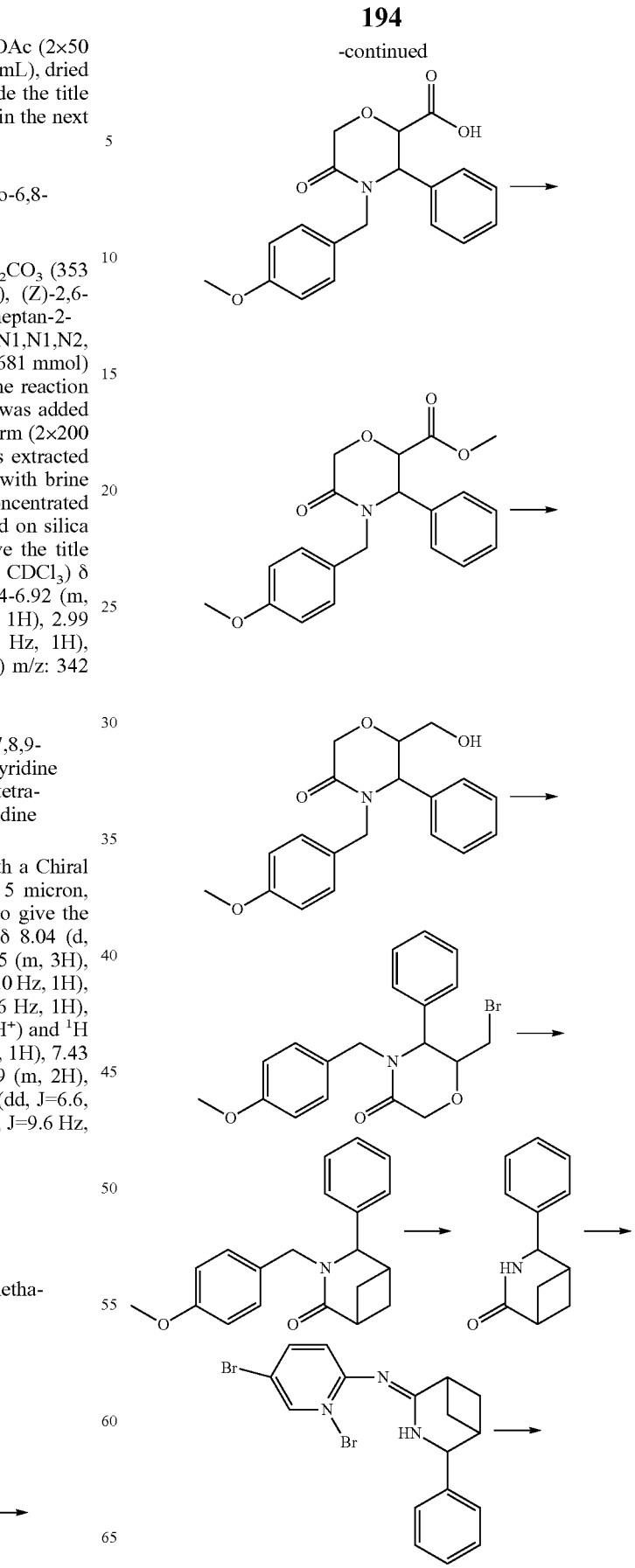

-continued

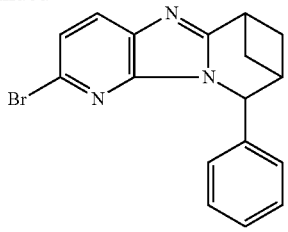 [SMILES: Brc1ccc2nc3n(c2n1)C(c1ccccc1)C1CC3C1]

Step 1: (E)-N-Benzylidene-1-(4-methoxyphenyl)methanamine

To a 500 mL round bottom flask was added 4-methoxybenzylamine (15 ml, 115 mmol) in CH$_2$Cl$_2$ (100 mL) at rt. Benzaldehyde (11.14 mL, 110 mmol) and MgSO$_4$ (26.4 g, 219 mmol) were added and the mixture stirred at rt for 96 h. The solution was filtered, concentrated, purified on silica gel and eluted with MTBE 0-20% over 60 min/DCM to give the title compound (18.40 g, 74.5%); $^1$H NMR (501 MHz, CDCl$_3$) δ 8.42 (t, J=1.5 Hz, 1H), 7.88-7.80 (m, 2H), 7.51-7.42 (m, 3H), 7.36-7.27 (m, 2H), 6.99-6.91 (m, 2H), 4.84-4.80 (m, 2H), 3.84 (s, 3H). MS (ESI) m/z: 226 (M+H)$^+$.

Step 2: 1-(4-Methoxybenzyl)-6-oxo-2-phenylpiperidine-3-carboxylic acid

To a 200 mL round bottom flask was added diglycolic anhydride (9.80 g, 76 mmol), (E)-N-benzylidene-1-(4-methoxyphenyl)methanamine (15.56 g, 69.1 mmol) in xylene (150 mL). The solution was heated to reflux (about 138° C.) for 2 h. The reaction was complete after heating for 3 h cooled to rt and extracted with 10% aqueous Na$_2$CO$_3$ (2×50 mL), water (2×50 mL), acidified with 1 N HCl to neutral and extracted with EtOAc (500 mL), dried over Na$_2$SO$_4$, filtered and concentrated in vacuo to afford the title compound which was used in the next step without purification. $^1$H NMR (501 MHz, DMSO-d$_6$) δ 7.45-7.37 (m, 2H), 7.31-7.16 (m, 2H), 7.18-7.00 (m, 3H), 6.91-6.75 (m, 2H), 5.13 (d, J=14.7 Hz, 1H), 4.76 (dd, J=27.5, 2.8 Hz, 1H), 4.61 (d, J=16.7 Hz, 1H), 4.44-4.28 (m, 2H), 3.74 (d, J=21.6 Hz, 3H), 3.43 (d, J=14.8 Hz, 1H). MS (ESI) m/z: 341 (M+H)$^+$.

Step 3: Methyl 1-(4-methoxybenzyl)-6-oxo-2-phenylpiperidine-3-carboxylate

To a 1 L round bottom flask was added 1-(4-methoxybenzyl)-6-oxo-2-phenylpiperidine-3-carboxylic acid (9.54 g, 28.1 mmol) in MeOH (200 mL) was added concentrated HCl (2 mL) and the solution was heated to 60° C. for 5 h. Then, the solution was cooled and concentrated. The reaction mixture was extracted with EtOAc (500 mL), washed with sat. NaHCO$_3$ (100 mL), brine (200 mL), dried over Na$_2$SO$_4$, filtered and concentrated. The residue was purified on silica gel and eluted with 0-20% MTBE/DCM over 60 min to give the title compound (7.35 g, 74.0%); $^1$H NMR (400 MHz, CDCl$_3$) δ 7.46-7.22 (m, 3H), 7.21-6.99 (m, 4H), 6.86 (dd, J=33.4, 8.5 Hz, 2H), 5.65-5.40 (m, 1H), 4.85 (dd, J=25.3, 4.4 Hz, 1H), 3.80-3.74 (m, 3H), 3.57-3.42 (m, 3H), 2.84-2.67 (m, 2H), 2.58 (ddd, J=18.2, 6.8, 4.2 Hz, 1H), 1-76-1.72 (m, 1H), 2.09-1.80 (m, 2H). MS (ESI) m/z: 354 (M+H)$^+$.

Step 4: 5-(Hydroxymethyl)-1-(4-methoxybenzyl)-6-phenylpiperidin-2-one

To a 500 mL round bottom flask was added methyl 1-(4-methoxybenzyl)-6-oxo-2-phenylpiperidine-3-carboxylate (7.35 g, 20.80 mmol) in THF (150 mL) and lithium borohydride (31.2 mL, 62.4 mmol) was added and stirred at rt. After 4 h the reaction was concentrated, extracted with EtOAc (500 mL) and washed with NaHCO$_3$ (200 mL), brine (100 mL), dried over Na$_2$SO$_4$, filtered and concentrated. The residue was purified on silica gel and eluted with DCM/MTBE 0-20% over 60 min to give the title compound (5.64 g, 83%); $^1$H NMR (400 MHz, CDCl$_3$) δ 7.42-7.24 (m, 3H), 7.22-7.01 (m, 4H), 6.93-6.73 (m, 2H), 5.49 (dd, J=14.5, 8.3 Hz, 1H), 4.32 (dd, J=33.0, 5.2 Hz, 1H), 3.46 (td, J=7.3, 4.6 Hz, 2H), 3.30-3.17 (m, 2H), 2.63-2.45 (m, 2H), 2.24 (t, J=5.1 Hz, 1H), 2.04-1.82 (m, 1H), 1.61 (dd, J=13.7, 6.8 Hz, 1H), 1.18 (s, 3H). MS (ESI) m/z: 326 (M+H)$^+$.

Step 5: 5-(Bromomethyl)-1-(4-methoxybenzyl)-6-phenylpiperidin-2-one

To a solution of 5-(hydroxymethyl)-1-(4-methoxybenzyl)-6-phenylpiperidin-2-one (5.64 g, 17.33 mmol) in DCM (120 mL) was cooled to 0° C. PPh$_3$ (10.100 g, 38.5 mmol) was added followed by N-bromosuccinimide (6.17 g, 34.7 mmol) in three portions. The reaction was warmed to rt. After 2 h, the reaction was washed with sat. NaHCO$_3$ (2×50 mL), brine (2×50 mL), dried over Na$_2$SO$_4$, filtered and concentrated in vacuo. The residue was purified on silica gel and eluted with 0-10% MTBE/DCM over 60 min wth 60 min hold to give the title compound (6.71 g, 100%); $^1$H NMR (400 MHz, CDCl$_3$) δ 7.47-7.20 (m, 3H), 7.20-6.95 (m, 4H), 6.95-6.72 (m, 2H), 5.52 (dd, J=14.6, 8.4 Hz, 1H), 4.37 (dd, J=34.1, 5.6 Hz, 1H), 3.88-3.71 (m, 3H), 3.41-3.14 (m, 2H), 2.59 (t, J=7.0 Hz, 2H), 2.15 (ddt, J=10.2, 6.1, 3.7 Hz, 1H), 2.03-1.88 (m, 1H), 1.82-1.68 (m, 1H), 1.19 (s, 1H). MS (ESI) m/z: 389 (M+H)$^+$.

Step 6: 3-(4-Methoxybenzyl)-4-phenyl-3-azabicyclo[3.1.1]heptan-2-one

To a 200 mL flask was added 5-(bromomethyl)-1-(4-methoxybenzyl)-6-phenylpiperidin-2-one (3.76 g, 9.68 mmol) in THF (100 mL) at −74° C. was added potassium bis(trimethylsilyl)amide (14.52 mL, 14.52 mmol) dropwise over 10 min and keeping the internal temperature below −74° C. After 20 min, the reaction was quenched with sat. NH$_4$Cl (10 mL) and stirred for 30 min. The reaction mixture was extracted with EtOAc (2×60 mL), washed with brine (2×20 mL), dried over Na$_2$SO$_4$, filtered and concentrated. The residue was purified on silica gel and eluted with MTBE/DCM 0-20% over 60 min to give the title compound (2.38 g, 80%); $^1$H NMR (500 MHz, DMSO-d$_6$) δ 7.43-7.35 (m, 2H), 7.35-7.26 (m, 1H), 7.26-7.19 (m, 2H), 6.99-6.89 (m, 2H), 6.88-6.77 (m, 2H), 5.28 (dd, J=14.8, 7.4 Hz, 1H), 4.44 (dd, J=10.7, 2.6 Hz, 1H), 3.72 (d, J=19.0 Hz, 3H), 2.72 (q, J=5.7 Hz, 1H), 2.60-2.44 (m, 2H), 2.33 (dt, J=8.9, 5.7 Hz, 1H), 1.94 (dt, J=9.4, 5.9 Hz, 1H), 1.78 (q, J=9.0 Hz, 1H), 1.57 (dt, J=23.7, 8.7 Hz, 1H). MS (ESI) m/z: 307 (M+H)$^+$.

Step 7: 4-Phenyl-3-azabicyclo[3.1.1]heptan-2-one

To a 200 mL round bottom flask was added 3-(4-methoxybenzyl)-4-phenyl-3-azabicyclo[3.1.1]heptan-2-one (2.0 g, 6.51 mmol) in MeCN (80 mL). The mixture was cooled to −10° C. and ceric ammonium nitrate (10.70 g, 19.52 mmol) about 1 M in water (30 mL) was added dropwise over 5 min so temperature did not exceed −4° C. The reaction was stirred for 1 h at −10° C. The reaction only shows a small amount of product by tlc. The solution was warmed to 0-5° C. and stirred for 1 h. Then, the reaction was warmed to rt and stirred for 1 h. Added 1.0 equivalent of ceric ammonium nitrate at rt. After 1 h at rt, the reaction mixture was extracted with MTBE (200 mL) and washed with brine (100 mL×2), dried over Na₂SO₄, filtered and concentrated. The residue was purified on silica gel and eluted with DCM/MTBE 0-20% over 40 min with 40 min hold to give the title compound (325 mg, 26.7%); ¹H NMR (400 MHz, DMSO-d₆) δ 7.75 (s, 1H), 7.45-7.29 (m, 4H), 7.31-7.20 (m, 1H), 4.74 (t, J=2.1 Hz, 1H), 2.63 (tq, J=4.2, 2.9, 2.1 Hz, 1H), 2.57-2.45 (m, 1H), 2.39 (dt, J=8.9, 5.9 Hz, 1H), 1.95 (dt, J=9.3, 5.9 Hz, 1H), 1.77 (t, J=8.6 Hz, 1H), 1.55 (dd, J=9.2, 8.3 Hz, 1H). MS (ESI) m/z: 188 (M+H)⁺.

Step 8: (Z)-2,6-Dibromo-N-(4-phenyl-3-azabicyclo [3.1.1]heptan-2-ylidene)pyridin-3-amine To a 50 mL round bottom flask was added 4-phenyl-3-azabicyclo[3.1.1]heptan-2-one (320 mg, 1.709 mmol) in DCE (10 mL). POCl₃ (0.159 mL, 1.709 mmol) was added and the mixture stirred at rt for 20 min. 2,6-Dibromopyridin-3-amine (474 mg, 1.880 mmol) was added as a solid and the mixture was stirred at 40° C. and then the temperature was raised to 45° C. The reaction was complete after 16 h. The reaction was concentrated and extracted with EtOAc (100 mL), washed with water (10 mL), brine (10 mL), dried over Na₂SO₄, filtered and concentrated to give the title compound (210 mg, 29%). Used without purification. MS (ESI) m/z: 422 (M+H)⁺.

Step 9: 2-Bromo-9-phenyl-6,7,8,9-tetrahydro-6,8-methanoimidazo[1,2-a:5,4-b']dipyridine To a 200 mL round bottom flask was added K₂CO₃ (354 mg, 2.56 mmol), CuI (65.1 mg, 0.342 mmol), (Z)-2,6-dibromo-N-(4-phenyl-3-azabicyclo[3.1.1]heptan-2-ylidene)pyridin-3-amine (720 mg, 1.710 mmol), N1,N1,N2,N2-tetramethylethane-1,2-diamine (0.103 mL, 0.684 mmol) in butyronitrile (12 mL) and DMSO (4.00 mL). The reaction was heated to 100° C. and was complete after 1 hour. Water was added (150 mL), extracted with chloroform (200 mL) and IPA (40 mL). The organic layer was extracted (2× chloroform/10% IPA). The organic layer was washed with brine (150 mL), dried over Na₂SO₄, filtered and concentrated. The residue was purified on silica gel and eluted with DCM/0-20% MTBE to give the title compound (365 mg, 62.8%); ¹H NMR (400 MHz, CDCl₃) δ 7.85 (dd, J=34.1, 8.3 Hz, 1H), 7.41-7.23 (m, 4H), 7.05-6.92 (m, 2H), 5.78 (d, J=2.7 Hz, 1H), 3.56 (q, J=5.5 Hz, 1H), 2.99 (qd, J=6.1, 2.7 Hz, 1H), 2.80 (dt, J=9.5, 5.9 Hz, 1H), 2.47-2.32 (m, 1H), 2.07-1.86 (m, 2H). MS (ESI) m/z: 341 (M+H)⁺.

Preparation #96

2-(2-Chloropyrimidin-5-yl)-9-phenyl-8,9-dihydro-6H-pyrido[3',2':4,5]imidazo-[2,1-c][1,4]oxazine

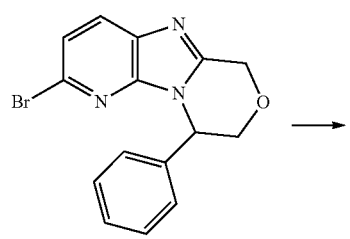

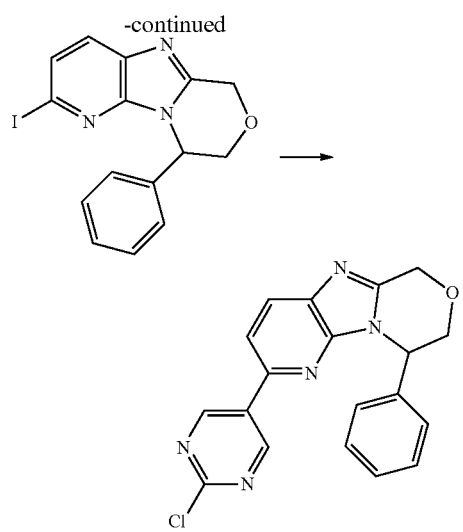

Step 1: 2-Iodo-9-phenyl-8,9-dihydro-6H-pyrido[3', 2':4,5]imidazo[2,1-c][1,4]oxazine To a solution of 7-bromo-4-phenyl-3,4-dihydro-1H-benzo[4,5]imidazo[2,1-c][1,4]oxazine (preparation #26) (0.4 g, 1.211 mmol) and CuI (0.012 g, 0.061 mmol) in 1,4-dioxane (1.2 mL) at rt was added NaI (0.363 g, 2.423 mmol) and DMEA (0.013 mL, 0.121 mmol). Reaction was placed in a sealed tube and heated to 110° C. The mixture was stirred for 60 h; then cooled to rt and transferred to a separatory funnel with DCM (100 mL). The solution was washed with 100 mL sat. NH₄Cl, 100 mL water; then dried over Na₂SO₄, filtered and concentrated to give the title compound which was used directly in the next reaction without further purification (0.380 g; 83%); ¹H NMR (400 MHz, DMSO-d₆) δ 7.77 (d, J=8.2 Hz, 1H), 7.59 (d, J=8.2 Hz, 1H), 7.35-7.20 (m, 3H), 7.10-7.01 (m, 2H), 5.72 (dd, J=5.0, 2.0 Hz, 1H), 5.15 (d, J=16.4 Hz, 1H), 4.98 (d, J=16.4 Hz, 1H), 4.29 (dd, J=12.0, 3.6 Hz, 1H), 4.11 (dd, J=12.0, 2.2 Hz, 1H); MS (DCI) m/z: 278 (M+H)⁺.

Step 2: 2-(2-Chloropyrimidin-5-yl)-9-phenyl-8,9-dihydro-6H-pyrido[3',2':4,5]imidazo[2,1-c][1,4]-oxazine To a solution of 2-iodo-9-phenyl-8,9-dihydro-6H-pyrido[3',2':4,5]imidazo[2,1-c][1,4]oxazine (0.380 g, 1.007 mmol) and (2-chloropyrimidin-5-yl)boronic acid (0.160 g, 1.007 mmol) in THF (4 mL) at rt was added Cs₂CO₃ (1.007 mL, 2.015 mmol), Pd₂(dba)₃ (0.090 g, 0.098 mmol) and 1,3,5,7-tetramethyl-6-phenyl-2,4,8-trioxa-6-phosphaadamantane (0.058 g, 0.198 mmol). The mixture was degassed (3× vacuum/purge with N₂) and heated to 60° C. After 1 h, the reaction was cooled to rt and concentrated. The residue taken up in CH₂Cl₂ and washed with water and brine; then dried (Na₂SO₄), filtered and concentrated. The residue was purified by chromatography on silica gel (100% DCM; then 10 to 50% THF/DCM) to give the title compound (0.296 g; 81%); ¹H NMR (400 MHz, THF-d8) δ 9.05 (s, 2H), 8.05 (d, J=8.3 Hz, 1H), 7.82 (d, J=8.3 Hz, 1H), 7.40-7.18 (m, 5H), 5.69 (t, J=4.3 Hz, 1H), 5.24-4.97 (m, 2H), 4.29 (ddd, J=80.1, 12.0, 4.3 Hz, 2H); MS (DCI) m/z: 364 (M+H)⁺.

Preparation #97

(R)-2'-Bromo-6',8'-dihydro-2H-spiro[benzofuran-3, 9'-pyrido[3',2':4,5]imidazo[2,1-c][1,4]oxazine] and (S)-2'-bromo-6',8'-dihydro-2H-spiro[benzofuran-3, 9'-pyrido[3',2':4,5]imidazo[2,1-c][1,4]oxazine]

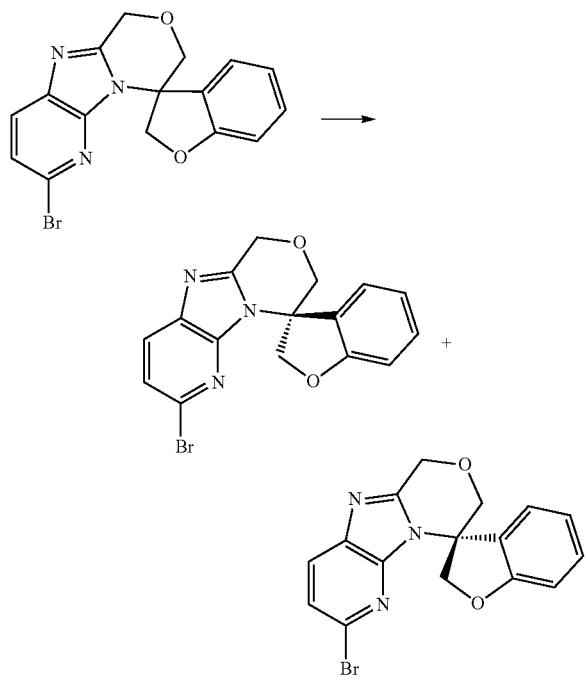

A racemic mixture of 2'-bromo-6',8'-dihydro-2H-spiro[benzofuran-3,9'-pyrido[3',2':4,5]imidazo[2,1-c][1,4]oxazine](1.5 g, Preparation #85) was separated via chiral SFC chromatography (Table 2, Method 20) to give (R)-2'-bromo-6',8'-dihydro-2H-spiro[benzofuran-3,9'-pyrido[3',2':4,5]imidazo[2,1-c][1,4]oxazine](0.40 g, 27%) $R_t$=5.5 min [Stereochemistry assignment based on TNFα activity of derivatives] and (S)-2'-bromo-6',8'-dihydro-2H-spiro[benzofuran-3,9'-pyrido[3',2':4,5]imidazo[2,1-c][1,4]oxazine] (0.55 g, 37%) $R_t$=5.9 min [Stereochemistry assignment based on TNFα activity of derivatives]; LC/MS (Table 1, Method ab) $R_t$=0.93 min; MS m/z: 358, 360 (M+H)+.

Preparation #98

(1S,4S)-4-(((4-Bromopyridin-2-yl)oxy)methyl)cyclohexanol and (1R,4R)-4-(((4-bromopyridin-2-yl)oxy)methyl)cyclohexanol

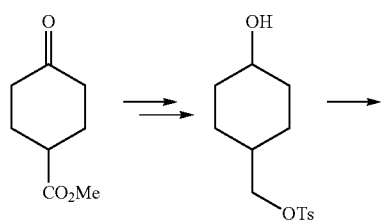

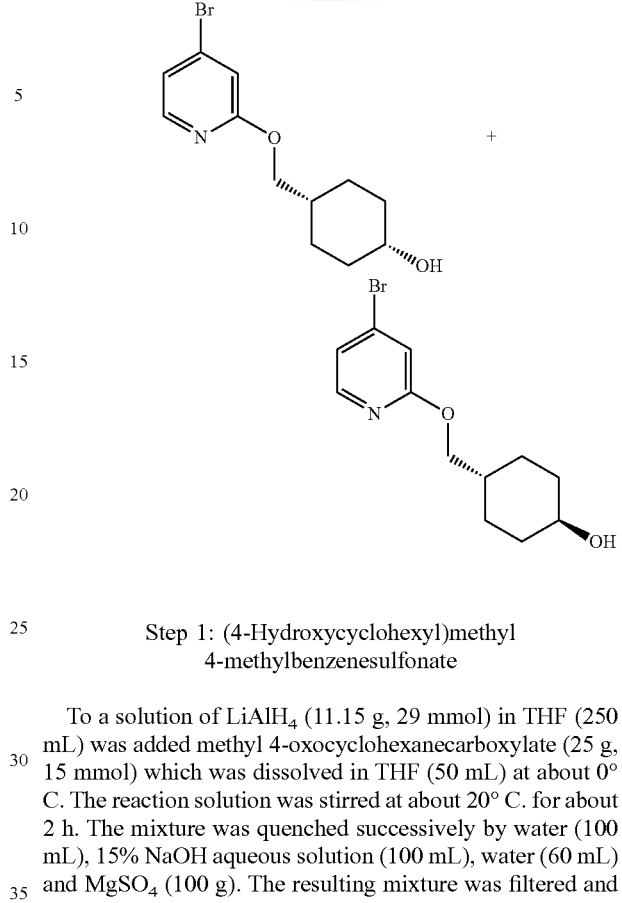

Step 1: (4-Hydroxycyclohexyl)methyl 4-methylbenzenesulfonate

To a solution of LiAlH$_4$ (11.15 g, 29 mmol) in THF (250 mL) was added methyl 4-oxocyclohexanecarboxylate (25 g, 15 mmol) which was dissolved in THF (50 mL) at about 0° C. The reaction solution was stirred at about 20° C. for about 2 h. The mixture was quenched successively by water (100 mL), 15% NaOH aqueous solution (100 mL), water (60 mL) and MgSO$_4$ (100 g). The resulting mixture was filtered and the filtrate was concentrated in vacuo to give the intermediate, 4-(hydroxymethyl)cyclohexanol (12.5 g). To a solution of 4-(hydroxymethyl)cyclohexanol (12.5 g, 86 mmol), TEA (13.1 g, 130 mmol), N,N-dimethylpyridin-4-amine (0.845 g, 6.9 mmol) in DCM (400 mL) was added a solution of 4-methylbenzene-1-sulfonyl chloride (11.53 g, 60.5 mmol) in DCM (50 mL) at about 0° C. The reaction mixture was stirred at about rt for about 2 h. The reaction was quenched by addition of about 100 mL of NH$_4$Cl at about rt and washed with DCM (3×100 mL). The organic were combined, dried over MgSO$_4$, filtered and concentrated under reduced pressure to give the title compound (19.5 g, 13% over two steps); $^1$H NMR (CDCl$_3$, 400 MHz) δ 0.77-1.09 (m, 1H), 1.16-1.83 (m, 8H), 1.97 (d, J=12.79 Hz, 1H), 2.45 (s, 2H), 2.96-3.12 (m, 1H), 3.38-3.61 (m, 1H), 3.70-4.08 (m, 2H), 7.35 (d, J 7.94 Hz, 2H), 7.65-7.83 (m, 2H).

Step 2: (1S,4S)-4-(((4-Bromopyridin-2-yl)oxy)methyl)cyclohexanol and (1R,4R)-4-(((4-bromopyridin-2-yl)oxy)methyl)cyclohexanol Two solutions of 4-bromopyridin-2-ol (7.34 g, 42.2 mmol) in DMF (200 mL) were prepared. To each solution was added (4-hydroxycyclohexyl) methyl 4-methylbenzenesulfonate (15 g, 52.7 mmol) and K$_2$CO$_3$ (7.29 g, 52.7 mmol) at rt. The reactions were stirred at about 70° C. for about 12 h. The reaction mixtures were combined, filtered, concentrated under reduced pressure, and the residue was purified by preparative HPLC (Table 1, Method aj) to give (1S,4S)-4-(((4-Bromopyridin-2-yl)oxy)methyl)cyclohexanol (2.12 g, 14%); LC/MS (Table 1, Method ak) $R_t$=3.09 min; MS m/z: 286, 288 (M+H)⁺ and (1R,4R)-4-(((4-bromopyridin-2-yl)oxy)methyl)cyclohexanol (1.47 g, 9.6%); LC/MS (Table 1, Method ak) $R_f$=3.18 min; MS m/z: 286, 288 (M+H)⁺.

Preparation #99

(1R,4R)-4-((4-Bromopyridin-2-yl)oxy)cyclohexan-1-ol and (1S,4S)-4-((4-bromopyridin-2-yl)oxy)cyclohexanol

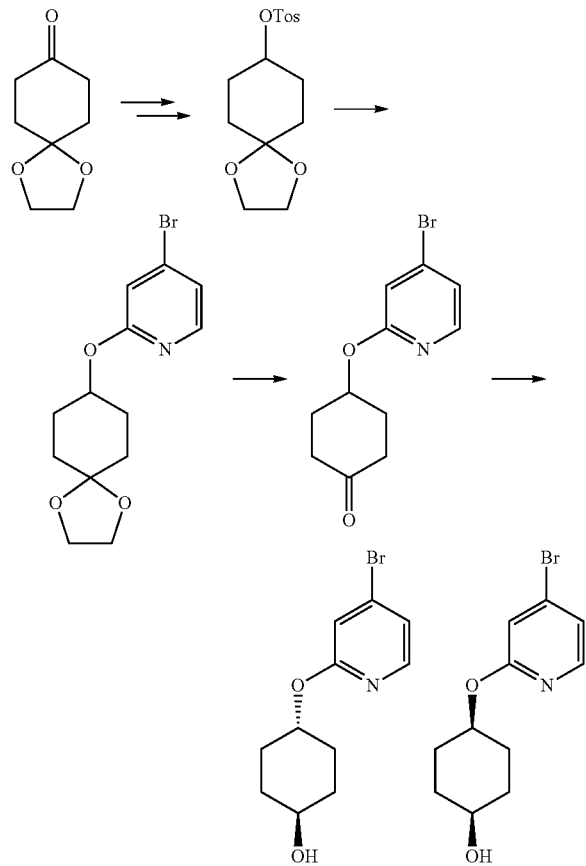

Step 1: 1,4-Dioxaspiro[4.5]decan-8-yl 4-methylbenzenesulfonate

To a mixture of 1,4-dioxaspiro[4.5]decan-8-one (60 g, 384 mmol) in MeOH (750 mL) was added NaBH₄ (43.6 g, 1.15 mol) slowly at about 0° C. under N₂ atmosphere. The reaction was stirred at about 25° C. for about 2. The reaction mixture was cooled to about 0° C. and water was added to quench the reaction. The reaction was concentrated to remove the MeOH and the residue was extracted with EtOAc (3×200 mL). The organics were combined, dried over MgSO₄, filtered and concentrated to give the intermediate, 1,4-dioxaspiro[4.5]decan-8-ol (57 g). To a solution of 1,4-dioxaspiro[4.5]decan-8-ol (57 g, 360 mmol), TEA (47.4 g, 468 mmol) and N,N-dimethylpyridin-4-amine (4.40 g, 36.0 mmol) in DCM (1 L) was added 4-methylbenzene-1-sulfonyl chloride (82 g, 432 mmol) at about 0° C., then the reaction mixture stirred under N₂ atmosphere at about 25° C. for about 12 h. The mixture was poured into water (500 mL), extracted with DCM (3×300 mL). The organic layers were combined, dried over MgSO₄, filtered and concentrated under reduced pressure. The crude product was purified by flash chromatography on silica gel (10:1-5:1 petroleum ether/EtOAc) to afford the title compound (110 g, 83% over two steps); ¹H NMR (CDCl₃, 400 MHz) δ 1.45-1.51 (m, 2 H), 1.69-1.83 (m, 6 H), 2.38 (s, 3 H), 3.84 (dd, J=7.72, 4.19 Hz, 4 H), 4.57 (dt, J=5.84, 3.03 Hz, 1 H), 7.26 (d, J=7.94 Hz, 2 H), 7.73 (d, J=8.38 Hz, 2 H)

Step 2: 2-(1,4-Dioxaspiro[4.5]decan-8-yloxy)-4-bromopyridine

A mixture of 1,4-dioxaspiro[4.5]decan-8-yl 4-methylbenzenesulfonate (55 g, 176 mmol), 4-bromopyridin-2-ol (27.8 g, 160 mmol) and Cs₂CO₃ (78 g, 240 mmol) in DMF (250 mL) was stirred at about 45° C. for about 28 h. The mixture was poured into ice water and extracted with EtOAc (3×100 mL). The organics were combined, washed with brine (2×50 mL), dried over MgSO₄, filtered, and concentrated under reduced pressure. The residue was purified by flash chromatography on silica gel (1:2 EtOAc/petroleum ether) to afford the title compound (27 g, 51%); ¹H NMR (CDCl₃, 400 MHz) δ 1.61-1.70 (m, 2 H), 1.82-1.99 (m, 6 H), 3.96 (t, J=3.09 Hz, 4 H), 5.14 (dt, J=6.73, 3.47 Hz, 1 H), 6.91 (s, 1H), 6.95-7.00 (m, 1 H), 7.94 (d, J=5.29 Hz, 1 H).

Step 3: 4-((4-Bromopyridin-2-yl)oxy)cyclohexan-1-one

The mixture of 2-(1,4-dioxaspiro[4.5]decan-8-yloxy)-4-bromopyridine (27 g, 86 mmol) and HCl (286 mL, 859 mmol) in THF (800 mL) was stirred at 25° C. for about 41 h. NaHCO₃ was added to the mixture to neutralize to pH 8. The mixture was extracted with EtOAc (3×250 mL), then the organics ere combined and washed with brine (3×150 mL), dried over Na₂SO₄, filtered, and concentrated under reduced pressure. The residue was triturated with petroleum ether (50 mL) to afford the title compound (18 g, 74%); ¹H NMR: (CDCl₃, 400 MHz) δ 2.07-2.29 (m, 4 H), 2.34-2.44 (m, 2 H), 2.58-2.68 (m, 2H), 5.39-5.49 (m, 1 H), 6.98 (s, 1 H), 7.04 (d, J=5.48 Hz, 1 H), 7.98 (d, J=5.48 Hz, 1 H).

Step 4

(1r,4r)-4-((4-Bromopyridin-2-yl)oxy)cyclohexan-1-ol and (1s, 4s)-4-((4-bromopyridin-2-yl)oxy)cyclohexanol Two solutions of 4-((4-bromopyridin-2-yl)oxy)cyclohexan-1-one (8.5 g, 31.5 mmol) in MeOH (100 mL) were prepared and NaBH₄ (2.38 g, 62.9 mmol) was added to both at about 0° C., then the mixture was stirred at rt for about 2 h. Water (100 mL) was added to quench the reaction. The reaction mixtures were concentrated under reduced pressure and the residue extracted with EtOAc (3×100 mL). The organic were combined dried over MgSO₄, filtered, concentrated under reduced pressure and the residue was purified by preparative HPLC (Table 1, Method al) to give (1r,4r)-4-((4-Bromopyridin-2-yl)oxy)cyclohexan-1-ol (5.87 g, yield 69%); ¹H NMR (DMSO-d₆, 400 MHz) δ 1.19-1.52 (m, 4H), 1.73-2.06 (m, 4H), 3.51 (td, J=9.15, 4.63 Hz, 1H), 4.58 (d, J=3.97 Hz, 1H), 4.87-4.99 (m, 1H), 7.04 (s, 1H), 7.18 (d, J=5.29 Hz, 1H), 8.06 (d, J=5.73 Hz, 1H), LC/MS (Table 1, Method ak) $R_f$=2.9 min; MS m/z: 272, 274 (M+H)⁺ and (1s, 4s)-4-((4-bromopyridin-2-yl)oxy)cyclohexanol (5.34 g, yield 61%); ¹H NMR (DMSO-d₆, 400 MHz) δ 1.47-1.93 (m, 8H), 3.62 (d, J=3.53 Hz, 1H), 4.49 (d, J=3.53 Hz, 1H), 4.95-5.08 (m, 1H), 7.05 (s, 1H), 7.16 (d, J=4.85 Hz, 1H), 8.04 (d, J=5.29 Hz, 1H), LC/MS (Table 1, Method ak) $R_t$=2.86 min; MS m/z: 272, 274 (M+H)$^+$.

Preparation #100

((1R,4R)-4-(((4-Bromopyridin-2-yl)oxy)methyl)cyclohexyl)methanol

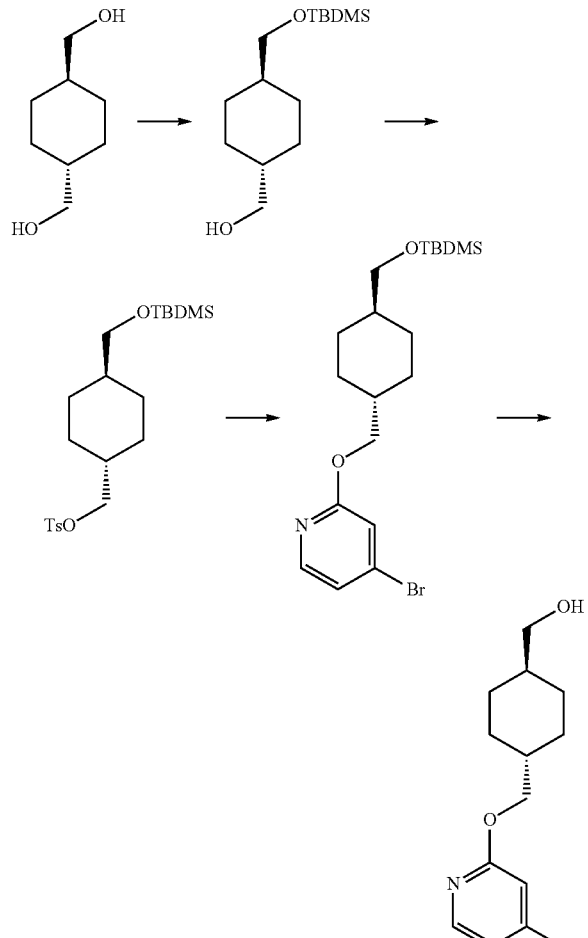

Step 1: ((1R,4R)-4-(((tert-Butyldimethylsilyl)oxy)methyl)cyclohexyl)methanol

To a 500-mL flask containing (1R,4R)-cyclohexane-1,4-diyldimethanol (80 g, 555 mmol) and 1H-imidazole (37.8 g, 555 mmol) in DMF (400 mL) was added to a solution of tert-butylchlorodimethylsilane (84 g, 555 mmol) in DMF (400 mL) at about 0° C. After addition, the reaction was allowed to stir at about 25° C. for about 16 h. The solution was poured into ice water (200 mL) and extracted with MTBE (3×100 mL). The organics were combined, concentrated in vacuo, and purified by flash chromatography on silica gel (1:2 EtOAc/petroleum ether) to afford the title compound (68 g, 45.1%); $^1$H NMR (400 MHz, CDCl$_3$) δ 0.03 (s, 6 H) 0.86-0.96 (m, 13 H) 1.34-1.58 (m, 3 H) 1.81 (d, J=8.61 Hz, 4 H) 3.42 (dd, J=17.61, 6.26 Hz, 4 H)

Step 2: ((1R,4R)-4-(((tert-Butyldimethylsilyl)oxy)methyl) cyclohexyl)methyl4-methylbenzenesulfonate To a flask containing ((1R,4R)-4-(((tert-butyldimethylsilyl)oxy)methyl)cyclohexyl) methanol (74 g, 272 mmol) and pyridine (64.5 g, 816 mmol) in DCM (800 mL) was added 4-methylbenzene-1-sulfonyl chloride (67.4 g, 354 mmol) at about 20° C. After addition, the reaction was allowed to stir at about 25° C. for about 16 h. The solution was poured into ice water (300 mL) and extracted with MTBE (3×150 mL). The organic were combined, washed with 1N HCl (2×150 mL), brine (3×200 mL), dried over Na$_2$SO$_4$, filtered, concentrated in vacuo, and purified by flash chromatography on silica gel (1:2 EtOAc/petroleum ether) to afford the title compound (90 g, 76%); $^1$H NMR (400 MHz, CDCl$_3$) δ 0.00 (s, 6 H) 0.89 (br. s., 13 H) 1.36 (d, J=3.09 Hz, 1 H) 1.59 (dd, J=6.39, 2.87 Hz, 1 H) 1.69-1.79 (m, 4 H) 2.43 (s, 3 H) 3.36 (d, J=6.17 Hz, 2 H) 3.80 (d, J=6.17 Hz, 2 H) 7.32 (d, J=7.94 Hz, 2 H) 7.76 (d, J=7.94 Hz, 2 H).

Step 3: 4-Bromo-2-(((1R,4R)-4-(((tert-butyldimethylsilyl)oxy)methyl)cyclohexyl)methoxy)pyridine The mixture of ((1R,4R)-4-(((tert-butyldimethylsilyl)oxy)methyl)cyclohexyl)methyl 4-methylbenzenesulfonate (45.8 g, 106 mmol), Cs$_2$CO$_3$ (43.0 g, 132 mmol) and 4-bromopyridin-2-ol (15.3 g, 88 mmol) in DMF (180 mL) was stirred at about 25° C. for about 50 h, then stirred at about 45° C. for about 16 h. The mixture was filtered and the filtrate was concentrated under reduced pressure. The residue was dissolved in EtOAc (500 mL), washed with water water (100 mL), brine (3×150 mL), dried over Na$_2$SO$_4$, and concentrated under reduced pressure to give crude product which was purified by flash chromatography on silica gel (1:20-1:5 EtOAc/petroleum ether) to afford the title compound (20 g, 52%); $^1$H NMR (400 MHz, CDCl$_3$) δ 0.04 (s, 6 H) 0.89 (s, 9 H) 0.93-1.12 (m, 4 H) 1.37-1.51 (m, 1 H) 1.65-1.77 (m, 1 H) 1.78-1.94 (m, 4 H) 3.41 (d, J=6.26 Hz, 2 H) 4.08 (d, J=6.65 Hz, 2 H) 6.94 (s, 1 H) 6.99 (d, J=5.48 Hz, 1 H) 7.96 (d, J=5.48 Hz, 1 H).

Step 4: ((1R,4R)-4-(((4-Bromopyridin-2-yl)oxy) methyl)cyclohexyl)methanol

The mixture of 4-bromo-2-(((1R,4R)-4-(((tert-butyldimethylsilyl)oxy)methyl)cyclohexyl) methoxy)pyridine (20.4 g, 46.8 mmol) and HCl (204 mL, 612 mmol) in THF (408 mL) was stirred at about 25° C. for about 2 h. NaHCO$_3$ was added to the mixture to neutralize to pH 7. The mixture was extracted with EtOAc (3×50 mL), the organics were combined, washed with brine (3×25 mL), dried over Na$_2$SO$_4$, and concentrated to give the crude product which was washed with petroleum ether (3×50 mL) to give the title compound (12.5 g, 87%); $^1$H NMR (400 MHz, CDCl$_3$) δ 0.85-1.05 (m, 4 H) 1.28 (br. s., 1H) 1.34-1.45 (m, 1 H) 1.59-1.71 (m, 1 H) 1.72-1.88 (m, 4 H) 3.38 (d, J=6.17 Hz, 2 H) 4.00 (d, J=6.62 Hz, 2 H) 6.85 (s, 1 H) 6.90 (d, J=5.29 Hz, 1 H) 7.86 (d, J=5.29 Hz, 1 H), LC/MS (Table 1, Method ak) $R_t$=2.86 min; MS m/z: 272, 274 (M+H)$^+$.

Preparation #101

(R)-2-(tert-Butoxy)-1-(2-methyl-4-(5-(4,4,5,5-tetramethyl-1,3,2-dioxaborolan-2-yl)pyrimidin-2-yl)piperazin-1-yl)ethanone

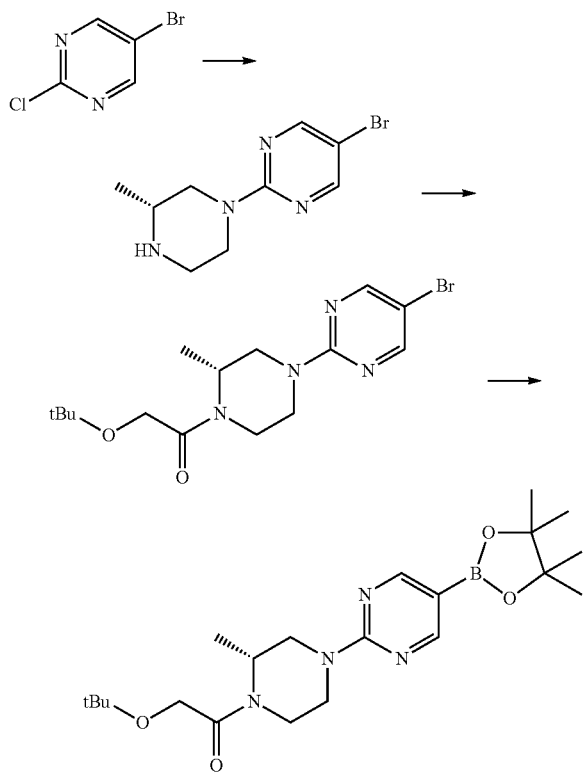

Step 1: (R)-5-Bromo-2-(3-methylpiperazin-1-yl)pyrimidine

EtOH (250 mL) was added to a mixture of 5-bromo-2-chloropyrimidine (5 g, 25.8 mmol) and (R)-2-methylpiperazine (2.74 g, 27.4 mmol) followed by the addition of TEA (9.98 mL, 71.6 mmol) under a nitrogen atmosphere. The reaction was stirred at about 78° C. for about 8 h. The reaction was cooled to about rt and concentrated under reduced pressure. The residue was triturated with 20:1 DCM/MeOH (150 mL) and stirred for 30 min. The solid was collected by filtration and dried under vacuum to afford title compound (5 g, 75%) as the HCl salt; $^1$H NMR (400 MHz, DMSO-$d_6$) δ 9.66 (br. s., 2H), 8.53 (s, 2H), 4.53 (d, J=13.7 Hz, 2H), 3.34-3.20 (m, 3H), 3.18-3.08 (m, 1H), 3.03-2.92 (m, 1H), 1.29 (d, J=6.2 Hz, 3H).

Step 2: (R)-1-(4-(5-Bromopyrimidin-2-yl)-2-methylpiperazin-1-yl)-2-(tert-butoxy)ethanone Five flasks were each charged with of 2-(tert-butoxy)acetic acid (5.14 g, 38.9 mmol), (R)-5-bromo-2-(3-methylpiperazin-1-yl)pyrimidine (10 g, 38.9 mmol), HOBT (6.25 g, 40.8 mmol), and EDC (7.83 g, 40.8 mmol) in DCM (120 mL). DIEA (25.1 g, 194 mmol) was added to each reaction mixture. The five reactions were stirred at about 25° C. for about 22 h. The reaction mixtures were combined and washed with sat. NaHCO$_3$ (2×500 mL), then with sat. NH$_4$Cl (2×500 mL), and water (500 mL). The organic layer was dried over Na$_2$SO$_4$, filtered and concentrated under reduced pressure. The crude product was purified by flash chromatography on silica gel (4-20% EtOAc/petroleum ether) to afford (28 g, 38%); $^1$H NMR (400 MHz, CDCl$_3$) δ 8.28 (s, 2H), 4.84-4.37 (m, 3H), 4.17-3.88 (m, 3H), 3.49-2.84 (m, 3H), 1.23 (s, 12H).

Step 3: (R)-2-(tert-Butoxy)-1-(2-methyl-4-(5-(4,4,5,5-tetramethyl-1,3,2-dioxaborolan-2-yl)pyrimidin-2-yl)piperazin-1-yl)ethanone Two flasks were each charged with (R)-1-(4-(5-bromopyrimidin-2-yl)-2-methylpiperazin-1-yl)-2-(tert-butoxy)ethanone (5 g, 13.47 mmol), KOAc (4.23 g, 43.1 mmol) and 4,4,4',4',5,5,5',5'-octamethyl-2,2'-bi(1,3,2-dioxaborolane) (10.26 g, 40.4 mmol) in 1,4-dioxane (60 mL) and degassed with a stream of nitrogen. PdCl$_2$(dppf) (0.69 g, 0.94 mmol) was added to each reaction mixture and they were further degassed for about 5 min. The mixtures were heated at about 95° C. for about 5 h. The two mixtures were cooled to about rt and combined. The solids were filtered off and rinsed with EtOAc. The filtrate was concentrated under reduced pressure and the residue was purified by column chromatography on silica gel (0-20% EtOAc in petroleum ether/DCM (1:1)) to give a crude product. The crude product was triturated with 5% of EtOAc in petroleum ether (50 mL) and stirred for 30 min. The solid was collected by filtration and dried under vacuum to give the title compound (5 g, 44% yield); $^1$H NMR (400 MHz, CDCl$_3$) δ 8.59 (s, 2H), 4.88-4.36 (m, 3H), 4.18-3.87 (m, 3H), 3.47-2.86 (m, 3H), 1.32 (s, 12H), 1.25-1.10 (m, 12H).

Preparation #102

(S)-2-(tert-Butoxy)-1-(2-methyl-4-(5-(4,4,5,5-tetramethyl-1,3,2-dioxaborolan-2-yl)pyrimidin-2-yl)piperazin-1-yl)ethanone

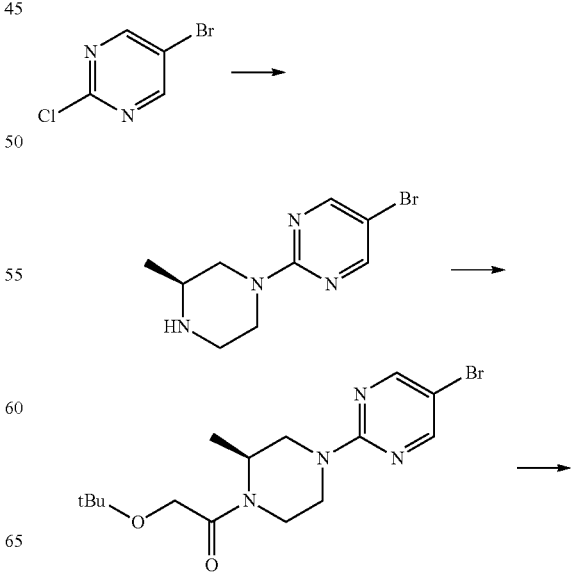

-continued

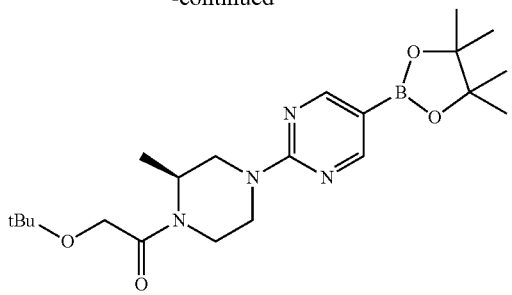

Step 1: (S)-5-Bromo-2-(3-methylpiperazin-1-yl)pyrimidine

The reaction was performed using (S)-2-methylpiperazine in a similar fashion to Preparation #101, step 1 to give the title compound (72%); $^1$H NMR (400 MHz, DMSO-$d_6$) δ 9.69 (br. s., 1H), 8.52 (s, 2H), 4.52 (d, J=13.7 Hz, 2H), 3.46-3.32 (m, 1H), 3.26 (d, J=15.0 Hz, 2H), 3.18-3.06 (m, 1H), 3.04-2.91 (m, 1H), 1.43-1.16 (m, 3H).

Step 2: (S)-1-(4-(5-Bromopyrimidin-2-yl)-2-methyl-piperazin-1-yl)-2-(tert-butoxy)ethanone The reaction was performed using (S)-5-bromo-2-(3-methylpiperazin-1-yl)pyrimidine in a similar fashion to Preparation #101, step 2 to give the title compound (41%); $^1$H NMR (400 MHz, CDCl$_3$) δ 8.30 (s, 2H), 4.89-3.92 (m, 6H), 3.51-2.84 (m, 3H), 1.28-1.14 (m, 12H).

Step 3: (S)-2-(tert-Butoxy)-1-(2-methyl-4-(5-(4,4,5,5-tetramethyl-1,3,2-dioxaborolan-2-yl)pyrimidin-2-yl)piperazin-1-yl)ethanone The reaction was performed using (S)-1-(4-(5-bromopyrimidin-2-yl)-2-methylpiperazin-1-yl)-2-(tert-butoxy)ethanone in a similar fashion to Preparation #101, step 3 to give the title compound (87%); $^1$H NMR (400 MHz, CDCl$_3$) δ 8.59 (s, 2H), 4.89-3.92 (m, 6H), 3.49-2.84 (m, 3H), 1.32 (s, 12H), 1.27-1.10 (m, 12H).

Preparation #103

2'-Bromo-6',8'-dihydrospiro[isochroman-4,9'-pyrido[3',2':4,5]imidazo[2,1-c][1,4]oxazine]

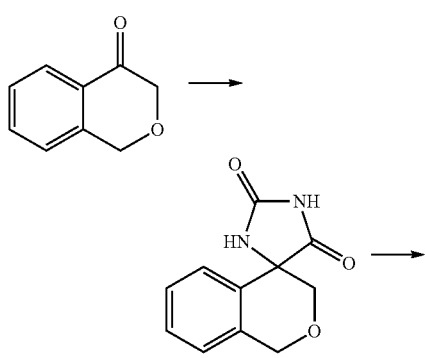

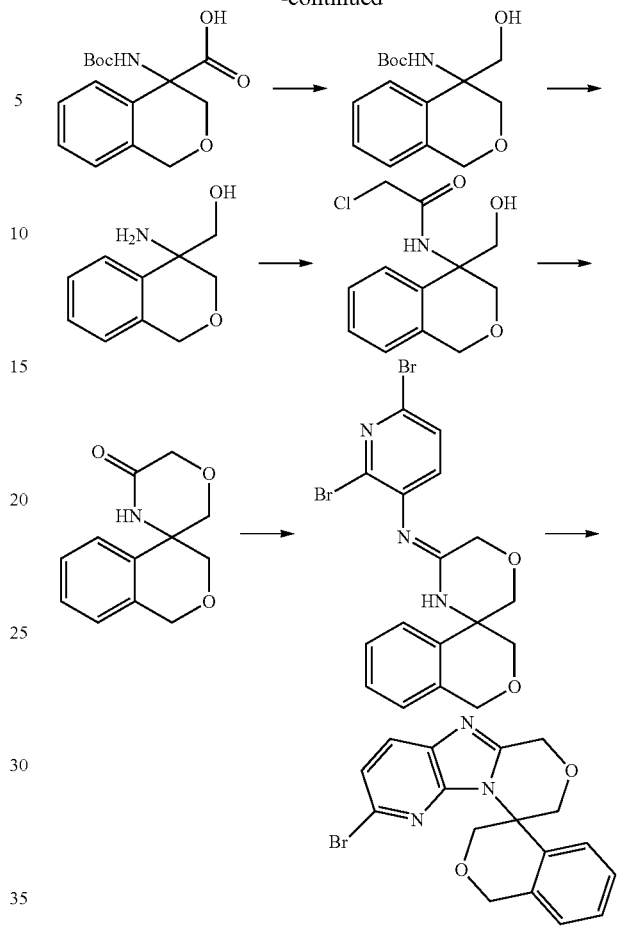

Step 1: Spiro[imidazolidine-4,4'-isochroman]-2,5-dione

To a solution of isochroman-4-one 1 (20 g, 135 mmol) in EtOH (150 mL) and water (150 mL) was added (NH$_4$)$_2$CO$_3$ (51.9 g, 540 mmol) and KCN (13.18 g, 202 mmol) at about 20° C. The resulting mixture was heated to about 65° C. for about 48 h. The mixture was concentrated under reduced pressure to 150 mL and filtered. The solid was dried under reduced pressure to give the title compound (20 g, 68%); $^1$H NMR (400 MHz, DMSO-$d_6$): δ 10.96 (br. s., 1H), 8.68 (s, 1H), 7.34-7.28 (m, 2H), 7.16-7.14 (m, 2H), 4.79-4.71 (m, 2H), 4.02-3.95 (m, 2H).

Step 2: 4-((tert-Butoxycarbonyl)amino)isochromane-4-carboxylic acid

To a solution of spiro[imidazolidine-4,4'-isochroman]-2,5-dione (20 g, 92 mmol) in water (140 mL) was added KOH (36.0 g, 642 mmol) at 20° C. The resulting mixture was heated to about 120° C. for about 72 h. Then the mixture was cooled to about 30° C. and di-tert-butyl dicarbonate (40.0 g, 183 mmol) was added. The mixture was further stirred at about 30° C. for about 12 h. The mixture was acidified by addition of 4 N HCl (186 mL) with stirring and then transferred to a separatory funnel with DCM (400 mL) and water (100 mL). The organic phase was separated amd concentrated under reduced pressure to get a residue, which was taken up in MBTE (140 mL) and washed with 1 N NaOH (367 mL). The aqueous phase was washed with MBTE. The aqueous phase was collected acidified with 1 M HCl (459 mL) and extracted with DCM (2×500 mL). The organics were combined, dried over $Na_2SO_4$, filtered and concentrated under reduced pressure to obtain the title compound (23 g, 86%); $^1$H NMR (400 MHz, DMSO-$d_6$): δ 12.82 (br. s., 1H), 7.55-7.53 (d, J=8.4 Hz, 1H), 7.32 (br. s., 1H), 7.29-7.27 (m, 2H), 7.08-7.07 (m, 1H), 4.69 (s, 2H), 4.21-4.12 (m, 2H), 1.38 (s, 9H).

Step 3: tert-Butyl (4-(hydroxymethyl)isochroman-4-yl)carbamate

To a solution of 4-((tert-butoxycarbonyl)amino)isochromane-4-carboxylic acid (10 g, 34.1 mmol) in anhydrous THF (300 mL) was added aluminum(III) lithium hydride (2.85 g, 75 mmol) in portions below about −5° C. Then the mixture was stirred at about 35° C. for about 12 h. The mixture was quenched with water (2.85 mL), 15% NaOH (2.85 mL) and water (8.55 mL) then filtered. The filtrate was concentrated under reduced pressure to get a residue, which was purified by flash column chromatography on silica gel (2-20% EtOAc/petroleum ether) to give the title compound (6.5 g, 68%); $^1$H NMR (400 MHz, DMSO-$d_6$): δ 7.27-7.25 (d, J=7.1 Hz, 1H), 7.23-7.09 (m, 2H), 7.01-7.00 (m, 1H), 6.56 (br. s., 1H), 5.04 (br. s., 1H), 4.72-4.63 (m, 2H), 3.99 (br. s., 2H), 3.57-3.52 (dd, J=7.3, 11.2 Hz, 1H), 3.38-3.33 (dd, J=5.5, 11.2 Hz, 1H), 1.30-0.97 (m, 9H).

Step 4: (4-Aminoisochroman-4-yl)methanol

To a solution of tert-butyl (4-(hydroxymethyl)isochroman-4-yl)carbamate acid (13 g, 46.5 mmol) in MBTE (260 mL) was added anhydrous MeOH (15.1 mL, 372 mmol) and acetyl chloride (7.41 mL, 140 mmol) at about 0° C. The resulting mixture was stirred at about 20° C. for about 12 h. The resulting solid, filtered, and dried under vacuum to give the title compound (6.5 g, 78%); $^1$H NMR (400 MHz, DMSO-$d_6$): δ 8.62 (br. s., 2H), 7.73-7.71 (m, 1H), 7.38-7.32 (m, 2H), 7.18-7.15 (m, 1H), 5.82 (br. s., 1H), 4.76 (s, 2H), 4.10-4.07 (d, J=11.9 Hz, 1H), 3.83-3.80 (m, 2H), 3.78-3.69 (m, 1H).

Step 5: 2-Chloro-N-(4-(hydroxymethyl)isochroman-4-yl)acetamide

To a solution of (4-aminoisochroman-4-yl)methanol (6.5 g, 36.3 mmol) in anhydrous THF (20 mL) was added TEA (11.12 mL, 80 mmol) and 2-chloroacetyl chloride (3.69 g, 32.6 mmol) below about −5° C. The resulting mixture was stirred at about 25° C. for about 2 h. The mixture was washed with water (50 mL) and extracted with EtOAc (3×30 mL). The organic layer was dried over $Na_2SO_4$, filtered, and concentrated under reduced pressure to get a residue, which was purified by flash column chromatography on silica gel (2-35% EtOAc/petroleum ether) to give the title compound (4.3 g, 46%); $^1$H NMR (400 MHz, DMSO-$d_6$): δ 8.06 (s, 1H), 7.26-7.24 (m, 1H), 7.18-7.16 (dd, J=3.3, 5.7 Hz, 2H), 7.06-6.99 (m, 1H), 5.37-5.34 (t, J=5.3 Hz, 1H), 4.70 (s, 2H), 4.11 (s, 2H), 4.06-4.03 (m, 1H), 3.98-3.96 (m, 1H), 3.70-3.96 (dd, J=5.1, 11.3 Hz, 1H), 3.47-3.43 (dd, J=5.1, 11.0 Hz, 1H).

Step 6: Spiro[isochromane-4,3'-morpholin]-5'-one

To a solution of 2-chloro-N-(4-(hydroxymethyl)isochroman-4-yl)acetamide 7 (1.075 g, 4.20 mmol) in 2-methylbutan-2-ol (30 mL) was added potassium 2-methylpropan-2-olate (1.415 g, 12.61 mmol) at about 20° C. The resulting mixture was stirred at about 25° C. for about 20 min. Then to the mixture was added MeOH (5 mL) and water (100 mL). The mixture was extracted with MTBE (30 mL) and the organic layer was washed with brine (100 mL). Three additional reactions were set up as described above. All four organic phases were combined, dried over with $Na_2SO_4$, filtered, and concentrated under reduced pressure to afford the title compound (3.6 g, 98%); $^1$H NMR (400 MHz, DMSO-$d_6$): δ 8.30 (s, 1H), 7.47-7.45 (d, J=7.5 Hz, 1H), 7.35-7.25 (m, 2H), 7.09-7.07 (d, J=7.5 Hz, 1H), 4.79-4.67 (m, 2H), 4.17-4.05 (m, 3H), 3.97-3.94 (d, J=11.9 Hz, 1H), 3.51-3.48 (m, 2H).

Step 7: (E)-N-(2,6-Dibromopyridin-3-yl)spiro[isochromane-4,3'-morpholin]-5'-imine To a solution of spiro[isochromane-4,3'-morpholin]-5'-one (1.8 g, 8.21 mmol) in 1,2-dichloroethane (32 mL) was added $POCl_3$ (1.51 g, 9.85 mmol) at about 20° C. and then the mixture was stirred for about 5 min. 2,6-Dibromopyridin-3-amine (2.48 g, 9.85 mmol) was added and the reaction mixture was heated to about 70° C. for about 2 h. One additional reaction was set up as described above. The two reaction mixtures were combined after cooling to about rt. The mixture was filtered and washed with 1,2-dichloroethane (15 mL), then the filtrate was transferred to a separatory funnel with DCM (20 mL). The mixture was washed with water (2×30 mL) and brine (2×30 mL). The organic phase was collected, dried over $Na_2SO_4$, filtered, and concentrated under reduced pressure to give the title compound (7 g, 94%); $^1$H NMR (400 MHz, DMSO-$d_6$): δ 10.15 (br. s., 1H), 7.98-7.87 (m, 2H), 7.67-7.62 (m, 1H), 7.38-7.31 (m, 2H), 7.17-7.11 (m, 1H), 5.05-4.92 (m, 2H), 4.83-4.76 (m, 1H), 4.72-4.64 (m, 1H), 4.17 (dd, J=5.1, 11.7 Hz, 2H), 3.81 (d, J=11.9 Hz, 1H), 3.56 (d, J=11.0 Hz, 1H).

Step 8: 2'-Bromo-6'H,8'H-spiro[isochromane-4,9'-pyrido[3',2':4,5]imidazo[2,1-c][1,4]oxazine]

To a solution of (E)-N-(2,6-dibromopyridin-3-yl)spiro[isochromane-4,3'-morpholin]-5'-imine (3.5 g, 7.72 mmol) in MeCN (52 mL) and DMSO (13 mL) was added N1,N1,N2,N2-tetramethylethane-1,2-diamine (0.449 g, 3.86 mmol), $K_2CO_3$ (1.28 g, 9.27 mmol) and CuI (0.147 g, 0.772 mmol) under $N_2$ at about 20° C. The resulting mixture was heated to about 75° C. for about 12 h. One additional reaction was set up as described above. Both mixtures were combined and concentrated to remove MeCN. To the residue was added water (100 mL) with stirring. After about 10 mins, the solid was filtered. The collected solid was dissolved in DCM (100 mL) and washed with brine (50 mL). The organic phase was dried over $Na_2SO_4$, filtered, and concentrated under reduced pressure to get crude product, which was purified by preparative HPLC (Table 1, Method ao) to afford the title compound (1.26 g, 42%); $^1$H NMR (400 MHz, $CDCl_3$): δ 7.80-7.78 (d, J=8.4 Hz, 1H), 7.30-7.24 (m, 2H), 7.15-7.09 (m, 2H), 6.76-6.74 (d, J=7.9 Hz, 1H), 5.18-5.02 (m, 3H), 4.92-4.89 (m, 1H), 4.63-4.60 (d, J=12.3 Hz, 1H), 4.46-4.43 (m, 1H), 4.35-4.33 (m, 1H), 3.86-3.82 (dd, J=1.8, 12.3 Hz, 1H), LC/MS (Table 1, Method af) $R_t$=2.26 min; MS m/z: 372, 374 $(M+H)^+$.

Preparation #104 tert-Butyl (2-(5-bromopyridin-2-yl)propan-2-yl)carbamate

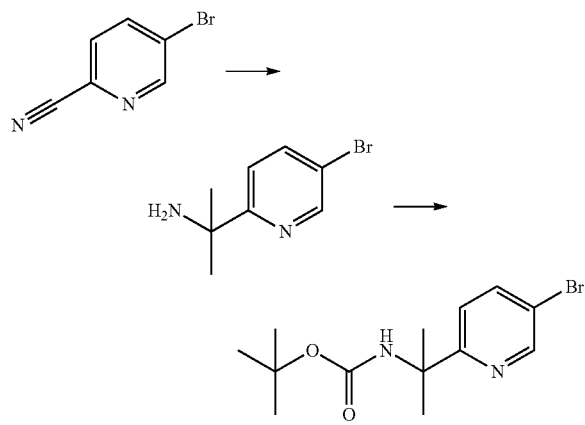

Step 1: 2-(5-Bromopyridin-2-yl)propan-2-amine

Methyl magnesium bromide (3 M in Et$_2$O) (4.00 mL, 12.0 mmol) was slowly added to a solution of 5-bromopicolinonitrile (1.00 g, 5.46 mmol) in toluene (13 mL) at about 0° C. After completion of addition, the ice bath was removed and the reaction was heated at about 100° C. for about 16 h. The reaction was cooled to rt then 2-methyl tetrahydrofuran (6 mL) was added and heating was continued at about 100° C. for about 1 h. The reaction was cooled to rt then methyl magnesium bromide (3 M in Et$_2$O) (4.00 mL, 12.0 mmol) was added. The reaction was heated at 100° C. for about 12 h. The reaction was allowed to cool to rt then was added carefully to ice cold stirring 2 N aq. HCl (50 mL, 100 mmol). The aqueous solution was extracted with EtOAc (2×50 mL) then the aqueous layer was basified with 5 N aq. sodium hydroxide (25.0 mL, 125 mmol). The aqueous layer was extracted with EtOAc (2×50 mL). The combined organic extracts were washed with sat. aq. NaCl (25 mL), dried over Na$_2$SO$_4$, filtered and concentrated under reduced pressure to give the title compound (0.53 g, 45%); LC/MS (Table 1, Method y) R$_t$=0.21 min; MS m/z: 215 and 217 (M+H)$^+$.

Step 2: tert-Butyl (2-(5-bromopyridin-2-yl)propan-2-yl)carbamate

A solution of sodium carbonate (0.197 g, 1.86 mmol) in water (3.0 mL) was added to a mixture of 2-(5-bromopyridin-2-yl)propan-2-amine (0.400 g, 1.86 mmol) in 1,4-dioxane (5.0 mL) and water (5.0 mL). The mixture was cooled in an ice bath then di-tert-butyl dicarbonate (0.406 g, 1.86 mmol) was added in one portion. About 5 min after the addition, the ice bath was removed and the reaction was stirred at rt for about 16 h. The reaction was extracted with EtOAc (2×20 mL). The combined organic layers were dried over Na$_2$SO$_4$, filtered and concentrated under reduced pressure. The residue was purified on silica gel using a gradient of 5-20% EtOAc in heptane to give the title compound (0.136 g, 23%); LC/MS (Table 1, Method y) R$_t$=1.52 min; MS m/z: 315 and 317 (M+H)$^+$.

Preparation #105

2'-Bromo-2,3-dihydro-6'H,8'H-spiro[indene-1,9'-pyrido[3',2':4,5]imidazo[2,1-c][1,4]oxazin]-3-ol

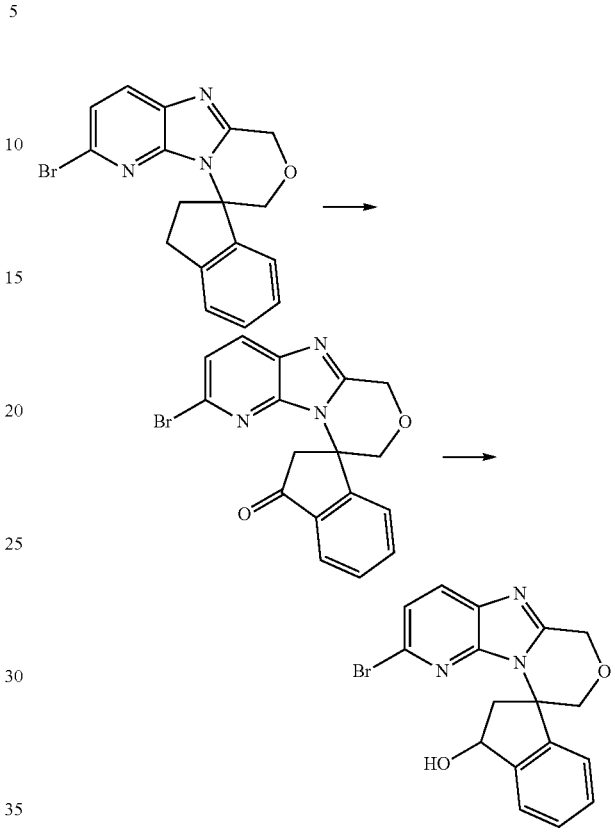

Step 1: 2'-Bromo-6'H,8'H-spiro[indene-1,9'-pyrido[3',2':4,5]imidazo[2,1-c][1,4]oxazin]-3(2H)-one In a 4 mL vial was mixed 2'-bromo-2,3,6',8'-tetrahydrospiro[indene-1,9'-pyrido[3',2':4,5]imidazo[2,1-c][1,4]oxazine](301 mg, 0.84 mmol, Preparation #92) and potassium peroxydisulfate (340 mg, 1.3 mmol) in MeCN (4.2 mL) and water (4.2 mL) to give a colorless solution. 1-(chloromethyl)-4-fluoro-1,4-diazabicyclo[2.2.2]octane-1,4-diium tetrafluoroborate (450 mg, 1.3 mmol) was added, and the reaction was stirred at rt for about 1 h before being stirred at about 75° C. for about 18 h. The reaction was purified by normal phase chromatography on silica gel (10-100% EtOAc/heptanes) to afford the title compound (78 mg, 25% yield); LC/MS (Table 1, method g) R$_t$=0.74 min; MS m/z: 370, 372 (M+H)$^+$.

Step 2: 2'-Bromo-2,3-dihydro-6'H,8'H-spiro[indene-1,9'-pyrido[3',2':4,5]imidazo[2,1-c][1,4]oxazin]-3-ol In a 4 mL vial was mixed 2'-bromo-6'H,8'H-spiro[indene-1,9'-pyrido[3',2':4,5]imidazo[2,1-c][1,4]oxazin]-3(2H)-one (31 mg, 0.081 mmol) and sodium cyanoborohydride (31 mg, 0.48 mmol) in MeOH (0.16 mL) to give a yellow solution. The reaction was stirred at rt for about 18 h. The reaction purified by reverse phase chromatography using a gradient of MeCN (A) and 0.1% TFA in water (B) at a flow rate of 50 mL/min (0-0.5 min 5% A, 0.5-8.5 min linear gradient 05-100% A, 8.7-10.7 min 100% A, 10.7-11 min linear gradient 100-05% A) to yield the title compound (31 mg, 95%); LC/MS (Table 1, method g) $R_t$=0.79 min; MS m/z: 372, 374 (M+H)$^+$.

Preparation #106

3-Methoxy-3-methyl-1-(4-(4,4,5,5-tetramethyl-1,3,2-dioxaborolan-2-yl)-3,6-dihydropyridin-1(2H)-yl)butan-1-one

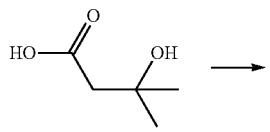

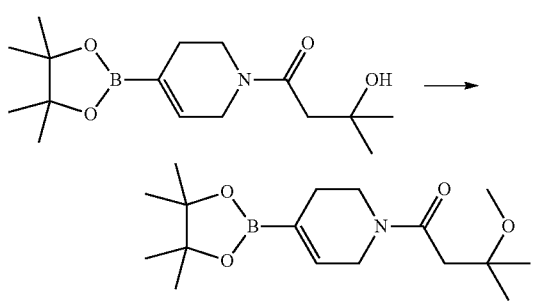

Step #1: 3-Hydroxy-3-methyl-1-(4-(4,4,5,5-tetramethyl-1,3,2-dioxaborolan-2-yl)-3,6-dihydropyridin-1(2H)-yl)butan-1-one To a solution of 3-hydroxy-3-methylbutanoic acid (7.94 g, 67.2 mmol), 1-ethyl-3-(3-dimethylaminopropyl)carbodiimide hydrochloride (14.05 g, 73.3 mmol) and N,N-dimethylpyridin-4-amine (26.1 g, 214 mmol) in DCM (700 mL) was added 4-(4,4,5,5-tetramethyl-1,3,2-dioxaborolan-2-yl)-1,2,3,6-tetrahydropyridine, HCl (15 g, 61.1 mmol). The reaction was stirred at 25° C. for 4 h. The reaction was diluted with DCM (500 mL), washed with 1N HCl (400 mL) and brine (400 mL), dried over Na$_2$SO$_4$, filtered, and concentrated under reduced pressure to give crude product, which was purified by column chromatography on silica gel (0-100% EtOAc/hexane) to give the title compound (4 g, 17.8%); 1H NMR (400 MHz, CDCl$_3$-d): δ 1.16-1.35 (m, 18 H), 2.20-2.30 (m, 2 H), 2.42 (d, J=15.44 Hz, 2H), 3.46 (t, J=5.73 Hz, 1 H), 3.63 (t, J=5.51 Hz, 1 H), 3.97 (q, J=2.65 Hz, 1 H), 4.12 (q, J=2.65 Hz, 1 H), 5.27 (d, J=12.35 Hz, 1 H), 6.35-6.54 (m, 1 H).

Step #2: 3-Methoxy-3-methyl-1-(4-(4,4,5,5-tetramethyl-1,3,2-dioxaborolan-2-yl)-3,6-dihydropyridin-1(2H)-yl)butan-1-one To a solution of 3-hydroxy-3-methyl-1-(4-(4,4,5,5-tetramethyl-1,3,2-dioxaborolan-2-yl)-5,6-dihydropyridin-1(2H)-yl)butan-1-one (2 g, 6.47 mmol) in THF (40 mL) was added NaH (0.388 g, 9.70 mmol) in portions at 0° C. and the reaction suspension was warmed and stirred at 20° C. for 30 min. Then the reaction suspension was cooled to 0° C. and a solution of iodomethane (1.84 g, 12.94 mmol) in THF (10 mL) was added dropwise. The reaction mixture was heated to 20° C. for 2 h. The mixture was poured into sat. NH$_4$Cl (100 mL) and a solid precipitated. The mixture was filtered and washed with water (3×50 mL) to give the crude product, which was purified by column chromatography on silica gel (0-100% EtOAc/hexane) to give the title compound (0.3 g, 13.3%); 1H NMR (400 MHz, MeOD-d$_4$): δ 1.22-1.31 (m, 18 H), 2.12-2.26 (m, 2 H), 2.60 (d, J=12.79 Hz, 2 H), 3.14-3.24 (m, 3 H), 3.57-3.65 (m, 2 H), 4.08 (d, J=3.09 Hz, 1 H), 4.20 (d, J=3.09 Hz, 1 H), 6.45 (d, J=8.38 Hz, 1 H).

Example #1

2-(5-(1-Phenyl-2,3-dihydro-1H-benzo[d]pyrrolo[1,2-a]imidazol-7-yl)pyrimidin-2-yl)propan-2-ol

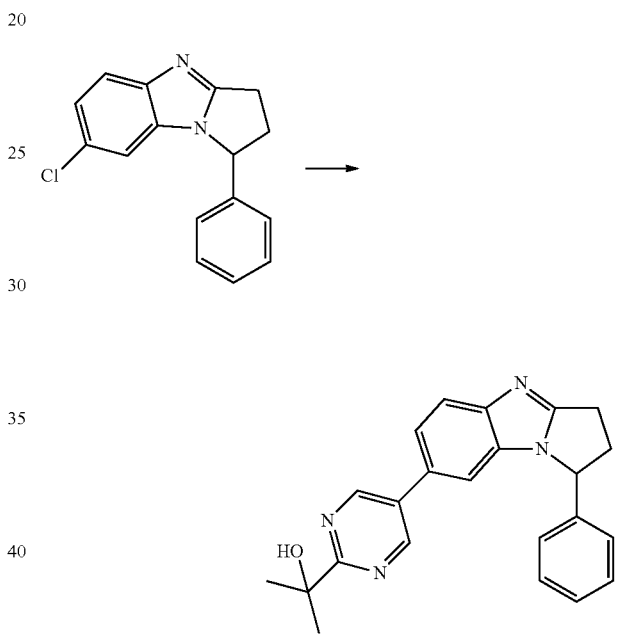

To a microwave tube were added 7-chloro-1-phenyl-2,3-dihydro-1H-benzo[d]pyrrolo[1,2-a]imidazole (0.062 g, 0.231 mmol, Preparation #5, step 1), 2-(5-(4,4,5,5-tetramethyl-1,3,2-dioxaborolan-2-yl)pyrimidin-2-yl)propan-2-ol (0.067 g, 0.254 mmol), PCy$_3$ (0.013 g, 0.046 mmol), Pd(dba)$_3$ (0.021 g, 0.023 mmol) and K$_3$PO$_4$ (0.098 g, 0.461 mmol) in a mixture of 1,4-dioxane (1 mL) and water (0.056 mL). The tube was degassed, purged with N$_2$, and heated at about 140° C. for about 1 h. The solvent was removed and the residue was partitioned between water and DCM. The organic phase was separated and concentrated under reduced pressure. The residue was purified by flash-column chromatography on silica gel (MeOH/DCM 0-10%) to afford the crude product. Analytically pure product was obtained by preparative HPLC (Table 1, Method o). The returned sample was dissolved in DCM and washed with sat. Na$_2$CO$_3$, separated, and the organics concentrated under vacuum to give the product (0.07 g, 82%); LC/MS (Table 1, Method e) $R_t$=1.22 min; MS m/z: 371 (M+H)$^+$. (TNF IC$_{50}$=A).

The compounds shown in Table A were synthesized in a manner similar to Example #1 from the corresponding boronic acid/boronate.

TABLE A

| Boronic acid/boronate | Product | Example # | R$_t$ min (Table 1, Method) | m/z (M + H)$^+$ | TNF IC$_{50}$ |
|---|---|---|---|---|---|
| (4-(N-Methylsulfamoyl)phenyl)-boronic acid | | A.1 | 0.6 (i) | 404 | A |
| (4-(Ethylsulfonyl)phenyl)boronic acid | | A.2 | 0.62 (i) | 403 | A |
| (4-(Morpholinosulfonyl)phenyl)boronic acid | | A.3 | 0.64 (i) | 460 | A |
| (4-(Methylsulfonamidomethyl)-phenyl)boronic acid | | A.4 | 0.6 (i) | 418 | A |
| 4,4,5,5-Tetramethyl-2-(4-(methylsulfonyl)phenyl)-1,3,2-dioxaborolane | | A.5 | 0.6 (i) | 389 | A |
| 4-(4,4,5,5-Tetramethyl-1,3,2-dioxaborolan-2-yl)benzenesulfonamide | | A.6 | 0.55 (i) | 390 | A |

TABLE A-continued

| Boronic acid/boronate | Product | Example # | R$_t$ min (Table 1, Method) | m/z (M + H)$^+$ | TNF IC$_{50}$ |
|---|---|---|---|---|---|
| (4-(Cyanomethyl)phenyl)boronic acid | 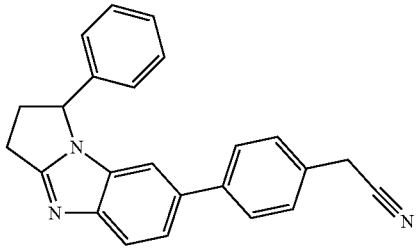 [SMILES: N#CCc1ccc(-c2ccc3nc4n(c3c2)C(c2ccccc2)CC4)cc1] | A.7 | 0.64 (i) | 350 | A |
| (2-Cyclopropylpyrimidin-5-yl)boronic acid | 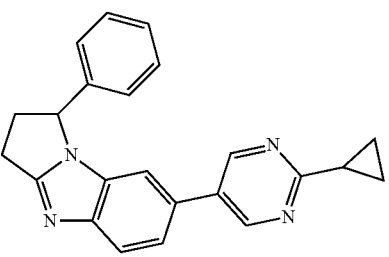 [SMILES: c1ccc(C2CCc3nc4ccc(-c5cnc(C6CC6)nc5)cc4n32)cc1] | A.8 | 0.61 (i) | 353 | A |
| (6-(Ethylsulfonyl)pyridin-3-yl)boronic acid | 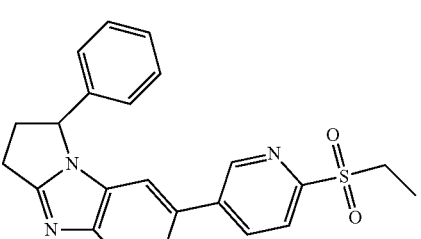 | A.9 | 0.58 (i) | 404 | A |
| N,N-Dimethyl-4-(4,4,5,5-tetramethyl-1,3,2-dioxaborolan-2-yl)benzamide | 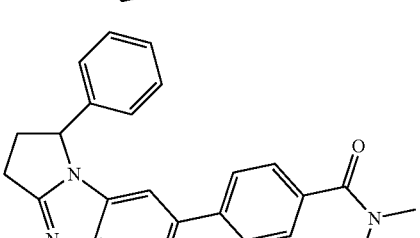 | A.10 | 0.59 (i) | 382 | A |
| (4-(Ethyl(methyl)carbamoyl)-phenyl)boronic acid | 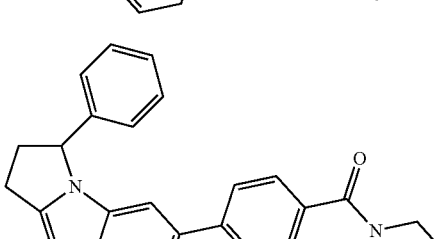 | A.11 | 0.63 (i) | 396 | A |
| N,N-Dimethyl-5-(4,4,5,5-tetramethyl-1,3,2-dioxaborolan-2-yl)pyridin-2-amine | 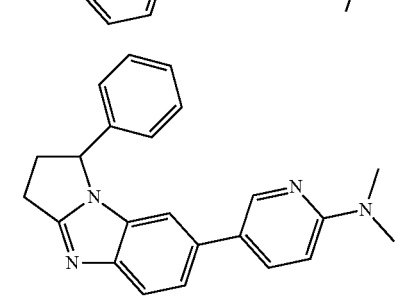 | A.12 | 0.47 (i) | 355 | B |

TABLE A-continued

| Boronic acid/boronate | Product | Example # | R$_t$ min (Table 1, Method) | m/z (M + H)$^+$ | TNF IC$_{50}$ |
|---|---|---|---|---|---|
| 2-Methyl-4-(4,4,5,5-tetramethyl-1,3,2-dioxaborolan-2-yl)pyridine | | A.13 | 0.45 (i) | 326 | B |
| 2-Methyl-5-(4,4,5,5-tetramethyl-1,3,2-dioxaborolan-2-yl)pyridine | | A.14 | 0.45 (i) | 326 | B |
| 3-ethoxy-5-(4,4,5,5-tetramethyl-1,3,2-dioxaborolan-2-yl)pyridine | | A.15 | 0.53 (i) | 356 | B |
| (6-(Methylthio)pyridin-3-yl)boronic acid | | A.16 | 0.63 (i) | 358 | B |
| 1-(5-(4,4,5,5-Tetramethyl-1,3,2-dioxaborolan-2-yl)pyridin-2-yl)piperazine | | A.17 | 0.44 (i) | 396 | B |
| 2-(3-(4,4,5,5-Tetramethyl-1,3,2-dioxaborolan-2-yl)phenoxy)acetonitrile | | A.18 | 0.66 (i) | 366 | B |

TABLE A-continued

| Boronic acid/boronate | Product | Example # | R$_t$ min (Table 1, Method) | m/z (M + H)$^+$ | TNF IC$_{50}$ |
|---|---|---|---|---|---|
| N-Cyclopropyl-4-(4,4,5,5-tetramethyl-1,3,2-dioxaborolan-2-yl)benzamide | | A.19 | 0.6 (i) | 394 | B |
| 1-Methyl-4-(5-(4,4,5,5-tetramethyl-1,3,2-dioxaborolan-2-yl)pyridin-2-yl)piperazine | | A.20 | 0.45 (i) | 410 | B |
| 3-((4-(4,4,5,5-Tetramethyl-1,3,2-dioxaborolan-2-yl)-1H-pyrazol-1-yl)methyl)pyridine | | A.21 | 0.47 (i) | 392 | B |
| Pyridin-3-ylboronic acid | | A.22 | 0.44 (i) | 312 | B |
| (2-Aminopyrimidin-5-yl)boronic acid | | A.23 | 0.55 (i) | 328 | B |
| Pyrimidin-5-ylboronic acid | | A.24 | 0.52 (i) | 313 | B |

TABLE A-continued

| Boronic acid/boronate | Product | Example # | R_t min (Table 1, Method) | m/z (M + H)+ | TNF IC_{50} |
|---|---|---|---|---|---|
| (5-Methylpyridin-3-yl)boronic acid | | A.25 | 0.46 (i) | 326 | B |
| N-((Tetrahydrofuran-2-yl)methyl)-4-(4,4,5,5-tetramethyl-1,3,2-dioxaborolan-2-yl)benzamide | | A.26 | 0.61 (i) | 438 | B |
| 5-(4,4,5,5-Tetramethyl-1,3,2-dioxaborolan-2-yl)pyridin-2-amine | | A.27 | 0.45 (i) | 327 | C |
| 1,5-Dimethyl-4-(4,4,5,5-tetramethyl-1,3,2-dioxaborolan-2-yl)-1H-pyrazole | | A.28 | 0.56 (i) | 329 | C |
| N,N-Dimethyl-3-(4,4,5,5-tetramethyl-1,3,2-dioxaborolan-2-yl)benzamide | | A.29 | 0.6 (i) | 382 | C |

TABLE A-continued

| Boronic acid/boronate | Product | Example # | R, min (Table 1, Method) | m/z (M + H)+ | TNF IC50 |
|---|---|---|---|---|---|
| (3-(Methylsulfonyl)phenyl)-boronic acid | | A.30 | 0.59 (i) | 389 | C |
| 3-(Methylsulfonyl)-5-(4,4,5,5-tetramethyl-1,3,2-dioxaborolan-2-yl)pyridine | | A.31 | 0.54 (i) | 390 | C |
| 2-Methyl-3-(4,4,5,5-tetramethyl-1,3,2-dioxaborolan-2-yl)pyridine | | A.32 | 0.44 (i) | 326 | C |
| (4-(Isopropylsulfonyl)phenyl)-boronic acid | | A.33 | 0.64 (i) | 417 | A |
| 2-(4-(4,4,5,5-Tetramethyl-1,3,2-dioxaborolan-2-yl)phenoxy)acetonitrile | | A.34 | 0.65 (i) | 366 | B |

TABLE A-continued

| Boronic acid/boronate | Product | Example # | R_t min (Table 1, Method) | m/z (M + H)+ | TNF IC_50 |
|---|---|---|---|---|---|
| (4-(Ethylcarbamoyl)phenyl)-boronic acid | | A.35 | 0.6 (i) | 382 | B |
| 4-(4,4,5,5-Tetramethyl-1,3,2-dioxaborolan-2-yl)benzamide | | A.36 | 0.53 (i) | 354 | B |
| 2-(Benzo[d][1,3]dioxol-5-yl)-4,4,5,5-tetramethyl-1,3,2-dioxaborolane | | A.37 | 0.67 (i) | 355 | B |
| 3-Methoxy-5-(4,4,5,5-tetramethyl-1,3,2-dioxaborolan-2-yl)pyridine | | A.38 | 0.49 (i) | 342 | B |
| N-(2-Methoxyethyl)-4-(4,4,5,5-tetramethyl-1,3,2-dioxaborolan-2-yl)benzamide | | A.39 | 0.58 (i) | 412 | B |

TABLE A-continued

| Boronic acid/boronate | Product | Example # | R$_t$ min (Table 1, Method) | m/z (M + H)$^+$ | TNF IC$_{50}$ |
|---|---|---|---|---|---|
| N-Methyl-4-(4,4,5,5-tetramethyl-1,3,2-dioxaborolan-2-yl)benzamide | | A.40 | 0.56 (i) | 368 | B |
| 2-(3-(4,4,5,5-Tetramethyl-1,3,2-dioxaborolan-2-yl)phenyl)acetonitrile | | A.41 | 0.65 (i) | 350 | B |
| (3-(Methylsulfonamidomethyl)-phenyl)boronic acid | | A.42 | 0.61 (i) | 418 | B |
| (3-(Methylcarbamoyl)phenyl)-boronic acid | | A.43 | 0.57 (i) | 368 | B |
| (3-(Ethyl(methyl)carbamoyl)-phenyl)boronic acid | | A.44 | 0.63 (i) | 396 | C |

TABLE A-continued

| Boronic acid/boronate | Product | Example # | R$_t$ min (Table 1, Method) | m/z (M + H)$^+$ | TNF IC$_{50}$ |
|---|---|---|---|---|---|
| N-(2-(Dimethylamino)ethyl)-3-(4,4,5,5-tetramethyl-1,3,2-dioxaborolan-2-yl)benzamide | | A.45 | 0.5 (i) | 425 | C |
| 1-Methyl-5-(4,4,5,5-tetramethyl-1,3,2-dioxaborolan-2-yl)pyridin-2(1H)-one | | A.46 | 0.51 (i) | 342 | C |
| 1-Methyl-3-(4,4,5,5-tetramethyl-1,3,2-dioxaborolan-2-yl)-1H-pyrrole | | A.47 | 0.64 (i) | 314 | C |

The compounds shown in Table B were synthesized in a manner similar to Example #1 from 2-(5-(4,4,5,5-tetramethyl-1,3,2-dioxaborolan-2-yl)pyrimidin-2-yl)propan-2-ol and the corresponding bromides or chlorides.

TABLE B

| Bromide/chloride | Product | Example # | R$_t$ min (Table 1, Method) | m/z (M + H)$^+$ | TNF IC$_{50}$ |
|---|---|---|---|---|---|
| 7-Chloro-1-(3-fluorophenyl)-2,3-dihydro-1H-benzo[d]pyrrolo[1,2-a]imidazole (Preparation #6) | | B.1 | 0.63 (e) | 389 | A |

TABLE B-continued

| Bromide/chloride | Product | Example # | R$_t$ min (Table 1, Method) | m/z (M + H)$^+$ | TNF IC$_{50}$ |
|---|---|---|---|---|---|
| 7-Chloro-1-(2,5-dimethylphenyl)-2,3-dihydro-1H-benzo[d]pyrrolo[1,2-a]imidazole (Preparation #7) | | B.2 | 1.10 (e) | 399 | A |

The compound shown in Table C was synthesized in a manner similar to Example #1 from (S)-7-chloro-1-phenyl-2,3-dihydro-1H-benzo[d]pyrrolo[1,2-a]imidazole (Preparation #5) and the corresponding boronic acid/boronate.

TABLE C

| Boronic acid/boronate | Product | Example # | R$_t$ min (Table 1, Method) | m/z (M + H)$^+$ | TNF IC$_{50}$ |
|---|---|---|---|---|---|
| 4-(5-(4,4,5,5-Tetramethyl-1,3,2-dioxaborolan-2-yl)pyrimidin-2-yl)morpholine | | C.1 | 1.32 (e) | 398 | C |

Example #2

(R)-2-(5-(1-Phenyl-2,3-dihydro-1H-benzo[d]pyrrolo[1,2-a]imidazol-7-yl)pyrimidin-2-yl)propan-2-ol

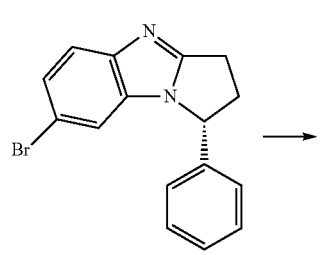

→

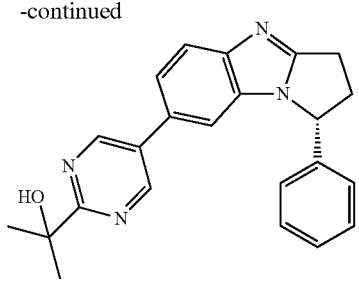

To a vial were added (R)-7-bromo-1-phenyl-2,3-dihydro-1H-benzo[d]pyrrolo[1,2-a]imidazole (0.220 g, 0.702 mmol, Preparation #4), 2-(5-(4,4,5,5-tetramethyl-1,3,2-dioxaborolan-2-yl)pyrimidin-2-yl)propan-2-ol (0.557 g, 2.107 mmol), K$_3$PO$_4$ (0.596 g, 2.81 mmol) in a mixture of 1,4-dioxane (4 mL) and MeOH (2.6 mL). The vial was degassed, Pd(PPh$_3$)$_4$ (0.081 g, 0.070 mmol) was added, purged with $N_2$, and heated at about 110° C. for about 1 h. The reaction was filtered through Celite® and concentrated under reduced pressure. The residue was purified by flash-column chromatography (MeOH/DCM 0-20%) followed by recrystallization from (DCM/heptane) to give the title compound (0.155 g, 60%); LC/MS (Table 1, Method f) $R_t$=0.72 min; MS m/z: 371 (M+H)$^+$. (TNF IC$_{50}$=A).

The compounds shown in Table D were synthesized in a manner similar to Example #2 from 4-(5-(4,4,5,5-tetramethyl-1,3,2-dioxaborolan-2-yl)pyrimidin-2-yl)morpholine and the corresponding bromides or chlorides.

TABLE D

| Bromide/chloride | Product | Example # | $R_t$ min (Table 1, Method) | m/z (M + H)$^+$ | TNF IC$_{50}$ |
|---|---|---|---|---|---|
| 8-Bromo-1-phenyl-1,2,3,4-tetrahydrobenzo[4,5]imidazo[1,2-a]pyridine (Preparation #9, step 1) | | D.1 | 1.29(e) | 412 | A |
| 7-Bromo-1-phenyl-2,3-dihydro-1H-benzo[d]pyrrolo[1,2-a]imidazole (Preparation #4, step 1) | | D.2 | 1.34 (e) | 398 | A |
| (R)-7-Bromo-1-phenyl-2,3-dihydro-1H-benzo[d]pyrrolo[1,2-a]imidazole (Preparation #4) | | D.3 | 1.06 (e) | 398 | A |
| 7-Bromo-4-phenyl-3,4-dihydro-2H-pyrano[2',3':4,5]imidazo[1,2-a]pyridine (Preparation #90) | | D.4 | 0.91 (ab) | 414 | B |

TABLE D-continued

| Bromide/chloride | Product | Example # | R_t min (Table 1, Method) | m/z (M + H)+ | TNF IC_50 |
|---|---|---|---|---|---|
| 7-bromo-4-(2-methoxyphenyl)-3,4-dihydro-2H-pyrano[2',3':4,5]imidazo[1,2-a]pyridine (Preparation # 92) | | D.5 | 0.86 (ab) | 444 | A |

The compounds shown in Table E were synthesized in a manner similar to Example #2 from 2-(5-(4,4,5,5-tetramethyl-1,3,2-dioxaborolan-2-yl)pyrimidin-2-yl)propan-2-ol and the corresponding bromides or chlorides.

TABLE E

| Bromide/chloride | Product | Example # | R_t min (Table 1, Method) | m/z (M + H)+ | TNF IC_50 |
|---|---|---|---|---|---|
| 8-Bromo-1-phenyl-1,2,3,4-tetrahydrobenzo[4,5]imidazo[1,2-a]pyridine (Preparation #9, step 1) | | E.1 | 1.18 (e) | 385 | A |
| 2-(2-Bromo-6,7,8,9-tetrahydrobenzo[4,5]imidazo[1,2-a]pyridin-9-yl)phenol (Preparation #11) | | E.2 | 1.04 (e) | 401 | C |
| 7-Bromo-1-(2-methoxyphenyl)-2,3-dihydro-1H-benzo[d]pyrrolo[1,2-a]imidazole (Preparation #42) | | E.3 | 0.69 (f) | 401 | A |

TABLE E-continued

| Bromide/chloride | Product | Example # | $R_t$ min (Table 1, Method) | m/z $(M + H)^+$ | TNF $IC_{50}$ |
|---|---|---|---|---|---|
| 2'-Bromo-6',8'-dihydro-2H-spiro[benzofuran-3,9'-pyrido[3',2':4,5]imidazo[2,1-c][1,4]oxazine] | | E.4 | 2.88 (ae) | 416 | A |
| 2'-Bromo-6',8'-dihydrospiro[chroman-4,9'-pyrido[3',2':4,5]imidazo[2,1-c][1,4]oxazine] | | E.5 | 2.90 (af) | 430 | B |

Example #3

7-(5-((R)-1-Phenyl-2,3-dihydro-1H-benzo[d]pyrrolo[1,2-a]imidazol-7-yl)pyrimidin-2-yl)hexahydroimidazo[1,5-a]pyrazin-3(2H)-one

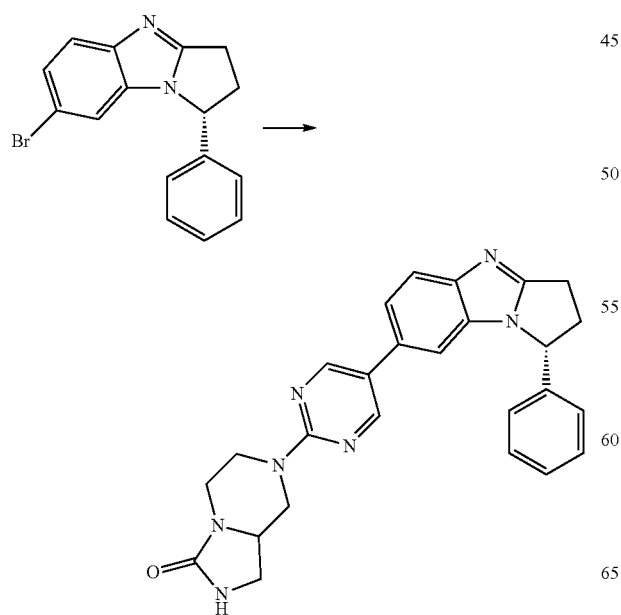

To a vial was added (2-chloropyrimidin-5-yl)boronic acid (0.030 g, 0.192 mmol), EtOH (1 mL), hexahydroimidazo[1,5-a]pyrazin-3(2H)-one hydrochloride (0.034 g, 0.192 mmol) and TEA (0.027 mL, 0.192 mmol). The mixture was heated at about 95° C. for about 1 h then (R)-7-bromo-1-phenyl-2,3-dihydro-1H-benzo[d]pyrrolo[1,2-a]imidazole (0.030 g, 0.096 mmol, Preparation #4), $Cs_2CO_3$ (0.062 g, 0.192 mmol), and SiliaCat® DPP-Pd (0.038 g, 9.58 μmol) were added. The contents were heated to about 95° C. for about 2 h. The reaction was cooled to rt, filtered, the filtercake washed with MeOH, and the filtrate concentrated to dryness. The crude product was purified by preparative HPLC (Table 1, Method 1) to give the title compound (0.021 g, 49%); LC/MS (Table 1, Method f) $R_t$=0.68 min; MS m/z: 452 $(M+H)^+$. (TNF $IC_{50}$=A).

The compounds shown in Table F were synthesized in a manner similar to Example #3 from (R)-7-bromo-1-phenyl-2,3-dihydro-1H-benzo[d]pyrrolo[1,2-a]imidazole (Preparation #4) and the corresponding amine.

TABLE F
| Amine | Product | Example # | R$_t$ min (Table 1, Method) | m/z (M + H)$^+$ | TNF IC$_{50}$ |
|---|---|---|---|---|---|
| 7-Azaspiro[3.5]nonan-2-ol hydrochloride | 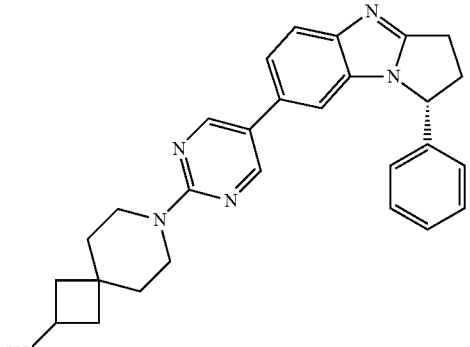 | F.1 | 0.71 (f) | 452 | A |
| 3,3-Difluoropiperidin-4-ol hydrochloride | 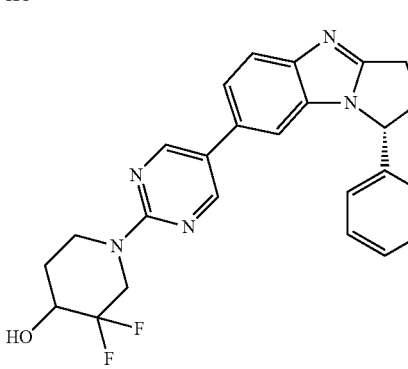 | F.2 | 0.67 (f) | 448 | A |
| Piperidin-4-ol | 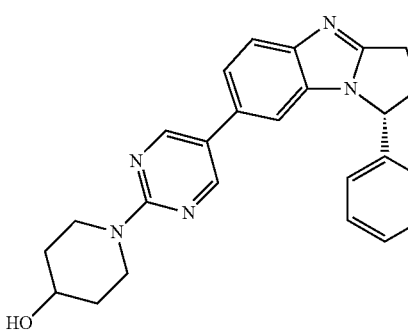 | F.3 | 0.85 (f) | 412 | A |
| Thiomorpholine 1,1-dioxide | 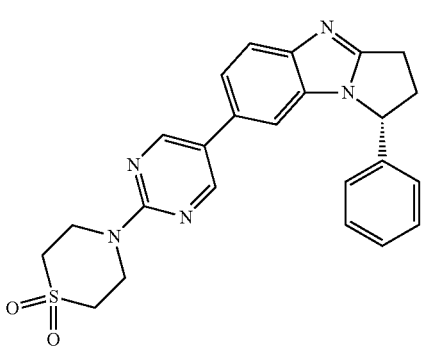 [SMILES: O=S1(=O)CCN(c2ncc(-c3ccc4nc5n(c4c3)[C@@H](c3ccccc3)CC5)cn2)CC1] | F.4 | 0.72 (f) | 446 | A |

Example #4

(S)-1-(5-(4-Phenyl-3,4-dihydro-1H-benzo[4,5]imidazo[2,1-c][1,4]oxazin-7-yl)pyrimidin-2-yl)piperidin-4-ol

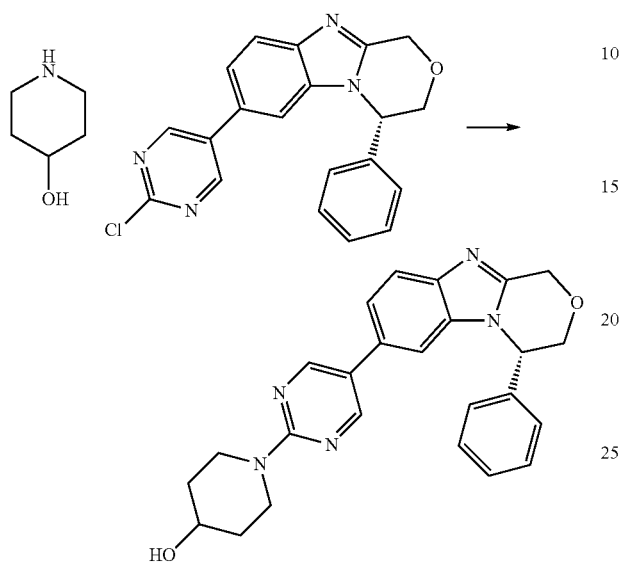

A vial was preloaded with piperidin-4-ol (0.020 g, 0.2 mmol). A stock solution of (S)-7-(2-chloropyrimidin-5-yl)-4-phenyl-3,4-dihydro-1H-benzo[4,5]imidazo[2,1-c][1,4]oxazine (0.055 M in 5% DIEA: 95% EtOH, 1 mL, 0.055 mmol, Preparation #35) was added to the vial. The vial was capped and the reaction mixture was heated to about 85° C. for about 16 h while stirring. The reaction mixture was then filtered, 1 mL of 1:1 DMSO/MeOH was added, and the contents were purified by preparative HPLC (Table 1, Method k) to afford the title compound (0.0098 g, 28%). LC/MS (Table 1, Method i) $R_t$=0.56 min; MS m/z: 428 (M+H)$^+$. (TNF IC$_{50}$=A).

The compounds shown in Table G were synthesized in a manner similar to Example #4 from (S)-7-(2-chloropyrimidin-5-yl)-4-phenyl-3,4-dihydro-1H-benzo[4,5]imidazo[2,1-c][1,4]oxazine (Preparation #35) and the corresponding amine.

TABLE G

| Amine | Product | Example # | $R_t$ min (Table 1, Method) | m/z (M + H)$^+$ | TNF IC$_{50}$ |
|---|---|---|---|---|---|
| 2,7-Diazaspiro[4.4]nonan-1-one hydrochloride | | G.1 | 0.54 (i) | 467 | B |
| 2-Methylmorpholine | | G.2 | 0.64 (i) | 428 | A |

TABLE G-continued

| Amine | Product | Example # | R$_t$ min (Table 1, Method) | m/z (M + H)$^+$ | TNF IC$_{50}$ |
|---|---|---|---|---|---|
| 2-(Piperidin-3-yl)acetic acid | | G.3 | 0.62 (i) | 470 | B |
| Piperidin-3-ylmethanol | | G.4 | 0.60 (i) | 442 | A |
| 3-(Piperazin-1-yl)propan-1-ol | | G.5 | 0.47 (i) | 471 | B |
| 1,3,8-Triazaspiro[4.5]decan-4-one | | G.6 | 0.48 (i) | 482 | B |

TABLE G-continued
| Amine | Product | Example # | R$_t$ min (Table 1, Method) | m/z (M + H)$^+$ | TNF IC$_{50}$ |
|---|---|---|---|---|---|
| 1-(Piperidin-4-yl)ethan-1-ol | 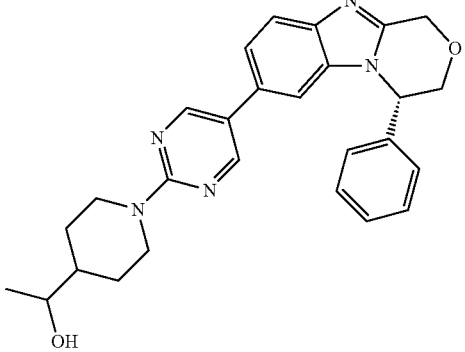 | G.7 | 0.61 (i) | 456 | B |
| 2-Oxa-7-azaspiro[3.5]nonane | 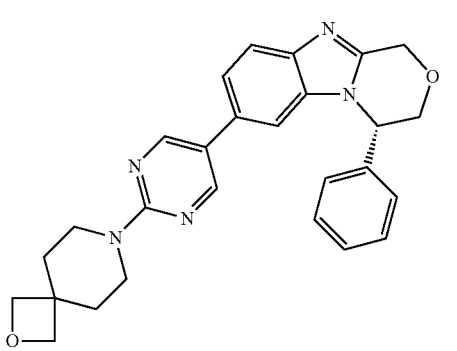 [SMILES: c1ccc([C@H]2COCc3nc4ccc(-c5cnc(N6CCC7(CC6)COC7)nc5)cc4n32)cc1] | G.8 | 0.62 (i) | 454 | A |
| 1,4-Diazepan-2-one | 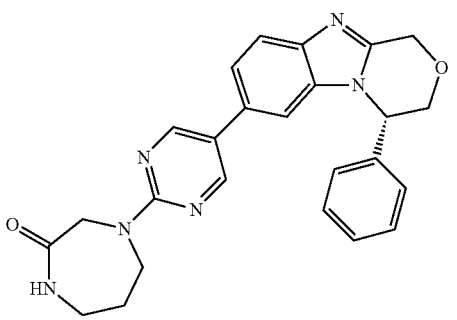 [SMILES: O=C1CN(c2ncc(-c3ccc4nc5n(c4c3)[C@@H](c3ccccc3)COC5)cn2)CCCN1] | G.9 | 0.55 (i) | 441 | B |
| 3-(Piperidin-4-yl)propanoic acid | 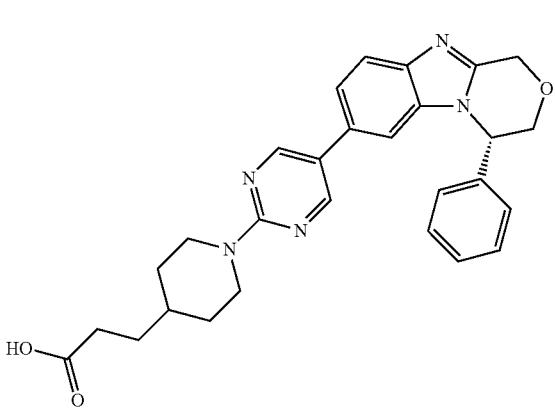 [SMILES: O=C(O)CCC1CCN(c2ncc(-c3ccc4nc5n(c4c3)[C@@H](c3ccccc3)COC5)cn2)CC1] | G.10 | 0.62 (i) | 484 | B |

TABLE G-continued
| Amine | Product | Example # | R<sub>t</sub> min (Table 1, Method) | m/z (M + H)+ | TNF IC$_{50}$ |
|---|---|---|---|---|---|
| Azepan-4-ol | 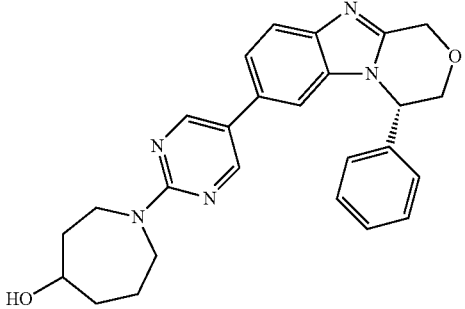 [SMILES: OC1CCCN(c2ncc(-c3ccc4nc5n(c4c3)[C@@H](c3ccccc3)COC5)cn2)CC1] | G.11 | 0.56 (i) | 442 | A |
| Piperazine-1-sulfonamide | 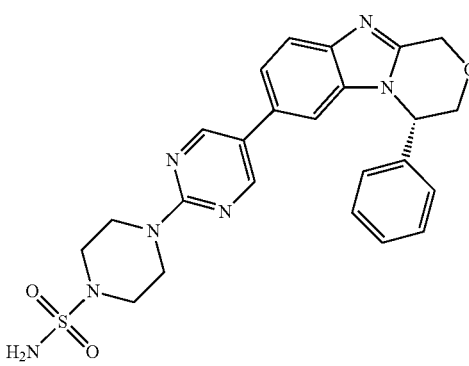 | G.12 | 0.57 (i) | 492 | A |
| 1-(1-Methylpiperidin-4-yl)piperazine | 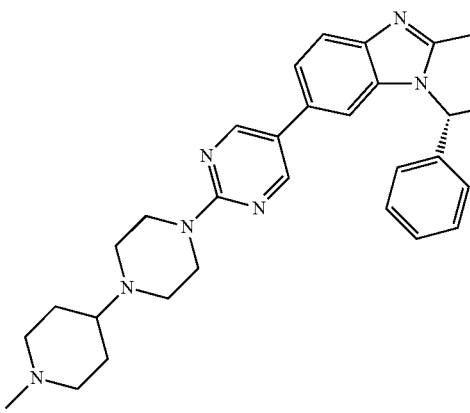 | G.13 | 0.45 (i) | 510 | B |
| (4-Fluoropiperidin-4-yl)methanol hydrochloride | 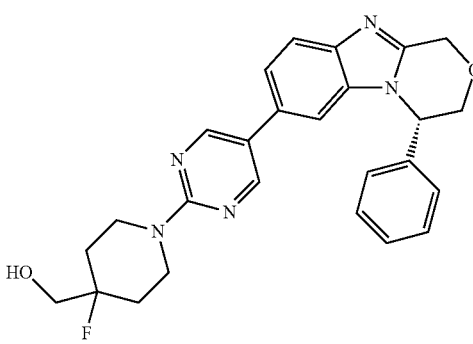 | G.14 | 0.59 (i) | 460 | A |

TABLE G-continued
| Amine | Product | Example # | $R_t$ min (Table 1, Method) | m/z (M + H)⁺ | TNF IC₅₀ |
|---|---|---|---|---|---|
| 2-(Trifluoromethyl)morpholine hydrochloride | 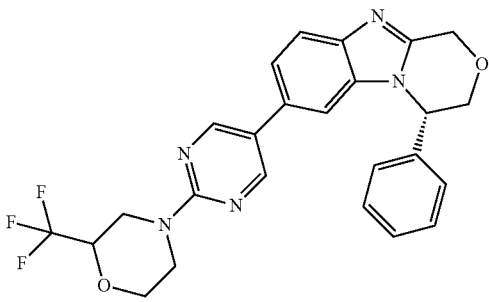 [SMILES: FC(F)(F)C1CN(c2ncc(-c3ccc4nc5n(c4c3)[C@@H](c3ccccc3)COC5)cn2)CCO1] | G.15 | 0.72 (i) | 482 | B |
| 2-Oxa-6-azaspiro[3.4]octane | 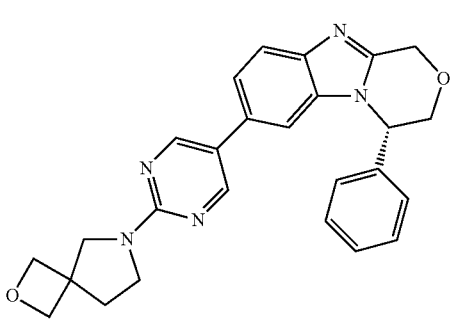 [SMILES: c1ccc([C@H]2COCc3nc4ccc(-c5cnc(N6CCC7(COC7)C6)nc5)cc4n32)cc1] | G.16 | 0.49 (i) | 440 | B |
| 4-(Azetidin-3-yl)morpholine hydrochloride | 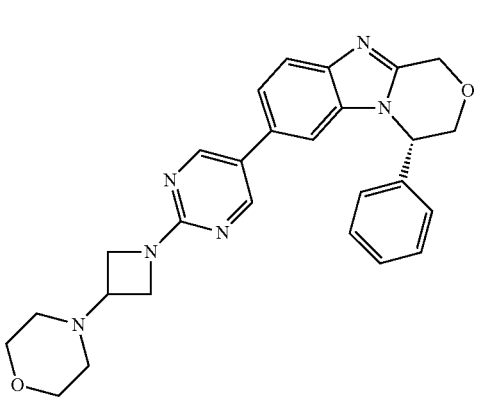 [SMILES: c1ccc([C@H]2COCc3nc4ccc(-c5cnc(N6CC(N7CCOCC7)C6)nc5)cc4n32)cc1] | G.17 | 0.46 (i) | 469 | C |
| (R)-3-(Methylsulfonyl)pyrrolidine | 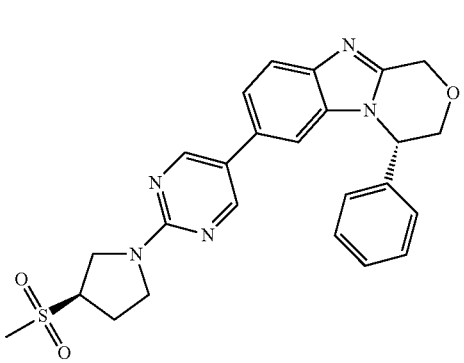 [SMILES: CS(=O)(=O)[C@@H]1CCN(c2ncc(-c3ccc4nc5n(c4c3)[C@@H](c3ccccc3)COC5)cn2)C1] | G.18 | 0.55 (i) | 476 | B |

TABLE G-continued

| Amine | Product | Example # | R_t min (Table 1, Method) | m/z (M + H)⁺ | TNF IC$_{50}$ |
|---|---|---|---|---|---|
| N-(Piperidin-4-yl)methanesulfonamide | | G.19 | 0.59 (i) | 505 | B |
| 4-(2-Hydroxyethyl)piperidin-4-ol hydrochloride | | G.20 | 0.53 (i) | 472 | A |
| 1-Methyl-4,4'-bipiperidine hydrochloride | | G.21 | 0.55 (i) | 509 | B |
| 4-Methylpiperidin-4-ol | | G.22 | 0.59 (i) | 442 | A |

TABLE G-continued

| Amine | Product | Example # | R$_t$ min (Table 1, Method) | m/z (M + H)$^+$ | TNF IC$_{50}$ |
|---|---|---|---|---|---|
| 2,6-Dimethylmorpholine | | G.23 | 0.68 (i) | 442 | B |
| 1-(Methylsulfonyl)piperazine hydrochloride | | G.24 | 0.61 (i) | 491 | A |
| (3S,4S)-Pyrrolidine-3,4-diol | | G.25 | 0.47 (i) | 430 | C |
| (3R,4R)-Pyrrolidine-3,4-diol | | G.26 | 0.47 (i) | 430 | C |

TABLE G-continued
| Amine | Product | Example # | R<sub>t</sub> min (Table 1, Method) | m/z (M + H)+ | TNF IC50 |
|---|---|---|---|---|---|
| Hexahydro-3H-oxazolo[3,4-a]pyrazin-3-one hydrochloride | 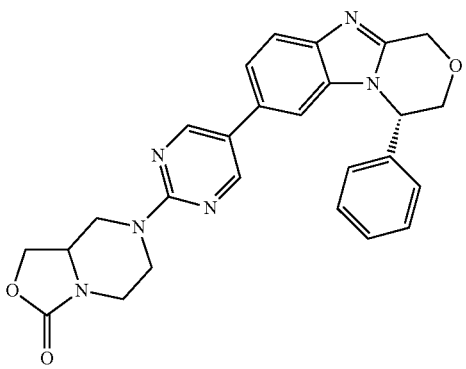 [SMILES: O=C1OCC2CN(c3ncc(-c4ccc5nc6n(c5c4)[C@@H](c4ccccc4)COC6)cn3)CCN12] | G.27 | 0.59 (i) | 469 | B |
| 5,6,7,8-Tetrahydro-[1,2,4]triazolo[4,3-a]pyrazine | 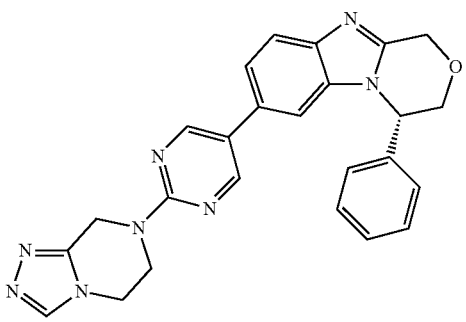 [SMILES: c1ccc([C@H]2COCc3nc4ccc(-c5cnc(N6CCn7cnnc7C6)nc5)cc4n32)cc1] | G.28 | 0.52 (i) | 451 | A |
| 3-(Methylsulfonyl)pyrrolidine | 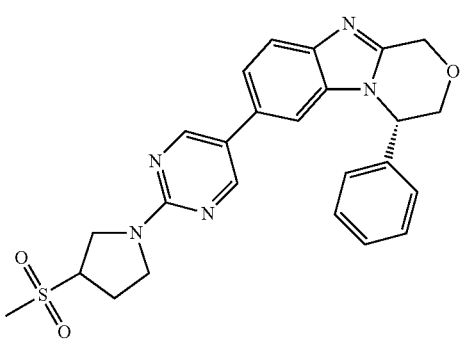 [SMILES: CS(=O)(=O)C1CCN(c2ncc(-c3ccc4nc5n(c4c3)[C@@H](c3ccccc3)COC5)cn2)C1] | G.29 | 0.55 (i) | 476 | B |
| Piperazin-2-one | 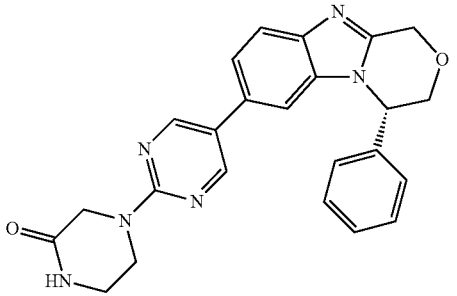 [SMILES: O=C1CN(c2ncc(-c3ccc4nc5n(c4c3)[C@@H](c3ccccc3)COC5)cn2)CCN1] | G.30 | 0.54 (i) | 427 | A |

TABLE G-continued

| Amine | Product | Example # | R$_t$ min (Table 1, Method) | m/z (M + H)$^+$ | TNF IC$_{50}$ |
|---|---|---|---|---|---|
| 3-(2-Hydroxyethyl)pyrrolidin-3-ol 2,2,2-trifluoroacetate | | G.31 | 0.5 (i) | 458 | B |
| 1,4-Oxazepane hydrochloride | | G.32 | 0.61 (i) | 428 | A |
| (4-(Methylsulfonyl)piperidin-4-yl)methanol | | G.33 | 0.56 (i) | 520 | B |
| 6-Azaspiro[3.4]octan-2-ol hydrochloride | | G.34 | 0.55 (i) | 454 | A |

TABLE G-continued

| Amine | Product | Example # | R$_t$ min (Table 1, Method) | m/z (M + H)$^+$ | TNF IC$_{50}$ |
|---|---|---|---|---|---|
| Morpholin-2-ylmethanol hydrochloride | | G.35 | 0.56 (i) | 444 | A |

The compounds shown in Table H were synthesized in a manner similar to Example #4 from 8-(2-chloropyrimidin-5-yl)-1-phenyl-1,2,3,4-tetrahydrobenzo[4,5]imidazo[1,2-a]pyridine (Preparation #9) and the corresponding amine.

TABLE H

| Amine | Product | Example # | R$_t$ min (Table 1, Method) | m/z (M + H)$^+$ | TNF IC$_{50}$ |
|---|---|---|---|---|---|
| Azetidine-3-carboxylic acid | | H.1 | 1.18 (e) | 426 | C |
| Isonipecotic acid | | H.2 | 1.32 (e) | 454 | B |

TABLE H-continued

| Amine | Product | Example # | R$_t$ min (Table 1, Method) | m/z (M + H)$^+$ | TNF IC$_{50}$ |
|---|---|---|---|---|---|
| Piperazin-2-one | | H.3 | 1.21 (e) | 425 | B |

Example #5

9-(2-Methoxyphenyl)-2-(2-morpholinopyrimidin-5-yl)-6,7,8,9-tetrahydrobenzo[4,5]imidazo[1,2-a]pyridin-9-ol

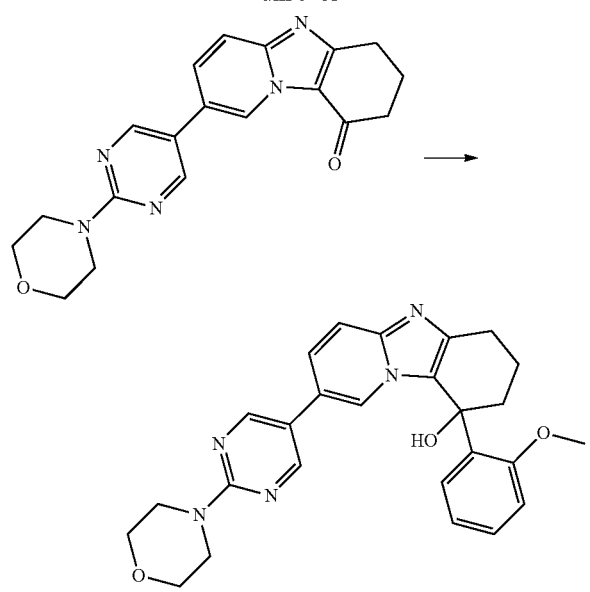

To a round bottom flask was added 2-(2-morpholinopyrimidin-5-yl)-7,8-dihydrobenzo[4,5]imidazo[1,2-a]pyridin-9(6H)-one (0.085 g, 0.243 mmol, Preparation #10) in THF (1 mL). To this stirring slurry under N$_2$ was added (2-methoxyphenyl)magnesium bromide (0.438 mL, 0.438 mmol). The mixture was stirred at rt for about 1 h. A precipitate formed in the reaction mixture upon the addition of sat. NH$_4$Cl and EtOAc. The solid was collected by filtration, washed with 10 mL water, EtOAc, and dried under vacuum. The filtrate was concentrated, diluted with DCM, washed with 10 mL water, filtered through a phase separator and concentrated. The filtrate residue was combined with the solid, dissolved in a 1:1 MeOH/DCM mixture, concentrated onto silica gel and purified via silica gel chromatography eluting with (0-10% MeOH/DCM) to give the title compound (0.08 g, 72%); LC/MS (Table 1, Method e) R$_t$=1.32 min.; MS m/z: 458 (M+H)$^+$. (TNF IC$_{50}$=B).

The compounds shown in Table I were synthesized in a manner similar to Example #5 from 2-(2-morpholinopyrimidin-5-yl)-7,8-dihydrobenzo[4,5]imidazo[1,2-a]pyridin-9(6H)-one (Preparation #10) and the corresponding Grignard.

TABLE I

| Grignard | Product | Example # | R$_t$ min (Table 1, Method) | m/z (M + H)$^+$ | TNF IC$_{50}$ |
|---|---|---|---|---|---|
| (3-Chlorophenyl)magnesium bromide | | I.1 | 1.35 (e) | 462 | B |

TABLE I-continued
| Grignard | Product | Example # | R$_t$ min (Table 1, Method) | m/z (M + H)$^+$ | TNF IC$_{50}$ |
|---|---|---|---|---|---|
| Phenylmagnesium bromide | 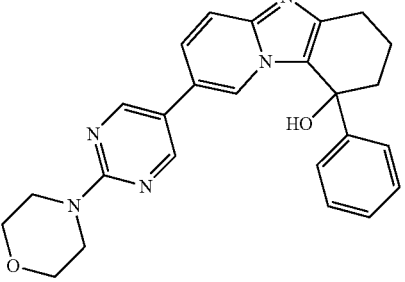 | I.2 | 1.30 (e) | 428 | B |
| m-Tolylmagnesium chloride | 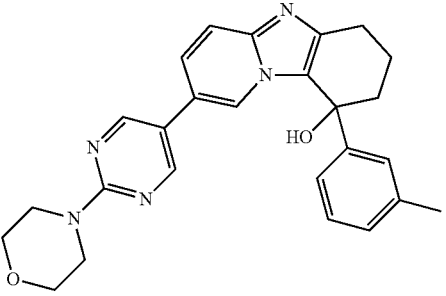 [SMILES: Cc1cccc(C2(O)CCCc3nc4ccc(-c5cnc(N6CCOCC6)nc5)cn4c32)c1] | I.3 | 0.75 (i) | 442 | B |
| (3-Fluorophenyl)magnesium bromide | 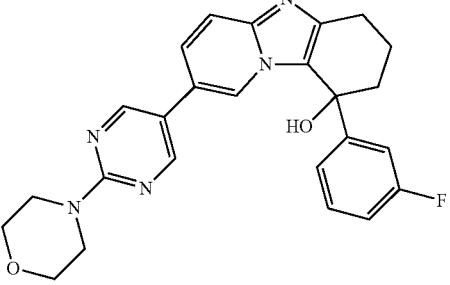 | I.4 | 0.74 (i) | 446 | B |
| (3-Fluoro-2-methylphenyl)magnesium chloride | 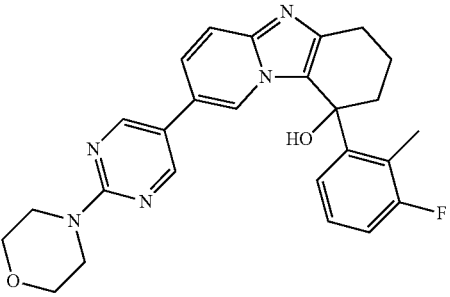 [SMILES: Cc1c(F)cccc1C1(O)CCCc2nc3ccc(-c4cnc(N5CCOCC5)nc4)cn3c21] | I.5 | 0.74 (i) | 460 | B |
| (4-Fluorophenyl)magnesium bromide | 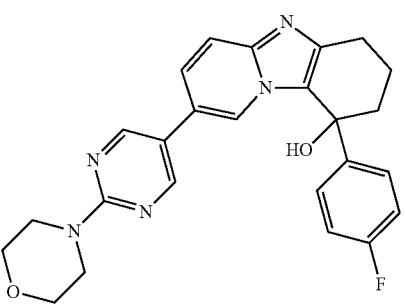 [SMILES: Cc1ccc(C2(O)CCCc3nc4ccc(-c5cnc(N6CCOCC6)nc5)cn4c32)cc1] | I.6 | 0.74 (i) | 446 | B |

TABLE I-continued

| Grignard | Product | Example # | R$_t$ min (Table 1, Method) | m/z (M + H)$^+$ | TNF IC$_{50}$ |
|---|---|---|---|---|---|
| (3-Chloro-5-fluorophenyl)magnesium bromide | | I.7 | 0.79 (i) | 480 | B |
| p-Tolylmagnesium bromide | | I.8 | 0.76 (i) | 442 | B |

The compounds shown in Table J were synthesized in a manner similar to Example #5 from 2-(2-morpholinopyrimidin-5-yl)-8,9-dihydro-6H-cyclohepta[4,5]imidazo[1,2-a]pyridin-10(7H)-one (Preparation #37) and the corresponding Grignard.

TABLE J

| Grignard | Product | Example # | R$_t$ min (Table 1, Method) | m/z (M + H)$^+$ | TNF IC$_{50}$ |
|---|---|---|---|---|---|
| (3-Fluorophenyl)magnesium bromide | | J.1 | 0.77 (i) | 460 | A |
| (3-Chlorophenyl)magnesium bromide | | J.2 | 0.77 (i) | 476 | B |

TABLE J-continued

| Grignard | Product | Example # | R$_t$ min (Table 1, Method) | m/z (M + H)$^+$ | TNF IC$_{50}$ |
|---|---|---|---|---|---|
| m-Tolylmagnesium chloride | | J.3 | 0.79 (i) | 456 | B |
| (4-Fluorophenyl)magnesium bromide | | J.4 | 0.78 (i) | 460 | B |
| (3-Chloro-5-fluorophenyl)magnesium bromide | | J.5 | 0.82 (i) | 494 | B |
| (4-Methoxyphenyl) magnesium bromide | | J.6 | 0.75 (i) | 472 | B |
| p-Tolylmagnesium bromide | | J.7 | 0.81 (i) | 456 | B |

TABLE J-continued

| Grignard | Product | Example # | R$_t$ min (Table 1, Method) | m/z (M + H)$^+$ | TNF IC$_{50}$ |
|---|---|---|---|---|---|
| (4-Chlorophenyl)magnesium bromide | | J.8 | 0.81 (i) | 476 | B |
| (3,5-Dimethoxyphenyl) magnesium chloride | | J.9 | 0.75 (i) | 502 | C |
| (3-Methoxyphenyl) magnesium bromide | | J.10 | 0.75 (i) | 472 | C |

The compound shown in Table K was synthesized in a manner similar to Preparation #11, step 2 from the corresponding alcohol.

TABLE K

| Alcohol | Product | Example # | R$_t$ min (Table 1, Method) | m/z (M + H)$^+$ | TNF IC$_{50}$ |
|---|---|---|---|---|---|
| 9-(3-Chlorophenyl)-2-(2-morpholinopyrimidin-5-yl)-6,7,8,9-tetrahydrobenzo[4,5]imidazo[1,2-a]pyridin-9-ol (Example #I.1) | | K.1 | 1.40 (e) | 446 | A |

Example #6

4-(5-(8-Phenyl-7,8-dihydro-6H-pyrrolo[2',1':2,3]imidazo[4,5-b]pyridin-2-yl)pyrimidin-2-yl)morpholine

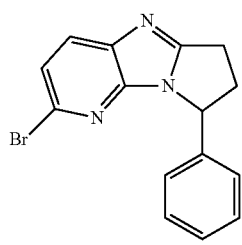

→

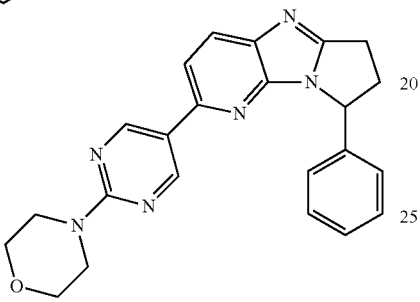

To a microwave tube were added (2-morpholinopyrimidin-5-yl)boronic acid (0.100 g, 0.477 mmol), 2-bromo-8-phenyl-7,8-dihydro-6H-pyrrolo[2',1':2,3]imidazo[4,5-b]pyridine (0.100 g. 0.318 mmol, Preparation #12) and 1,4-dioxane (2 mL). 2M $Na_2CO_3$ (1 mL) was added followed by $Pd(dppf)Cl_2$ (0.023 g, 0.032 mmol). The tube was degassed with $N_2$ and heated in a microwave at about 135° C. for about 40 min. The reaction mixture was filtered through Celite® and the filtrate was evaporated to dryness. The residue was purified by preparative HPLC (Table 1, Method j) to give the product (0.09 g, 6%); LC/MS (Table 1, Method d) $R_t$=0.71 min; MS m/z: 399 (M+H)⁺. (TNF $IC_{50}$=A).

The compounds shown in Table L were synthesized in a manner similar to Example #6 from 2-bromo-8-phenyl-7,8-dihydro-6H-pyrrolo[2',1':2,3]imidazo[4,5-b]pyridine (Preparation #12) and the corresponding boronic acids/boronates.

TABLE L

| Boronic acid/boronate | Product | Example # | $R_t$ min (Table 1, Method) | m/z (M + H)⁺ | TNF $IC_{50}$ |
|---|---|---|---|---|---|
| 2-(2-Hydroxypropan-2-yl)pyrimidin-5-ylboronic acid | | L.1 | 0.65 (d) | 372 | A |
| 2-(3-Oxopiperazin-1-yl)pyrimidin-5-ylboronic acid (Preparation #21) | | L.2 | 0.57 (d) | 412 | A |

TABLE L-continued

| Boronic acid/boronate | Product | Example # | R$_t$ min (Table 1, Method) | m/z (M + H)$^+$ | TNF IC$_{50}$ |
|---|---|---|---|---|---|
| (2-(4-Hydroxypiperidin-1-yl)pyrimidin-5-yl)boronic acid (Preparation #22) | | L.3 | 0.67 (d) | 413 | A |
| 7-(5-(4,4,5,5-Tetramethyl-1,3,2-dioxaborolan-2-yl)pyrimidin-2-yl)hexahydroimidazo[1,5-a]pyrazin-3(2H)-one (Preparation #62) | | L.4 | 0.72 (d) | 453 | A |

The compounds shown in Table M were synthesized in a manner similar to Example #6 from 2-bromo-8-(3-fluorophenyl)-7,8-dihydro-6H-pyrrolo[2',1':2,3]imidazo[4,5-b]pyridine (Preparation #13) and the corresponding boronic acids/boronates.

TABLE M

| Boronic acid/boronate | Product | Example # | R$_t$ min (Table 1, Method) | m/z (M + H)$^+$ | TNF IC$_{50}$ |
|---|---|---|---|---|---|
| 2-Morpholinopyrimidin-5-ylboronic acid | | M.1 | 0.83 (d) | 417 | A |

TABLE M-continued

| Boronic acid/boronate | Product | Example # | R$_t$ min (Table 1, Method) | m/z (M + H)$^+$ | TNF IC$_{50}$ |
|---|---|---|---|---|---|
| 2-(2-Hydroxypropan-2-yl)pyrimidin-5-ylboronic acid | | M.2 | 0.70 (d) | 390 | A |
| 2-(3-Oxopiperazin-1-yl)pyrimidin-5-ylboronic acid (Preparation #21) | | M.3 | 0.66 (d) | 430 | A |
| 2-(4-Hydroxypiperidin-1-yl)pyrimidin-5-yl)boronic acid (Preparation #22) | | M.4 | 0.68 (d) | 431 | A |
| 7-(5-(4,4,5,5-Tetramethyl-1,3,2-dioxaborolan-2-yl)pyrimidin-2-yl)hexahydroimidazo[1,5-a]pyrazin-3(2H)-one (Preparation #62) | | M.5 | 0.75 (d) | 471 | A |

The compounds shown in Table N were synthesized in a manner similar to Example #6 from 2-bromo-8-(2,5-dimethylphenyl)-7,8-dihydro-6H-pyrrolo[2',1':2,3]imidazo[4,5-b]pyridine (Preparation #17) and the corresponding boronic acids/boronates.

TABLE N

| Boronic acid/boronate | Product | Example # | R$_t$ min (Table 1, Method) | m/z (M + H)$^+$ | TNF IC$_{50}$ |
|---|---|---|---|---|---|
| 2-Morpholinopyrimidin-5-ylboronic acid | | N.1 | 0.77 (d) | 427 | A |
| 2-(3-Oxopiperazin-1-yl)pyrimidin-5-ylboronic acid (Preparation #21) | | N.2 | 0.70 (d) | 440 | A |
| (2-(4-Hydroxypiperidin-1-yl)pyrimidin-5-yl)boronic acid (Preparation #22) | | N.3 | 0.73 (d) | 441 | A |
| 7-(5-(4,4,5,5-tetramethyl-1,3,2-dioxaborolan-2-yl)pyrimidin-2-yl)hexahydroimidazo[1,5-a]pyrazin-3(2H)-one (Preparation #62) | | N.4 | 0.78 (d) | 481 | A |

The compounds shown in Table O were synthesized in a manner similar to Example #6 from 2-bromo-9-phenyl-6,7,8,9-tetrahydroimidazo[1,2-a:5,4-b']dipyridine (Preparation #18) and the corresponding boronic acids/boronates.

TABLE O

| Boronic acid/boronate | Product | $R_t$ min (Table 1, Example # Method) | m/z (M + H)$^+$ | TNF IC$_{50}$ |
|---|---|---|---|---|
| 2-Morpholinopyrimidin-5-ylboronic acid | | O.1  0.72 (d) | 413 | A |
| 2-(2-Hydroxypropan-2-yl)pyrimidin-5-ylboronic acid | | O.2  0.76 (d) | 386 | A |
| 2-(3-Oxopiperazin-1-yl)pyrimidin-5-ylboronic acid (Preparation #21) | | O.3  0.57 (d) | 426 | A |
| (2-(4-Hydroxypiperidin-1-yl)pyrimidin-5-yl)boronic acid (Preparation #22) | | O.4  0.67 (d) | 427 | A |

The compounds shown in Table P were synthesized in a manner similar to Example #6 from 3-bromo-6-phenyl-7,8-dihydro-6H-pyrrolo[1',2':1,2]imidazo[4,5-c]pyridine (Preparation #19) and the corresponding boronic acids/boronates.

TABLE P

| Boronic acid/boronate | Product | Example # | R$_t$ min (Table 1, Method) | m/z (M + H)$^+$ | TNF IC$_{50}$ |
|---|---|---|---|---|---|
| 2-Morpholinopyrimidin-5-ylboronic acid | 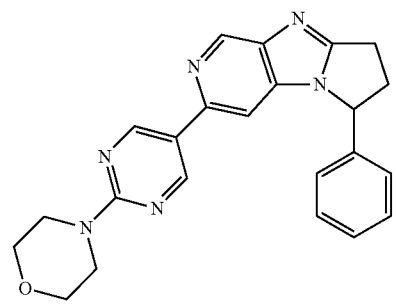 [SMILES: c1ccc(C2CCc3nc4cnc(-c5cnc(N6CCOCC6)nc5)cc4n32)cc1] | P.1 | 0.67 (d) | 399 | B |
| 2-(2-Hydroxypropan-2-yl)pyrimidin-5-ylboronic acid | 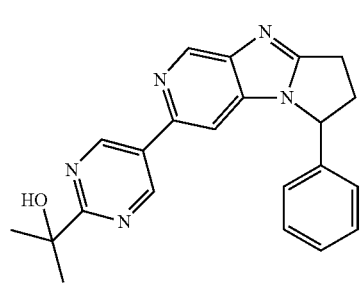 [SMILES: CC(C)(O)c1ncc(-c2cc3c(cn2)nc2n3C(c3ccccc3)CC2)cn1] | P.2 | 0.64 (d) | 372 | B |
| 2-(3-Oxopiperazin-1-yl)pyrimidin-5-ylboronic acid (Preparation #21) | 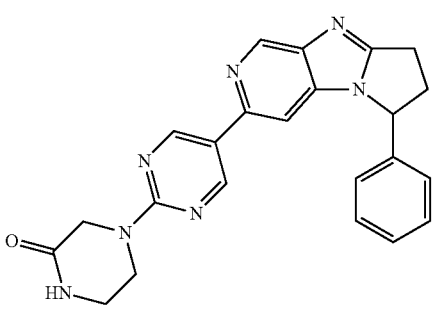 | P.3 | 0.61 (d) | 412 | C |

The compound shown in Table Q was synthesized in a manner similar to Example #6 from 3-chloro-6-phenyl-6,7,8,9-tetrahydroimidazo[1,2-a:4,5-b']dipyridine (Preparation #20) and the corresponding boronic acids/boronates.

TABLE Q

| Boronic acid/boronate | Product | Example # | $R_r$ min (Table 1, Method) | m/z (M + H)$^+$ | TNF IC$_{50}$ |
|---|---|---|---|---|---|
| 2-(3-Oxopiperazin-1-yl)pyrimidin-5-ylboronic acid (Preparation #21) | | Q.1 | 0.64 (d) | 426 | C |

Example #7 and #8

Ethyl 2-[[5-[9-(2-methoxyphenyl)-6,7,8,9-tetrahydropyrido[1,2-a]benzimidazol-2-yl]pyrimidin-2-yl]amino]acetate and 2-((5-(9-(2-methoxyphenyl)-6,7,8,9-tetrahydrobenzo[4,5]imidazo[1,2-a]pyridin-2-yl)pyrimidin-2-yl)amino)acetic acid

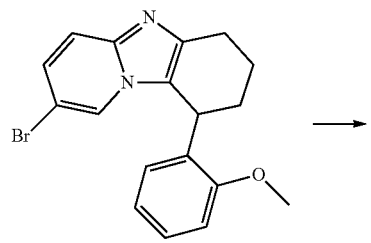

→

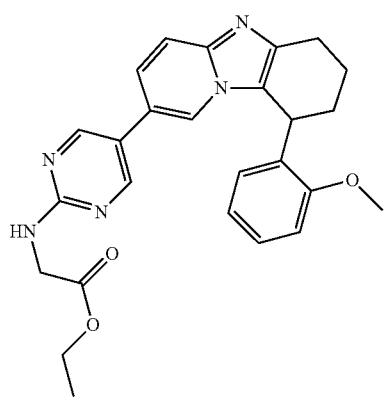

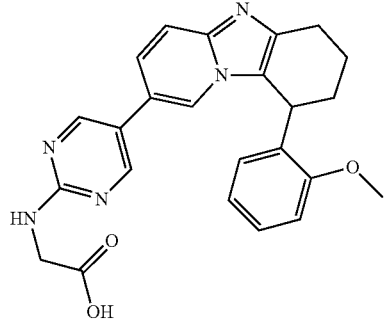

A mixture of 2-bromo-9-(2-methoxyphenyl)-6,7,8,9-tetrahydrobenzo[4,5]imidazo[1,2-a]pyridine (0.048 g, 0.134 mmol, Preparation #11, step 2)), ethyl 2-((5-(4,4,5,5-tetramethyl-1,3,2-dioxaborolan-2-yl)pyrimidin-2-yl)amino)acetate (0.0578 g, 0.188 mmol), Pd(dppf)Cl$_2$.DCM (0.011 g, 0.013 mmol), 2 M aq. Na$_2$CO$_3$ (0.228 mL, 0.457 mmol) and 0.3 mL of 1,4-dioxane were heated in a microwave oven at about 110° C. for about 35 min. The reaction mixture was cooled down to rt. The mixture was partitioned between EtOAc (20 mL) and water (5 mL). The layers were separated and the aqueous layer extracted with EtOAc (3×15 mL). The combined organic layers were dried over Na$_2$SO$_4$, filtered, and concentrated under reduced pressure. The crude material was purified by preparative HPLC (Table 1 Method k) to give ethyl 2-[[5-[9-(2-methoxyphenyl)-6,7,8,9-tetrahydropyrido[1,2-a]benzimidazol-2-yl]pyrimidin-2-yl]amino]acetate (0.007 g, 11%); LC/MS (Table 1, Method d) R$_t$=0.87 min; MS m/z: 458 (M+H)$^+$ (TNF IC$_{50}$=A) and 2-((5-(9-(2-methoxyphenyl)-6,7,8,9-tetrahydrobenzo[4,5]imidazo[1,2-a]pyridin-2-yl)pyrimidin-2-yl)amino)acetic acid (0.012 g, 21%); LC/MS (Table 1, Method d) R$_t$=0.77 min; MS m/z: 430 (M+H)$^+$. (TNF IC$_{50}$=B).

The compound shown in Table R was synthesized in a manner similar to Example #7 and the corresponding boronic acids/boronates.

TABLE R

| Boronic acid/boronate | Product | Example # | R, min (Table 1, Method) | m/z (M + H)+ | TNF IC50 |
|---|---|---|---|---|---|
| Methyl 2-((5-(4,4,5,5-tetramethyl-1,3,2-dioxaborolan-2-yl)pyridin-2-yl)oxy)acetate | 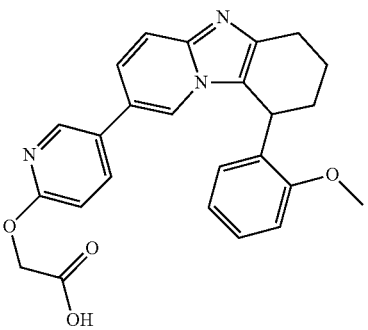 [SMILES: COc1ccccc1C1CCCc2nc3ccc(-c4ccc(OCC(=O)O)nc4)cn3c21] | R.1 | 0.75 (d) | 430 | A |

The compounds shown in Table S were synthesized in a manner similar to Example #7 from 2-bromo-10-(2-methoxyphenyl)-7,8,9,10-tetrahydro-6H-cyclohepta[4,5]imidazo[1,2-a]pyridine (Preparation #3) and the corresponding boronic acid/boronate.

TABLE S

| Boronic acid/boronate | Product | Example # | R, min (Table 1, Method) | m/z (M + H)+ | TNF IC50 |
|---|---|---|---|---|---|
| (2-Morpholinopyrimidin-5-yl)boronic acid | 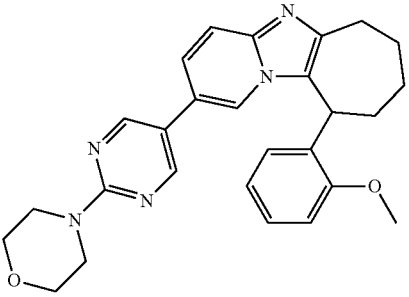 [SMILES: COc1ccccc1C1CCCCc2nc3ccc(-c4cnc(N5CCOCC5)nc4)cn3c21] | S.1 | 1.09 (d) | 456 | A |
| Ethyl 2-((5-(4,4,5,5-tetramethyl-1,3,2-dioxaborolan-2-yl)pyrimidin-2-yl)amino)acetate | 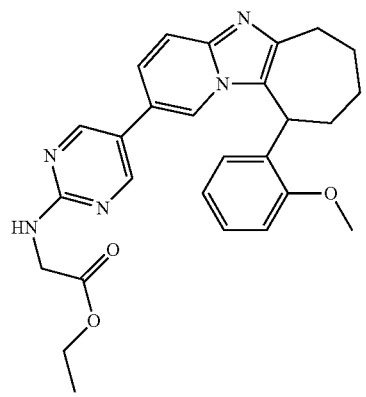 [SMILES: CCOC(=O)CNc1ncc(-c2ccc3nc4c(n3c2)C(c2ccccc2OC)CCCC4)cn1] | S.2 | 0.90 (d) | 472 | B |

TABLE S-continued

| Boronic acid/boronate | Product | Example # | R<sub>t</sub> min (Table 1, Method) | m/z (M + H)+ | TNF IC50 |
|---|---|---|---|---|---|
| Ethyl 2-((5-(4,4,5,5-tetramethyl-1,3,2-dioxaborolan-2-yl)pyrimidin-2-yl)amino)acetate | | S.3 | 0.81 (d) | 444 | B |
| 2-(5-(4,4,5,5-Tetramethyl-1,3,2-dioxaborolan-2-yl)pyrimidin-2-yl)propan-2-ol | | S.4 | 0.80 (d) | 429 | A |

The compounds shown in Table T were synthesized in a manner similar to Example #6 from 7-bromo-4-phenyl-3,4-dihydro-1H-benzo[4,5]imidazo[2,1-c][1,4]oxazine (Preparation #26) and the corresponding boronic acid/boronate.

TABLE T

| Boronic acid/boronate | Product | Example # | R<sub>t</sub> min (Table 1, Method) | m/z (M + H)+ | TNF IC50 |
|---|---|---|---|---|---|
| (5-Fluoro-6-methoxypyridin-3-yl)boronic acid | | T.1 | 0.67 (i) | 376 | B |
| (6-(Methylsulfonyl)pyridin-3-yl)boronic acid | | T.2 | 0.57 (i) | 406 | B |

TABLE T-continued

| Boronic acid/boronate | Product | Example # | R$_t$ min (Table 1, Method) | m/z (M + H)$^+$ | TNF IC$_{50}$ |
|---|---|---|---|---|---|
| 6-(4,4,5,5-Tetramethyl-1,3,2-dioxaborolan-2-yl)-[1,2,5]oxadiazolo[3,4-b]pyridine | | T.3 | 0.66 (i) | 370 | B |
| (6-(2,2,2-Trifluoroethoxy)pyridin-3-yl)boronic acid | | T.4 | 0.74 (i) | 426 | B |
| 2-Isopropoxy-5-(4,4,5,5-tetramethyl-1,3,2-dioxaborolan-2-yl)pyridine | | T.5 | 0.70 (i) | 386 | B |
| N-(5-(4,4,5,5-Tetramethyl-1,3,2-dioxaborolan-2-yl)pyridin-2-yl)acetamide | | T.6 | 0.52 (i) | 385 | C |
| (6-Methoxy-5-methylpyridin-3-yl)boronic acid | | T.7 | 0.68 (i) | 372 | B |

TABLE T-continued

| Boronic acid/boronate | Product | Example # | R, min (Table 1, Method) | m/z (M + H)+ | TNF IC50 |
|---|---|---|---|---|---|
| (5-(2-Methyl-1H-imidazol-1-yl)pyrazin-2-yl)boronic acid | 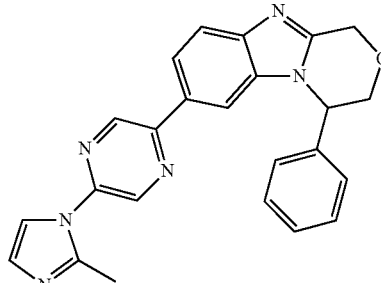 | T.8 | 0.50 (i) | 409 | B |
| (5-(1H-Imidazol-1-yl)pyrazin-2-yl)boronic acid | 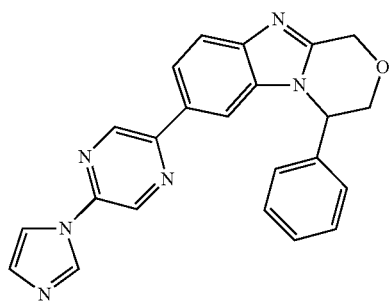 [SMILES: c1ccc(C2COCc3nc4ccc(-c5cnc(-n6ccnc6)cn5)cc4n32)cc1] | T.9 | 0.49 (i) | 395 | B |
| 1-(5-(4,4,5,5-Tetramethyl-1,3,2-dioxaborolan-2-yl)pyridin-2-yl)piperazine | 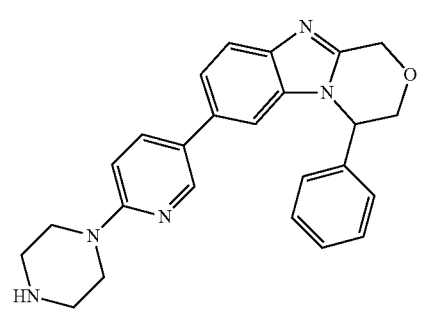 [SMILES: c1ccc(C2COCc3nc4ccc(-c5ccc(N6CCNCC6)nc5)cc4n32)cc1] | T.10 | 0.45 (i) | 412 | B |
| 4-Methyl-7-(4,4,5,5-tetramethyl-1,3,2-dioxaborolan-2-yl)-3,4-dihydro-2H-pyrido[3,2-b][1,4]oxazine | 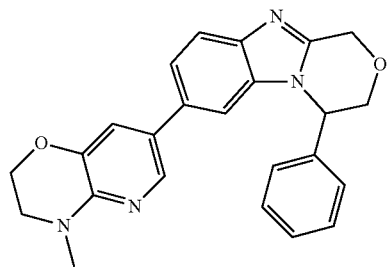 [SMILES: CN1CCOc2cc(-c3ccc4nc5n(c4c3)C(c3ccccc3)COC5)cnc21] | T.11 | 0.50 (i) | 399 | B |
| 4-(3-Methyl-5-(4,4,5,5-tetramethyl-1,3,2-dioxaborolan-2-yl)pyridin-2-yl)morpholine | 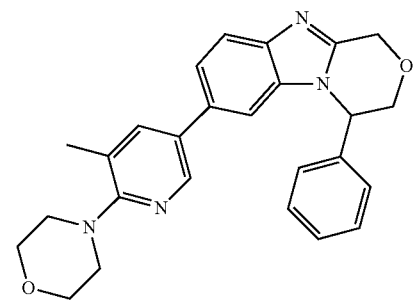 [SMILES: Cc1cc(-c2ccc3nc4n(c3c2)C(c2ccccc2)COC4)cnc1N1CCOCC1] | T.12 | 0.54 (i) | 427 | B |

TABLE T-continued

| Boronic acid/boronate | Product | Example # | R, min (Table 1, Method) | m/z (M + H)+ | TNF IC50 |
|---|---|---|---|---|---|
| 1-(4-(5-(4,4,5,5-Tetramethyl-1,3,2-dioxaborolan-2-yl)pyridin-2-yl)piperazin-1-yl)ethan-1-one | 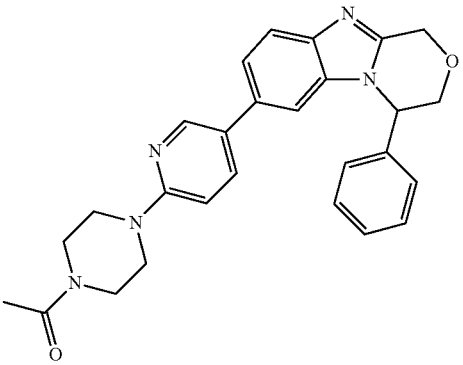 [SMILES: CC(=O)N1CCN(c2ccc(-c3ccc4nc5n(c4c3)C(c3ccccc3)COC5)cn2)CC1] | T.13 | 0.48 (i) | 454 | B |
| N,N-Dimethyl-5-(4,4,5,5-tetramethyl-1,3,2-dioxaborolan-2-yl)pyrimidin-2-amine | 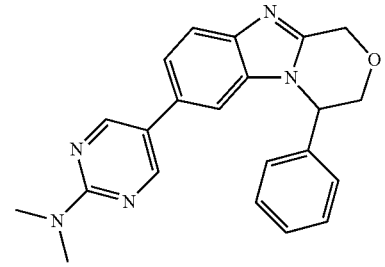 [SMILES: CN(C)c1ncc(-c2ccc3nc4n(c3c2)C(c2ccccc2)COC4)cn1] | T.14 | 0.58 (i) | 372 | B |
| 5-(4,4,5,5-Tetramethyl-1,3,2-dioxaborolan-2-yl)pyrimidine-2-carbonitrile | 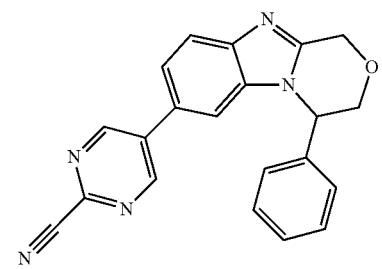 [SMILES: N#Cc1ncc(-c2ccc3nc4n(c3c2)C(c2ccccc2)COC4)cn1] | T.15 | 0.63 (i) | 354 | B |
| 5-(4,4,5,5-Tetramethyl-1,3,2-dioxaborolan-2-yl)picolinonitrile | 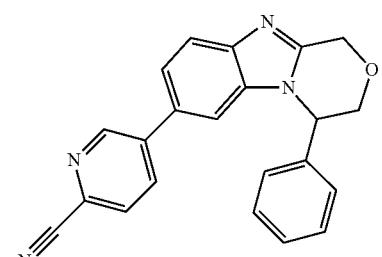 | T.16 | 0.62 (i) | 353 | B |
| N-Cyclopentyl-5-(4,4,5,5-tetramethyl-1,3,2-dioxaborolan-2-yl)pyrimidin-2-amine | 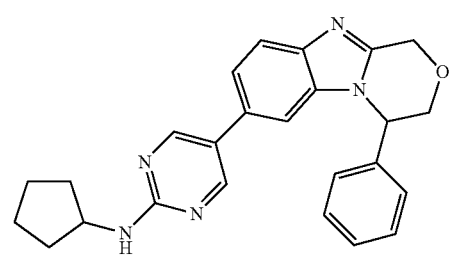 [SMILES: c1ccc(C2COCc3nc4ccc(-c5cnc(NC6CCCC6)nc5)cc4n32)cc1] | T.17 | 0.64 (i) | 412 | B |

TABLE T-continued

| Boronic acid/boronate | Product | Example # | R, min (Table 1, Method) | m/z (M + H)+ | TNF IC50 |
|---|---|---|---|---|---|
| 2-Methyl-5-(4,4,5,5-tetramethyl-1,3,2-dioxaborolan-2-yl)pyridine | | T.18 | 0.47 (i) | 342 | B |
| 7-(4,4,5,5-Tetramethyl-1,3,2-dioxaborolan-2-yl)pyrido[2,3-b]pyrazine | | T.19 | 0.55 (i) | 380 | C |
| 1-Methyl-4-(5-(4,4,5,5-tetramethyl-1,3,2-dioxaborolan-2-yl)pyridin-2-yl)piperazine | | T.20 | 0.46 (i) | 426 | B |
| (5-(1H-Pyrazol-1-yl)pyrazin-2-yl)boronic acid | | T.21 | 0.66 (i) | 395 | B |
| (2-Methoxypyrimidin-5-yl)boronic acid | | T.22 | 0.58 (i) | 358 | B |

TABLE T-continued

| Boronic acid/boronate | Product | Example # | R$_t$ min (Table 1, Method) | m/z (M + H)$^+$ | TNF IC$_{50}$ |
|---|---|---|---|---|---|
| (2-(1H-Pyrazol-1-yl)pyrimidin-5-yl)boronic acid | | T.23 | 0.60 (i) | 395 | B |
| N-Cyclopropyl-5-(4,4,5,5-tetramethyl-1,3,2-dioxaborolan-2-yl)pyrimidin-2-amine | | T.24 | 0.55 (i) | 384 | B |
| (6-Morpholinopyridin-3-yl)boronic acid | | T.25 | 0.49 (i) | 413 | A |
| 5-(4,4,5,5-Tetramethyl-1,3,2-dioxaborolan-2-yl)pyrimidine | | T.26 | 0.53 (i) | 329 | C |
| N,N-Dimethyl-3-((5-(4,4,5,5-tetramethyl-1,3,2-dioxaborolan-2-yl)pyridin-2-yl)oxy)propan-1-amine | | T.27 | 0.50 (i) | 429 | C |

TABLE T-continued

| Boronic acid/boronate | Product | Example # | R, min (Table 1, Method) | m/z (M + H)+ | TNF IC50 |
|---|---|---|---|---|---|
| N-(2-Morpholinoethyl)-5-(4,4,5,5-tetramethyl-1,3,2-dioxaborolan-2-yl)pyridin-2-amine | | T.28 | 0.45 (i) | 456 | C |
| 6-(4,4,5,5-Tetramethyl-1,3,2-dioxaborolan-2-yl)furo[3,2-b]pyridine | | T.29 | 0.56 (i) | 368 | B |
| (6-Isopropoxy-5-methylpyridin-3-yl)boronic acid | | T.30 | 0.76 (i) | 400 | B |
| (2-Methylpyrimidin-5-yl)boronic acid | | T.31 | 0.55 (i) | 343 | B |
| 3-Methyl-6-(4,4,5,5-tetramethyl-1,3,2-dioxaborolan-2-yl)-3H-imidazo[4,5-b]pyridine | | T.32 | 0.50 (i) | 382 | C |

TABLE T-continued

| Boronic acid/boronate | Product | Example # | R, min (Table 1, Method) | m/z (M + H)+ | TNF IC50 |
|---|---|---|---|---|---|
| 5-(4,4,5,5-Tetramethyl-1,3,2-dioxaborolan-2-yl)-2-(trifluoromethyl)pyridine | | T.33 | 0.71 (i) | 396 | B |
| 1-Methyl-4-(3-methyl-5-(4,4,5,5-tetramethyl-1,3,2-dioxaborolan-2-yl)pyridin-2-yl)piperazine | | T.34 | 0.50 (i) | 440 | B |
| (2-(2-Hydroxypropan-2-yl)pyrimidin-5-yl)boronic acid | | T.35 | 1.24 (e) | 387 | A |

The compounds shown in Table U were synthesized in a manner similar to Example #6 from 4-(5-(4,4,5,5-tetramethyl-1,3,2-dioxaborolan-2-yl)pyrimidin-2-yl)morpholine and the corresponding bromide/chloride.

TABLE U

| Bromide/chloride | Product | Example # | R, min (Table 1, Method) | m/z (M + H)+ | TNF IC50 |
|---|---|---|---|---|---|
| 7-Bromo-4-(2,5-difluorophenyl-3,4-dihydro-1H-benzo[4,5]imidazo[2,1-c][1,4]oxazine (Preparation #28) | | U.1 | 1.11 (n) | 450 | A |

TABLE U-continued

| Bromide/chloride | Product | Example # | R$_t$ min (Table 1, Method) | m/z (M + H)$^+$ | TNF IC$_{50}$ |
|---|---|---|---|---|---|
| 7-Bromo-4-((3-fluoro)phenyl-3,4-dihydro-1H-benzo[4,5]imidazo[2,1-c][1,4]oxazine (Preparation #30) | | U.2 | 1.10 (n) | 432 | B |

Example #9

7-(5-((S)-4-Phenyl-3,4-dihydro-1H-benzo[4,5]imidazo[2,1-c][1,4]oxazin-7-yl)pyrimidin-2-yl)hexahydroimidazo[1,5-a]pyrazin-3(2H)-one

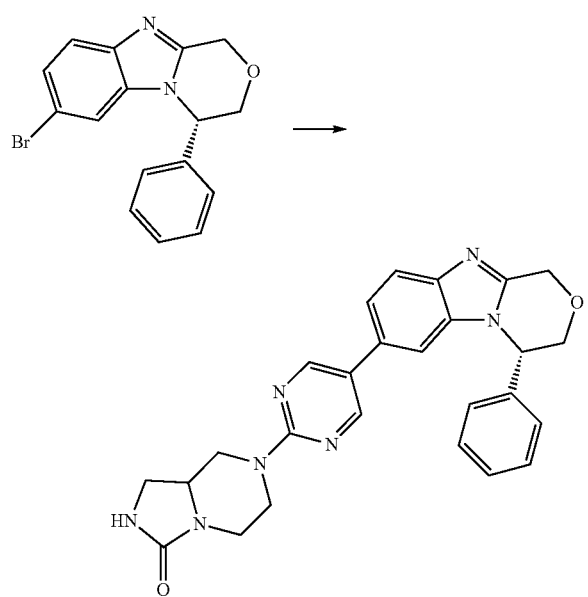

To a vial was added (2-chloropyrimidin-5-yl)boronic acid (0.096 g, 0.608 mmol), EtOH (2 mL), and hexahydroimidazo[1,5-a]pyrazin-3(2H)-one hydrochloride (0.086 g, 0.608 mmol) followed by the addition of TEA (0.109 mL, 0.790 mmol). The contents were heated at about 95° C. for about 2 h. The mixture was then added to a second vial preloaded with (S)-7-bromo-4-phenyl-3,4-dihydro-1H-benzo[4,5]imidazo[2,1-c][1,4]oxazine (0.100 g, 0.304 mmol, Preparation #24), 2M Cs$_2$CO$_3$ (0.304 mL, 0.608 mmol), and SiliaCat® DPP-Pd (0.122 g, 0.030 mmol, 0.25 mmol/g load, SiliCycle Cat#R390-100). The contents were heated at about 95° C. for about 4 h, the mixture was cooled to rt, concentrated onto silica gel and purified by flash-column chromatography on silica gel (1-10% DCM/MeOH) to give the title compound (0.085 g, 60%); LC/MS (Table 1, Method n) R$_t$=1.01 min; MS m/z: 468 (M+H)$^+$. (TNF IC$_{50}$=A).

The compounds shown in Table V were synthesized in a manner similar to Example #9 from hexahydroimidazo[1,5-a]pyrazin-3(2H)-one hydrochloride and the corresponding bromide/chloride.

TABLE V

| Bromide/chloride | Product | Example # | R$_t$ min (Table 1, Method) | m/z (M + H)$^+$ | TNF IC$_{50}$ |
|---|---|---|---|---|---|
| 7-Bromo-4-((3-fluoro)phenyl-3,4-dihydro-1H-benzo[4,5]imidazo[2,1-c][1,4]oxazine (Preparation #30) | | V.1 | 1.04 (n) | 486 | A |

TABLE V-continued

| Bromide/chloride | Product | Example # | R$_t$ min (Table 1, Method) | m/z (M + H)$^+$ | TNF IC$_{50}$ |
|---|---|---|---|---|---|
| 7-Bromo-4-(2-chlorophenyl)-3,4-dihydro-1H-benzo[4,5]imidazo[2,1-c][1,4]oxazine (Preparation #32) | | V.2 | 0.88 (f) | 502 | A |
| 7-Bromo-1,2',3,3'-tetrahydrospiro[benzo[4,5]imidazo[2,1-c][1,4]oxazine-4,1'-indene] (Preparation #34) | | V.3 | 0.87 (f) | 494 | A |

The compounds shown in Table W were synthesized in a manner similar to Example #9 from (S)-7-bromo-4-phenyl-3,4-dihydro-1H-benzo[4,5]imidazo[2,1-c][1,4]oxazine (Preparation #24) and the corresponding amine.

TABLE W

| Amine | Product | Example # | R$_t$ min (Table 1, Method) | m/z (M + H)$^+$ | TNF IC$_{50}$ |
|---|---|---|---|---|---|
| 3,3-Difluoropiperidin-4-ol | | W.1 | 0.77 (f) | 464 | A |

TABLE W-continued
| Amine | Product | Example # | R$_t$ min (Table 1, Method) | m/z (M + H)$^+$ | TNF IC$_{50}$ |
|---|---|---|---|---|---|
| 7-Azaspiro[3.5]nonan-2-ol | 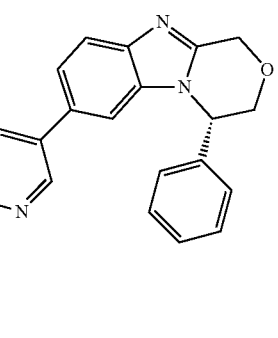 | W.2 | 0.80 (f) | 468 | A |
| Thiomorpholine 1,1-dioxide | 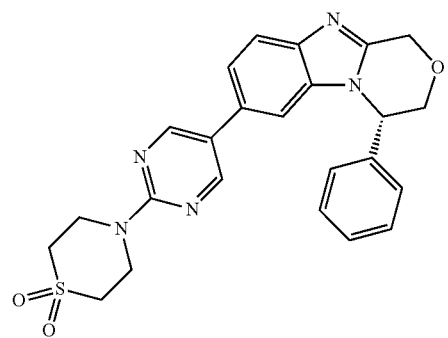 [SMILES: O=S1(=O)CCN(c2ncc(-c3ccc4nc5n(c4c3)[C@@H](c3ccccc3)COC5)cn2)CC1] | W.3 | 0.78 (f) | 462 | A |
| 7-Azaspiro[3.5]nonan-1-ol | 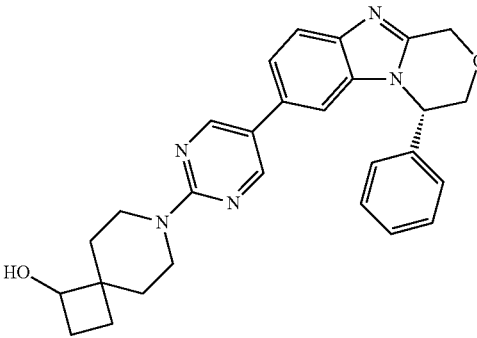 | W.4 | 0.63(i) | 468 | |
| 2-Hydroxy-1-(piperazin-1-yl)ethanone | 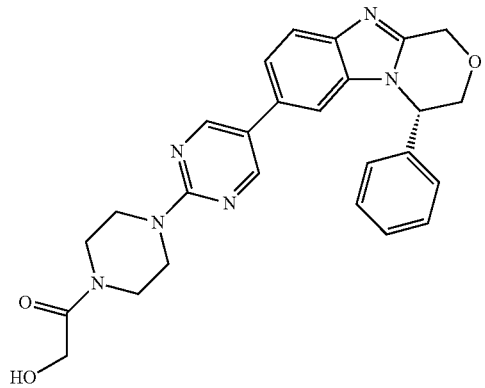 [SMILES: O=C(CO)N1CCN(c2ncc(-c3ccc4nc5n(c4c3)[C@@H](c3ccccc3)COC5)cn2)CC1] | W.5 | 0.55(i) | 471 | |

The compounds shown in Table X were synthesized in a manner similar to Example #9 from 7-bromo-4-(3-fluorophenyl)-3,4-dihydro-1H-benzo[4,5]imidazo[2,1-c][1,4]oxazine (Preparation #30) and the corresponding amine.

TABLE X

| Amine | Product | R<sub>t</sub> min (Table 1, Example # Method) | m/z (M + H)<sup>+</sup> | TNF IC<sub>50</sub> |
|---|---|---|---|---|
| 3,3-Difluoropiperidin-4-ol | | X.1  1.08 (n) | 482 | A |
| 7-Azaspiro[3.5]nonan-2-ol | | X.2  1.07 (n) | 486 | A |
| 1,4-Oxazepane | | X.3  1.08 (n) | 446 | A |

Example #10

2-(5-(1-(2-Methoxyphenyl)-2,3-dihydro-1H-cyclopenta[4,5]imidazo[1,2-a]pyridin-7-yl)pyrimidin-2-yl)propan-2-ol

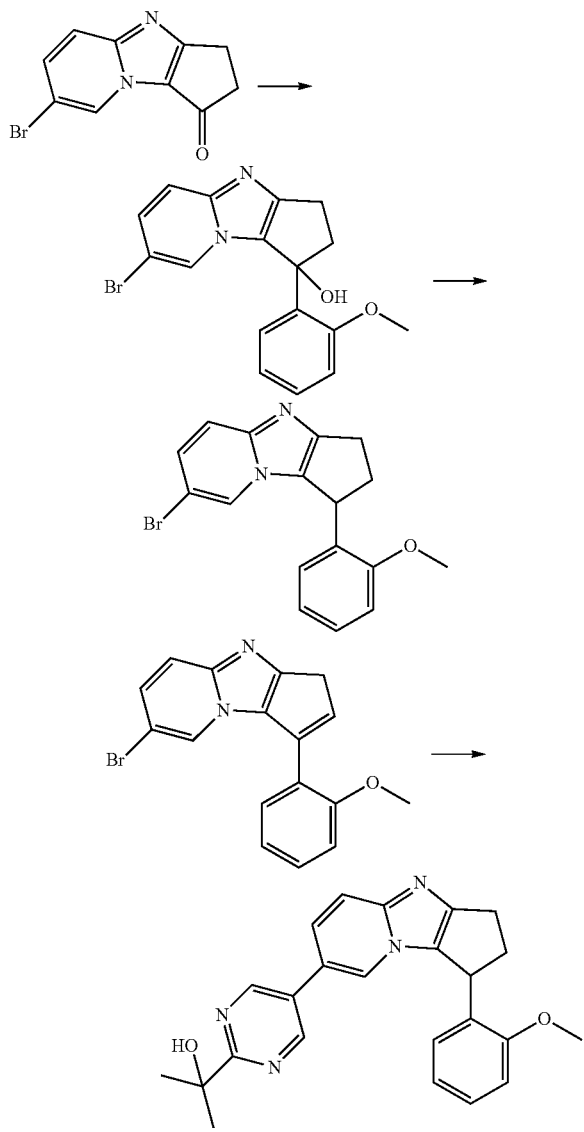

Step 1: 7-Bromo-1-(2-methoxyphenyl)-2,3-dihydro-1H-cyclopenta[4,5]imidazo[1,2-a]pyridin-1-ol To a round flask was added 7-bromo-2,3-dihydro-1H-cyclopenta[4,5]imidazo[1,2-a]pyridin-1-one (0.500 g, 1.99 mmol, Preparation #2) in THF (20 mL). To this stirring solution at about 0° C. under a $N_2$ atmosphere was added (2-methoxyphenyl)magnesium bromide (2.59 mL, 2.59 mmol). The reaction was warmed to rt and stirred for about 1 h. The reaction was quenched with sat. $NH_4Cl$ and extracted with EtOAc. The organics were collected, washed with water, filtered through a phase separator, and concentrated to afford the crude product (0.72 g, 101%); LC/MS (Table 1, Method e) $R_t$=1.37 min.; MS m/z: 341, 343 $(M-H_2O)^+$.

Step 2: 2-(5-(1-(2-Methoxyphenyl)-2,3-dihydro-1H-cyclopenta[4,5]imidazo[1,2-a]pyridin-7-yl)pyrimidin-2-yl)propan-2-ol To 7-bromo-1-(2-methoxyphenyl)-2,3-dihydro-1H-cyclopenta[4,5]imidazo[1,2-a]pyridin-1-ol (0.41 g, 1.141 mmol) in DCM (10 mL) was added TES (0.638 mL, 3.99 mmol) and $BF_3.OEt_2$ (0.477 mL, 3.77 mmol) over about 5 min. The reaction was stirred for about 1 h at about −78° C. under a $N_2$ atmosphere. The reaction was warmed to rt over about 30 min. The mixture was diluted with sat. $NaHCO_3$ and the organic layer was collected. The aqueous layer was extracted with DCM (2×10 mL), the combined organics were filtered through a phase separator, and concentrated under reduced pressure. The residue was purified by flash-column chromatography on silica gel (EtOAc/heptane 40-100%) to give a 1:0.6 mixture of 7-bromo-1-(2-methoxyphenyl)-2,3-dihydro-1H-cyclopenta[4,5]imidazo[1,2-a]pyridine and 7-bromo-1-(2-methoxyphenyl)-3H-cyclopenta[4,5]imidazo[1,2-a]pyridine (0.23 g). A vial was charged with the crude mixture (0.23 g), 2-(5-(4,4,5,5-tetramethyl-1,3,2-dioxaborolan-2-yl)pyrimidin-2-yl)propan-2-ol (0.177 g, 0.670 mmol), $K_3PO_4$ (0.284 g, 1.340 mmol) in a mixture of 1,4-dioxane (2 mL) and MeOH (1.3 mL). The vial was degassed, $Pd(PPh_3)_4$ (0.077 g, 0.067 mmol) was added, purged with $N_2$, and heated at about 110° C. for about 1 h. The reaction was cooled to rt, filtered through Celite®, and concentrated under reduced pressure. The crude product was purified by preparative HPLC (Table 1, Method p) to provide the title compound (0.076 g, 17%); LC/MS (Table 1, Method e) $R_t$=1.00 min.; MS m/z: 401 $(M+H)^+$. (TNF $IC_{50}$=A).

Examples #11 and 12

(S)-2-(5-(1-(2-Methoxyphenyl)-2,3-dihydro-1H-cyclopenta[4,5]imidazo[1,2-a]pyridin-7-yl)pyrimidin-2-yl)propan-2-ol and (R)-2-(5-(1-(2-methoxyphenyl)-2,3-dihydro-1H-cyclopenta[4,5]imidazo[1,2-a]pyridin-7-yl)pyrimidin-2-yl)propan-2-ol

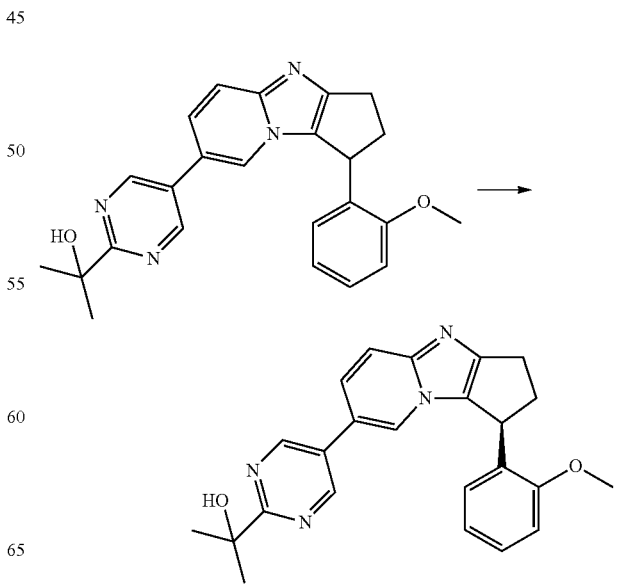

-continued

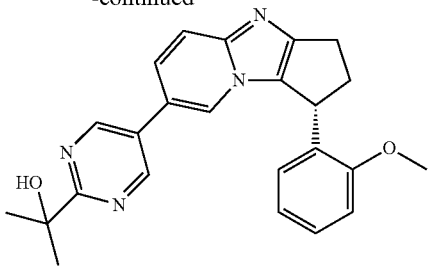

A racemic mixture of 2-(5-(1-(2-methoxyphenyl)-2,3-dihydro-1H-cyclopenta[4,5]imidazo[1,2-a]pyridin-7-yl)pyrimidin-2-yl)propan-2-ol (Example #10) was separated via chiral SFC [Table 2, Method 3] to give (S)-2-(5-(1-(2-methoxyphenyl)-2,3-dihydro-1H-cyclopenta[4,5]imidazo[1,2-a]pyridin-7-yl)pyrimidin-2-yl)propan-2-ol (0.027 g, 39%, OR=positive); LC/MS (Table 1, Method e) $R_t$=1.04 min.; MS m/z: 401 (M+H)$^+$ (TNF IC$_{50}$=C) and (R)-2-(5-(1-(2-methoxyphenyl)-2,3-dihydro-1H-cyclopenta [4,5]imidazo[1,2-a]pyridin-7-yl)pyrimidin-2-yl)propan-2-ol (0.029 g, 42%, OR=negative) [Stereochemistry assignment based on optical rotation]; LC/MS (Table 1, Method e) $R_t$=1.04 min.; MS m/z: 401 (M+H)$^+$. (TNF IC$_{50}$=A)

The compounds shown in Table Y were separated via chiral SFC in a manner similar to Examples #11 and 12.

TABLE Y

Chiral Separation of Stereoisomers

| Stereoisomers [Chiral Separation Method] | Structure | Example # | $R_t$ min (Table 1, Method) | m/z (M + H)$^+$ | TNF IC$_{50}$ |
|---|---|---|---|---|---|
| 4-(5-(1-Phenyl-1,2,3,4-tetrahydrobenzo[4,5]imidazo[1,2-a]pyridin-8-yl)pyrimidin-2-yl)morpholine (Example #D.1) [Table 2, Method 4, $R_t$ = 8.11 min, Stereochemistry assignment based on TNFα activity] | 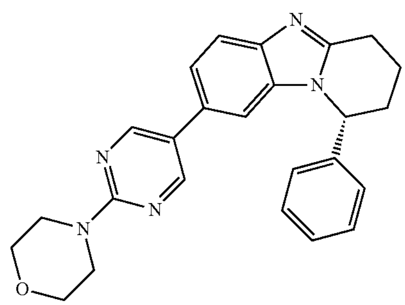 [SMILES: c1ccc([C@H]2CCCc3nc4ccc(-c5cnc(N6CCOCC6)nc5)cc4n32)cc1] | Y.1 | 1.28 (e) | 412 | A |
| 2-(5-(1-Phenyl-1,2,3,4-tetrahydrobenzo[4,5]imidazo[1,2-a]pyridin-8-yl)pyrimidin-2-yl)propan-2-ol (Example #E.1) [Table 2, Method 5, $R_t$ = 3.3 min, Stereochemistry assignment based on TNFα activity] | 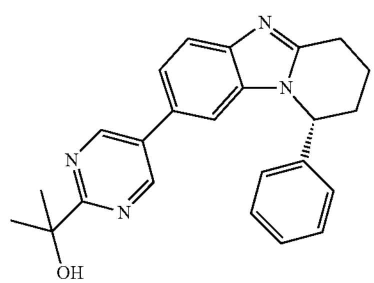 | Y.2 | 1.17 (e) | 385 | A |
| 2-(5-(1-Phenyl-1,2,3,4-tetrahydrobenzo[4,5]imidazo[1,2-a]pyridin-8-yl)pyrimidin-2-yl)propan-2-ol (Example #E.1) [Table 2, Method 5, $R_t$ = 2.7 min, Stereochemistry assignment based on TNFα activity] | 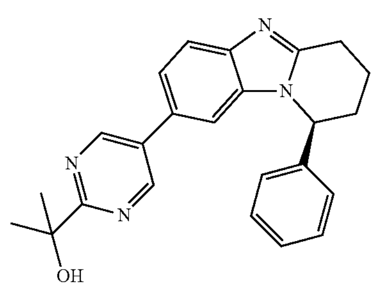 [SMILES: CC(C)(O)c1ncc(-c2ccc3nc4n(c3c2)[C@H](c2ccccc2)CCC4)cn1] | Y.3 | 1.17 (e) | 385 | B |
| 2-(5-(1-Phenyl-2,3-dihydro-1H-benzo[d]pyrrolo[1,2-a]imidazol-7-yl)pyrimidin-2-yl)propan-2-ol (Example #1) [Table 2, Method 7, $R_t$ = 5.30 min, OR = negative, Stereochemistry assignment based on optical rotation] | 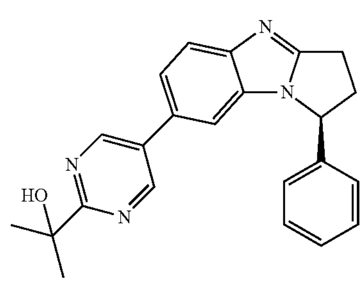 [SMILES: CC(C)(O)c1ncc(-c2ccc3nc4n(c3c2)[C@H](c2ccccc2)CC4)cn1] | Y.4 | 1.24 (e) | 371 | C |

TABLE Y-continued

Chiral Separation of Stereoisomers

| Stereoisomers [Chiral Separation Method] | Structure | Example # | $R_t$ min (Table 1, Method) | m/z (M + H)$^+$ | TNF IC$_{50}$ |
|---|---|---|---|---|---|
| 2-(5-(9-(2-Methoxyphenyl)-6,7,8,9-tetrahydrobenzo[4,5]imidazo[1,2-a]pyridin-2-yl)pyrimidin-2-yl)propan-2-ol (synthesized in a manner similar to Example #3 from 2-bromo-9-(2-methoxyphenyl)-6,7,8,9-tetrahydrobenzo[4,5]imidazo[1,2-a]pyridine (Preparation #11, step 2) and 2-(5-(4,4,5,5-tetramethyl-1,3,2-dioxaborolan-2-yl)pyrimidin-2-yl)propan-2-ol) [Table 2, Method 8, $R_t$ = 4.2 min, OR = negative, Stereochemistry assignment based on optical rotation] | 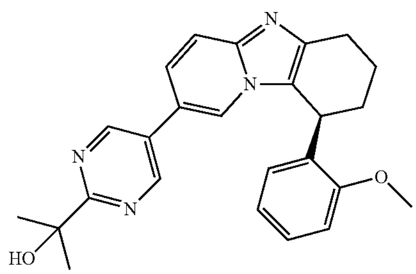 [SMILES: COc1ccccc1[C@@H]1CCCc2nc3ccc(-c4cnc(C(C)(C)O)nc4)cn3c21] | Y.5 | 1.06 (e) | 415 | B |
| 2-(5-(9-(2-Methoxyphenyl)-6,7,8,9-tetrahydrobenzo[4,5]imidazo[1,2-a]pyridin-2-yl)pyrimidin-2-yl)propan-2-ol (synthesized in a manner similar to Example #3 from 2-bromo-9-(2-methoxyphenyl)-6,7,8,9-tetrahydrobenzo[4,5]imidazo[1,2-a]pyridine (Preparation #11, step 2) and 2-(5-(4,4,5,5-tetramethyl-1,3,2-dioxaborolan-2-yl)pyrimidin-2-yl)propan-2-ol) [Table 2, Method 8, $R_t$ = 4.9 min, OR = positive, Stereochemistry assignment based on optical rotation] | 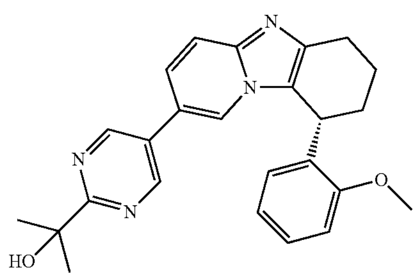 [SMILES: COc1ccccc1[C@H]1CCCc2nc3ccc(-c4cnc(C(C)(C)O)nc4)cn3c21] | Y.6 | 1.06 (e) | 415 | A |
| 4-(3-Fluorophenyl)-7-(2-morpholinopyrimidin-5-yl)-3,4-dihydro-1H-benzo[4,5]imidazo[2,1-c][1,4]oxazine (Example #U.2) [Table 2, Method 6, $R_t$ = 5.9 min, Stereochemistry assignment based on TNFα activity] | 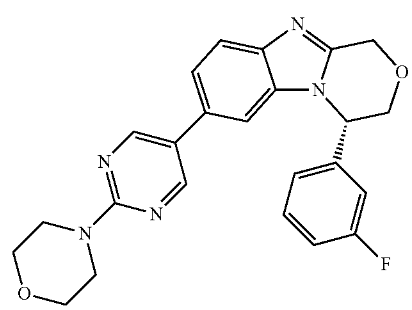 [SMILES: Fc1cccc([C@H]2COCc3nc4ccc(-c5cnc(N6CCOCC6)nc5)cc4n32)c1] | Y.7 | 0.81 (f) | 432 | A |
| 2-(5-(1-(2,5-Dimethylphenyl)-2,3-dihydro-1H-benzo[d]pyrrolo[1,2-a]imidazol-7-yl)pyrimidin-2-yl)propan-2-ol (Example #B.2) [Table 2, Method 14, $R_t$ = 8.40 min, Stereochemistry assignment based on TNFα activity] | 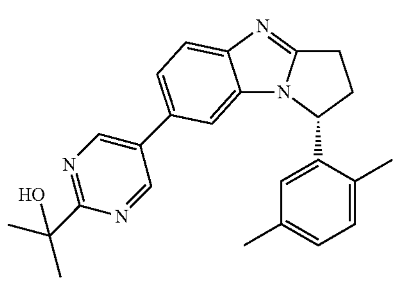 | Y.8 | 0.89 (f) | 399 | A |
| 2-(5-(1-(2,5-Dimethylphenyl)-2,3-dihydro-1H-benzo[d]pyrrolo[1,2-a]imidazol-7-yl)pyrimidin-2-yl)propan-2-ol (Example #B.2) [Table 2, Method 14, $R_t$ = 6.85 min, Stereochemistry assignment based on TNFα activity] | 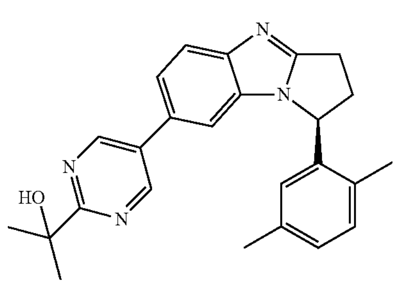 [SMILES: Cc1ccc(C)c([C@@H]2CCc3nc4ccc(-c5cnc(C(C)(C)O)nc5)cc4n32)c1] | Y.9 | 0.78 (f) | 399 | B |

TABLE Y-continued

Chiral Separation of Stereoisomers

| Stereoisomers [Chiral Separation Method] | Structure | Example # | R$_t$ min (Table 1, Method) | m/z (M + H)$^+$ | TNF IC$_{50}$ |
|---|---|---|---|---|---|
| 4-(5-(8-Phenyl-7,8-dihydro-6H-pyrrolo[2',1':2,3]imidazo[4,5-b]pyridin-2-yl)pyrimidin-2-yl)morpholine (Example #6) [Table 2, Method 12, R$_t$ = 8.12 min, Stereochemistry assignment based on TNFα activity] | 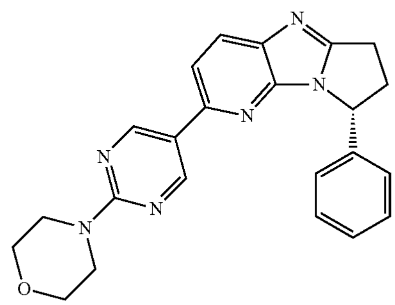 [SMILES: c1ccc([C@H]2CCc3nc4ccc(-c5cnc(N6CCOCC6)nc5)nc4n32)cc1] | Y.10 | 0.77 (f) | 399 | A |
| 1-(5-(8-phenyl-7,8-dihydro-6H-pyrrolo[2',1':2,3]imidazo[4,5-b]pyridin-2-yl)pyrimidin-2-yl)piperidin-4-ol (Example #L.3) [Table 2, Method 12, R$_t$ = 14.2 min, Stereochemistry assignment based on TNFα activity] | 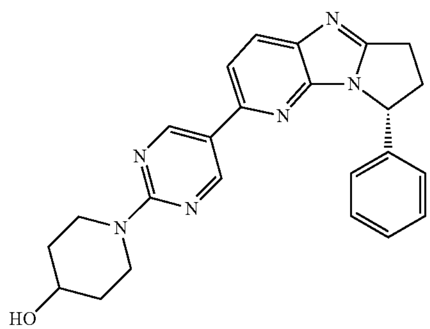 [SMILES: OC1CCN(c2ncc(-c3ccc4nc5n(c4n3)[C@@H](c3ccccc3)CC5)cn2)CC1] | Y.11 | 0.65 (f) | 413 | A |
| 1-(5-(8-(3-fluorophenyl)-7,8-dihydro-6H-pyrrolo[2',1':2,3]imidazo[4,5-b]pyridin-2-yl)pyrimidin-2-yl)piperidin-4-ol (Example #M.4) [Table 2, Method 12, R$_t$ = 6.1 min, Stereochemistry assignment based on TNFα activity] | 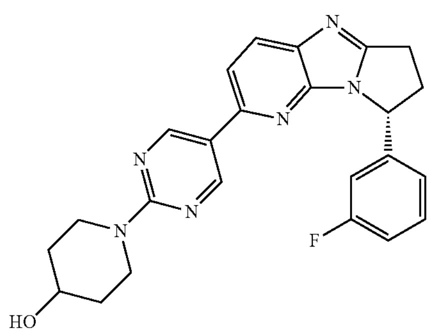 [SMILES: OC1CCN(c2ncc(-c3ccc4nc5n(c4n3)[C@@H](c3cccc(F)c3)CC5)cn2)CC1] | Y.12 | 0.65 (f) | 413 | A |
| 2-(5-(6',8'-Dihydro-2H-spiro[benzofuran-3,9'-pyrido[3',2':4,5]imidazo[2,1-c][1,4]oxazin]-2'-yl)pyrimidin-2-yl)propan-2-ol (Example #E.4) [Table 2, 17, R$_t$ = 4.8 min, Stereochemistry assignment based on TNFα activity] | 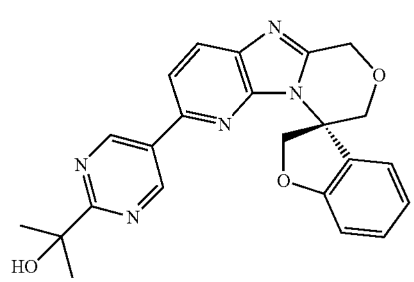 [SMILES: CC(C)(O)c1ncc(-c2ccc3nc4n(c3n2)[C@@]2(COC4)COc3ccccc32)cn1] | Y.13 | 0.88 (z) | 416 | A |
| 2-(5-(6',8'-Dihydrospiro[chroman-4,9'-pyrido[3',2':4,5]imidazo[2,1-c][1,4]oxazin]-2'-yl)pyrimidin-2-yl)propan-2-ol (Example #E.5) [Table 2, 18, R$_t$ = 4.4 min, Stereochemistry assignment based on TNFα activity] | 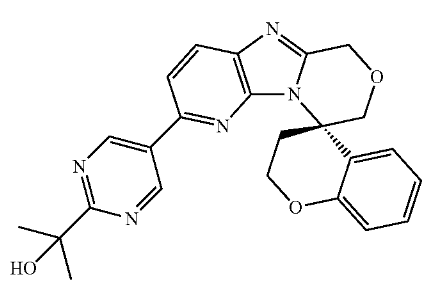 [SMILES: CC(C)(O)c1ncc(-c2ccc3nc4n(c3n2)[C@]2(CCOc3ccccc32)COC4)cn1] | Y.14 | 0.83 (y) | 430 | A |

TABLE Y-continued

Chiral Separation of Stereoisomers

| Stereoisomers<br>[Chiral Separation Method] | Structure | Example # | $R_t$ min (Table 1, Method) | m/z (M + H)+ | TNF IC$_{50}$ |
|---|---|---|---|---|---|
| 2-(5-(6',8'-Dihydrospiro[chroman-4,9'-pyrido[3',2':4,5]imidazo[2,1-c][1,4]oxazin]-2'-yl)pyrimidin-2-yl)propan-2-ol (Example #E.5) [Table 2, 18, $R_t$ = 2.9 min, Stereochemistry assignment based on TNFα activity] | 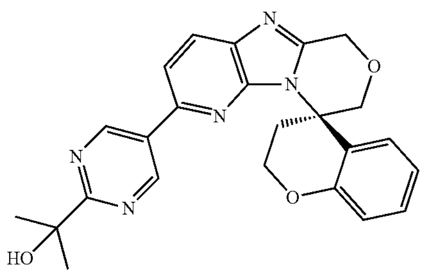 [SMILES: CC(C)(O)c1ncc(-c2ccc3nc4n(c3n2)[C@@]2(CCOc3ccccc32)COC4)cn1] | Y.15 | 0.83 (y) | 430 | B |

Example #13

(S)-2-(5-(4-(2-(Difluoromethoxy)phenyl)-3,4-dihydro-H-benzo[4,5]imidazo[2,1-c][1,4]oxazin-7-yl)pyrimidin-2-yl)propan-2-ol

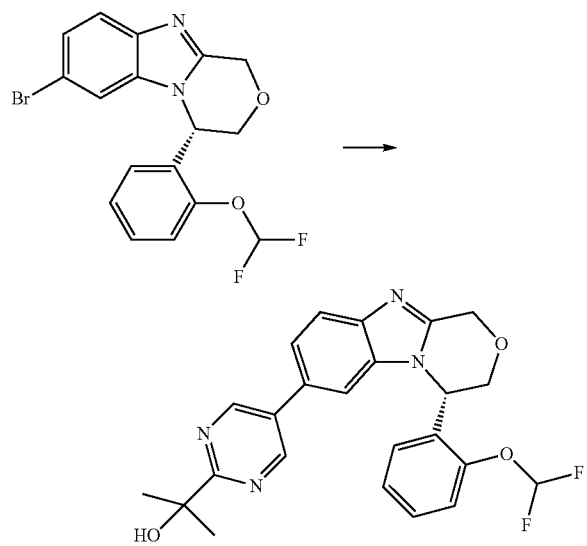

A mixture of (S)-7-bromo-4-(2-(difluoromethoxy)phenyl)-3,4-dihydro-1H-benzo[4,5]imidazo[2,1-c][1,4]oxazine (0.15 g, 0.38 mmol, Preparation #36), 2-(5-(4,4,5,5-tetramethyl-1,3,2-dioxaborolan-2-yl)pyrimidin-2-yl)propan-2-ol (0.20 g, 0.76 mmol), Pd(dppf)Cl$_2$.DCM (0.031 g, 0.038 mmol), 2 M aqueous Na$_2$CO$_3$ (0.47 mL, 0.95 mmol), and 1,4-dioxane (1.0 mL) were heated in a microwave oven at about 135° C. for about 1 h. The reaction mixture was cooled to rt and partitioned between EtOAc and brine (3 mL each). The layers were separated and the aqueous layer was extracted with EtOAc (2×3 mL). The combined organic layers were dried over Na$_2$SO$_4$, filtered, and concentrated under reduced pressure. The crude product was purified via silica gel chromatography eluting with 0-100% EtOAc in heptane to give impure title compound that was further purified via silica gel chromatography eluting with 0-50% DCM/MeOH/NH$_4$OH (90:9:1) in DCM to give the title compound (0.070 g, 41%); LC/MS (Table 1, Method f) $R_t$=2.27 min; MS m/z: 453 (M+H)+; $^1$H NMR (400 MHz, DMSO-d$_6$) δ 8.91 (s, 2H), 7.79 (d, J=8.3 Hz, 1H), 7.61 (dd, J=8.4, 1.8 Hz, 1H), 7.60-7.21 (m, 4H), 7.13 (td, J=7.5, 1.2 Hz, 1H), 6.69 (dd, J=7.8, 1.7 Hz, 1H), 5.98 (t, J=3.8 Hz, 1H), 5.19 (d, J=15.9 Hz, 1H), 5.08 (d, J=15.8 Hz, 1H), 5.05 (s, 1H), 4.43 (dd, J=11.9, 4.1 Hz, 1H), 4.15 (dd, J=12.0, 3.5 Hz, 1H), 1.50 (s, 6H). (TNF IC$_{50}$=A)

The compounds shown in Table Z were synthesized in a manner similar to Example #13 from the corresponding bromide.

TABLE Z

| Bromide | Product | Example # | $R_t$ min (Table 1, Method) | m/z (M + H)+ | TNF IC$_{50}$ |
|---|---|---|---|---|---|
| (S)-7-Bromo-4-(2-methoxyphenyl)-3,4-dihydro-1H-benzo[4,5]imidazo[2,1-c][1,4]oxazine (Preparation #60) | | Z.1 | 2.10 (g) | 417 | A |

TABLE Z-continued

| Bromide | Product | Example # | R$_t$ min (Table 1, Method) | m/z (M + H)$^+$ | TNF IC$_{50}$ |
|---|---|---|---|---|---|
| 7-Bromo-4-(2,6-dichlorophenyl)-3,4-dihydro-1H-benzo[4,5]imidazo[2,1-c][1,4]oxazine (Preparation #50) | | Z.2 | 2.27 (g) | 455, 457 | A |
| 7-Bromo-4-(2-methoxyphenyl)-3,4-dihydro-2H-pyrano[2',3':4,5]imidazo[1,2-a]pyridine (Preparation #91) | | Z.3 | 0.82 (ab) | 417 | B |

Example #14

4-(5-(9-(2-Methoxyphenyl)-6,7-dihydrobenzo[4,5]imidazo[1,2-a]pyridin-2-yl)pyrimidin-2-yl)morpholine

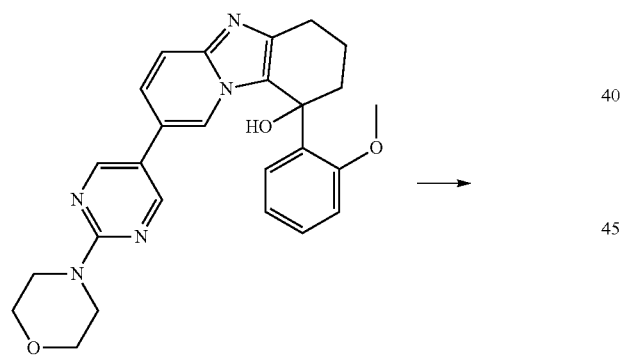

To a mixture of 9-(2-methoxyphenyl)-2-(2-morpholinopyrimidin-5-yl)-6,7,8,9-tetrahydrobenzo[4,5]-imidazo[1,2-a]pyridin-9-ol (0.07 g, 0.153 mmol, Example #5) in DCM (1 mL) was added BF$_3$·OEt$_2$ (0.064 mL, 0.505 mmol) and TES (0.086 mL, 0.535 mmol). The reaction was stirred for about 30 min at rt then MeOH was added to dissolve a minor amount of precipitate. The mixture was washed with sat. NaHCO$_3$, the organic layer was collected and the aqueous layer was extracted with DCM (10 mL). The combined organic layers were dried over MgSO$_4$, filtered, and concentrated under reduced pressure to give the title compound (0.05 g, 74%); LC/MS (Table 1, Method e) R$_t$=1.39 min.; MS m/z: 440 (M+H)$^+$. (TNF IC$_{50}$=C).

Example #15

4-(5-(9-(2-Methoxyphenyl)-6,7,8,9-tetrahydrobenzo[4,5]imidazo[1,2-a]pyridin-2-yl)pyrimidin-2-yl)morpholine

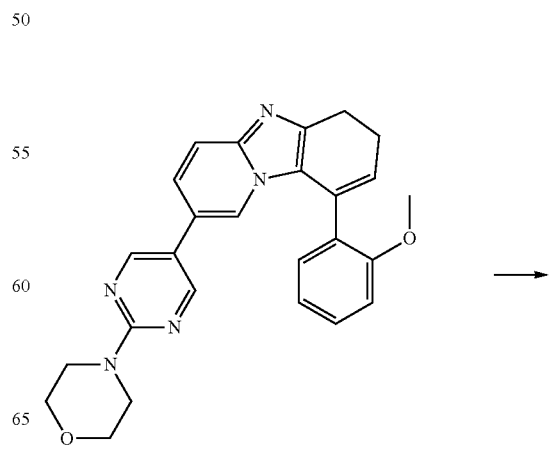

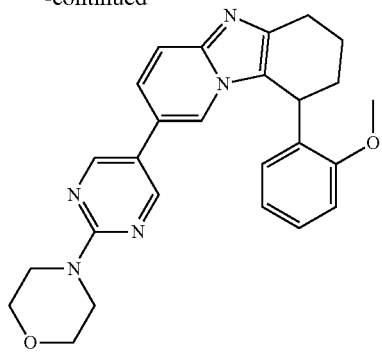

4-(5-(9-(2-Methoxyphenyl)-6,7-dihydrobenzo[4,5]imidazo[1,2-a]pyridin-2-yl)pyrimidin-2-yl)morpholine (0.04 g, 0.091 mmol, Example #14) and THF (10 mL) were added to 5% Pd/C (0.01 g, 0.042 mmol) in a 50 mL pressure bottle and stirred at rt for about 16 h at about 30 psi. The reaction was heated to about 50° C. for about 16 h. The reaction was filtered and concentrated onto silica gel. The crude material was purified by flash-column chromatography on silica gel (MeOH/DCM 0-10%) to give the title compound (0.01 g, 21%); LC/MS (Table 1, Method e) $R_t$=1.46 min.; MS m/z: 442 (M+H)$^+$. (TNF IC$_{50}$=A).

Example #16

2-(5-(9-(2-Methoxyphenyl)-6,7,8,9-tetrahydrobenzo[4,5]imidazo[1,2-a]pyridin-2-yl)pyrimidin-2-yl)propan-2-ol

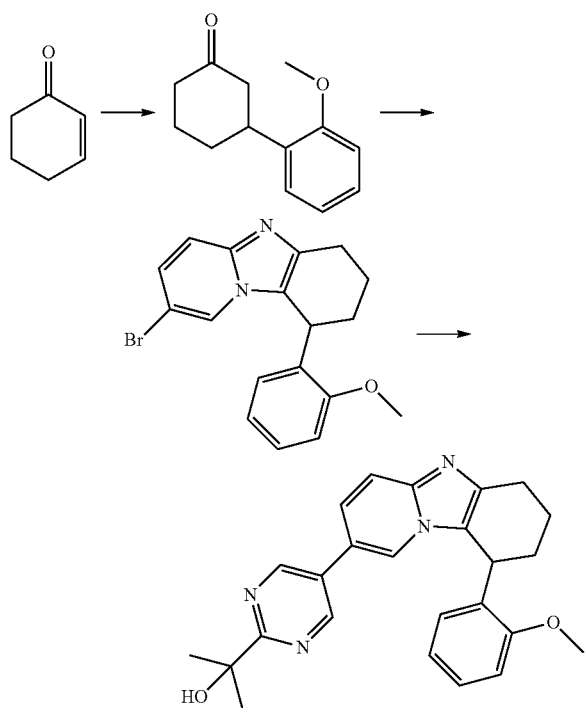

Step 1: 3-(2-Methoxyphenyl)cyclohexanone

Argon was bubbled through 1,4-dioxane (52 mL) for 10 min, then (2-methoxyphenyl)boronic acid (6.38 g, 42.0 mmol), 2,2'-bis(diphenylphosphino)-1,1'-binaphthalene (0.423 g, 0.680 mmol), and bis(norbornadiene)rhodium(I) tetrafluoroboranate (0.239 g, 0.640 mmol) were added and argon bubbling continued for about 5 min. The mixture was stirred at rt for about 2 h under argon, then to the suspension was added water (8 mL), cyclohex-2-enone (3.87 mL, 40 mmol), and TEA (5.58 mL, 40.0 mmol). The reaction mixture was stirred at rt overnight. The mixture was diluted with EtOAc and filtered through a Celite® pad and the filtrate was concentrated and partitioned between water and DCM. The crude was purified by flash-column chromatography on silica gel (0-50% EtOAc/heptane) to give the title compound (5.5 g, 67%); $^1$H NMR (400 MHz, DMSO-d$_6$) δ 7.29 7.09 (m, 2H), 7.00 6.87 (m, 2H), 6.73 2.59 (d, J=12.8 Hz, 1H), 2.44 2.14 (m, 3H), 2.02 (ddq, J=13.1, 6.5, 3.4 Hz, 1H), 1.85 (td, J=8.8, 3.3 Hz, 2H), 1.67 (dtdd, J=12.9, 8.6, 6.5, 4.6 Hz, 1H).

Step 2: 2-Bromo-9-(2-methoxyphenyl)-6,7,8,9-tetrahydrobenzo[4,5]imidazo[1,2-a]pyridine To a clear solution of 3-(2-methoxyphenyl)cyclohexanone (1.6 g, 7.83 mmol) in AcOH (20 mL), Br$_2$ (0.888 mL, 17.23 mmol) was added. The solution was stirred at about 50° C. for about 6 h. Solvent and excess Br$_2$ was removed under vacuum. The residue was dissolved in AcOH (8 mL) and treated with 5-bromopyridin-2-amine (1.355 g, 7.83 mmol), then the mixture was irradiated with microwave at about 150° C. for about 3 h. The solvent was removed and the residue was passed through silica gel to give the crude title compound (0.20 g, 7%); LC/MS (Table 1, Method d) $R_t$=0.67 min; MS m/z: 357, 359 (M+H)$^+$ Step 3: 2-(5-(9-(2-Methoxyphenyl)-6,7,8,9-tetrahydrobenzo[4,5]imidazo[1,2-a]pyridin-2-yl)pyrimidin-2-yl)propan-2-ol To a degassed mixture of 2-bromo-9-(2-methoxyphenyl)-6,7,8,9-tetrahydrobenzo[4,5]imidazo[1,2-a]pyridine (0.18 g, 0.252 mmol), K$_3$PO$_4$ (0.160 g, 0.756 mmol) and 2-(5-(4,4,5,5-tetramethyl-1,3,2-dioxaborolan-2-yl)pyrimidin-2-yl)propan-2-ol (0.399 g, 0.756 mmol) in 1,4-dioxane (1.5 mL) and MeOH (1.0 mL) was added Pd(PPh$_3$)$_4$ (0.029 g, 0.025 mmol). The reaction vessel was sealed and heated with microwave at about 110° C. for about 120 min. The suspension was filtered and the filtrate was concentrated and purified by preparative HPLC (Table 1, Method j) to give the title compound (0.020 g, 19%); LC/MS (Table 1, Method d) $R_t$=0.69 min; MS m/z: 415 (M+H)$^+$. $^1$H NMR (400 MHz, DMSO-d$_6$) δ 8.86 (s, 2H), 7.81 (dd, J=1.8, 0.9 Hz, 1H), 7.70-7.49 (m, 2H), 7.20 (ddd, J=9.0, 7.5, 1.7 Hz, 1H), 7.07 (dd, J=8.4, 1.1 Hz, 1H), 6.71 (td, J=7.5, 1.1 Hz, 1H), 6.29 (dd, J=7.6, 1.7 Hz, 1H), 5.05 (s, 1H), 4.79 (t, J=5.1 Hz, 1H), 3.88 (s, 3H), 2.86-2.76 (m, 2H), 2.14-2.22 (m, 1H), 1.94-2.00 (m, 1H),1.67-1.80 (m, 2H),1.47 (s, 6H). (TNF IC$_{50}$=A).

Example #17

2-(5-(1-Cyclohexyl-2,3-dihydro-1H-benzo[d]pyrrolo[1,2-a]imidazol-7-yl)pyrimidin-2-yl)propan-2-ol

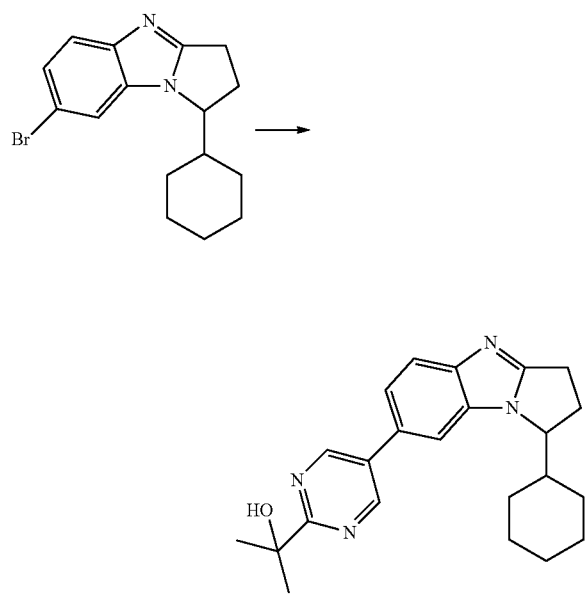 [SMILES: Brc1ccc2nc3n(c2c1)C(C1CCCCC1)CC3 ; CC(C)(O)c1ncc(-c2ccc3nc4n(c3c2)C(C2CCCCC2)CC4)cn1]

To a vial was added (2-(2-hydroxypropan-2-yl)pyrimidin-5-yl)boronic acid (0.282 g, 1.551 mmol), EtOH (5 mL), $Cs_2CO_3$ (0.505 g, 1.551 mmol) followed by the addition of SiliaCat® DPP-Pd (0.207 g, 0.052 mmol) and 7-bromo-1-cyclohexyl-2,3-dihydro-1H-benzo[d]pyrrolo[1,2-a]imidazole (0.165 g, 0.517 mmol, Preparation #8). The contents were heated at about 95° C. for about 2 h. The reaction was cooled to rt, filtered, the filter cake washed with MeOH, and the filtrate concentrated to dryness. The crude product was purified by preparative HPLC (Table 1, Method m). The sample was dissolved in DCM, washed with aq. $NaHCO_3$, filtered through a phase separator and concentrated to give the title compound (0.034 g, 17%); LC/MS (Table 1, Method f) $R_t$=0.69 min; MS m/z: 377 (M+H)$^+$. (TNF $IC_{50}$=A).

Example #18

8-Phenyl-2-(4-(pyrimidin-2-yl)piperazin-1-yl)-7,8-dihydro-6H-pyrrolo[2',1':2,3]imidazo[4,5-b]pyridine

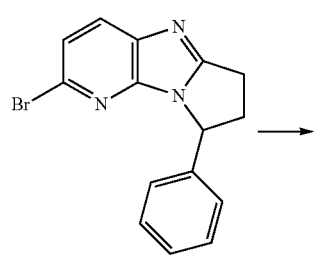

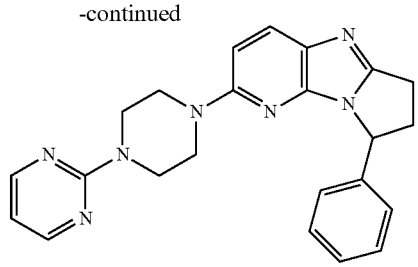

To a microwave tube was added 2-bromo-8-phenyl-7,8-dihydro-6H-pyrrolo[2',1':2,3]imidazo[4,5-b]pyridine (0.1 g, 0.318 mmol, Preparation #12), 2-(piperazin-1-yl)pyrimidine (0.078 g, 0.477 mmol), xantphos (0.039 g, 0.067 mmol), Pd(OAc)$_2$ (0.007 g, 0.032 mmol), $Cs_2CO_3$ (0.259 g, 0.796 mmol) and 1,4-dioxane (2 mL). The mixture was purged with $N_2$ and then heated for about 1 h in a microwave at about 135° C. The reaction was cooled to rt, filtered through Celite® and evaporated to dryness. The resulting residue was purified by preparative HPLC (Table 1, Method j) to give the title compound (0.065 g, 51.4%); LC/MS (Table 1, Method d) $R_t$=0.68 min; MS m/z: 398 (M+H)$^+$. (TNF $IC_{50}$=B).

Example #19

7-(2-Morpholinopyrimidin-5-yl)-4-phenyl-3,4-dihydro-1H-benzo[4,5]imidazo[2,1-c][1,4]oxazine

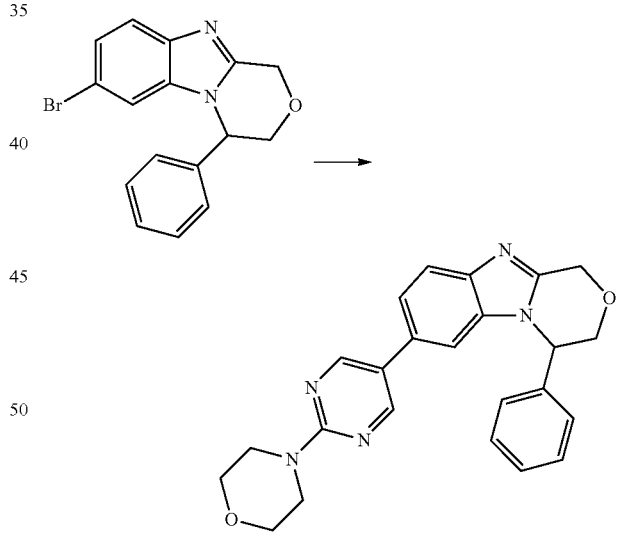

In a 4 mL vial equipped with a magnetic stirrer was added 7-bromo-4-phenyl-3,4-dihydro-1H-benzo[4,5]imidazo[2,1-c][1,4]oxazine (0.100 g, 0.304 mmol, Preparation #26), 4-(5-(4,4,5,5-tetramethyl-1,3,2-dioxaborolan-2-yl)pyrimidin-2-yl)morpholine (0.133 g, 0.456 mmol), and Pd(dppf)Cl$_2$.DCM (0.024 g, 0.030 mmol). 4 mL of dry, degassed 1,4-dioxane was added to the vial followed by the addition of 1M $Cs_2CO_3$ (0.600 mL, 0.6 mmol). The vial was sealed and heated at about 100° C. for about 4 h. The mixture was filtered through Celite®, and evaporated to dryness, and purified by flash-column chromatography on silica gel (1-10% MeOH/DCM) to obtain the title compound (0.071 g, 64%); LC/MS (Table 1, Method e) $R_t$=1.36 min; MS m/z: 414 (M+H)⁺. (TNF IC$_{50}$=A).

Examples #20 and #21

(R)-7-(2-Morpholinopyrimidin-5-yl)-4-phenyl-3,4-dihydro-1H-benzo[4,5]imidazo[2,1-c][1,4]oxazine and (S)-7-(2-morpholinopyrimidin-5-yl)-4-phenyl-3,4-dihydro-1H-benzo[4,5]imidazo[2,1-c][1,4]oxazine)

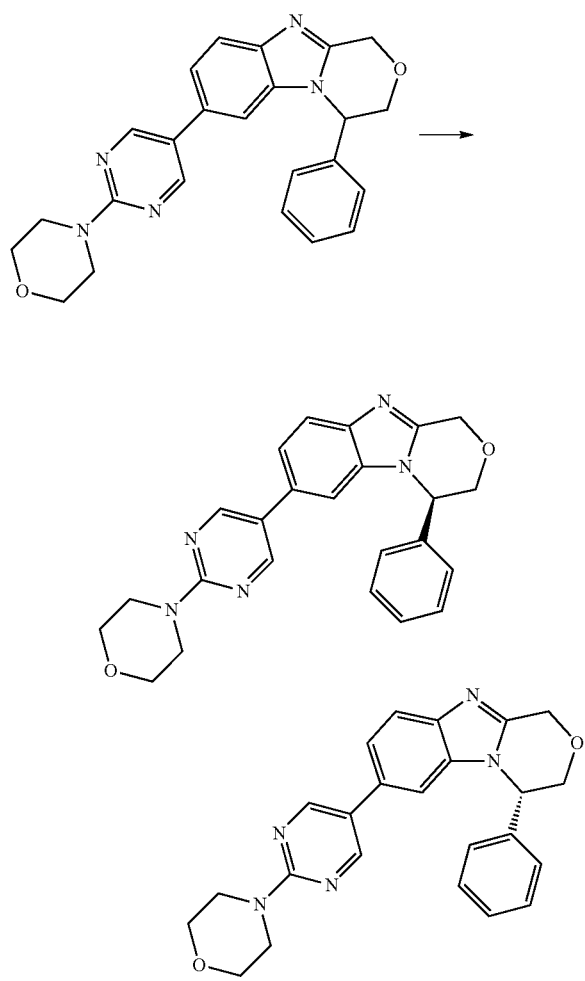

A racemic mixture of 7-(2-morpholinopyrimidin-5-yl)-4-phenyl-3,4-dihydro-1H-benzo[4,5]imidazo[2,1-c][1,4]oxazine (Example #19) was separated via chiral SFC (Table 2, Method 6) to give (R)-7-(2-morpholinopyrimidin-5-yl)-4-phenyl-3,4-dihydro-1H-benzo[4,5]imidazo[2,1-c][1,4]oxazine; LC/MS (Table 1, Method e) $R_t$=1.36 min; MS m/z: 414 (M+H)⁺. (TNF IC$_{50}$=C) and (S)-7-(2-morpholinopyrimidin-5-yl)-4-phenyl-3,4-dihydro-1H-benzo[4,5]imidazo[2,1-c][1,4]oxazine; [Stereochemistry assignment based on TNFα FP binding assay activity]; LC/MS (Table 1, Method e) $R_t$=1.36 min; MS m/z: 414 (M+H)⁺. (TNF IC$_{50}$=A)

Example #22

1-(5-(4-Phenyl-3,4-dihydro-1H-benzo[4,5]imidazo[2,1-c][1,4]oxazin-7-yl)pyrimidin-2-yl)piperidine-4-carboxylic acid

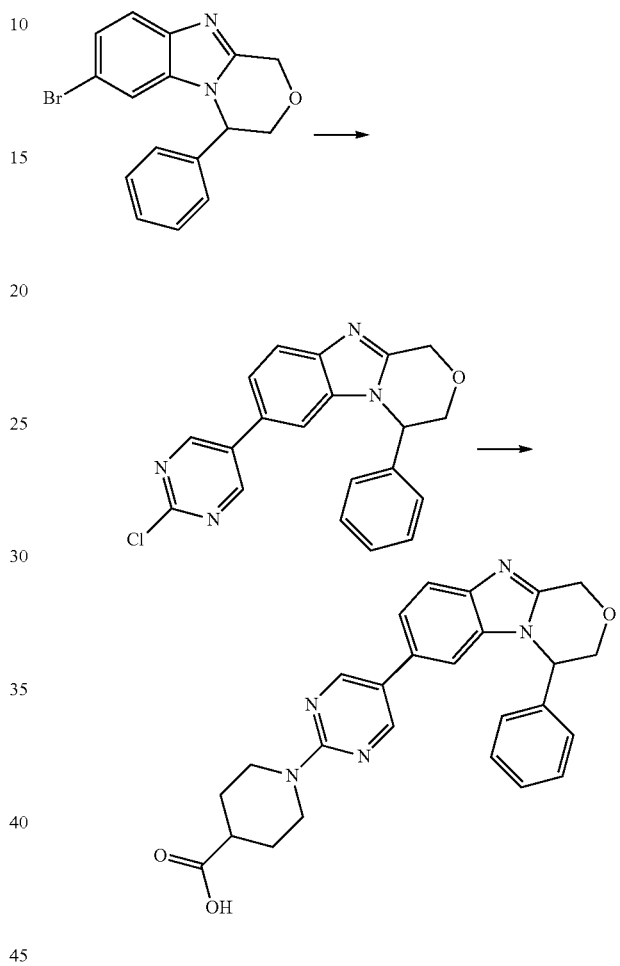

In a vial equipped with a magnetic stirrer was added 7-bromo-4-phenyl-3,4-dihydro-1H-benzo[4,5]imidazo[2,1-c][1,4]oxazine (0.050 g, 0.152 mmol, Preparation #26), 2-chloro-5-(4,4,5,5-tetramethyl-1,3,2-dioxaborolan-2-yl)pyrimidine (0.073 g, 0.304 mmol), and Pd(dppf)Cl$_2$.DCM (0.012 g, 0.015 mmol). 2 mL of dry, degassed 1,4-dioxane was added to the vial followed by the addition of 1M Cs$_2$CO$_3$ (0.300 mL, 0.6 mmol). The vial was sealed and heated at about 140° C. for about 30 min. The reaction mixture was filtered through Celite® and evaporated to dryness to give crude 7-(2-chloropyrimidin-5-yl)-4-phenyl-3,4-dihydro-1H-benzo[4,5]imidazo[2,1-c][1,4]oxazine. The crude material was redissolved in EtOH (2 mL) and DIEA (0.079 g, 0.608 mmol) was added followed by the addition of piperidine-4-carboxylic acid (0.039 g, 0.608 mmol). The reaction mixture was heated at about 90° C. for about 3 h, then cooled to rt, filtered through Celite®, and evaporated to dryness. The resulting residue was purified by preparative HPLC (Table 1, Method k) to give the title compound (0.019 g, 28%); LC/MS (Table 1, Method f) $R_t$=0.68 min; MS m/z: 456 (M+H)⁺. (TNF IC$_{50}$=B).

Example #23

5-(9-(2-Methoxyphenyl)-6,7,8,9-tetrahydrobenzo[4,5]imidazo[1,2-a]pyridin-2-yl)thiophene-2-carboxylic acid

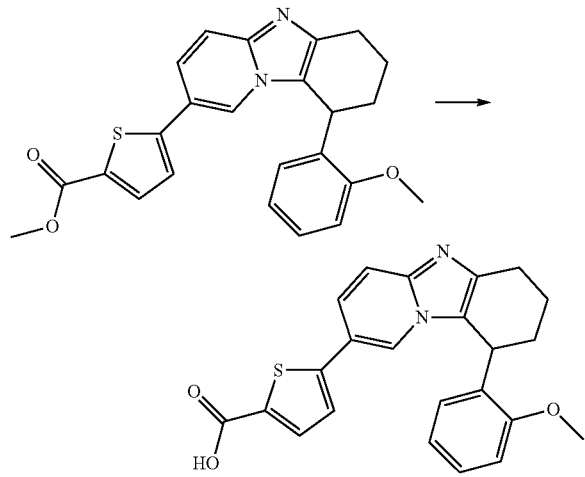

To methyl 5-(9-(2-methoxyphenyl)-6,7,8,9-tetrahydrobenzo[4,5]imidazo[1,2-a]pyridin-2-yl)thiophene-2-carboxylate (0.025 g, 0.060 mmol, synthesized in a similar manner to Example #7 from 2-bromo-9-(2-methoxyphenyl)-6,7,8,9-tetrahydrobenzo[4,5]imidazo[1,2-a]pyridine (Preparation #11, step 2) and methyl 5-(4,4,5,5-tetramethyl-1,3,2-dioxaborolan-2-yl)thiophene-2-carboxylate) was added a mixture of MeOH/water (0.5 mL/0.25 mL) followed by LiOH (0.0114 g, 0.478 mmol). This was stirred at rt for about 5 h. Then MeOH was evaporated under reduced pressure. The residue was acidified (about pH 5) with 1N HCl, extracted with 25% IPA/CHCl$_3$ (20 mL), the organic phase was dried and concentrated under reduced pressure. The residue was purified by preparative HPLC (Table 1, Method q) to give the title compound (0.003 g, 12%). LC/MS (Table 1, Method e) R$_t$=1.38 min; MS m/z: 405 (M+H)$^+$. (TNF IC$_{50}$=B)

Example #24

(R)-7-(5-((R)-1-Phenyl-2,3-dihydro-1H-benzo[d]pyrrolo[1,2-a]imidazol-7-yl)pyrimidin-2-yl)hexahydroimidazo[1,5-a]pyrazin-3(2H)-one

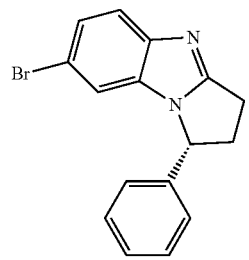

-continued

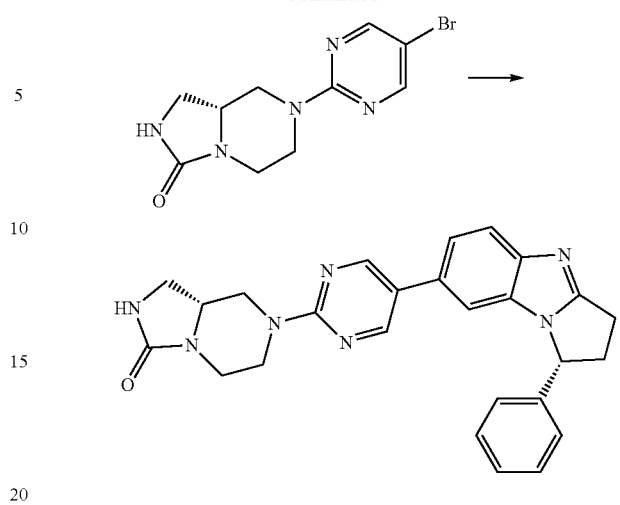

A mixture of bis(pinacolato)diboron (0.114 g, 0.447 mmol), (R)-7-(5-bromopyrimidin-2-yl)hexahydroimidazo[1,5-a]pyrazin-3(2H)-one (0.072 g, 0.241 mmol, Preparation #39), KOAc (0.063 g, 0.644 mmol), Pd(dppf)Cl$_2$ (0.012 g, 0.017 mmol), and 1,4-dioxane (2 mL) was evacuated then back-filled with N$_2$ three times then purged with N$_2$ for about 10 min. The mixture was warmed to about 95° C. After about 3 h, the mixture was allowed to cool to rt and (R)-7-bromo-1-phenyl-2,3-dihydro-1H-benzo [d]pyrrolo[1,2-a]imidazole (0.07 g, 0.224 mmol, Preparation #4), Cs$_2$CO$_3$ (0.182 g, 0.559 mmol), and PdCl$_2$(PPh$_3$)$_2$(0.012 g, 0.017 mmol) were added in one portion. Water (0.5 mL) was added and the reaction was evacuated then back-filled with N$_2$ three times then purged with N$_2$ for about 10 min. The mixture was warmed to 95° C. After about 3 h, the mixture was allowed to cool to rt and stirred at rt for about 10 h. Water (15 mL) and DCM (20 mL) were added, the mixture was filtered, and then the layers were separated. The aqueous layer was extracted with DCM (2×20 mL). The combined organics were dried over Mg$_2$SO$_4$, filtered and concentrated. The crude product was purified via silica gel chromatography (0-5% MeOH/DCM) to give the title compound (0.065 g, 64%); LC/MS (Table 1, Method s) R$_t$=2.27 min; MS m/z: 452 (M+H)$^+$. (TNF IC$_{50}$=A)

Example #25

(S)-7-(5-((R)-1-Phenyl-2,3-dihydro-1H-benzo[d]pyrrolo[1,2-a]imidazol-7-yl)pyrimidin-2-yl)hexahydroimidazo[1,5-a]pyrazin-3(2H)-one

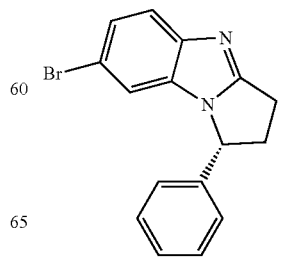

-continued

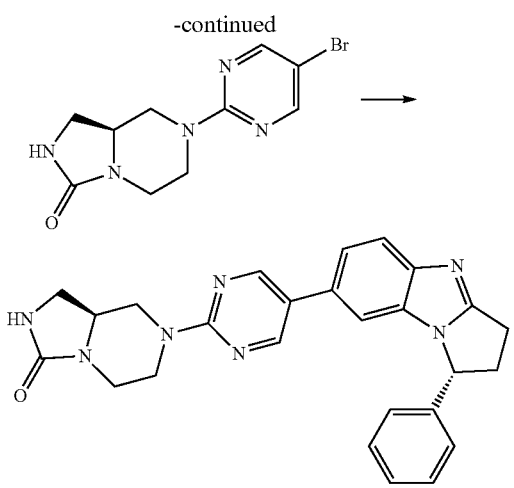

A mixture of bis(pinacolato)diboron (0.114 g, 0.447 mmol), (S)-7-(5-bromopyrimidin-2-yl)hexahydroimidazo[1,5-a]pyrazin-3(2H)-one (0.072 g, 0.241 mmol, Preparation #39), KOAc (0.063 g, 0.644 mmol), Pd(dppf)Cl$_2$ (0.012 g, 0.017 mmol), and 1,4-dioxane (2 mL) was evacuated then back-filled with N$_2$ three times then purged with N$_2$ for about 10 min. The mixture was warmed to about 95° C. After about 3 h, the mixture was allowed to cool to rt and (R)-7-bromo-1-phenyl-2,3-dihydro-1H-benzo [d]pyrrolo[1,2-a]imidazole (0.07 g, 0.224 mmol, Preparation #4), Cs$_2$CO$_3$ (0.182 g, 0.559 mmol), and PdCl$_2$(PPh$_3$)$_2$(0.012 g, 0.017 mmol) were added in one portion. Water (0.5 mL) was added and the reaction was evacuated then back-filled with N$_2$ three times then purged with N$_2$ for about 10 min. The mixture was warmed to 95° C. After about 3 h, the mixture was allowed to cool to rt and stirred at rt for about 10 h. Water (15 mL) and DCM (20 mL) were added, the mixture was filtered, and then the layers were separated. The aqueous layer was extracted with DCM (2×20 mL). The combined organics were dried over Mg$_2$SO$_4$, filtered and concentrated. The crude product was purified via silica gel chromatography (0-5% MeOH/DCM) to give the title compound (0.078 g, 77%); LC/MS (Table 1, Method s) R$_t$=2.25 min; MS m/z: 452 (M+H)$^+$. (TNF IC$_{50}$=A)

The compounds shown in Table AA were synthesized in a manner similar to Example #25 from (R)-7-bromo-1-phenyl-2,3-dihydro-1H-benzo[d]pyrrolo[1,2-a]imidazole (Preparation #49) and the corresponding bromides.

TABLE AA

| Bromide | Structure | Example # | R$_t$ min (Table 1, Method) | m/z (M + H)$^+$ | TNF IC$_{50}$ |
|---|---|---|---|---|---|
| 4-(5-Bromopyrimidin-2-yl)tetrahydro-2H-pyran-4-ol (Preparation #45) | 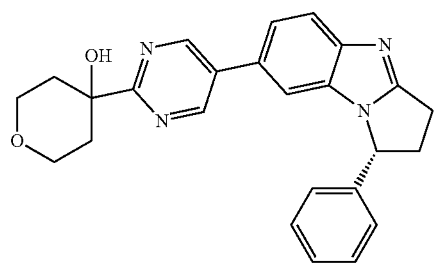 [SMILES: OC1(c2ncc(-c3ccc4nc5n(c4c3)[C@@H](c3ccccc3)CC5)cn2)CCOCC1] | AA.1 | 0.66 (f) | 413 | A |
| 1-(5-Bromopyrimidin-2-yl)cyclobutanol (Preparation #46) | 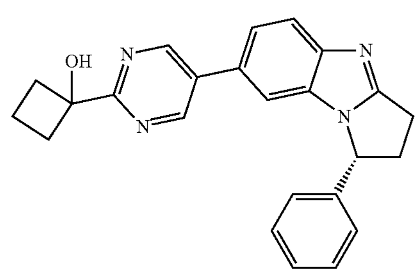 [SMILES: OC1(c2ncc(-c3ccc4nc5n(c4c3)[C@@H](c3ccccc3)CC5)cn2)CCC1] | AA.2 | 0.71 (f) | 383 | A |
| 3-(5-Bromopyrimidin-2-yl)oxetan-3-ol (Preparation #47) | 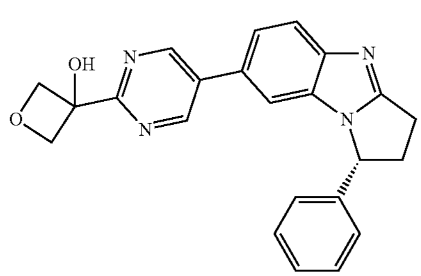 [SMILES: OC1(c2ncc(-c3ccc4nc5n(c4c3)[C@@H](c3ccccc3)CC5)cn2)COC1] | AA.3 | 0.62 (f) | 385 | A |

TABLE AA-continued

| Bromide | Structure | Example # | R$_t$ min (Table 1, Method) | m/z (M + H)$^+$ | TNF IC$_{50}$ |
|---|---|---|---|---|---|
| 4-Bromo-2-((tetrahydro-2H-pyran-4-yl)oxy)pyridine (Preparation #48) | 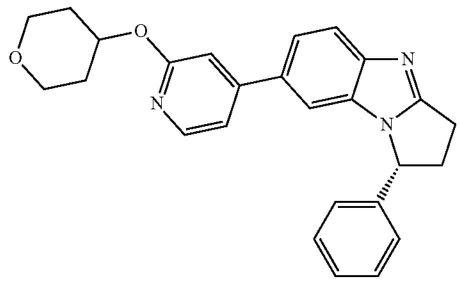 [SMILES: c1ccc([C@H]2CCc3nc4ccc(-c5ccnc(OC6CCOCC6)c5)cc4n32)cc1] | AA.4 | 0.75 (f) | 412 | A |

The compounds shown in Table AB were synthesized in a manner similar to Example #6 from (S)-2-bromo-9-phenyl-8,9-dihydro-6H-pyrido[3',2':4,5]imidazo[2,1-c][1,4]oxazine (Preparation #56) and the corresponding boronic acids/boronates.

TABLE AB

| Boronic acid/boronate | Product | Example # | R$_t$ min (Table 1, Method) | m/z (M + H)$^+$ | TNF IC$_{50}$ |
|---|---|---|---|---|---|
| 2-Morpholinopyrimidin-5-ylboronic acid | | AB.1 | 0.75 (d) | 416 | A |
| 2-(2-Hydroxypropan-2-yl)pyrimidin-5-ylboronic acid | | AB.2 | 0.71 (d) | 388 | A |
| 2-(3-Oxopiperazin-1-yl)pyrimidin-5-ylboronic acid (Preparation #21) | | AB.3 | 0.67 (d) | 428 | A |

TABLE AB-continued

| Boronic acid/boronate | Product | Example # | R$_t$ min (Table 1, Method) | m/z (M + H)$^+$ | TNF IC$_{50}$ |
|---|---|---|---|---|---|
| (2-(4-Hydroxypiperidin-1-yl)pyrimidin-5-yl)boronic acid (Preparation #22) | | AB.4 | 0.74 (d) | 429 | A |
| 7-(5-(4,4,5,5-Tetramethyl-1,3,2-dioxaborolan-2-yl)pyrimidin-2-yl)hexahydroimidazo[1,5-a]pyrazin-3(2H)-one (Preparation #62) | | AB.5 | 0.76 (d) | 469 | A |

The compound shown in Table AC was synthesized in a manner similar to Example #6 from (S)-2-bromo-9-(2-methoxyphenyl)-8,9-dihydro-6H-pyrido[3',2':4,5]imidazo[2,1-c][1,4]oxazine (Preparation #57) and the corresponding boronic acid/boronate.

TABLE AC

| Boronic acid/boronate | Product | Example # | R$_t$ min (Table 1, Method) | m/z (M + H)$^+$ | TNF IC$_{50}$ |
|---|---|---|---|---|---|
| (2-(4-Hydroxypiperidin-1-yl)pyrimidin-5-yl)boronic acid (Preparation #22) | | AC.1 | 0.72 (d) | 459 | A |

The compounds shown in Table AD were synthesized in a manner similar to Example #6 from 7-bromo-1-(2-methoxyphenyl)-2,3-dihydro-1H-benzo[d]pyrrolo[1,2-a]imidazole (Preparation #58) and the corresponding boronic acids/boronate.

TABLE AD

| Boronic acid/boronate | Product | Example # | R$_t$ min (Table 1, Method) | m/z (M + H)$^+$ | TNF IC$_{50}$ |
|---|---|---|---|---|---|
| (2-(4-Hydroxypiperidin-1-yl)pyrimidin-5-yl)boronic acid (Preparation #22) | 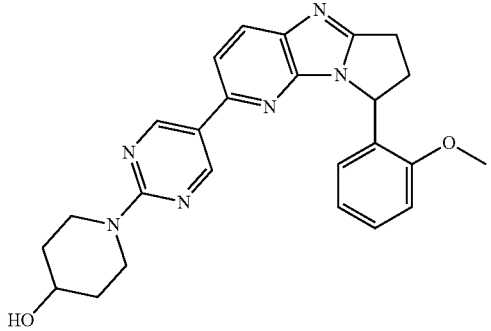 [SMILES: COc1ccccc1C1CCc2nc3ccc(-c4cnc(N5CCC(O)CC5)nc4)nc3n21] | AD.1 | 0.74 (d) | 443 | A |
| 7-(5-(4,4,5,5-Tetramethyl-1,3,2-dioxaborolan-2-yl)pyrimidin-2-yl)hexahydroimidazo[1,5-a]pyrazin-3(2H)-one (Preparation #62) | 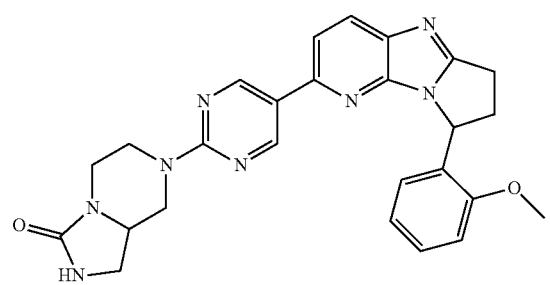 [SMILES: COc1ccccc1C1CCc2nc3ccc(-c4cnc(N5CCN6C(=O)NCC6C5)nc4)nc3n21] | AD.2 | 0.66 (d) | 483 | A |

The compound shown in Table AE was synthesized in a manner similar to Example #6 from 2-bromo-9-(2-methoxyphenyl)-6,7,8,9-tetrahydroimidazo[1,2-a:5,4-b']dipyridine (Preparation #54) and the corresponding boronic acid/boronate.

TABLE AE

| Boronic acid/boronate | Product | Example # | R$_t$ min (Table 1, Method) | m/z (M + H)$^+$ | TNF IC$_{50}$ |
|---|---|---|---|---|---|
| (2-(4-Hydroxypiperidin-1-yl)pyrimidin-5-yl)boronic acid (Preparation #22) | 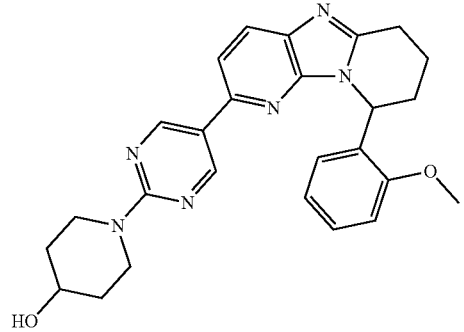 [SMILES: COc1ccccc1C1CCCc2nc3ccc(-c4cnc(N5CCC(O)CC5)nc4)nc3n21] | AE.1 | 0.78 (d) | 457 | A |

The compounds shown in Table AF were synthesized in a manner similar to Example #24 from (R)-7-(5-bromopyrimidin-2-yl)hexahydroimidazo[1,5-a]pyrazin-3(2H)-one (Preparation #39, OR=negative) and the corresponding bromide.

TABLE AF

| Bromide | Structure | Example # | R_t min (Table 1, Method) | m/z (M + H)+ | TNF IC_{50} |
|---|---|---|---|---|---|
| (R)-7-Bromo-4-phenyl-3,4-dihydro-1H-pyrano[3',4':4,5]imidazo[1,2-a]pyridine (Preparation #67) | 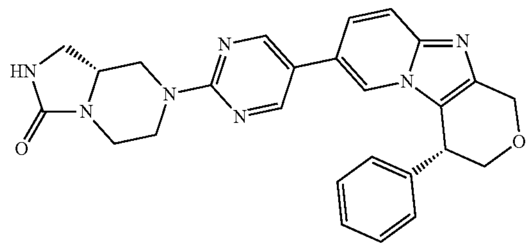 [SMILES: O=C1NC[C@@H]2CN(c3ncc(-c4ccc5nc6c(n5c4)[C@@H](c4ccccc4)COC6)cn3)CCN12] | AF.1 | 1.64 (w) | 468 | A |
| (R)-2-Bromo-9-phenyl-8,9-dihydro-6H-pyrano[3',4':4,5]imidazo[1,2-b]pyridazine (Preparation #68) | 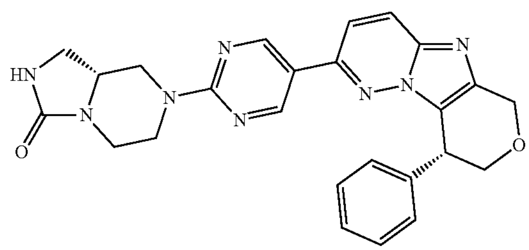 [SMILES: O=C1NC[C@@H]2CN(c3ncc(-c4ccc5nc6c(n5n4)[C@@H](c4ccccc4)COC6)cn3)CCN12] | AF.2 | 1.73 (w) | 469 | A |

The compound shown in Table AG was synthesized in a manner similar to Example #2 from (1-(2-methoxyphenyl)-2,3-dihydro-1H-cyclopenta[4,5]imidazo[1,2-a]pyridin-7-yl)boronic acid (Preparation #51) and the corresponding bromides or chlorides.

TABLE AG

| Bromide/chloride | Structure | Example # | R_t min (Table 1, Method) | m/z (M + H)+ | TNF IC_{50} |
|---|---|---|---|---|---|
| 4-(5-Bromopyrimidin-2-yl)morpholine | 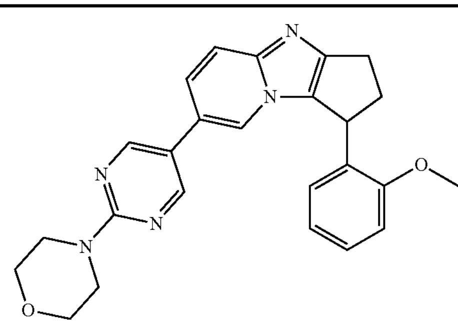 | AG.1 | 0.89 (f) | 428 | A |

The compounds shown in Table AH were synthesized in a manner similar to Example #3 from hexahydroimidazo[1,5-a]pyrazin-3(2H)-one hydrochloride and the corresponding bromide.

TABLE AH

| Bromide | Structure | Example # | $R_t$ min (Table 1, Method) | m/z (M + H)+ | TNF IC$_{50}$ |
|---|---|---|---|---|---|
| 7-Bromo-4-(2-fluorophenyl)-3,4-dihydro-1H-benzo[4,5]imidazo[2,1-c][1,4]oxazine (Preparation #75) | 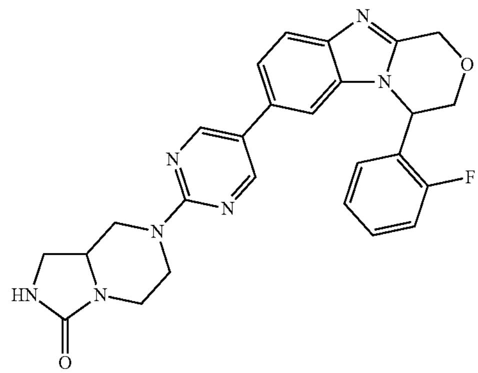 [SMILES: O=C1NCC2CN(c3ncc(-c4ccc5nc6n(c5c4)C(c4ccccc4F)COC6)cn3)CCN12] | AH.1 | 0.74 (f) | 486 | A |
| 7-Bromo-4-(3-chlorophenyl)-3,4-dihydro-1H-benzo[4,5]imidazo[2,1-c][1,4]oxazine (Preparation #77) | 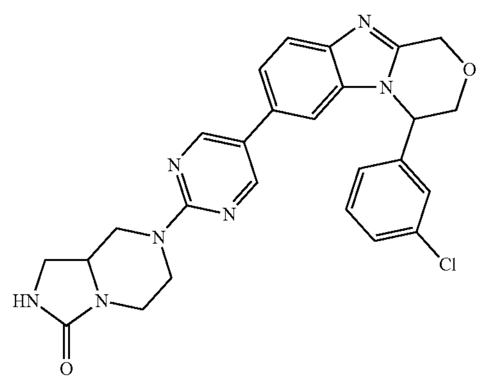 [SMILES: O=C1NCC2CN(c3ncc(-c4ccc5nc6n(c5c4)C(c4cccc(Cl)c4)COC6)cn3)CCN12] | AH.2 | 0.77 (f) | 502 | A |
| (S)-7-Bromo-4-(2-chlorophenyl)-3,4-dihydro-1H-benzo[4,5]imidazo[2,1-c][1,4]oxazine (Preparation #73) | 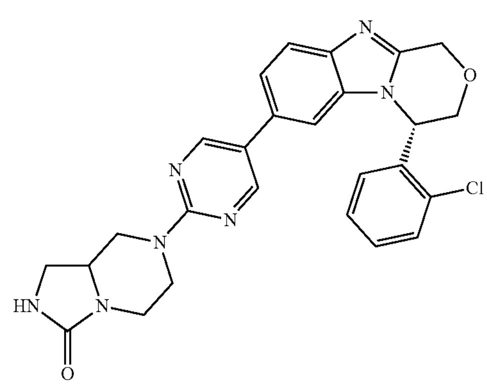 [SMILES: O=C1NCC2CN(c3ncc(-c4ccc5nc6n(c5c4)[C@@H](c4ccccc4Cl)COC6)cn3)CCN12] | AH.3 | 0.74 (f) | 502 | A |

TABLE AH-continued

| Bromide | Structure | Example # | R$_t$ min (Table 1, Method) | m/z (M + H)$^+$ | TNF IC$_{50}$ |
| --- | --- | --- | --- | --- | --- |
| 7-Bromo-4-(3-(trifluoromethyl)phenyl)-3,4-dihydro-1H-benzo[4,5]imidazo[2,1-c][1,4]oxazine (Preparation #79) | 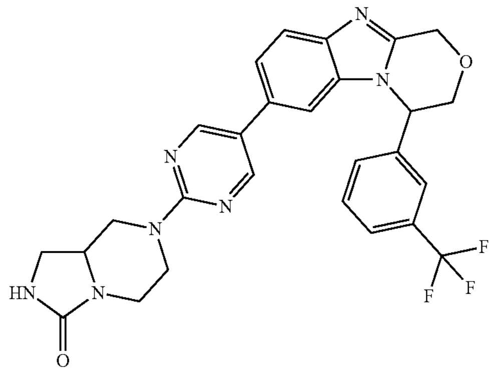 [SMILES: O=C1NCC2CN(c3ncc(-c4ccc5nc6n(c5c4)C(c4cccc(C(F)(F)F)c4)COC6)cn3)CCN12] | AH.4 | 0.81 (f) | 536 | A |
| (R)-2-Bromo-8-cyclohexyl-7,8-dihydro-6H-pyrrolo[2',1':2,3]imidazo[4,5-b]pyridine (Preparation #80) | 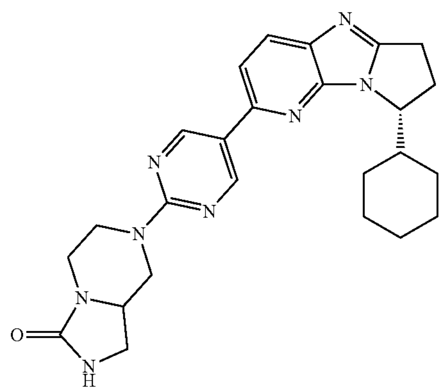 [SMILES: O=C1NCC2CN(c3ncc(-c4ccc5nc6n(c5n4)[C@@H](C4CCCCC4)CC6)cn3)CCN12] | AH.5 | 1.08 (x) | 459 | A |
| 2-Bromo-8-cyclohexyl-7,8-dihydro-6H-pyrrolo[2',1':2,3]imidazo[4,5-b]pyridine (Preparation #80, step 3) | 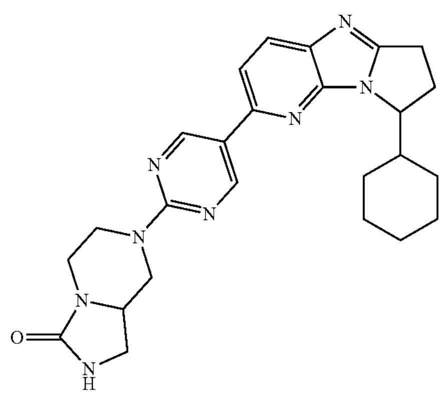 [SMILES: O=C1NCC2CN(c3ncc(-c4ccc5nc6n(c5n4)C(C4CCCCC4)CC6)cn3)CCN12] | AH.6 | 1.04 (x) | 459 | A |
| 2-Bromo-9-(2-fluorophenyl)-8,9-dihydro-6H-pyrido[3',2':4,5]imidazo[2,1-c][1,4]oxazine (Preparation #14) | 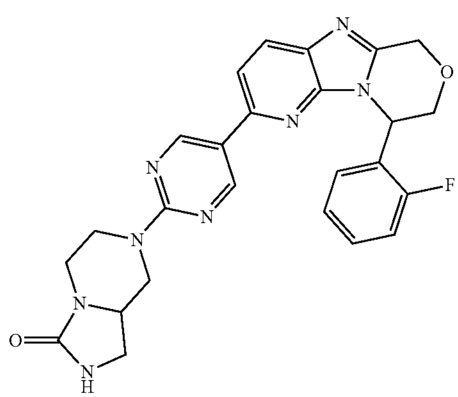 [SMILES: O=C1NCC2CN(c3ncc(-c4ccc5nc6n(c5n4)C(c4ccccc4F)COC6)cn3)CCN12] | AH.7 | 1.01 (f) | 487 | A |

TABLE AH-continued

| Bromide | Structure | Example # | R, min (Table 1, Method) | m/z (M + H)+ | TNF IC50 |
|---|---|---|---|---|---|
| 2-Bromo-9-(3-fluorophenyl)-8,9-dihydro-6H-pyrido[3',2':4,5]imidazo[2,1-c][1,4]oxazine (Preparation #15) | 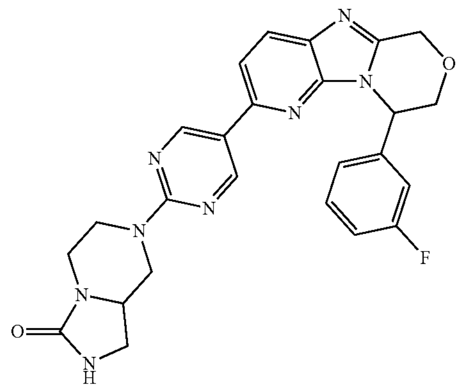 [SMILES: O=C1NCC2CN(c3ncc(-c4ccc5nc6n(c5n4)C(c4cccc(F)c4)COC6)cn3)CCN12] | AH.8 | 0.81 (f) | 487 | A |
| 2-Bromo-8-methyl-8-phenyl-7,8-dihydro-6H-pyrrolo[2',1':2,3]imidazo[4,5-b]pyridine (Preparation #16) | 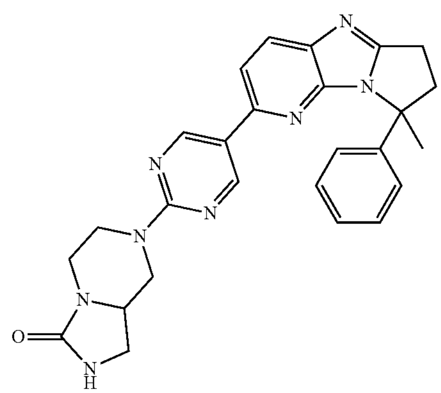 [SMILES: CC1(c2ccccc2)CCc2nc3ccc(-c4cnc(N5CCN6C(=O)NCC6C5)nc4)nc3n21] | AH.9 | 0.76 (e) | 467 | A |

The compounds shown in Table AI were synthesized in a manner similar to Example #3 from piperidin-4-ol and the corresponding bromide/chloride.

TABLE AI

| Bromide/chloride | Structure | Example # | R, min (Table 1, Method) | m/z (M + H)+ | TNF IC50 |
|---|---|---|---|---|---|
| 2-Bromo-9-(3-fluorophenyl)-8,9-dihydro-6H-pyrido[3',2':4,5]imidazo[2,1-c][1,4]oxazine (Preparation #15) | 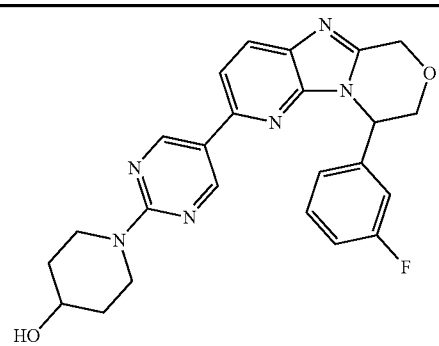 | AI.1 | 0.78 (e) | 447 | A |

The compounds shown in Table AJ were synthesized in a manner similar to Example #3 from 2-bromo-9-(2-methoxyphenyl)-6,7,8,9-tetrahydrobenzo[4,5]imidazo[1,2-a]pyridine (Preparation #11, step 2) and the corresponding amine.

TABLE AJ

| Amine | Product | Example # | $R_t$ min (Table 1) | m/z ESI+ (M + H)+ | TNF IC$_{50}$ |
|---|---|---|---|---|---|
| Piperidin-4-ol | | AJ.1 | 1.09 (x) | 456 | A |
| Azepan-4-ol | | AJ.2 | 1.10 (x) | 470 | A |
| (4-Fluoropiperidin-4-yl)methanol hydrochloride | | AJ.3 | 1.07 (x) | 488 | A |
| 3,3-Difluoropiperidin-4-ol | | AJ.4 | 1.41 (f) | 492 | A |

TABLE AJ-continued

| Amine | Product | Example # | R$_t$ min (Table 1) | m/z ESI+ (M + H)$^+$ | TNF IC$_{50}$ |
|---|---|---|---|---|---|
| 4-Methylpiperidin-4-ol | | AJ.5 | 1.41 (f) | 470 | A |
| Hexahydroimidazo[1,5-a]pyrazin-3(2H)-one | | AJ.6 | 1.01 (x) | 496 | A |
| 1,4-Oxazepane hydrochloride | | AJ.7 | 1.12 (x) | 456 | A |
| 7-Azaspiro[3.5]nonan-2-ol hydrochloride | | AJ.8 | 1.16 (x) | 496 | A |

Example #26

(R)-7-(5-((S)-4-Phenyl-3,4-dihydro-1H-benzo[4,5]imidazo[2,1-c][1,4]oxazin-7-yl)pyrimidin-2-yl)hexahydroimidazo[1,5-a]pyrazin-3(2H)-one

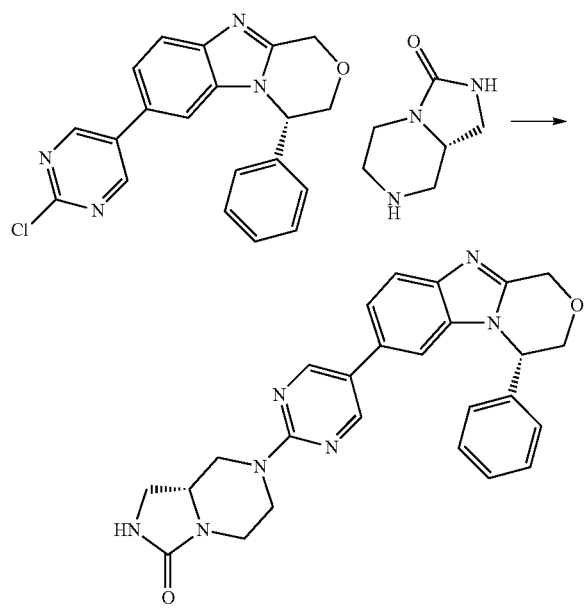

To a 4 mL vial with magnetic stirrer was added (S)-7-(2-chloropyrimidin-5-yl)-4-phenyl-3,4-dihydro-1H-benzo[4,5]imidazo[2,1-c][1,4]oxazine (0.075 g, 0.207 mmol, Preparation #35) followed by the addition of (S)-hexahydroimidazo[1,5-a]pyrazin-3(2H)-one (0.029 g, 0.207 mmol, Preparation #41) and DIEA (0.060 mL, 0.344 mmol). The reaction was allowed to heat to about 100° C. overnight. A precipitate formed and was dissolved by the addition of DCM. The solution was then concentrated onto dry silica gel and purified by flash chromatography (1-10% MeOH/DCM) to give the title compound (0.029 g, 30%); LC/MS (Table 1, Method f) $R_t$=0.72 min; MS m/z: 468 (M+H)$^+$. (TNF IC$_{50}$=A)

Example #27

(S)-7-(5-((S)-4-Phenyl-3,4-dihydro-1H-benzo[4,5]imidazo[2,1-c][1,4]oxazin-7-yl)pyrimidin-2-yl)hexahydroimidazo[1,5-a]pyrazin-3(2H)-one

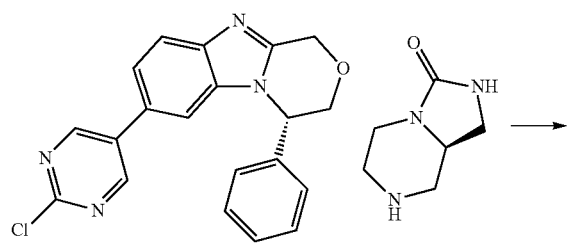

-continued

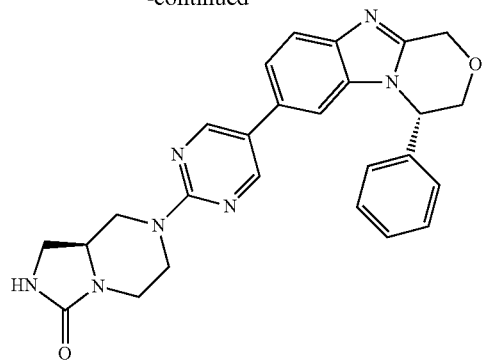

To a 4 mL vial with magnetic stirrer was added (S)-7-(2-chloropyrimidin-5-yl)-4-phenyl-3,4-dihydro-1H-benzo[4,5]imidazo[2,1-c][1,4]oxazine (0.075 g, 0.207 mmol, Preparation #35) followed by the addition of (R)-hexahydroimidazo[1,5-a]pyrazin-3(2H)-one (0.029 g, 0.207 mmol, Preparation #40) and DIEA (0.060 mL, 0.344 mmol). The reaction was allowed to heat to about 100° C. overnight. A precipitate formed and was dissolved by the addition of DCM. The solution was then concentrated onto dry silica gel and purified by flash chromatography (1-10% MeOH/DCM) to produce the title compound (0.042 g, 44%); LC/MS (Table 1, Method f) $R_t$=0.72 min; MS m/z: 468 (M+H)$^+$. (TNF IC$_{50}$=A)

Example #28

2-(5-(1-(Pyridin-2-yl)-2,3-dihydro-1H-benzo[d]pyrrolo[1,2-a]imidazol-7-yl)pyrimidin-2-yl)propan-2-ol

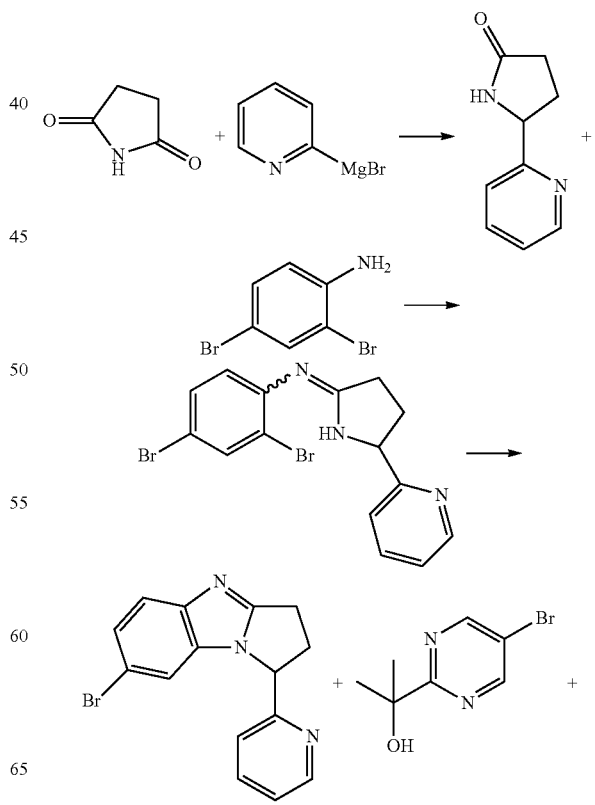

-continued

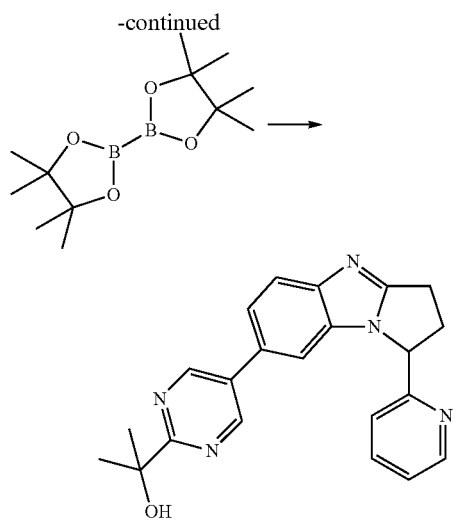

Step 1: 5-(Pyridin-2-yl)pyrrolidin-2-one

A mixture of pyrrolidine-2,5-dione (0.50 g, 5.05 mmol) in dry DCM (10 mL) was added to pyridin-2-ylmagnesium bromide (about 1 M in THF, 11 mL, 11.00 mmol) cooled to −78° C. After about 5 min, the dry-ice bath was removed and the resulting mixture was stirred at rt. After about 19 h, sodium cyanoborohydride (0.381 g, 6.06 mmol) was added followed by a slow addition of 6 M HCl solution to keep the pH between 3 and 4. After about 4 h, the reaction was neutralized with 2 N NaOH and partitioned between EtOAc (50 mL) and brine (25 mL). The layers were separated. The aqueous layer was extracted with additional EtOAc (2×25 mL). The aqueous layer was basified with 2 N NaOH to about pH 10 and extracted with additional EtOAc (3×50 mL) followed by EtOAc/MeOH (3:1, 3×50 mL). The combined organic layers were washed with brine, dried over MgSO$_4$, filtered, and concentrated under reduced pressure to give crude title compound (0.55 g); LC/MS (Table 1, Method g) R$_t$=0.22 min.; MS m/z: 163 (M+H)$^+$.

Step 2: 2,4-Dibromo-N-(5-(pyridin-2-yl)pyrrolidin-2-ylidene)aniline

To a mixture of 5-(pyridin-2-yl)pyrrolidin-2-one (0.55 g, 3.4 mmol) in toluene (9 mL) was added POCl$_3$ (0.316 mL, 3.39 mmol) and 2,4-dibromoaniline (0.851 g, 3.39 mmol). The reaction mixture was heated to about 110° C. After about 2 h, the reaction mixture was cooled to rt, concentrated under reduced pressure and partitioned between EtOAc (100 mL) and 1 M NaOH (50 mL). The combined aqueous layers were washed with brine (30 mL), dried over MgSO$_4$, filtered, and concentrated under reduced pressure to give crude title compound (0.88 g); LC/MS (Table 1, Method g) R$_t$=1.87 min.; MS m/z: 394, 396, 398 (M+H)$^+$.

Step 3: 7-Bromo-1-(pyridin-2-yl)-2,3-dihydro-1H-benzo[d]pyrrolo[1,2-a]imidazole To a solution of 2,4-dibromo-N-(5-(pyridin-2-yl)pyrrolidin-2-ylidene)aniline (0.88 g, 2.2 mmol) in MeCN (15 mL) was added K$_2$CO$_3$ (0.369 g, 2.67 mmol), DMEA (0.048 mL, 0.44 mmol) and CuI (0.042 g, 0.22 mmol). The reaction was heated at about 80° C. After about 15 h, the reaction was cooled to rt, diluted with DCM (20 mL) and filtered through Florisil® (10 g). The filtrate was concentrated under reduced pressure to give a crude residue that was purified via silica gel chromatography eluting with 0-100% DCM/MeOH/NH$_4$OH (90:9:1) in DCM to give impure title compound (0.11 g); LC/MS (Table 1, Method h) R$_t$=1.85 min.; MS m/z: 314, 316 (M+H)$^+$.

Step 4: 2-(5-(1-(Pyridin-2-yl)-2,3-dihydro-1H-benzo[d]pyrrolo[1,2-a]imidazol-7-yl)pyrimidin-2-yl)propan-2-ol To a 20 mL vial charged with 2-(5-bromopyrimidin-2-yl)propan-2-ol (0.090 g, 0.41 mmol), bis(pinacolato)diboron (0.210 g, 0.828 mmol), KOAc (0.103 g, 1.05 mmol) and 1,4-dioxane (2.4 mL) was added Pd(dppf)Cl$_2$.CH$_2$Cl$_2$ (0.018 g, 0.022 mmol). Then the vial was stirred in a preheated block at about 95° C. After about 1 h, the reaction mixture was cooled to rt and transferred to a 20 mL vial containing 7-bromo-1-(pyridin-2-yl)-2,3-dihydro-1H-benzo[d]pyrrolo[1,2-a]imidazole (0.10 g, 0.32 mmol), Cs$_2$CO$_3$ (0.26 g, 0.80 mmol), Pd(dppf)Cl$_2$.DCM (0.013 g, 0.016 mmol) and water (0.60 mL). The reaction mixture was heated in a preheated block at about 100° C. After about 1 h, the reaction mixture was cooled to rt and partitioned between EtOAc (5 mL) and water (5 mL). The layers were separated and the aqueous layer was extracted with EtOAc (2×5 mL). The combined organic layers were washed with brine, dried over MgSO$_4$, filtered, and concentrated under reduced pressure. The crude product was dissolved in DCM and purified via silica gel chromatography eluting with 50-100% DCM/MeOH/NH$_4$OH (90:9:1) in DCM to give the title compound (0.041 g, about 2% over 4 steps). LC/MS (Table 1, Method h) R$_t$=1.82 min; MS m/z: 372 (M+H)$^+$; 1H NMR (400 MHz, DMSO-d$_6$) δ 8.97 (s, 2H), 8.58-8.49 (m, 1H), 7.83 (td, J=7.7, 1.8 Hz, 1H), 7.70 (d, J=8.4 Hz, 1H), 7.53 (dd, J=8.4, 1.8 Hz, 1H), 7.45 (dt, J=7.9, 1.1 Hz, 1H), 7.41 (d, J=1.7 Hz, 1H), 7.33 (ddd, J=7.6, 4.8, 1.1 Hz, 1H), 5.78 (dd, J=8.0, 4.0 Hz, 1H), 5.05 (s, 1H), 3.29-3.03 (m, 3H), 2.82-2.64 (m, 1H), 1.51 (s, 6H). (TNF IC$_{50}$=B)

Example #29

2-(5-(8-(Pyridin-2-yl)-7,8-dihydro-6H-pyrrolo[2',1':2,3]imidazo[4,5-b]pyridin-2-yl)pyrimidin-2-yl)propan-2-ol

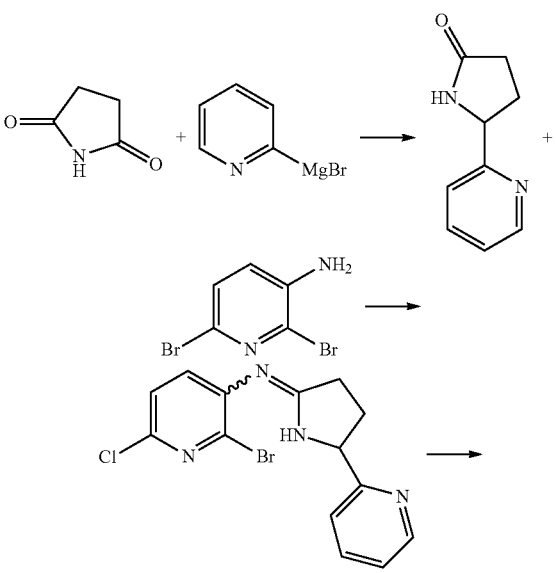

-continued

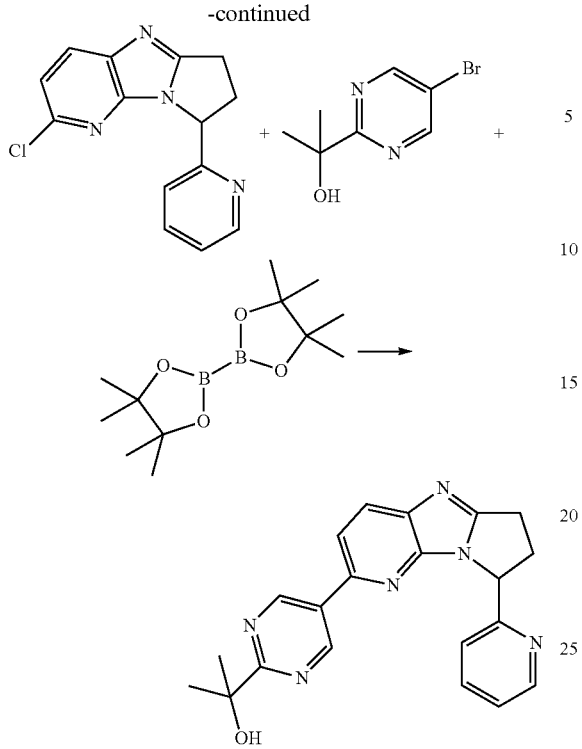

The reaction sequence was performed in a similar fashion to Example #28 substituting 2,6-dibromopyridin-3-amine for 2,4-dibromoaniline in step 2 to give the title compound (about 1% over 4 steps); LC/MS (Table 1, Method g) $R_t$=1.76 min; MS m/z: 373 (M+H)$^+$; $^1$H NMR (400 MHz, DMSO-d$_6$) δ 9.20 (s, 2H), 8.55-8.46 (m, 1H), 8.10 (d, J=8.3 Hz, 1H), 7.90 (d, J=8.4 Hz, 1H), 7.89-7.83 (m, 1H), 7.56 (d, J=7.8 Hz, 1H), 7.38-7.31 (m, 1H), 5.86 (dd, J=7.6, 4.3 Hz, 1H), 5.07 (s, 1H), 3.28-3.08 (m, 3H), 2.86-2.68 (m, 1H), 1.50 (s, 6H). (TNF IC$_{50}$=B)

Example #30

(R)-7-(5-((R)-1-Phenyl-2,3-dihydro-1H-benzo[d]pyrrolo[1,2-a]imidazol-7-yl)pyrimidin-2-yl)hexahydroimidazo[1,5-a]pyrazin-3(2H)-one

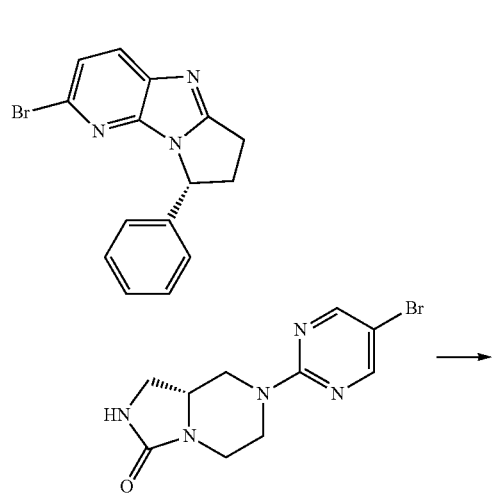

-continued

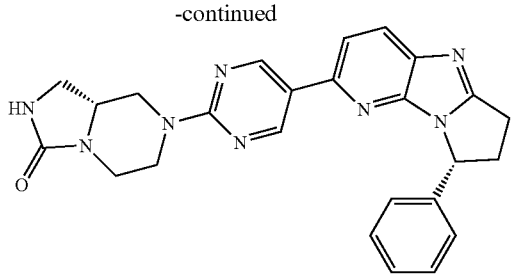

The reaction was performed from (R)-2-bromo-8-phenyl-7,8-dihydro-6H-pyrrolo[2',1':2,3]imidazo[4,5-b]pyridine (0.28 g, 0.89 mmol, Preparation #52) with (R)-7-(5-bromopyrimidin-2-yl)hexahydroimidazo[1,5-a]pyrazin-3(2H)-one (0.29 g, 0.96 mmol, Preparation #39) in a similar fashion to Preparation #24, to give the title compound (0.17 g, 41%); LC/MS (Table 1, Method d) $R_t$=0.71 min; MS m/z: 453 (M+H)$^+$ LC/MS (TNF IC$_{50}$=A)

Example #31

(S)-7-(5-((R)-8-Phenyl-7,8-dihydro-6H-pyrrolo[2',1':2,3]imidazo[4,5-b]pyridin-2-yl)pyrimidin-2-yl)hexahydroimidazo[1,5-a]pyrazin-3(2H)-one The reaction was performed from (R)-2-bromo-8-phenyl-7,8-dihydro-6H-pyrrolo[2',1':2,3]imidazo[4,5-b]pyridine (0.28 g, 0.89 mmol, Preparation #52) with (S)-7-(5-bromopyrimidin-2-yl)hexahydroimidazo[1,5-a]pyrazin-3(2H)-one (0.29 g, 0.96 mmol, Preparation #39) in a similar fashion to Preparation #24, to give the title compound (0.13 g, 32%); LC/MS (Table 1, Method d) $R_t$=0.71 min; MS m/z: 453 (M+H)$^+$ LC/MS (TNF IC$_{50}$=A)

Example #32

2-(5-(4-(2-Methoxyphenyl)-3,4-dihydro-1H-pyrano[3',4':4,5]imidazo[1,2-a]pyridin-7-yl)pyrimidin-2-yl)propan-2-ol

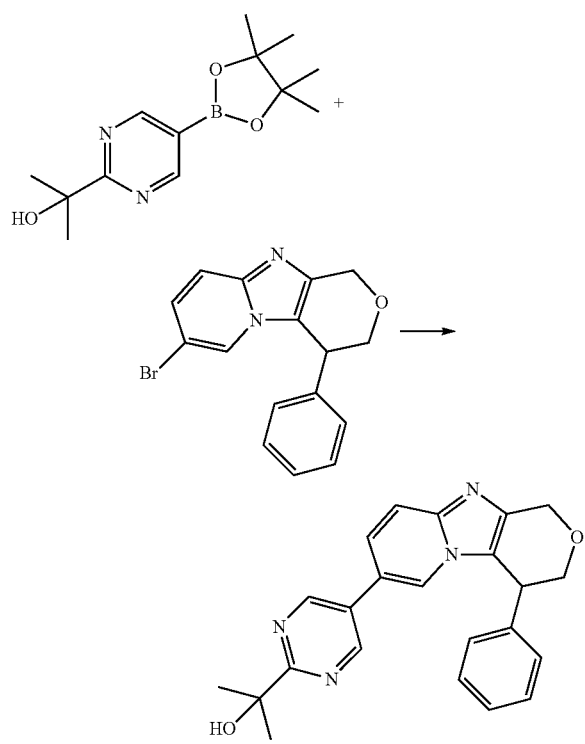

A mixture of 2-(5-(4,4,5,5,-tetramethyl-1,3,2-dioxaborolan-2-yl)propan-2-ol (48 mg, 0.184 mmol), 7-bromo-4-(2-methoxyphenyl)-3,4-dihydro-1H-pyran[3',4':4,5]imidazo[1,2-a]pyridine (22 mg, 0.060 mmol, Preparation #63), Pd(PPh₃)₄(0.007 g, 0.01 mmol), potassium phosphate (52 mg, 0.245 mmol) and 0.735 mL of 1,4-dioxane and 0.49 mL of water were heated in a microwave oven at about 110° C. for about 60 min. The reaction mixture was cooled to rt. The mixture was filtered through Celite® and concentrated under reduced pressure. The crude material was purified by preparative HPLC (Table 1 Method k) to afford the title compound (0.009 g, 21%) LC/MS (Table 1, Method f) $R_f$=0.65 min; MS m/z: 417 (M+H)⁺ (TNF IC₅₀=A)

Example #33

1-(5-(8-Phenyl-7,8-dihydro-6H-cyclopenta[4,5]imidazo[1,2-b]pyridazin-2-yl)pyrimidin-2-yl)piperidin-4-ol

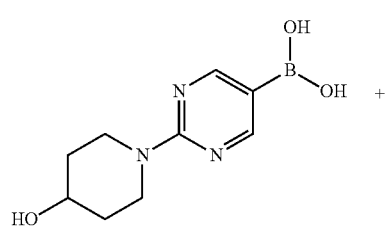

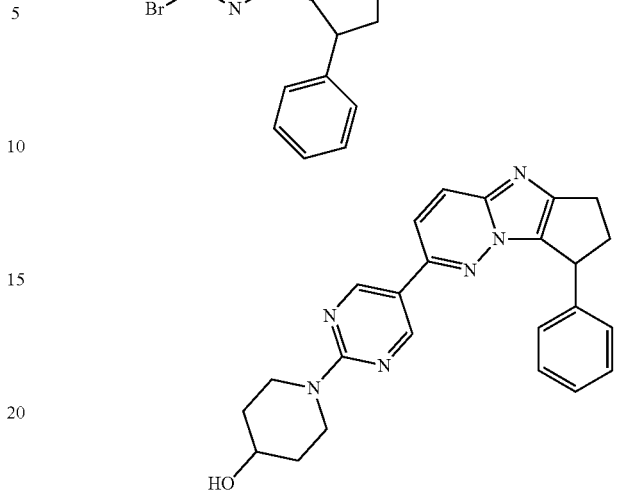

A mixture of (2-(4-hydroxypiperidin-1-yl)pyrimidin-5-yl)boronic acid (0.057 g, 0.26 mmol, Preparation #22), 2-bromo-8-phenyl-7,8-dihydro-6H-cyclopenta[4,5]imidazo[1,2-b]pyridazine (0.040 g, 0.13 mmol, Preparation #65), Pd(dppf)Cl₂.DCM (0.009 g, 0.013 mmol), 2 M aq. Na₂CO₃ (0.60 mL, 0.90 mmol) and 1.2 mL of 1,4-dioxane were heated in a microwave oven at about 135° C. for about 60 min. The reaction mixture was cooled down to rt. The mixture was filtered through Celite® and concentrated under reduced pressure. The crude material was purified by preparative HPLC (Table 1 Method k) to afford the target compound (0.003 g, 4.8%) LC/MS (Table 1, Method f) $R_f$=0.74 min; MS m/z: 412 (M)+(TNF IC₅₀=A)

Example #34

7-(5-(8-(2-Methoxyphenyl)-7,8-dihydro-6H-cyclopenta[4,5]imidazo[1,2-b]pyridazin-2-yl)pyrimidin-2-yl)hexahydroimidazo[1,5-a]pyrazine-3(2H)-one

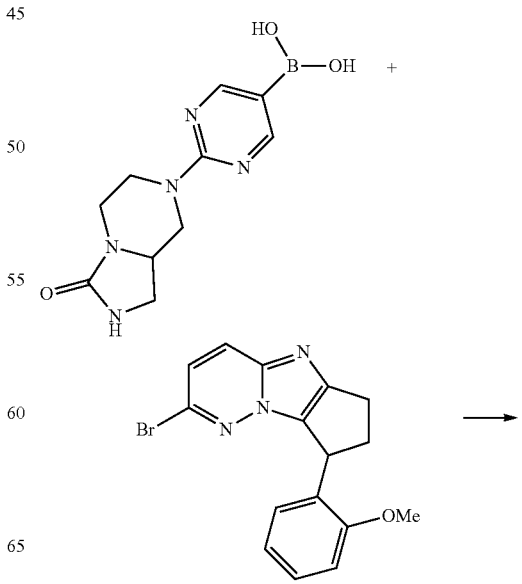

-continued

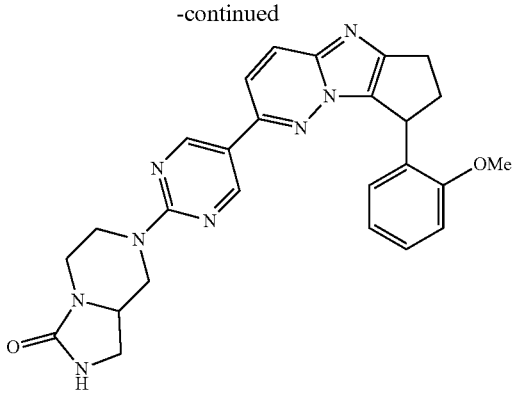

A mixture of (2-(3-oxohexahydroimidazo[1,5-a]pyrazin-7(1H)-yl)pyrimidin-5-yl)boronic acid (0.14 g, 0.54 mmol, Prepared in a similar manner to Preparation #21 hexahydroimidazo[1,5-a]pyrazin-3(2H)-one hydrochloride and 2-chloropyrimidine-5-boronic acid), 2-bromo-8-phenyl-7,8-dihydro-6H-cyclopenta [4,5]imidazo[1,2-b]pyridazine (0.062 g, 0.18 mmol, Preparation #66), Pd(dppf)Cl$_2$.DCM (0.014 g, 0.018 mmol), 2 M aq. Na$_2$CO$_3$ (0.31 mL, 0.61 mmol) and 0.45 mL of 1,4-dioxane were heated in a microwave oven at about 135° C. for about 60 min. The reaction mixture was cooled down to rt. The mixture was filtered through Celite® and concentrated under reduced pressure. The residue was purified by column chromatography on silica (0-10% MeOH/DCM) to afford the title compound (0.004 g, 4.6%) LC/MS (Table 1, Method f) R$_t$=0.72 min; MS m/z: 483 (M+H)$^+$ (TNF IC$_{50}$=A)

Example #35

7-(5-(4-(2-(Trifluoromethyl)phenyl)-3,4-dihydro-1H-benzo[4,5]imidazo[2,1-c][1,4]oxazin-7-yl)pyrimidin-2-yl)hexahydroimidazo[1,5-a]pyrazin-3(2H)-one

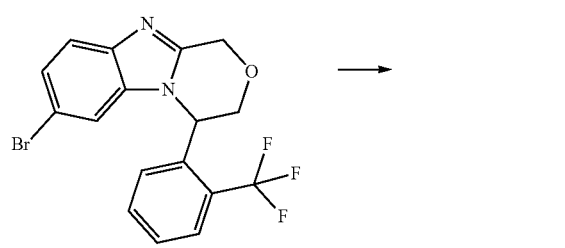

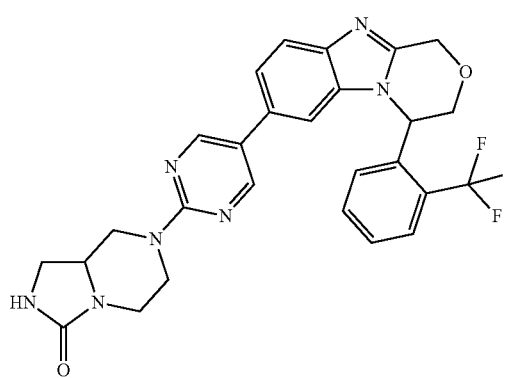

To a vial was added (2-chloropyrimidin-5-yl)boronic acid (0.041 g, 0.262 mmol), EtOH (2 mL), and hexahydroimidazo[1,5-a]pyrazin-3(2H)-one hydrochloride (0.046 g, 0.262 mmol) followed by the addition of TEA (0.42 mL, 0.300 mmol). The contents were heated at about 95° C. for about 2 h. The mixture was then added to a second vial preloaded with 7-bromo-4-(2-(trifluoromethyl)phenyl)-3,4-dihydro-1H-benzo[4,5]imidazo[2,1-c][1,4]oxazine (0.040 g, 0.101 mmol, Preparation #71), 2M Cs$_2$CO$_3$ (0.101 mL, 0.201 mmol), and SiliaCat® DPP-Pd (0.041 g, 0.010 mmol, 0.25 mmol/g load, SiliCycle Cat#R390-100). The contents were heated at about 95° C. for about 4 h, the mixture was cooled to rt, concentrated onto silica gel and purified by flash-column chromatography on silica gel (1-10% DCM/MeOH). The fractions were dried and then dissolved in 1 mL DCM. 1 mL of 4N hydrochloric acid in 1,4-dioxane was added and after stirring for 30 min the contents were dried under vacuum to give the title compound (0.037 g, 61%) as an HCl salt; LC/MS (Table 1, Method f) R$_t$=0.83 min; MS m/z: 536 (M+H)$^+$. (TNF IC$_{50}$=A).

Example #36

(S)-7-(5-(4-Phenyl-3,4-dihydro-1H-benzo[4,5]imidazo[2,1-c][1,4]oxazin-7-yl)pyrimidin-2-yl)-7-azaspiro[3.5]nonan-2-amine

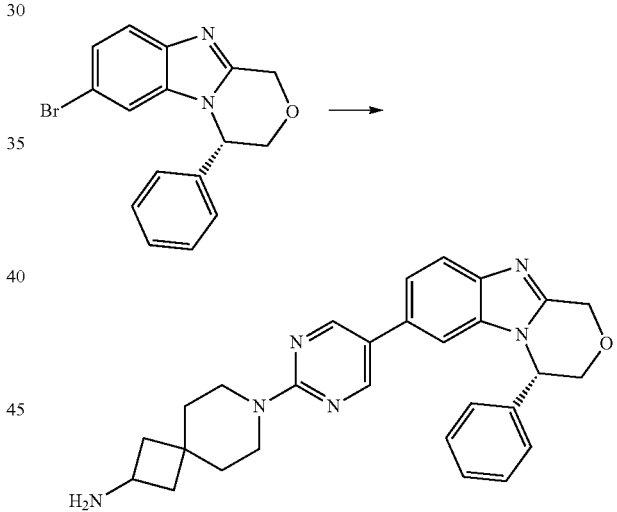

To a vial was added (2-chloropyrimidin-5-yl)boronic acid (0.049 g, 0.317 mmol), EtOH (2 mL), and tert-butyl 7-azaspiro[3.5]nonan-2-ylcarbamate (0.056 g, 0.317 mmol) followed by the addition of TEA (0.42 mL, 0.30 mmol). The contents were heated at about 95° C. for about 2 h. The mixture was then added to a second vial preloaded with (S)-7-bromo-4-phenyl-3,4-dihydro-1H-benzo[4,5]imidazo[2,1-c][1,4]oxazine (0.040 g, 0.12 mmol, Preparation #24), 2M Cs$_2$CO$_3$ (0.12 mL, 0.24 mmol), and SiliaCat® DPP-Pd (0.049 g, 0.012 mmol, 0.25 mmol/g load, SiliCycle Cat#R390-100). The contents were heated at about 95° C. for about 4 h, the mixture was cooled to rt and filtered through Celite®. The to the filtrate was added 2 mL of 4 N HCl in 1,4-dioxane and the reaction was allowed to proceed for about 4 hours. The contents were then dried under nitrogen stream and redissolved in 50% DMSO/MeOH (2 mL). The crude material was purified by preparative HPLC (Table 1 Method k) to give the title compound (0.009 g, 9%); LC/MS (Table 1, Method f) $R_t$=0.53 min; MS m/z: 467 (M+H)$^+$. (TNF IC$_{50}$=A).

Example #37

(S)-7-(2-((1R,6S)-3,10-Diazabicyclo[4.3.1]decan-1-yl)pyrimidin-5-yl)-4-phenyl-3,4-dihydro-1H-benzo[4,5]imidazo[2,1-c][1,4]oxazine

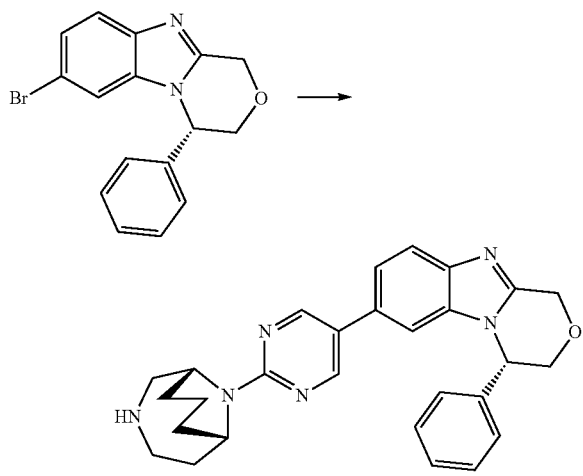

The title compound was synthesized in a manner similar to Example #36 from (S)-7-bromo-4-phenyl-3,4-dihydro-1H-benzo[4,5]imidazo[2,1-c][1,4]oxazine (Preparation #24) and (1R,6S)-tert-butyl 3,10-diazabicyclo[4.3.1]decane-3-carboxylate. LC/MS (Table 1, Method i) $R_t$=0.58 min; MS m/z: 467 (M+H)$^+$. (TNF IC$_{50}$=A).

Example #38

2-(5-(1-(Tetrahydro-2H-pyran-4-yl)-2,3-dihydro-1H-benzo[d]pyrrolo[1,2-a]imidazol-7-yl)pyrimidin-2-yl)propan-2-ol

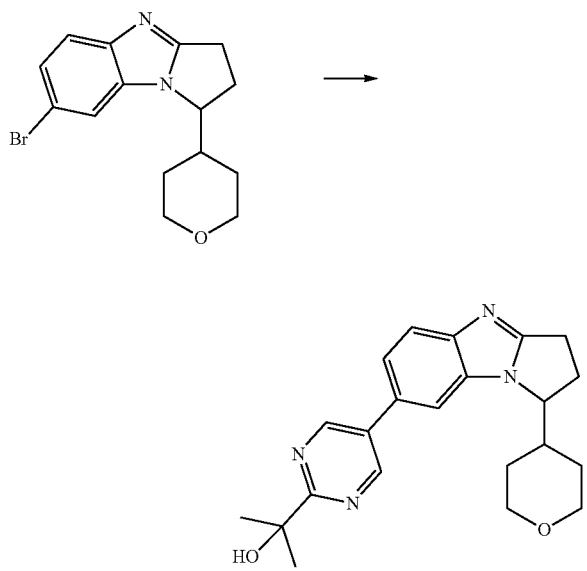 [SMILES: Brc1ccc2nc3n(c2c1)C(C1CCOCC1)CC3 ; CC(C)(O)c1ncc(-c2ccc3nc4n(c3c2)C(C2CCOCC2)CC4)cn1]

A microwave vial charged with 2-(5-bromopyrimidin-2-yl)propan-2-ol (0.026 g, 0.121 mmol), 4,4,4',4',5,5,5',5'-octamethyl-2,2'-bi(1,3,2-dioxaborolane) (0.062 g, 0.243 mmol), KOAc (0.028 g, 0.280 mmol) and 1,4-dioxane (0.7 mL) was added Pd(dppf)Cl$_2$.DCM (0.0046 g, 5.60 µmol). Then the vial was stirred in a preheated oil bath at about 95° C. After about 1.5 h, the reaction mixture was cooled to rt. To the mixture was added 7-bromo-1-(tetrahydro-2H-pyran-4-yl)-2,3-dihydro-1H-benzo[d]pyrrolo[1,2-a]imidazole (0.03 g, 0.093 mmol, Preparation #61), Cs$_2$CO$_3$ (0.076 g, 0.233 mmol), Pd(dppf)Cl$_2$.DCM (0.0046 g, 5.60 µmol) and water (0.175 mL). Then the vial was heated in a preheated oil bath at about 95° C. After about 1 h, the reaction mixture was cooled to rt and partitioned between EtOAc (5 mL) and water (5 mL). The layers were separated and the aqueous layer extracted with EtOAc (2×10 mL). The combined organic layers were washed with brine, dried over Na$_2$SO$_4$, filtered, and concentrated under reduced pressure. The crude material was dissolved in DCM and purified via silica gel chromatography eluting with 0-5% MeOH with 0.5% TEA/DCM to give the title compound (0.010 g); LC/MS (Table 1, Method f) $R_t$=0.63 min; MS m/z: 379 (M+H)$^+$. (TNF IC$_{50}$=C).

Example #39

2-(5-(8-Methyl-8-phenyl-7,8-dihydro-6H-pyrrlo[2',1':2,3]imidazo[4,5-b]pyridin-2-yl)pyrimidin-2-yl)propan-2-ol

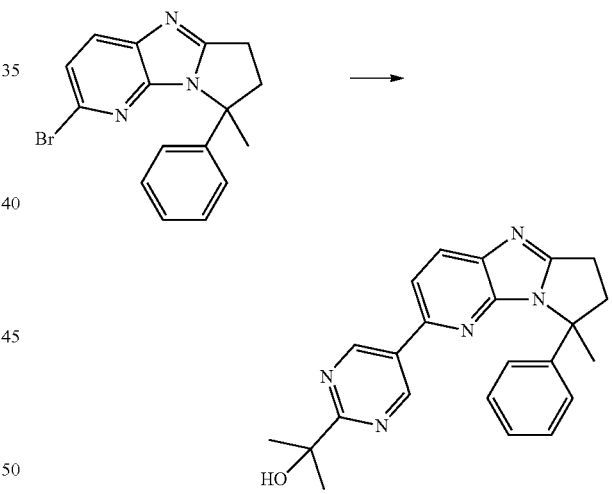

To a vial charged with 2-(5-bromopyrimidin-2-yl)propan-2-ol (43.0 mg, 0.198 mmol), 4,4,4',4',5,5,5',5'-octamethyl-2,2'-bi(1,3,2-dioxaborolane) (101 mg, 0.396 mmol), KOAc (49.3 mg, 0.503 mmol) and 1,4-dioxane (1 mL) was added Pd(dppf)Cl$_2$.DCM (7.5 mg, 9.14 µmol). The vial was stirred in a preheated oil bath at about 95° C. After about 1.5 h, the reaction was cooled to rt. 2-Bromo-8-methyl-8-phenyl-7,8-dihydro-6H-pyrrolo[2',1':2,3]imidazo[4,5-b]pyridine (50 mg, 0.152 mmol, Preparation #16), Cs$_2$CO$_3$ (124 mg, 0.381 mmol), Pd(dppf)Cl$_2$.DCM (7.5 mg, 9.14 µmol) and water (0.250 mL) were added and the mixture was reheated in a preheated oil bath at about 95° C. The reaction was cooled to rt after about 50 min and partioned between EtOAc and water. The layers were separated and the aqueous layer extracted with EtOAc (2×50 mL). The combined organic layers were washed with brine, dried over Na$_2$SO$_4$, filtered, and concentrated under reduced pressure. The crude product was purified by preprarative HPLC (Table 1, Method ao) to give the title compound (0.074 g, 95%). LC/MS (Table 1, Method e) R$_t$=0.75 min; MS m/z: 386 (M+H)$^+$ (TNF IC$_{50}$=A).

Example #40

((R)-1-(5-((R)-8-Phenyl-7,8-dihydro-6H-pyrrolo[2',1':2,3]imidazo[4,5-b]pyridin-2-yl)pyrimidin-2-yl)pyrrolidin-2-yl)methanol

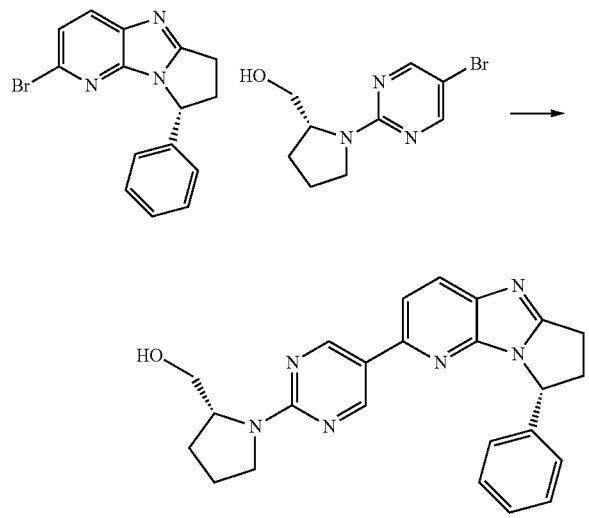

A mixture of bis(pinacolato)diboron (0.146 g, 0.575 mmol), (R)-(1-(5-bromopyrimidin-2-yl)pyrrolidin-2-yl)methanol (0.123 g, 0.477 mmol, synthesized in a manner similar to Preparation #39, step 1 from 5-bromo-2-chloropyrimidine and D-prolinol), KOAc (0.0942 g, 0.960 mmol), PdCl$_2$dppf (0.0198 g, 0.027 mmol), and 1,4-dioxane (2.5 mL) was heated under an atmosphere of N$_2$ at about 95° C. for about 2 h then cooled to rt. (R)-2-Bromo-8-phenyl-7,8-dihydro-6H-pyrrolo[2',1':2,3]imidazo[4,5-b]pyridine (0.0998 g, 0.318 mmol, Preparation #52), Cs$_2$CO$_3$ (0.264 g, 0.810 mmol), PdCl$_2$(PPh$_3$)$_2$ (0.0183 g, 0.026 mmol) and water (0.625 mL) were added. The mixture was warmed to 85° C. for about 3 h under an atmosphere of nitrogen. The mixture was cooled to rt then water (10 mL) and DCM (10 mL) were added. The mixture was filtered rinsing with 10 mL of DCM. The filtrate layers were separated. The aqueous layer was extracted with DCM (2×10 mL). The combined organics were dried over Na$_2$SO$_4$, filtered and concentrated. The crude material was purified via flash chromatography on silica gel (0-50% DCM/MeOH) to give the title compound (0.087 g, 65%); LC/MS (Table 1, Method r) R$_t$=1.92 min; MS m/z: 413. (TNF IC$_{50}$=B).

The compounds shown in Table AK were synthesized in a manner similar to Example #40 from (R)-2-bromo-8-phenyl-7,8-dihydro-6H-pyrrolo[2',1':2,3]imidazo[4,5-b]pyridine (Preparation #52) and the corresponding bromide/chloride.

TABLE AK

| Bromide/chloride | Product | Example # | R$_t$ min (Table 1, Method) | m/z (M + H)$^+$ | TNF IC$_{50}$ |
|---|---|---|---|---|---|
| (S)-(1-(5-Bromopyrimidin-2-yl)pyrrolidin-2-yl)methanol (synthesized in a manner similar to Preparation #39, step 1 from 5-bromo-2-chloropyrimidine and L-prolinol) | | AK.1 | 1.04 (z) | 413 | B |
| 4-Bromo-1-(2-(methylsulfonyl)ethyl)pyridin-2(1H)-one (synthesized as described in PCT Int. Appl., 2008141119 from 4-bromopyridin-2-ol and (methylsulfonyl)ethane) | | AK.2 | 1.61 (r) | 435 | C |

TABLE AK-continued

| Bromide/chloride | Product | Example # | R$_t$ min (Table 1, Method) | m/z (M + H)$^+$ | TNF IC$_{50}$ |
|---|---|---|---|---|---|
| 4-Bromo-1-(2-hydroxy-2-methylpropyl)pyridin-2(1H)-one (synthesized as described in PCT Int. Appl, WO 2009/134400) from 4-bromopyridin-2(1H)-one and 2,2-dimethyl-oxirane) | | AK.3 | 1.66 (r) | 401 | C |

The compounds shown in Table AL were synthesized in a manner similar to Example #40 from (R)-2-chloro-8-phenyl-7,8-dihydro-6H-pyrrolo[2',1':2,3]imidazo[4,5-b]pyridine (Preparation #81) and the corresponding bromide/chloride.

TABLE AL

| Bromide/chloride | Product | Example # | R$_t$ min (Table 1, Method) | m/z (M + H)$^+$ | TNF IC$_{50}$ |
|---|---|---|---|---|---|
| 1-(5-Bromopyrimidin-2-yl)ethanol (synthesized as described in US2013/252938 A1 from 5-bromo-2-iodopyrimidine and acetaldehyde) | | AL.1 | 1.68 (r) | 358 | B |
| 1-(5-Bromopyrimidin-2-yl)-2-cyclopropylethanol (synthesized in a manner similar to 1-(5-bromopyrimidin-2-yl)ethanol as described in US2013/252938 A1 from 5-bromo-2-iodopyrimidine and 2-cyclopropylacetaldehyde) | | AL.2 | 2.00 (r) | 398 | B |
| (5-Bromopyrimidin-2-yl)(tetrahydro-2H-pyran-4-yl)methanol (synthesized in a manner similar to 1-(5-bromopyrimidin-2-yl)ethanol as described in US2013/252938 A1 from 5-bromo-2-iodopyrimidine and tetrahydro-2H-pyran-4-carbaldehyde) | | AL.3 | 1.69 (r) | 428 | B |

TABLE AL-continued

| Bromide/chloride | Product | Example # | R$_t$ min (Table 1, Method) | m/z (M + H)$^+$ | TNF IC$_{50}$ |
|---|---|---|---|---|---|
| 1-(5-Bromopyrimidin-2-yl)-1-(tetrahydro-2H-pyran-4-yl)ethanol (synthesized in a manner similar to 1-(5-bromopyrimidin-2-yl)ethanol as described in US2013/252938 A1 from 5-bromo-2-iodopyrimidine and 1-(tetrahydro-2H-pyran-4-yl)ethanone) | | AL.4 | 1.99 (r) | 442 | B |
| 2-(5-Bromopyrimidin-2-yl)-1-cyclopropylpropan-2-ol (synthesized in a manner similar to 1-(5-bromopyrimidin-2-yl)ethanol as described in US2013/252938 A1 from 5-bromo-2-iodopyrimidine and 1-cyclopropylpropan-2-one | | AL.5 | 2.29 (r) | 412 | B |

The compounds shown in Table AM were synthesized in a manner similar to Example #40 from (R)-2-chloro-8-(3-methoxyphenyl)-7,8-dihydro-6H-pyrrolo[2',1':2,3]imidazo[4,5-b]pyridine (Preparation #82) and the corresponding bromide/chloride.

TABLE AM

| Bromide/chloride | Product | Example # | R$_t$ min (Table 1, Method) | m/z (M + H)$^+$ | TNF IC$_{50}$ |
|---|---|---|---|---|---|
| (R)-7-(5-Bromopyrimidin-2-yl)hexahydroimidazo[1,5-a]pyrazin-3(2H)-one (Preparation #39) | | AM.1 | 1.76 (r) | 483 | A |
| (R)-1-(4-(5-Bromopyrimidin-2-yl)-2-methylpiperazin-1-yl)ethanone | | AM.2 | 1.82 (r) | 484 | A |

The compound shown in Table AN were synthesized in a manner similar to Example #40 from (S)-2-chloro-8-(3-methoxyphenyl)-7,8-dihydro-6H-pyrrolo[2',1':2,3]imidazo[4,5-b]pyridine (Preparation #82) and the corresponding bromide/chloride.

TABLE AN

| Bromide/chloride | Product | Example # | $R_t$ min (Table 1, Method) | m/z (M + H)⁺ | TNF IC$_{50}$ |
|---|---|---|---|---|---|
| (R)-7-(5-Bromopyrimidin-2-yl)hexahydroimidazo[1,5-a]pyrazin-3(2H)-one (Preparation #39) | | AN.1 | 1.67 (r) | 483 | C |

The compounds shown in Table AO were synthesized in a manner similar to Example #40 from (R)-2-chloro-8-(2-methoxyphenyl)-7,8-dihydro-6H-pyrro[2',1':2,3]imidazo[4,5-b]pyridine (Preparation #83) and the corresponding bromide/chloride

TABLE AO

| Bromide/chloride | Product | Example # | $R_t$ min (Table 1, Method) | m/z (M + H)⁺ | TNF IC$_{50}$ |
|---|---|---|---|---|---|
| (R)-7-(5-Bromo-pyrimidin-2-yl)hexahydro-imidazo[1,5-a]pyrazin-3(2H)-one (Preparation #39) | | AO.1 | 1.87 (v) | 483 | A |
| (S)-7-(5-Bromo-pyrimidin-2-yl)hexahydro-imidazo[1,5-a]pyrazin-3(2H)-one (Preparation #39) | | AO.2 | 1.87 (v) | 483 | A |
| 1-(5-Bromo-pyrimidin-2-yl)piperidin-4-ol | | AO.3 | 1.93 (v) | 443 | A |

TABLE AO-continued

| Bromide/chloride | Product | Example # | R, min (Table 1, Method) | m/z (M + H)+ | TNF IC50 |
|---|---|---|---|---|---|
| (R)-1-(4-(5-Bromopyrimidin-2-yl)-2-methyl-piperazin-1-yl)-2-hydroxy-ethanone (synthesized in a similar manner to Example #43 from glycolic acid and (R)-5-bromo-2-(3-methyl-piperazin-1-yl)pyrimidine dihydrochloride (synthesized in a manner similar to Example #41, step to from (R)-tert-butyl 4-(5-bromopyrimidin-2-yl)-2-methyl-piperazine-1-carboxylate (synthesized in a manner similar to Preparation #39, step 1 from 5-bromo-2-chloropyrimidine and (R)-tert-butyl 4-(5-bromopyrimidin-2-yl)-2-methyl-piperazine-1-carboxylate))) | | AO.4 | 1.92 (v) | 500 | A |

The compounds shown in Table AP were synthesized in a manner similar to Example #40 from (S)-2-chloro-8-(2-methoxyphenyl)-7,8-dihydro-6H-pyrrolo[2',1':2,3]imidazo[4,5-b]pyridine (Preparation #83) and the corresponding bromide/chloride

TABLE AP

| Bromide/chloride | Product | Example # | R, min (Table 1, Method) | m/z (M + H)+ | TNF IC50 |
|---|---|---|---|---|---|
| (R)-7-(5-Bromo-pyrimidin-2-yl)hexahydro-imidazo[1,5-a]pyrazin-3(2H)-one (Preparation #39) | | AP.1 | 1.87 (v) | 483 | B |

Example #41

1-((R)-2-Methyl-4-(5-((R)-8-phenyl-7,8-dihydro-6H-pyrrolo[2',1':2,3]imidazo[4,5-b]pyridin-2-yl)pyrimidin-2-yl)piperazin-1-yl)ethanone

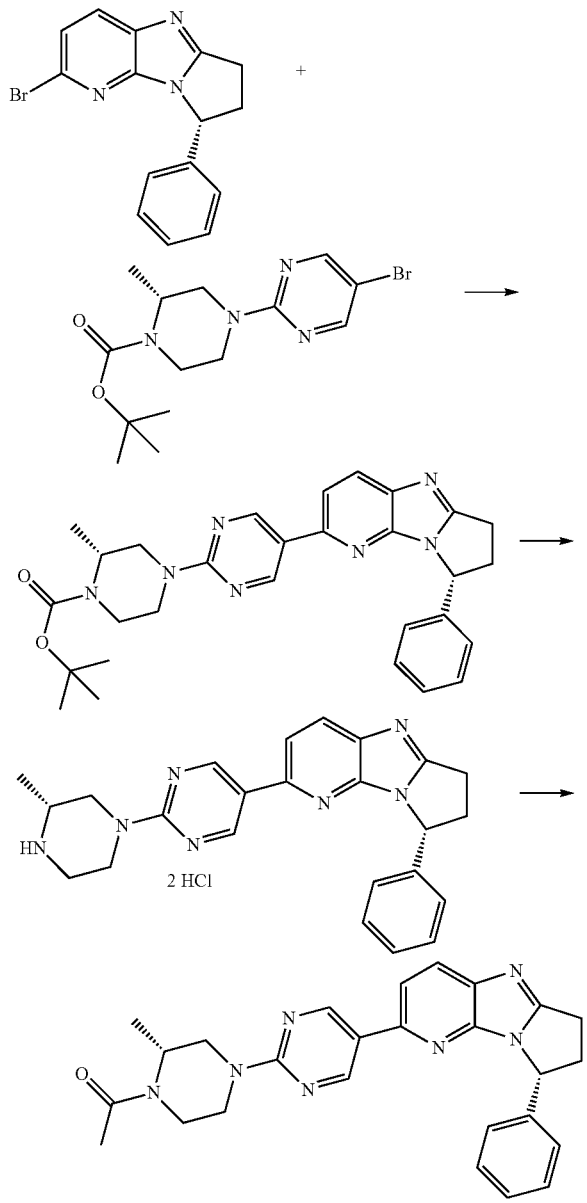

Step 1: (R)-tert-Butyl 2-methyl-4-(5-((R)-8-phenyl-7,8-dihydro-6H-pyrrolo[2',1':2,3]imidazo[4,5-b]pyridin-2-yl)pyrimidin-2-yl)piperazine-1-carboxylate The title compound was synthesized in a manner similar to Example #40 from (R)-2-bromo-8-phenyl-7,8-dihydro-6H-pyrrolo[2',1':2,3]imidazo[4,5-b]pyridine (Preparation #52) and (R)-tert-butyl 4-(5-bromopyrimidin-2-yl)-2-methylpiperazine-1-carboxylate (synthesized in a manner similar to Preparation #39, step 1 from 5-bromo-2-chloropyrimidine and (R)-tert-butyl 4-(5-bromopyrimidin-2-yl)-2-methylpiperazine-1-carboxylate); LC/MS (Table 1, Method z) $R_t$=1.87 min; MS m/z: 595 (M+H)⁺.

Step 2: (R)-2-(2-((R)-3-Methylpiperazin-1-yl)pyrimidin-5-yl)-8-phenyl-7,8-dihydro-6H-pyrrolo[2',1':2,3]imidazo[4,5-b]pyridine dihydrochloride To a solution of (S)-tert-butyl 4-(5-(1-(2-(difluoromethoxy)-5-methylbenzyl)-2-methyl-3-oxo-2,3-dihydro-1H-indazol-6-yl)pyrimidin-2-yl)-2-methylpiperazine-1-carboxylate (0.501 g, 0.843 mmol) and 1,4-dioxane (5 mL) was added 4 M HCl in 1.4-dioxane (3.0 mL, 12.0 mmol). The mixture was stirred for about 14 h then diluted with MeOH (3 mL). The mixture was stirred for about 30 min then concentrated under reduced pressure and dried under vacuum to give the title compound (0.459 g, 100%); LC/MS (Table 1, Method z) $R_t$=0.97 min; MS m/z: 495(M+H)⁺.

Step 3: 1-((R)-2-Methyl-4-(5-((R)-8-phenyl-7,8-dihydro-6H-pyrrolo[2',1':2,3]imidazo[4,5-b]pyridin-2-yl)pyrimidin-2-yl)piperazin-1-yl)ethanone To a mixture of (R)-2-(2-((R)-3-methylpiperazin-1-yl)pyrimidin-5-yl)-8-phenyl-7,8-dihydro-6H-pyrrolo[2',1':2,3]imidazo[4,5-b]pyridine dihydrochloride (0.117 g, 0.242 mmol), TEA (0.4 mL, 2.87 mmol) and N,N-dimethylpyridin-4-amine (2.95 mg, 0.024 mmol) in DCM (5 mL) was added acetic anhydride (0.1 mL, 1.060 mmol). The mixture was stirred at rt for 1 h then partitioned between sat. NaHCO₃ (10 mL) and DCM (20 mL). The aqueous layer was extracted with DCM (20 mL) then the combined organic layers were dried over Na₂SO₄, filtered and concentrated under reduced pressure. The material was purified via flash chromatography on silica gel (0-4% MeOH/DCM) to give the title compound; (0.071 g, 62%); LC/MS (Table 1, Method v) $R_t$=1.94 min; MS m/z: 454 (M+H)⁺. (TNF IC₅₀=A).

Example #42

1-((S)-2-Methyl-4-(5-((R)-8-phenyl-7,8-dihydro-6H-pyrrolo[2',1':2,3]imidazo[4,5-b]pyridin-2-yl)pyrimidin-2-yl)piperazin-1-yl)ethanone

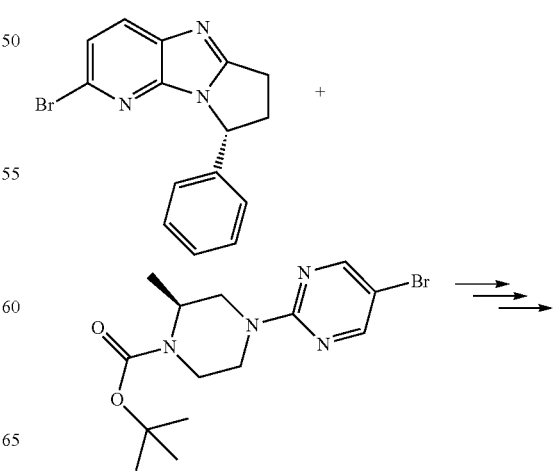

377
-continued

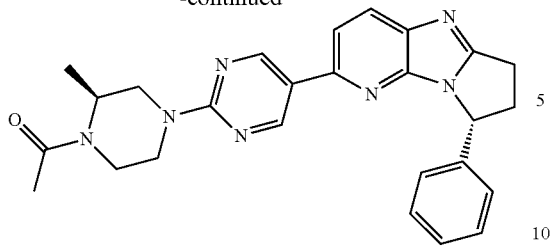

The title compound was synthesized in a manner similar to Example #41 steps 1 through 3 from (R)-2-bromo-8-phenyl-7,8-dihydro-6H-pyrrolo[2',1':2,3]imidazo[4,5-b]pyridine (Preparation #52) and (S)-tert-butyl 4-(5-bromopyrimidin-2-yl)-2-methylpiperazine-1-carboxylate (synthesized in a manner similar to Preparation #39, step 1 from 5-bromo-2-chloropyrimidine and (S)-tert-butyl 4-(5-bromopyrimidin-2-yl)-2-methylpiperazine-1-carboxylate); LC/MS (Table 1, Method z) $R_t$=1.94 min; MS m/z: 454 (M+H)$^+$. (TNF IC$_{50}$=A).

Example #43

2-Hydroxy-1-((R)-2-methyl-4-(5-((R)-8-phenyl-7,8-dihydro-6H-pyrrolo[2',1':2,3]imidazo[4,5-b]pyridin-2-yl)pyrimidin-2-yl)piperazin-1-yl)ethanone

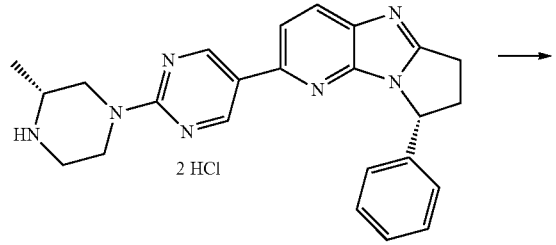

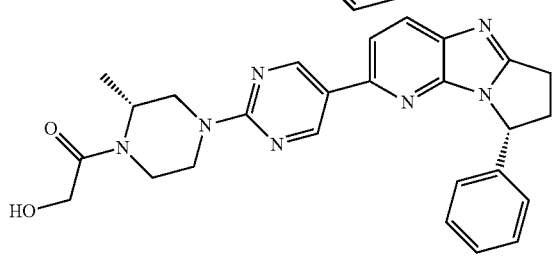

To a mixture of (R)-2-(2-((R)-3-methylpiperazin-1-yl)pyrimidin-5-yl)-8-phenyl-7,8-dihydro-6H-pyrrolo[2',1':2,3]imidazo[4,5-b]pyridine dihydrochloride (0.269 g, 0.654 mmol, Example #41, step 2) in DMF (3.48 mL) was added 2-hydroxyacetic acid (0.065 g, 0.850 mmol), 1-[bis(dimethylamino)methylene]-1H-1,2,3-triazolo[4,5-b]pyridinium 3-oxid hexafluorophosphate (0.298 g, 0.784 mmol) and TEA (0.528 mL, 3.79 mmol). The mixture was stirred at rt for about 1 h then partitioned between DCM (10 mL) and water (5 mL). The aqueous layer was extracted with DCM (5 mL) then the combined organics were dried over MgSO$_4$, filtered and concentrated under reduced pressure. The material was purified via flash chromatography on silica gel (0-50% MeOH/CH$_2$Cl$_2$) to give the title compound; LC/MS (Table 1, Method v) $R_t$=1.79 min; MS m/z: 470 (M+H)$^+$. (TNF IC$_{50}$=A).

378

Example #44

1-((R)-4-(5-((R)-8-(3-(Hydroxymethyl)phenyl)-7,8-dihydro-6H-pyrrolo[2',1':2,3]imidazo[4,5-b]pyridin-2-yl)pyrimidin-2-yl)-2-methylpiperazin-1-yl)ethanone

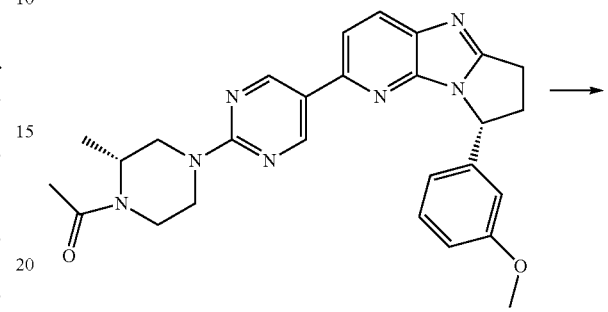

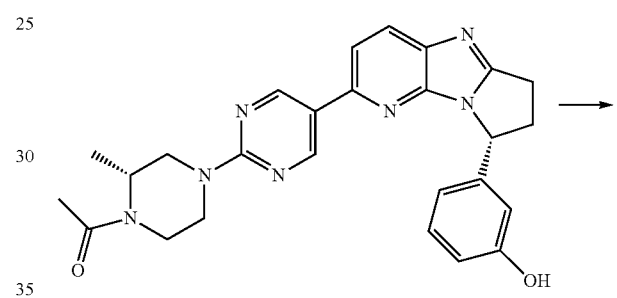

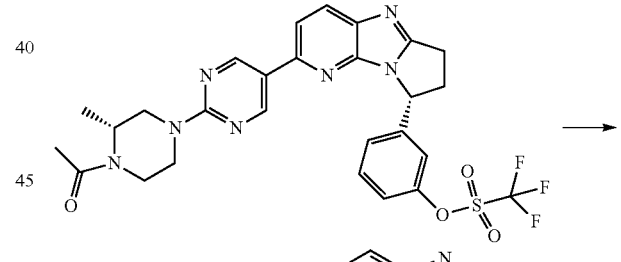

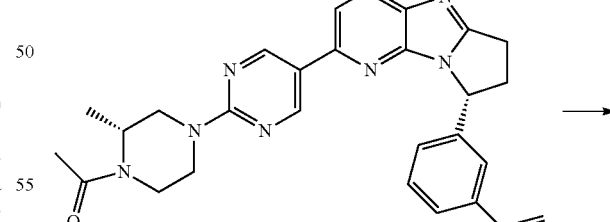

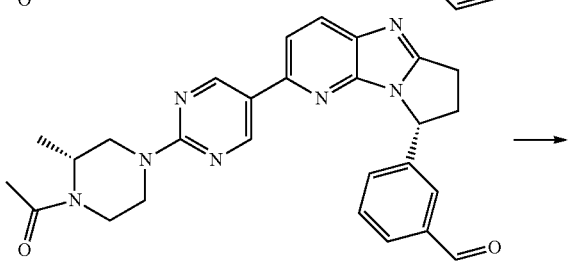

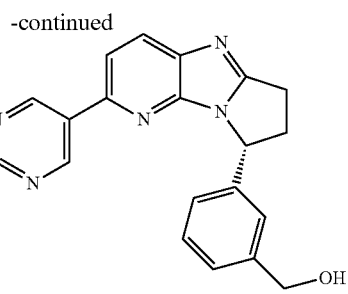

Step 1: 1-((R)-4-(5-((R)-8-(3-Hydroxyphenyl)-7,8-dihydro-6H-pyrrolo[2',1':2,3]imidazo[4,5-b]pyridin-2-yl)pyrimidin-2-yl)-2-methylpiperazin-1-yl)ethanone A solution of 1-((R)-4-(5-((R)-8-(3-methoxyphenyl)-7,8-dihydro-6H-pyrrolo[2',1':2,3]imidazo[4,5-b]pyridin-2-yl)pyrimidin-2-yl)-2-methylpiperazin-1-yl)ethanone (0.750 g, 1.551 mmol, Example #AM.2) in DCM (10 mL) was cooled to about 0° C. then tribromoborane (1 M in DCM) (10.86 mL, 10.86 mmol) was added, maintaining the reaction temperature below about 4° C. The mixture was stirred at about 0° C. for about 30 min. MeOH (20 mL) was added to the mixture which was then allowed to warm to rt. Solvents were removed under reduced pressure then the residue was partitioned between DCM (40 mL) and sat. NaHCO₃. The organic layer was washed with water (20 mL), dried over Na₂SO₄, filtered and concentrated to give the title compound which was used directly in the next step (0.804 g, 110%); LC/MS (Table 1, Method z) R$_t$=1.05 min; MS m/z: 470 (M+H)$^+$.

Step 2: 3-((R)-2-(2-((R)-4-Acetyl-3-methylpiperazin-1-yl)pyrimidin-5-yl)-7,8-dihydro-6H-pyrrolo[2',1':2,3]imidazo[4,5-b]pyridin-8-yl)phenyl trifluoromethanesulfonate 1-((R)-4-(5-((R)-8-(3-Hydroxyphenyl)-7,8-dihydro-6H-pyrrolo[2',1':2,3]imidazo[4,5-b]pyridin-2-yl)pyrimidin-2-yl)-2-methylpiperazin-1-yl)ethanone (0.728 g, 1.550 mmol) was dissolved in a DMF (10 mL) then treated with 1,1,1-trifluoro-N-phenyl-N-((trifluoromethyl)sulfonyl)methanesulfonamide (0.609 g, 1.706 mmol) and DIEA (0.542 mL, 3.10 mmol). After about 2.5 h a second portion of 1,1,1-trifluoro-N-phenyl-N-((trifluoromethyl)sulfonyl)methanesulfonamide (0.222 g, 0.620 mmol) was added. The mixture was stirred for about 14 h then the solvents were removed under reduced pressure. The residue was partitioned between EtOAc and sat. NaHCO₃. The organic solution was dried over Na₂SO₄, filtered and concentrated under reduced pressure. The material was purified via flash chromatography on silica gel (0-8% MeOH/DCM) to give the title compound (0.802 g, 86%); LC/MS (Table 1, Method z) Rt=1.47 min; MS m/z: 602 (M+H)$^+$.

Step 3: 1-((R)-2-Methyl-4-(5-((R)-8-(3-vinylphenyl)-7,8-dihydro-6H-pyrrolo[2',1':2,3]imidazo[4,5-b]pyridin-2-yl)pyrimidin-2-yl)piperazin-1-yl)ethanone A solution of 3-((R)-2-(2-((R)-4-acetyl-3-methylpiperazin-1-yl)pyrimidin-5-yl)-7,8-dihydro-6H-pyrrolo[2',1':2,3] imidazo[4,5-b]pyridin-8-yl)phenyl trifluoromethanesulfonate (0.835 g, 1.388 mmol), vinylboronic acid pinacol ester (0.283 mL, 1.666 mmol), and Cs₂CO₃ (1.131 g, 3.47 mmol) in 1,4-dioxane (18 mL) and water (3.60 mL) was degassed with a stream of nitrogen. PdCl₂(PPh₃)₂ (0.057 g, 0.081 mmol) was added and the mixture was further degassed for about 5 min with nitrogen. The mixture was heated to about 85° C. under nitrogen for about 2.5 h. The mixture was cooled to rt then the organic layer was decanted. The organic solution was concentrated to dryness along with silica gel then the sample was purified via flash chromatography on silica gel (0-8% MeOH/DCM) to give the title compound (0.746 g, 89%); LC/MS (Table 1, Method z) R$_t$=1.39 min; MS m/z: 480 (M+H)$^+$.

Step 4: 3-((R)-2-(2-((R)-4-acetyl-3-methylpiperazin-1-yl)pyrimidin-5-yl)-7,8-dihydro-6H-pyrrolo[2',1':2,3]imidazo[4,5-b]pyridin-8-yl)benzaldehyde A mixture of 1-((R)-2-methyl-4-(5-((R)-8-(3-vinylphenyl)-7,8-dihydro-6H-pyrrolo[2',1':2,3]imidazo[4,5-b]pyridin-2-yl)pyrimidin-2-yl)piperazin-1-yl)ethanone (0.735 g, 1.364 mmol) and 4-methylmorpholine 4-oxide (0.479 g, 4.09 mmol) in THF (10 mL) was cooled in an ice bath and osmium(VIII) oxide (0.535 mL, 0.068 mmol, 4 wt % in water) was added. The mixture was stirred at rt overnight then sodium periodate (0.438 g, 2.046 mmol) was added. The mixture was stirred at rt for about 3 h then partitioned between EtOAc (100 mL) and water (100 mL). The layers were separated and the aqueous layer was extracted with EtOAc (50 mL). The combined organic solutions were dried over Na₂SO₄, filtered and concentrated. The material was purified via flash chromatography on silica gel (0-8% MeOH/DCM) to give the title compound (0.381 g, 58%); LC/MS (Table 1, Method z) R$_t$=1.11 min; MS m/z: 482 (M+H)$^+$.

Step 5: 1-((R)-4-(5-((R)-8-(3-(Hydroxymethyl)phenyl)-7,8-dihydro-6H-pyrrolo[2',1':2,3]imidazo[4,5-b]pyridin-2-yl)pyrimidin-2-yl)-2-methylpiperazin-1-yl)ethanone A solution of 3-((R)-2-(2-((R)-4-acetyl-3-methylpiperazin-1-yl)pyrimidin-5-yl)-7,8-dihydro-6H-pyrrolo[2',1':2,3] imidazo[4,5-b]pyridin-8-yl)benzaldehyde (0.220 g, 0.457 mmol) in MeOH (4 mL) was cooled to about 0° C. then sodium tetrahydroborate (0.020 g, 0.529 mmol) was added in one portion then the mixture was allowed to warm to rt. EtOAc (20 mL) and water (5 mL) were added to the mixture then the layers were separated. The aqueous layer was extracted with EtOAc (3×20 mL) then the combined organic solutions were dried over Na₂SO₄, filtered and concentrated. The material was purified by flash chromatography on silica gel (0-10% MeOH/DCM) to give the title compound (0.182 g, 82%); LC/MS (Table 1, Method r) R$_t$=1.50 min; MS m/z: 484 (M+H)$^+$. (TNF IC$_{50}$=A).

Example #45

1-((R)-4-(5-((R)-8-(3-(Hydroxymethyl)phenyl)-7,8-dihydro-6H-pyrrolo[2',1':2,3]imidazo[4,5-b]pyridin-2-yl)pyrimidin-2-yl)-2-methylpiperazin-1-yl)ethanone

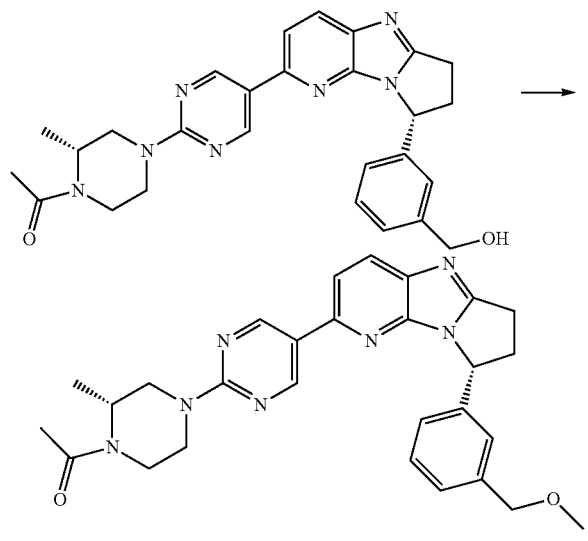

To a suspension of NaH (60 wt %) (0.008 g, 0.200 mmol) in THF (1 mL) was added a solution of 1-((R)-4-(5-((R)-8-(3-(hydroxymethyl)phenyl)-7,8-dihydro-6H-pyrrolo[2',1':2,3]imidazo[4,5-b]pyridin-2-yl)pyrimidin-2-yl)-2-methylpiperazin-1-yl)ethanone (0.05 g, 0.103 mmol, Example #44) in THF (1 mL). The mixture was stirred for about 5 min then iodomethane (0.032 mL, 0.517 mmol) was added. The mixture was stirred for about 5 h then concentrated under reduced pressure. Water (0.5 mL) was added to the residue then the mixture was extracted with DCM (2×3 mL). The organic solution was purified directly by flash chromatography on silica gel (0-10% MeOH/DCM) to give the title compound (0.019 g, 37%); LC/MS (Table 1, Method r) $R_t$=1.75 min; MS m/z: 498 (M+H)$^+$. (TNF IC$_{50}$=B).

Example #46

(S)-1-(5-((R)-8-Phenyl-7,8-dihydro-6H-pyrrolo[2',1':2,3]imidazo[4,5-b]pyridin-2-yl)pyrimidin-2-yl)piperidin-4-yl 2-amino-3-methylbutanoate

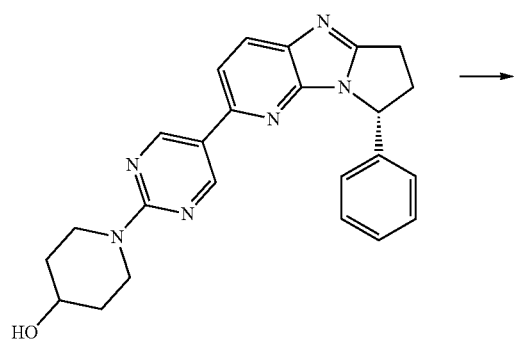

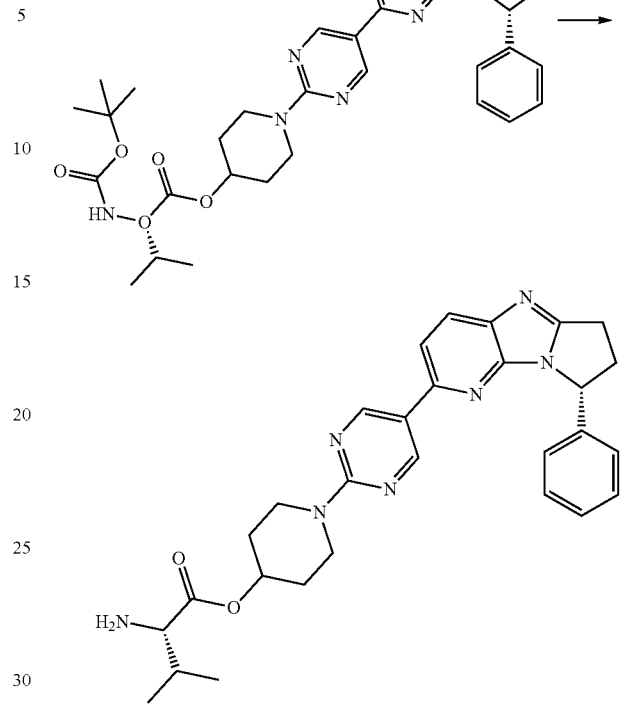

Step 1: (S)-1-(5-((R)-8-Phenyl-7,8-dihydro-6H-pyrrolo[2',1':2,3]imidazo[4,5-b]pyridin-2-yl)pyrimidin-2-yl)piperidin-4-yl 2-((tert-butoxycarbonyl)amino)-3-methylbutanoate A mixture of (S)-2-((tert-butoxycarbonyl)amino)-3-methylbutanoic acid (0.047 g, 0.218 mmol), (R)-1-(5-(8-phenyl-7,8-dihydro-6H-pyrrolo[2',1':2,3]imidazo[4,5-b]pyridin-2-yl)pyrimidin-2-yl)piperidin-4-ol (0.075 g, 0.182 mmol), 4-dimethyl amino pyridine (6.66 mg, 0.055 mmol), and 1-ethyl-3-(3-dimethylaminopropyl)carbodiimide (0.052 g, 0.273 mmol) in DMF (2 mL) was stirred at rt for about 7 h. An additional portion of (S)-2-((tert-butoxycarbonyl)amino)-3-methylbutanoic acid (0.047 g, 0.218 mmol) and EDC (0.052 g, 0.273 mmol) were added and stirring continued for about 24 h. The reaction mixture was partitioned between EtOAc (10 mL) and water (10 mL). After separating the layers the aqueous phase was extracted with EtOAc (2×5 mL). The combined organic phases were washed with 20% aqueous citric acid, sat. NaHCO$_3$ (15 mL) and brine (15 mL) then dried over Na$_2$SO$_4$, filtered, and concentrated under reduced pressure. The residue was purified via flash chromatography on silica gel (0-5% DCM/MeOH) to give the title compound (0.072 g, 64.7%); LC/MS (Table 1, Method z) $R_t$=1.82 min; MS m/z: 612 (M+H)$^+$.

Step 2: (S)-1-(5-((R)-8-Phenyl-7,8-dihydro-6H-pyrrolo[2',1':2,3]imidazo[4,5-b]pyridin-2-yl)pyrimidin-2-yl)piperidin-4-yl 2-amino-3-methylbutanoate (S)-1-(5-((R)-8-Phenyl-7,8-dihydro-6H-pyrrolo[2,1':2,3]imidazo[4,5-b]pyridin-2-yl)pyrimidin-2-yl)piperidin-4-yl 2-((tert-butoxycarbonyl)amino)-3-methylbutanoate (0.072 g, 0.118 mmol) was treated with 4N HCl in 1,4-dioxane (0.5 mL, 2.0 mmol). The mixture was stirred at rt for about 30 min then concentrated under reduced pressure to give the title compound (0.044 g, 73%); LC/MS (Table 1, Method r) $R_t$=1.72 min; MS m/z: 512 (M+H)$^+$. (TNF IC$_{50}$=B).

Example #46.1

(R)-1-(5-(8-Phenyl-7,8-dihydro-6H-pyrrolo[2',1':2,3] imidazo[4,5-b]pyridin-2-yl)pyrimidin-2-yl)piperidin-4-yl dihydrogen phosphate hydrochloride

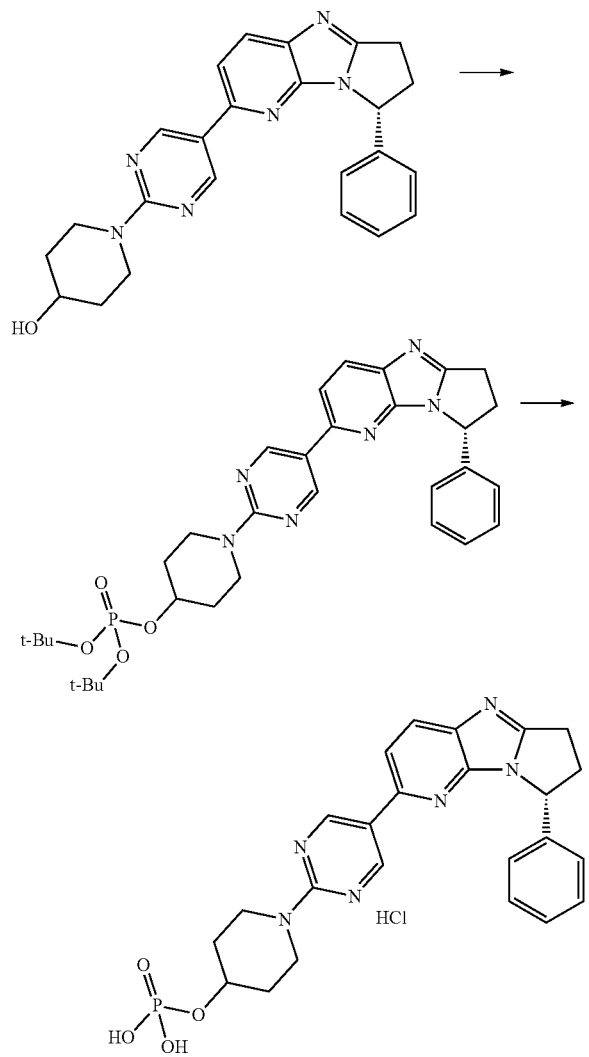

Step 1: (R)-di-tert-Butyl (1-(5-(8-phenyl-7,8-dihydro-6H-pyrrolo[2',1':2,3]imidazo[4,5-b]pyridin-2-yl)pyrimidin-2-yl)piperidin-4-yl) phosphate A solution of (R)-1-(5-(8-phenyl-7,8-dihydro-6H-pyrrolo[2',1':2,3]imidazo[4,5-b]pyridin-2-yl)pyrimidin-2-yl)piperidin-4-ol (0.080 g, 0.194 mmol), imidazole (0.013 g, 0.194 mmol) and imidazole hydrochloride (0.030 g, 0.291 mmol) in DMF (2 mL) was treated with di-tert-butyl N,N-diisopropylphosphoramidite (0.061 mL, 0.194 mmol). The resulting solution was stirred at ambient temperature for about 17 h then additional di-tert-butyl N,N-diisopropylphosphoramid-ite (0.061 mL, 0.194 mmol), imidazole (0.013 g, 0.194 mmol) and imidazole hydrochloride (0.030 g, 0.291 mmol) were added. The mixture was stirred for about 90 min then cooled to about 0° C. and treated with 30 wt % hydrogen peroxide (0.10 mL, 0.882 mmol). The mixture was warmed to rt and stirred for about 15 h. The mixture was partitioned between EtOAc (10 mL) and water (10 mL) then the aqueous phase was extracted with EtOAc (2×5 mL). The combined organic phases were washed with water and brine (10 mL each), dried over Na$_2$SO$_4$, filtered, and concentrated under reduced pressure. The material was purified via flash chromatography on silica gel followed by preparative reverse phase chromatography to give the title compound; (0.078 g, 66.5%); LC/MS (Table 1, Method z) $R_t$=1.67 min; MS m/z: 605 (M+H)$^+$.

Step 2: (R)-1-(5-(8-Phenyl-7,8-dihydro-6H-pyrrolo [2',1':2,3]imidazo[4,5-b]pyridin-2-yl)pyrimidin-2-yl) piperidin-4-yl dihydrogen phosphate hydrochloride (R)-di-tert-Butyl (1-(5-(8-phenyl-7,8-dihydro-6H-pyrrolo[2',1':2,3]imidazo[4,5-b]pyridin-2-yl)pyrimidin-2-yl)piperidin-4-yl) phosphate (0.078 g, 0.129 mmol) was treated with 4 N HCl in 1,4-dioxane (1 mL, 4.00 mmol). The mixture was stirred at rt for about 30 min then concentrated under reduced pressure to give the title compound (0.066 g, 97%); LC/MS (Table 1, Method r) $R_t$=1.39 min; MS m/z: 493 (M+H)$^+$. (TNF IC$_{50}$=B).

Example #47

(R)-8-Phenyl-2-(2-((tetrahydro-2H-pyran-4-yl)oxy) pyridin-4-yl)-7,8-dihydro-6H-pyrrolo[2',1':2,3]imidazo[4,5-b]pyridine

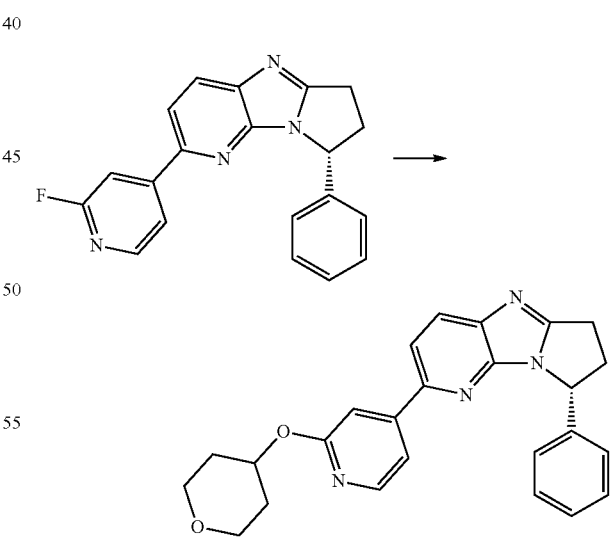

Tetrahydro-2H-pyran-4-ol (0.046 g, 0.454 mmol) was taken into DMF (1 mL) followed by the addition of NaH (0.018 g, 0.454 mmol). The mixture was stirred for about 10 min, then (R)-2-(2-fluoropyridin-4-yl)-8-phenyl-7,8-dihydro-6H-pyrrolo[2',1':2,3]imidazo[4,5-b]pyridine (0.05 g, 0.151 mmol, Preparation #84) in DMF (1 mL) was added and the mixture was heated at about 120° C. for about 40 min in a microwave. The reaction was cooled to rt, a few drops of water was added, and the mixture was concentrated under reduced pressure. The residue dissolved was purified by prep-HPLC (Table 1, Method aq) to afford the product (0.02 g, 35%); LC/MS (Table 1, Method ab) $R_t$=0.83 min; MS m/z: 413 (M+H)$^+$. (TNF IC$_{50}$=A).

The compounds shown in Table AQ were synthesized in a manner similar to Example #47 from the corresponding alcohol.

TABLE AQ

| Alcohol | Product | Example # | $R_t$ min (Table 1, Method) | m/z (M + H)$^+$ | TNF IC$_{50}$ |
|---|---|---|---|---|---|
| Cyclopentane-1,3-diol | | AQ.1 | 0.88 (ab) | 413 | A |
| Cyclohexane-1,4-diol | | AQ.2 | 0.80 (ab) | 427 | A |
| Oxetan-3-ol | | AQ.3 | 0.82 (ab) | 385 | B |
| Cyclohexane-1,3-diol | | AQ.4 | 0.82 (ab) | 427 | B |
| Oxetan-3-ylmethanol | | AQ.5 | 0.91 (ab) | 399 | B |

TABLE AQ-continued

| Alcohol | Product | Example # | R*t* min (Table 1, Method) | m/z (M + H)+ | TNF IC50 |
|---|---|---|---|---|---|
| (R)-1-Methyl-pyrrolidin-3-ol | | AQ.6 | 0.66 (ab) | 412 | B |
| Ethane-1,2-diol | | AQ.7 | 0.78 (ab) | 373 | B |
| (S)-1-Methyl-pyrrolidin-3-ol | | AQ.8 | 0.84 (ab) | 412 | B |

The compounds shown in Table AR were synthesized in a manner similar to Example #47 from the corresponding alcohol, substituting THF for DMF.

TABLE AR

| Alcohol | Product | Example # | R*t* min (Table 1, Method) | m/z (M + H)+ | TNF IC50 |
|---|---|---|---|---|---|
| cis-1,4-Cyclohexanediol | | AR.1 | 0.94 (ac) | 427 | B |

Example #48

(8R)-8-Phenyl-2-(2-((tetrahydro-2H-pyran-3-yl)oxy)pyridin-4-yl)-7,8-dihydro-6H-pyrrolo[2',1':2,3]imidazo[4,5-b]pyridine

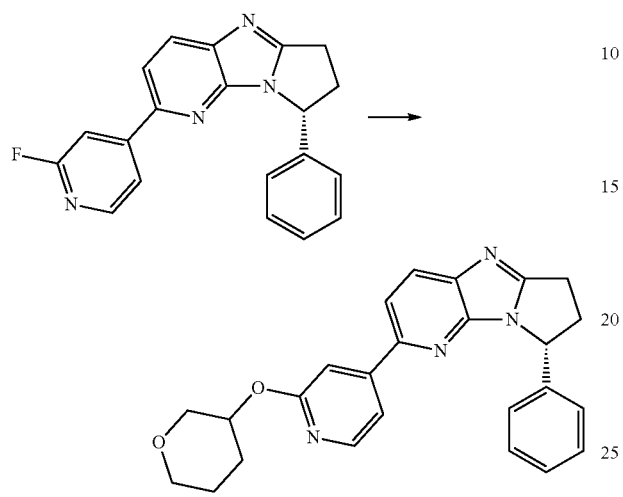

Tetrahydro-2H-pyran-3-ol (0.051 g, 0.499 mmol was taken into THF (1 mL) followed by the addition of 1M potassium butoxide in THF (0.5 mL, 0.5 mmol). The mixture was stirred for about 10 min, then (R)-2-(2-fluoropyridin-4-yl)-8-phenyl-7,8-dihydro-6H-pyrrolo[2',1':2,3]imidazo[4,5-b]pyridine (0.055 g, 0.166 mmol, Preparation #84) in THF (1 mL) was added and the mixture was heated at about 120° C. for about 20 min in a microwave. The reaction was cooled to rt, quenched with water and extracted with 100 mL EtOAc. The organics were collected, passed through a phase separator, concentrated under reduced pressure and the residue purified via silica gel chromatography eluting with 75-100% EtOAc/heptanes to afford the title compound (0.03 g, 45%); LC/MS (Table 1, Method ab) $R_t$=0.89 min; MS m/z: 413 (M+H)$^+$. (TNF IC$_{50}$=B).

The compounds shown in Table AS were synthesized in a manner similar to Example #48 from the corresponding alcohol.

TABLE AS

| Alcohol | Product | Example # | $R_t$ min (Table 1, Method) | m/z (M + H)$^+$ | TNF IC$_{50}$ |
|---|---|---|---|---|---|
| Tetrahydro-furan-3-ol | | AS.1 | 0.85 (ab) | 399 | B |
| Cyclopentanol | | AS.2 | 0.93 (ab) | 397 | B |
| Cyclohexanol | | AS.3 | 0.98 (ab) | 411 | B |

TABLE AS-continued

| Alcohol | Product | Example # | R$_t$ min (Table 1, Method) | m/z (M + H)$^+$ | TNF IC$_{50}$ |
|---|---|---|---|---|---|
| Methyl 4-hydroxycyclohexanecarboxylate | | AS.4 | 0.94 (ab) | 469 | B |
| Methyl 3-hydroxycyclopentanecarboxylate | | AS.5 | 0.91 (ab) | 455 | B |
| Butan-1-ol | | AS.6 | 0.96 (ab) | 485 | B |
| 3-Hydroxycyclopentanecarbonitrile | | AS.7 | 0.80 (ab) | 422 | B |

Example #49

(R)-8-Phenyl-2-(2-((S)-pyrrolidin-3-yloxy)pyridin-4-yl)-7,8-dihydro-6H-pyrrolo[2',1':2,3]imidazo[4,5-b]pyridine)

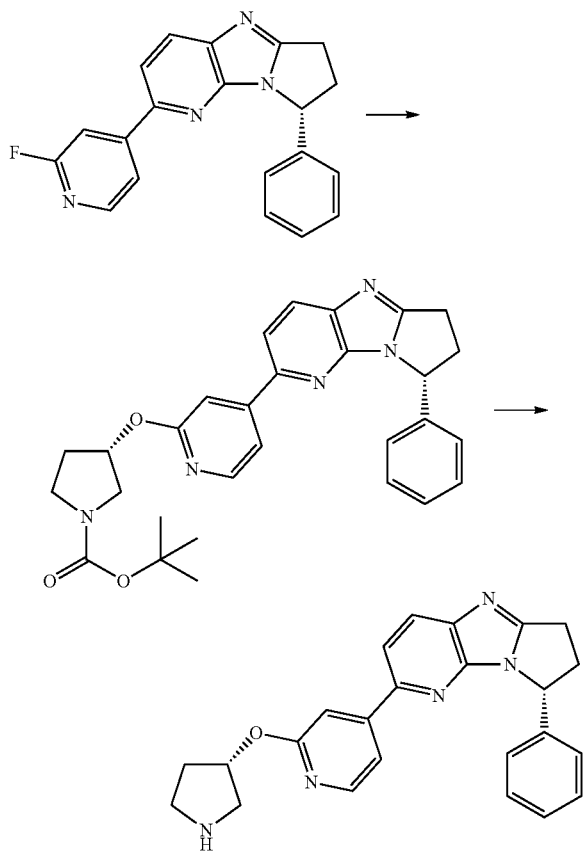

Step 1: (S)-tert-Butyl 3-((4-((R)-8-phenyl-7,8-dihydro-6H-pyrrolo[2',1':2,3]imidazo[4,5-b]pyridin-2-yl)pyridin-2-yl)oxy)pyrrolidine-1-carboxylate The reaction was performed from (R)-2-(2-fluoropyridin-4-yl)-8-phenyl-7,8-dihydro-6H-pyrrolo[2',1':2,3]imidazo[4,5-b]pyridine (0.045 g, 0.136 mmol, Preparation #84) with (S)-tert-butyl 3-hydroxypyrrolidine-1-carboxylate (0.051 g, 0.272 mmol) in a similar fashion to Example #47, to give the title compound (0.036 g, 53%); LC/MS (Table 1, Method ab) $R_t$=0.91 min.; MS m/z: 498 (M+H)$^+$.

Step 2: (R)-8-Phenyl-2-(2-((S)-pyrrolidin-3-yloxy)pyridin-4-yl)-7,8-dihydro-6H-pyrrolo[2',1':2,3]imidazo[4,5-b]pyridine To a solution of (S)-tert-butyl 3-((4-((R)-8-phenyl-7,8-dihydro-6H-pyrrolo[2',1':2,3]imidazo[4,5-b]pyridin-2-yl)pyridin-2-yl)oxy)pyrrolidine-1-carboxylate (0.034 g, 0.068 mmol) in 1,4-dioxane (1 mL) was added 4M HCl in 1,4-dioxane (0.17 mL, 0.683 mmol) The reaction was stirred at rt for about 1 h. The solvent was removed under reduced pressure and the residue was triturated with diethylether (2×1 mL). The resulting solid was collected by filtration, washed with diethylether, and dried to afford the title compound (0.03 g, 101%); LC/MS (Table 1, Method ab) $R_t$=0.73 min.; MS m/z: 398 (M+H)$^+$. (TNF IC$_{50}$=B).

The compounds shown in Table AT were synthesized in a manner similar to Example #49 from the corresponding alcohol.

TABLE AT

| Alcohol | Product | Example # | $R_t$ min (Table 1, Method) | m/z (M + H)$^+$ | TNF IC$_{50}$ |
|---|---|---|---|---|---|
| tert-Butyl 3-hydroxy-piperidine-1-carboxylate | | AT.1 | 0.77 (ab) | 412 | B |
| (R)-tert-Butyl 3-hydroxy-pyrrolidine-1-carboxylate | | AT.2 | 0.72 (ab) | 398 | B |

TABLE AT-continued

| Alcohol | Product | Example # | R$_t$ min (Table 1, Method) | m/z (M + H)$^+$ | TNF IC$_{50}$ |
|---|---|---|---|---|---|
| tert-Butyl 1-hydroxy-6-azaspiro[3.4]octane-6-carboxylate | | AT.3 | 0.78 (ab) | 438 | B |
| tert-Butyl 2-hydroxy-6-azaspiro[3.4]octane-6-carboxylate | | AT.4 | 0.76 (ab) | 438 | B |
| tert-Butyl 1-hydroxy-6-azaspiro[3.5]nonane-6-carboxylate | | AT.4 | 0.81 (ab) | 452 | B |

Example #50

1-(5-(6',8'-Dihydro-2H-spiro[benzofuran-3,9'-pyrido[3',2':4,5]imidazo[2,1-c][1,4]oxazin]-2'-yl)pyrimidin-2-yl)piperidin-4-ol

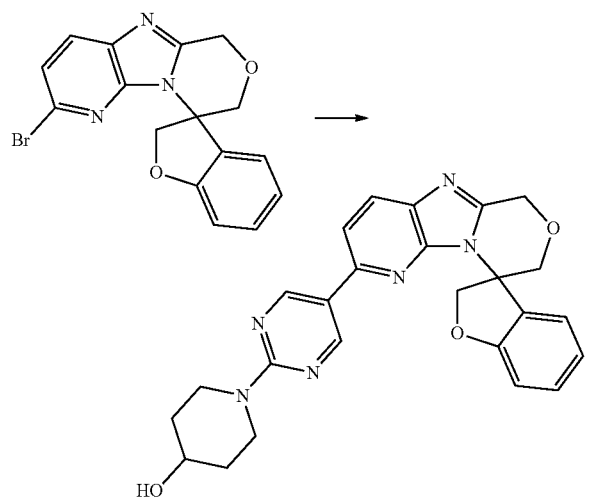

To a vial was added 2-chloro-5-(4,4,5,5-tetramethyl-1,3,2-dioxaborolan-2-yl)pyrimidine (0.050 g, 0.209 mmol), EtOH (0.5 mL), and piperidin-4-ol (0.021 g, 0.209 mmol), followed by the addition of TEA (0.067 mL, 0.276 mmol). The contents were heated at about 95° C. for about 2 h. The mixture was cooled to rt and concentrated under reduced pressure. 2'-Bromo-6',8'-dihydro-2H-spiro[benzofuran-3,9'-pyrido[3',2':4,5]imidazo[2,1-c][1,4]oxazine](0.03 g, 0.084 mmol, Preparation #85), PdCl$_2$(PPh$_3$)$_2$(5.9 mg, 8.38 mol), Cs$_2$CO$_3$ (0.068 g, 0.209 mmol), 1,4-dioxane (0.5 mL) and water (0.25 mL) were added to the residue, and the reaction was stirred at about 90° C. overnight. The mixture was cooled to rt, and the organic layer was filtered through a silica gel pad, rinsing with 1,4-dioxane. The filtrate was concentrated under reduced pressure and purified via chromatography eluting with 0-10% MeOH/DCM to give the title compound (0.017 g, 45%); LC/MS (Table 1, Method ac) R$_t$=0.87 min; MS m/z: 457 (M+H)$^+$. (TNF IC$_{50}$=A).

The compounds shown in Table AU were synthesized in a manner similar to Example #50 from the amine.

TABLE AU

| Amine | Product | Example # | R$_t$ min (Table 1, Method) | m/z (M + H)$^+$ | TNF IC$_{50}$ |
|---|---|---|---|---|---|
| (S)-Hexa-hydroimidazo[1,5-a]pyrazin-3(2H)-one (Preparation #41) | | AU.1 | 0.88 (ac) | 497 | A |
| 3-Amino-cyclobutan-1-ol | | AU.2 | 0.56 (ai) | 443 | B |
| Tetrahydro-furan-3-amine | | AU.3 | 0.61 (ai) | 443 | B |
| Piperidin-3-ol | | AU.4 | 0.61 (ai) | 457 | A |
| 1-Methyl-piperazine | | AU.5 | 0.53 (ai) | 456 | B |

Example #51

2'-(2-Morpholinopyrimidin-5-yl)-6',8'-dihydro-2H-spiro[benzofuran-3,9'-pyrido[3',2':4,5]imidazo[2,1-c][1,4]oxazine]

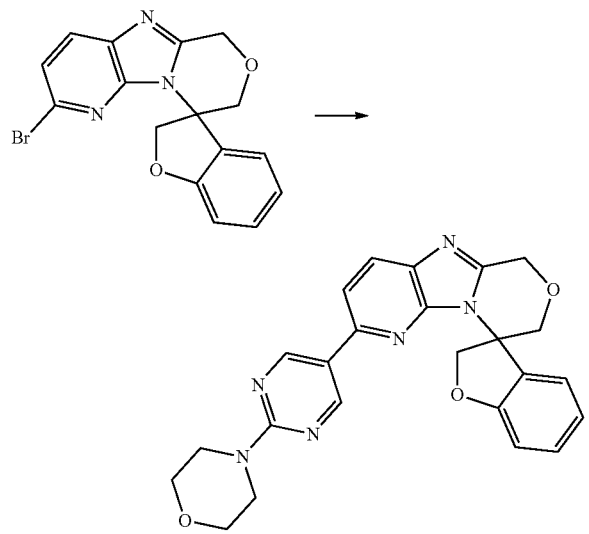

A vial was charged with 2'-bromo-6',8'-dihydro-2H-spiro[benzofuran-3,9'-pyrido[3',2':4,5]imidazo[2,1-c][1,4]oxazine](0.02 g, 0.056 mmol, Preparation #85), (2-morpholinopyrimidin-5-yl)boronic acid (0.013 g, 0.061 mmol), $Cs_2CO_3$ (0.045 g, 0.140 mmol) and $PdCl_2(PPh_3)_2$ (3.9 mg, 5.58 µmol) followed by water (0.25 mL) and 1,4-dioxane (0.5 mL). The vial was degassed with $N_2$ and heated at about 85° C. for about 2 h. The mixture was cooled to rt, and the organic layer was filtered through a silica gel pad, rinsing with 1,4-dioxane. The filtrate was concentrated under reduced pressure and purified via chromatography eluting with 0-100% EtOAc/Heptanes to give the title compound (0.016 g, 65%); LC/MS (Table 1, Method ab) $R_t$=0.87 min; MS m/z: 443 (M+H)$^+$. (TNF $IC_{50}$=A).

Example #52

1-(5-(1,2',3,3'-Tetrahydrospiro[benzo[4,5]imidazo[2,1-c][1,4]oxazine-4,1'-inden]-7-yl)pyrimidin-2-yl)piperidin-4-ol

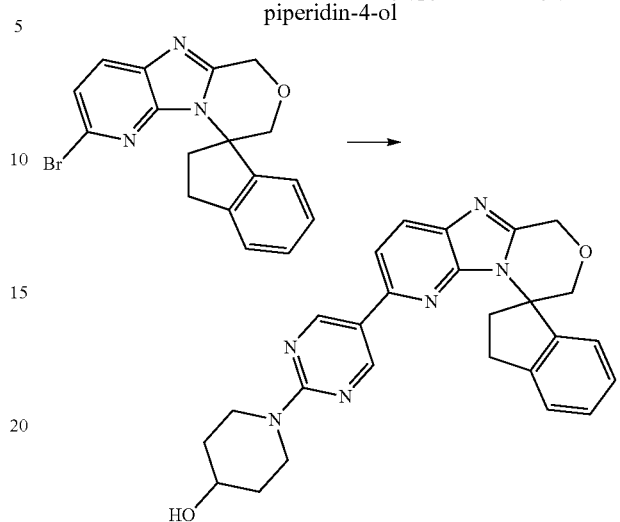

To a vial was added (2-chloropyrimidin-5-yl)boronic acid (0.200 g, 1.263 mmol), EtOH (3 mL), and piperidin-4-ol (128 mg, 1.263 mmol) followed by the addition of TEA (196 µL, 1.404 mmol). The contents were heated at about 80° C. for about 0.5 h. The mixture was then added to 2-5 mL microwave vial preloaded with 2'-bromo-2,3,6',8'-tetrahydrospiro[indene-1,9'-pyrido[3',2':4,5]imidazo[2,1-c][1,4]oxazine](0.100 g, 0.281 mmol, Preparation #92) and SiliaCat® DPP-Pd (0.112 g, 0.028 mmol, 0.25 mmol/g load, SiliCycle Cat#R390-100). The final volume of EtOH was brought to 4 mL and 1M $Cs_2CO_3$ (0.101 mL, 0.201 mmol) was added. The vial was capped and the contents were heated via microwave irradiation (Biotage Initiator) at 130° C. for 20 min. The contents were cooled and concentrated directly onto silica gel and purified by flash chromatography (1-10% DCM/MeOH, 40 g Redisep Gold). Fractions were concentrated to yield title compound (0.085 g, 66%) as a white solid; LC/MS (Table 1, Method f) $R_t$=0.87 min; MS m/z: 455 (M+H)$^+$. (TNF $IC_{50}$=A).

The compounds shown in Table AV were synthesized in a manner similar to Example #52 from the corresponding amines.

TABLE AV

| Amine | Product | Example # | $R_t$ min (Table 1, Method) | m/z (M + H)$^+$ | TNF $IC_{50}$ |
|---|---|---|---|---|---|
| Piperidin-3-ylmethanol | (structure) | AV.1 | 5.31 (ah) | 469 | A |

TABLE AV-continued
| Amine | Product | Example # | R$_t$ min (Table 1, Method) | m/z (M + H)$^+$ | TNF IC$_{50}$ |
|---|---|---|---|---|---|
| (S)-Hexa-hydroimi-dazo[1,5-a]pyrazin-3(2H)-one (Preparation #41) | 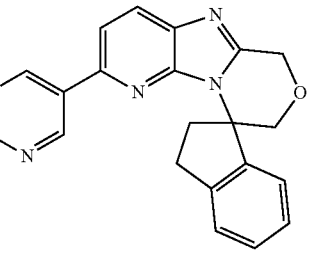 | AV.2 | 4.63 (ah) | 495 | A |
| 1,4-Oxazepane | 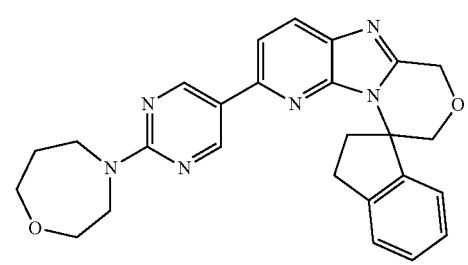 [SMILES: c1ccc2c(c1)CCC21COCc2nc3ccc(-c4cnc(N5CCCOCC5)nc4)nc3n21] | AV.3 | 5.53 (ah) | 455 | A |
| 3,3-Difluoro-piperidin-4-ol | 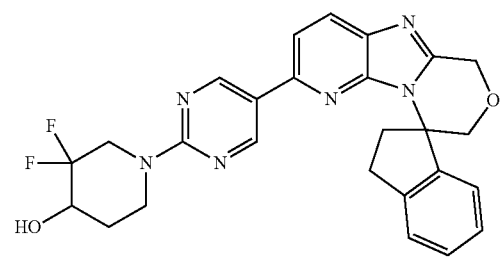 [SMILES: OC1CCN(c2ncc(-c3ccc4nc5n(c4n3)C3(CCc4ccccc43)COC5)cn2)CC1(F)F] | AV.4 | 5.41 (ah) | 491 | A |
| 2-Hydroxy-1-(piperazin-1-yl)propan-1-one | 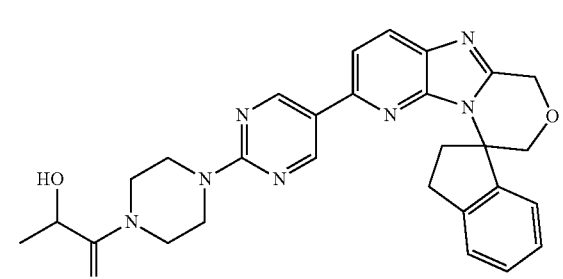 | AV.5 | 4.66 (ah) | 512 | A |
| 2-Hydroxy-1-(piperazin-1-yl)ethan-1-one | 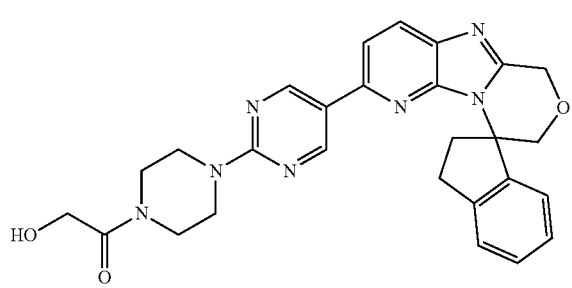 [SMILES: O=C(CO)N1CCN(c2ncc(-c3ccc4nc5n(c4n3)C3(CCc4ccccc43)COC5)cn2)CC1] | AV.6 | 4.50 (ah) | 498 | A |

TABLE AV-continued

| Amine | Product | Example # | R, min (Table 1, Method) | m/z (M + H)+ | TNF IC50 |
|---|---|---|---|---|---|
| (4-Fluoro-piperidin-4-yl)methanol | 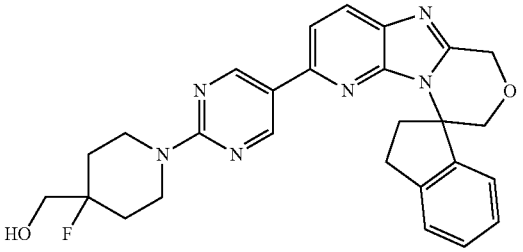 [SMILES: OCC1(F)CCN(c2ncc(-c3ccc4nc5n(c4n3)C3(CCc4ccccc43)COC5)cn2)CC1] | AV.7 | 5.24 (ah) | 487 | A |
| Morpholine | 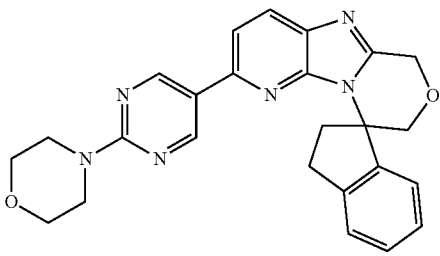 [SMILES: c1ccc2c(c1)CCC21COCc2nc3ccc(-c4cnc(N5CCOCC5)nc4)nc3n21] | AV.8 | 5.51 (ah) | 441 | A |
| Azepan-4-ol | 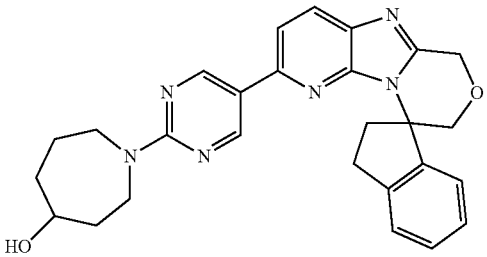 [SMILES: OC1CCCN(c2ncc(-c3ccc4nc5n(c4n3)C3(CCc4ccccc43)COC5)cn2)CC1] | AV.9 | 4.88 (ah) | 469 | A |

Example #53

(R)-1-((4,4-Difluorocyclohexyl)methyl)-4-(8-phenyl-7,8-dihydro-6H-pyrrolo[2',1':2,3]imidazo[4,5-b]pyridin-2-yl)pyridin-2(1H)-one

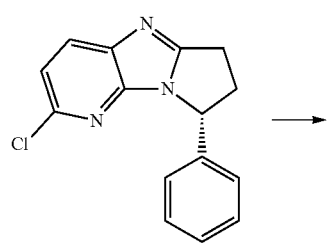

In a 4 mL vial with magnetic stirrer was added (1-((4,4-difluorocyclohexyl)methyl)-2-oxo-1,2-dihydropyridin-4-yl)boronic acid (81 mg, 0.3 mmol), (R)-2-chloro-8-phenyl-7,8-dihydro-6H-pyrrolo[2',1':2,3]imidazo[4,5-b]pyridine (30 mg, 0.111 mmol, Preparation #81,), and 1,1'-bis(diphenylphosphino)ferrocene-palladium(II)dichloride dichloromethane complex (9.1 mg, 0.011 mmol) followed by the addition of 1.5 mL degassed 1,4-dioxane and finally Cs$_2$CO$_3$ (300 μL, 1 M, 0.300 mmol). This mixture was heated to 100° C. overnight. The reaction mixture was then filtered through Celite®. The crude material was purified by preparative HPLC (Table 1, Method k) to give the title compound (0.009 g, 9%) as an TFA salt; LC/MS (Table 1, Method i) R$_t$=0.71 min; MS m/z: 461 (M+H)+. (TNF IC50=B).

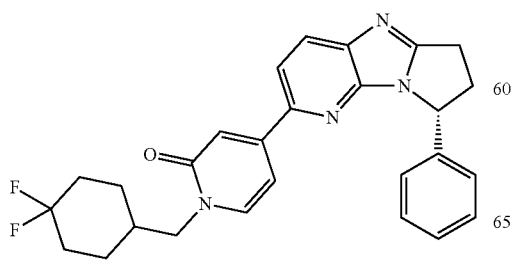

The title compounds shown in table AW were synthesized in a manner similar to Example #53 from (R)-2-chloro-8-phenyl-7,8-dihydro-6H-pyrrolo[2',1':2,3]imidazo[4,5-b]pyridine (Preparation #81) and the corresponding boronic acid/boronate

TABLE AW

| Boronic acid/boronate | Product | Example # | R$_t$ min (Table 1, Method) | m/z (M + H)$^+$ | TNF IC$_{50}$ |
|---|---|---|---|---|---|
| (1-((4,4-Difluorocyclohexyl)methyl)-2-oxo-1,2-dihydropyridin-4-yl)boronic acid | | AW.1 | 0.71 (i) | 461 | B |
| 1-(2-Methoxyethyl)-4-(4,4,5,5-tetramethyl-1,3,2-dioxaborolan-2-yl)pyridin-2(1H)-one | | AW.2 | 0.59 (i) | 387 | B |
| (2-Oxo-1-((tetrahydro-2H-pyran-4-yl)methyl)-1,2-dihydropyridin-4-yl)boronic acid | | AW.3 | 0.60 (i) | 427 | B |
| (2-Oxo-1-(tetrahydrofuran-3-yl)-1,2-dihydropyridin-4-yl)boronic acid | | AW.4 | 0.59 (i) | 378 | B |

TABLE AW-continued

| Boronic acid/boronate | Product | Example # | R, min (Table 1, Method) | m/z (M + H)+ | TNF IC50 |
|---|---|---|---|---|---|
| 1-(Tetrahydro-2H-pyran-4-yl)-4-(4,4,5,5-tetramethyl-1,3,2-dioxaborolan-2-yl)pyridin-2(1H)-one | | AW.5 | 0.59 (i) | 413 | C |
| 1-(Tetrahydro-2H-pyran-4-yl)-4-(4,4,5,5-tetramethyl-1,3,2-dioxaborolan-2-yl)-1H-pyrazole | | AW.6 | 0.72 (i) | 386 | B |

Example #54

4-((4-(6',8'-dihydro-2H-spiro[benzofuran-3,9'-pyrido[3',2':4,5]imidazo[2,1-c][1,4]oxazin]-2'-yl)pyridin-2-yl)oxy)cyclohexanol

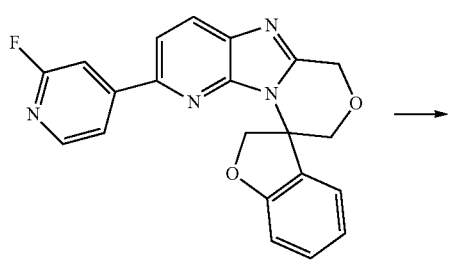

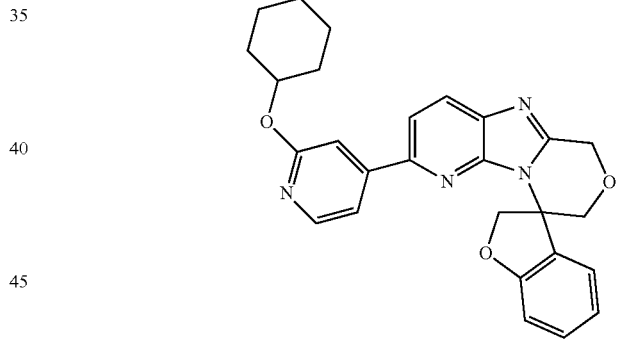

A microwave vial was charged with cyclohexane-1,4-diol (0.186 g, 1.603 mmol) and DMF (3 mL), next NaH (0.075 g, 1.870 mmol) was added and reaction stirred at rt for about 10 min then 2'-(2-fluoropyridin-4-yl)-6',8'-dihydro-2H-spiro[benzofuran-3,9'-pyrido[3',2':4,5]imidazo[2,1-c][1,4]oxazine](0.2 g, 0.534 mmol, Preparation #87) was added and vial was irradiated for about 45 min at about 120° C. Reaction quenched with slow addition of water and extracted with DCM (30 mL), organic washed with water and brine and dried over MgSO$_4$, then filtered and evaporated under reduced pressure to give a residue. The residue was purified on silica gel chromatography (0-15% MeOH/DCM over 25 min) to give the title compound (0.095 g, 35%). LC/MS (Table 1, Method i) R$_f$=0.78 min; MS m/z: 471 (M+H)$^+$. (TNF IC$_{50}$=A).

TABLE AX

| Alcohol | Product | Example # | R$_t$ min (Table 1, Method) | m/z (M + H)$^+$ | TNF IC$_{50}$ |
|---|---|---|---|---|---|
| trans-1,4-Cyclohexane-diol | | AX.1 | 0.78 (i) | 471 | A |
| cis-1,4-Cyclohexane-diol | | AX.2 | 0.78 (i) | 471 | B |
| 1,3-Cyclo-pentanediol | | AX.3 | 0.78 (i) | 457 | A |

The compounds shown in Table AX were synthesized in a manner similar to Example #54 from the corresponding alcohol.

Example #55

(R)-1-(5-(3-fluoro-8-phenyl-7,8-dihydro-6H-pyrrolo[2',1':2,3]imidazo[4,5-b]pyridin-2-yl)pyrimidin-2-yl)piperidin-4-ol

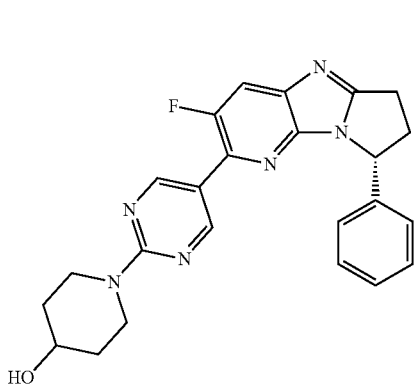 [SMILES: OC1CCN(c2ncc(-c3nc4c(cc3F)nc3n4[C@@H](c4ccccc4)CC3)cn2)CC1]

A round-bottom flask under nitrogen was charged with 1-(5-bromopyrimidin-2-yl)-4-piperidinol (0.525 g, 2.033 mmol, ArkPharm), bis(pinacolato)diboron (0.715 g, 2.82 mmol), 1,1'-bis(diphenylphosphino)-ferrocene-palladium(II)dichloride-dichloromethane complex (0.128 g, 0.156 mmol) and KOAc (0.460 g, 4.69 mmol) next anhydrous 1,4-dioxane (10 mL) was added and mixture was degassed for 10 min, next the flask was heated to 95° C. in an oil bath for 2.5 h. Next the flask was cooled to rt and (R)-2-chloro-3-fluoro-8-phenyl-7,8-dihydro-6H-pyrrolo[2',1':2,3]imidazo[4,5-b]pyridine (0.45 g, 1.564 mmol, Preparation #88), $Cs_2CO_3$ (1.274 g, 3.91 mmol) and bis(triphenylphosphine)palladium(II)dichloride (0.110 g, 0.156 mmol) were added next 1,4-dioxane (1 mL) and water (3.00 mL) were added and reaction mixture was degased with nitrogen for 10 min and heated in an oil bath at 95° C. After 15 h, reaction was cooled to rt and diluted with EtOAc (70 mL) and filtered over a pad of Celite® then the organic was washed with a saturated solution of sodium bicarbonate, water and brine, next organic was dried over $MgSO_4$, filtered and evaporated under reduced pressure. The residue was purified on silica gel chromatography using a gradient of DCM to 10% of MeOH over 30 min to give a solid. LC/MS (Table 1, Method i) $R_t$=0.78 min; MS m/z: 431 (M+H)$^+$, (TNF $IC_{50}$=A).

Example #56

2-(2-morpholinopyrimidin-5-yl)-9-phenyl-7,9-dihydro-6H-pyrano[4',3':4,5]imidazo[1,2-b]pyridazine

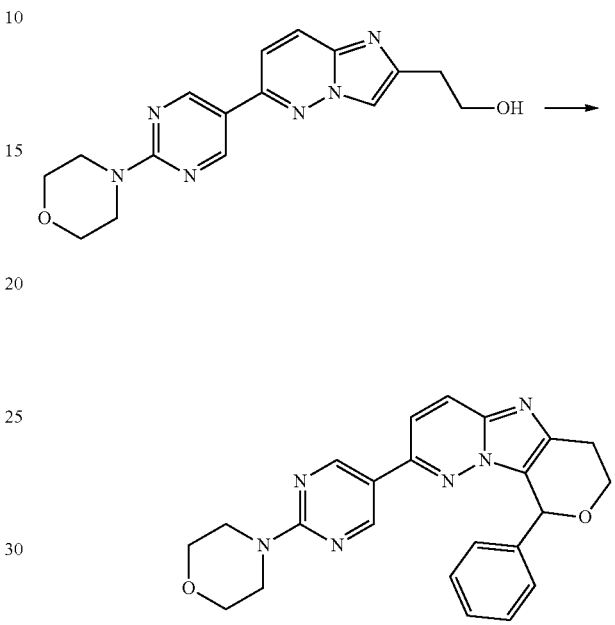

To a solution of 2-(6-(2-morpholinopyrimidin-5-yl)imidazo[1,2-b]pyridazin-2-yl)ethanol (Preparation #89, 0.076 g, 0.233 mmol) in MeCN (5 mL), p-toluenemethanesulfonic acid monohydrate (0.022 g, 0.116 mmol) and (dimethoxymethyl)benzene (0.078 g, 0.512 mmol) were added and the reaction mixture heated at 90° C. for 4 h. The reaction was cooled and diluted with sat. $NaHCO_3$ and extracted with DCM (3×10 mL). The combined organics were washed with brine, dried over $MgSO_4$, filtered and concentrated under reduced pressure. The residue was purified by column chromatography on silica gel eluting with a gradient of 0-10% MeOH/DCM to give a light green solid (37 mg, 38%). LC/MS (Table 1, Method i) $R_t$=0.88 min; MS m/z: 415 (M+H)$^+$ (TNF $IC_{50}$=B).

TABLE AY

| Ketal | Product | Example # | $R_t$ min (Table 1, Method) | m/z (M + H)$^+$ | TNF $IC_{50}$ |
|---|---|---|---|---|---|
| 1,1-Dimethoxy-cyclohexane | | AY.1 | 0.86 (i) | 407 | B |

TABLE AY-continued

| Ketal | Product | Example # | R$_t$ min (Table 1, Method) | m/z (M + H)$^+$ | TNF IC$_{50}$ |
|---|---|---|---|---|---|
| 4,4-Dimethoxy-chromane | 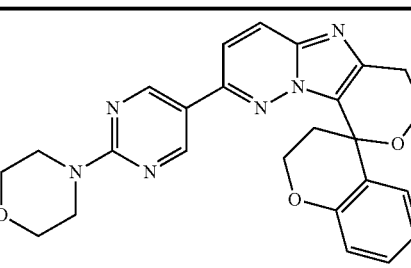 | AY.2 | 0.84 (i) | 457 | A |

The compounds shown in Table AY were synthesized in a manner similar to Example #56 from the corresponding ketals. The ketals were synthesized in a manner similar to the following preparation unless commercially available.

Ketal Preparation: p-Toluenesulfonic acid monohydrate (0.024 g, 0.125 mmol) was added at once to a solution of 3-phenylcyclopentanone (0.20 g, 1.248 mmol) and trimethyl orthoformate (0.479 mL, 4.37 mmol) in anhydrous MeOH (5 mL) reaction stirred at rt for 12 h. The reaction was diluted with DCM (25 mL) and washed with sat. NaHCO$_3$, then brine, the organic dried over MgSO$_4$, filtered and concentrated under reduced pressure. The crude ketal was used as is in the synthesis of compounds of Table AY.

Example #57 trans-4-((4-(4-(2-Methoxyphenyl)-3,4-dihydro-2H-pyrano[2',3':4,5]imidazo[1,2-a]pyridin-7-yl)pyridin-2-yl)oxy)cyclohexanol

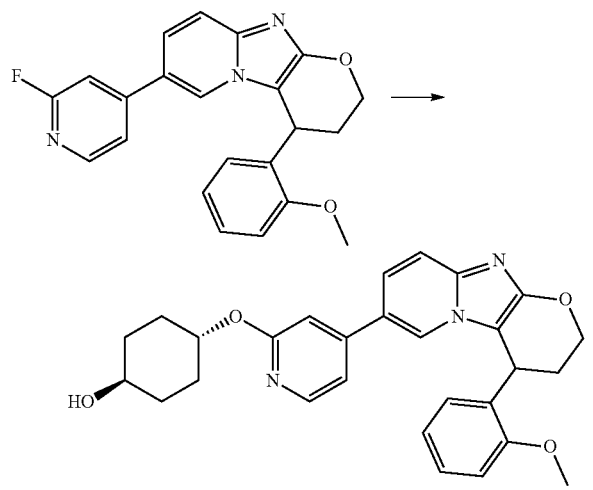

A 5 mL microwave vial was charged with 60% sodium hydride (70 mg, 1.750 mmol) and trans-1,4-cyclohexanediol (180 mg, 1.550 mmol), purged with nitrogen, added DMF (2 mL), and stirred the mixture for 10 min at ambient temperature. A solution of 7-(2-fluoropyridin-4-yl)-4-(2-methoxyphenyl)-3,4-dihydro-2H-pyrano[2',3':4,5]imidazo[1,2-a]pyridine (151 mg, 0.402 mmol, Preparation #93) in DMF (2 mL) was added, and heated at 120° C. for 105 min. Quenched with water (50 mL), extracted twice with EtOAc, washed with 10 mL brine, and dried over Na$_2$SO$_4$. Chromatographed on a Grace Reveleris 24 g column, eluted with 0-100% 3:1 EtOAc:EtOH in 1:1 DCM:Heptane (30 mL/min), affording the title compound (83.4 mg, 44.0%); $^1$H NMR (400 MHz, DMSO-d$_6$) δ 8.09 (dd, J=5.4, 0.6 Hz, 1H), 7.93 (dd, J=1.9, 1.0 Hz, 1H), 7.54 (dd, J=9.3, 1.8 Hz, 1H), 7.50 (dd, J=9.3, 1.0 Hz, 1H), 7.21 (ddd, J=8.2, 7.4, 1.7 Hz, 1H), 7.09-7.02 (m, 2H), 6.90 (dd, J=1.6, 0.8 Hz, 1H), 6.73 (td, J=7.5, 1.1 Hz, 1H), 6.44 (dd, J=7.6, 1.7 Hz, 1H), 4.95-4.85 (m, 1H), 4.82 (dd, J=6.2, 3.5 Hz, 1H), 4.54 (d, J=4.2 Hz, 1H), 4.25 (ddd, J=11.2, 4.8, 3.2 Hz, 1H), 3.95 (td, J=11.0, 2.1 Hz, 1H), 3.87 (s, 3H), 3.52-3.42 (m, 1H), 2.42-2.31 (m, 1H), 2.09-2.02 (m, 1H), 2.02-1.93 (m, 2H), 1.84-1.75 (m, 2H), 1.46-1.32 (m, 2H), 1.32-1.18 (m, 2H). MS (ESI+) m/z 472 (M+H). LC/MS (Table 1, ab) R$_t$=0.86 min; MS m/z: 472 (M+H)$^+$ (TNF IC$_{50}$=A).

Example #58

(8aS)-7-(5-(9-Phenyl-8,9-dihydro-6H-pyrido[3',2':4,5]imidazo[2,1-c][1,4]oxazin-2-yl)pyrimidin-2-yl)hexahydroimidazo[1,5-a]pyrazin-3(2H)-one

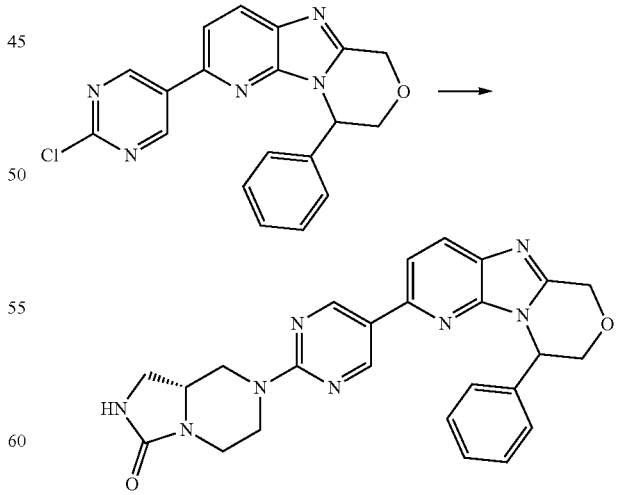

2-(2-Chloropyrimidin-5-yl)-9-phenyl-8,9-dihydro-6H-pyrido[3',2':4,5]imidazo[2,1-c][1,4]oxazine (35 mg, 0.096 mmol, Preparation #96) and (S)-hexahydroimidazo[1,5-a]pyrazin-3(2H)-one (14 mg, 0.096 mmol, Preparation #41)

were mixed in EtOH (0.25 mL), and TEA (0.19 mmol, 0.027 mL) was added. The reaction was heated to 95° C. for 2 h before being concentrated. The crude residue was dissolved in MeOH, filtered and purified by reverse phase chromatography eluting with 5-100% MeCN/0.1% NH$_4$OAc in H$_2$O over 10 min to yield the title compound (1.2 mg, 2.7%); LC/MS (Table 1, method ah) R$_t$=4.44 min; MS m/z: 469 (M+H)$^+$. (TNF IC$_{50}$=A).

The compounds shown in Table AZ were synthesized in a manner similar to Example #58 from the corresponding amine.

TABLE AZ

| Amine | Product | Example # | R$_t$ min (Table 1, Method) | m/z (M + H)$^+$ | TNF IC$_{50}$ |
|---|---|---|---|---|---|
| 3,3-Difluoro-piperidin-4-ol | | AZ.1 | 5.37 (ah) | 465 | A |
| Piperidin-4-ol | | AZ.2 | 4.42 (ah) | 429 | A |
| 1,4-Oxazepane | | AZ.3 | 5.12 (ah) | 429 | B |
| Piperidin-3-ylmethanol | | AZ.4 | 4.81 (ah) | 443 | A |
| (4-Fluoro-piperidin-4-yl)methanol | | AZ.5 | 4.67 (ah) | 461 | A |

TABLE AZ-continued

| Amine | Product | Example # | R, min (Table 1, Method) | m/z (M + H)+ | TNF IC50 |
|---|---|---|---|---|---|
| 2-Hydroxy-1-(piperazin-1-yl)propan-1-one | | AZ.6 | 4.42 (ah) | 486 | B |
| 2-Hydroxy-1-(piperazin-1-yl)ethan-1-one | | AZ.7 | 4.31 (ah) | 472 | A |

Example #59

2'-(2-(Piperazin-1-yl)pyrimidin-5-yl)-6'H,8'H-spiro[chromane-4,9'-pyrido[3',2':4,5]imidazo[2,1-c][1,4]oxazine]

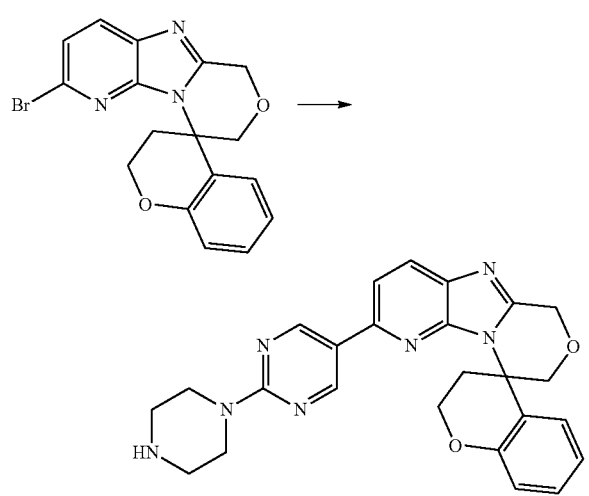

In a 4 mL vial was mixed 4,4,4',4',5,5,5',5'-octamethyl-2,2'-bi(1,3,2-dioxaborolane) (63 mg, 0.25 mmol), 5-bromo-2-(piperazin-1-yl)pyrimidine (45 mg, 0.19 mmol), Pd(Cl$_2$)dppf (18 mg, 0.025) and KOAc (41 mg, 0.42 mmol) in 1,4-dioxane (0.7 mL). The reaction was purged with N$_2$ for a few minutes and then stirred at 95° C. for 2 h before being cooled to rt. 2'-bromo-6'H,8'H-spiro[chromane-4,9'-pyrido[3',2':4,5]imidazo[2,1-c][1,4]oxazine](31 mg, 0.087 mmol, Preparation #86), PdCl$_2$(PPh$_3$)$_2$(5.8 mg, 0.0087 mmol) and Cs$_2$CO$_3$ (67 mg, 0.22 mmol) were added to the reaction mixture. 1.4-Dioxane (0.15 mL) and H$_2$O (0.22 mL) were added. The reaction was purged with N$_2$ for a few minutes and stirred at 85° C. for 18 h before being cooled to rt, filtered and concentrated. The residue was dissolved in 1:1 MeOH/DMSO and purified by reverse phase chromatography using a gradient of MeCN (A) and 0.1% TFA in water (B) at a flow rate of 50 mL/min (0-0.5 min 5% A, 0.5-8.5 min linear gradient 05-100% A, 8.7-10.7 min 100% A, 10.7-11 min linear gradient 100-05% A) to yield the title compound. (17 mg, 18%); LC/MS (Table 1, method ai) R$_t$=0.52 min; MS m/z: 456 (M+H)+. (TNF IC$_{50}$=B).

The compounds shown in Table BA were synthesized in a manner similar to Example #59 from the corresponding bromide.

TABLE BA

| Bromide | Product | Example # | R_t min (Table 1, Method) | m/z (M + H)+ | TNF IC_{50} |
|---|---|---|---|---|---|
| 5-Bromo-2-methoxy-pyrimidine | | BA.1 | 0.62 (ai) | 402 | B |
| 5-Bromo-2-ethoxy-pyrimidine | | BA.2 | 0.69 (ai) | 416 | A |
| 5-Bromo-2-(methylsulfonyl)pyrimidine | | BA.3 | 0.63 (ai) | 450 | B |
| 1-(5-Bromopyrimidin-2-yl)-1,4-diazepane | | BA.4 | 0.52 (ai) | 470 | B |
| 5-Bromo-N-isopropyl-pyrimidn-2-amine | | BA.5 | 0.65 (ai) | 429 | B |
| 4-(5-Bromopyrimidin-2-yl)morpholine | | BA.6 | 0.64 (ai) | 457 | A |

TABLE BA-continued

| Bromide | Product | Example # | R$_t$ min (Table 1, Method) | m/z (M + H)$^+$ | TNF IC$_{50}$ |
|---|---|---|---|---|---|
| 2-(5-Bromopyrimidin-2-yl)propan-2-ol | | BA.7 | 0.65 (ai) | 430 | B |
| 4-Bromo-2-((tetrahydro-2H-pyran-4-yl)oxy)pyridine | | BA.8 | 0.66 (ai) | 471 | A |

Example #60

5-(6'H,8'H-Spiro[chromane-4,9'-pyrido[3',2':4,5]imidazo[2,1-c][1,4]oxazin]-2'-yl)-N-(tetrahydrofuran-3-yl)pyrimidin-2-amine

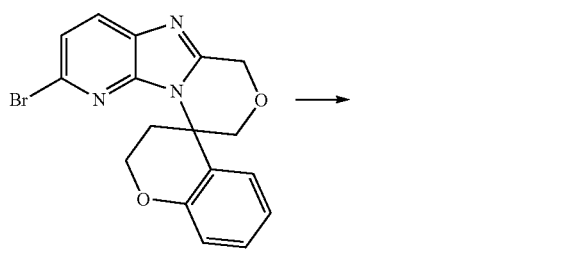

In a 4 mL vial was mixed the 2-chloro-5-(4,4,5,5-tetramethyl-1,3,2-dioxaborolan-2-yl)pyrimidine (61 mg, 0.25 mmol), tetrahydrofuran-3-amine (22 mg, 0.25 mmol) and TEA (46 uL, 0.36 mmol) in EtOH (0.3 mL). The reaction was heated to 95° C. for 2 h before being cooled and concentrated. To the crude residue was added the 2'-bromo-6'H,8'H-spiro[chromane-4,9'-pyrido[3',2':4,5]imidazo[2,1-c][1,4]oxazine](39 mg, 0.10 mmol, Preparation #86), Pd$_2$(dba)$_3$ (9.6 mg, 0.010 mmol), 1,3,5,7-Tetramethyl-2,4,8-trioxa-6-phospha-adamantane (6.1 mg, 0.020 mmol) and Cs$_2$CO$_3$ (74.8 mg, 0.25 mmol). THF (1 mL) and H$_2$O (0.25 mL) were added, and the reaction was stirred at 60° C. for 18 h before being cooled to rt and concentrated. The residue was dissolved in 1:1 MeOH/DMSO and purified by reverse phase chromatography using a gradient of MeCN (A) and 0.1% TFA in H$_2$O (B) at a flow rate of 50 mL/min (0-0.5 min 5% A, 0.5-8.5 min linear gradient 05-100% A, 8.7-10.7 min 100% A, 10.7-11 min linear gradient 100-05% A) to yield the title compound. (39 mg, 33%); LC/MS (Table 1, method ai) R$_t$=0.61 min; MS m/z: 457 (M+H)$^+$. (TNF IC$_{50}$=B).

The compounds shown in Table BB were synthesized in a manner similar to Example #60 from the corresponding amine.

TABLE BB

| Amine | Product | Example # | R$_t$ min (Table 1, Method) | m/z (M + H)$^+$ | TNF IC$_{50}$ |
|---|---|---|---|---|---|
| (S)-Hexahydro-imidazo[1,5-a]pyrazin-3(2H)-one (Preparation #41) | | BB.1 | 0.62 (ai) | 511 | A |
| Piperidin-4-ol | | BB.2 | 0.54 (ai) | 471 | A |
| Piperidin-3-ol | | BB.3 | 0.60 (ai) | 471 | A |
| Azetidin-3-ol | | BB.4 | 0.55 (ai) | 443 | A |
| Pyrrolidin-3-ol | | BB.5 | 0.56 (ai) | 457 | A |
| 3-Aminocyclo-butan-1-ol | | BB.6 | 0.56 (ai) | 457 | B |

TABLE BB-continued

| Amine | Product | Example # | R$_t$ min (Table 1, Method) | m/z (M + H)$^+$ | TNF IC$_{50}$ |
|---|---|---|---|---|---|
| 3-Methyl-azetidin-3-ol | | BB.7 | 0.57 (ai) | 457 | B |
| 1-Methyl-piperazine | | BB.8 | 0.54 (ai) | 470 | B |

Example #61

(R)-8-Phenyl-2-(2-(((tetrahydro-2H-pyran-4-yl)methoxy)pyridin-4-yl)-7,8-dihydro-6H-pyrrolo[2',1':2,3]imidazo[4,5-b]pyridine

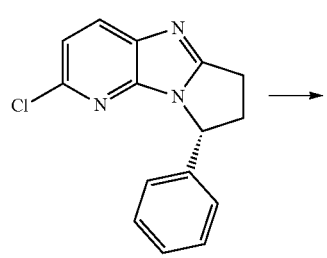

→

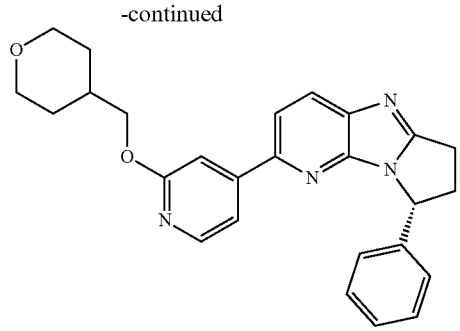

4,4,4',4',5,5,5',5'-octamethyl-2,2'-bi(1,3,2-dioxaborolane) (34 mg, 0.13 mmol), 4-bromo-2-((tetrahydro-2H-pyran-4-yl)methoxy)pyridine (28 mg, 0.10 mmol), Pd(Cl)$_2$dppf (8.4 mg, 0.01 mmol) and KOAc (33.4, 0.32 mmol) were mixed in 1,4-dioxane (0.2 mL) and stirred at 95° C. for 2 h. The reaction was cooled to rt. (R)-2-chloro-8-phenyl-7,8-dihydro-6H-pyrrolo[2',1':2,3]imidazo[4,5-b]pyridine (22 mg, 0.088 mmol, Preparation #81), Pd(Cl)$_2$(PPh$_3$)$_2$ (6.1 mg, 0.0192 mmol) and Cs$_2$CO$_3$ (68 mg, 0.22 mmol) were added. 1,4-Dioxane (0.3 mL) and H$_2$O (0.2 mL) were added, and the reaction was heated to 85° C. for 18 h before being cooled to rt and concentrated. The residue was dissolved in 1:1 MeOH/DMSO and purified by reverse phase chromatography using a gradient of MeCN (A) and 0.1% TFA in H$_2$O (B) at a flow rate of 50 mL/min (0-0.5 min 5% A, 0.5-8.5 min linear gradient 05-100% A, 8.7-10.7 min 100% A, 10.7-11 min linear gradient 100-05% A) to yield the title compound. (4.9 mg, 9.4%); LC/MS (Table 1, method ai) R$_t$=0.65 min; MS m/z: 427 (M+H)$^+$. (TNF IC$_{50}$=B).

The compounds shown in Table BC were synthesized in a manner similar to Example #61 from the corresponding bromide.

TABLE BC

| Bromide | Product | Example # | R$_t$ min (Table 1, Method) | m/z (M + H)$^+$ | TNF IC$_{50}$ |
|---|---|---|---|---|---|
| 4-Bromo-2-(2-methoxyethoxy)pyridine | | BC.1 | 0.61 (ai) | 387 | B |
| 1-((4-Bromopyridin-2-yl)oxy)-2-methylpropan-2-ol | | BC.2 | 0.60 (ai) | 401 | B |

Example #62

(R)-8-Phenyl-2-(1,2,3,6-tetrahydropyridin-4-yl)-7,8-dihydro-6H-pyrrolo [2',1':2,3]imidazo[4,5-b]pyridine

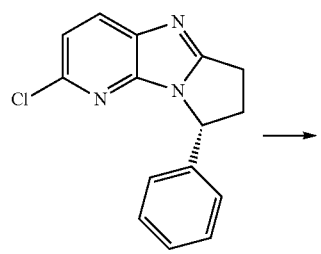

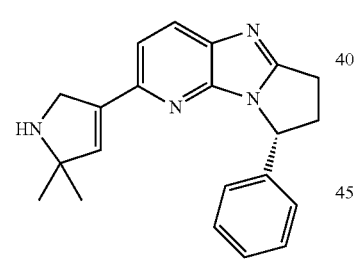

(R)-2-Chloro-8-phenyl-7,8-dihydro-6H-pyrrolo[2',1':2,3]imidazo[4,5-b]pyridine (25 mg, 0.061 mmol, Preparation #81), tert-butyl 2,2-dimethyl-4-(4,4,5,5-tetramethyl-1,3,2-dioxaborolan-2-yl)-2,5-dihydro-1H-pyrrole-1-carboxylate (31 mg, 0.11 mmol), PdCl$_2$dppf (11 mg, 0.013 mmol) and Cs$_2$CO$_3$ (52 mg, 0.13 mmol) were mixed in a vial and purged with N$_2$. THF (0.5 mL) was added, and the reaction was stirred at 65° C. for 18 h before being cooled. The crude reaction mixture was concentrated, and TFA (0.020 mL, 0.19 mmol) and DCM (0.25 mL) were added. The reaction was stirred for 1 h at rt before being concentrated. The crude residue was dissolved in 1:1 MeOH/DMSO and purified by reverse phase chromatography eluting with 5-100% MeCN/H$_2$O (with 0.1% TFA) over 10 min to yield the title compound (1.5 mg, 6%); LC/MS (Table 1, method ag) R$_t$=2.67 min; MS m/z: 331 (M+H)$^+$. (TNF IC$_{50}$=C).

Example #63

2-(5-(9-Phenyl-6,7,8,9-tetrahydro-6,8-methanoimidazo[1,2-a:5,4-b']dipyridin-2-yl)pyrimidin-2-yl)propan-2-ol

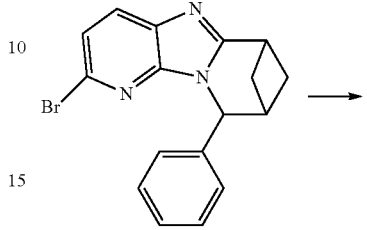

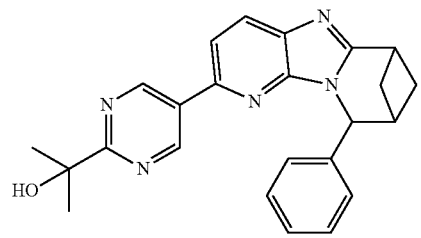

In a 20 mL vial was mixed 2-(5-bromopyrimidin-2-yl)propan-2-ol (34 mg, 0.15 mmol), 4,4,4',4',5,5,5',5'-octamethyl-2,2'-bi(1,3,2-dioxaborolane) (52 mg, 0.21 mmol), PdCl$_2$dppf (11 mg, 0.015 mmol) and KOAc (33 mg, 0.34 mmol) in 1,4-dioxane (0.69 mL) to give a suspension. The reaction was purged with N$_2$. The reaction was stirred at 95° C. for 2 h. The reaction was cooled to rt. 2-Bromo-9-phenyl-6,7,8,9-tetrahydro-6,8-methanoimidazo[1,2-a:5,4-b']dipyridine (35 mg, 0.11 mmol, Preparation #95) and PdCl$_2$(PPh$_3$)$_2$ (7.2 mg, 0.011 mmol) and cesium carbonate (84 mg, 0.26 mmol) were added in 1,4-dioxane (0.12 mL) and H$_2$O (0.18 mL). The reaction was purged with N$_2$, and the mixture was heated to 85° C. for 18 h. The reaction mixture was cooled and concentrated. The crude residue was dissolved in 1:1 MeOH/DMSO and purified by reverse phase chromatography eluting with 5-100% MeCN/H$_2$O with 0.1% TFA over 10 min to yield the title compound (39 mg, 96%); LC/MS (Table 1, method ag) R$_t$=3.91 min; MS m/z: 398 (M+H)$^+$. (TNF IC$_{50}$=B).

The compound shown in Table BD was synthesized in a manner similar to Example #63 from the corresponding bromide.

TABLE BD

| Bromide | Product | Example # | R_t min (Table 1, Method) | m/z (M + H)+ | TNF IC50 |
|---|---|---|---|---|---|
| 4-Bromo-2-((tetrahydro-2H-pyran-4-yl)oxy)pyridine | | BD.1 | 4.58 (ag) | 439 | B |

Example #64

1-(5-(9-Phenyl-6,7,8,9-tetrahydro-6,8-methanoimidazo[1,2-a:5,4-b']dipyridin-2-yl)pyrimidin-2-yl)piperidin-4-ol

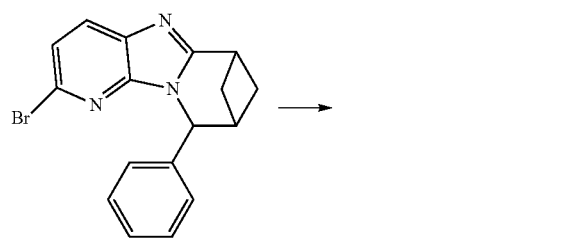

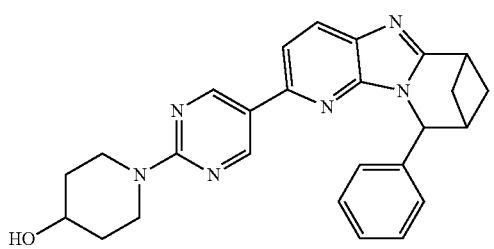

In a 4 mL vial was mixed piperidin-4-ol (26 mg, 0.26 mmol), 2-chloro-5-(4,4,5,5-tetramethyl-1,3,2-dioxaborolan-2-yl)pyrimidine (62 mg, 0.26 mmol) and TEA (0.082 mL, 0.34 mmol) in EtOH (0.30 mL) to give an orange solution. The reaction was heated to 95° C. for 2 h. The reaction was concentrated. To the crude residue was added 2-bromo-9-phenyl-6,7,8,9-tetrahydro-6,8-methanoimidazo[1,2-a:5,4-b']dipyridine (35 mg, 0.11 mmol, Preparation #95), Pd$_2$(dba)$_3$ (9.4 mg, 0.011 mmol), (1S,3R,5R,7S)-1,3,5,7-tetramethyl-8-phenyl-2,4,6-trioxa-8-phosphaadamantane (6.1 mg, 0.021 mmol) and cesium carbonate (74 mg, 0.23 mmol). THF (1 mL) and H$_2$O (0.25 mL) were added, and the reaction was stirred at 60° C. for 18 h. The reaction mixture was cooled and concentrated. The crude residue was dissolved in 1:1 MeOH/DMSO and purified by reverse phase chromatography eluting with 5-100% MeCN/H$_2$O with 0.1% TFA over 10 min to yield the title compound (8.9 mg, 19%); LC/MS (Table 1, method ag) R$_t$=3.62 min; MS m/z: 439 (M+H)+. (TNF IC$_{50}$=B).

The compound shown in Table BE was synthesized in a manner similar to Example #64 from the corresponding amine.

TABLE BE

| Amine | Product | Example # | R_t min (Table 1, Method) | m/z (M + H)+ | TNF IC50 |
|---|---|---|---|---|---|
| Morpholine | | BE.1 | 4.13 (ag) | 425 | B |

Example #65

2'-(5,5-Dimethyl-2,5-dihydro-1H-pyrrol-3-yl)-6',8'-dihydro-2H-spiro[benzofuran-3,9'-pyrido[3',2':4,5]imidazo[2,1-c][1,4]oxazine]

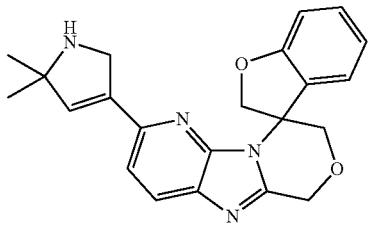 [SMILES: CC1(C)C=C(c2ccc3nc4n(c3n2)C2(COC4)COc3ccccc32)CN1]

2'-Bromo-6',8'-dihydrospiro[chroman-4,9'-pyrido[3',2':4,5]imidazo[2,1-c][1,4]oxazine](15 mg, 0.043 mmol, Preparation #85), tert-butyl 2,2-dimethyl-4-(4,4,5,5-tetramethyl-1,3,2-dioxaborolan-2-yl)-2,5-dihydro-1H-pyrrole-1-carboxylate (16 mg, 0.051 mmol), $PdCl_2dppf$ (5.5 mg, 0.0069 mmol) and $Cs_2CO_3$ (27 mg, 0.067 mmol) were mixed in a 4 mL vial. The reaction was purged with $N_2$, and THF was added.

The reaction was heated to 65° C. for 18 h. The reaction was cooled to rt and concentrated. The crude residue was dissolved in 1:1 TFA/DCM (0.25 mL each). The reaction was stirred at rt for 1 h before being concentrated. The crude residue was dissolved in 1:1 MeOH/DMSO and purified by reverse phase chromatography eluting with 5-100% MeCN/$H_2O$ with 0.1% TFA over 10 min to yield the title compound (7.9 mg, 67%); LC/MS (Table 1, method ag) $R_t$=3.10 min; MS m/z: 375 (M+H)$^+$. (TNF $IC_{50}$=B).

The compounds shown in Table BF were synthesized in a manner similar to Example #65 from the corresponding boronic ester.

TABLE BF

| Boronic ester | Product | Example # | $R_t$ min (Table 1, Method) | m/z (M + H)$^+$ | TNF $IC_{50}$ |
|---|---|---|---|---|---|
| tert-Butyl 3-(4,4,5,5-tetramethyl-1,3,2-dioxaborolan-2-yl)-2,5-dihydro-1H-pyrrole-1-carboxylate | | BF.1 | 2.87 (ag) | 347 | B |
| tert-Butyl methyl(2-oxo-2-(4-(4,4,5,5-tetramethyl-1,3,2-dioxaborolan-2-yl)-3,6-Dihydropyridin-1(2H)-yl)ethyl)carbamate | | BF.2 | 3.02 (ag) | 432 | B |

Example #66

2'-(2-(Piperazin-1-yl)pyrimidin-5-yl)-2H,6'H,8'H-spiro[benzofuran-3,9'-pyrido[3',2':4,5]imidazo[2,1-c][1,4]oxazine]

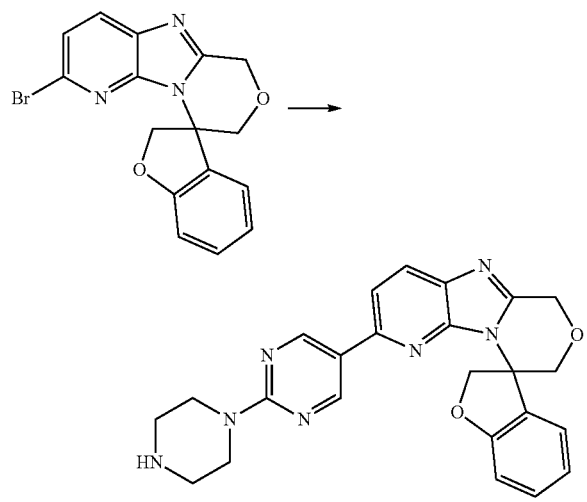

In a 4 mL vial was mixed the 4,4,4',4',5,5,5',5'-octamethyl-2,2'-bi(1,3,2-dioxaborolane) (36 mg, 0.14 mmol), 5-bromo-2-(piperazin-1-yl)pyrimidine (26 mg, 0.11 mmol), PdCl$_2$dppf (15.6 mg, 0.026 mmol) and KOAc (46 mg, 0.56 mmol). 1,4-dioxane (0.5 mL) was added, and the reaction was purged with nitrogen. After being stirred at 95° C. for 2 h, the reaction was cooled to rt. 2'-bromo-6',8'-dihydrospiro[chroman-4,9'-pyrido[3',2':4,5]imidazo[2,1-c][1,4]oxazine](31 mg, 0.088 mmol, Preparation #85), PdCl$_2$(PPh$_3$)$_2$ (6.2 mg, 0.0089 mmol) and Cs$_2$CO$_3$ (72 mg, 0.27 mmol) were added. 1,4-dioxane (0.15 mL) and H$_2$O (0.2 mL) were added. The reaction was purged with N$_2$ and heated to 85° C. for 18 h before being cooled to rt and concentrated. The residue was dissolved in 1:1 MeOH/DMSO and purified by reverse phase chromatography using a gradient of MeCN (A) and 0.1% TFA in H$_2$O (B) at a flow rate of 50 mL/min (0-0.5 min 5% A, 0.5-8.5 min linear gradient 05-100% A, 8.7-10.7 min 100% A, 10.7-11 min linear gradient 100-05% A) to yield the title compound. (21 mg, 41%); LC/MS (Table 1, Method ai) R$_t$=0.53 min; MS m/z: 442 (M+H)$^+$. (TNF IC$_{50}$=B).

The compounds shown in Table BG were synthesized in a manner similar to Example #66 from the corresponding bromide.

TABLE BG

| Bromide | Product | Example # | R$_t$ min (Table 1, Method) | m/z (M + H)$^+$ | TNF IC$_{50}$ |
|---|---|---|---|---|---|
| 4-Bromo-2-((tetrahydro-2H-pyran-4-yl)oxy)pyridine | | BG.1 | 0.67 (ai) | 457 | B |
| 5-Bromo-2-methoxypyrimidine | | BG.2 | 0.66 (ai) | 388 | B |
| (S)-1-(4-(5-Bromopyrimidin-2-yl)-2-methylpiperazin-1-yl)-2-(tert-butoxy)ethan-1-one | | BG.3 | 0.74 (ai) | 570 | B |

TABLE BG-continued

| Bromide | Product | Example # | $R_t$ min (Table 1, Method) | m/z (M + H)+ | TNF IC$_{50}$ |
|---|---|---|---|---|---|
| (S)-1-(4-(5-Bromo-pyrimidin-2-yl)-3-methyl-piperazin-1-yl)-2-(tert-butoxy)ethan-1-one | 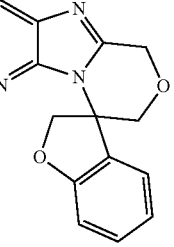 | BG.4 | 0.74 (ai) | 570 | B |
| (R)-1-(4-(5-Bromo-pyrimidin-2-yl)-3-methyl-piperazin-1-yl)-2-(tert-butoxy)ethan-1-one | 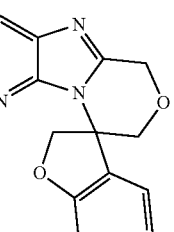 | BG.5 | 0.74 (ai) | 570 | B |
| (R)-1-(4-(5-Bromo-pyrimidin-2-yl)-2-methyl-piperazin-1-yl)-2-(tert-butoxy)ethan-1-one | 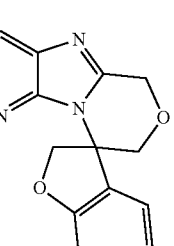 | BG.6 | 0.74 (ai) | 570 | A |

Example #67

1-((2S)-4-(5-(2H,6'H,8'H-Spiro[benzofuran-3,9'-pyrido[3',2':4,5]imidazo[2,1-c][1,4]oxazin]-2'-yl)pyrimidin-2-yl)-2-methylpiperazin-1-yl)-2-hydroxy-ethan-1-one

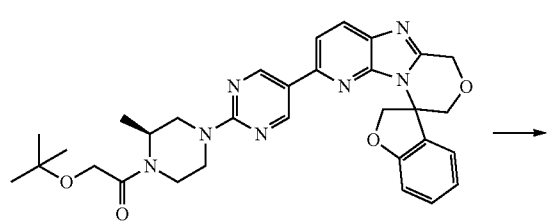

→

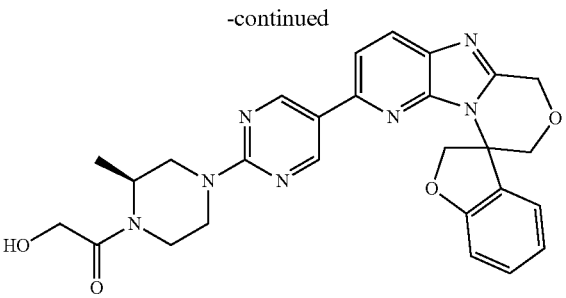

2-(tert-Butoxy)-1-((2S)-4-(5-(6',8'-dihydro-2H-spiro[benzofuran-3,9'-pyrido[3',2':4,5]imidazo[2,1-c][1,4]oxazin]-2'-yl)pyrimidin-2-yl)-2-methylpiperazin-1-yl)ethanone (21 mg, 0.035 mmol, Example #BG.3) was dissolved in DCM (0.35 mL) and TFA (0.35 mL) and stirred for 1 h at rt. The reaction was concentrated. The crude residue was dissolved in DMSO and purified by reverse phase chromatography eluting with 5-100% MeCN/H$_2$O (with 0.1% TFA) over 10 min to yield the title compound (8.9 mg, 49%); LC/MS (Table 1, method ag) R$_t$=4.06 min; MS m/z: 514 (M+H)+. (TNF IC$_{50}$=A).

The compounds shown in Table BH were synthesized in a manner similar to Example #67 from the corresponding ether.

TABLE BH

| Ether | Product | Example # | R$_t$ min (Table 1, Method) | m/z (M + H)$^+$ | TNF IC$_{50}$ |
|---|---|---|---|---|---|
| 1-((3S)-4-(5-(2H,6'H,8'H-Spiro[benzofuran-3,9'-pyrido[3',2':4,5]imidazo[2,1-c][1,4]oxazin]-2'-yl)pyrimidin-2-yl)-3-methylpiperazin-1-yl)-2-(tert-butoxy)ethan-1-one (Example #BG.4) | | BH.1 | 4.06 (ag) | 514 | A |
| 1-((3R)-4-(5-(2H,6'H,8'H-Spiro[benzofuran-3,9'-pyrido[3',2':4,5]imidazo[2,1-c][1,4]oxazin]-2'-yl)pyrimidin-2-yl)-3-methylpiperazin-1-yl)-2-(tert-butoxy)ethan-1-one (Example #BG.5) | | BH.2 | 4.06 (ag) | 514 | A |
| 1-((2R)-4-(5-(2H,6'H,8'H-Spiro[benzofuran-3,9'-pyrido[3',2':4,5]imidazo 2,1-c][1,4]oxazin]-2'-yl)pyrimidin-2-yl)-2-methylpiperazin-1-yl)-2-(tert-butoxy)ethan-1-one (Example #BG.6) | | BH.3 | 4.06 (ag) | 514 | A |

Example #68

2-(5-(2,3-Dihydro-6'H,8'H-spiro[indene-1,9'-pyrido[3',2':4,5]imidazo[2,1-c][1,4]oxazin]-2'-yl)pyrimidin-2-yl)propan-2-ol

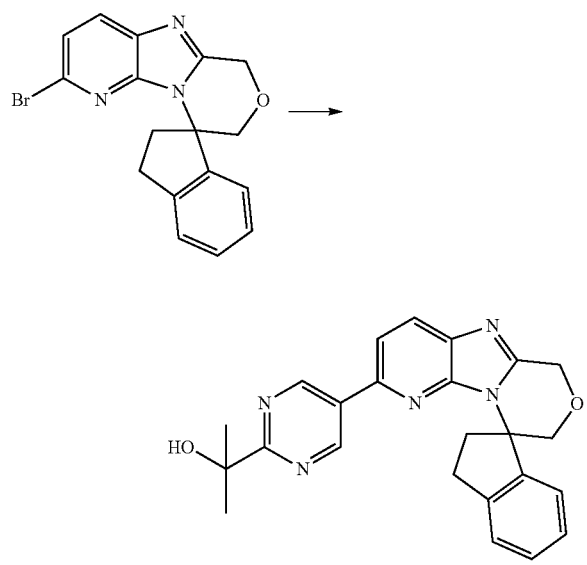 [SMILES: Brc1ccc2nc3n(c2n1)C1(CCc2ccccc21)COC3 ; CC(C)(O)c1ncc(-c2ccc3nc4n(c3n2)C2(CCc3ccccc32)COC4)cn1]

2-(5-Bromopyrimidin-2-yl)propan-2-ol (460 mg, 2.1 mmol), 4,4,4',4',5,5,5',5'-octamethyl-2,2'-bi(1,3,2-dioxaborolane) (710 mg, 2.8 mmol), Pd(Cl)$_2$dppf (110 mg, 0.14 mmol) and potassium acetate (460 mg, 4.6 mmol) were mixed in 1,4-dioxane (1.8 mL) to give an orange suspension. The reaction was purged with N$_2$. The reaction was stirred at 95° C. for 2 h. The reaction was cooled to rt. 2'-bromo-2,3,6',8'-tetrahydrospiro[indene-1,9'-pyrido[3',2':4,5]imidazo[2,1-c][1,4]oxazine](490 mg, 1.4 mmol, Preparation #92) and PdCl$_2$(PPh$_3$)$_2$(99 mg, 0.140 mmol) and cesium carbonate (1.1 g, 3.5 mmol) were added in 1,4-dioxane (1.9 mL) and H$_2$O (2.8 mL). The reaction was purged with N$_2$, and the mixture was heated to 85° C. for 18 h. The reaction mixture was cooled. H$_2$O (5 mL) was added, and the layers were separated. The aqueous layer was extracted with DCM (3×5 mL), and the combined organics were concentrated. The crude oil was purified (0-25% MeOH/CH$_2$Cl$_2$) to yield the title compound. (340 mg, 59%). LC/MS (Table 1, method g). R$_t$=0.82 min; MS m/z: 414 (M+H)$^+$. (TNF IC$_{50}$=A).

Example #69

2'-(2-(2-Hydroxypropan-2-yl)pyrimidin-5-yl)-6',8'-dihydrospiro[indene-1,9'-pyrido[3',2':4,5]imidazo[2,1-c][1,4]oxazin]-3(2H)-one

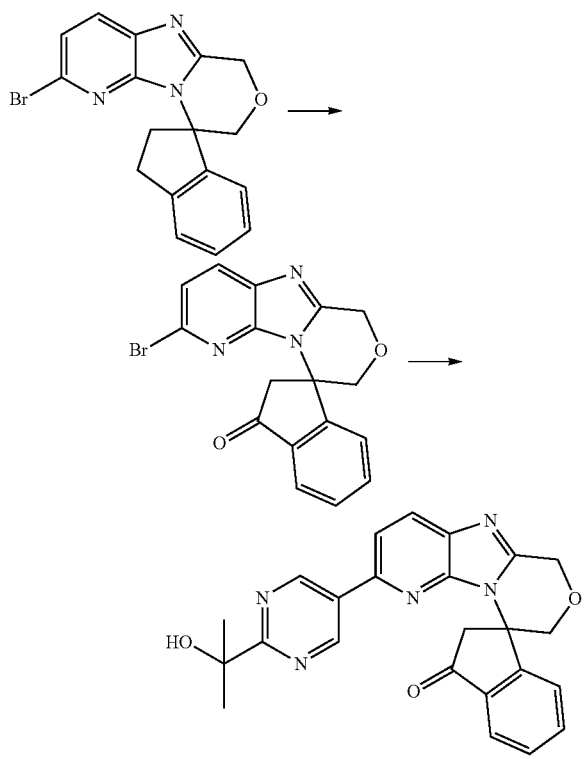

Step 1: 2'-Bromo-6',8'-dihydrospiro[indene-1,9'-pyrido[3',2':4,5]imidazo[2,1-c][1,4]oxazin]-3(2H)-one In a 4 mL vial was mixed 2'-bromo-2,3,6',8'-tetrahydrospiro[indene-1,9'-pyrido[3',2':4,5]imidazo[2,1-c][1,4]oxazine](150 mg, 0.42 mmol, Preparation #92) and potassium peroxydisulfate (170 mg, 0.63 mmol) in MeCN (2.1 mL) and $H_2O$ (2.1 mL) to give a colorless solution. 1-(chloromethyl)-4-fluoro-1,4-diazabicyclo[2.2.2]octane-1,4-diium tetrafluoroborate (220 mg, 0.63 mmol) was added, and the reaction was stirred at room temperature for 30 min before being heated to 80° C. for 18 h. The reaction was concentrated, and DCM (2 mL) and $H_2O$ (2 mL) were added. The aqueous layer was extracted with DCM (3×2 mL). The combined organics were filtered through a phase separator and concentrated. The reaction was purified (5-25% MeOH/$CH_2Cl_2$) to give the title compound (13.7 mg, 8.8%). LC/MS (Table 1, method g) $R_t$=0.73 min; MS m/z: 370, 372 $(M+H)^+$.

Step 2: 2'-(2-(2-Hydroxypropan-2-yl)pyrimidin-5-yl)-6',8'-dihydrospiro[indene-1,9'-pyrido[3',2':4,5]imidazo[2,1-c][1,4]oxazin]-3(2H)-one In a 4 mL vial was mixed 2-(5-bromopyrimidin-2-yl)propan-2-ol (5.5 mg, 0.026 mmol), 4,4,4',4',5,5,5',5'-octamethyl-2,2'-bi(1,3,2-dioxaborolane) (8.6 mg, 0.034 mmol), Pd(dppf)(Cl)$_2$ (1.8 mg, 0.0025 mmol) and KOAc (5.5 mg, 0.056 mmol) in 1,4-dioxane (0.23 mL). The reaction was purged with $N_2$. The reaction was stirred at 95° C. for 2 h before being cooled to rt. 2'-bromo-6',8'-dihydrospiro[indene-1,9'-pyrido[3',2':4,5]imidazo[2,1-c][1,4]oxazin]-3(2H)-one (6.3 mg, 0.017 mmol), PdCl$_2$(PPh$_3$)$_2$(1.8 mg, 0.0025 mmol) and Cs$_2$CO$_3$ (13 mg, 0.043 mmol) were added. 1,4-dioxane (0.23 mL) and water (68 µL) were added. The reaction was purged with $N_2$, and the mixture was heated to 85° C. for 18 h. The reaction was concentrated, dissolved in MeOH and filtered. The sample was purified by reverse phase chromatography (MeCN/0.1% TFA in $H_2O$, 5-100% over 10 min at 40 mL/min). LC/MS (Table 1, method g) $R_t$=0.70 min; MS m/z: 428 $(M+H)^+$. (TNF IC$_{50}$=B).

Example #70

2-(5-((6R,8S,9S)-9-Phenyl-6,7,8,9-tetrahydro-6,8-epoxyimidazo[1,2-a:5,4-b']dipyridin-2-yl)pyrimidin-2-yl)propan-2-ol

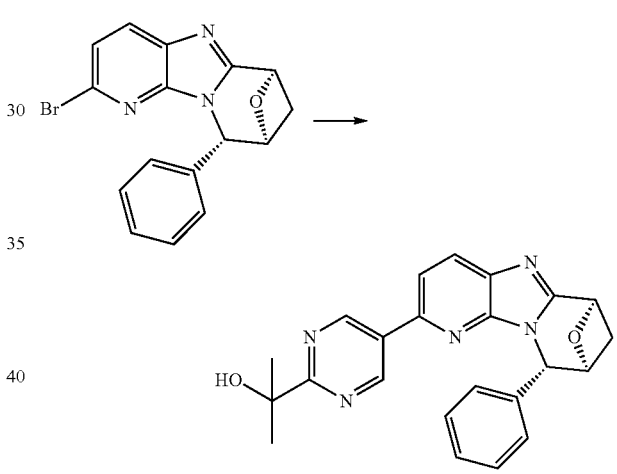

In a 20 mL vial was mixed 2-(5-bromopyrimidin-2-yl)propan-2-ol (19 mg, 0.088 mmol), 4,4,4',4',5,5,5',5'-octamethyl-2,2'-bi(1,3,2-dioxaborolane) (29 mg, 0.12 mmol), and Pd(Cl)$_2$dppf (4.3 mg, 0.0058 mmol) and KOAc (19 mg, 0.19 mmol) in 1,4-dioxane (0.39 mL) to give a black suspension. The reaction was purged with $N_2$. The reaction was stirred at 95° C. for 2 h. The reaction was cooled to rt. (6R,8S,9S)-2-bromo-9-phenyl-6,7,8,9-tetrahydro-6,8-epoxyimidazo[1,2-a:5,4-b']dipyridine (20 mg, 0.058 mmol, Preparation #94), PdCl$_2$(PPh$_3$)$_2$(4.1 mg, 0.0058 mmol) and Cs$_2$CO$_3$ (48 mg, 0.15 mmol) were added in 1,4-dioxane (0.080 mL) and $H_2O$ (0.120 mL). The reaction was purged with $N_2$, and the mixture was heated to 85° C. for 18 h. The sample was diluted with 1:1 DMSO/MeOH and purified by reverse phase chromatography. A gradient of MeCN (A) and 0.1% TFA in $H_2O$ (B) was used, at a flow rate of 50 mL/min (0-1.0 min 5% A, 1.0-8.5 min linear gradient 5-100% A, 8.5-11.5 min 100% A, 11.5-12.0 min linear gradient 95-5% A) to yield the title compound (2.1 mg, 9.0%). LC/MS (Table 1, method g). $R_t$=0.78 min; MS m/z: 400 $(M+H)^+$. (TNF IC$_{50}$=C).

Example #71

1-(5-((6R,8S,9S)-9-Phenyl-6,7,8,9-tetrahydro-6,8-epoxyimidazo[1,2-a:5,4-b']dipyridin-2-yl)pyrimidin-2-yl)piperidin-4-ol

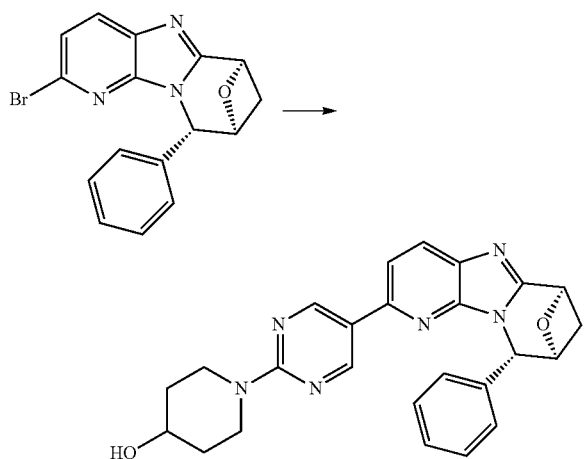

2-Chloro-5-(4,4,5,5-tetramethyl-1,3,2-dioxaborolan-2-yl)pyrimidine (41 mg, 0.17 mmol) and piperidin-4-ol (17 mg, 0.17 mmol) were mixed in EtOH. TEA (0.031 mL, 0.22 mmol) was added, and the reaction was heated to 95° C. for 2 h before being cooled and concentrated. (6R,8S,9S)-2-bromo-9-phenyl-6,7,8,9-tetrahydro-6,8-epoxyimidazo[1,2-a:5,4-b']dipyridine (19 mg, 0.11 mmol, Preparation #94), Cs$_2$CO$_3$ (18 mg, 0.11 mmol), Pd$_2$(dba)$_3$ (5.1 mg, 0.011 mmol) and (1S,3R,5R,7S)-1,3,5,7-tetramethyl-8-phenyl-2,4,6-trioxa-8-phosphaadamantane (3.2 mg, 0.021 mmol) were added to the crude residue and mixed in 4:1 THF/H$_2$O (0.5 mL total). The reaction was stirred at 60° C. for 18 h before being cooled and concentrated. The sample was diluted with 1:1 DMSO/MeOH, filtered and purified by reverse phase chromatography. A gradient of MeCN (A) and 0.1% NH$_4$OAc in H$_2$O (B) was used, at a flow rate of 50 mL/min (0-1.0 min 5% A, 1.0-8.5 min linear gradient 5-100% A, 8.5-11.5 min 100% A, 11.5-12.0 min linear gradient 95-5% A) to yield the title compound (1.2 mg, 1.6%). LC/MS (Table 1, method ai). R$_f$=0.63 min; MS m/z: 441 (M+H)$^+$. (TNF IC$_{50}$=C).

Example #72

2'-(2-(2-Hydroxypropan-2-yl)pyrimidin-5-yl)-2,3-dihydro-6'H,8'H-spiro[indene-1,9'-pyrido[3',2':4,5]imidazo[2,1-c][1,4]oxazin]-6'-ol

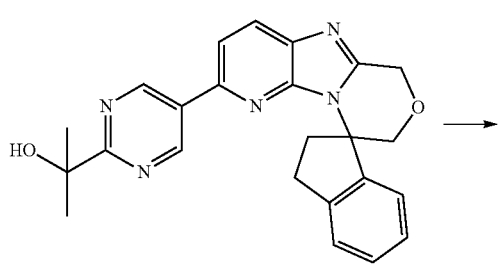

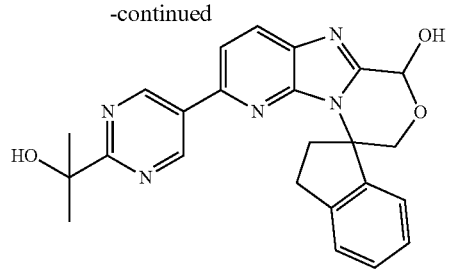

In a 4 mL vial was dissolved 2-(5-(2,3-dihydro-6'H,8'H-spiro[indene-1,9'-pyrido[3',2':4,5]imidazo[2,1-c][1,4]oxazin]-2'-yl)pyrimidin-2-yl)propan-2-ol (41 mg, 0.099 mmol, Example #68) in DMSO (0.25 mL, (ratio 1.25 M with respect to 2-iodoxybenzoic acid) to give a brown suspension. 2-iodoxybenzoic acid (83 mg, 0.30 mmol) was added, and the reaction was heated to 95° C. for 24 h. Another 3 equivalent of 2-iodoxybenzoic acid (83 mg, 0.3 mmol) was added, and the reaction was heated at about 85° C. for about 24 h. The sample was diluted with 1:1 DMSO/MeOH and purified by reverse phase chromatography. A gradient of MeCN (A) and 0.1% TFA in H$_2$O (B) was used, at a flow rate of 50 mL/min (0-1.0 min 5% A, 1.0-8.5 min linear gradient 5-100% A, 8.5-11.5 min 100% A, 11.5-12.0 min linear gradient 95-5% A) to yield the title compound (7.5 mg, 18%). LC/MS (Table 1, method g) R$_f$=6.43 min; MS m/z: 430 (M+H)$^+$. (TNF IC$_{50}$=B).

Example #73

2'-(1-(Pyrimidin-4-yl)-1,2,3,6-tetrahydropyridin-4-yl)-2H,6'H,8'H-spiro[benzofuran-3,9'-pyrido[3',2':4,5]imidazo[2,1-c][1,4]oxazine]

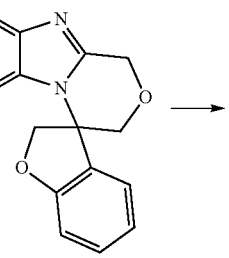

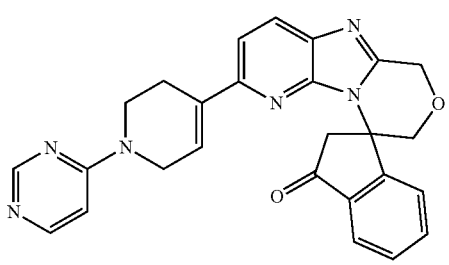

2'-Bromo-6',8'-dihydro-2H-spiro[benzofuran-3,9'-pyrido[3',2':4,5]imidazo[2,1-c][1,4]oxazine](0.015 mg, 0.042 mmol, Preparation #85), 4-(4-(4,4,5,5-tetramethyl-1,3,2-dioxaborolan-2-yl)-3,6-dihydropyridin-1(2H)-yl)pyrimidine (14 mg, 0.051 mmol), PdCl$_2$dppf (5.5 mg, 0.0063 mmol) and Cs$_2$CO$_3$ (27 mg, 0.084 mmol) were mixed in a 4 mL vial. The reaction was purged with N$_2$, and THF (0.5 mL) was added. The reaction was heated to about 65° C. for about 18 h. The reaction was cooled to rt and concentrated. The crude residue was dissolved in 1:1 MeOH/DMSO and purified by reverse phase chromatography using a gradient of MeCN (A) and 0.1% TFA in water (B) at a flow rate of 50 mL/min (0-0.5 min 5% A, 0.5-8.5 min linear gradient 05-100% A, 8.7-10.7 min 100% A, 10.7-11 min linear gradient 100-05% A) to yield the title compound (5.1 mg, 27%); LC/MS (Table 1, method ai) R$_t$=0.55 min; MS m/z: 439 (M+H)$^+$. (TNF IC$_{50}$=B).

The compound shown in Table BI was synthesized in a manner similar to Example #73 from the corresponding boronic ester.

TABLE BI

| Boronic ester | Product | Example # | R$_t$ min (Table 1, Method) | m/z (M + H)$^+$ | TNF IC$_{50}$ |
|---|---|---|---|---|---|
| 3-Methoxy-3-methyl-1-(4-(4,4,5,5-tetramethyl-1,3,2-dioxaborolan-2-yl)-3,6-dihydropyridin-1(2H)-yl)butan-1-one (Preparation #106) | | BI.1 | 0.68 (ai) | 475 | B |

The compounds shown in Table BJ were synthesized in a manner similar to Example #50 from (S)-2'-bromo-6',8'-dihydro-2H-spiro[benzofuran-3,9'-pyrido[3',2':4,5]imidazo[2,1-c][1,4]oxazine](Preparation #97) and the corresponding amine.

TABLE BJ

| Amine | Product | Example # | R$_t$ min (Table 1, Method) | m/z (M + H)$^+$ | TNF IC$_{50}$ |
|---|---|---|---|---|---|
| Piperidin-4-ol | | BJ.1 | 0.76 (ab) | 457 | A |
| (S)-Hexahydro-imidazo[1,5-a]pyrazin-3(2H)-one (Preparation #41) | | BJ.2 | 0.79 (ab) | 498 | A |

Example #74

(1S,4r)-4-((4-((S)-6',8'-Dihydro-2H-spiro[benzofuran-3,9'-pyrido[3',2':4,5]imidazo[2,1-c][1,4]oxazin]-2'-yl)pyridin-2-yl)oxy)cyclohexanol

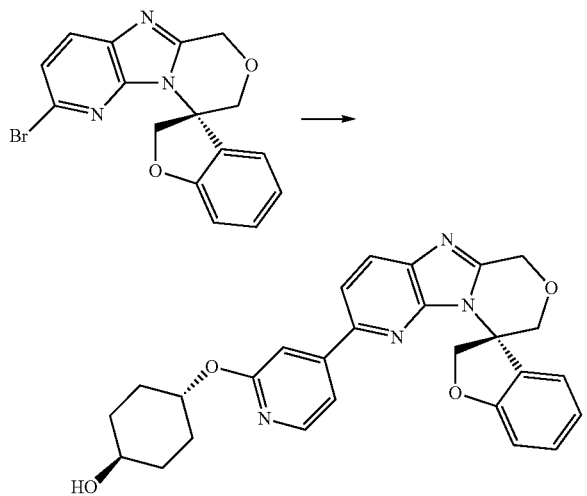

A mixture of 4,4,4',4',5,5,5',5'-octamethyl-2,2'-bi(1,3,2-dioxaborolane) (0.043 g, 0.168 mmol), (1r,4r)-4-((4-bromopyridin-2-yl)oxy)cyclohexanol (0.034 g, 0.126 mmol), KOAc (0.025 g, 0.251 mmol), PdCl$_2$(dppf) (4.90 mg, 6.70 mol), and 1,4-dioxane (2 mL) was purged with nitrogen three times and then degassed for about 5 min. The mixture was placed in a preheated oil bath at about 95° C. and stirred for about 2 h. The reaction was cooled to ambient temperature and (S)-2'-bromo-6',8'-dihydro-2H-spiro [benzofuran-3,9'-pyrido[3',2':4,5]imidazo[2,1-c][1,4]oxazine](0.03 g, 0.084 mmol, Preparation #97), Cs$_2$CO$_3$ (0.068 g, 0.209 mmol), water (0.500 mL) and PdCl$_2$(PPh$_3$)$_2$(4.1 mg, 5.86 mol) were added. The reaction mixture was purged with nitrogen for about 10 min and placed in a preheated oil bath at about 85° C. and for about 16 h. The reaction was cooled to about rt and the aqueous layer was removed. The organics were filtered through a silica gel pad, rinsing with 1,4-dioxane, and concentrated under reduced pressure. The crude product was purified by flash chromatography on silica gel (40-100% EtOAc/heptanes) to afford the title compound (0.034 g, 86%); LC/MS (Table 1, Method ab) R$_t$=0.77 min; MS m/z: 471 (M+H)$^+$. (TNF IC$_{50}$=A)

The compounds shown in Table BK were synthesized in a manner similar to Example #74 from (R)-2-chloro-8-phenyl-7,8-dihydro-6H-pyrrolo[2',1':2,3]imidazo[4,5-b]pyridine (Preparation #81) and the corresponding bromide.

TABLE BK

| Bromide | Product | Example # | R$_t$ min (Table 1, Method) | m/z (M + H)$^+$ | TNF IC$_{50}$ |
|---|---|---|---|---|---|
| (1S,4S)-4-(((4-Bromopyridin-2-yl)oxy)methyl)cyclohexanol (Preparation #98) | | BK.1 | 0.95 (an) | 441 | A |
| (1R,4R)-4-(((4-Bromopyridin-2-yl)oxy)methyl)cyclohexanol (Preparation #98) | | BK.2 | 0.94 (an) | 441 | B |

TABLE BK-continued

| Bromide | Product | Example # | R, min (Table 1, Method) | m/z (M + H)+ | TNF IC50 |
|---|---|---|---|---|---|
| ((1R,4R)-4-(((4-Bromopyridin-2-yl)oxy)methyl)cyclohexyl)methanol (Preparation #100) | 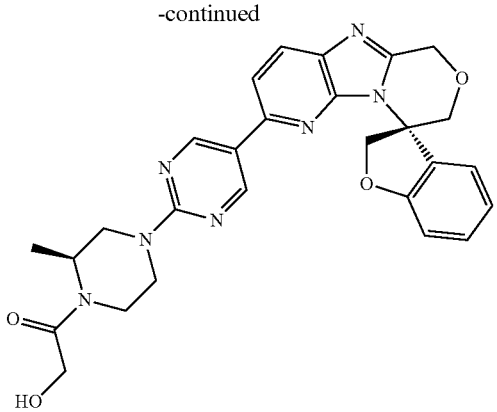 | BK.3 | 0.98 (an) | 455 | B |

Example #75

1-((S)-4-(5-((S)-6',8'-Dihydro-2H-spiro[benzofuran-3,9'-pyrido[3',2':4,5]imidazo[2,1-c][1,4]oxazin]-2'-yl)pyrimidin-2-yl)-2-methylpiperazin-1-yl)-2-hydroxyethanone

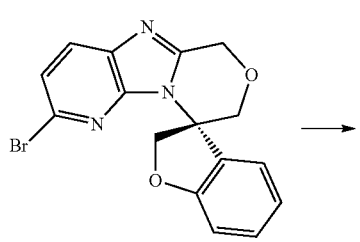

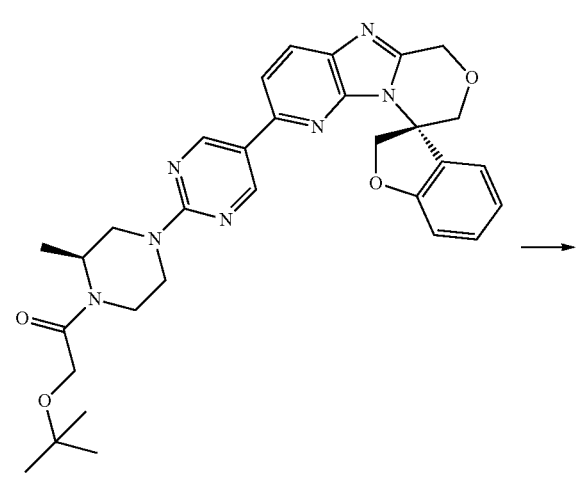

Step 1: 2-(tert-Butoxy)-1-((S)-4-(5-((S)-6',8'-dihydro-2H-spiro[benzofuran-3,9'-pyrido[3',2':4,5]imidazo[2,1-c][1,4]oxazin]-2'-yl)pyrimidin-2-yl)-2-methylpiperazin-1-yl)ethanone A solution of (S)-2'-bromo-6',8'-dihydro-2H-spiro[benzofuran-3,9'-pyrido[3',2':4,5]imidazo[2,1-c][1,4]oxazine] (0.143 g, 0.399 mmol, Preparation #97), (S)-2-(tert-butoxy)-1-(2-methyl-4-(5-(4,4,5,5-tetramethyl-1,3,2-dioxaborolan-2-yl)pyrimidin-2-yl)piperazin-1-yl)ethanone (0.184 g, 0.439 mmol, Preparation #102), Cs₂CO₃ (0.325 g, 0.998 mmol) and PdCl₂(PPh₃)₂ (0.028 g, 0.040 mmol) in one portion followed by water (0.500 mL) and 1,4-dioxane (2 mL). The reaction was degassed and purged with nitrogen and then heated at about 85° C. for about 2 h. The reaction was cooled to rt and the aqueous layer was removed. The organic layers were filtered through a silica gel pad, rinsing with 1,4-dioxane, concentrated under reduced pressure, and purified by flash chromatography on silica gel (40-100% EtOAc/heptanes) to afford the title compound (0.21 g, 94%); LC/MS (Table 1, Method ab) $R_t$=0.92 min; MS m/z: 570 (M+H)+.

Step 2: 1-((S)-4-(5-((S)-6',8'-Dihydro-2H-spiro[benzofuran-3,9'-pyrido[3',2':4,5]imidazo[2,1-c][1,4]oxazin]-2'-yl)pyrimidin-2-yl)-2-methylpiperazin-1-yl)-2-hydroxyethanone To a solution of 2-(tert-butoxy)-1-((S)-4-(5-((S)-6',8'-dihydro-2H-spiro[benzofuran-3,9'-pyrido[3',2':4,5]imidazo[2, 1-c][1,4]oxazin]-2'-yl)pyrimidin-2-yl)-2-methylpiperazin-1-yl)ethanone (0.21 g, 0.369 mmol) in DCM (2 mL) was added with TFA (2 mL) and the mixture was stirred for about 15 min, the reaction was concentrated under reduced pressure and the residue was suspended between sat.NaHCO₃ and DCM. The organics were passed through a phase separator, concentrated under reduced pressure, and purified by flash chromatography on silica gel (0-10% MeOH/DCM) to afford the title compound (0.15 g, 79%); LC/MS (Table 1, Method ab) R$_f$=0.79 min; MS m/z: 514 (M+H)⁺. (TNF IC$_{50}$=A)

The compound shown in Table BL was synthesized in a manner similar to Example #75 from (S)-2'-bromo-6',8'-dihydro-2H-spiro[benzofuran-3,9'-pyrido[3',2':4,5]imidazo[2,1-c][1,4]oxazine](Preparation #97) and the corresponding boronic acids/boronates.

TABLE BL

| Boronic acids/boronates | Product | Example # | R$_f$ min (Table 1, Method) | m/z (M + H)⁺ | TNF IC$_{50}$ |
|---|---|---|---|---|---|
| (R)-2-(tert-Butoxy)-1-(2-methyl-4-(5-(4,4,5,5-tetramethyl-1,3,2-dioxaborolan-2-yl)pyrimidin-2-yl)piperazin-1-yl)ethanone (Preparation #101) | | BL.1 | 0.77 (ab) | 514 | A |

The compounds shown in Table BM were synthesized in a manner similar to Example #75 from (R)-2'-bromo-6',8'-dihydro-2H-spiro[benzofuran-3,9'-pyrido[3',2':4,5]imidazo[2,1-c][1,4]oxazine](Preparation #97) and the corresponding boronic acids/boronates.

TABLE BM

| Boronic acids/boronates | Product | Example # | R$_f$ min (Table 1, Method) | m/z (M + H)⁺ | TNF IC$_{50}$ |
|---|---|---|---|---|---|
| (R)-2-(tert-Butoxy)-1-(2-methyl-4-(5-(4,4,5,5-tetramethyl-1,3,2-dioxaborolan-2-yl)pyrimidin-2-yl)piperazin-1-yl)ethanone (Preparation #101) | | BM.1 | 0.77 (ab) | 514 | B |

TABLE BM-continued

| Boronic acids/boronates | Product | Example # | R, min (Table 1, Method) | m/z (M + H)+ | TNF IC50 |
|---|---|---|---|---|---|
| (S)-2-(tert-Butoxy)-1-(2-methyl-4-(5-(4,4,5,5-tetramethyl-1,3,2-dioxaborolan-2-yl)pyrimidin-2-yl)piperazin-1-yl)ethanone (Preparation #102) | | BM.2 | 0.77 (ab) | 514 | B |

Example #76

(R)-8-Phenyl-2-(1-(pyrimidin-4-yl)-1,2,3,6-tetrahydropyridin-4-yl)-7,8-dihydro-6H-pyrrolo [2',1':2,3] imidazo[4,5-b]pyridine

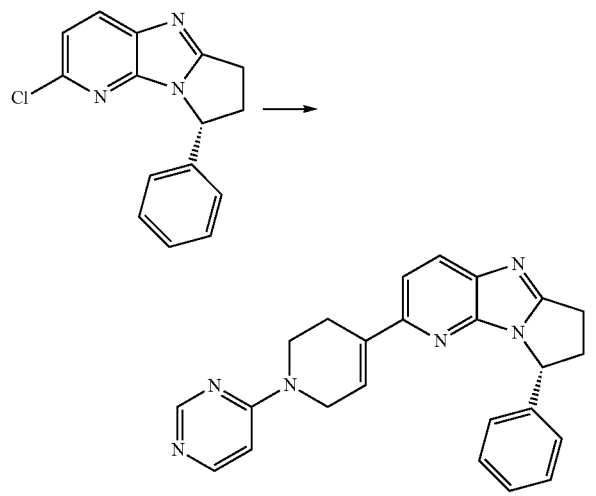

(R)-2-Chloro-8-phenyl-7,8-dihydro-6H-pyrrolo[2',1':2,3] imidazo[4,5-b]pyridine (25 mg, 0.079 mmol, Preparation #81), 4-(4-(4,4,5,5-tetramethyl-1,3,2-dioxaborolan-2-yl)-3,6-dihydropyridin-1(2H)-yl)pyrimidine (27 mg, 0.096 mmol), PdCl$_2$dppf (11 mg, 0.017 mmol) and Cs$_2$CO$_3$ (52 mg, 0.16 mmol) were mixed in a 4 mL vial. The reaction was purged with N$_2$, and THF (0.5 mL) was added. The reaction was heated to about 65° C. for about 18 h. The reaction was cooled to rt and concentrated. The crude residue was dissolved in 1:1 MeOH/DMSO and purified by reverse phase chromatography using a gradient of MeCN (A) and 0.1% TFA in water (B) at a flow rate of 50 mL/min (0-0.5 min 5% A, 0.5-8.5 min linear gradient 05-100% A, 8.7-10.7 min 100% A, 10.7-11 min linear gradient 100-05% A) to yield the title compound (2.3 mg, 7.3%); LC/MS (Table 1, method ai) R$_t$=0.49 min; MS m/z: 395 (M+H)+. (TNF IC$_{50}$=B).

The compound shown in Table BN was synthesized in a manner similar to Example #76 from the corresponding boronic ester.

TABLE BN

| Boronic ester | Product | Example # | R, min (Table 1, Method) | m/z (M + H)+ | TNF IC50 |
|---|---|---|---|---|---|
| Methyl 2-(4-(4,4,5,5-tetramethyl-1,3,2-dioxaborolan-2-yl)cyclohex-3-en-1-yl)acetate | | BN.1 | 0.67, ai | 388 | B |

The compounds shown in Table BO were synthesized in a manner similar to Example #50 from 2'-bromo-6',8'-dihydrospiro[isochroman-4,9'-pyrido[3',2':4,5]imidazo[2,1-c][1,4]oxazine](Preparation #103) and the corresponding amine.

TABLE BO

| Amine | Product | Example # | $R_t$ min (Table 1, Method) | m/z (M + H)⁺ | TNF IC$_{50}$ |
|---|---|---|---|---|---|
| Piperidin-4-ol | | BO.1 | 0.76 (ab) | 471 | B |
| (S)-Hexahydro-imidazo[1,5-a]pyrazin-3(2H)-one (Preparation #41) | | BO.2 | 0.76 (ab) | 511 | A |

The compounds shown in Table BP were synthesized in a manner similar to Example #51 from 2'-bromo-6',8'-dihydrospiro[isochroman-4,9'-pyrido[3',2':4,5]imidazo[2,1-c][1,4]oxazine](Preparation #103) and the corresponding boronic acids/boronates.

TABLE BP

| Boronic acids/boronates | Product | Example # | $R_t$ min (Table 1, Method) | m/z (M + H)⁺ | TNF IC$_{50}$ |
|---|---|---|---|---|---|
| 4-(5-(4,4,5,5-Tetramethyl-1,3,2-dioxaborolan-2-yl)pyrimidin-2-yl)morpholine | | BP.1 | 0.83 (ab) | 457 | B |

Example #77

1-(5-(8-Methyl-8-phenyl-7,8-dihydro-6H-pyrrolo[2',1':2,3]imidazo[4,5-b]pyridin-2-yl)pyrimidin-2-yl)piperidin-4-ol

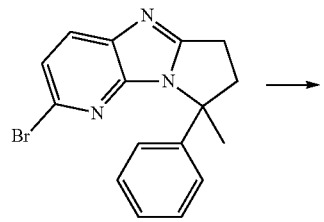

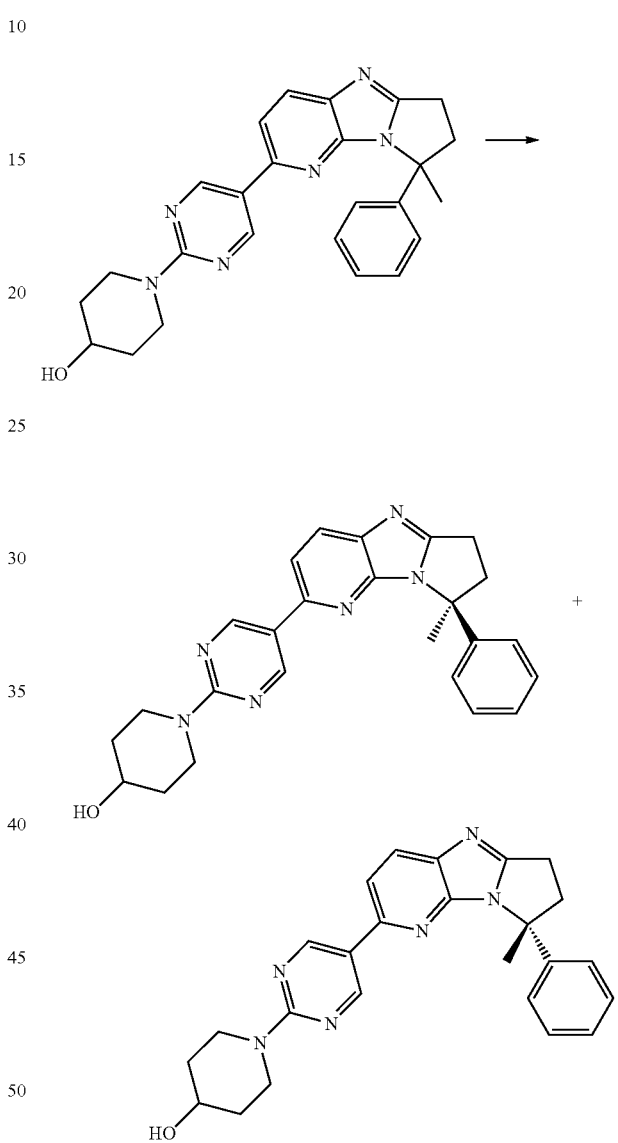

To a vial was added (2-chloropyrimidin-5-yl)boronic acid (48.2 mg, 0.305 mmol), EtOH (1 mL) and piperidin-4-ol (30.8 mg, 0.305 mmol) followed by the addition of TEA (0.042 mL, 0.305 mmol). The mixture was heated at about 95° C. for about 2 h. The reaction was cooled to rt and to the solution was added 2-bromo-8-methyl-8-phenyl-7,8-dihydro-6H-pyrrolo[2',1':2,3]imidazo[4,5-b]pyridine (50 mg, 0.152 mmol, Preparation #16), $Cs_2CO_3$ (99 mg, 0.305 mmol), and Siliacat Pd-DPP (60.9 mg, 0.015 mmol). The mixture was heated to about 95° C. for about 2. The reaction was cooled to rt, filtered, the filter cake wash with MeOH, and the filtate concentrated under reduced pressure. The crude product was purified by preparative HPLC (Table 1, Method ap) to afford the title compound (56 mg, 86%); LC/MS (Table 1, method e) $R_t$=0.75 min; MS m/z: 427 $(M+H)^+$. (TNF $IC_{50}$=A).

Example #78

(S)-1-(5-(8-Methyl-8-phenyl-7,8-dihydro-6H-pyrrolo[2',1':2,3]imidazo[4,5-b]pyridin-2-yl)pyrimidin-2-yl)piperidin-4-ol and (R)-1-(5-(8-methyl-8-phenyl-7,8-dihydro-6H-pyrrolo[2',1':2,3]imidazo[4,5-b]pyridin-2-yl)pyrimidin-2-yl)piperidin-4-ol A racemic mixture of 1-(5-(8-methyl-8-phenyl-7,8-dihydro-6H-pyrrolo[2',1':2,3]imidazo[4,5-b]pyridin-2-yl)pyrimidin-2-yl)piperidin-4-ol (0.054 g, Example #77) was separated via chiral SFC (Table 2, Method 21) to give (S)-1-(5-(8-methyl-8-phenyl-7,8-dihydro-6H-pyrrolo[2',1':2,3]imidazo[4,5-b]pyridin-2-yl)pyrimidin-2-yl)piperidin-4-ol (0.006 g, 14%); $R_t$=3.8 min (TNF $IC_{50}$=C) and (R)-1-(5-(8-methyl-8-phenyl-7,8-dihydro-6H-pyrrolo[2',1':2,3]imidazo[4,5-b]pyridin-2-yl)pyrimidin-2-yl)piperidin-4-ol (0.014 g, 33%); $R_t$=5.0 min [Stereochemistry arbitarily assigned]; LC/MS (Table 1, Method ab) $R_t$=0.75 min; MS m/z: 427 $(M+H)^+$. (TNF $IC_{50}$=A).

Example #79

(S)-2-(5-(8-Methyl-8-phenyl-7,8-dihydro-6H-pyrrolo[2',1':2,3]imidazo[4,5-b]pyridin-2-yl)pyrimidin-2-yl)propan-2-ol and (R)-2-(5-(8-methyl-8-phenyl-7,8-dihydro-6H-pyrrolo [2',1':2,3]imidazo[4,5-b]pyridin-2-yl)pyrimidin-2-yl)propan-2-ol

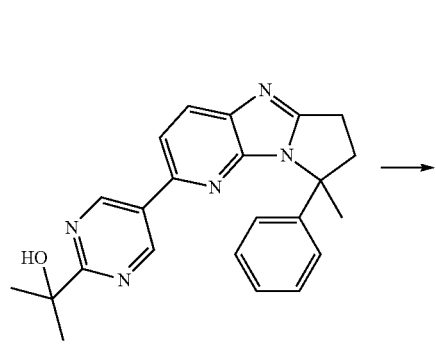

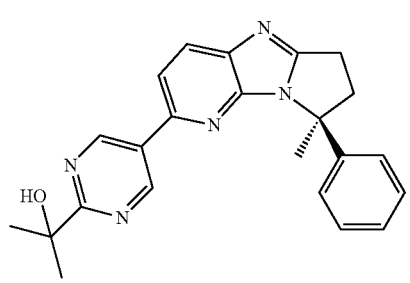

+

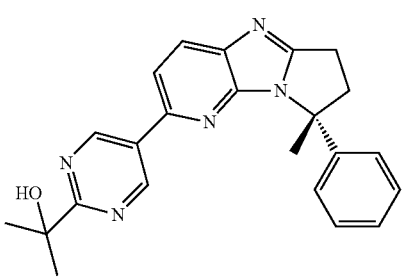

A racemic mixture of 2-(5-(8-methyl-8-phenyl-7,8-dihydro-6H-pyrrlo[2',1':2,3]imidazo[4,5-b]pyridin-2-yl)pyrimidin-2-yl)propan-2-ol (0.053 g, Example #39) was separated via chiral SFC (Table 2, Method 22) to give (S)-2-(5-(8-methyl-8-phenyl-7,8-dihydro-6H-pyrrolo[2',1':2,3]imidazo[4,5-b]pyridin-2-yl)pyrimidin-2-yl)propan-2-ol (0.01 g, 19%); $R_t$=4.3 min (TNF IC$_{50}$=C) $R_t$=0.75 min; MS m/z: 427 (M+H)$^+$ and (R)-2-(5-(8-methyl-8-phenyl-7,8-dihydro-6H-pyrrolo[2',1':2,3]imidazo[4,5-b]pyridin-2-yl)pyrimidin-2-yl)propan-2-ol (0.013 g, 25%); R, =4.8 min [Stereochemistry arbitarily assigned]; LC/MS (Table 1, Method ab) $R_t$=0.75 min; MS m/z: 427 (M+H)$^+$. (TNF IC$_{50}$=A).

Example #80

2-(5-(2,3-Dihydro-6'H,8'H-spiro[indene-1,9'-pyrido[3',2':4,5]imidazo[2,1-c][1,4]oxazin]-2'-yl)pyrimidin-2-yl)propan-2-amine

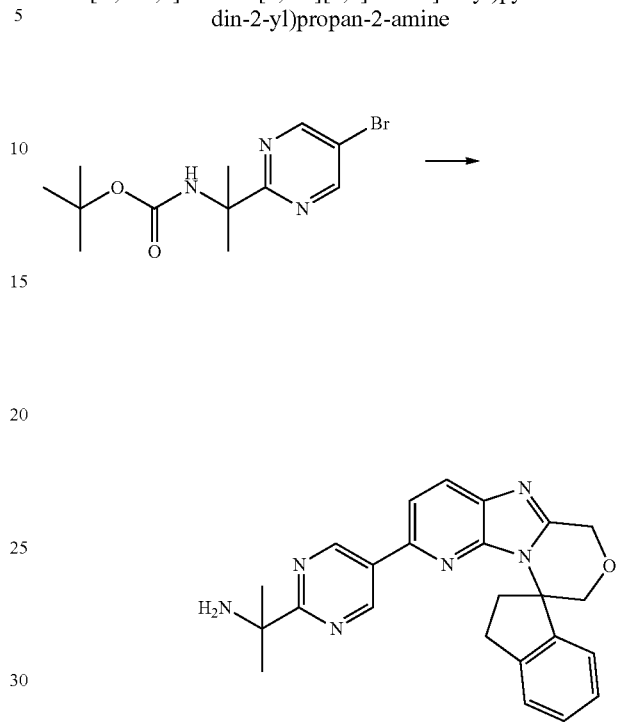

In a 4 mL vial was mixed 4,4,4',4',5,5,5',5'-octamethyl-2,2'-bi(1,3,2-dioxaborolane) (39 mg, 0.16 mmol), tert-butyl (2-(5-bromopyridin-2-yl)propan-2-yl)carbamate (37 mg, 0.12 mmol, Preparation #104), PdCl$_2$dppf (8.6 mg, 0.012 mmol) and KOAc (21 mg, 0.22 mmol) in 1,4-dioxane (0.7 mL). The reaction was purged with N$_2$ for 5 min and then stirred at about 95° C. for about 2 h before being cooled to rt. 2'-Bromo-2,3-dihydro-6'H,8'H-spiro[indene-1,9'-pyrido[3',2':4,5]imidazo[2,1-c][1,4]oxazine](35 mg, 0.098 mmol, Preparation #34), PdCl$_2$(PPh$_3$)$_2$(6.9 mg, 0.0098 mmol) and Cs$_2$CO$_3$ (80 mg, 0.25 mmol) were added to the reaction mixture followed by 1,4-dioxane (0.15 mL) and water (0.20 mL). The reaction was purged with N$_2$ for a few minutes and stirred at about 85° C. for about 18 h before being cooled to rt, filtered and concentrated. To the crude residue was added DCM (0.2 mL) and TFA (0.1 mL). The reaction was stirred at about 35° C. for about 18 h before being concentrated. The residue was dissolved in 1:1 MeOH/DMSO and purified by reverse phase chromatography using a gradient of MeCN (A) and 0.1% TFA in water (B) at a flow rate of 50 mL/min (0-0.5 min 5% A, 0.5-8.5 min linear gradient 05-100% A, 8.7-10.7 min 100% A, 10.7-11 min linear gradient 100-05% A) to yield the title compound (38 mg, 94%). LC/MS (Table 1, method ag) $R_t$=3.08 min; MS m/z: 413 (M+H)$^+$. (TNF IC$_{50}$: A).

The compounds shown in Table BQ were synthesized in a manner similar to Example #80 from the corresponding bromide/chloride.

TABLE BQ

| Bromide/chloride | Product | Example # | R$_f$ min (Table 1, Method) | m/z (M + H)$^+$ | TNF IC$_{50}$ |
|---|---|---|---|---|---|
| (R)-2-Chloro-8-phenyl-7,8-dihydro-6H-pyrrolo[2',1':2,3]imidazo[4,5-b]pyridine (Preparation #81) | | BQ.1 | 2.69 (ag) | 371 | B |
| (S)-2'-Bromo-6',8'-dihydro-2H-spiro[benzofuran-3,9'-pyrido[3',2':4,5]imidazo[2,1-c][1,4]oxazine] (Preparation #97) | | BQ.2 | 3.08 (ag) | 415 | nt |

Example #81

2'-(2-(2-Hydroxypropan-2-yl)pyrimidin-5-yl)-2,3,6',8'-tetrahydrospiro[indene-1,9'-pyrido[3',2':4,5]imidazo[2,1-c][1,4]oxazin]-3-ol

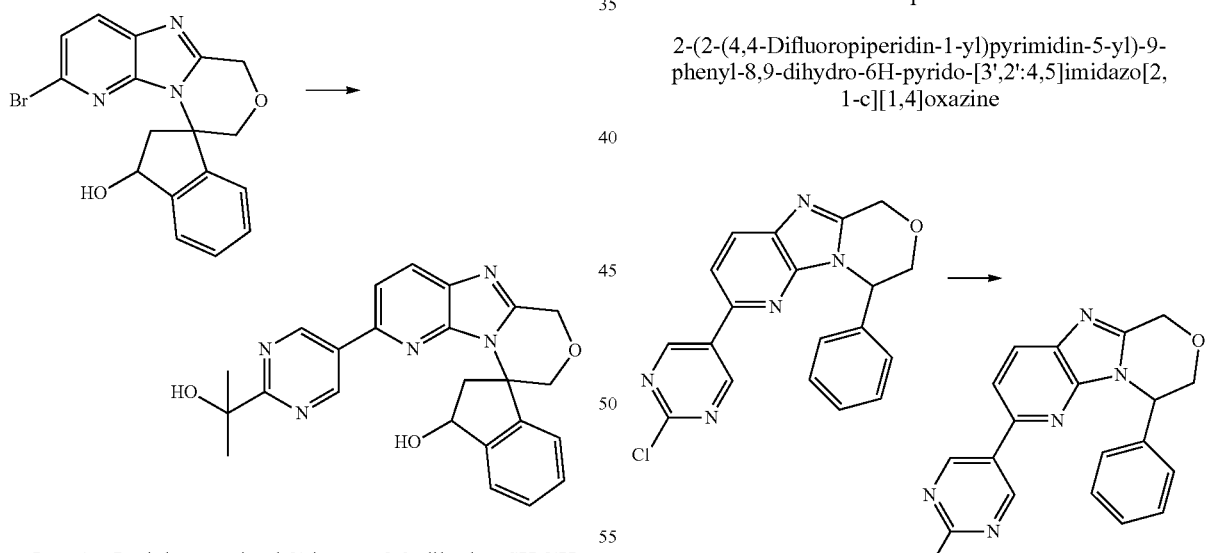

In a 4 mL vial was mixed 2'-bromo-2,3-dihydro-6'H,8'H-spiro[indene-1,9'-pyrido[3',2':4,5]imidazo[2,1-c][1,4]oxazin]-3-ol (5.1 mg, 0.013 mmol, Preparation #105), (2-(2-hydroxypropan-2-yl)pyrimidin-5-yl)boronic acid (4.9 mg, 0.027 mmol), Pd$_2$(dba)$_3$ (2.5 mg, 0.0027 mmol), (1S,3R,5R,7S,9S)-1,3,5,7-tetramethyl-9-phenyl-2,4,6-trioxa-9-phosphaadamantane (0.79 mg, 0.0027 µmol) and Cs$_2$CO$_3$ (4.4 mg, 0.013 mmol). The vial was purged with N$_2$. THF (0.22 mL) and water (0.054 mL) were added to give a suspension. The reaction was stirred at about 60° C. for about 18 h. The reaction was concentrated, dissolved in 1:1 DMSO/MeOH and filtered. The mixture was purified by reverse phase chromatography using a gradient of MeCN (A) and 0.1% TFA in water (B) at a flow rate of 50 mL/min (0-0.5 min 5% A, 0.5-8.5 min linear gradient 05-100% A, 8.7-10.7 min 100% A, 10.7-11 min linear gradient 100-05% A) to yield the title compound (2.8 mg, 49%). LC/MS (Table 1, method ag) R$_f$=3.55 min; MS m/z: 430 (M+H)$^+$. (TNF IC$_{50}$=B).

Example #82

2-(2-(4,4-Difluoropiperidin-1-yl)pyrimidin-5-yl)-9-phenyl-8,9-dihydro-6H-pyrido-[3',2':4,5]imidazo[2,1-c][1,4]oxazine To a solution of 2-(2-chloropyrimidin-5-yl)-9-phenyl-8,9-dihydro-6H-pyrido[3',2':4,5]imidazo-[2,1-c][1,4]oxazine (Preparation #96, 0.295 g, 0.811 mmol) and KF (0.146 g, 2.51 mmol) in DMF (4 mL) at rt was added DIEA (0.220 g, 1.703 mmol) and 4,4-difluoropiperidine (0.118 g, 0.973 mmol). The reaction was heated to 110° C. and stirred overnight. The mixture was cooled to rt, water added, the mixture wasd stirred for 15 min and then filtered. The solid material was subjected to reverse phase HPLC to provide the desired compound (0.205 g, 56%); $^1$H NMR (400 MHz, DMSO-d$_6$) δ 8.82 (s, 2H), 8.05 (d, J=8.4 Hz, 1H), 7.75 (d, J=8.4 Hz, 1H), 7.39-7.14 (m, 5H), 5.74 (t, J=3.8 Hz, 1H), 5.19 (d, J=16.1 Hz, 1H), 5.05 (d, J=16.1 Hz, 1H), 4.37 (dd, J=12.0, 4.1 Hz, 1H), 4.12 (dd, J=12.1, 3.7 Hz, 1H), 3.91 (t, J=5.8 Hz, 4H), 1.98 (tt, J=13.7, 5.7 Hz, 4H); MS (ESI) m/z: 449 (M+H)$^+$ (TNF IC$_{50}$=A).

Example #83

(1R,4R)-4-((4-((R)-8-Phenyl-7,8-dihydro-6H-pyrrolo[2',1':2,3]imidazo[4,5-b]pyridin-2-yl)pyridin-2-yl)oxy)cyclohexanol (A-1684504.0)

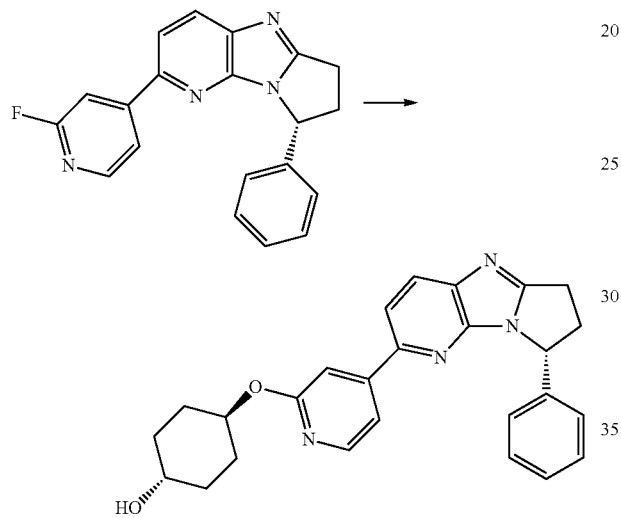

(1R,4R)-Cyclohexane-1,4-diol (0.105 g, 0.908 mmol) was taken into THF (5 mL) followed by the addition of potassium 2-methylpropan-2-olate in THF (0.91 mL, 0.91 mmol). The mixture was stirred for about 10 min, then (R)-2-(2-fluoropyridin-4-yl)-8-phenyl-7,8-dihydro-6H-pyrrolo[2',1':2,3]imidazo[4,5-b]pyridine (0.15 g, 0.454 mmol, Preparation #84) in THF (5 mL) was added and the mixture was heated at about 120° C. for about 20 min in a single mode microwave. The reaction was cooled to rt and water was added to quench the reaction. The mixture was extracted with EtOAc, dried over MgSO$_4$, concentrated under reduced pressure, and purified by flash chromatography on silica gel (0-5% MeOH/DCM) to give the title compound (0.021 g, 10.8%); LC/MS (Table 1, Method ab) R$_t$=0.82 min; MS m/z: 427 (M+H)$^+$. (TNF IC$_{50}$=A).

What is claimed:

1. A compound of Formula (I):

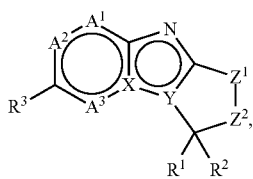

or a pharmaceutically acceptable salt or stereoisomer thereof, wherein:

R$^1$ is H or (C$_1$-C$_3$)alkyl;

R$^2$ is phenyl, tetrahydropyranyl, pyridinyl or cyclohexyl, each of which is optionally substituted with 1 to 3 groups selected from the group consisting of halogen, —CN, —NR$^f$, —OR$^f$, —CF$_3$, —(C$_1$-C$_6$)alkyl, —(C$_1$-C$_6$)haloalkyl, —(C$_1$-C$_6$)alkylene-OR$^f$, —(C$_1$-C$_6$)alkylene-NR$^f$R$^f$, and —(C$_1$-C$_6$)haloalkoxy, wherein R$^f$ is H or —(C$_1$-C$_6$)alkyl;

A$^1$ and A$^2$ are independently C(R$^{A2}$);

A$^3$ is N;

X is C and Y is N;

Z$^1$ is —C(R$^z$)$_2$- and Z$^2$ is —C(R$^z$)$_2$—;

R$^3$ is —R$^{3a}$—R$^{3b}$, wherein:

R$^{3a}$ is aryl, saturated or partially saturated heterocyclyl, or heteroaryl;

R$^{3b}$ is H, CF$_3$, CN, —C(O)OH, —C(O)N(R$^a$)$_2$, optionally substituted (C$_1$-C$_3$)alkyl, optionally substituted (C$_3$-C$_6$)cycloalkyl, —CH$_2$-optionally substituted heteroaryl, —N(R$^a$)$_2$, —N(R$^c$)S(O)$_2$-optionally substituted (C$_1$-C$_3$)alkyl, —OR$^a$, —S-optionally substituted (C$_1$-C$_3$)alkyl, —S(O)$_2$-optionally substituted (C$_1$-C$_3$)alkyl, —S(O)$_2$—N(R$^c$)$_2$, —S(O)$_2$-morpholinyl, optionally substituted azepanyl, optionally substituted 6-azaspiro[3.4]nonanyl, optionally substituted 7-azaspiro[3.5]nonanyl, optionally substituted azaspiro[3.4]octanyl, optionally substituted azetidinyl, optionally substituted 2,7-diazaspiro[4.4]nonanyl, optionally substituted diazepanyl, optionally substituted 3,10-diazabicyclo[4.3.1]decanyl, optionally substituted oxetanyl, hexahydroimidazo[1,2-a]pyrimidin-2(3H)-one, optionally substituted imidazolyl, hexahydroimidazo[1,2-c]pyrimidin-2(3H)-one, optionally substituted hexahydroimidazo[1,5-a]pyrazin-3(2H)-one, optionally substituted hexahydroimidazo[1,5-c]pyrazin-3(2H)-one, optionally substituted morpholinyl, optionally substituted oxazolo[3,4-a]pyrazine-3-one, 1,4-oxepanyl, optionally substituted piperazinyl, optionally substituted piperidinyl, optionally substituted pyrazinyl, optionally substituted pyrazolyl, optionally substituted pyrimidinyl, optionally substituted pyrrolidinyl, tetrahydro-1H-oxazolo[3,4-a]pyrazin-3(5H)-one, optionally substituted tetrahydropyranyl, thiomorpholinyl 1,1-dioxide, 5,6,7,8-tetrahydro- [1,2,4]triazolo[4,3-a]pyrazinyl, or optionally substituted 1,3,8-triazaspiro[4.5]decanyl;

R$^a$ is selected from the group consisting of H, optionally substituted (C$_1$-C$_5$)alkyl, —C(O)-optionally substituted (C$_1$-C$_5$)alkyl, optionally substituted —(CH$_2$)$_p$-(C$_3$-C$_6$)cycloalkyl and —(CH$_2$)$_p$-optionally substituted heterocyclyl; and R$^c$ is selected from the group consisting of H, optionally substituted (C$_1$-C$_5$)alkyl, optionally substituted —(CH$_2$)$_p$-(C$_3$-C$_6$)cycloalkyl, and —(CH$_2$)$_p$-optionally substituted heterocyclyl;

provided a substituted R$^{3b}$ group is substituted by one or more substituents independently selected from the group consisting of —F, —CH$_3$,—CH$_2$OH, —CN, —CH$_2$C(O)OCH$_2$CH$_3$, —C(O)CH$_2$OH, —C(O)CH$_3$, —C(O)OH, —NH$_2$, —N(H)S(O)$_2$CH$_3$, —OH, and =O;

each instance of R$^{A2}$ is independently H, CF$_3$, halo, or (C$_1$-C$_3$)alkyl;

each instance of R$^z$ is independently H, F, CF$_3$, —OH or (C$_1$-C$_3$)alkyl; and each instance of p is independently 0, 1 or 2;

further provided:

heterocyclyl is (i) a non-aromatic, saturated or unsaturated, monocyclic, bicyclic, tricyclic, or spirocyclic ring, having 5 to 12 ring atoms including at least one ring nitrogen, oxygen, or sulfur atom, or (ii) an azetidinyl ring; and heteroaryl is an aromatic, monocyclic, bicyclic, or tricyclic ring, having 5 to 12 ring atoms including at least one nitrogen, oxygen, or sulfur atom.

2. The compound of claim 1, or a pharmaceutically acceptable salt or stereoisomer thereof, wherein R$^2$ is phenyl substituted with 1 group selected from the group consisting of halogen, —CN, —NR$^f$, —OR$^f$, —CF$_3$, —(C$_1$-C$_6$)alkyl, —(C$_1$-C$_6$)haloalkyl, —(C$_1$-C$_6$)alkylene-OR$^f$, —(C$_1$-C$_6$)alkylene-NR$^f$R$^f$, and -(C$_1$-C$_6$)haloalkoxy, wherein R$^f$ is H or —(C$_1$-C$_6$)alkyl; and R$^1$ is H.

3. The compound of claim 2, or a pharmaceutically acceptable salt or stereoisomer thereof, wherein R$^2$ is phenyl substituted with 1 group selected from the group consisting of halogen, —OR$^f$, —(C$_1$-C$_6$)alkyl, and —(C$_1$-C$_6$)haloalkoxy, and R$^1$ is H.

4. The compound of claim 1, or a pharmaceutically acceptable salt or stereoisomer thereof, wherein R$^{3a}$ is phenyl, imidazo[4,5-b]pyridinyl, [1,2,5]oxadiazolo[3,4-b]pyridinyl, piperazinyl, piperidinyl, pyrimidinyl, pyridinyl, pyrazinyl, pyridine-2(1H)-one, 3,4-dihydro-2H -pyrido[3,2 -b][1,4]oxazinyl, furo[3,2 -b]pyridinyl benzo [d][1,3]dioxolyl, 1H-pyrazolyl, 3,4-dihydro- 2 H-pyrido[3,2 -b][1,4]oxazinyl, pyrrolyl, [1,2,5]oxadiazolo[3,4-b]pyridinyl, pyrido[2,3 -b]pyrazinyl, 3H-imidazo[4,5-b]pyridinyl, pyridine- 2(1H)-onyl, or thienyl.

5. The compound of claim 1, or a pharmaceutically acceptable salt or stereoisomer thereof, wherein R$^{3b}$ is (C$_1$-C$_3$)alkyl optionally substituted by one or more substituents independently selected from the group consisting of —F, —CH$_3$, —CH$_2$OH, —CN, —CH$_2$C(O)OCH$_2$CH$_3$, —C(O)CH$_2$OH, —C(O)CH$_3$, —C(O)OH, —NH$_2$, —N(H)S(O)$_2$CH$_3$, —OH, and =O.

6. The compound of claim 1, or a pharmaceutically acceptable salt or stereoisomer thereof, wherein R$^{3a}$ is phenyl, piperazinyl, piperidinyl, pyrimidinyl, pyridinyl, 3,4 -dihydro- 2H-pyrido [3,2 -b][1,4]oxazinyl, furo [3,2-b]pyridinyl, benzo[d][1,3]dioxolyl, or thienyl.

7. The compound of claim 1, or a pharmaceutically acceptable salt or stereoisomer thereof, wherein R$^{3b}$ is CF$_3$, CN, —C(O)OH, —C(O)N(H)$_2$—C(O)N(H)(cyclopropyl), optionally substituted (C$_1$-C$_3$)alkyl, optionally substituted cyclobutyl, optionally substituted cyclopropyl, —N(H)(optionally substituted (C$_1$-C$_3$ )alkyl), —N(optionally substituted (C$_1$-C$_3$)alkyl))$_2$, —N(H)(cyclopropyl), —N(H)(cyclopentyl), —N(R$^c$)S(O)$_2$-optionally substituted (C$_1$-C$_3$)alkyl, —O-tetrahydropyranyl, —O-optionally substituted (C$_1$-C$_3$) alkyl, —S—CH$_3$, —S(O)$_2$—CH$_3$, —S(O)$_2$—N(R$^c$)$_2$,—S(O)$_2$-morpholinyl, optionally substituted azepanyl, optionally substituted 6-azaspiro[3.4]nonanyl, optionally substituted 7-azaspiro[3.5]nonanyl, optionally substituted azaspiro[3.4]octanyl, optionally substituted 2,7-diazaspiro[4.4]nonanyl, optionally substituted diazepanyl, optionally substituted 3,10-diazabicyclo[4.3.1]decanyl, optionally substituted oxetanyl, hexahydroimidazo[1,2-a]pyrimidin-2(3H)-one, optionally substituted imidazolyl, hexahydroimidazo[1,2-c]pyrimidin- 2(3H)-one, optionally substituted hexahydroimidazo[1,5-a]pyrazin-3(2H)-one, optionally substituted hexahydroimidazo[1,5-c]pyrazin- 3(2H)—one, optionally substituted morpholinyl, optionally substituted oxazolo[3,4-a]pyrazine- 3-one, 1,4-oxepanyl, optionally substituted piperazinyl, optionally substituted piperidinyl, optionally substituted pyrazinyl, optionally substituted pyrazolyl, optionally substituted pyrimidinyl, optionally substituted pyrrolidinyl, tetrahydro-1H-oxazolo[3,4-a]pyrazin-3(5H)-one, optionally substituted tetrahydropyranyl, thiomorpholinyl 1,1-dioxide, 5,6,7,8-tetrahydro- [1,2,4]triazolo[4,3-a]pyrazinyl, or optionally substituted 1,3,8-triazaspiro[4.5]decanyl, provided a substituted R$^{3b}$ group is substituted by one or more substituents independently selected from the group consisting of —F, —CH$_3$, —CH$_2$OH, —CN, —CH$_2$C(O)OCH$_2$CH$_3$, —C(O)CH$_2$OH, —C(O)CH$_3$, —C(O)OH, —NH$_2$,—N(H)S(O)$_2$CH$_3$, —OH, and =O.

8. The compound of claim 1, or a pharmaceutically acceptable salt or stereoisomer thereof, wherein a substituted R$^{3b}$ group is substituted by one or more substituents independently selected from the group consisting of —NH$_2$, —OH, and =O.

9. The compound of claim 1, or a pharmaceutically acceptable salt or stereoisomer thereof, wherein R$^{3a}$ is pyrimidinyl.

10. The compound of claim 1, or a pharmaceutically acceptable salt or stereoisomer thereof, wherein R$^{3b}$ is optionally substituted (C$_1$-C$_3$)alkyl, optionally substituted cyclobutyl, —O-optionally substituted (C$_1$-C$_3$)alkyl, —S(O)$_2$-optionally substituted (C$_1$-C$_3$)alkyl, —S(O)$_2$—N(H)(optionally substituted (C$_1$-C$_3$)alkyl), optionally substituted azepanyl, optionally substituted 7-azaspiro[3.5]nonanyl, optionally substituted 3,10-diazabicyclo[4.3.1]decanyl, optionally substituted oxetanyl, optionally substituted hexahydroimidazo[1,5-a]pyrazin-3(2H)-one, optionally substituted morpholinyl, 1,4-oxepanyl, optionally substituted piperazinyl, optionally substituted piperidinyl, optionally substituted tetrahydropyranyl, or thiomorpholinyl 1,1-dioxide, provided a substituted R$^{3b}$ group is substituted by one or more substituents independently selected from the group consisting of —F, —CH$_3$, —CH$_2$OH, —CN, —CH$_2$C(O)OCH$_2$CH$_3$, —C(O)CH$_2$OH, —C(O)CH$_3$, —C(O)OH, —NH$_2$, —N(H)S(O)$_2$CH$_3$, —OH, and =O.

11. The compound of claim 1, or a pharmaceutically acceptable salt or stereoisomer thereof, wherein a substituted R$^{3b}$ is substituted by one or more substituents independently selected from the group consisting of —CH$_3$, —CH$_2$OH, —C(O)OCH$_2$CH$_3$, —C(O)OH, —NH$_2$,—OH, and =O.

12. The compound of claim 1 selected from the group consisting of

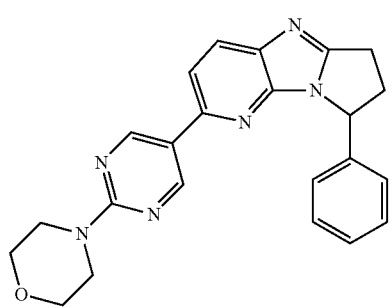

467
-continued
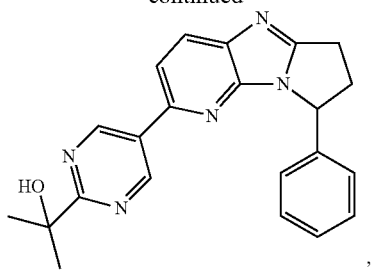
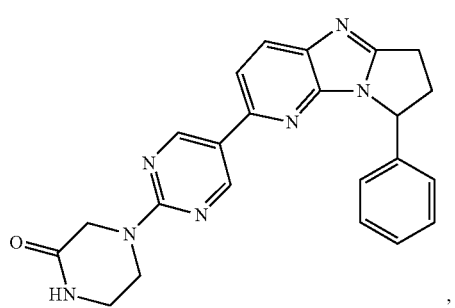
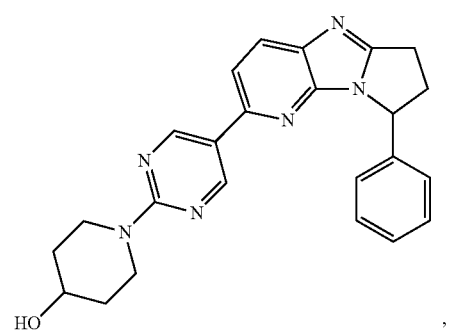
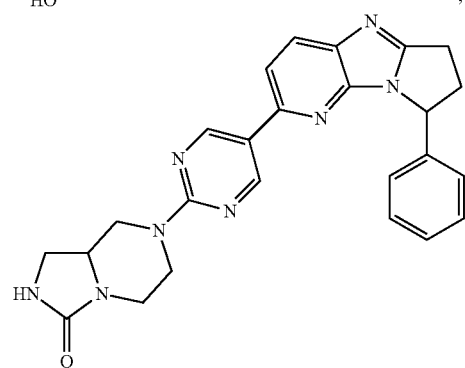
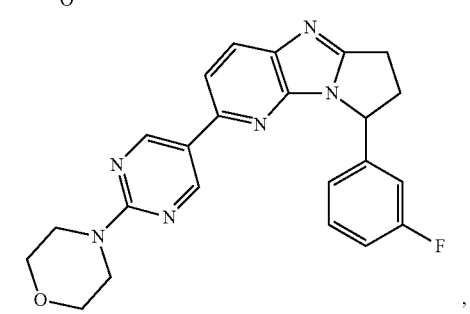
468
-continued
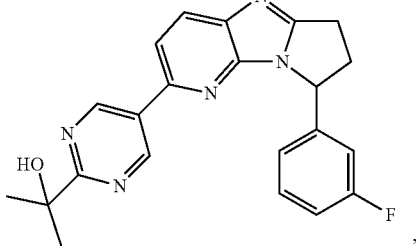
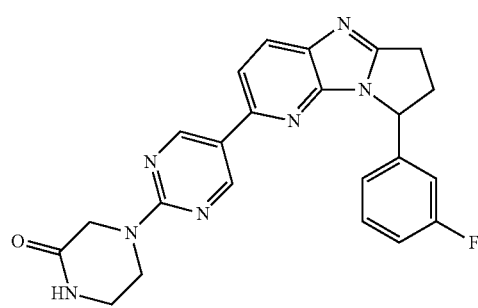
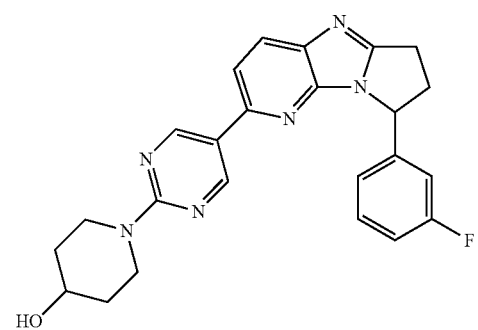
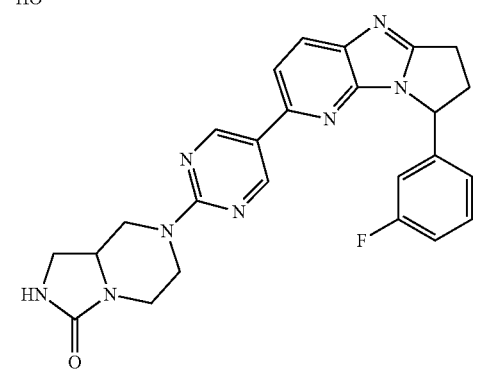
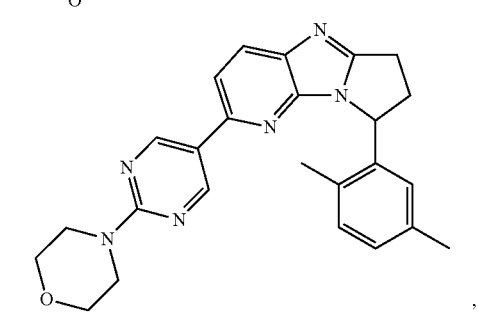

469
-continued
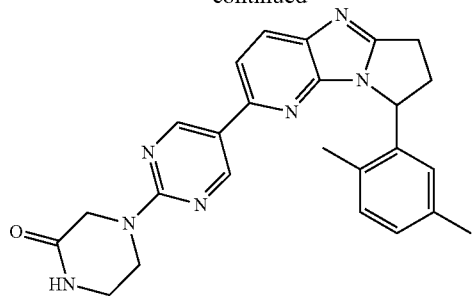
,
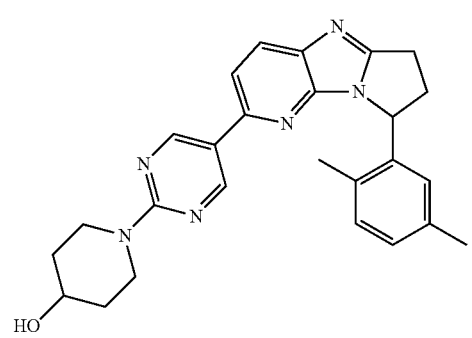
,
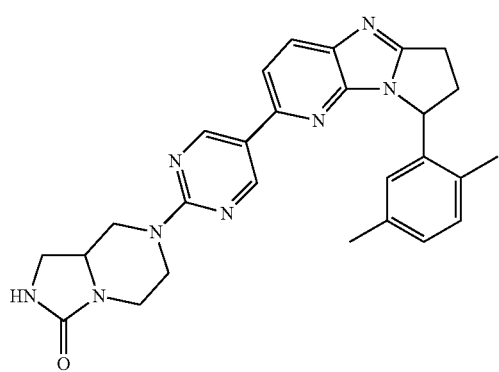
,
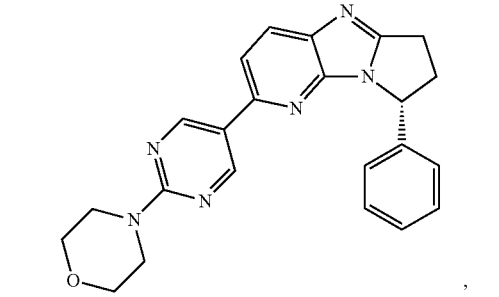
,
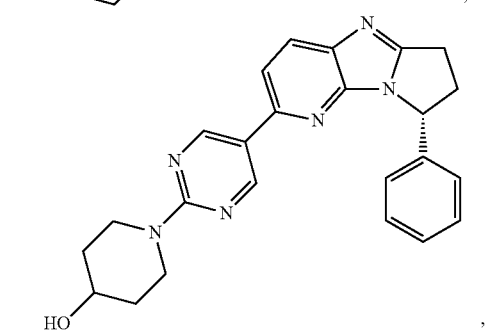
,
470
-continued
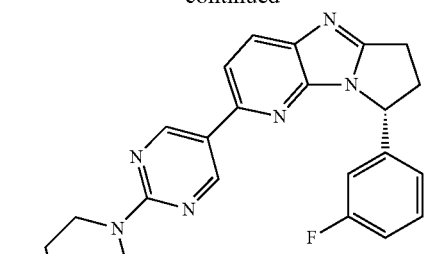
,
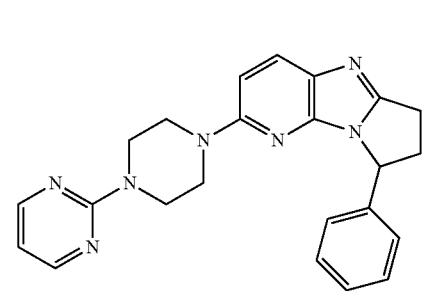
,
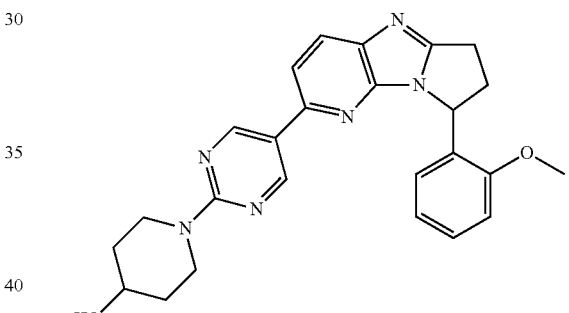
,
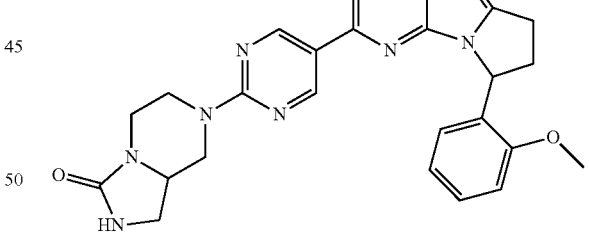
,
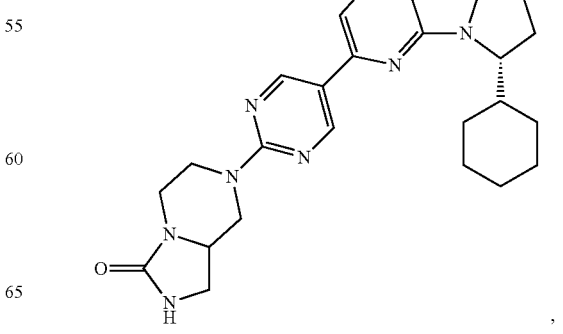
, -continued

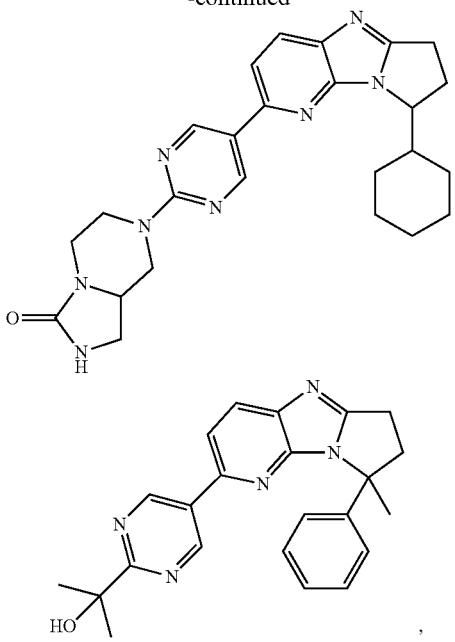

and pharmaceutically acceptable salts thereof.

13. The compound of claim 1, or a pharmaceutically acceptable salt or stereoisomer thereof,
wherein:
$R^1$ is H;
$R^2$ is phenyl optionally substituted with 1 to 3 groups selected from the group consisting of halogen, —CN, —NR$^f$, —OR$^f$, —CF$_3$, —(C$_1$-C$_6$)alkyl, —(C$_1$-C$_6$)haloalkyl, —(C$_1$-C$_6$)alkylene-OR$^f$, —(C$_1$-C$_6$)alkylene-NR$^f$R$^f$, and —(C$_1$-C$_6$)haloalkoxy, wherein R$^f$ is H or —(C$_1$-C$_6$)alkyl;
$A^1$ and $A^2$ are independently C(R$^{A2}$), wherein each instance of R$^{A2}$ is independently H or halo;
$Z^1$ is —C(R$^z$)$_2$- and $Z^2$ is —C(R$^z$)$_2$-, wherein each instance of R$^z$ is independently H, F, or —OH; and
$R^3$ is —R$^{3a}$—R$^{3b}$, wherein:
R$^{3a}$ is aryl or heteroaryl; and
R$^{3b}$ is CF$_3$, CN, —C(O)OH, —C(O)N(R$^a$)$_2$, optionally substituted (C$_1$-C$_3$)alkyl, optionally substituted (C$_3$-C$_6$)cycloalkyl, —CH$_2$-optionally substituted heteroaryl, —N(R$^a$)$_2$, —N(R$^c$)S(O)$_2$-optionally substituted (C$_1$-C$_3$)alkyl, —OR$^a$, —S-optionally substituted (C$_1$-C$_3$)alkyl, —S(O)$_2$-optionally substituted (C$_1$-C$_3$)alkyl, —S(O)$_2$—N(R$^c$)$_2$, —S(O)$_2$-morpholinyl, optionally substituted azepanyl, optionally substituted 6-azaspiro[3.4]nonanyl, optionally substituted 7-azaspiro[3.5]nonanyl, optionally substituted azaspiro[3.4]octanyl, optionally substituted azetidinyl, optionally substituted 2,7-diazaspiro[4.4]nonanyl, optionally substituted diazepanyl, optionally substituted 3,10-diazabicyclo[4.3.1]decanyl, optionally substituted oxetanyl, hexahydroimidazo[1,2-a]pyrimidin- 2(3H)-one, optionally substituted imidazolyl, hexahydroimidazo[1,2-c]pyrimidin-2(3H)-one, optionally substituted hexahydroimidazo[1,5-a]pyrazin-3(2H)-one, optionally substituted hexahydroimidazo[1,5-c]pyrazin-3(2H)-one, optionally substituted morpholinyl, optionally substituted oxazolo[3,4-a]pyrazine- 3-one, 1,4-oxepanyl, optionally substituted piperazinyl, optionally substituted piperidinyl, optionally substituted pyrazinyl, optionally substituted pyrazolyl, optionally substituted pyrimidinyl, optionally substituted pyrrolidinyl, tetrahydro-1H-oxazolo[3,4-a]pyrazin-3(5H)-one, optionally substituted tetrahydropyranyl, thiomorpholinyl 1,1-dioxide, 5,6,7,8-tetrahydro-[1,2,4]triazolo[4,3-a]pyrazinyl, or optionally substituted 1,3,8-triazaspiro[4.5]decanyl;
R$^a$ is selected from the group consisting of H, optionally substituted (C$_1$-C$_5$)alkyl, —C(O)-optionally substituted (C$_1$-C$_5$)alkyl, optionally substituted —(CH$_2$)$_p$-(C$_3$-C$_6$)cycloalkyl and -(CH$_2$)$_p$-optionally substituted heterocyclyl; and
R$_c$ is selected from the group consisting of H, optionally substituted (C$_1$-C$_5$)alkyl, optionally substituted —(CH$_2$)$_p$-(C$_3$-C$_6$)cycloalkyl, and -(CH$_2$)$_p$-optionally substituted heterocyclyl;
provided a substituted R$^{3b}$ group is substituted by one or more substituents independently selected from the group consisting of —F, —CH$_3$, —CH$_2$OH, —CN, —CH$_2$ C(O)OCH$_2$CH$_3$, —C(O)CH$_2$OH, —C(O)CH$_3$, —C(O)OH, —NH$_2$, —N(H)S(O)$_2$CH$_3$, —OH, and =O.

14. The compound of claim 13, or a pharmaceutically acceptable salt or stereoisomer thereof, wherein each instance of R$^{A2}$ is H.

15. The compound of claim 13, or a pharmaceutically acceptable salt or stereoisomer thereof, wherein each instance of R$^z$ is H.

16. The compound of claim 13, or a pharmaceutically acceptable salt or stereoisomer thereof, wherein R$^{3a}$ is heteroaryl.

17. The compound of claim 13, or a pharmaceutically acceptable salt or stereoisomer thereof,
wherein:
each instance of R$^{A2}$ is H;
each instance of R$^z$ is H; and
R$^{3a}$ is heteroaryl.

18. The compound of claim 13, or a pharmaceutically acceptable salt or stereoisomer thereof, wherein R$^{3b}$ is (C$_1$-C$_3$)alkyl substituted by one or more substituents independently selected from the group consisting of —F, —CH$_3$, —CH$_2$OH, —CN, —CH$_2$C(O)OCH$_2$CH$_3$, —C(O)CH$_2$OH, —C(O)CH$_3$, —C(O)OH, —NH$_2$, —N(H)S(O)$_2$CH$_3$, —OH, and =O.

19. The compound of claim 13, or a pharmaceutically acceptable salt or stereoisomer thereof,
wherein:
each instance of R$^{A2}$ is H;
each instance of R$^z$ is H;
R$^{3a}$ is heteroaryl; and
R$^{3b}$ is (C$_1$-C$_3$)alkyl substituted by one or more substituents independently selected from the group consisting of —F, —CH$_3$, —CH$_2$OH, —CN, —CH$_2$C(O)OCH$_2$CH$_3$, —C(O)CH$_2$OH, —C(O)CH$_3$, —C(O)OH, —NH$_2$, —N(H)S(O)$_2$CH$_3$, —OH, and =O.

* * * * *